US011993612B2

(12) United States Patent
Jensen et al.

(10) Patent No.: US 11,993,612 B2
(45) Date of Patent: May 28, 2024

(54) LRRK2 INHIBITORS

(71) Applicant: H. Lundbeck A/S, Valby (DK)

(72) Inventors: Thomas Jensen, Valby (DK); Mikkel Jessing, Valby (DK); Wanwan Yu, Valby (DK); David Rodriguez Diaz, Valby (DK); Jacob Nielsen, Valby (DK); Christopher Richard Jones, Valby (DK); Thomas Andersen, Valby (DK); Mikkel Fog Jacobsen, Valby (DK)

(73) Assignee: H. Lundbeck A/S, Valby (DK)

( * ) Notice: Subject to any disclaimer, the term of this patent is extended or adjusted under 35 U.S.C. 154(b) by 0 days.

(21) Appl. No.: 18/331,289

(22) Filed: Jun. 8, 2023

(65) Prior Publication Data
US 2023/0416272 A1    Dec. 28, 2023

Related U.S. Application Data

(63) Continuation of application No. 18/049,802, filed on Oct. 26, 2022, now Pat. No. 11,780,851.

(30) Foreign Application Priority Data

Oct. 27, 2021  (EP) .................................... 21204970
Oct. 13, 2022  (EP) .................................... 22201380

(51) Int. Cl.
*C07D 498/22* (2006.01)

(52) U.S. Cl.
CPC ........ *C07D 498/22* (2013.01); *C07B 2200/05* (2013.01)

(58) Field of Classification Search
None
See application file for complete search history.

(56) References Cited

U.S. PATENT DOCUMENTS

| 11,780,851 B2 | 10/2023 | Jensen et al. |
| 2014/0005183 A1 | 1/2014 | Galatsis et al. |
| 2016/0031905 A1 | 2/2016 | Hoflack et al. |
| 2017/0240565 A1 | 8/2017 | Hoflack et al. |
| 2023/0144725 A1 | 5/2023 | Jensen et al. |

FOREIGN PATENT DOCUMENTS

| WO | WO 2013/046029 A1 | 4/2013 |
| WO | WO 2014/134772 A1 | 9/2014 |
| WO | WO 2014/134774 A1 | 9/2014 |
| WO | WO 2014/137719 A1 | 9/2014 |
| WO | WO 2014/137723 A1 | 9/2014 |
| WO | WO 2014/137725 A1 | 9/2014 |
| WO | WO 2014/137728 A1 | 9/2014 |
| WO | WO 2014/140235 A1 | 9/2014 |
| WO | WO 2015/026683 A1 | 2/2015 |
| WO | WO 2015/073344 A1 | 5/2015 |
| WO | WO 2015/092592 A1 | 6/2015 |
| WO | WO 2015/113451 A1 | 8/2015 |
| WO | WO 2015/113452 A1 | 8/2015 |
| WO | WO 2016/036586 A1 | 3/2016 |
| WO | WO 2016/042089 A1 | 3/2016 |
| WO | WO 2016/130920 A2 | 8/2016 |
| WO | WO 2017/012576 A1 | 1/2017 |
| WO | WO 2017/087905 A1 | 5/2017 |
| WO | WO 2017/106771 A1 | 6/2017 |
| WO | WO 2017/156493 A1 | 9/2017 |
| WO | WO 2017/218843 A1 | 12/2017 |
| WO | WO 2018/137573 A1 | 8/2018 |
| WO | WO 2018/137593 A1 | 8/2018 |
| WO | WO 2018/137607 A1 | 8/2018 |
| WO | WO 2018/155916 A2 | 8/2018 |
| WO | WO 2018/217946 A1 | 11/2018 |
| WO | WO 2019/012093 A1 | 1/2019 |
| WO | WO 2019/074809 A1 | 4/2019 |
| WO | WO 2019/074810 A1 | 4/2019 |
| WO | WO 2019/112269 A1 | 6/2019 |
| WO | WO 2020/106685 A1 | 5/2020 |
| WO | WO 2023/222005 A1 | 11/2023 |
| WO | WO 2023/224894 A1 | 11/2023 |

OTHER PUBLICATIONS

Deng et al., Leucine-rich repeat kinase 2 inhibitors: a patent review (2006-2011). Expert Opin Ther Pat. Dec. 2012;22(12):1415-26. Epub Nov. 6, 2012.

Ding et al., Discovery of 4-ethoxy-7H-pyrrolo[2,3-d]pyrimidin-2-amines as potent, selective and orally bioavailable LRRK2 inhibitors. Bioorg Med Chem Lett. May 15, 2018;28(9):1615-1620. Epub Mar. 19, 2018.

Ding et al., Leucine-rich repeat kinase 2 inhibitors: a patent review (2014-present). Expert Opin Ther Pat. Apr. 2020;30(4):275-286. Epub Feb. 18, 2020.

Domingos et al., Targeting leucine-rich repeat kinase 2 (LRRK2) for the treatment of Parkinson's disease. Future Med Chem. Aug. 2019;11(15):1953-1977.

Estrada et al., Discovery of highly potent, selective, and brain-penetrable leucine-rich repeat kinase 2 (LRRK2) small molecule inhibitors. J Med Chem. Nov. 26, 2012;55(22):9416-33. Epub Oct. 15, 2012.

(Continued)

*Primary Examiner* — Samantha L Shterengarts

(74) *Attorney, Agent, or Firm* — Wolf, Greenfield & Sacks, P.C.

(57) ABSTRACT

The present invention is directed to compounds of formula I

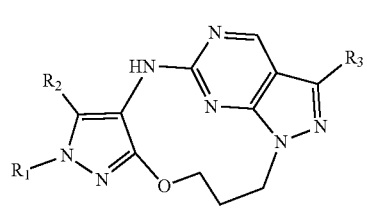

The compounds are considered useful for the treatment of diseases associated with LRRK2 such as Parkinson's disease.

19 Claims, No Drawings

(56) References Cited

OTHER PUBLICATIONS

Estrada et al., Discovery of highly potent, selective, and brain-penetrant aminopyrazole leucine-rich repeat kinase 2 (LRRK2) small molecule inhibitors. J Med Chem. Feb. 13, 2014;57(3):921-36. Epub Jan. 15, 2014.

Galatsis, P. Leucine-rich repeat kinase 2 inhibitors: a patent review (2014-2016). Expert Opin Ther Pat. Jun. 2017;27(6):667-676. Epub Jan. 31, 2017.

Hatcher et al., Discovery of a Pyrrolopyrimidine (JH-II-127), a Highly Potent, Selective, and Brain Penetrant LRRK2 Inhibitor. ACS Med Chem Lett. Apr. 7, 2015;6(5):584-9.

Henderson et al., Discovery and preclinical profiling of 3-[4-(morpholin-4-yl)-7H-pyrrolo[2,3-d]pyrimidin-5-yl]benzonitrile (PF-06447475), a highly potent, selective, brain penetrant, and in vivo active LRRK2 kinase inhibitor. J Med Chem. Jan. 8, 2015;58(1):419-32. Epub Nov. 17, 2014.

Kethiri et al., Leucine-rich repeat kinase 2 inhibitors: a review of recent patents (2011-2013). Expert Opin Ther Pat. Jul. 2014;24(7):745-57. Epub Jun. 11, 2014.

Scott et al., Discovery of a 3-(4-Pyrimidinyl) Indazole (MLi-2), an Orally Available and Selective Leucine-Rich Repeat Kinase 2 (LRRK2) Inhibitor that Reduces Brain Kinase Activity. J Med Chem. Apr. 13, 2017;60(7):2983-2992. Epub Mar. 16, 2017.

U.S. Appl. No. 18/049,802, filed Oct. 26, 2022, Granted, U.S. Pat. No. 11,780,851.

U.S. Appl. No. 18/467,162, filed Sep. 14, 2023, Pending.

LRRK2 INHIBITORS

CROSS-REFERENCE TO RELATED APPLICATIONS

This application is a Continuation application of U.S. application Ser. No. 18/049,802, filed Oct. 26, 2022, which claims priority to European Application No. 21204970.4, filed Oct. 27, 2021, and European Application No. 22201380.7, filed Oct. 13, 2022, the entire contents of the aforementioned applications are hereby incorporated herein by reference.

FIELD OF THE INVENTION

The present invention relates to compounds which are LRRK2 inhibitors and thus useful in therapy, and to pharmaceutical composition comprising said compounds.

BACKGROUND OF THE INVENTION

Parkinson's disease (PD) is a neurodegenerative disease. It is the second most common neurodegenerative disease after Alzheimer's disease and affects more than 1% of the population above the age of 65. Parkinson's disease is clinically characterised by resting tremor, bradykinesia, muscular rigidity and postural instability. In addition to motor symptoms, other symptoms such as neuropsychiatric symptoms are also present in many patients, and in late stages of the disease, Parkinson's disease dementia commonly develops. Pathologically, the disease is characterised by loss of dopaminergic neurons with consequent decrease in dopamine levels in the brain and by aggregation of the protein α-synuclein in the dopaminergic neurons. These aggregations, called Lewy bodies, are composed of insoluble α-synuclein phosphorylated at serine-129 and ubiquitin.

Current Parkinson's disease therapeutic intervention strategies aim at increasing the dopamine levels by administration of levodopa or monoamine oxidase B inhibitors. As an alternative, dopamine agonists are administered to stimulate dopaminergic receptors, an effect similar to that obtained by increasing the dopamine levels. Although these therapies provide significant symptomatic benefit to the patient, they are also associated with adverse side effects and often become ineffective after prolonged treatment and progression of the underlying disease. Importantly, none of the existing therapies addresses the underlying and disease-causing problem, i.e. the progressive loss of dopaminergic neurons.

Leucine-rich repeat kinase 2 (LRRK2) is a 2527 amino acid protein involved in catalysing protein phosphorylation. Evidence is mounting for a relationship between LRRK2 and the pathogenesis of Parkinson's disease. Single nucleotide polymorphisms that alter amino acids in functional domains of LRRK2 have been shown to cause familiar and sporadic Parkinson's disease. Several such pathogenic variants have been identified including G2019S, I2020T, N1437H, R1441C, R1441G, R1441H and Y1699C (Shu et al., A Comprehensive Analysis of Population Differences in LRRK2 Variant Distribution in Parkinson's Disease, Front Aging Neurosci., 11:13, 2019; Chittoor-Vinod et al., Genetic and Environmental Factors Influence the Pleomorphy of LRRK2 Parkinsonism, Int. J. Mol. Sci., 2021, 22, 1045). The most common pathogenic form of LRRK2-associated Parkinson's disease is the amino acid substitution G2019S in the kinase domain of the LRRK2 protein. G2019S Parkinson's disease is inherited in an autosomal dominant fashion suggesting a gain-of-function mutation of the LRRK2 protein. In support of this notion, biochemical studies have shown that both G2019S and other pathogenic LRRK2 variants lead to an increased kinase activity of LRRK2 (West et al, Parkinson's disease-associated mutations in leucine-rich repeat kinase 2 augment kinase activity, Proc. Nat. Acad. Sci, 102, 16842-16847, 2005; Chittoor-Vinod et al., Genetic and Environmental Factors Influence the Pleomorphy of LRRK2 Parkinsonism, Int. J. Mol. Sci., 2021, 22, 1045). The clinical and pathological features of Parkinson's disease associated with LRRK2 mutations are very similar to those of idiopathic Parkinson's disease (Trinh et al., A comparative study of Parkinson's disease and leucine-rich repeat kinase 2 p.G2019S parkinsonism, Neurobiol. Aging., 35(5), 1125-31, 2014). This strongly suggests a causal involvement of overactive LRRK2 in the pathogenesis of Parkinson's disease in patients with such activating mutations in LRRK2 and that inhibitors of LRRK2 could be used as disease modifying treatment in familiar Parkinson's disease.

In addition to the rare high-penetrance exonic LRRK2 variants mentioned above, there are also common LRRK2 variants with lower but significant association with Parkinson's disease showing that LRRK2 also contributes to idiopathic Parkinson's disease. These include very common single-nucleotide polymorphisms in the LRRK2 promotor region, where the Parkinson's disease associated variants appear to be associated with increased LRRK2 expression at least in some cell types (Nails et al., Identification of novel risk loci, causal insights, and heritable risk for Parkinson's disease: a meta-analysis of genome-wide association studies, Lancet Neurol, 2019, 18, 1091-1102; Sun et al., Genetic Variants Associated With Neurodegenerative Diseases Regulate Gene Expression in Immune Cell CD14+ Monocytes, Front Genet., 2018, 18, 9:666; Langston et al., Association of a Common Genetic Variant with Parkinson's Disease is Propagated through Microglia, bioRxiv, 2021) suggesting that LRRK2 inhibition might be relevant. Further, investigations of common exonic polymorphic variants have highlighted several LRRK2 Parkinson's disease risk variants including the A419V and G2385R that are common in the Asian population (Shu et al., A Comprehensive Analysis of Population Differences in LRRK2 Variant Distribution in Parkinson's Disease, Front Aging Neurosci., 11:13, 2019). There is also a protective variant of LRRK2 with reduced kinase activity such as the LRRK2 N551K R1398H variant (Wang et al., Understanding LRRK2 kinase activity in preclinical models and human subjects through quantitative analysis of LRRK2 and pT73 Rab10, Scientific Reports, 2021, 11:12900), which lends further support to the potential of LRRK2 inhibition in idiopathic Parkinson's disease by showing that wild-type LRRK2 activity is not optimal in a Parkinson's disease context. Functionally, LRRK2 affects trafficking of lysosomes and other vesicles through phosphorylation of RAB GTPases, and PD-associated genes are enriched for genes involved in lysosomal function and autophagy (Chang et al., A meta-analysis of genome-wide association studies identifies 17 new Parkinson's disease risk loci, Nat Genet., 2017, 49(10): 1511-1516). Two genes associated with Parkinson's disease, VPS35 and RAB29, have been shown to directly interact with LRRK2 biology as they increase LRRK2 activity (Taylor et al., Advances in elucidating the function of leucine-rich repeat protein kinase-2 in normal cells and Parkinson's disease, Curr Opin Cell Biol., 2020, 63:102-113), and as mentioned above, LRRK2 associated Parkinson's disease is very similar to idiopathic PD. Together this strongly supports the relevance of LRRK2 inhibition in treatment of idiopathic PD.

Several lines of evidence suggest that LRRK2 activity may impact α-synuclein pathology development after seeding with α-synuclein (O'Hara et al., LRRK2 and α-Synuclein: Distinct or Synergistic Players in Parkinson's Disease?, Front Neurosci., 2020, 17; 14:577).

In addition to strengthening the case for potential of LRRK2 inhibitors for treatment of Parkinson's disease, this indicates potential of LRRK2 inhibitors for treatment of other synucleinopathies including Lewy body dementia and multiple system atrophy.

LRRK2 is highly expressed in white blood cells and spleen suggesting a potential for LRRK2 inhibitors for treatment of aberrant immune responses. This is further supported by genetic association of LRRK2 with such diseases particularly inflammatory bowel diseases including Crohn's disease and leprosy (Liu et al., Association analyses identify 38 susceptibility loci for inflammatory bowel disease and highlight shared genetic risk across populations, Nat Genet., 2015, 47(9):979-986; Rastegar et al., Leucine Rich Repeat Kinase 2 and Innate Immunity, Front Neurosci., 2020, 10; 14:193). Thus, LRRK2 inhibitors may have potential for treatment of these diseases.

Both from the pharmaceutical industry and academic labs there has been a high interest in developing potent selective LRRK2 inhibitors due to its great promise in treating Parkinson's disease.

The historic development of LRRK2 inhibitors is well described in the literature (Delgado et al., N-bridged 5,6-bicyclic pyridines: Recent applications in central nervous system disorders, European Journal of Medicinal Chemistry 97 (2015) 719-731); Xiao Ding & Feng Ren (2020) Leucine-rich repeat kinase 2 inhibitors: a patent review (2014-present), Expert Opinion on Therapeutic patents, 30:4, 275-286). Even though a lot of focus has been on designing new LRRK2 inhibitors from the pharmaceutical industry and academic labs, the task of designing a brain penetrant, potent, selective LRRK2 inhibitor remains a challenging task for the medicinal chemistry community (Delgado et al., N-bridged 5,6-bicyclic pyridines: Recent applications in central nervous system disorders, European Journal of Medicinal Chemistry 97 (2015) 719-731).

Despite the tremendous efforts from pharmaceutical industry and academic labs only two molecules (DNL201 and DNL151) from Denali Therapeutics have reached clinical phase (Xiao Ding & Feng Ren (2020) Leucine-rich repeat kinase 2 inhibitors: a patent review (2014-present), Expert Opinion on Therapeutic patents, 30:4, 275-286).

Against this background there is still a highly unmet need to provide a LRRK2 inhibitor with good pharmacokinetic properties, whilst maintaining high potency and good selectivity.

SUMMARY OF THE INVENTION

The present inventors have surprisingly found that certain 5,7-(azenometheno)dipyrazolo[3,4-b:5',1'-g][1]oxa[4,6,8] triazacycloundecine compounds are LRRK2 inhibitors. Accordingly, in a first aspect of the invention is provided a compound of formula I, or a pharmaceutically acceptable salt thereof, wherein:

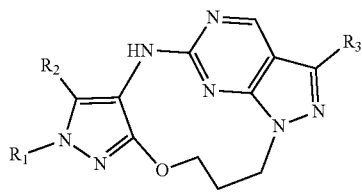

$R_1$ is $CH_2R_4$ or $R_4$;
$R_2$ is a $C_1$-$C_3$ alkyl, an isotopically labelled $C_1$-$C_3$ alkyl, a $C_3$-$C_6$cycloalkyl, or a $C_1$-$C_3$ haloalkyl;
$R_3$ is halogen, cyano, a O—$C_1$-$C_3$ haloalkyl, a $C_1$-$C_3$ haloalkyl, a $C_3$-$C_6$cycloalkyl, or a $C_1$-$C_3$ alkyl;
$R_4$ is a 4- to 7-membered heterocycle having 1-2 heteroatoms independently selected from oxygen and nitrogen; a $C_1$-$C_3$alkyl, a $C_1$-$C_3$ cyanoalkyl, a $C_1$-$C_3$ haloalkyl, or a $C_3$-$C_6$cycloalkyl; or $R_4$ is a bicyclic 8-membered heterocycle having 1-2 heteroatoms independently selected from oxygen and nitrogen;
wherein each heterocycle or cycloalkyl is unsubstituted or substituted with 1, 2, or 3 groups independently selected from the group consisting of cyano, deuterium, halogen, $C_1$-$C_3$ alkyl, an isotopically labelled $C_1$-$C_3$ alkyl, a O—$C_1$-$C_3$ haloalkyl, a O—$C_1$-$C_3$ alkyl, or a $C_1$-$C_3$ haloalkyl.

In some embodiments of the invention, $R_1$ is $CH_2R_4$.
In some embodiments of the invention, $R_1$ is $R_4$.
In some embodiments of the invention, the compound is a compound of formula Ia, or a pharmaceutically acceptable salt thereof, wherein:

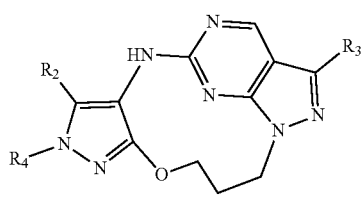

In some embodiments of the invention, $R_2$ is selected from a $C_1$-$C_3$ alkyl, an isotopically labelled $C_1$-$C_3$ alkyl or a $C_3$-$C_6$cycloalkyl.
In some embodiments of the invention, $R_2$ is selected from —$CH_3$, —$CH_2CH_3$, —$CD_3$, or cyclopropyl.
In some embodiments of the invention, $R_2$ is $C_1$-$C_3$ alkyl.
In some embodiments of the invention, $R_2$ is methyl.
In some embodiments of the invention, $R_2$ is ethyl.
In some embodiments of the invention, $R_2$ is an isotopically labelled $C_1$-$C_3$ alkyl.
In some embodiments of the invention, $R_2$ is selected from the group consisting of —$CD_3$ or -$CD_2CD_3$.
In some embodiments of the invention, $R_2$ is —$CD_3$.
In some embodiments of the invention, $R_2$ is cyclopropyl.
In some embodiments of the invention, $R_3$ is $C_1$-$C_3$ haloalkyl.
In some embodiments of the invention, $R_3$ is CF3.
In some embodiments of the invention, $R_3$ is halogen.
In some embodiments of the invention, $R_3$ is chloro.
In some embodiments of the invention, $R_3$ is bromo.
In some embodiments of the invention, $R_3$ is cyano.
In some embodiments of the invention, $R_3$ is a $C_3$-$C_6$cycloalkyl.

In some embodiments of the invention, $R_3$ is cyclopropyl.

In some embodiments of the invention, $R_4$ is a 4- to 6-membered heterocycle having one oxygen atom, wherein the 4- to 6-membered heterocycle is unsubstituted or substituted with one group selected from the group consisting of cyano, deuterium, halogen, $C_1$-$C_3$ alkyl, an isotopically labelled $C_1$-$C_3$ alkyl, O—$C_1$-$C_3$ haloalkyl, O—$C_1$-$C_3$ alkyl, or $C_1$-$C_3$ haloalkyl.

In some embodiments of the invention, $R_4$ is a 4- to 6-membered heterocycle having one oxygen atom, wherein the 4- to 6-membered heterocycle is unsubstituted or substituted with one group selected from the group consisting of deuterium, halogen, $C_1$-$C_3$ alkyl, or an isotopically labelled $C_1$-$C_3$ alkyl.

In some embodiments of the invention, $R_4$ is 6-membered heterocycle having one oxygen atom, wherein the 6-membered heterocycle is unsubstituted or substituted with one group selected from the group consisting of deuterium, halogen, $C_1$-$C_3$ alkyl, or an isotopically labelled $C_1$-$C_3$ alkyl.

In some embodiments of the invention, $R_4$ is 6-membered heterocycle having one oxygen atom, wherein the 6-membered heterocycle is unsubstituted or substituted with two groups independently selected from the group consisting of deuterium, halogen, $C_1$-$C_3$ alkyl, or an isotopically labelled $C_1$-$C_3$ alkyl.

In some embodiments of the invention, $R_4$ is selected from the group consisting of:

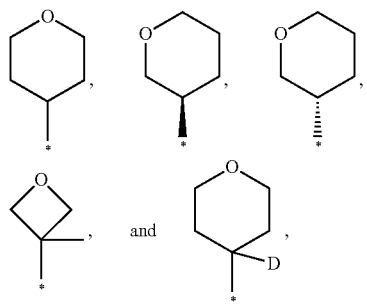

wherein * denotes the attachment point.

In some embodiments of the invention, $R_4$ is selected from the group consisting of: CH3

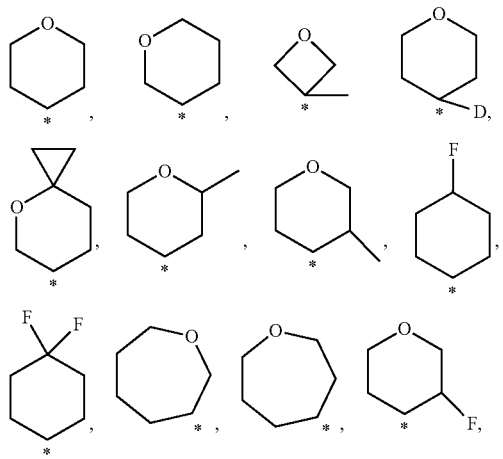

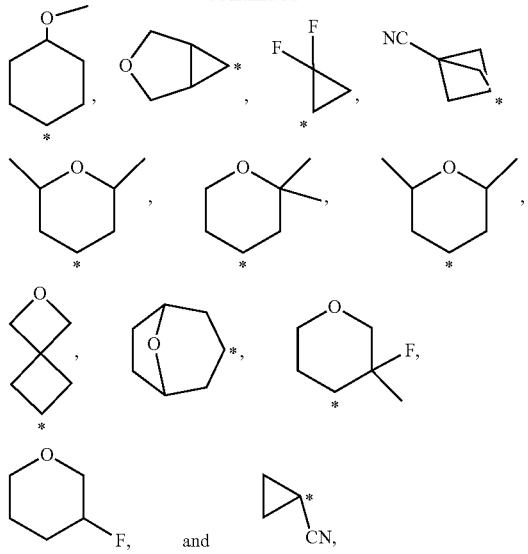

wherein * denotes the attachment point.

In some embodiments of the invention, $R_4$ is tetrahydropyran.

In some embodiments of the invention, $R_4$ is unsubstituted tetrahydropyran.

In some embodiments of the invention, $R_4$ is tetrahydro-2H-pyran-4-yl.

In some embodiments of the invention, $R_4$ is tetrahydro-2H-pyran-3-yl.

In some embodiments of the invention, $R_4$ is 4-oxaspiro [2.5]octan-7-yl.

In some embodiments of the invention, the 8-membered heterocycle is an unsubstituted 8-membered spirocyclic heterocycle.

In some embodiments of the invention, the bicyclic 8-membered heterocycle contains one oxygen.

In some embodiments of the invention, the bicyclic 8-membered heterocycle contains one oxygen and is a spirocyclic heterocycle.

In some embodiments of the invention, the compound is a compound of formula Ib, or a pharmaceutically acceptable salt thereof, wherein:

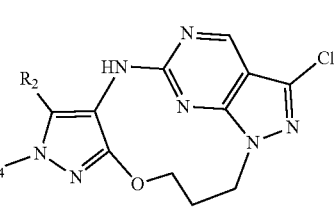

$R_2$ is a $C_1$-$C_3$ alkyl, an isotopically labelled $C_1$-$C_3$ alkyl, a $C_3$-$C_6$cycloalkyl, or a $C_1$-$C_3$ haloalkyl;

$R_4$ is a 4- to 7-membered heterocycle having 1-2 heteroatoms independently selected from oxygen and nitrogen, a $C_1$-$C_3$alkyl, a $C_1$-$C_3$ cyanoalkyl, a $C_1$-$C_3$ haloalkyl, or a $C_3$-$C_6$cycloalkyl;

wherein each heterocycle or cycloalkyl is unsubstituted or substituted with 1 group selected from the groups selected from cyano, deuterium, halogen, a $C_1$-$C_3$ alkyl, an isotopically labelled $C_1$-$C_3$ alkyl, a O—$C_1$-$C_3$ haloalkyl, a O—$C_1$-$C_3$ alkyl, or a $C_1$-$C_3$ haloalkyl.

In some embodiments of the invention, $R_2$ is selected from —$CH_3$, —$CH_2CH_3$, —$CD_3$, or cyclopropyl.

In some embodiments of the invention, the compound is a compound of formula Ic, or a pharmaceutically acceptable salt thereof, wherein:

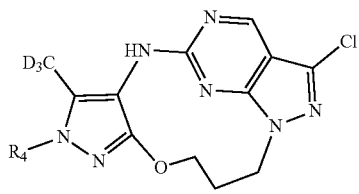

Ic $R_4$ is a 4- to 7-membered heterocycle having 1-2 heteroatoms independently selected from oxygen and nitrogen, a $C_1$-$C_3$alkyl, a $C_1$-$C_3$ cyanoalkyl, a $C_1$-$C_3$ haloalkyl, or a $C_3$-$C_6$ cycloalkyl; wherein each heterocycle or cycloalkyl is unsubstituted or substituted with 1 group selected from the groups selected from cyano, deuterium, halogen, a $C_1$-$C_3$ alkyl, an isotopically labelled $C_1$-$C_3$ alkyl, a O—$C_1$-$C_3$ haloalkyl, a O—$C_1$-$C_3$ alkyl, or a $C_1$-$C_3$ haloalkyl.

In some embodiments of the invention, the compound is a compound of formula Id, or a pharmaceutically acceptable salt thereof, wherein:

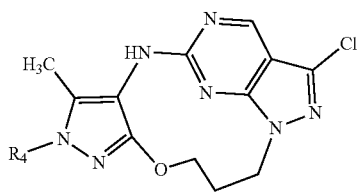

Id $R_4$ is a 4- to 7-membered heterocycle having 1-2 heteroatoms independently selected from oxygen and nitrogen, a $C_1$-$C_3$alkyl, a $C_1$-$C_3$ cyanoalkyl, a $C_1$-$C_3$ haloalkyl, or a $C_3$-$C_6$ cycloalkyl; wherein each heterocycle or cycloalkyl is unsubstituted or substituted with 1 group selected from the groups selected from cyano, deuterium, halogen, a $C_1$-$C_3$ alkyl, an isotopically labelled $C_1$-$C_3$ alkyl, a O—$C_1$-$C_3$ haloalkyl, a O—$C_1$-$C_3$ alkyl, or a $C_1$-$C_3$ haloalkyl.

In some embodiments of the invention, the 4- to 7-membered heterocycle is an unsubstituted 6-7 membered spirocyclic heterocycle.

In some embodiments of the invention, the 4- to 7-membered heterocycle is an unsubstituted 6-7 membered bridged heterocycle.

In some embodiments of the invention, the compound is selected from the group consisting of:

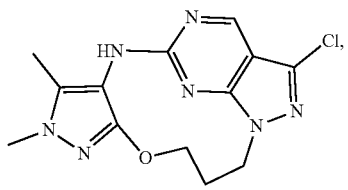

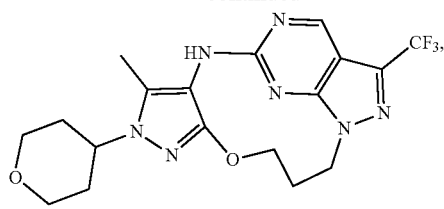

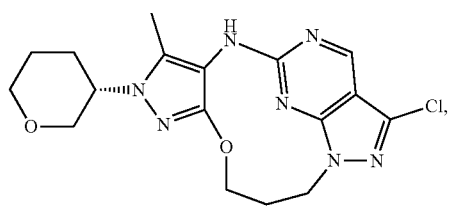

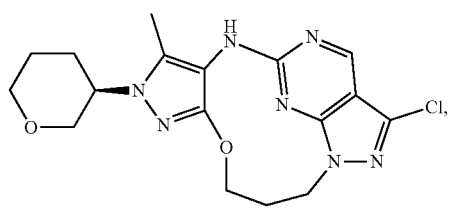

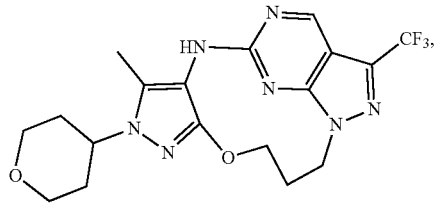

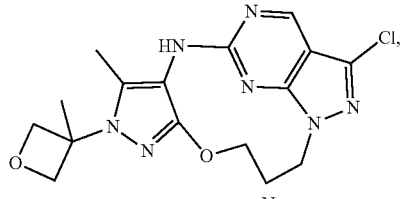

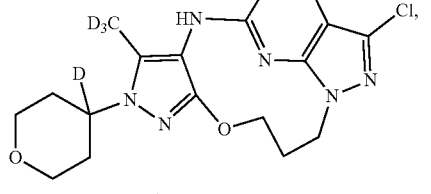

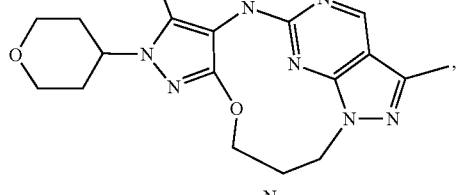

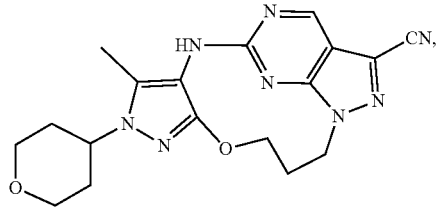

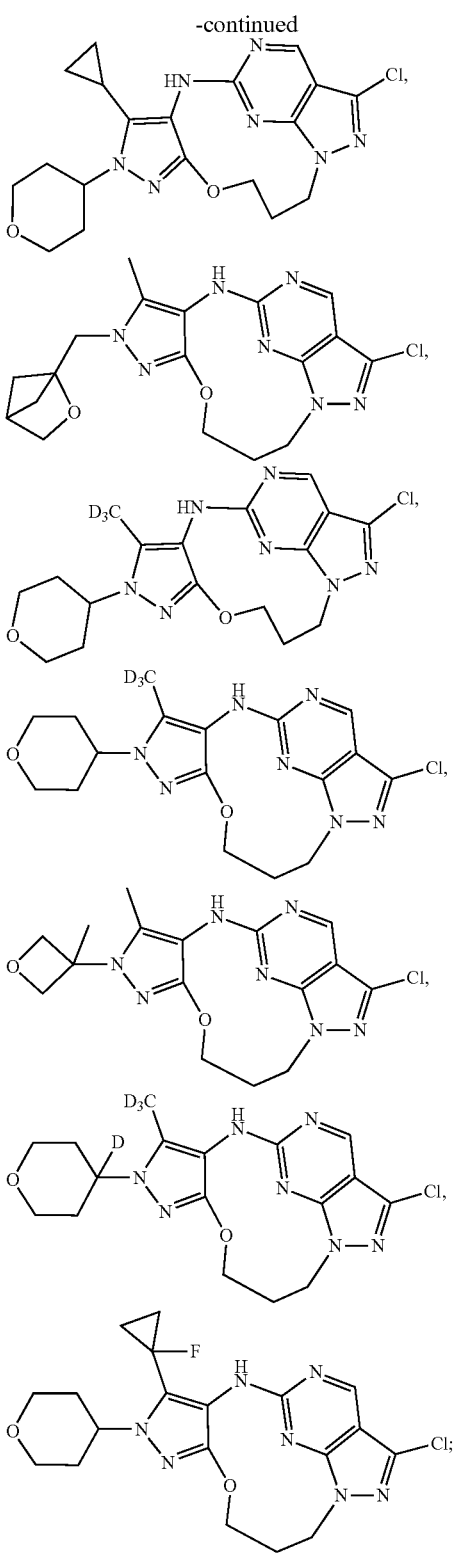

or a pharmaceutically acceptable salt thereof.

In some embodiments of the invention, the compound is selected from the group consisting of:

8-Chloro-2,3-dimethyl-2,4,12,13-tetrahydro-11H-5,7-(azenometheno)dipyrazolo-[3,4-b:5',1'-g][1]oxa[4,6,8]triazacycloundecine;

8-Chloro-3-methyl-2-(tetrahydro-2H-pyran-4-yl)-2,4,12,13-tetrahydro-11H-5,7-(azenometheno)dipyrazolo[3,4-b:5',1'-g][1]oxa[4,6,8]triazacycloundecine;

(R)-8-chloro-3-methyl-2-(tetrahydro-2H-pyran-3-yl)-2,4,12,13-tetrahydro-11H-5,7-(azenometheno)dipyrazolo[3,4-b:5',1'-g][1]oxa[4,6,8]triazacycloundecine;

(S)-8-chloro-3-methyl-2-(tetrahydro-2H-pyran-3-yl)-2,4,12,13-tetrahydro-11H-5,7-(azenometheno)dipyrazolo[3,4-b:5',1'-g][1]oxa[4,6,8]triazacycloundecine;

3-Methyl-2-(tetrahydro-2H-pyran-4-yl)-8-(trifluoromethyl)-2,4,12,13-tetrahydro-11H5,7-(azenometheno)dipyrazolo[3,4-b:5',1'-g][1]oxa[4,6,8]triazacycloundecine;

8-Bromo-3-methyl-2-(tetrahydro-2H-pyran-4-yl)-2,4,12,13-tetrahydro-11H-5,7-(azenometheno)dipyrazolo[3,4-b:5',1'-g][1]oxa[4,6,8]triazacycloundecine;

8-Cyclopropyl-3-methyl-2-(tetrahydro-2H-pyran-4-yl)-2,4,12,13-tetrahydro-11H-5,7-(azenometheno)dipyrazolo[3,4-b:5',1'-g][1]oxa[4,6,8]triazacycloundecine;

3,8-Dimethyl-2-(tetrahydro-2H-pyran-4-yl)-2,4,12,13-tetrahydro-11H-5,7-(azenometheno)dipyrazolo[3,4-b:5',1'-g][1]oxa[4,6,8]triazacycloundecine;

3-Methyl-2-(tetrahydro-2H-pyran-4-yl)-2,4,12,13-tetrahydro-11H-5,7-(azenometheno)dipyrazolo[3,4-b:5',1'-g][1]oxa[4,6,8]triazacycloundecine-8-carbonitrile;

8-Chloro-3-cyclopropyl-2-(tetrahydro-2H-pyran-4-yl)-2,4,12,13-tetrahydro-11H-5,7-(azenometheno)dipyrazolo[3,4-b:5',1'-g][1]oxa[4,6,8]triazacycloundecine;

2-((2-Oxabicyclo[2.1.1]hexan-1-yl)methyl)-8-chloro-3-methyl-2,4,12,13-tetrahydro-11H-5,7-(azenometheno)dipyrazolo[3,4-b:5',1'-g][1]oxa[4,6,8]triazacycloundecine;

8-Chloro-3-methyl-2-((3-methyloxetan-3-yl)methyl)-2,4,12,13-tetrahydro-11H-5,7-(azenometheno)dipyrazolo[3,4-b:5',1'-g][1]oxa[4,6,8]triazacycloundecine;

8-Chloro-3-(methyl-d3)-2-(tetrahydro-2H-pyran-4-yl)-2,4,12,13-tetrahydro-11H-5,7-(azenometheno)dipyrazolo[3,4-b:5',1'-g][1]oxa[4,6,8]triazacycloundecine;

8-Chloro-3-methyl-2-(3-methyloxetan-3-yl)-2,4,12,13-tetrahydro-11H-5,7-(azenometheno)dipyrazolo[3,4-b:5',1'-g][1]oxa[4,6,8]triazacycloundecine;

8-Chloro-3-(methyl-d3)-2-(tetrahydro-2H-pyran-4-yl-4-d)-2,4,12,13-tetrahydro-11H5,7-(azenometheno)dipyrazolo[3,4-b:5',1'-g][1]oxa[4,6,8]triazacycloundecine; and 8-Chloro-3-(1-fluorocyclopropyl)-2-(tetrahydro-2H-pyran-4-yl)-2,4,12,13-tetrahydro-11H-5,7-(azenometheno)dipyrazolo[3,4-b:5',1'-g][1]oxa[4,6,8]triazacycloundecine; or a pharmaceutically acceptable salt thereof.

In some embodiments of the invention, the compound is selected from the group consisting of:

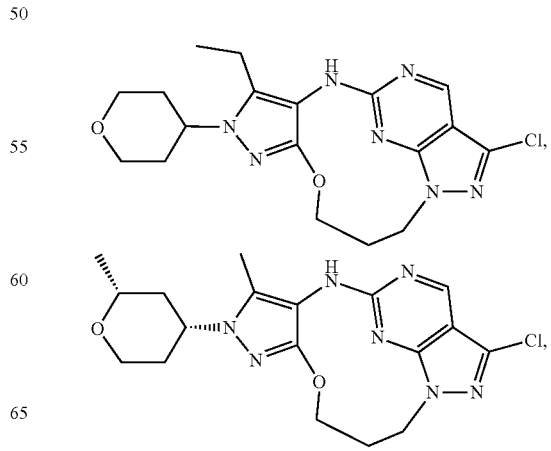

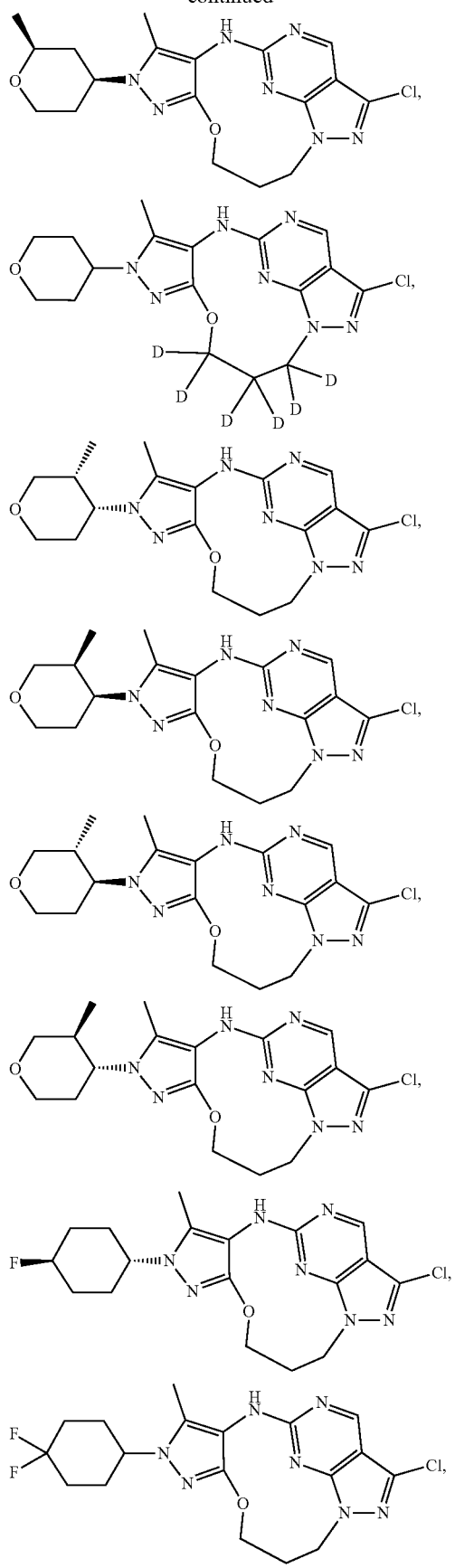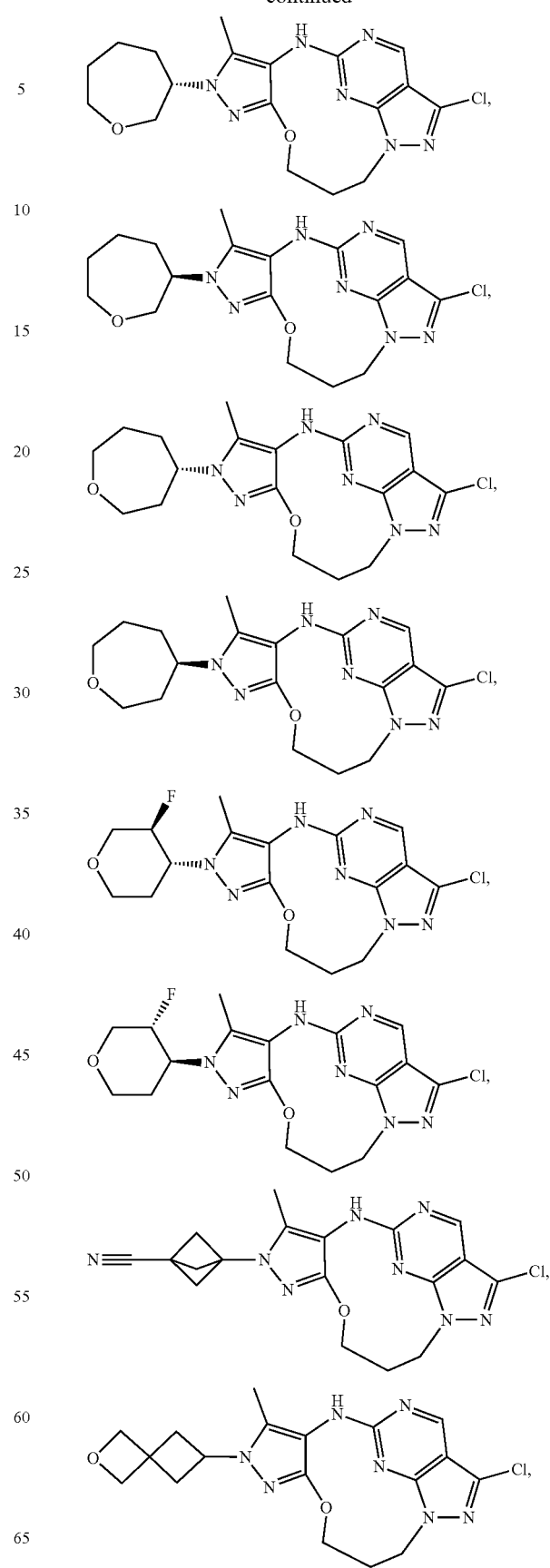

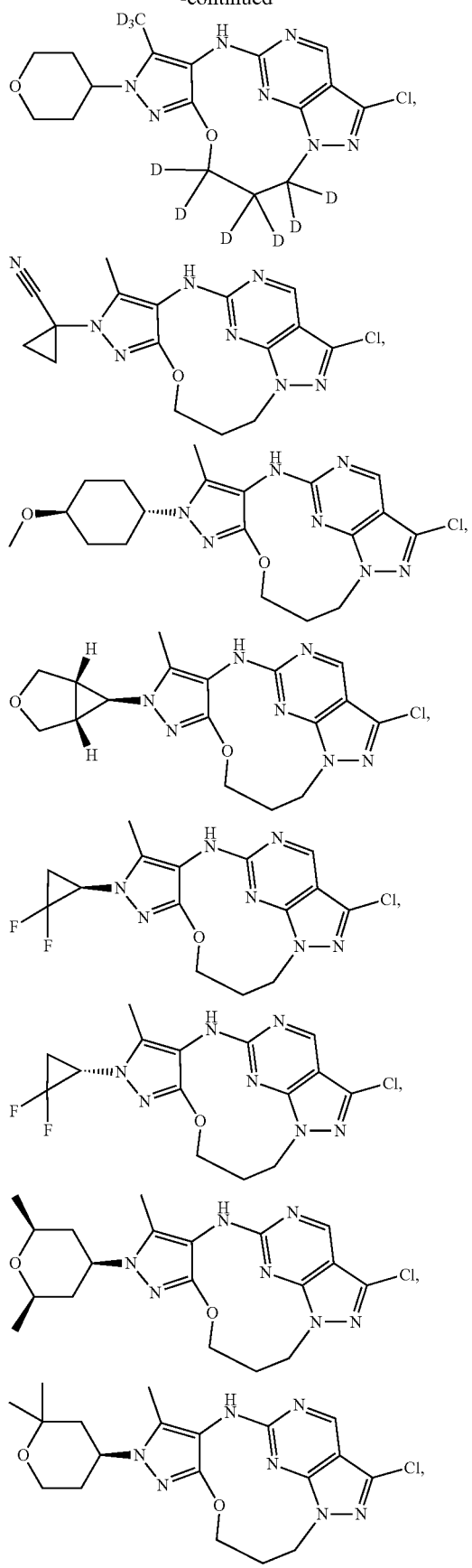
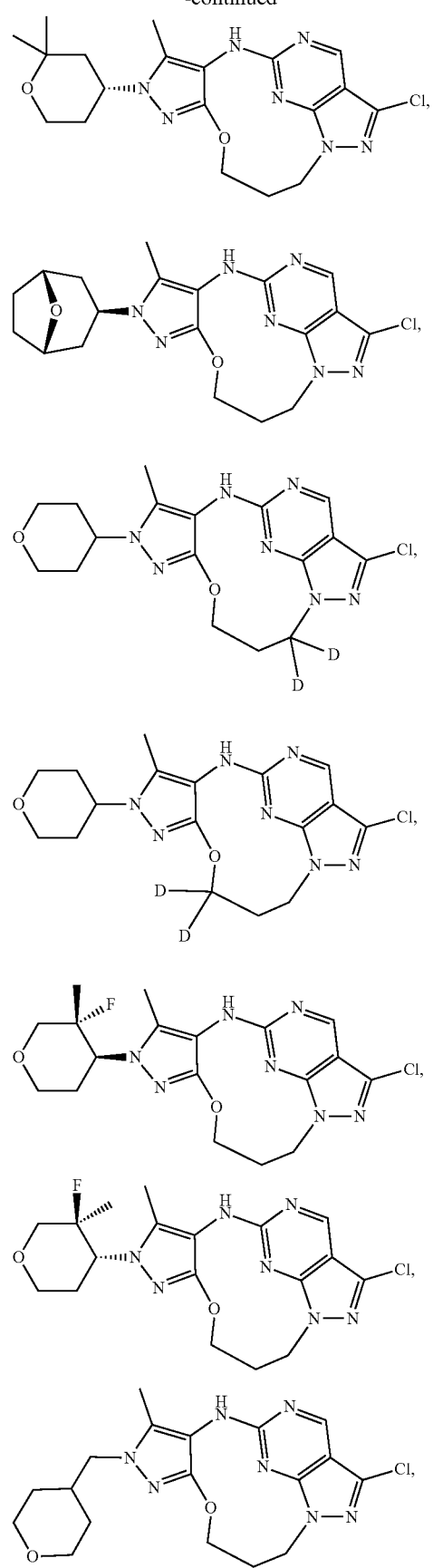

-continued
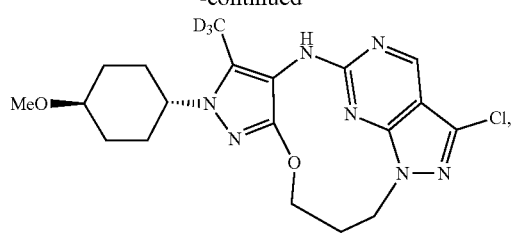
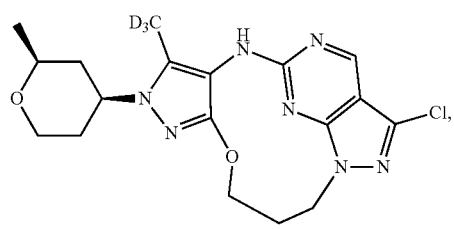
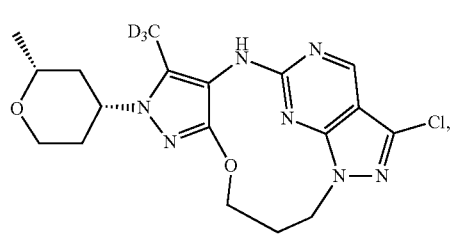
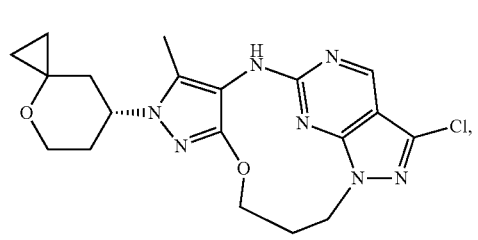
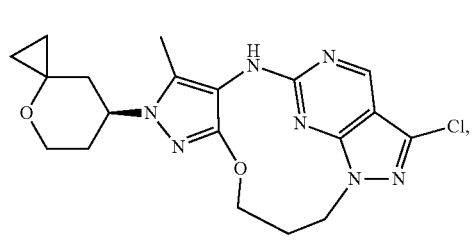
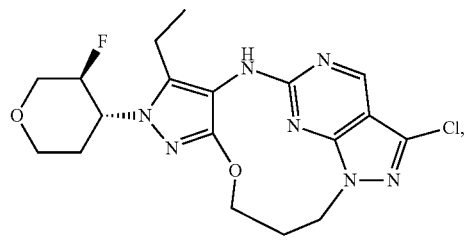
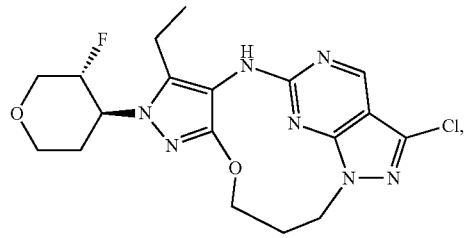
-continued
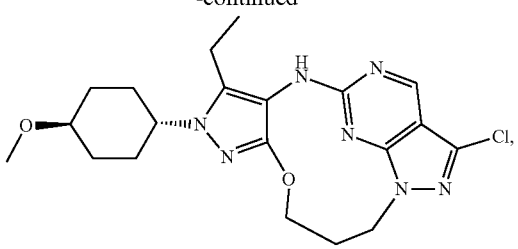
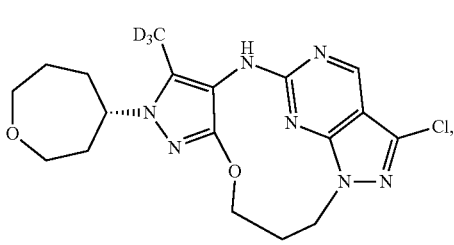
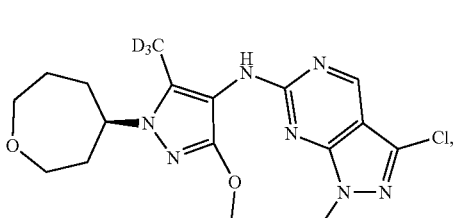
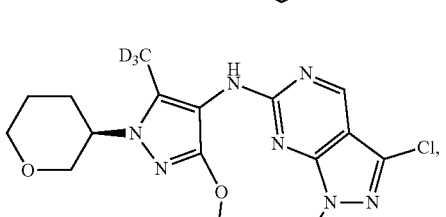
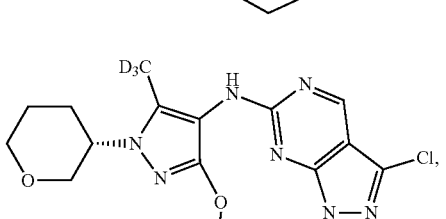
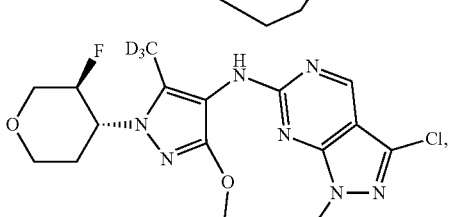
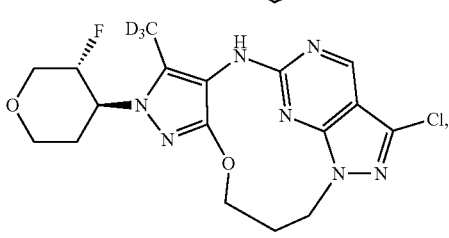

-continued

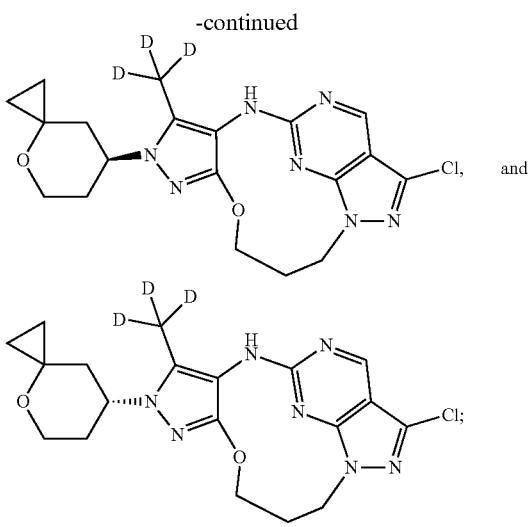

or a pharmaceutically acceptable salt thereof.

In some embodiments of the invention, the compound is selected from the group consisting of:

8-Chloro-3-ethyl-2-(tetrahydro-2H-pyran-4-yl)-2,4,12,13-tetrahydro-11H-5,7-(azenometheno)dipyrazolo[3,4-b:5',1'-g][1]oxa[4,6,8]triazacycloundecane:

8-Chloro-3-methyl-2-((2R,4R)-2-methyltetrahydro-2H-pyran-4-yl)-2,4,12,13-tetrahydro-11H-5,7-(azenometheno)dipyrazolo[3,4-b:5',1'-g][1]oxa[4,6,8]triazacycloundecine;

8-Chloro-3-methyl-2-((2S,4S)-2-methyltetrahydro-2H-pyran-4-yl)-2,4,12,13-tetrahydro-11H-5,7-(azenometheno)dipyrazolo[3,4-b:5',1'-g][1]oxa[4,6,8]triazacycloundecine;

8-Chloro-3-methyl-2-(tetrahydro-2H-pyran-4-yl)-2,4,12,13-tetrahydro-11H-5,7-(azenometheno)dipyrazolo[3,4-b:5',1'-g][1]oxa[4,6,8]triazacycloundecine-11,11,12,12,13,13-$d_6$;

8-Chloro-3-methyl-2-((3R,4S)-3-methyltetrahydro-2H-pyran-4-yl)-2,4,12,13-tetrahydro-11H-5,7-(azenometheno)dipyrazolo[3,4-b:5',1'-g][1]oxa[4,6,8]triazacycloundecine;

8-Chloro-3-methyl-2-((3S,4R)-3-methyltetrahydro-2H-pyran-4-yl)-2,4,12,13-tetrahydro-11H-5,7-(azenometheno)dipyrazolo[3,4-b:5',1'-g][1]oxa[4,6,8]triazacycloundecine;

8-Chloro-3-methyl-2-((3S,4S)-3-methyltetrahydro-2H-pyran-4-yl)-2,4,12,13-tetrahydro-11H-5,7-(azenometheno)dipyrazolo[3,4-b:5',1'-g][1]oxa[4,6,8]triazacycloundecine;

8-Chloro-3-methyl-2-((3R,4R)-3-methyltetrahydro-2H-pyran-4-yl)-2,4,12,13-tetrahydro-11H-5,7-(azenometheno)dipyrazolo[3,4-b:5',1'-g][1]oxa[4,6,8]triazacycloundecine;

8-Chloro-2-((1r,4r)-4-fluorocyclohexyl)-3-methyl-2,4,12,13-tetrahydro-11H-5,7-(azenometheno)dipyrazolo[3,4-b:5',1'-g][1]oxa[4,6,8]triazacycloundecine;

8-Chloro-2-(4,4-difluorocyclohexyl)-3-methyl-2,4,12,13-tetrahydro-11H-5,7-(azenometheno)dipyrazolo[3,4-b:5',1'-g][1]oxa[4,6,8]triazacycloundecine;

(R)-8-Chloro-3-methyl-2-(oxepan-3-yl)-2,4,12,13-tetrahydro-11H-5,7-(azenometheno)dipyrazolo[3,4-b:5',1'-g][1]oxa[4,6,8]triazacycloundecine;

(S)-8-Chloro-3-methyl-2-(oxepan-3-yl)-2,4,12,13-tetrahydro-11H-5,7-(azenometheno)dipyrazolo[3,4-b:5',1'-g][1]oxa[4,6,8]triazacycloundecine;

(R)-8-Chloro-3-methyl-2-(oxepan-4-yl)-2,4,12,13-tetrahydro-11H-5,7-(azenometheno)dipyrazolo[3,4-b:5',1'-g][1]oxa[4,6,8]triazacycloundecine;

(S)-8-Chloro-3-methyl-2-(oxepan-4-yl)-2,4,12,13-tetrahydro-11H-5,7-(azenometheno)dipyrazolo[3,4-b:5',1'-g][1]oxa[4,6,8]triazacycloundecine;

8-Chloro-2-((3S,4R)-3-fluorotetrahydro-2H-pyran-4-yl)-3-methyl-2,4,12,13-tetrahydro-11H-5,7-(azenometheno)dipyrazolo[3,4-b:5',1'-g][1]oxa[4,6,8]triazacycloundecine;

8-Chloro-2-((3R,4S)-3-fluorotetrahydro-2H-pyran-4-yl)-3-methyl-2,4,12,13-tetrahydro-11H-5,7-(azenometheno)dipyrazolo[3,4-b:5',1'-g][1]oxa[4,6,8]triazacycloundecine;

3-(8-Chloro-3-methyl-12,13-dihydro-11H-5,7-(azenometheno)dipyrazolo[3,4-b:5',1'-g][1]oxa[4,6,8]triazacycloundecin-2(4H)-yl)bicyclo[1.1.1]pentane-1-carbonitrile;

8-Chloro-3-methyl-2-(2-oxaspiro[3.3]heptan-6-yl)-2,4,12,13-tetrahydro-11H-5,7-(azenometheno)dipyrazolo[3,4-b:5',1'-g][1]oxa[4,6,8]triazacycloundecine;

8-Chloro-3-(methyl-$d_3$)-2-(tetrahydro-2H-pyran-4-yl)-2,4,12,13-tetrahydro-11H-5,7-(azenometheno)dipyrazolo[3,4-b:5',1'-g][1]oxa[4,6,8]triazacycloundecine-11,11,12,12,13,13-$d_6$;

1-(8-Chloro-3-methyl-12,13-dihydro-11H-5,7-(azenometheno)dipyrazolo[3,4-b:5',1'-g][1]oxa[4,6,8]triazacycloundecin-2(4H)-yl)cyclopropane-1-carbonitrile;

8-Chloro-2-((1r,4r)-4-methoxycyclohexyl)-3-methyl-2,4,12,13-tetrahydro-11H-5,7-(azenometheno)dipyrazolo[3,4-b:5',1'-g][1]oxa[4,6,8]triazacycloundecine;

2-((1R,5S,6r)-3-Oxabicyclo[3.1.0]hexan-6-yl)-8-chloro-3-methyl-2,4,12,13-tetrahydro-11H-5,7-(azenometheno)dipyrazolo[3,4-b:5',1'-g][1]oxa[4,6,8]triazacycloundecine;

(R)-8-Chloro-2-(2,2-difluorocyclopropyl)-3-methyl-2,4,12,13-tetrahydro-11H-5,7-(azenometheno)dipyrazolo[3,4-b:5',1'-g][1]oxa[4,6,8]triazacycloundecine;

(S)-8-Chloro-2-(2,2-difluorocyclopropyl)-3-methyl-2,4,12,13-tetrahydro-11H-5,7-(azenometheno)dipyrazolo[3,4-b:5',1'-g][1]oxa[4,6,8]triazacycloundecine;

8-chloro-2-((2R,4r,6S)-2,6-dimethyltetrahydro-2H-pyran-4-yl)-3-methyl-2,4,12,13-tetrahydro-11H-5,7-(azenometheno)dipyrazolo[3,4-b:5',1'-g][1]oxa[4,6,8]triazacycloundecine;

(R)-8-Chloro-2-(2,2-dimethyltetrahydro-2H-pyran-4-yl)-3-methyl-2,4,12,13-tetrahydro-11H-5,7-(azenometheno)dipyrazolo[3,4-b:5',1'-g][1]oxa[4,6,8]triazacycloundecine;

(S)-8-Chloro-2-(2,2-dimethyltetrahydro-2H-pyran-4-yl)-3-methyl-2,4,12,13-tetrahydro-11H-5,7-(azenometheno)dipyrazolo[3,4-b:5',1'-g][1]oxa[4,6,8]triazacycloundecine;

2-((1R,3s,5S)-8-Oxabicyclo[3.2.1]octan-3-yl)-8-chloro-3-methyl-2,4,12,13-tetrahydro-11H-5,7-(azenometheno)dipyrazolo[3,4-b:5',1'-g][1]oxa[4,6,8]triazacycloundecine;

8-Chloro-3-methyl-2-(tetrahydro-2H-pyran-4-yl)-2,4,12,13-tetrahydro-11H-5,7-(azenometheno)dipyrazolo[3,4-b:5',1'-g][1]oxa[4,6,8]triazacycloundecine-11,11-$d_2$;

8-Chloro-3-methyl-2-(tetrahydro-2H-pyran-4-yl)-2,4,12,13-tetrahydro-11H-5,7-(azenometheno)dipyrazolo[3,4-b:5',1'-g][1]oxa[4,6,8]triazacycloundecine-13,13-$d_2$;

8-Chloro-2-((3R,4S)-3-Fluoro-3-methyltetrahydro-2H-pyran-4-yl)-3-methyl-2,4,12,13-tetrahydro-11H-5,7-(azenometheno)dipyrazolo[3,4-b:5',1'-g][1]oxa[4,6,8]triazacycloundecine;

8-Chloro-2-((3S,4R)-3-Fluoro-3-methyltetrahydro-2H-pyran-4-yl)-3-methyl-2,4,12,13-tetrahydro-11H-5,7-(azenometheno)dipyrazolo[3,4-b:5',1'-g][1]oxa[4,6,8]triazacycloundecine;

8-Chloro-3-methyl-2-((tetrahydro-2H-pyran-4-yl)methyl)-2,4,12,13-tetrahydro-11H5,7-(azenometheno)dipyrazolo[3,4-b:5',1'-g][1]oxa[4,6,8]triazacycloundecine;

8-Chloro-2-((1r,4r)-4-methoxycyclohexyl)-3-(methyl-d₃)-2,4,12,13-tetrahydro-11H-5,7-(azenometheno)dipyrazolo[3,4-b:5',1'-g][1]oxa[4,6,8]triazacycloundecine;

8-Chloro-3-(methyl-d₃)-2-((2R,4R)-2-methyltetrahydro-2H-pyran-4-yl)-2,4,12,13-tetrahydro-11H-5,7-(azenometheno)dipyrazolo[3,4-b:5',1'-g][1]oxa[4,6,8]triazacycloundecine;

8-Chloro-3-(methyl-d₃)-2-((2S,4S)-2-methyltetrahydro-2H-pyran-4-yl)-2,4,12,13-tetrahydro-11H-5,7-(azenometheno)dipyrazolo[3,4-b:5',1'-g][1]oxa[4,6,8]triazacycloundecine;

(R)-8-Chloro-3-methyl-2-(4-oxaspiro[2.5]octan-7-yl)-2,4,12,13-tetrahydro-11H-5,7-(azenometheno)dipyrazolo[3,4-b:5',1'-g][1]oxa[4,6,8]triazacycloundecine;

(S)-8-Chloro-3-methyl-2-(4-oxaspiro[2.5]octan-7-yl)-2,4,12,13-tetrahydro-11H-5,7-(azenometheno)dipyrazolo[3,4-b:5',1'-g][1]oxa[4,6,8]triazacycloundecine;

8-Chloro-3-ethyl-2-((3R,4S)-3-fluorotetrahydro-2H-pyran-4-yl)-2,4,12,13-tetrahydro-11H-5,7-(azenometheno)dipyrazolo[3,4-b:5',1'-g][1]oxa[4,6,8]triazacycloundecine;

8-Chloro-3-ethyl-2-((3S,4R)-3-fluorotetrahydro-2H-pyran-4-yl)-2,4,12,13-tetrahydro-11H-5,7-(azenometheno)dipyrazolo[3,4-b:5',1'-g][1]oxa[4,6,8]triazacycloundecine;

8-Chloro-3-ethyl-2-((1r,4r)-4-methoxycyclohexyl)-2,4,12,13-tetrahydro-11H-5,7-(azenometheno)dipyrazolo[3,4-b:5',1'-g][1]oxa[4,6,8]triazacycloundecine;

(R)-8-Chloro-3-(methyl-d₃)-2-(oxepan-4-yl)-2,4,12,13-tetrahydro-11H-5,7-(azenometheno)dipyrazolo[3,4-b:5',1'-g][1]oxa[4,6,8]triazacycloundecine;

(S)-8-Chloro-3-(methyl-d₃)-2-(oxepan-4-yl)-2,4,12,13-tetrahydro-11H-5,7-(azenometheno)dipyrazolo[3,4-b:5',1'-g][1]oxa[4,6,8]triazacycloundecine;

(R)-8-Chloro-3-(methyl-d3)-2-(tetrahydro-2H-pyran-3-yl)-2,4,12,13-tetrahydro-11H5,7-(azenometheno)dipyrazolo[3,4-b:5',1'-g][1]oxa[4,6,8]triazacycloundecine;

(S)-8-Chloro-3-(methyl-d3)-2-(tetrahydro-2H-pyran-3-yl)-2,4,12,13-tetrahydro-11H5,7-(azenometheno)dipyrazolo[3,4-b:5',1'-g][1]oxa[4,6,8]triazacycloundecine;

8-Chloro-2-((3R,4S)-3-fluorotetrahydro-2H-pyran-4-yl)-3-(methyl-d₃)-2,4,12,13-tetrahydro-11H-5,7-(azenometheno)dipyrazolo[3,4-b:5',1'-g][1]oxa[4,6,8]triazacycloundecine;

8-chloro-2-((3S,4R)-3-fluorotetrahydro-2H-pyran-4-yl)-3-(methyl-d₃)-2,4,12,13-tetrahydro-11H-5,7-(azenometheno)dipyrazolo[3,4-b:5',1'-g][1]oxa[4,6,8]triazacycloundecine;

(R)-8-chloro-3-(methyl-d₃)-2-(4-oxaspiro[2.5]octan-7-yl)-2,4,12,13-tetrahydro-11H-5,7-(azenometheno)dipyrazolo[3,4-b:5',1'-g][1]oxa[4,6,8]triazacycloundecine; and (S)-8-chloro-3-(methyl-d₃)-2-(4-oxaspiro[2.5]octan-7-yl)-2,4,12,13-tetrahydro-11H-5,7-(azenometheno)dipyrazolo[3,4-b:5',1'-g][1]oxa[4,6,8]triazacycloundecine; or a pharmaceutically acceptable salt thereof.

In some embodiments of the invention, the compound is

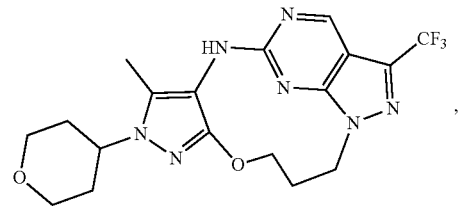 [SMILES: Cc1c2c(nn1C1CCOCC1)OCCCn1nc(C(F)(F)F)c3cnc(nc31)N2]

or a pharmaceutically acceptable salt.

In some embodiments of the invention, the compound is

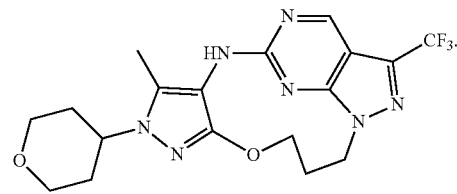 [SMILES: Cc1c2c(nn1C1CCOCC1)OCCCn1nc(C(F)(F)F)c3cnc(nc31)N2]

In some embodiments of the invention, the compound is

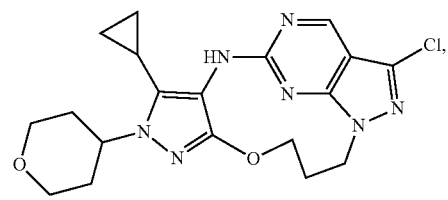 [SMILES: Clc1nn2c3nc(ncc13)Nc1c(nn(C3CCOCC3)c1C1CC1)OCCC2]

or a pharmaceutically acceptable salt.

In some embodiments of the invention, the compound is

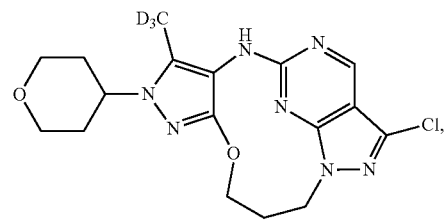 [SMILES: [2H]C([2H])([2H])c1c2c(nn1C1CCOCC1)OCCCn1nc(Cl)c3cnc(nc31)N2]

or a pharmaceutically acceptable salt.

In some embodiments of the invention, the compound is

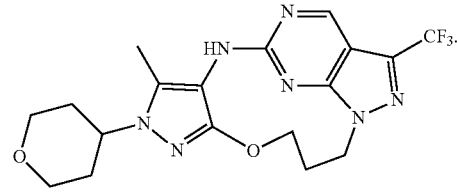 [SMILES: Cc1c2c(nn1C1CCOCC1)OCCCn1nc(C(F)(F)F)c3cnc(nc31)N2]

In some embodiments of the invention, the compound is

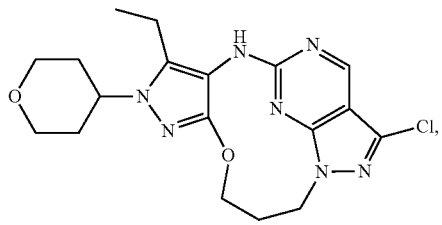

or a pharmaceutically acceptable salt thereof.

In some embodiments of the invention, the compound is

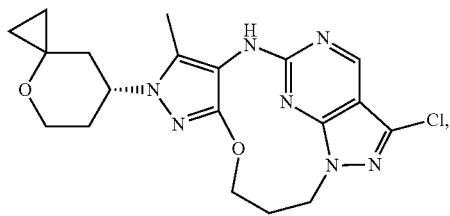 [SMILES: Cc1c2c(nn1[C@@H]1CCOC3(CC3)C1)OCCCn1nc(Cl)c3cnc(nc31)N2]

or a pharmaceutically acceptable salt thereof.

In some embodiments of the invention, the compound is

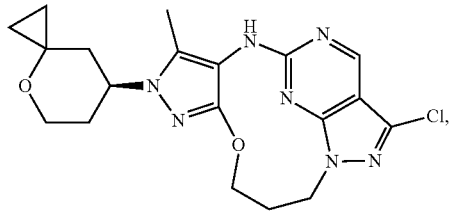 [SMILES: Cc1c2c(nn1[C@H]1CCOC3(CC3)C1)OCCCn1nc(Cl)c3cnc(nc31)N2]

or a pharmaceutically acceptable salt thereof.

In some embodiments of the invention, the compound is

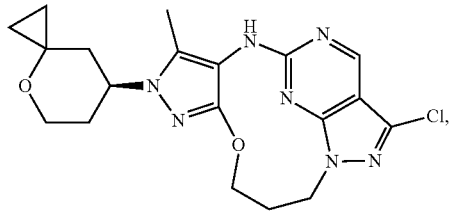 [SMILES: Cc1c2c(nn1[C@H]1CCOC3(CC3)C1)OCCCn1nc(Cl)c3cnc(nc31)N2]

or a pharmaceutically acceptable salt thereof.

In some embodiments of the invention, the compound is

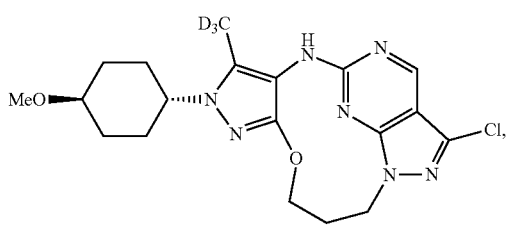 [SMILES: [2H]C([2H])([2H])c1c2c(nn1[C@H]1CC[C@H](OC)CC1)OCCCn1nc(Cl)c3cnc(nc31)N2]

or a pharmaceutically acceptable salt thereof.

In some embodiments of the invention, the compound is

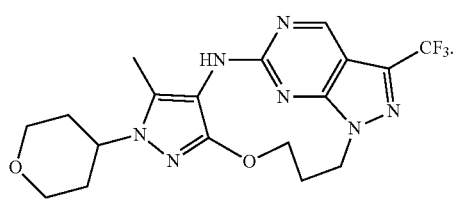 [SMILES: Cc1c2c(nn1C1CCOCC1)OCCCn1nc(C(F)(F)F)c3cnc(nc31)N2]

In some embodiments of the invention, the compound is

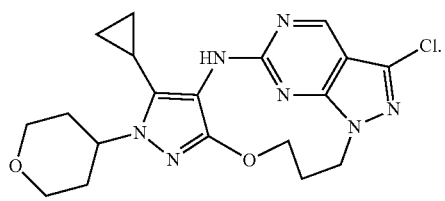 [SMILES: Clc1nn2c3nc(ncc13)Nc1c(nn(C3CCOCC3)c1C1CC1)OCCC2]

In some embodiments of the invention, the compound is

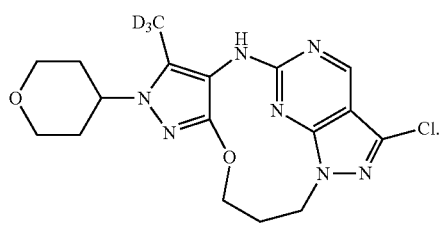 [SMILES: [2H]C([2H])([2H])c1c2c(nn1C1CCOCC1)OCCCn1nc(Cl)c3cnc(nc31)N2]

In some embodiments of the invention, the compound is

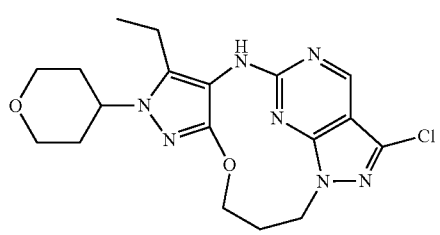 [SMILES: CCc1c2c(nn1C1CCOCC1)OCCCn1nc(Cl)c3cnc(nc31)N2]

In some embodiments of the invention, the compound is

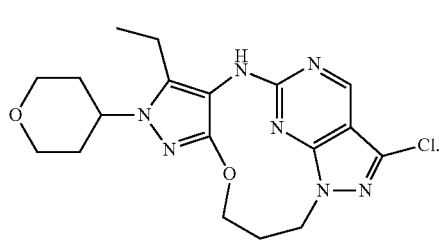 [SMILES: CCc1c2c(nn1C1CCOCC1)OCCCn1nc(Cl)c3cnc(nc31)N2]

In some embodiments of the invention, the compound is

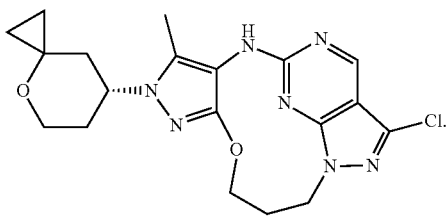 [SMILES: Cc1c2c(nn1[C@@H]1CCOC3(CC3)C1)OCCCn1nc(Cl)c3cnc(nc31)N2]

In some embodiments of the invention, the compound is

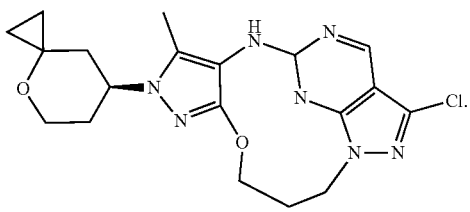

In some embodiments of the invention, the compound is

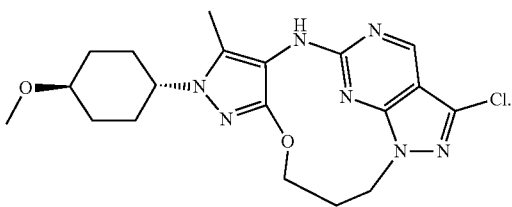 [SMILES: CO[C@H]1CC[C@H](n2nc3c(c2C)Nc2ncc4c(Cl)nn(c4n2)CCCO3)CC1]

In some embodiments of the invention, the compound is

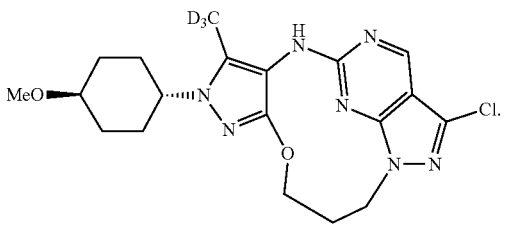 [SMILES: [2H]C([2H])([2H])c1c2c(nn1[C@H]1CC[C@H](OC)CC1)OCCCn1nc(Cl)c3cnc(nc31)N2]

In a further aspect, the invention provides a pharmaceutical composition comprising a compound of formula I, Ia, Ib, Ic, Id, A or Aa as disclosed herein or pharmaceutically acceptable salts thereof and one or more pharmaceutically acceptable carriers.

In a further aspect, the invention provides compounds of formula I, Ia, Ib, Ic, Id, A or Aa as disclosed herein or pharmaceutically acceptable salt thereof for use in therapy.

In a further aspect, the invention provides compounds of formula I, Ia, Ib, Ic, Id, A or Aa as disclosed herein or pharmaceutically acceptable salt thereof for use in the treatment of a disease associated with LRRK2 such as Parkinson's disease.

In a further aspect, the invention relates to the use of a compound of formula I, Ia, Ib, Ic, Id, A or Aa as disclosed herein or pharmaceutically acceptable salt thereof in the manufacture of a medicament for use in the treatment of a disease associated with LRRK2 such as Parkinson's disease In a further aspect, the invention relates to a method for the treatment of a disease associated with LRRK2 such as Parkinson disease, the method comprising the administration of a therapeutically effective amount of a compound of formula I, Ia, Ib, Ic, Id, A or Aa as disclosed herein or pharmaceutically acceptable salt thereof to a patient in need thereof.

DETAILED DESCRIPTION OF THE INVENTION

The inventors of the present disclosure have surprisingly identified new compounds that are LRRK2 inhibitors. The compounds are listed in table 1. As can be seen from the examples of the present disclosure, the compounds were demonstrated to possess a low clearance and a high brain penetrance, while maintaining a high potency and selectivity for LRRK2 and having good pharmacokinetics. As has been demonstrated in the historic literature of LRRK2 inhibitors, as presented above, identification of compound having such characteristics is by no means trivial.

TABLE 1

| Compounds of the invention | | |
|---|---|---|
| Compound number | Name | Structure |
| 1 | 8-Chloro-2,3-dimethyl-2,4,12,13-tetrahydro-11H-5,7-(azenometheno)dipyrazolo-[3,4-b:5',1'-g][1]oxa[4,6,8]triazacycloundecine | 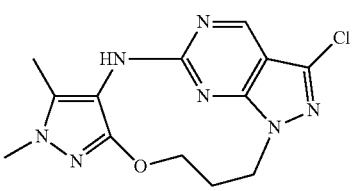 [SMILES: Cc1c2c(nn1C)OCCCn1nc(Cl)c3cnc(nc31)N2] |

TABLE 1-continued

Compounds of the invention

| Compound number | Name | Structure |
|---|---|---|
| 2 | 8-Chloro-3-methyl-2-(tetrahydro-2H-pyran-4-yl)-2,4,12,13-tetrahydro-11H-5,7-(azenometheno)dipyrazolo[3,4-b:5',1'-g][1]oxa[4,6,8]triazacycloundecine | 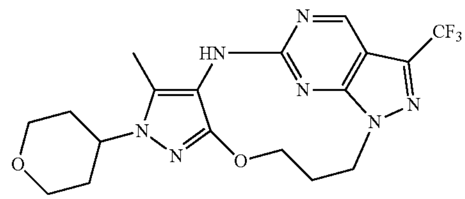 [SMILES: Cc1c2c(nn1C1CCOCC1)OCCCn1nc(C(F)(F)F)c3cnc(nc31)N2] |
| 3 | (R)-8-chloro-3-methyl-2-(tetrahydro-2H-pyran-3-yl)-2,4,12,13-tetrahydro-11H-5,7-(azenometheno)dipyrazolo[3,4-b:5',1'-g][1]oxa[4,6,8]triazacycloundecine; or (S)-8-chloro-3-methyl-2-(tetrahydro-2H-pyran-3-yl)-2,4,12,13-tetrahydro-11H-5,7-(azenometheno)dipyrazolo[3,4-b:5',1'-g][l]oxa[4,6,8]triazacycloundecine | or |
| 4 | (R)-8-chloro-3-methyl-2-(tetrahydro-2H-pyran-3-yl)-2,4,12,13-tetrahydro-11H-5,7-(azenometheno)dipyrazolo[3,4-b:5',1'-g][l]oxa[4,6,8]triazacycloundecine; or (S)-8-chloro-3-methyl-2-(tetrahydro-2H-pyran-3-yl)-2,4,12,13-tetrahydro-11H-5,7-(azenometheno)dipyrazolo[3,4-b:5',1'-g][l]oxa[4,6,8]triazacycloundecine | or |
| 5 | 3-Methyl-2-(tetrahydro-2H-pyran-4-yl)-8-(trifluoromethyl)-2,4,12,13-tetrahydro-11H-5,7-(azenometheno)dipyrazolo[3,4-b:5',1'-g][1]oxa[4,6,8]triazacycloundecine | 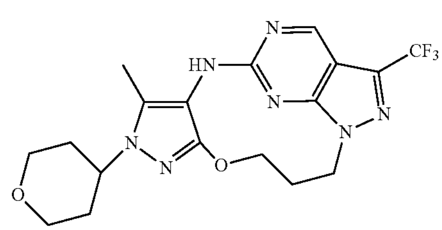 [SMILES: Cc1c2c(nn1C1CCOCC1)OCCCn1nc(C(F)(F)F)c3cnc(nc31)N2] |

TABLE 1-continued

Compounds of the invention

| Compound number | Name | Structure |
|---|---|---|
| 6 | 8-Bromo-3-methyl-2-(tetrahydro-2H-pyran-4-yl)-2,4,12,13-tetrahydro-11H-5,7-(azenometheno)dipyrazolo[3,4-b:5',1'-g][1]oxa[4,6,8]triazacycloundecine | 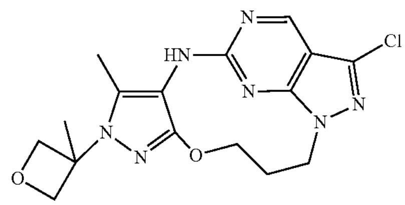 [SMILES: Cc1c2c(nn1C1(C)COC1)OCCCn1nc(Cl)c3cnc(nc31)N2] |
| 7 | 8-Cyclopropyl-3-methyl-2-(tetrahydro-2H-pyran-4-yl)-2,4,12,13-tetrahydro-11H-5,7-(azenometheno)dipyrazolo[3,4-b:5',1'-g][1]oxa[4,6,8]triazacycloundecine | 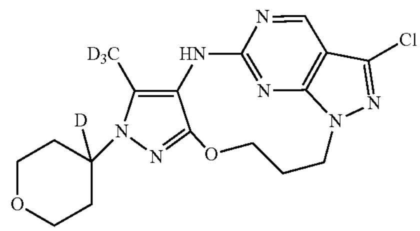 [SMILES: [2H]C([2H])([2H])c1c2c(nn1C1([2H])CCOCC1)OCCCn1nc(Cl)c3cnc(nc31)N2] |
| 8 | 3,8-Dimethyl-2-(tetrahydro-2H-pyran-4-yl)-2,4,12,13-tetrahydro-11H-5,7-(azenometheno)dipyrazolo[3,4-b:5',1'-g][1]oxa[4,6,8]triazacycloundecine | 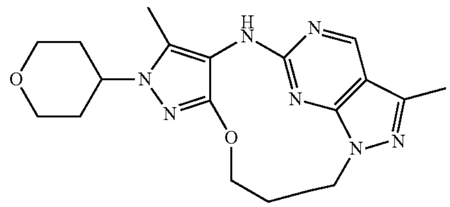 [SMILES: Cc1nn2c3nc(ncc13)Nc1c(nn(C3CCOCC3)c1C)OCCCC2] |
| 9 | 3-Methyl-2-(tetrahydro-2H-pyran-4-yl)-2,4,12,13-tetrahydro-11H-5,7-(azenometheno)dipyrazolo[3,4-b:5',1'-g][1]oxa[4,6,8]triazacycloundecine-8-carbonitrile | 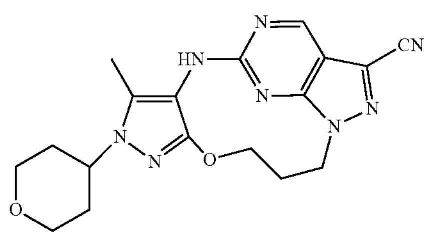 [SMILES: Cc1c2c(nn1C1CCOCC1)OCCCn1nc(C#N)c3cnc(nc31)N2] |
| 10 | 8-Chloro-3-cyclopropyl-2-(tetrahydro-2H-pyran-4-yl)-2,4,12,13-tetrahydro-11H-5,7-(azenometheno)dipyrazolo[3,4-b:5',1'-g][1]oxa[4,6,8]triazacycloundecine | 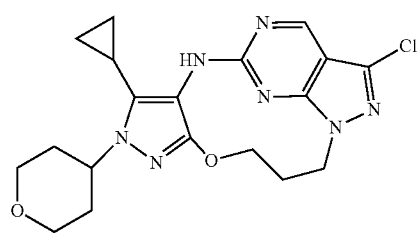 [SMILES: Clc1nn2c3nc(ncc13)Nc1c(nn(C3CCOCC3)c1C1CC1)OCCC2] |
| 11 | 2-((2-Oxabicyclo[2.1.1]hexan-1-yl)methyl)-8-chloro-3-methyl-2,4,12,13-tetrahydro-11H-5,7-(azenometheno)dipyrazolo[3,4-b:5',1'-g][1]oxa[4,6,8]triazacycloundecine | 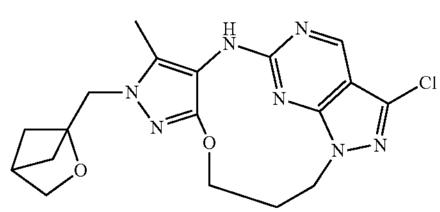 [SMILES: Cc1c2c(nn1CC13CC(CO1)C3)OCCCn1nc(Cl)c3cnc(nc31)N2] |

TABLE 1-continued

Compounds of the invention

| Compound number | Name | Structure |
|---|---|---|
| 12 | 8-Chloro-3-methyl-2-((3-methyloxetan-3-yl)methyl)-2,4,12,13-tetrahydro-11H-5,7-(azenometheno)dipyrazolo[3,4-b:5',1'-g][1]oxa[4,6,8]triazacycloundecine | 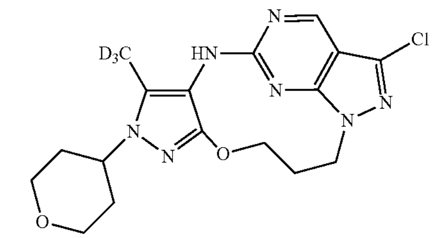 [SMILES: [2H]C([2H])([2H])c1c2c(nn1C1CCOCC1)OCCCn1nc(Cl)c3cnc(nc31)N2] |
| 13 | 8-Chloro-3-(methyl-d3)-2-(tetrahydro-2H-pyran-4-yl)-2,4,12,13-tetrahydro-11H-5,7-(azenometheno)dipyrazolo[3,4-b:5',1'-g][1]oxa[4,6,8]triazacycloundecine | 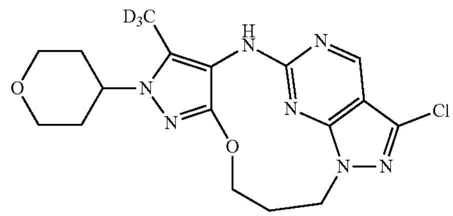 [SMILES: [2H]C([2H])([2H])c1c2c(nn1C1CCOCC1)OCCCn1nc(Cl)c3cnc(nc31)N2] |
| 14 | 8-Chloro-3-methyl-2-(3-methyloxetan-3-yl)-2,4,12,13-tetrahydro-11H-5,7-(azenometheno)dipyrazolo[3,4-b:5',1'-g][1]oxa[4,6,8]triazacycloundecine | 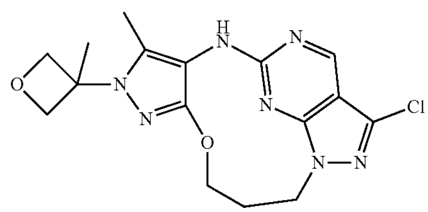 [SMILES: Cc1c2c(nn1C1(C)COC1)OCCCn1nc(Cl)c3cnc(nc31)N2] |
| 15 | 8-Chloro-3-(methyl-d3)-2-(tetrahydro-2H-pyran-4-yl-4-d)-2,4,12,13-tetrahydro-11H-5,7-(azenometheno)dipyrazolo[3,4-b:5',1'-g][1]oxa[4,6,8]triazacycloundecine | 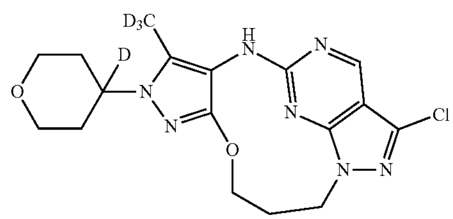 [SMILES: [2H]C([2H])([2H])c1c2c(nn1C1([2H])CCOCC1)OCCCn1nc(Cl)c3cnc(nc31)N2] |
| 16 | 8-Chloro-3-(1-fluorocyclopropyl)-2-(tetrahydro-2H-pyran-4-yl)-2,4,12,13-tetrahydro-11H-5,7-(azenometheno)dipyrazolo[3,4-b:5',1'-g][1]oxa[4,6,8]triazacycloundecine | 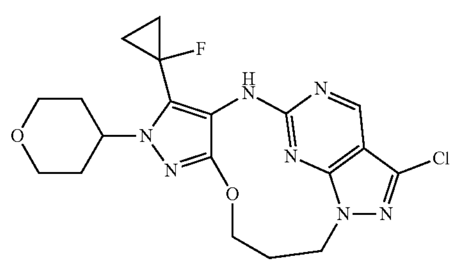 [SMILES: FC1(c2c3c(nn2C2CCOCC2)OCCCn2nc(Cl)c4cnc(nc42)N3)CC1] |
| 17 | 8-Chloro-3-ethyl-2-(tetrahydro-2H-pyran-4-yl)-2,4,12,13-tetrahydro-11H-5,7-(azenometheno)dipyrazolo[3,4-b:5',1'-g][1]oxa[4,6,8]triazacycloundecine | 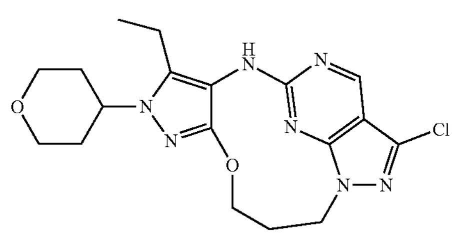 [SMILES: CCc1c2c(nn1C1CCOCC1)OCCCn1nc(Cl)c3cnc(nc31)N2] |

TABLE 1-continued

Compounds of the invention

| Compound number | Name | Structure |
|---|---|---|
| 18 | 8-Chloro-3-methyl-2-((2R,4R)-2-methyltetrahydro-2H-pyran-4-yl)-2,4,12,13-tetrahydro-11H-5,7-(azenometheno)dipyrazolo[3,4-b:5',1'-g][1]oxa[4,6,8]triazacycloundecine; or 8-Chloro-3-methyl-2-((2S,4S)-2-methyltetrahydro-2H-pyran-4-yl)-2,4,12,13-tetrahydro-11H-5,7-(azenometheno)dipyrazolo[3,4-b:5',1'-g][1]oxa[4,6,8]triazacycloundecine | or |
| 19 | 8-Chloro-3-methyl-2-((2R,4R)-2-methyltetrahydro-2H-pyran-4-yl)-2,4,12,13-tetrahydro-11H-5,7-(azenometheno)dipyrazolo[3,4-b:5',1'-g][1]oxa[4,6,8]triazacycloundecine; or 8-Chloro-3-methyl-2-((2S,4S)-2-methyltetrahydro-2H-pyran-4-yl)-2,4,12,13-tetrahydro-11H-5,7-(azenometheno)dipyrazolo[3,4-b:5',1'-g][1]oxa[4,6,8]triazacycloundecine | or |
| 20 | 8-Chloro-3-methyl-2-(tetrahydro-2H-pyran-4-yl)-2,4,12,13-tetrahydro-11H-5,7-(azenometheno)dipyrazolo[3,4-b:5',1'-g][1]oxa[4,6,8]triazacycloundecine-11,11,12,12,13,13-$d_6$ | 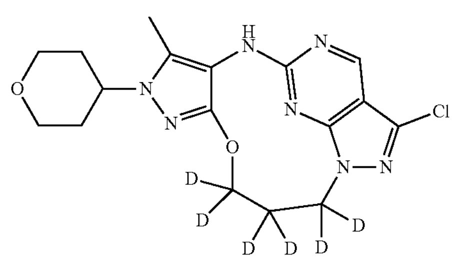 [SMILES: [2H]C1([2H])Oc2nn(C3CCOCC3)c(C)c2Nc2ncc3c(Cl)nn(c3n2)C([2H])([2H])C1([2H])[2H]] |

TABLE 1-continued

Compounds of the invention

| Compound number | Name | Structure |
|---|---|---|
| 21 | 8-Chloro-3-methyl-2-((3R,4S)-3-methyltetrahydro-2H-pyran-4-yl)-2,4,12,13-tetrahydro-11H-5,7-(azenometheno)dipyrazolo[3,4-b:5',1'-g][1]oxa[4,6,8]triazacycloundecine; or 8-Chloro-3-methyl-2-((3S,4R)-3-methyltetrahydro-2H-pyran-4-yl)-2,4,12,13-tetrahydro-11H-5,7-(azenometheno)dipyrazolo[3,4-b:5',1'-g][1]oxa[4,6,8]triazacycloundecine; or 8-Chloro-3-methyl-2-((3S,4S)-3-methyltetrahydro-2H-pyran-4-yl)-2,4,12,13-tetrahydro-11H-5,7-(azenometheno)dipyrazolo[3,4-b:5',1'-g][1]oxa[4,6,8]triazacycloundecine; or 8-Chloro-3-methyl-2-((3R,4R)-3-methyltetrahydro-2H-pyran-4-yl)-2,4,12,13-tetrahydro-11H-5,7-(azenometheno)dipyrazolo[3,4-b:5',1'-g][1]oxa[4,6,8]triazacycloundecine | [structure] or [structure] or [structure] or [structure] |

TABLE 1-continued

Compounds of the invention

| Compound number | Name | Structure |
|---|---|---|
| 22 | 8-Chloro-3-methyl-2-((3R,4S)-3-methyltetrahydro-2H-pyran-4-yl)-2,4,12,13-tetrahydro-11H-5,7-(azenometheno)dipyrazolo[3,4-b:5',1'-g][1]oxa[4,6,8]triazacycloundecine; or 8-Chloro-3-methyl-2-((3S,4R)-3-methyltetrahydro-2H-pyran-4-yl)-2,4,12,13-tetrahydro-11H-5,7-(azenometheno)dipyrazolo[3,4-b:5',1'-g][1]oxa[4,6,8]triazacycloundecine; or 8-Chloro-3-methyl-2-((3S,4S)-3-methyltetrahydro-2H-pyran-4-yl)-2,4,12,13-tetrahydro-11H-5,7-(azenometheno)dipyrazolo[3,4-b:5',1'-g][1]oxa[4,6,8]triazacycloundecine; or 8-Chloro-3-methyl-2-((3R,4R)-3-methyltetrahydro-2H-pyran-4-yl)-2,4,12,13-tetrahydro-11H-5,7-(azenometheno)dipyrazolo[3,4-b:5',1'-g][1]oxa[4,6,8]triazacycloundecine | or<br><br>or<br><br>or |

TABLE 1-continued

Compounds of the invention

| Compound number | Name | Structure |
|---|---|---|
| 23 | 8-Chloro-3-methyl-2-((3R,4S)-3-methyltetrahydro-2H-pyran-4-yl)-2,4,12,13-tetrahydro-11H-5,7-(azenometheno)dipyrazolo[3,4-b:5',1'-g][1]oxa[4,6,8]triazacycloundecine; or 8-Chloro-3-methyl-2-((3S,4R)-3-methyltetrahydro-2H-pyran-4-yl)-2,4,12,13-tetrahydro-11H-5,7-(azenometheno)dipyrazolo[3,4-b:5',1'-g][1]oxa[4,6,8]triazacycloundecine; or 8-Chloro-3-methyl-2-((3S,4S)-3-methyltetrahydro-2H-pyran-4-yl)-2,4,12,13-tetrahydro-11H-5,7-(azenometheno)dipyrazolo[3,4-b:5',1'-g][1]oxa[4,6,8]triazacycloundecine; or 8-Chloro-3-methyl-2-((3R,4R)-3-methyltetrahydro-2H-pyran-4-yl)-2,4,12,13-tetrahydro-11H-5,7-(azenometheno)dipyrazolo[3,4-b:5',1'-g][1]oxa[4,6,8]triazacycloundecine | or<br><br>or<br><br>or |

TABLE 1-continued

Compounds of the invention

| Compound number | Name | Structure |
|---|---|---|
| 24 | 8-Chloro-3-methyl-2-((3R,4S)-3-methyltetrahydro-2H-pyran-4-yl)-2,4,12,13-tetrahydro-11H-5,7-(azenometheno)dipyrazolo[3,4-b:5',1'-g][1]oxa[4,6,8]triazacycloundecine; or 8-Chloro-3-methyl-2-((3S,4R)-3-methyltetrahydro-2H-pyran-4-yl)-2,4,12,13-tetrahydro-11H-5,7-(azenometheno)dipyrazolo[3,4-b:5',1'-g][1]oxa[4,6,8]triazacycloundecine; or 8-Chloro-3-methyl-2-((3S,4S)-3-methyltetrahydro-2H-pyran-4-yl)-2,4,12,13-tetrahydro-11H-5,7-(azenometheno)dipyrazolo[3,4-b:5',1'-g][1]oxa[4,6,8]triazacycloundecine; or 8-Chloro-3-methyl-2-((3R,4R)-3-methyltetrahydro-2H-pyran-4-yl)-2,4,12,13-tetrahydro-11H-5,7-(azenometheno)dipyrazolo[3,4-b:5',1'-g][1]oxa[4,6,8]triazacycloundecine | 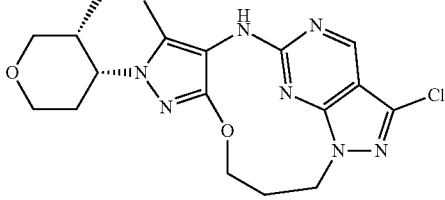<br>or<br>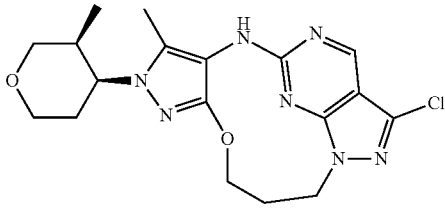 [SMILES: Cc1c2c(nn1[C@H]1CCOC[C@H]1C)OCCCn1nc(Cl)c3cnc(nc31)N2]<br>or<br>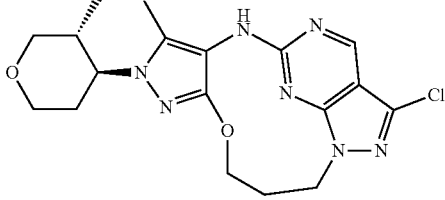<br>or<br> |
| 25 | 8-Chloro-2-((1r,4r)-4-fluorocyclohexyl)-3-methyl-2,4,12,13-tetrahydro-11H-5,7-(azenometheno)dipyrazolo[3,4-b:5',1'-g][1]oxa[4,6,8]triazacycloundecine | 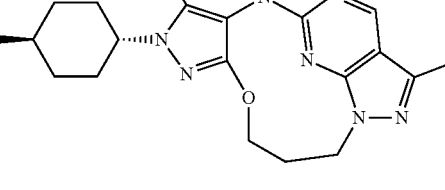 |
| 26 | 8-Chloro-2-(4,4-difluorocyclohexyl)-3-methyl-2,4,12,13-tetrahydro-11H-5,7-(azenometheno)dipyrazolo[3,4-b:5',1'-g][1]oxa[4,6,8]triazacycloundecine | 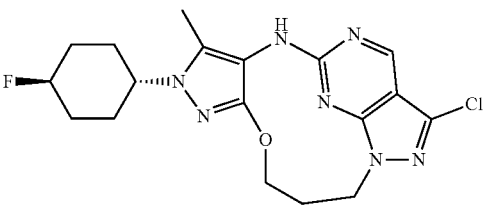 [SMILES: Cc1c2c(nn1[C@H]1CC[C@H](F)CC1)OCCCn1nc(Cl)c3cnc(nc31)N2] |

TABLE 1-continued

Compounds of the invention

| Compound number | Name | Structure |
| --- | --- | --- |
| 27 | (R)-8-Chloro-3-methyl-2-(oxepan-3-yl)-2,4,12,13-tetrahydro-11H-5,7-(azenometheno)dipyrazolo[3,4-b:5',1'-g][1]oxa[4,6,8]triazacycloundecine; or (S)-8-Chloro-3-methyl-2-(oxepan-3-yl)-2,4,12,13-tetrahydro-11H-5,7-(azenometheno)dipyrazolo[3,4-b:5',1'-g][1]oxa[4,6,8]triazacycloundecine | 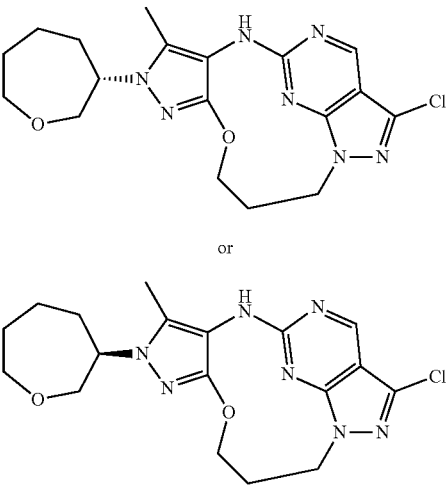<br>or<br>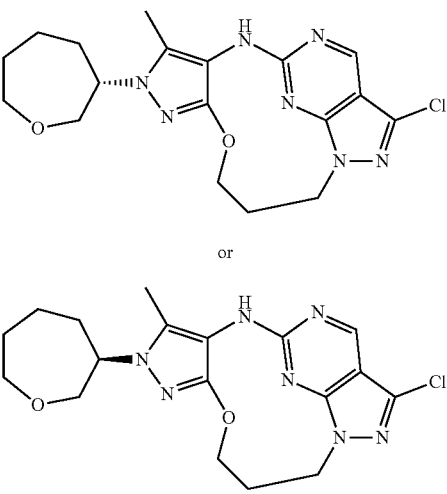 |
| 28 | (R)-8-Chloro-3-methyl-2-(oxepan-3-yl)-2,4,12,13-tetrahydro-11H-5,7-(azenometheno)dipyrazolo[3,4-b:5',1'-g][1]oxa[4,6,8]triazacycloundecine; or (S)-8-Chloro-3-methyl-2-(oxepan-3-yl)-2,4,12,13-tetrahydro-11H-5,7-(azenometheno)dipyrazolo[3,4-b:5',1'-g][1]oxa[4,6,8]triazacycloundecine | 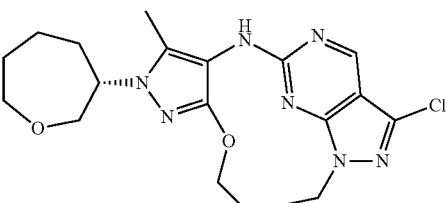<br>or<br>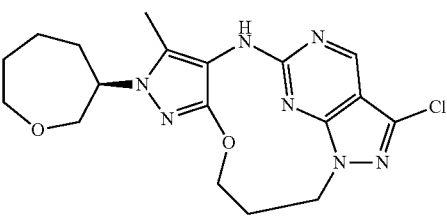 [SMILES: Cc1c2c(nn1[C@@H]1CCCCOC1)OCCCn1nc(Cl)c3cnc(nc31)N2] |
| 29 | (R)-8-Chloro-3-methyl-2-(oxepan-4-yl)-2,4,12,13-tetrahydro-11H-5,7-(azenometheno)dipyrazolo[3,4-b:5',1'-g][1]oxa[4,6,8]triazacycloundecine; or (S)-8-Chloro-3-methyl-2-(oxepan-4-yl)-2,4,12,13-tetrahydro-11H-5,7-(azenometheno)dipyrazolo[3,4-b:5',1'-g][1]oxa[4,6,8]triazacycloundecine | 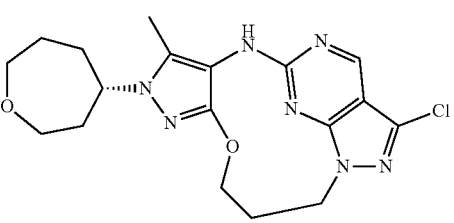 [SMILES: Cc1c2c(nn1[C@H]1CCCOCC1)OCCCn1nc(Cl)c3cnc(nc31)N2]<br>or<br>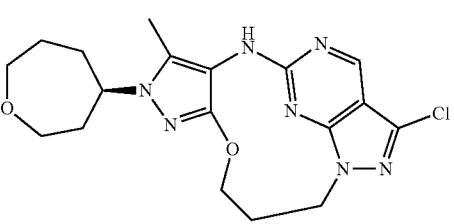 [SMILES: Cc1c2c(nn1[C@@H]1CCCOCC1)OCCCn1nc(Cl)c3cnc(nc31)N2] |

TABLE 1-continued

Compounds of the invention

| Compound number | Name | Structure |
|---|---|---|
| 30 | (R)-8-Chloro-3-methyl-2-(oxepan-4-yl)-2,4,12,13-tetrahydro-11H-5,7-(azenometheno)dipyrazolo[3,4-b:5',1'-g][1]oxa[4,6,8]triazacycloundecine; or (S)-8-Chloro-3-methyl-2-(oxepan-4-yl)-2,4,12,13-tetrahydro-11H-5,7-(azenometheno)dipyrazolo[3,4-b:5',1'-g][1]oxa[4,6,8]triazacycloundecine | 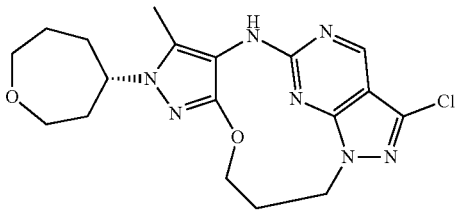 [SMILES: Cc1c2c(nn1[C@H]1CCCOCC1)OCCCn1nc(Cl)c3cnc(nc31)N2]<br>or<br>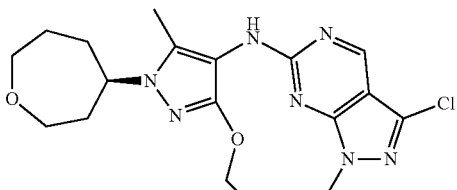 |
| 31 | 8-Chloro-2-((3S,4R)-3-fluorotetrahydro-2H-pyran-4-yl)-3-methyl-2,4,12,13-tetrahydro-11H-5,7-(azenometheno)dipyrazolo[3,4-b:5',1'-g][1]oxa[4,6,8]triazacycloundecine; or 8-Chloro-2-((3R,4S)-3-fluorotetrahydro-2H-pyran-4-yl)-3-methyl-2,4,12,13-tetrahydro-11H-5,7-(azenometheno)dipyrazolo[3,4-b:5',1'-g][1]oxa[4,6,8]triazacycloundecine | 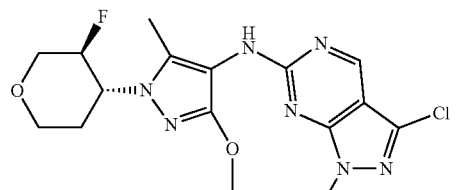<br>or<br>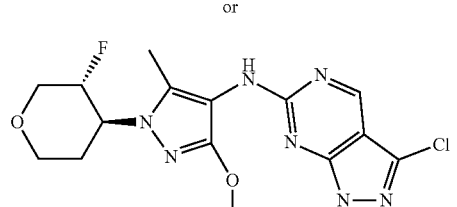 |
| 32 | 8-Chloro-2-((3S,4R)-3-fluorotetrahydro-2H-pyran-4-yl)-3-methyl-2,4,12,13-tetrahydro-11H-5,7-(azenometheno)dipyrazolo[3,4-b:5',1'-g][1]oxa[4,6,8]triazacycloundecine; or 8-Chloro-2-((3R,4S)-3-fluorotetrahydro-2H-pyran-4-yl)-3-methyl-2,4,12,13-tetrahydro-11H-5,7-(azenometheno)dipyrazolo[3,4-b:5',1'-g][1]oxa[4,6,8]triazacycloundecine | 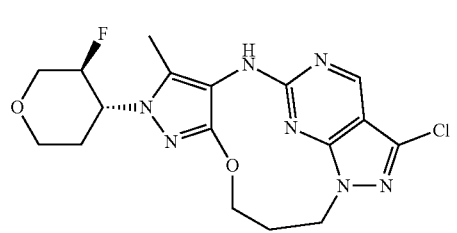 [SMILES: Cc1c2c(nn1[C@@H]1CCOC[C@H]1F)OCCCn1nc(Cl)c3cnc(nc31)N2]<br>or<br>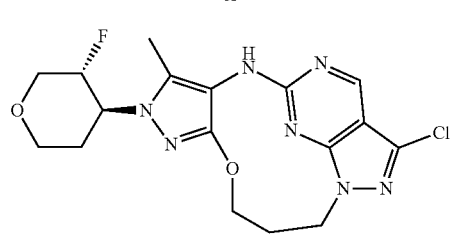 |

TABLE 1-continued

Compounds of the invention

| Compound number | Name |
|---|---|
| 33 | 3-(8-Chloro-3-methyl-12,13-dihydro-11H-5,7-(azenometheno)dipyrazolo[3,4-b:5',1'-g][1]oxa[4,6,8]triazacycloundecin-2(4H)-yl)bicyclo[1.1.1]pentane-1-carbonitrile |
| 34 | 8-Chloro-3-methyl-2-(2-oxaspiro[3.3]heptan-6-yl)-2,4,12,13-tetrahydro-11H-5,7-(azenometheno)dipyrazolo[3,4-b:5',1'-g][1]oxa[4,6,8]triazacycloundecine |
| 35 | 8-Chloro-3-(methyl-d₃)-2-(tetrahydro-2H-pyran-4-yl)-2,4,12,13-tetrahydro-11H-5,7-(azenometheno)dipyrazolo[3,4-b:5',1'-g][1]oxa[4,6,8]triazacycloundecine-11,11,12,12,13,13-d₆ |
| 36 | 1-(8-Chloro-3-methyl-12,13-dihydro-11H-5,7-(azenometheno)dipyrazolo[3,4-b:5',1'-g][1]oxa[4,6,8]triazacycloundecin-2(4H)-yl)cyclopropane-1-carbonitrile |
| 37 | 8-Chloro-2-((1r,4r)-4-methoxycyclohexyl)-3-methyl-2,4,12,13-tetrahydro-11H-5,7-(azenometheno)dipyrazolo[3,4-b:5',1'-g][1]oxa[4,6,8]triazacycloundecine |
| 38 | 2-((1R,5S,6r)-3-Oxabicyclo[3.1.0]hexan-6-yl)-8-chloro-3-methyl-2,4,12,13-tetrahydro-11H-5,7-(azenometheno)dipyrazolo[3,4-b:5',1'-g][1]oxa[4,6,8]triazacycloundecine |

TABLE 1-continued

Compounds of the invention

| Compound number | Name | Structure |
|---|---|---|
| 39 | (R)-8-Chloro-2-(2,2-difluorocyclopropyl)-3-methyl-2,4,12,13-tetrahydro-11H-5,7-(azenometheno)dipyrazolo[3,4-b:5',1'-g][1]oxa[4,6,8]triazacycloundecine; or (S)-8-Chloro-2-(2,2-difluorocyclopropyl)-3-methyl-2,4,12,13-tetrahydro-11H-5,7-(azenometheno)dipyrazolo[3,4-b:5',1'-g][1]oxa[4,6,8]triazacycloundecine | 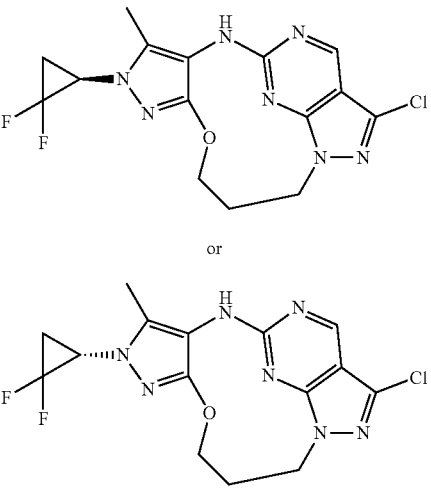<br>or<br>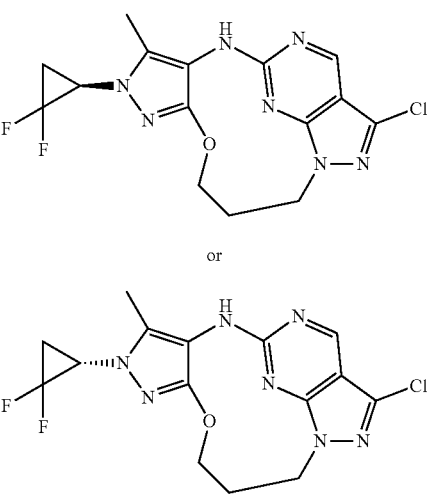 |
| 40 | (R)-8-Chloro-2-(2,2-difluorocyclopropyl)-3-methyl-2,4,12,13-tetrahydro-11H-5,7-(azenometheno)dipyrazolo[3,4-b:5',1'-g][1]oxa[4,6,8]triazacycloundecine; or (S)-8-Chloro-2-(2,2-difluorocyclopropyl)-3-methyl-2,4,12,13-tetrahydro-11H-5,7-(azenometheno)dipyrazolo[3,4-b:5',1'-g][1]oxa[4,6,8]triazacycloundecine | 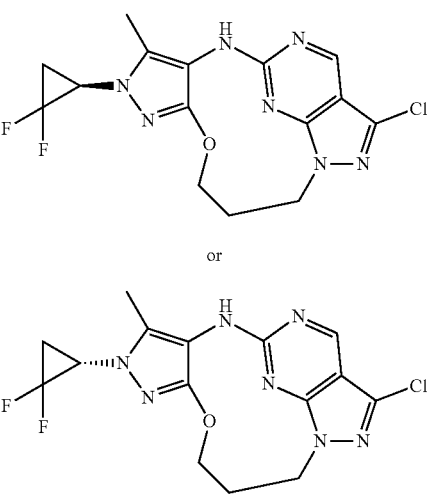<br>or<br> |
| 41 | 8-chloro-2-((2R,4r,6S)-2,6-dimethyltetrahydro-2H-pyran-4-yl)-3-methyl-2,4,12,13-tetrahydro-11H-5,7-(azenometheno)dipyrazolo[3,4-b:5',1'-g][1]oxa[4,6,8]triazacycloundecine | 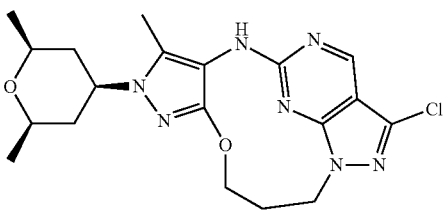 [SMILES: Cc1c2c(nn1[C@H]1C[C@@H](C)O[C@@H](C)C1)OCCCn1nc(Cl)c3cnc(nc31)N2] |

TABLE 1-continued

Compounds of the invention

| Compound number | Name | Structure |
|---|---|---|
| 42 | (R)-8-Chloro-2-(2,2-dimethyltetrahydro-2H-pyran-4-yl)-3-methyl-2,4,12,13-tetrahydro-11H-5,7-(azenometheno)dipyrazolo[3,4-b:5',1'-g][1]oxa[4,6,8]triazacycloundecine; or (S)-8-Chloro-2-(2,2-dimethyltetrahydro-2H-pyran-4-yl)-3-methyl-2,4,12,13-tetrahydro-11H-5,7-(azenometheno)dipyrazolo[3,4-b:5',1'-g][1]oxa[4,6,8]triazacycloundecine | 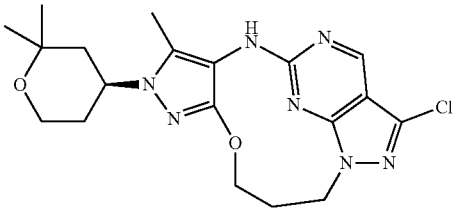 or 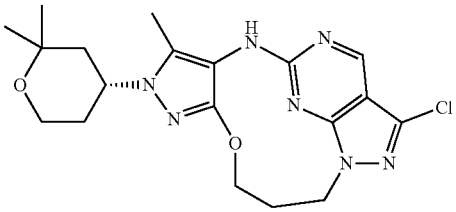 [SMILES: Cc1c2c(nn1[C@@H]1CCOC(C)(C)C1)OCCCn1nc(Cl)c3cnc(nc31)N2] |
| 43 | (R)-8-Chloro-2-(2,2-dimethyltetrahydro-2H-pyran-4-yl)-3-methyl-2,4,12,13-tetrahydro-11H-5,7-(azenometheno)dipyrazolo[3,4-b:5',1'-g][1]oxa[4,6,8]triazacycloundecine; or (S)-8-Chloro-2-(2,2-dimethyltetrahydro-2H-pyran-4-yl)-3-methyl-2,4,12,13-tetrahydro-11H-5,7-(azenometheno)dipyrazolo[3,4-b:5',1'-g][1]oxa[4,6,8]triazacycloundecine | 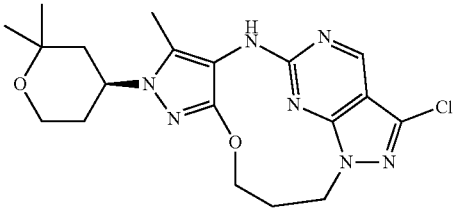 [SMILES: Cc1c2c(nn1[C@H]1CCOC(C)(C)C1)OCCCn1nc(Cl)c3cnc(nc31)N2] or 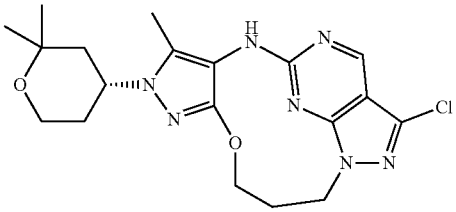 [SMILES: Cc1c2c(nn1[C@@H]1CCOC(C)(C)C1)OCCCn1nc(Cl)c3cnc(nc31)N2] |
| 44 | 2-((1R,3s,5S)-8-Oxabicyclo[3.2.1]octan-3-yl)-8-chloro-3-methyl-2,4,12,13-tetrahydro-11H-5,7-(azenometheno)dipyrazolo[3,4-b:5',1'-g][1]oxa[4,6,8]triazacycloundecine | 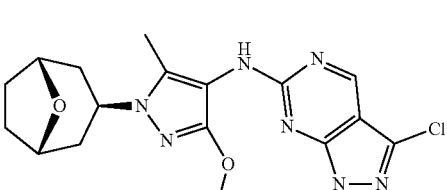 |
| 45 | 8-Chloro-3-methyl-2-(tetrahydro-2H-pyran-4-yl)-2,4,12,13-tetrahydro-11H-5,7-(azenometheno)dipyrazolo[3,4-b:5',1'-g][1]oxa[4,6,8]triazacycloundecine-11,11-$d_2$ | 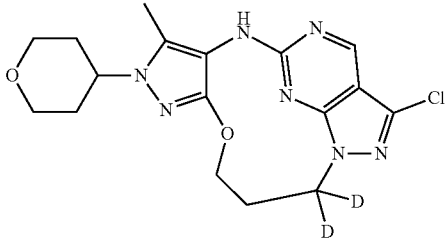 [SMILES: [2H]C1([2H])CCOc2nn(C3CCOCC3)c(C)c2Nc2ncc3c(Cl)nn1c3n2] |

TABLE 1-continued

Compounds of the invention

| Compound number | Name |
|---|---|
| 46 | 8-Chloro-3-methyl-2-(tetrahydro-2H-pyran-4-yl)-2,4,12,13-tetrahydro-11H-5,7-(azenometheno)dipyrazolo[3,4-b:5',1'-g][1]oxa[4,6,8]triazacycloundecine-13,13-d₂ |
| 47 | 8-Chloro-2-((3R,4S)-3-Fluoro-3-methyltetrahydro-2H-pyran-4-yl)-3-methyl-2,4,12,13-tetrahydro-11H-5,7-(azenometheno)dipyrazolo[3,4-b:5',1'-g][1]oxa[4,6,8]triazacycloundecine; or 8-Chloro-2-((3S,4R)-3-Fluoro-3-methyltetrahydro-2H-pyran-4-yl)-3-methyl-2,4,12,13-tetrahydro-11H-5,7-(azenometheno)dipyrazolo[3,4-b:5',1'-g][1]oxa[4,6,8]triazacycloundecine |
| 48 | 8-Chloro-2-((3R,4S)-3-Fluoro-3-methyltetrahydro-2H-pyran-4-yl)-3-methyl-2,4,12,13-tetrahydro-11H-5,7-(azenometheno)dipyrazolo[3,4-b:5',1'-g][1]oxa[4,6,8]triazacycloundecine; or 8-Chloro-2-((3S,4R)-3-Fluoro-3-methyltetrahydro-2H-pyran-4-yl)-3-methyl-2,4,12,13-tetrahydro-11H-5,7-(azenometheno)dipyrazolo[3,4-b:5',1'-g][1]oxa[4,6,8]triazacycloundecine |
| 49 | 8-Chloro-3-methyl-2-((tetrahydro-2H-pyran-4-yl)methyl)-2,4,12,13-tetrahydro-11H-5,7-(azenometheno)dipyrazolo[3,4-b:5',1'-g][1]oxa[4,6,8]triazacycloundecine |

TABLE 1-continued

Compounds of the invention

| Compound number | Name | Structure |
|---|---|---|
| 50 | 8-Chloro-2-((1r,4r)-4-methoxycyclohexyl)-3-(methyl-d₃)-2,4,12,13-tetrahydro-11H-5,7-(azenometheno)dipyrazolo[3,4-b:5',1'-g][1]oxa[4,6,8]triazacycloundecine | 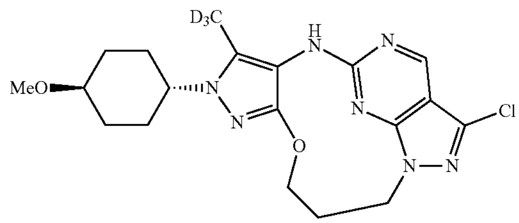 [SMILES: [2H]C([2H])([2H])c1c2c(nn1[C@H]1CC[C@H](OC)CC1)OCCCn1nc(Cl)c3cnc(nc31)N2] |
| 51 | 8-Chloro-3-(methyl-d₃)-2-((2R,4R)-2-methyltetrahydro-2H-pyran-4-yl)-2,4,12,13-tetrahydro-11H-5,7-(azenometheno)dipyrazolo[3,4-b:5',1'-g][1]oxa[4,6,8]triazacycloundecine; or 8-Chloro-3-(methyl-d₃)-2-((2S,4S)-2-methyltetrahydro-2H-pyran-4-yl)-2,4,12,13-tetrahydro-11H-5,7-(azenometheno)dipyrazolo[3,4-b:5',1'-g][1]oxa[4,6,8]triazacycloundecine | or |
| 52 | 8-Chloro-3-(methyl-d₃)-2-((2R,4R)-2-methyltetrahydro-2H-pyran-4-yl)-2,4,12,13-tetrahydro-11H-5,7-(azenometheno)dipyrazolo[3,4-b:5',1'-g][1]oxa[4,6,8]triazacycloundecine; or 8-Chloro-3-(methyl-d₃)-2-((2S,4S)-2-methyltetrahydro-2H-pyran-4-yl)-2,4,12,13-tetrahydro-11H-5,7-(azenometheno)dipyrazolo[3,4-b:5',1'-g][1]oxa[4,6,8]triazacycloundecine | or |

TABLE 1-continued

Compounds of the invention

| Compound number | Name | Structure |
|---|---|---|
| 53 | (R)-8-Chloro-3-methyl-2-(4-oxaspiro[2.5]octan-7-yl)-2,4,12,13-tetrahydro-11H-5,7-(azenometheno)dipyrazolo[3,4-b:5',1'-g][1]oxa[4,6,8]triazacycloundecine; or (S)-8-Chloro-3-methyl-2-(4-oxaspiro[2.5]octan-7-yl)-2,4,12,13-tetrahydro-11H-5,7-(azenometheno)dipyrazolo[3,4-b:5',1'-g][1]oxa[4,6,8]triazacycloundecine | 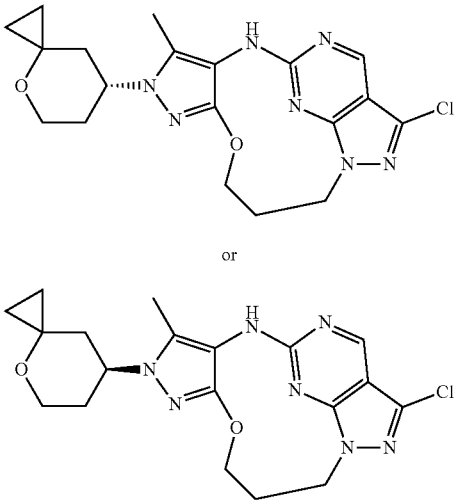 or 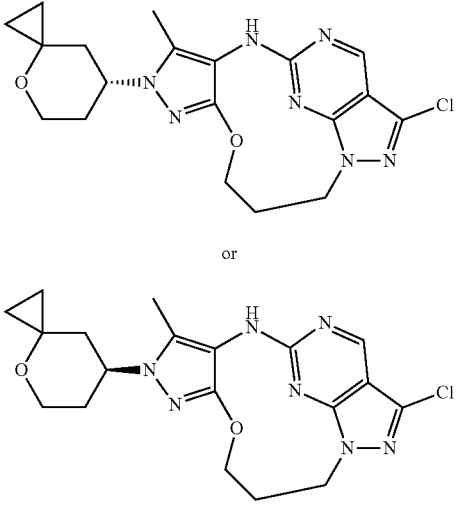 |
| 54 | (R)-8-Chloro-3-methyl-2-(4-oxaspiro[2.5]octan-7-yl)-2,4,12,13-tetrahydro-11H-5,7-(azenometheno)dipyrazolo[3,4-b:5',1'-g][1]oxa[4,6,8]triazacycloundecine; or (S)-8-Chloro-3-methyl-2-(4-oxaspiro[2.5]octan-7-yl)-2,4,12,13-tetrahydro-11H-5,7-(azenometheno)dipyrazolo[3,4-b:5',1'-g][1]oxa[4,6,8]triazacycloundecine | 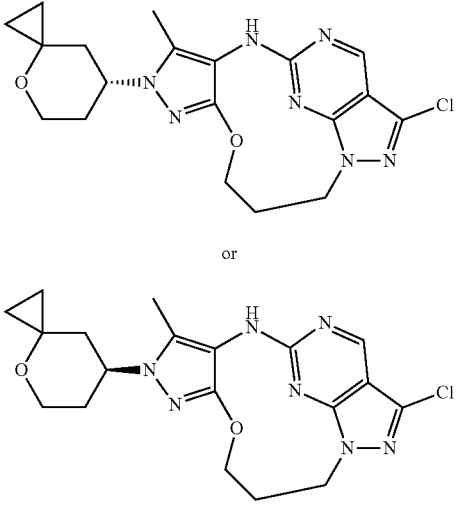 or 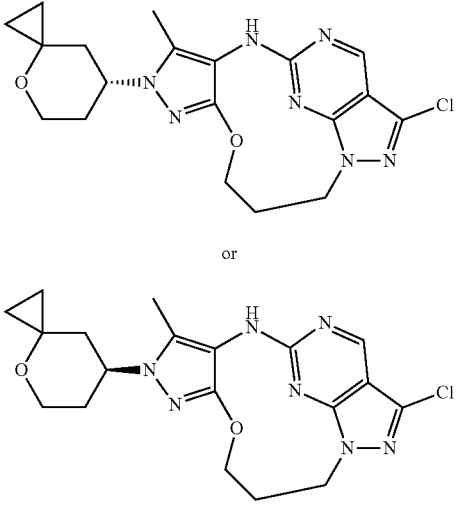 |

TABLE 1-continued

Compounds of the invention

| Compound number | Name | Structure |
|---|---|---|
| 55 | 8-Chloro-3-ethyl-2-((3R,4S)-3-fluorotetrahydro-2H-pyran-4-yl)-2,4,12,13-tetrahydro-11H-5,7-(azenometheno)dipyrazolo[3,4-b:5',1'-g][1]oxa[4,6,8]triazacycloundecine; or 8-Chloro-3-ethyl-2-((3S,4R)-3-fluorotetrahydro-2H-pyran-4-yl)-2,4,12,13-tetrahydro-11H-5,7-(azenometheno)dipyrazolo[3,4-b:5',1'-g][1]oxa[4,6,8]triazacycloundecine | 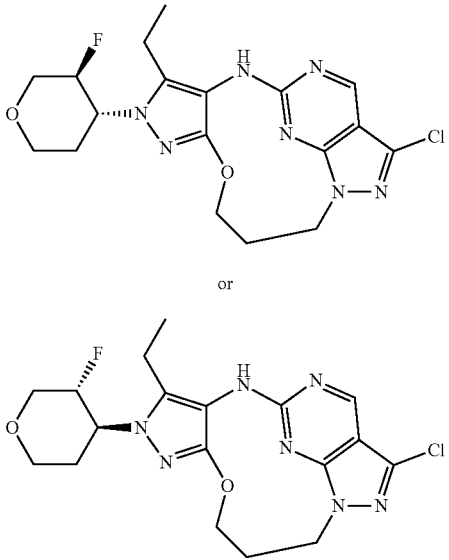<br>or<br>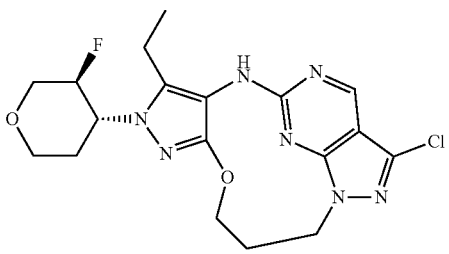 [SMILES: CCc1c2c(nn1[C@@H]1CCOC[C@H]1F)OCCCn1nc(Cl)c3cnc(nc31)N2] |
| 56 | 8-Chloro-3-ethyl-2-((3R,4S)-3-fluorotetrahydro-2H-pyran-4-yl)-2,4,12,13-tetrahydro-11H-5,7-(azenometheno)dipyrazolo[3,4-b:5',1'-g][1]oxa[4,6,8]triazacycloundecine; or 8-Chloro-3-ethyl-2-((3S,4R)-3-fluorotetrahydro-2H-pyran-4-yl)-2,4,12,13-tetrahydro-11H-5,7-(azenometheno)dipyrazolo[3,4-b:5',1'-g][1]oxa[4,6,8]triazacycloundecine | 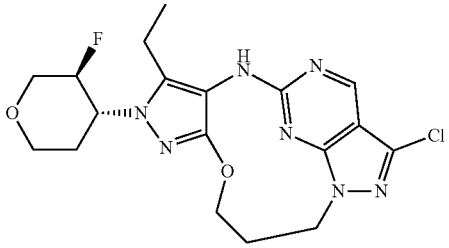 [SMILES: CCc1c2c(nn1[C@@H]1CCOC[C@H]1F)OCCCn1nc(Cl)c3cnc(nc31)N2]<br>or<br>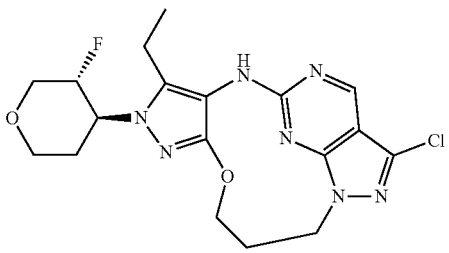 [SMILES: CCc1c2c(nn1[C@H]1CCOC[C@@H]1F)OCCCn1nc(Cl)c3cnc(nc31)N2] |
| 57 | 8-Chloro-3-ethyl-2-((1r,4r)-4-methoxycyclohexyl)-2,4,12,13-tetrahydro-11H-5,7-(azenometheno)dipyrazolo[3,4-b:5',1'-g][1]oxa[4,6,8]triazacycloundecine | 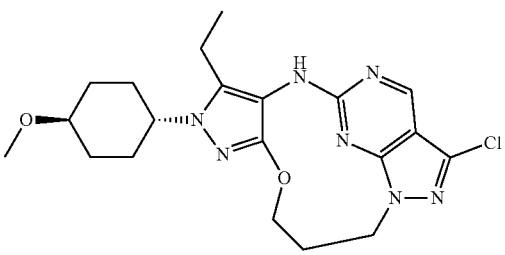 [SMILES: CCc1c2c(nn1[C@H]1CC[C@H](OC)CC1)OCCCn1nc(Cl)c3cnc(nc31)N2] |

TABLE 1-continued

Compounds of the invention

| Compound number | Name | Structure |
|---|---|---|
| 58 | (R)-8-Chloro-3-(methyl-d₃)-2-(oxepan-4-yl)-2,4,12,13-tetrahydro-11H-5,7-(azenometheno)dipyrazolo[3,4-b:5',1'-g][1]oxa[4,6,8]triazacycloundecine; or (S)-8-Chloro-3-(methyl-d₃)-2-(oxepan-4-yl)-2,4,12,13-tetrahydro-11H-5,7-(azenometheno)dipyrazolo[3,4-b:5',1'-g][1]oxa[4,6,8]triazacycloundecine | 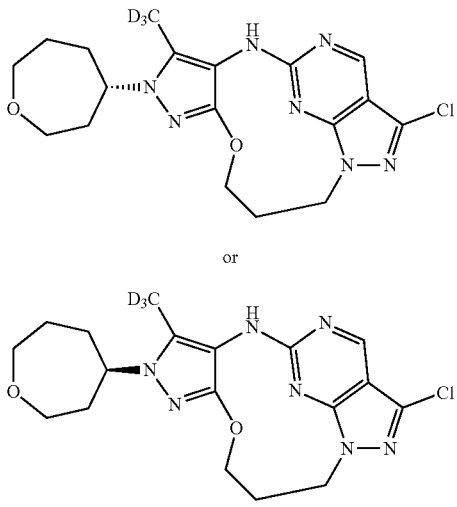 |
| 59 | (R)-8-Chloro-3-(methyl-d₃)-2-(oxepan-4-yl)-2,4,12,13-tetrahydro-11H-5,7-(azenometheno)dipyrazolo[3,4-b:5',1'-g][1]oxa[4,6,8]triazacycloundecine; or (S)-8-Chloro-3-(methyl-d₃)-2-(oxepan-4-yl)-2,4,12,13-tetrahydro-11H-5,7-(azenometheno)dipyrazolo[3,4-b:5',1'-g][1]oxa[4,6,8]triazacycloundecine | 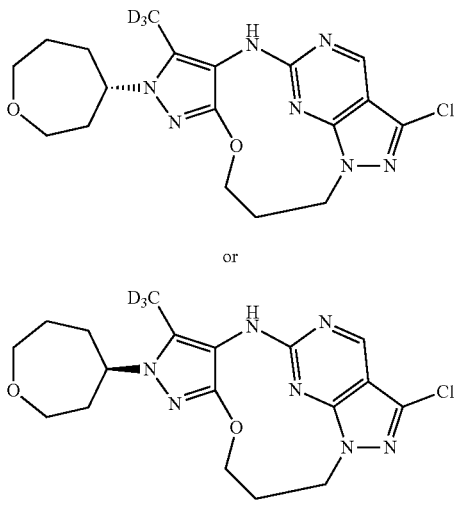 |
| 60 | (R)-8-Chloro-3-(methyl-d3)-2-(tetrahydro-2H-pyran-3-yl)-2,4,12,13-tetrahydro-11H-5,7-(azenometheno)dipyrazolo[3,4-b:5',1'-g][1]oxa[4,6,8]triazacycloundecine; or (S)-8-Chloro-3-(methyl-d3)-2-(tetrahydro-2H-pyran-3-yl)-2,4,12,13-tetrahydro-11H-5,7-(azenometheno)dipyrazolo[3,4-b:5',1'-g][1]oxa[4,6,8]triazacycloundecine | 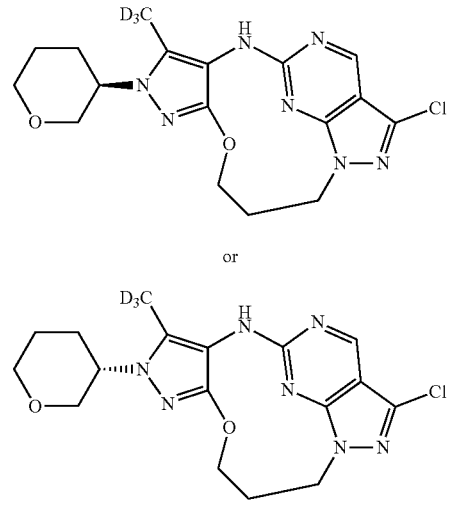 |

TABLE 1-continued

Compounds of the invention

| Compound number | Name | Structure |
|---|---|---|
| 61 | (R)-8-Chloro-3-(methyl-d3)-2-(tetrahydro-2H-pyran-3-yl)-2,4,12,13-tetrahydro-11H-5,7-(azenometheno)dipyrazolo[3,4-b:5',1'-g][1]oxa[4,6,8]triazacycloundecine; or (S)-8-Chloro-3-(methyl-d3)-2-(tetrahydro-2H-pyran-3-yl)-2,4,12,13-tetrahydro-11H-5,7-(azenometheno)dipyrazolo[3,4-b:5',1'-g][1]oxa[4,6,8]triazacycloundecine | or |
| 62 | 8-Chloro-2-((3R,4S)-3-fluorotetrahydro-2H-pyran-4-yl)-3-(methyl-d$_3$)-2,4,12,13-tetrahydro-11H-5,7-(azenometheno)dipyrazolo[3,4-b:5',1'-g][1]oxa[4,6,8]triazacycloundecine; or 8-chloro-2-((3S,4R)-3-fluorotetrahydro-2H-pyran-4-yl)-3-(methyl-d$_3$)-2,4,12,13-tetrahydro-11H-5,7-(azenometheno)dipyrazolo[3,4-b:5',1'-g][1]oxa[4,6,8]triazacycloundecine | or |
| 63 | (8-Chloro-2-((3R,4S)-3-fluorotetrahydro-2H-pyran-4-yl)-3-(methyl-d$_3$)-2,4,12,13-tetrahydro-11H-5,7-(azenometheno)dipyrazolo[3,4-b:5',1'-g][1]oxa[4,6,8]triazacycloundecine; or 8-chloro-2-((3S,4R)-3-fluorotetrahydro-2H-pyran-4-yl)-3-(methyl-d$_3$)-2,4,12,13-tetrahydro-11H-5,7-(azenometheno)dipyrazolo[3,4-b:5',1'-g][1]oxa[4,6,8]triazacycloundecine | or |

TABLE 1-continued

Compounds of the invention

| Compound number | Name | Structure |
|---|---|---|
| 64 | (R)-8-chloro-3-(methyl-d₃)-2-(4-oxaspiro[2.5]octan-7-yl)-2,4,12,13-tetrahydro-11H-5,7-(azenometheno)dipyrazolo[3,4-b:5',1'-g][1]oxa[4,6,8]triazacycloundecine; or (S)-8-chloro-3-(methyl-d₃)-2-(4-oxaspiro[2.5]octan-7-yl)-2,4,12,13-tetrahydro-11H-5,7-(azenometheno)dipyrazolo[3,4-b:5',1'-g][1]oxa[4,6,8]triazacycloundecine | *(structure shown)* or *(structure shown)* |
| 65 | (R)-8-chloro-3-(methyl-d₃)-2-(4-oxaspiro[2.5]octan-7-yl)-2,4,12,13-tetrahydro-11H-5,7-(azenometheno)dipyrazolo[3,4-b:5',1'-g][1]oxa[4,6,8]triazacycloundecine; or (S)-8-chloro-3-(methyl-d3)-2-(4-oxaspiro[2.5]octan-7-yl)-2,4,12,13-tetrahydro-11H-5,7-(azenometheno)dipyrazolo[3,4-b:5',1'-g][1]oxa[4,6,8]triazacycloundecine | *(structure shown)* or *(structure shown)* |

Definitions

In the present context, "alkyl" is intended to indicate a straight or branched saturated hydrocarbon. In particular, $C_1$-$C_3$-alkyl is intended to indicate such hydrocarbon having 1, 2 or 3 carbon atoms in the longest continuous carbon chain. Typical alkyl groups include, but are not limited to, methyl, ethyl, propyl, isopropyl, butyl, isobutyl, t-butyl and the like.

As used herein, the term "isotopically labelled alkyl group" means that either the carbon or the hydrogen atom(s) in the alkyl group is replaced with a corresponding isotope such as $^{13}$ and/or $^{14}C$ for carbon atom(s), or deuterium or tritium for hydrogen atom(s). In an embodiment of the invention the hydrogen atoms of the alkyl group are all replaced by deuterium. Representative examples of isotopically labelled alkyl include but are not limited to —$CD_3$, —$CD_2CD_3$. In a preferred embodiment, the isotopically labelled $C_1$-$C_3$-alkyl is —$CD_3$.

The term "alkylene," as used herein, refers to a divalent group derived from a straight or branched chain hydrocarbon of 1 to 10 carbon atoms, for example, of 2 to 5 carbon atoms. Representative examples of alkylene include, but are not limited to, —$CH_2$—, —$CH_2CH_2$—, —$CH_2CH_2CH_2$—, —$CH_2CH(CH_3)CH_2$—, —$CH_2CH_2CH_2CH_2$—, —$CH_2CH(CH_3)CH_2CH_2$—, —$CH(CH_3)$— and —$CH_2CH_2CH_2CH_2CH_2$—.

The term "alkoxy" as used herein refers to a group of formula —O-alkyl, wherein alkyl is defined as above. In particular, $C_1$-$C_3$-alkoxy is intended to indicate a hydrocarbon having 1, 2 or 3 carbon atoms. Examples of alkoxy groups include, but are not limited to, methoxy, ethoxy, propoxy, butoxy, isobutoxy, t-butoxy and the like.

The term "haloalkyl" or "haloalkoxy" is intended to refer to an alkyl or alkoxy group as defined hereinabove with 1, 2 or 3 hydrogens replaced by a halogen. Representative examples include but are not limited to $CH_2F$, $CHF_2$ $CF_3$, $OCF_3$, $OCH_2F$, and $OCHF_2$. In the present application "haloalkoxy" may also be referred to as "O-haloalkyl", such as for example "O—$C_1$-$C_3$ haloalkyl".

Similarly, the term "fluoroalkyl" is intended to refer to an alkyl group as defined hereinabove, with 1, 2, or 3 hydrogens replaced by fluoro. Representative examples include but are not limited to —$CF_3$.

In the present context, "halogen" is intended to indicate members of the $7^{th}$ main group of the periodic table of the elements, such as fluoro, bromo and chloro.

The term "heteroatom" is intended to mean sulfur, oxygen or nitrogen.

The term "cyano" as used herein, means at least one —CN group is appended to the parent molecular moiety.

The term "cyanoalkyl" as used herein is intended to indicate an alkyl group as defined herein, wherein at least one —CN group is appended to the parent molecular moiety.

The term "cyclic" as used herein refers to any cyclic structure, including heterocyclic, aromatic and heteroaromatic non-fused ring systems. The term "membered" is meant to denote the number of skeletal atoms that constitute the ring. Thus, for example, pyridyl, pyranyl, and pyrimidinyl are six-membered rings and pyrrolyl, and tetrahydrofuranyl are five-membered rings.

The term "cycloalkyl," as used herein, refers to a carbocyclic ring system containing three to ten carbon atoms, zero heteroatoms and zero double bonds. The cycloalkyl may be monocyclic or bicyclic, wherein the bicyclic ring is joined bridged, fused, or spirocyclic.

The terms "heterocycle", "heterocyclic" and "heterocyclyl" as used herein, alone or in combination, refers to saturated or unsaturated nonaromatic rings containing from 4 to 7 ring atoms where one or more of the ring atoms are heteroatoms. The heterocycle may be monocyclic or bicyclic, wherein the bicyclic ring is joined bridged, fused, or spirocyclic. In some embodiments if explicitly stated, the term "heterocycle", "heterocyclic" and "heterocyclyl" may refer to a saturated or unsaturated nonaromatic ring containing 8 ring atoms where one or more of the ring atoms are heteroatoms. Such 8-membered heterocycle is a bicyclic ring, wherein the bicyclic ring is joined bridged, fused, or spirocyclic.

In the present context, the term "therapeutically effective amount" of a compound is intended to indicate an amount sufficient to alleviate or partially arrest the clinical manifestations of a given disease and its complications in a therapeutic intervention comprising the administration of said compound. An amount adequate to accomplish this is defined as "therapeutically effective amount". Effective amounts for each purpose will depend on the severity of the disease or injury as well as the weight and general state of the subject. It will be understood that determining an appropriate dosage may be achieved using routine experimentation, e.g. by constructing a matrix of values and testing different points in the matrix, which is all within the ordinary skills of a trained physician.

In the present context, the term "treatment" and "treating" means the management and care of a patient for the purpose of combating a disease. The term is intended to include the full spectrum of treatments for a given disease from which the patient is suffering, such as administration of the active compound to alleviate the symptoms or complications, to delay the progression of the disease, to alleviate or relief the symptoms and complications, and/or to cure or eliminate the disease. The patient to be treated is preferably a mammal, in particular a human being. In the present context, "disease" can be used synonymous with disorder, condition, malfunction, dysfunction and the like.

The use of the terms "a" and "an" and "the" and similar referents in the context of describing the invention are to be construed to cover both the singular and the plural, unless otherwise indicated herein or clearly contradicted by context. For example, the phrase "the compound" is to be understood as referring to various "compounds" of the invention or particular described aspect, unless otherwise indicated.

The description herein of any aspect or aspect of the invention using terms such as "comprising", "having," "including," or "containing" with reference to an element or elements is intended to provide support for a similar aspect or aspect of the invention that "consists of", "consists essentially of", or "substantially comprises" that particular element or elements, unless otherwise stated or clearly contradicted by context (e.g., a composition described herein as comprising a particular element should be understood as also describing a composition consisting of that element, unless otherwise stated or clearly contradicted by context).

Embodiments of the Invention

In the following, embodiments of the invention are disclosed. The first embodiment is denoted E1, the second embodiment is denoted E2 and so forth.

E1. A compound of formula I, or a pharmaceutically acceptable salt thereof, wherein:

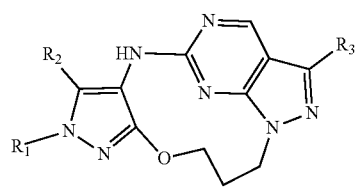

I $R_1$ is $CH_2R_4$ or $R_4$;
$R_2$ is a $C_1$-$C_3$ alkyl, an isotopically labelled $C_1$-$C_3$ alkyl, a $C_3$-$C_6$ cycloalkyl, or a $C_1$-$C_3$ haloalkyl;
$R_3$ is halogen, cyano, a O—$C_1$-$C_3$ haloalkyl, a $C_1$-$C_3$ haloalkyl, a $C_3$-$C_6$ cycloalkyl, or a $C_1$-$C_3$ alkyl;
$R_4$ is a 4- to 7-membered heterocycle having 1-2 heteroatoms independently selected from oxygen and nitrogen; a $C_1$-$C_3$alkyl, a $C_1$-$C_3$ cyanoalkyl, a $C_1$-$C_3$ haloalkyl, or a $C_3$-$C_6$ cycloalkyl;
or $R_4$ is a bicyclic 8-membered heterocycle having 1-2 heteroatoms independently selected from oxygen and nitrogen;
wherein each heterocycle or cycloalkyl is unsubstituted or substituted with 1, 2, or 3 groups independently selected from the group consisting of cyano, deuterium, halogen, $C_1$-$C_3$ alkyl, an isotopically labelled $C_1$-$C_3$ alkyl, a O—$C_1$-$C_3$ haloalkyl, a O—$C_1$-$C_3$ alkyl, or a $C_1$-$C_3$ haloalkyl.

E2. The compound of embodiment E1, or a pharmaceutically acceptable salt thereof, wherein $R_1$ is $CH_2R_4$.

E3. The compound of embodiment E1, wherein the compound is a compound of formula Ia, or a pharmaceutically acceptable salt thereof

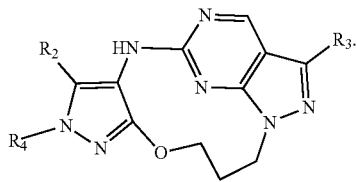

E4. The compound of any one of embodiments E1-E3, or a pharmaceutically acceptable salt thereof, wherein R₂ is selected from a C₁-C₃ alkyl, an isotopically labelled C₁-C₃ alkyl or a C₃-C₆ cycloalkyl.

E5. The compound of any one of embodiments E1-E4, or a pharmaceutically acceptable salt thereof, wherein R₂ is selected from —CH₃, —CH₂CH₃, —CD₃, or cyclopropyl.

E6. The compound of any one of embodiments E1-E4, or a pharmaceutically acceptable salt thereof, wherein R₂ is C₁-C₃ alkyl.

E7. The compound of any one of embodiments E1-E4, or a pharmaceutically acceptable salt thereof, wherein R₂ is methyl.

E8. The compound of any one of embodiments E1-E4, or a pharmaceutically acceptable salt thereof, wherein R₂ is ethyl.

E9. The compound of any one of embodiments E1-E4, or a pharmaceutically acceptable salt thereof, wherein R₂ is an isotopically labelled C₁-C₃ alkyl.

E10. The compound of embodiment E1-E4, or a pharmaceutically acceptable salt thereof, wherein R₂ is selected from the group consisting of —CD₃ or —CD₂CD₃.

E11. The compound of embodiment E10, or a pharmaceutically acceptable salt thereof, wherein R₂ is —CD₃.

E12. The compound of any one of embodiments E1-E4, or a pharmaceutically acceptable salt thereof, wherein R₂ is cyclopropyl.

E13. The compound of any one of embodiments E1-E12, or a pharmaceutically acceptable salt thereof, wherein R₃ is C₁-C₃ haloalkyl.

E14. The compound of embodiment E13, or a pharmaceutically acceptable salt thereof, wherein R₃ is CF3.

E15. The compound of any one of embodiments E1-E12, or a pharmaceutically acceptable salt thereof, wherein R₃ is halogen.

E16. The compound of embodiment E15, or a pharmaceutically acceptable salt thereof, wherein R₃ is chloro.

E17. The compound of embodiment E15, or a pharmaceutically acceptable salt thereof, wherein R₃ is bromo.

E18. The compound of any one of embodiments E1-E12, or a pharmaceutically acceptable salt thereof, wherein R₃ is cyano.

E19. The compound of any one of embodiment E1-E13, or a pharmaceutically acceptable salt thereof, wherein R₃ is a C₃-C₆cycloalkyl.

E20. The compound of embodiment E19, or a pharmaceutically acceptable salt thereof, wherein R₃ is cyclopropyl.

E21. The compound of any one of embodiments E1-E20, or a pharmaceutically acceptable salt thereof, wherein R₄ is a 4- to 6-membered heterocycle having one oxygen atom, wherein the 4- to 6-membered heterocycle is unsubstituted or substituted with two groups independently selected from the list consisting of cyano, deuterium, halogen, C₁-C₃ alkyl, an isotopically labelled C₁-C₃ alkyl or C₁-C₃ haloalkyl.

E22. The compound of any one of embodiments E1-E20, or a pharmaceutically acceptable salt thereof, wherein R₄ is a 4- to 6-membered heterocycle having one oxygen atom, wherein the 4- to 6-membered heterocycle is unsubstituted or substituted with 1 group selected from the group consisting of cyano, deuterium, halogen, C₁-C₃ alkyl, an isotopically labelled C₁-C₃ alkyl, O—C₁-C₃ haloalkyl, O—C₁-C₃ alkyl, or C₁-C₃ haloalkyl.

E23. The compound of any one of embodiments E1-E20, or a pharmaceutically acceptable salt thereof, wherein R₄ is a 4- to 6-membered heterocycle having one oxygen atom, wherein the 4- to 6-membered heterocycle is unsubstituted or substituted with 1 group selected from the group consisting of deuterium, halogen, C₁-C₃ alkyl, or an isotopically labelled C₁-C₃ alkyl.

E24. The compound of any one of embodiments E1-E20, or a pharmaceutically acceptable salt thereof, wherein R₄ is 6-membered heterocycle having one oxygen atom, wherein the 6-membered heterocycle is unsubstituted or substituted with 1 group selected from the group consisting of deuterium, halogen, C₁-C₃ alkyl, or an isotopically labelled C₁-C₃ alkyl.

E25. The compound of any one of embodiments E1-E20, or a pharmaceutically acceptable salt thereof, wherein R₄ is selected from the group consisting of:

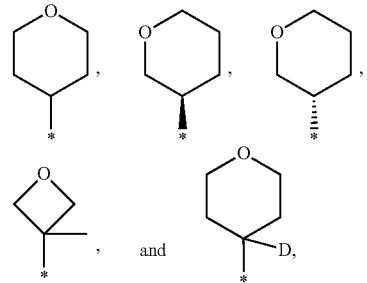

wherein * denotes the attachment point.

E26. The compound of any one of embodiments E1-E20, or a pharmaceutically acceptable salt thereof, wherein R₄ is selected from the group consisting of: CH₃,

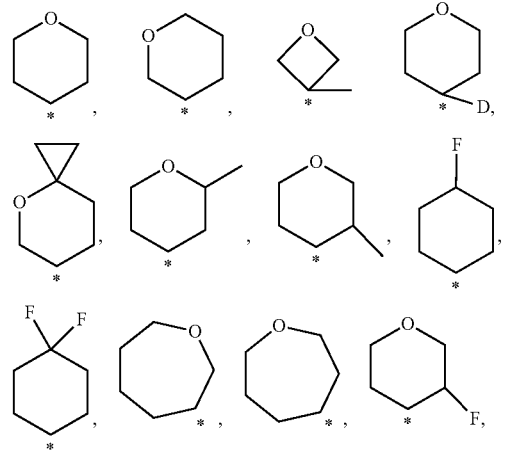

-continued

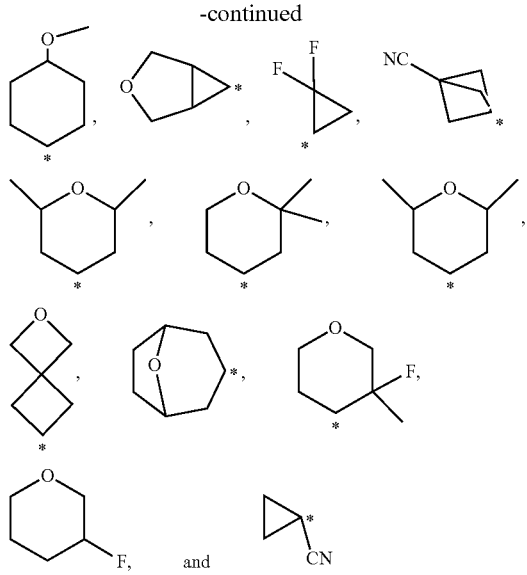

wherein * denotes the attachment point.

E27. The compound of any one of embodiments E1-E20, or a pharmaceutically acceptable salt thereof, wherein $R_4$ is unsubstituted tetrahydropyran.

E28. The compound of any one of embodiments E1-E20, or a pharmaceutically acceptable salt thereof, wherein $R_4$ is tetrahydro-2H-pyran-4-yl.

E29. The compound of any one of embodiments E1-E20, or a pharmaceutically acceptable salt thereof, wherein $R_4$ is tetrahydro-2H-pyran-3-yl.

E30. The compound of any one of embodiments E1-E20, or a pharmaceutically acceptable salt thereof, wherein $R_4$ is 4-oxaspiro[2.5]octan-7-yl.

E31. The compound of any one of embodiments E1-E20, or a pharmaceutically acceptable salt thereof, wherein the 8-membered heterocycle is an unsubstituted 8-membered spirocyclic heterocycle.

E32. The compound of embodiments E31, or a pharmaceutically acceptable salt thereof, wherein the bicyclic 8-membered heterocycle contains one oxygen.

E33. The compound of embodiments E31, or a pharmaceutically acceptable salt thereof, wherein the bicyclic 8-membered heterocycle contains one oxygen and is a spirocyclic heterocycle.

E34. The compound of embodiment E1, wherein the compound is a compound of formula Ib, or a pharmaceutically acceptable salt thereof, wherein:

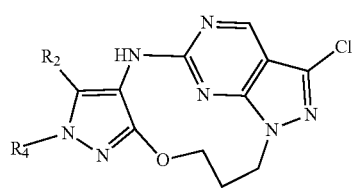

Ib $R_2$ is a $C_1$-$C_3$ alkyl, an isotopically labelled $C_1$-$C_3$ alkyl, a $C_3$-$C_6$cycloalkyl, or a $C_1$-$C_3$ haloalkyl;

$R_4$ is a 4- to 7-membered heterocycle having 1-2 heteroatoms independently selected from oxygen and nitrogen, a $C_1$-$C_3$alkyl, a $C_1$-$C_3$ cyanoalkyl, a $C_1$-$C_3$ haloalkyl, or a $C_3$-$C_6$cycloalkyl;

wherein each heterocycle or cycloalkyl is unsubstituted or substituted with 1 group selected from the groups selected from cyano, deuterium, halogen, a $C_1$-$C_3$ alkyl, an isotopically labelled $C_1$-$C_3$ alkyl, a O—$C_1$-$C_3$ haloalkyl, a O—$C_1$-$C_3$ alkyl, or a $C_1$-$C_3$ haloalkyl.

E35. The compound of embodiments E34, or a pharmaceutically acceptable salt thereof, wherein $R_2$ is selected from —$CH_3$, —$CH_2CH_3$, —$CD_3$, or cyclopropyl.

E36. The compound of embodiment E1, wherein the compound is a compound of formula Ic, or a pharmaceutically acceptable salt thereof, wherein:

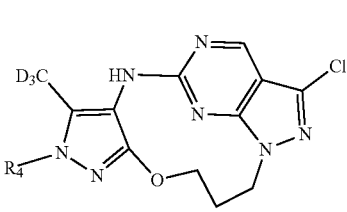

Ic $R_4$ is a 4- to 7-membered heterocycle having 1-2 heteroatoms independently selected from oxygen and nitrogen, a $C_1$-$C_3$alkyl, a $C_1$-$C_3$ cyanoalkyl, a $C_1$-$C_3$ haloalkyl, or a $C_3$-$C_6$cycloalkyl;

wherein each heterocycle or cycloalkyl is unsubstituted or substituted with 1 group selected from the groups selected from cyano, deuterium, halogen, a $C_1$-$C_3$ alkyl, an isotopically labelled $C_1$-$C_3$ alkyl, a O—$C_1$-$C_3$ haloalkyl, a O—$C_1$-$C_3$ alkyl, or a $C_1$-$C_3$ haloalkyl.

E37. The compound of embodiment E1, wherein the compound is a compound of formula Id, or a pharmaceutically acceptable salt thereof, wherein:

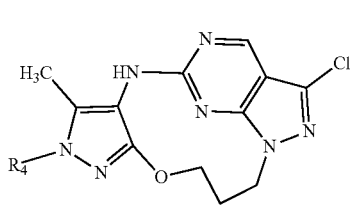

Id $R_4$ is a 4- to 7-membered heterocycle having 1-2 heteroatoms independently selected from oxygen and nitrogen, a $C_1$-$C_3$alkyl, a $C_1$-$C_3$ cyanoalkyl, a $C_1$-$C_3$ haloalkyl, or a $C_3$-$C_6$cycloalkyl;

wherein each heterocycle or cycloalkyl is unsubstituted or substituted with 1 group selected from the groups selected from cyano, deuterium, halogen, a $C_1$-$C_3$ alkyl, an isotopically labelled $C_1$-$C_3$ alkyl, a O—$C_1$-$C_3$ haloalkyl, a O—$C_1$-$C_3$ alkyl, or a $C_1$-$C_3$ haloalkyl.

E38. The compound of any one of embodiments E30-E31, or a pharmaceutically acceptable salt thereof, wherein the 4- to 7-membered heterocycle is an unsubstituted 6-7 membered spirocyclic heterocycle.

E39. The compound of any one of embodiments E30-E31, or a pharmaceutically acceptable salt thereof, wherein the 4- to 7-membered heterocycle is an unsubstituted 6-7 membered bridged heterocycle.

E40. The compound of embodiment E1, wherein the compound is selected from the group consisting of:

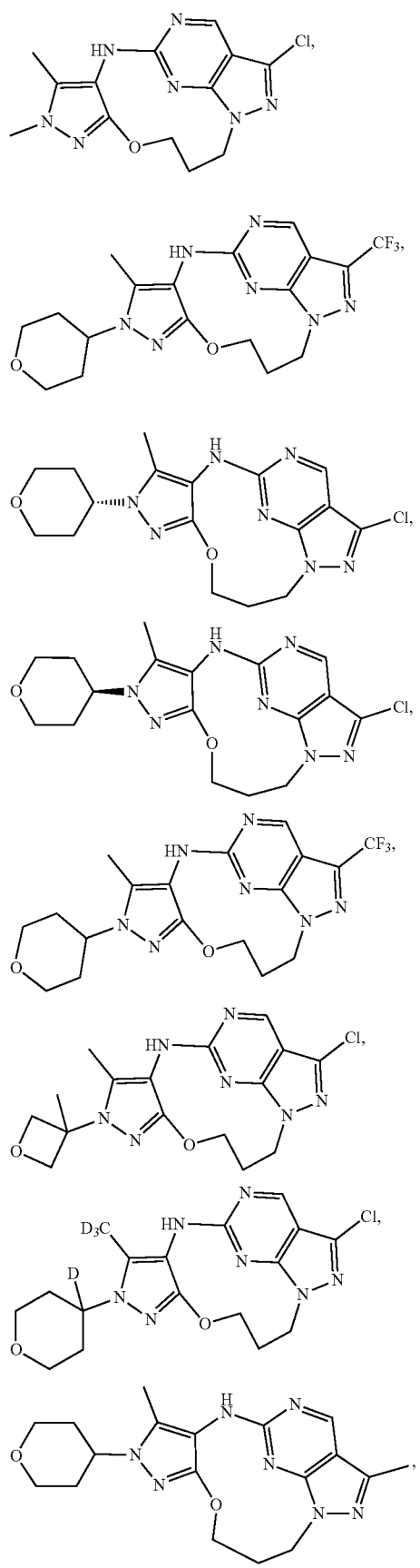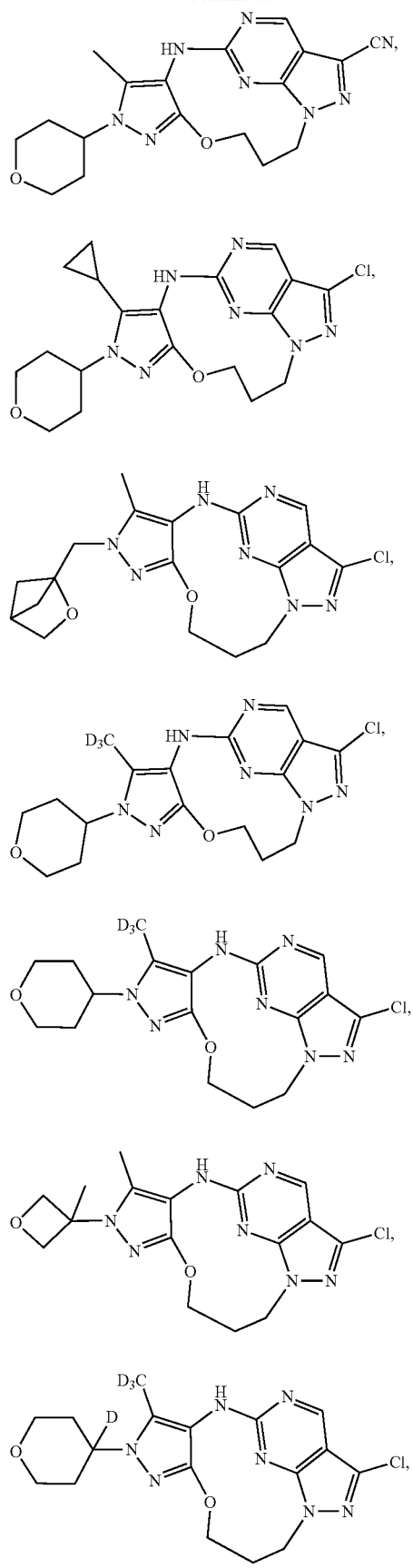

-continued

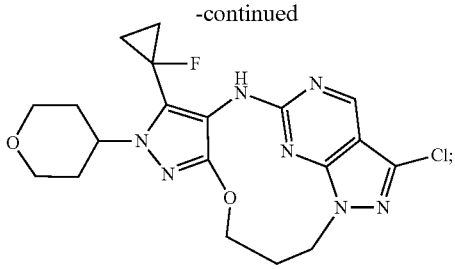

or a pharmaceutically acceptable salt thereof.

E41. The compound of embodiment E1, wherein the compound is selected from the group consisting of:

8-Chloro-2,3-dimethyl-2,4,12,13-tetrahydro-11H-5,7-(azenometheno)dipyrazolo-[3,4-b:5',1'-g][1]oxa[4,6,8]triazacycloundecine;

8-Chloro-3-methyl-2-(tetrahydro-2H-pyran-4-yl)-2,4,12,13-tetrahydro-11H-5,7-(azenometheno)dipyrazolo[3,4-b:5',1'-g][1]oxa[4,6,8]triazacycloundecine;

(R)-8-chloro-3-methyl-2-(tetrahydro-2H-pyran-3-yl)-2,4,12,13-tetrahydro-11H-5,7-(azenometheno)dipyrazolo[3,4-b:5',1'-g][1]oxa[4,6,8]triazacycloundecine;

(S)-8-chloro-3-methyl-2-(tetrahydro-2H-pyran-3-yl)-2,4,12,13-tetrahydro-11H-5,7-(azenometheno)dipyrazolo[3,4-b:5',1'-g][1]oxa[4,6,8]triazacycloundecine;

3-Methyl-2-(tetrahydro-2H-pyran-4-yl)-8-(trifluoromethyl)-2,4,12,13-tetrahydro-11H5,7-(azenometheno)dipyrazolo[3,4-b:5',1'-g][1]oxa[4,6,8]triazacycloundecine;

8-Bromo-3-methyl-2-(tetrahydro-2H-pyran-4-yl)-2,4,12,13-tetrahydro-11H-5,7-(azenometheno)dipyrazolo[3,4-b:5',1'-g][1]oxa[4,6,8]triazacycloundecine;

8-Cyclopropyl-3-methyl-2-(tetrahydro-2H-pyran-4-yl)-2,4,12,13-tetrahydro-11H-5,7-(azenometheno)dipyrazolo[3,4-b:5',1'-g][1]oxa[4,6,8]triazacycloundecine;

3,8-Dimethyl-2-(tetrahydro-2H-pyran-4-yl)-2,4,12,13-tetrahydro-11H-5,7-(azenometheno)dipyrazolo[3,4-b:5',1'-g][1]oxa[4,6,8]triazacycloundecine;

3-Methyl-2-(tetrahydro-2H-pyran-4-yl)-2,4,12,13-tetrahydro-11H-5,7-(azenometheno)dipyrazolo[3,4-b:5',1'-g][1]oxa[4,6,8]triazacycloundecine-8-carbonitrile;

8-Chloro-3-cyclopropyl-2-(tetrahydro-2H-pyran-4-yl)-2,4,12,13-tetrahydro-11H-5,7-(azenometheno)dipyrazolo[3,4-b:5',1'-g][1]oxa[4,6,8]triazacycloundecine;

2-((2-Oxabicyclo[2.1.1]hexan-1-yl)methyl)-8-chloro-3-methyl-2,4,12,13-tetrahydro-11H-5,7-(azenometheno)dipyrazolo[3,4-b:5',1'-g][1]oxa[4,6,8]triazacycloundecine;

8-Chloro-3-methyl-2-((3-methyloxetan-3-yl)methyl)-2,4,12,13-tetrahydro-11H-5,7-(azenometheno)dipyrazolo[3,4-b:5',1'-g][1]oxa[4,6,8]triazacycloundecine;

8-Chloro-3-(methyl-d3)-2-(tetrahydro-2H-pyran-4-yl)-2,4,12,13-tetrahydro-11H-5,7-(azenometheno)dipyrazolo[3,4-b:5',1'-g][1]oxa[4,6,8]triazacycloundecine;

8-Chloro-3-methyl-2-(3-methyloxetan-3-yl)-2,4,12,13-tetrahydro-11H-5,7-(azenometheno)dipyrazolo[3,4-b:5',1'-g][1]oxa[4,6,8]triazacycloundecine;

8-Chloro-3-(methyl-d3)-2-(tetrahydro-2H-pyran-4-yl-4-d)-2,4,12,13-tetrahydro-11H5,7-(azenometheno)dipyrazolo[3,4-b:5',1'-g][1]oxa[4,6,8]triazacycloundecine; and 8-Chloro-3-(1-fluorocyclopropyl)-2-(tetrahydro-2H-pyran-4-yl)-2,4,12,13-tetrahydro-11H-5,7-(azenometheno)dipyrazolo[3,4-b:5',1'-g][1]oxa[4,6,8]triazacycloundecine; or a pharmaceutically acceptable salt thereof.

E42. The compound of embodiment E1, wherein the compound is selected from the group consisting of:

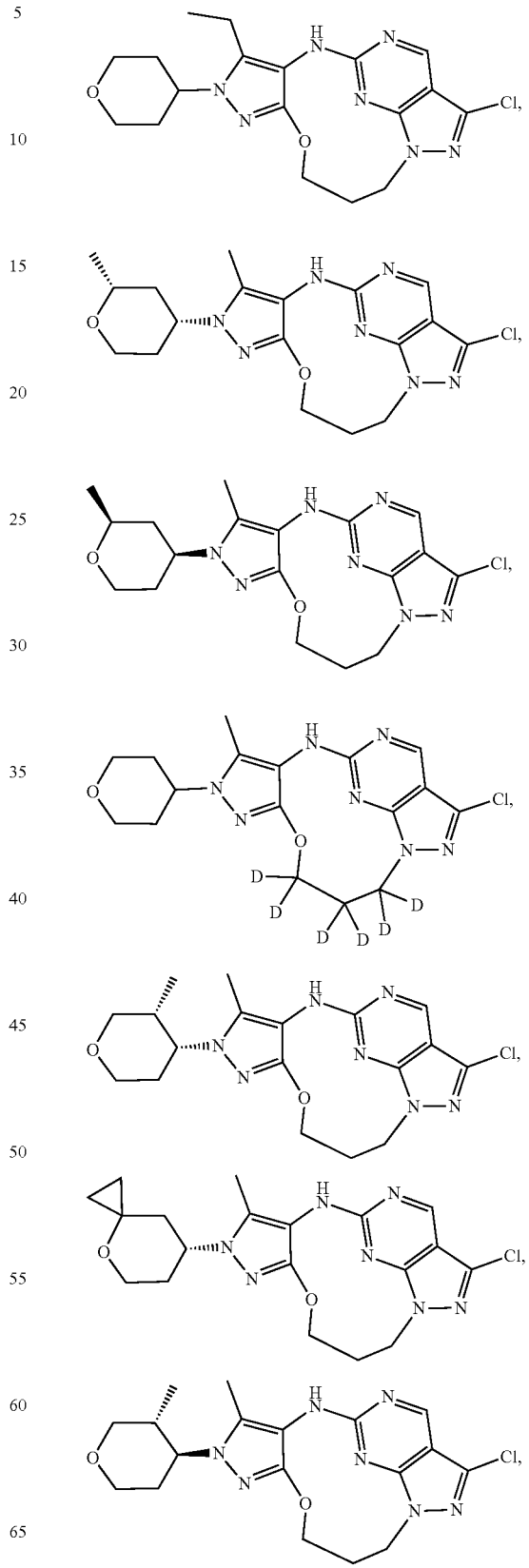

75
-continued
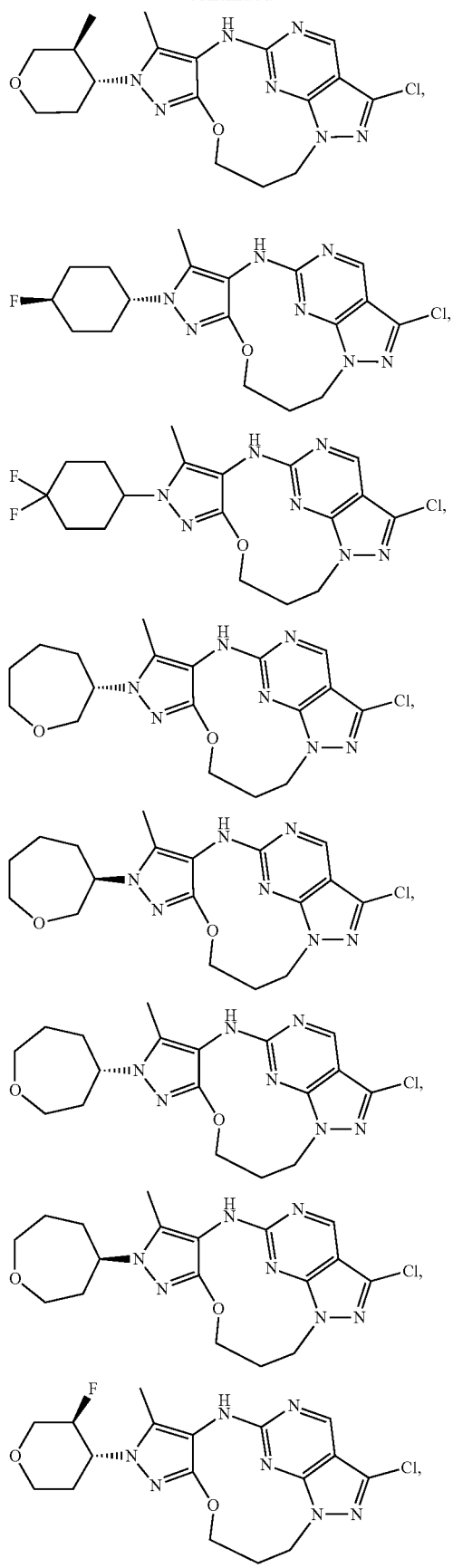
76
-continued
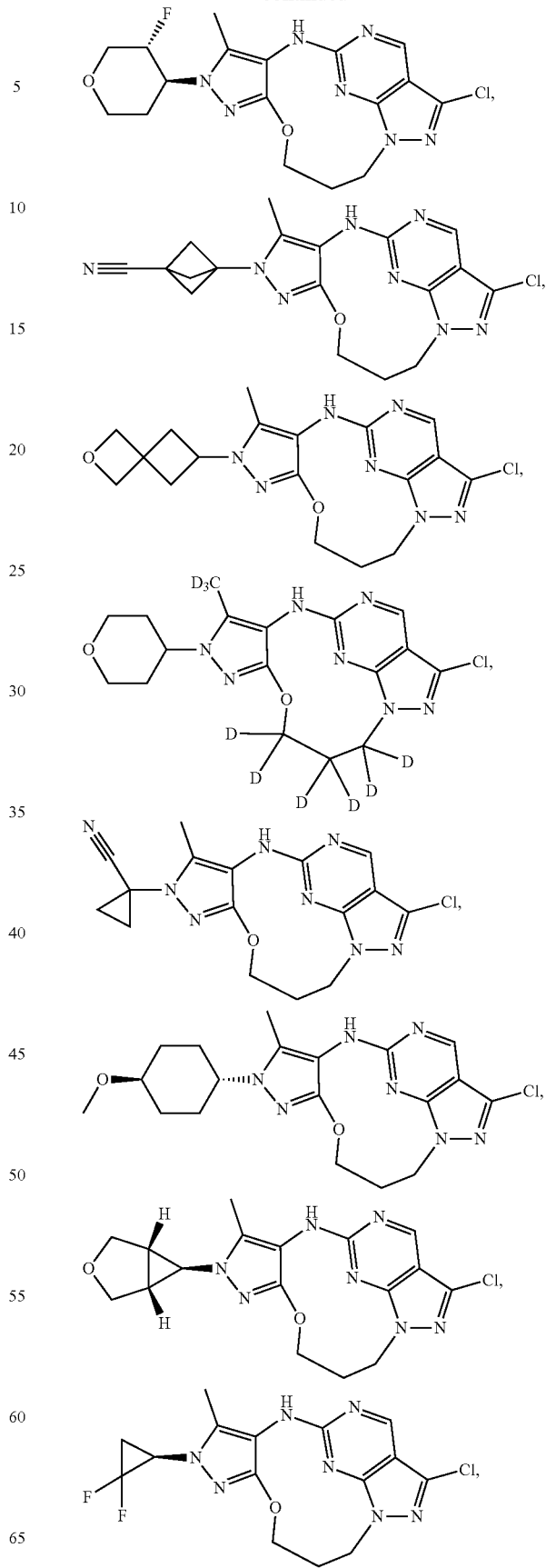

77
-continued
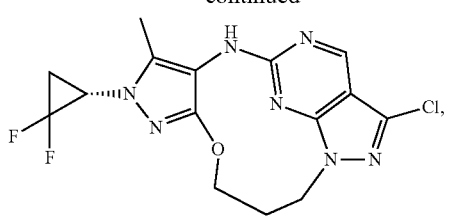
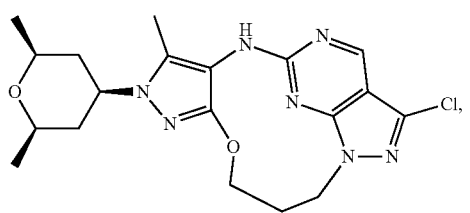
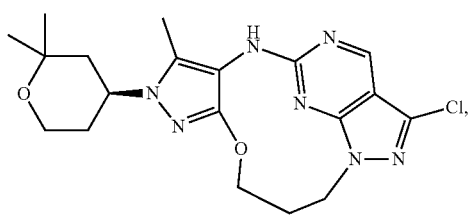
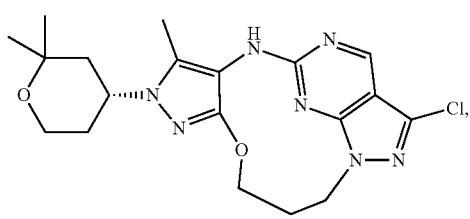
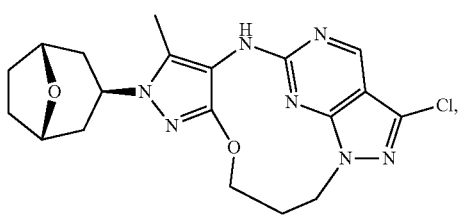
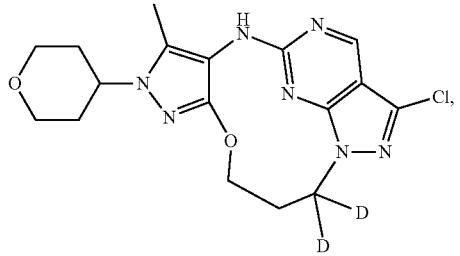
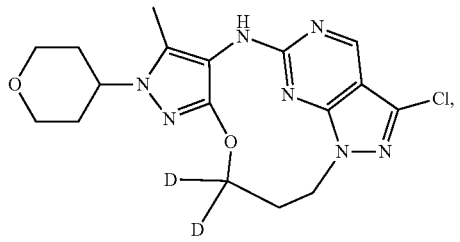
78
-continued
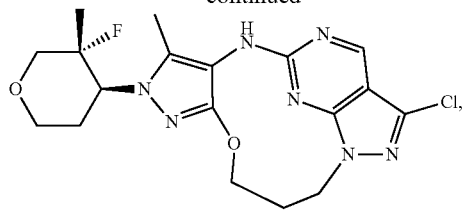
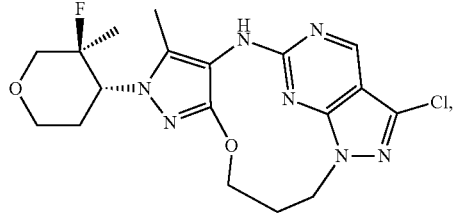
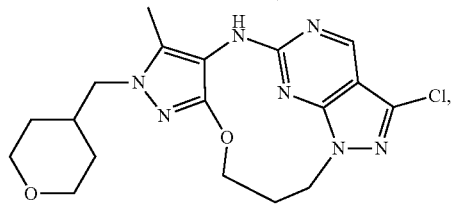
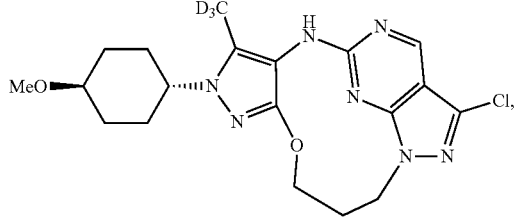
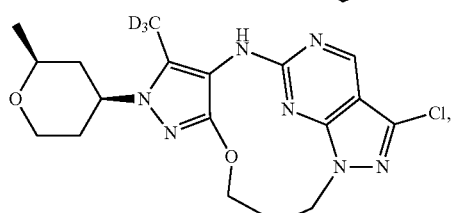
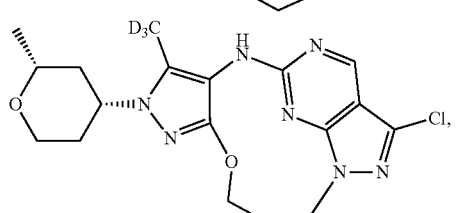
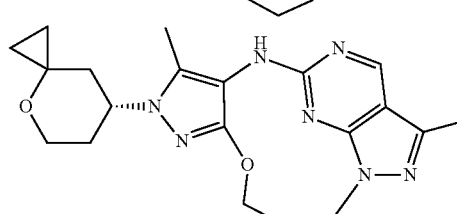
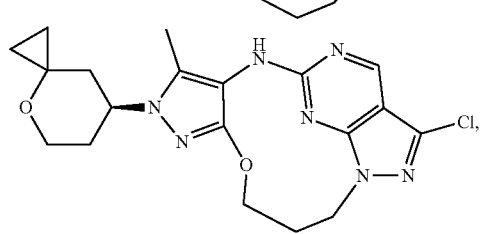

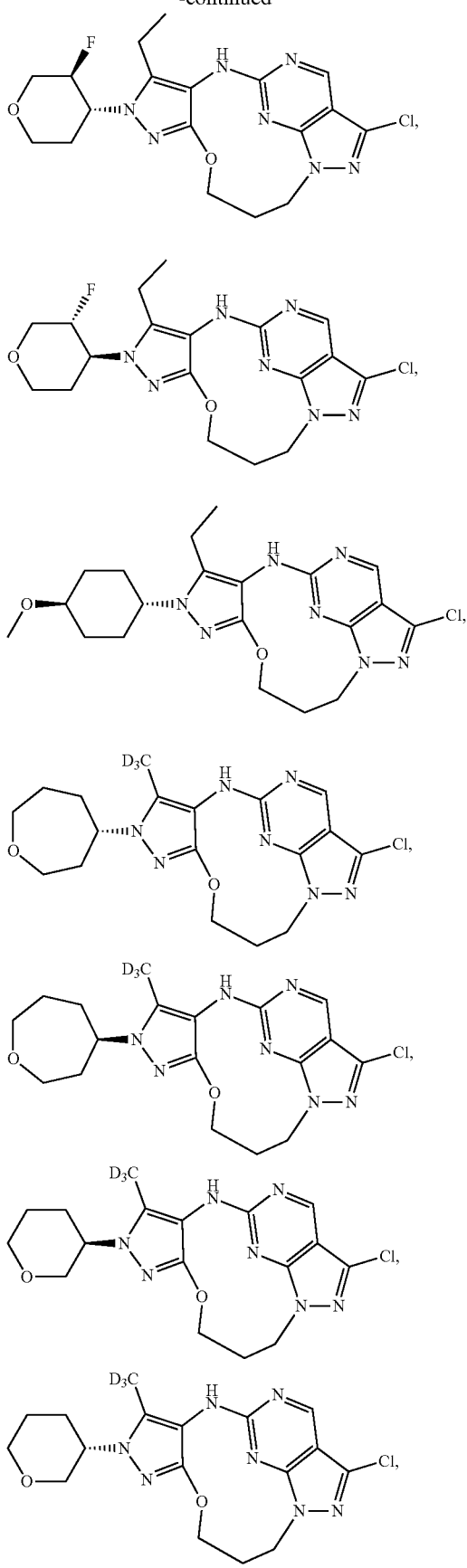
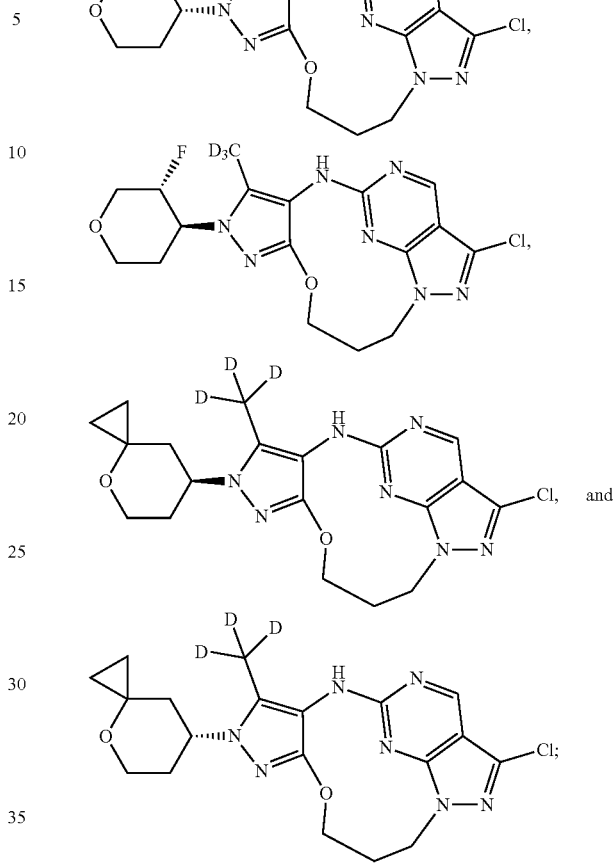

or a pharmaceutically acceptable salt thereof.

E43. The compound of embodiment E1, wherein the compound is selected from the group consisting of:

8-Chloro-3-ethyl-2-(tetrahydro-2H-pyran-4-yl)-2,4,12,13-tetrahydro-11H-5,7-(azenometheno)dipyrazolo[3,4-b:5',1'-g][1]oxa[4,6,8]triazacycloundecine;

8-Chloro-3-methyl-2-((2R,4R)-2-methyltetrahydro-2H-pyran-4-yl)-2,4,12,13-tetrahydro-11H-5,7-(azenometheno)dipyrazolo[3,4-b:5',1'-g][1]oxa[4,6,8]triazacycloundecine;

8-Chloro-3-methyl-2-((2S,4S)-2-methyltetrahydro-2H-pyran-4-yl)-2,4,12,13-tetrahydro-11H-5,7-(azenometheno)dipyrazolo[3,4-b:5',1'-g][1]oxa[4,6,8]triazacycloundecine;

8-Chloro-3-methyl-2-(tetrahydro-2H-pyran-4-yl)-2,4,12,13-tetrahydro-11H-5,7-(azenometheno)dipyrazolo[3,4-b:5',1'-g][1]oxa[4,6,8]triazacycloundecine-11,11,12,12,13,13-$d_6$;

8-Chloro-3-methyl-2-((3R,4S)-3-methyltetrahydro-2H-pyran-4-yl)-2,4,12,13-tetrahydro-11H-5,7-(azenometheno)dipyrazolo[3,4-b:5',1'-g][1]oxa[4,6,8]triazacycloundecine;

8-Chloro-3-methyl-2-((3S,4R)-3-methyltetrahydro-2H-pyran-4-yl)-2,4,12,13-tetrahydro-11H-5,7-(azenometheno)dipyrazolo[3,4-b:5',1'-g][1]oxa[4,6,8]triazacycloundecine;

8-Chloro-3-methyl-2-((3S,4S)-3-methyltetrahydro-2H-pyran-4-yl)-2,4,12,13-tetrahydro-11H-5,7-(azenometheno)dipyrazolo[3,4-b:5',1'-g][1]oxa[4,6,8]triazacycloundecine;

8-Chloro-3-methyl-2-((3R,4R)-3-methyltetrahydro-2H-pyran-4-yl)-2,4,12,13-tetrahydro-11H-5,7-(azenometheno)dipyrazolo[3,4-b:5',1'-g][1]oxa[4,6,8]triazacycloundecine;

8-Chloro-2-((1r,4r)-4-fluorocyclohexyl)-3-methyl-2,4,12,13-tetrahydro-11H-5,7-(azenometheno)dipyrazolo[3,4-b:5',1'-g][1]oxa[4,6,8]triazacycloundecine;

8-Chloro-2-(4,4-difluorocyclohexyl)-3-methyl-2,4,12,13-tetrahydro-11H-5,7-(azenometheno)dipyrazolo[3,4-b:5',1'-g][1]oxa[4,6,8]triazacycloundecine;

(R)-8-Chloro-3-methyl-2-(oxepan-3-yl)-2,4,12,13-tetrahydro-11H-5,7-(azenometheno)dipyrazolo[3,4-b:5',1'-g][1]oxa[4,6,8]triazacycloundecine;

(S)-8-Chloro-3-methyl-2-(oxepan-3-yl)-2,4,12,13-tetrahydro-11H-5,7-(azenometheno)dipyrazolo[3,4-b:5',1'-g][1]oxa[4,6,8]triazacycloundecine;

(R)-8-Chloro-3-methyl-2-(oxepan-4-yl)-2,4,12,13-tetrahydro-11H-5,7-(azenometheno)dipyrazolo[3,4-b:5',1'-g][1]oxa[4,6,8]triazacycloundecine;

(S)-8-Chloro-3-methyl-2-(oxepan-4-yl)-2,4,12,13-tetrahydro-11H-5,7-(azenometheno)dipyrazolo[3,4-b:5',1'-g][1]oxa[4,6,8]triazacycloundecine;

8-Chloro-2-((3S,4R)-3-fluorotetrahydro-2H-pyran-4-yl)-3-methyl-2,4,12,13-tetrahydro-11H-5,7-(azenometheno)dipyrazolo[3,4-b:5',1'-g][1]oxa[4,6,8]triazacycloundecine;

8-Chloro-2-((3R,4S)-3-fluorotetrahydro-2H-pyran-4-yl)-3-methyl-2,4,12,13-tetrahydro-11H-5,7-(azenometheno)dipyrazolo[3,4-b:5',1'-g][1]oxa[4,6,8]triazacycloundecine;

3-(8-Chloro-3-methyl-12,13-dihydro-11H-5,7-(azenometheno)dipyrazolo[3,4-b:5',1'-g][1]oxa[4,6,8]triazacycloundecin-2(4H)-yl)bicyclo[1.1.1]pentane-1-carbonitrile;

8-Chloro-3-methyl-2-(2-oxaspiro[3.3]heptan-6-yl)-2,4,12,13-tetrahydro-11H-5,7-(azenometheno)dipyrazolo[3,4-b:5',1'-g][1]oxa[4,6,8]triazacycloundecine;

8-Chloro-3-(methyl-ds)-2-(tetrahydro-2H-pyran-4-yl)-2,4,12,13-tetrahydro-11H-5,7-(azenometheno)dipyrazolo[3,4-b:5',1'-g][1]oxa[4,6,8]triazacycloundecine-11,11,12,12,13,13-d6;

1-(8-Chloro-3-methyl-12,13-dihydro-11H-5,7-(azenometheno)dipyrazolo[3,4-b:5',1'-g][1]oxa[4,6,8]triazacycloundecin-2(4H)-yl)cyclopropane-1-carbonitrile;

8-Chloro-2-((1r,4r)-4-methoxycyclohexyl)-3-methyl-2,4,12,13-tetrahydro-11H-5,7-(azenometheno)dipyrazolo[3,4-b:5',1'-g][1]oxa[4,6,8]triazacycloundecine;

2-((1R,5S,6r)-3-Oxabicyclo[3.1.0]hexan-6-yl)-8-chloro-3-methyl-2,4,12,13-tetrahydro-11H-5,7-(azenometheno)dipyrazolo[3,4-b:5',1'-g][1]oxa[4,6,8]triazacycloundecine;

(R)-8-Chloro-2-(2,2-difluorocyclopropyl)-3-methyl-2,4,12,13-tetrahydro-11H-5,7-(azenometheno)dipyrazolo[3,4-b:5',1'-g][1]oxa[4,6,8]triazacycloundecine;

(S)-8-Chloro-2-(2,2-difluorocyclopropyl)-3-methyl-2,4,12,13-tetrahydro-11H-5,7-(azenometheno)dipyrazolo[3,4-b:5',1'-g][1]oxa[4,6,8]triazacycloundecine;

8-chloro-2-((2R,4r,6S)-2,6-dimethyltetrahydro-2H-pyran-4-yl)-3-methyl-2,4,12,13-tetrahydro-11H-5,7-(azenometheno)dipyrazolo[3,4-b:5',1'-g][1]oxa[4,6,8]triazacycloundecine;

(R)-8-Chloro-2-(2,2-dimethyltetrahydro-2H-pyran-4-yl)-3-methyl-2,4,12,13-tetrahydro-11H-5,7-(azenometheno)dipyrazolo[3,4-b:5',1'-g][1]oxa[4,6,8]triazacycloundecine;

(S)-8-Chloro-2-(2,2-dimethyltetrahydro-2H-pyran-4-yl)-3-methyl-2,4,12,13-tetrahydro-11H-5,7-(azenometheno)dipyrazolo[3,4-b:5',1'-g][1]oxa[4,6,8]triazacycloundecine;

2-((1R,3s,5S)-8-Oxabicyclo[3.2.1]octan-3-yl)-8-chloro-3-methyl-2,4,12,13-tetrahydro-11H-5,7-(azenometheno)dipyrazolo[3,4-b:5',1'-g][1]oxa[4,6,8]triazacycloundecine;

8-Chloro-3-methyl-2-(tetrahydro-2H-pyran-4-yl)-2,4,12,13-tetrahydro-11H-5,7-(azenometheno)dipyrazolo[3,4-b:5',1'-g][1]oxa[4,6,8]triazacycloundecine-11,11-d$_2$;

8-Chloro-3-methyl-2-(tetrahydro-2H-pyran-4-yl)-2,4,12,13-tetrahydro-11H-5,7-(azenometheno)dipyrazolo[3,4-b:5',1'-g][1]oxa[4,6,8]triazacycloundecine-13,13-d$_2$;

8-Chloro-2-((3R,4S)-3-Fluoro-3-methyltetrahydro-2H-pyran-4-yl)-3-methyl-2,4,12,13-tetrahydro-11H-5,7-(azenometheno)dipyrazolo[3,4-b:5',1'-g][1]oxa[4,6,8]triazacycloundecine;

8-Chloro-2-((3S,4R)-3-Fluoro-3-methyltetrahydro-2H-pyran-4-yl)-3-methyl-2,4,12,13-tetrahydro-11H-5,7-(azenometheno)dipyrazolo[3,4-b:5',1'-g][1]oxa[4,6,8]triazacycloundecine;

8-Chloro-3-methyl-2-((tetrahydro-2H-pyran-4-yl)methyl)-2,4,12,13-tetrahydro-11H5,7-(azenometheno)dipyrazolo[3,4-b:5',1'-g][1]oxa[4,6,8]triazacycloundecine;

8-Chloro-2-((1r,4r)-4-methoxycyclohexyl)-3-(methyl-d$_3$)-2,4,12,13-tetrahydro-11H-5,7-(azenometheno)dipyrazolo[3,4-b:5',1'-g][1]oxa[4,6,8]triazacycloundecine;

8-Chloro-3-(methyl-d$_3$)-2-((2R,4R)-2-methyltetrahydro-2H-pyran-4-yl)-2,4,12,13-tetrahydro-11H-5,7-(azenometheno)dipyrazolo[3,4-b:5',1'-g][1]oxa[4,6,8]triazacycloundecine;

8-Chloro-3-(methyl-d$_3$)-2-((2S,4S)-2-methyltetrahydro-2H-pyran-4-yl)-2,4,12,13-tetrahydro-11H-5,7-(azenometheno)dipyrazolo[3,4-b:5',1'-g][1]oxa[4,6,8]triazacycloundecine;

(R)-8-Chloro-3-methyl-2-(4-oxaspiro[2.5]octan-7-yl)-2,4,12,13-tetrahydro-11H-5,7-(azenometheno)dipyrazolo[3,4-b:5',1'-g][1]oxa[4,6,8]triazacycloundecine;

(S)-8-Chloro-3-methyl-2-(4-oxaspiro[2.5]octan-7-yl)-2,4,12,13-tetrahydro-11H-5,7-(azenometheno)dipyrazolo[3,4-b:5',1'-g][1]oxa[4,6,8]triazacycloundecine;

8-Chloro-3-ethyl-2-((3R,4S)-3-fluorotetrahydro-2H-pyran-4-yl)-2,4,12,13-tetrahydro-11H-5,7-(azenometheno)dipyrazolo[3,4-b:5',1'-g][1]oxa[4,6,8]triazacycloundecine;

8-Chloro-3-ethyl-2-((3S,4R)-3-fluorotetrahydro-2H-pyran-4-yl)-2,4,12,13-tetrahydro-11H-5,7-(azenometheno)dipyrazolo[3,4-b:5',1'-g][1]oxa[4,6,8]triazacycloundecine;

8-Chloro-3-ethyl-2-((1r,4r)-4-methoxycyclohexyl)-2,4,12,13-tetrahydro-11H-5,7-(azenometheno)dipyrazolo[3,4-b:5',1'-g][1]oxa[4,6,8]triazacycloundecine;

(R)-8-Chloro-3-(methyl-d$_3$)-2-(oxepan-4-yl)-2,4,12,13-tetrahydro-11H-5,7-(azenometheno)dipyrazolo[3,4-b:5',1'-g][1]oxa[4,6,8]triazacycloundecine;

(S)-8-Chloro-3-(methyl-d$_3$)-2-(oxepan-4-yl)-2,4,12,13-tetrahydro-11H-5,7-(azenometheno)dipyrazolo[3,4-b:5',1'-g][1]oxa[4,6,8]triazacycloundecine;

(R)-8-Chloro-3-(methyl-d3)-2-(tetrahydro-2H-pyran-3-yl)-2,4,12,13-tetrahydro-11H5,7-(azenometheno)dipyrazolo[3,4-b:5',1'-g][1]oxa[4,6,8]triazacycloundecine;

(S)-8-Chloro-3-(methyl-d3)-2-(tetrahydro-2H-pyran-3-yl)-2,4,12,13-tetrahydro-11H5,7-(azenometheno)dipyrazolo[3,4-b:5',1'-g][1]oxa[4,6,8]triazacycloundecine;

8-Chloro-2-((3R,4S)-3-fluorotetrahydro-2H-pyran-4-yl)-3-(methyl-d₃)-2,4,12,13-tetrahydro-11H-5,7-(azenometheno)dipyrazolo[3,4-b:5',1'-g][1]oxa[4,6,8]triazacycloundecine;

8-chloro-2-((3S,4R)-3-fluorotetrahydro-2H-pyran-4-yl)-3-(methyl-d₃)-2,4,12,13-tetrahydro-11H-5,7-(azenometheno)dipyrazolo[3,4-b:5',1'-g][1]oxa[4,6,8]triazacycloundecine;

(R)-8-chloro-3-(methyl-d₃)-2-(4-oxaspiro[2.5]octan-7-yl)-2,4,12,13-tetrahydro-11H-5,7-(azenometheno)dipyrazolo[3,4-b:5',1'-g][1]oxa[4,6,8]triazacycloundecine; and (S)-8-chloro-3-(methyl-d₃)-2-(4-oxaspiro[2.5]octan-7-yl)-2,4,12,13-tetrahydro-11H-5,7-(azenometheno)dipyrazolo[3,4-b:5',1'-g][1]oxa[4,6,8]triazacycloundecine; or a pharmaceutically acceptable salt thereof.

E44. The compound of embodiment E1, wherein the compound is

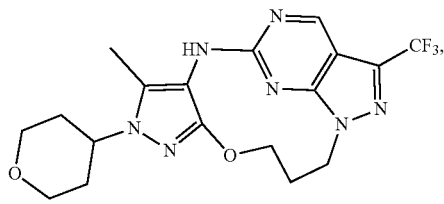

or a pharmaceutically acceptable salt.

E45. The compound of embodiment E1, or a pharmaceutically acceptable salt, wherein the compound is

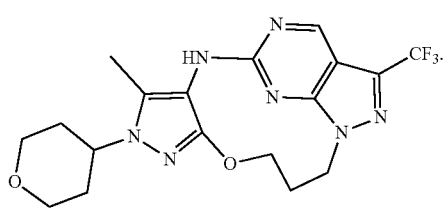

E46. The compound of embodiment E1, wherein the compound is

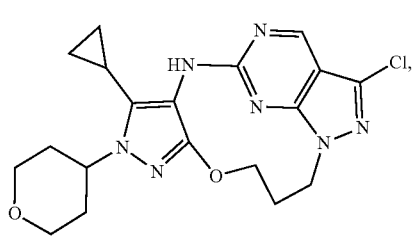 [SMILES: Clc1nn2c3nc(ncc13)Nc1c(nn(C3CCOCC3)c1C1CC1)OCCC2]

or a pharmaceutically acceptable salt.

E47. The compound of embodiment E1, wherein the compound is

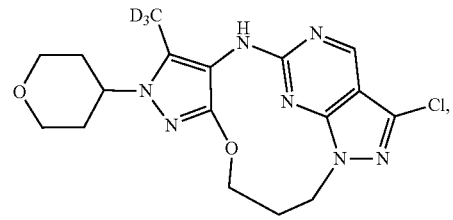 [SMILES: [2H]C([2H])([2H])c1c2c(nn1C1CCOCC1)OCCCn1nc(Cl)c3cnc(nc31)N2]

or a pharmaceutically acceptable salt.

E48. The compound of embodiment E1, wherein the compound is

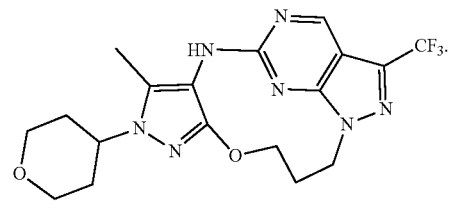 [SMILES: Cc1c2c(nn1C1CCOCC1)OCCCn1nc(C(F)(F)F)c3cnc(nc31)N2]

E49. The compound of embodiment E1, wherein the compound is

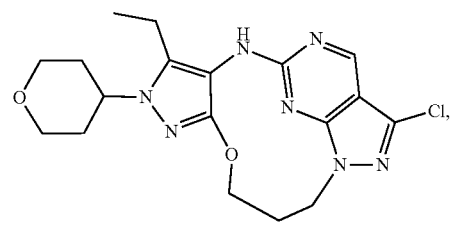 [SMILES: CCc1c2c(nn1C1CCOCC1)OCCCn1nc(Cl)c3cnc(nc31)N2]

or a pharmaceutically acceptable salt thereof.

E50. The compound of embodiment E1, wherein the compound is

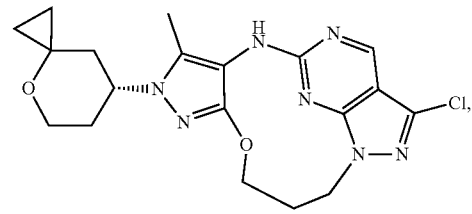 [SMILES: Cc1c2c(nn1[C@@H]1CCOC3(CC3)C1)OCCCn1nc(Cl)c3cnc(nc31)N2]

or a pharmaceutically acceptable salt thereof.

E51. The compound of embodiment E1, wherein the compound is

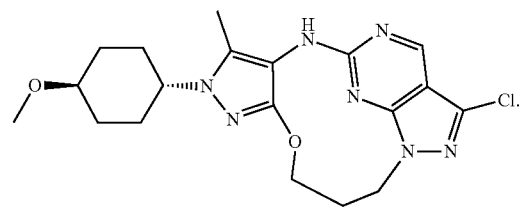 [SMILES: CO[C@H]1CC[C@H](n2nc3c(c2C)Nc2ncc4c(Cl)nn(c4n2)CCCO3)CC1]

E52. The compound of embodiment E1, wherein the compound is

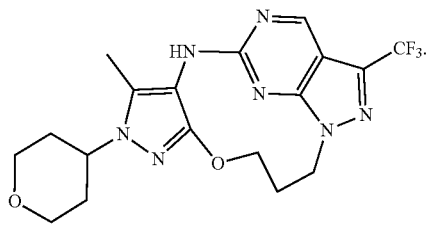 [SMILES: Cc1c2c(nn1C1CCOCC1)OCCCn1nc(C(F)(F)F)c3cnc(nc31)N2]

E53. The compound of embodiment E1, wherein the compound is

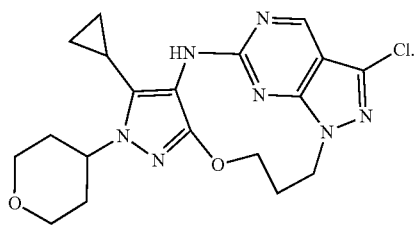 [SMILES: Clc1nn2c3nc(ncc13)Nc1c(nn(C3CCOCC3)c1C1CC1)OCCC2]

E54. The compound of embodiment E1, wherein the compound is

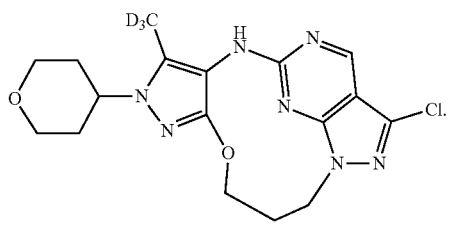 [SMILES: [2H]C([2H])([2H])c1c2c(nn1C1CCOCC1)OCCCn1nc(Cl)c3cnc(nc31)N2]

E55. The compound of embodiment E1, wherein the compound is

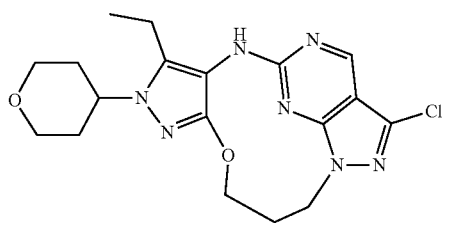 [SMILES: CCc1c2c(nn1C1CCOCC1)OCCCn1nc(Cl)c3cnc(nc31)N2]

E56. The compound of embodiment E1, wherein the compound is

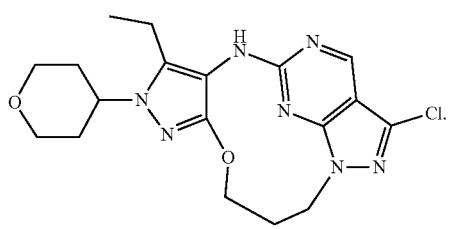 [SMILES: CCc1c2c(nn1C1CCOCC1)OCCCn1nc(Cl)c3cnc(nc31)N2]

E57. The compound of embodiment E1, wherein the compound is

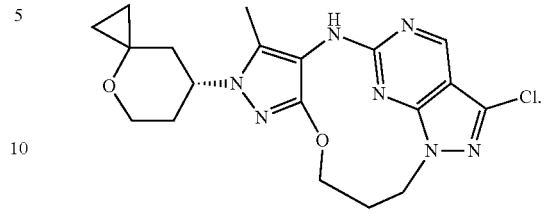

E58. The compound of embodiment E1, wherein the compound is

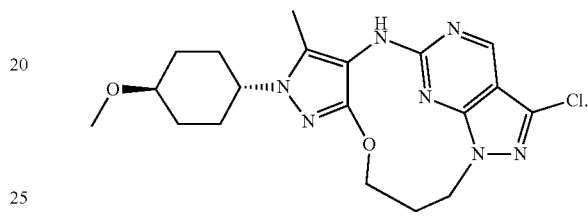

E59. A pharmaceutical composition comprising a compound according to any one of the previous embodiments E1 to E58 and one or more pharmaceutically acceptable carriers.

E60. The compound according to any one of embodiments E1 to E58, or a pharmaceutically acceptable salt thereof for use in therapy.

E61. The compound according to any one of embodiments E1 to E58, or a pharmaceutically acceptable salt thereof, for use in the treatment of a disease or disorder in the central nervous system selected from Lewy body dementia, multiple system atrophy, and Parkinson's disease.

E62. The compound according to embodiment E61, or a pharmaceutically acceptable salt thereof, wherein the Parkinson's disease is idiopathic Parkinson's disease, sporadic Parkinson's disease, Parkinson's disease in patients carrying a G2019S mutation in LRRK2, or Parkinson's disease in patients carrying one or more LRRK2 non-coding variants selected from rs76904798-T and Rs1491942-G.

E63. The compound according to embodiment E61, or a pharmaceutically acceptable salt thereof, wherein the Parkinson's disease is idiopathic Parkinson's disease, sporadic Parkinson's disease or Parkinson's disease in patients carrying one or more mutated forms of LRRK2 selected from G2019S, 12020T, M1646T, G2385R, A419V, N551K, R1398H, K1423K, R1441G, R1441H, R1441C, R1628P, S1647T, Y1699C, 12020T and Y2189C.

E64. The compound according to embodiment E61, or a pharmaceutically acceptable salt thereof, wherein the Parkinson's disease is idiopathic Parkinson's disease, sporadic Parkinson's disease or Parkinson's disease in patients carrying a G2019S mutation in LRRK2.

E65. The compound according to embodiment E61, or a pharmaceutically acceptable salt thereof, wherein the Parkinson's disease is idiopathic Parkinson's disease, sporadic Parkinson's disease or Parkinson's disease in patients carrying one or more LRRK2 non-coding variants selected from rs76904798-T and Rs1491942-G.

E66. The compound according to any one of embodiments E1 to E58, or a pharmaceutically acceptable salt thereof, for use in the treatment of a disease or disorder characterized by increased LRRK2 kinase activity or by expression of one or more mutated forms of LRRK2 selected from G2019S, I2020T, M1646T, G2385R, A419V, N551K, R1398H, K1423K, R1441G, R1441H, R1441C, R1628P, S1647T, Y1699C, I2020T and Y2189C or one or more LRRK2 non-coding variants alone or in combination selected from rs76904798-T and Rs1491942-G.

E67. Use of a compound according to any one of embodiment E1 to E58, or a pharmaceutically acceptable salt thereof, in the manufacture of a medicament for the treatment of a disease or disorder in the central nervous system selected from Lewy body dementia, multiple system atrophy or Parkinson's disease.

E68. A method for the treatment of a disease or disorder in the central nervous system selected from Lewy body dementia, multiple system atrophy or Parkinson's disease comprising the administration of a therapeutically effective amount of a compound, or a pharmaceutically acceptable salt thereof, according to any one of embodiments E1 to E58 to a patient in need thereof.

The compounds of the present invention may have one or more asymmetric centres and it is intended that any optical isomers (i.e. enantiomers or diastereomers) as separated, pure or partially purified optical isomers and any mixtures thereof including racemic mixtures, i.e. a mixture of stereoisomers, are included within the scope of the invention.

In this context is understood that when specifying the enantiomeric form, the compound is in enantiomeric excess, e.g. essentially in a pure form. Accordingly, one embodiment of the invention relates to a compound of the invention having an enantiomeric excess (ee) of at least 60%, at least 70%, at least 80%, at least 85%, at least 90%, at least 96%, preferably at least 98%.

Racemic forms can be resolved into the optical antipodes by known methods, for example by separation of diastereomeric salts thereof with an optically active acid and liberating the optically active amine compound by treatment with a base. Another method for resolving racemates into the optical antipodes is based upon chromatography on an optically active matrix. The compounds of the present invention may also be resolved by the formation of diastereomeric derivatives. Additional methods for the resolution of optical isomers, known to those skilled in the art, may be used. Such methods include those discussed by J. Jaques, A. Collet and S. Wilen in "Enantiomers, Racemates, and Resolutions", John Wiley and Sons, New York (1981). Optically active compounds can also be prepared from optically active starting materials. Absolute stereochemistry may be determined by methods known to the skilled person, such as vibrational circular dichroism (VCD) Spectroscopic analysis.

Furthermore, when a double bond or a fully or partially saturated ring system is present in the molecule geometric isomers may be formed. It is intended that any geometric isomers as separated, pure or partially purified geometric isomers or mixtures thereof are included within the scope of the invention. Likewise, molecules having a bond with restricted rotation may form geometric isomers. These are also intended to be included within the scope of the present invention.

Furthermore, some of the compounds of the present invention may exist in different tautomeric forms and it is intended that any tautomeric forms that the compounds are able to form are included within the scope of the present invention.

Included in this invention are also isotopically labelled compounds, wherein one or more atoms are represented by an atom of the same element having an atomic mass or mass number different from the atomic mass or mass number usually found in nature (e.g., $^{2}H$, $^{11}C$, $^{13}C$, $^{15}N$, $^{18}F$ and the like). Particular mention is made of $^{2}H$ substituted compounds i.e. compounds wherein one or more H atoms are represented by deuterium.

In one embodiment of the invention a compound of formula I, Ia, Ib, Ic, Id, A or Aa is isotopically labelled. In a further embodiment of the invention, one or more of the hydrogen atoms of the compound of formula I, Ia, Ib, Ic, Id, A or Aa are represented by deuterium. It is recognized that elements are present in natural isotopic abundances in most synthetic compounds and result in inherent incorporation of deuterium. However, the natural isotopic abundance of hydrogen isotopes such as deuterium is immaterial (about 0.015%) relative to the degree of stable isotopic substitution of compounds indicated herein. Thus, as used herein, designation of an atom as deuterium at a position indicates that the abundance of deuterium is significantly greater than the natural abundance of deuterium. Any atom not designated as a particular isotope is intended to represent any stable isotope of that atom, as will be apparent to the ordinarily skilled artisan.

In one embodiment, designation of a position as "D" in a compound has a minimum deuterium incorporation of greater than about 60% at that position such as greater than about 70% at that position such as greater than about 80% at that position such as greater than about 85% at that position. In a further embodiment, designation of a position as "D" in a compound has a minimum deuterium incorporation of greater than about 90% at that position such as greater than about 95% at that position such as greater than about 97% at that position such as greater than about 99% at that position.

Pharmaceutically Acceptable Salts

The compounds of this invention are generally utilized as the free substance or as a pharmaceutically acceptable salt thereof. When a compound of formula I, Ia, Ib, Ic, Id, A or Aa contains a free base, such salts may be prepared in a conventional manner by treating a solution or suspension of a free base of formula I, Ia, Ib, Ic, Id, A or Aa with a molar equivalent of a pharmaceutically acceptable acid. Representative examples of suitable organic and inorganic acids are described below.

Pharmaceutically acceptable salts in the present context are intended to indicate nontoxic, i.e. physiologically acceptable salts. The term pharmaceutically acceptable salts includes salts formed with inorganic and/or organic acids such as hydrochloric acid, hydrobromic acid, phosphoric acid, nitrous acid, sulphuric acid, benzoic acid, citric acid, gluconic acid, lactic acid, maleic acid, succinic acid, tartaric acid, acetic acid, propionic acid, oxalic acid, maleic acid, fumaric acid, glutamic acid, pyroglutamic acid, salicylic acid, salicylic acid and sulfonic acids, such as methanesulfonic acid, ethanesulfonic acid, toluenesulfonic acid and benzene-sulfonic acid. Some of the acids listed above are di- or tri-acids, i.e. acids containing two or three acidic hydrogens, such as phosphoric acid, sulphuric acid, fumaric acid and maleic acid. Di- and tri-acids may form 1:1, 1:2 or 1:3 (tri-acids) salts, i.e. a salt formed between two or three molecules of the compound of the present invention and one molecule of the acid.

The term pharmaceutically acceptable salts include salts formed with inorganic and/or organic bases, such as alkali metal bases, such as sodium hydroxide, lithium hydroxide, potassium hydroxide, alkaline earth bases, such as calcium hydroxide and magnesium hydroxide, and organic bases, such as trimethylamine. Some of the bases listed above are di- or tri-bases, i.e. bases able to receive two or three acidic hydrogens, such as calcium hydroxide and magnesium hydroxide. Di- and tri-bases may form 1:1 or 1:2 salts, i.e. a salt formed between two molecules of the compound of the present invention and one molecule of the base.

Additional examples of useful acids and bases to form pharmaceutically acceptable salts can be found e.g. in Stahl and Wermuth (Eds.) "Handbook of Pharmaceutical salts. Properties, selection, and use", Wiley-VCH, 2008.

Pharmaceutical Composition

The above-mentioned compounds or pharmaceutically acceptable salts may be in a composition as the sole active ingredient or in combination with other active ingredients. Additionally, one or more pharmaceutically acceptable carriers or diluents may be in the composition.

The pharmaceutical compositions may be specifically formulated for administration by any suitable route such as the oral, rectal, nasal, pulmonary, topical (including buccal and sublingual), transdermal, intracisternal, intraperitoneal, vaginal and parenteral (including subcutaneous, intramuscular, intrathecal, intravenous and intradermal) route, the oral route being preferred. It will be appreciated that the preferred route will depend on the general condition and age of the subject to be treated, the nature of the condition to be treated and the active ingredient chosen.

Pharmaceutical compositions for oral administration include solid dosage forms such as capsules, tablets, dragees, pills, lozenges, powders and granules. Where appropriate, they can be prepared with coatings.

Liquid dosage forms for oral administration include solutions, emulsions, suspensions, syrups and elixirs.

Pharmaceutical compositions for parenteral administration include sterile aqueous and nonaqueous injectable solutions, dispersions, suspensions or emulsions as well as sterile powders to be reconstituted in sterile injectable solutions or dispersions prior to use.

Other suitable administration forms include suppositories, sprays, ointments, creams, gels, inhalants, dermal patches, implants, etc.

Conveniently, the compounds of the invention are administered in a unit dosage form containing said compounds in an amount of about 0.1 to 500 mg, such as 10 mg, 50 mg, 100 mg, 150 mg, 200 mg or 250 mg of a compound of the present invention.

For parenteral administration, solutions of the compound of the invention in sterile aqueous solution, aqueous propylene glycol, aqueous vitamin E or sesame or peanut oil may be employed. Such aqueous solutions should be suitably buffered if necessary and the liquid diluent first rendered isotonic with sufficient saline or glucose. The aqueous solutions are particularly suitable for intravenous, intramuscular, subcutaneous and intraperitoneal administration. The sterile aqueous media employed are all readily available by standard techniques known to those skilled in the art.

Suitable pharmaceutical carriers include inert solid diluents or fillers, sterile aqueous solutions and various organic solvents. Examples of solid carriers are lactose, terra alba, sucrose, cyclodextrin, talc, gelatine, agar, pectin, acacia, magnesium stearate, stearic acid and lower alkyl ethers of cellulose. Examples of liquid carriers are syrup, peanut oil, olive oil, phosphor lipids, fatty acids, fatty acid amines, polyoxyethylene and water. The pharmaceutical compositions formed by combining the compound of the invention and the pharmaceutically acceptable carriers are then readily administered in a variety of dosage forms suitable for the disclosed routes of administration.

Formulations of the present invention suitable for oral administration may be presented as discrete units such as capsules or tablets, each containing a predetermined amount of the active ingredient, and which may include a suitable excipient. Furthermore, the orally available formulations may be in the form of a powder or granules, a solution or suspension in an aqueous or non-aqueous liquid, or an oil-in-water or water-in-oil liquid emulsion.

If a solid carrier is used for oral administration, the preparation may be tablet, e.g. placed in a hard gelatine capsule in powder or pellet form or in the form of a troche or lozenge. The amount of solid carrier may vary but will usually be from about 25 mg to about 1 g.

If a liquid carrier is used, the preparation may be in the form of a syrup, emulsion, soft gelatine capsule or sterile injectable liquid such as an aqueous or non-aqueous liquid suspension or solution.

Tablets may be prepared by mixing the active ingredient with ordinary adjuvants and/or diluents followed by compression of the mixture in a conventional tabletting machine. Examples of adjuvants or diluents comprise corn starch, potato starch, talcum, magnesium stearate, gelatine, lactose, gums, and the like. Any other adjuvants or additives usually used for such purposes such as colourings, flavourings, preservatives etc. may be used provided that they are compatible with the active ingredients.

Treating Diseases

As established above, LRRK2 inhibitors may be used in the treatment of Parkinson's disease and particular mention is made of Parkinson's disease associated with mutations in LRRK2, such as Gly2019Ser. Moreover, LRRK2 inhibitors are also expected to be useful in the treatment of other diseases which are associated with LRRK2. LRRK2 has been identified as a core component in Lewy bodies and is thus expected to be useful in the treatment of Lewy body dementia [*Neuropathol. Appl. Neurobiol.*, 34, 272-283, 2008]. Expression of LRRK2 mRNA is highly enriched in brain, lungs, kidney, spleen and blood suggesting that functional impact of increased LRRK2 activity is likely to be most relevant in pathogenic and pathologic conditions associated with those regions. Support for that notion can be found in studies showing an increased risk of nonskin cancer in LRRK2 Gly2019Ser mutation carriers and especially for renal and lung cancer [*Mov. Disorder*, 25, 2536-2541, 2010]. Over-expression of LRRK2 by chromosomal amplification has also been identified in papillary renal and thyroid carcinomas. Also, genetic association of LRRK2 has been reported for diseases where aberrant responses of the immune system are involved. This is the case for inflammatory bowel diseases such as Crohn's disease and ulcerative colitis as well as for leprosy [Nat. Genet. 42, 1118-1125, 2010; *Inflamm. Bowel Dis.* 16, 557-558, 2010; *N. Engl. J. Med.* 361, 2609-2618, 2009; *Inflamm. Bowel Dis*].

Thus, in an embodiment is provided a compound, or pharmaceutically acceptable salt thereof, or a pharmaceutical composition according to the invention for use in the treatment of a disease in the central nervous system selected from Lewy body dementia, multiple system atrophy or Parkinson's disease.

In an embodiment the disease in the central nervous system is Parkinson's disease.

In an embodiment the Parkinson's disease is idiopathic Parkinson's disease, sporadic Parkinson's disease or Parkinson's disease in patients carrying a G2019S mutation in LRRK2.

In an embodiment the Parkinson's disease is idiopathic Parkinson's disease.

In an embodiment the Parkinson's disease is sporadic Parkinson's disease.

In an embodiment the Parkinson's disease is in patients carrying a G2019S mutation in LRRK2.

In a further embodiment, the compounds, or pharmaceutically acceptable salt thereof as outlined in formula I, Ia, Ib, Ic, Id, A or Aa hereinabove, or compositions comprising said compounds may be used in the treatment of cancer or an immune related disorder.

In some embodiments, the cancer diseases may reside in the brain, lungs, kidney and spleen or blood organs such as renal cancer, lung cancer, skin cancer, and papillary renal and thyroid carcinomas.

In some embodiments, the immune related disorder may in one embodiment be Crohn's disease, ulcerative colitis, tuberculosis or leprosy.

According to an embodiment of the invention, the treatment may be in a patient with an increased LRRK2 kinase activity or carrying one or more mutated forms of LRRK2 such as G2019S, I2020T, M1646T, G2385R, A419V, N551K, R1398H, K1423K, R1441G, R1441H, R1441C, R1628P, S1647T, Y1699C, I2020T or Y2189C.

In one embodiment, the compound of the present invention is administered in an amount from about 0.001 mg/kg body weight to about 100 mg/kg body weight per day. In particular, daily dosages may be in the range of 0.01 mg/kg body weight to about 50 mg/kg body weight per day. The exact dosages will depend upon the frequency and mode of administration, the sex, the age, the weight, and the general condition of the subject to be treated, the nature and the severity of the condition to be treated, any concomitant diseases to be treated, the desired effect of the treatment and other factors known to those skilled in the art.

A typical oral dosage for adults will be in the range of 1-1000 mg/day of a compound, or pharmaceutically acceptable salt thereof of the present invention, such as 1-500 mg/day.

The compounds, or pharmaceutically acceptable salt thereof of the present invention may be administered alone as a pure compound or in combination with pharmaceutically acceptable carriers or excipients, in either single or multiple doses. The pharmaceutical compositions according to the invention may be formulated with pharmaceutically acceptable carriers or diluents as well as any other known adjuvants and excipients in accordance with conventional techniques such as those disclosed in Remington: The Science and Practice of Pharmacy, 22$^{nd}$ Edition, Pharmaceutical Press, 2012. In the present context, "excipient", "carrier", "diluent", "adjuvant" and the like are used synonymously and are intended to mean the same.

All references, including publications, patent applications, and patents, cited herein are hereby incorporated by reference in their entirety and to the same extent as if each reference were individually and specifically indicated to be incorporated by reference and were set forth in its entirety herein (to the maximum extent permitted by law), regardless of any separately provided incorporation of particular documents made elsewhere herein.

Item List

In the following, items of the invention are disclosed. The first item is denoted I1, the second item is denoted I2 and so forth.

I1. A compound of formula A, or a pharmaceutically acceptable salt thereof, wherein:

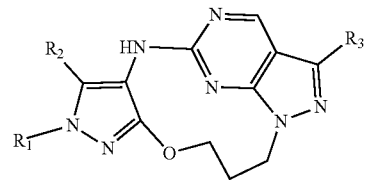

A $R_1$ is $CH_2R_4$ or $R_4$;
$R_2$ is a $C_1$-$C_3$ alkyl, an isotopically labelled $C_1$-$C_3$ alkyl, a $C_3$-$C_6$ cycloalkyl, or a $C_1$-$C_3$ haloalkyl;
$R_3$ is halogen, cyano, a O—$C_1$-$C_3$ haloalkyl, a $C_1$-$C_3$ haloalkyl, a $C_3$-$C_6$ cycloalkyl, or a $C_1$-$C_3$ alkyl;
$R_4$ is a 4- to 7-membered heterocycle having 1-2 heteroatoms independently selected from oxygen and nitrogen; a $C_1$-$C_3$ alkyl, a $C_1$-$C_3$ cyanoalkyl, a $C_1$-$C_3$ haloalkyl, or a $C_3$-$C_6$ cycloalkyl;
wherein each heterocycle or cycloalkyl is unsubstituted or substituted with 1, 2, or 3 groups independently selected from the group consisting of cyano, deuterium, halo, $C_1$-$C_3$ alkyl, an isotopically labelled $C_1$-$C_3$ alkyl, a O—$C_1$-$C_3$ haloalkyl, a O—$C_1$-$C_3$ alkyl, or a $C_1$-$C_3$ haloalkyl.

I2. The compound of item I1, wherein the compound is a compound of formula Aa, or a pharmaceutically acceptable salt thereof, wherein:

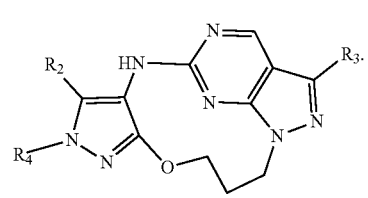

Aa

I3. The compound of any one of items I1 to I2, or a pharmaceutically acceptable salt thereof, wherein $R_2$ is selected from a $C_1$-$C_3$ alkyl, an isotopically labelled $C_1$-$C_3$ alkyl or a $C_3$-$C_6$ cycloalkyl.

I4. The compound of any one of items I1 to I3, or a pharmaceutically acceptable salt thereof, wherein $R_2$ is an isotopically labelled $C_1$-$C_3$ alkyl.

I5. The compound of any one of items I1 to I4, or a pharmaceutically acceptable salt thereof, wherein $R_2$ is —$CD_3$.

I6. The compound of any one of items I1 to I5, or a pharmaceutically acceptable salt thereof, wherein $R_3$ is halogen.

I7. The compound of any one of items I1 to I5, or a pharmaceutically acceptable salt thereof, wherein $R_3$ is chloro.

I8. The compound of any one of items I1 to I7, or a pharmaceutically acceptable salt thereof, wherein $R_4$ is a 4- to 6-membered heterocycle having one oxygen atom, wherein the 4- to 6-membered heterocycle is unsubstituted or substituted with 1 group selected from the list consisting of cyano, deuterium, halo, $C_1$-$C_3$ alkyl, an isotopically labelled $C_1$-$C_3$ alkyl or $C_1$-$C_3$ haloalkyl.

I9. The compound of any one of items I1 to I8, or a pharmaceutically acceptable salt thereof, wherein $R_4$ is selected from the group consisting of:

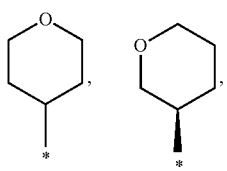
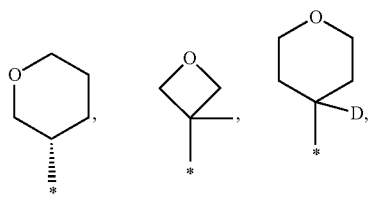
wherein * denotes the attachment point.
I10. The compound of any one of items I1 to I9, or a pharmaceutically acceptable salt thereof, wherein R₄ is unsubstituted tetrahydro-2H-pyran-4-yl.
I11. The compound of claim 1 selected from the list of:
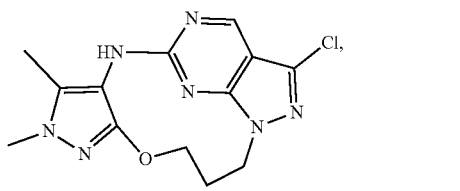
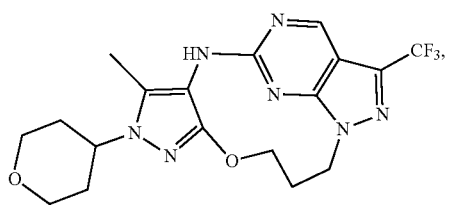
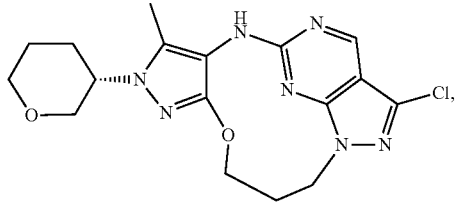
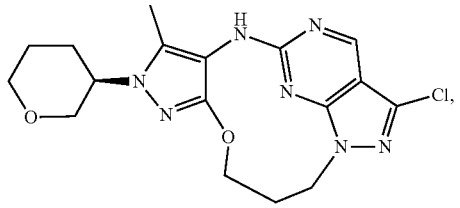
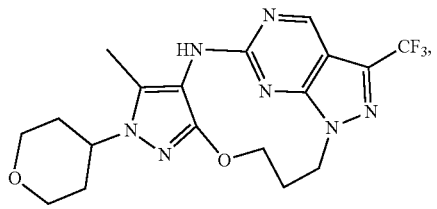
-continued
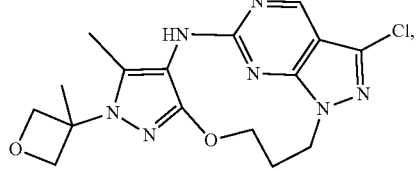
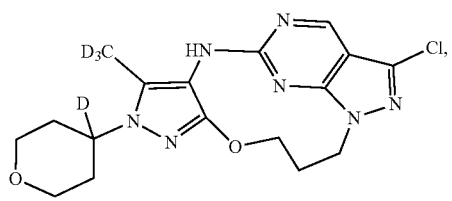
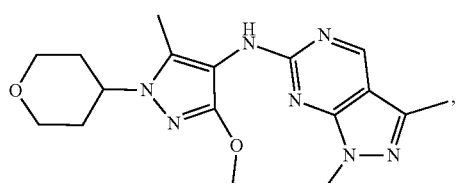
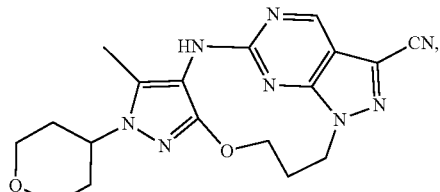
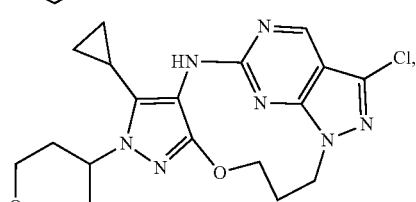
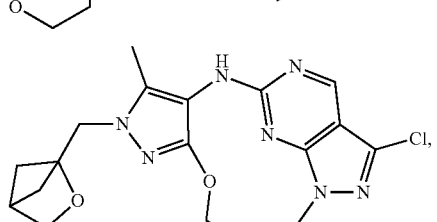
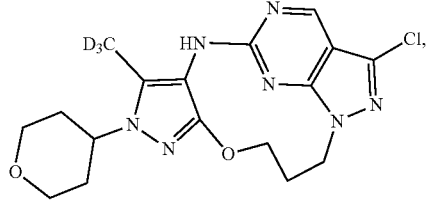
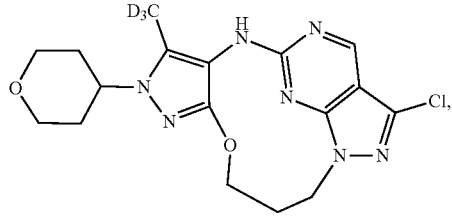

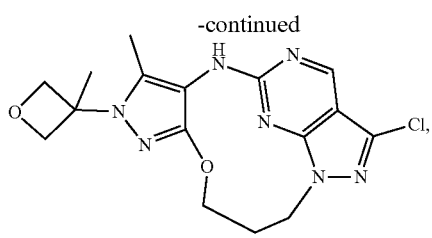

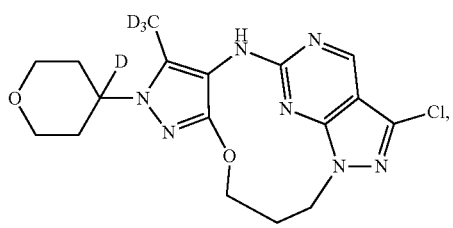
and

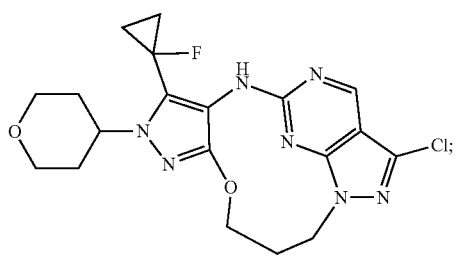

or a pharmaceutically acceptable salt thereof.

I12. A pharmaceutical composition comprising a compound according to any one of the previous items I1 to I11 and one or more pharmaceutically acceptable carriers or diluents.

I13. A compound, or a pharmaceutically acceptable salt thereof according to any one of items I1 to I11 for use in therapy.

I14. A compound of any one of items I1 to I11, or a pharmaceutically acceptable salt thereof, for use in the treatment of a disease in the central nervous system selected from Lewy body dementia, multiple system atrophy, or Parkinson's disease.

I15. The compound of any one of items I1 to I11, or a pharmaceutically acceptable salt thereof, wherein the Parkinson's disease is idiopathic Parkinson's disease, sporadic Parkinson's disease or Parkinson's disease in patients carrying a G2019S mutation in LRRK2.

I16. The compound according to any one of items I1 to I11, or a pharmaceutically acceptable salt thereof, for use in the treatment of a disease or disorder characterized by increased LRRK2 kinase activity or by expression of one or more mutated forms of LRRK2 selected from G2019S, I2020T, M1646T, G2385R, A419V, N551K, R1398H, K1423K, R1441G, R1441H, R1441C, R1628P, S1647T, Y1699C, I2020T and Y2189C or a LRRK2 non-coding variant alone or in combination selected from rs76904798-T and Rs1491942-G.

I17. Use of a compound of any one of items I1 to I11, or a pharmaceutically acceptable salt thereof, in the manufacture of a medicament for the treatment of a disease or disorder in the central nervous system selected from Lewy body dementia, multiple system atrophy, or Parkinson's disease.

I18. The use according to item I17 wherein the Parkinson's disease is idiopathic Parkinson's disease, sporadic Parkinson's disease or Parkinson's disease in patients carrying a G2019S mutation in LRRK2, or Parkinson's disease in patients carrying one or more LRRK2 non-coding variants selected from rs76904798-T and Rs1491942-G.

I19. A method for the treatment of a disease or disorder in the central nervous system selected from Lewy body dementia, multiple system atrophy or Parkinson's disease comprising the administration of a therapeutically effective amount of compound of any one of items I1 to I11, or a pharmaceutically acceptable salt thereof, to a patient in need thereof.

I20. The method according to item i19, wherein the Parkinson's disease is idiopathic Parkinson's disease, sporadic Parkinson's disease, Parkinson's disease in patients carrying a G2019S mutation in LRRK2, or Parkinson's disease in patients carrying one or more LRRK2 non-coding variants alone selected from rs76904798-T and Rs1491942-G.

Experimental Section

Preparation of the Compounds of the Invention

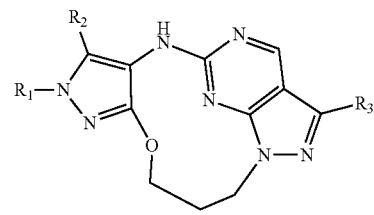

The compounds of formula I, Ia, Ib, Ic, Id, A or Aa may be prepared by methods described below, together with synthetic methods known in the art of organic chemistry, or modifications that are familiar to those of ordinary skill in the art. For example, the methods describe the use of selective protecting groups during the synthesis of the compounds of the invention. One skilled in the art would be able to select the appropriate protecting group for a particular reaction. Methods for protection and deprotection of such groups are well known in the art and may be found in Watts and Green et al., Protective Groups in Organic Synthesis, 2006, 4$^{th}$ Edition, Wiley Interscience, New York. The starting materials used herein are available commercially or may be prepared by routine methods known in the art, such as those method described in standard reference books such as "Compendium of Organic Synthetic Methods, Vol. I-XII" (published by Wiley Interscience). Preferred methods include, but are not limited to, those described below. The schemes are representative of methods useful in synthesizing the compounds of the present invention. They are not to constrain the scope of the invention in any way.

Method 1:

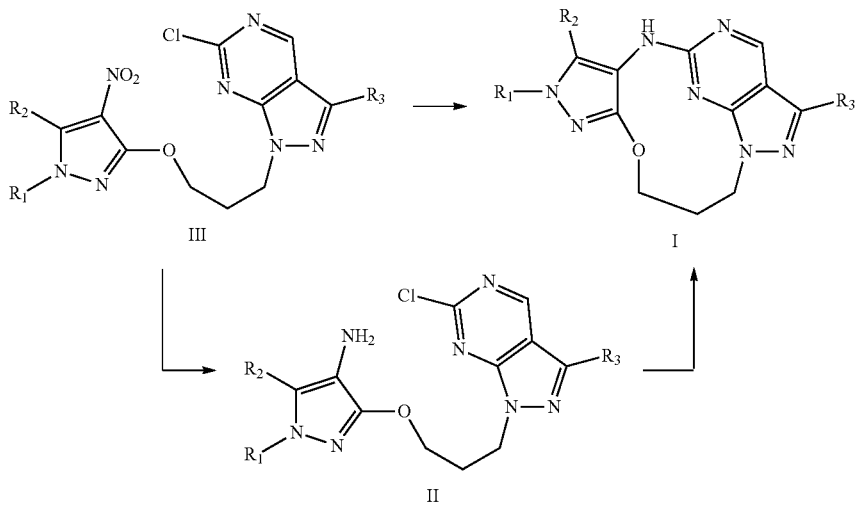

In brief, compounds of formula I can be prepared according to scheme 1. The compounds of formula I can for example be prepared through a one pot procedure by reducing an intermediate of type III with iron and ammonium chloride in a suitable solvent e.g. a mixture of ethanol and water as described for Example 1. Alternatively, an intermediate of type III can be reduced using e.g. sodium dithionite in the presence of a base such as potassium hydrogen carbonate in a solvent such as a mixture of water and tetrahydrofuran to afford an aminopyrazole intermediate of type II. An intermediate of type II can be cyclized to afford compounds of formula I in the presence of a base e.g. potassium fluoride and a solvent such as dimethylsulfoxide as detailed for Example 16.

Method 2:

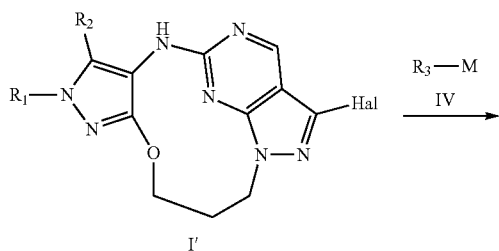

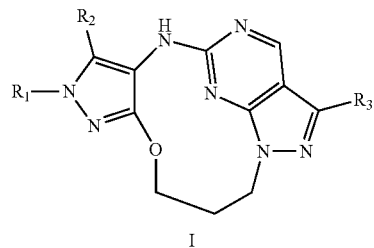

Alternatively, compounds of formula I can be prepared from a compound of formula I' (i.e. a compound of type I wherein $R^3$=halogen e.g. Br) according to scheme 2. The compounds of formula I can be prepared by employing a cross-coupling reaction between an intermediate of type I' and an organometallic alkyl intermediate IV (wherein M is for example Bpin, $B(OH)_2$, $Sn(n-Bu)_3$ or $SnMe_3$, ZnBr or ZnCl). The coupling is exemplified by but not limited to a Negishi-type cross-coupling reaction. The reaction can be performed by reacting an intermediate of type I' with an organozinc intermediate IV in which M=ZnBr or ZnCl in the presence of a catalyst like di-μ-iodobis(tri-t-butylphosphino)dipalladium(I) and a suitable solvent such as a mixture of toluene and tetrahydrofuran as described for Example 7.

Method 3:

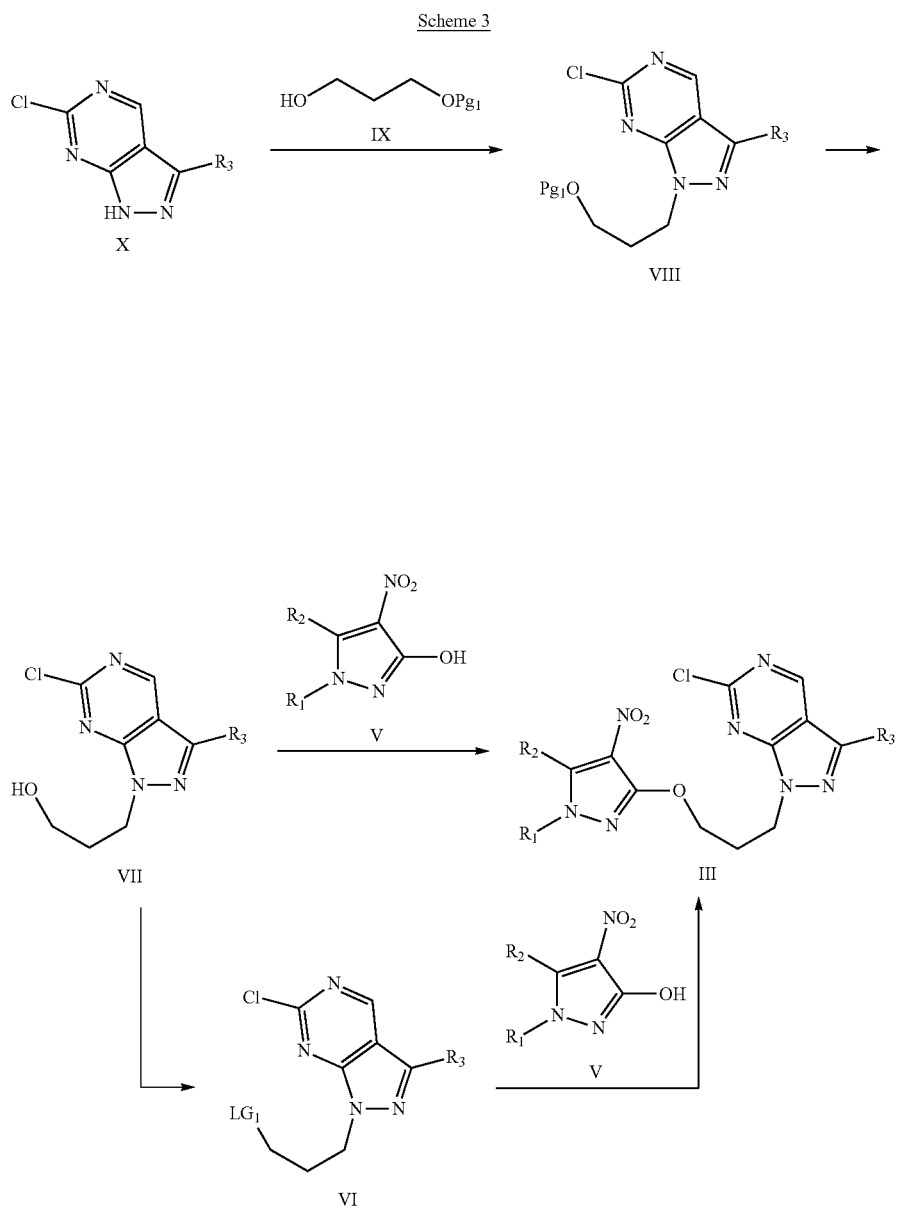

Scheme 3

A nitropyrazole intermediate of type III can be prepared according to scheme 3 starting from a pyrazolopyrimidine intermediate of type X. An intermediate of type X can be reacted with e.g. an alcohol such as IX (wherein $Pg_1$ is for example TBS) under Mitsunobu-type conditions employing for example diisopropyl azodicarboxylate and triphenylphosphine in a solvent such as tetrahydrofuran to afford an intermediate of type VIII. Intermediates of type VIII (wherein $Pg_1$ is for example TBS) can be converted into an alcohol intermediate of type VII using for example an acid such as aqueous hydrochloric acid in an appropriate solvent such as a mixture of tetrahydrofuran and water, as described in the synthesis of 3-(3,6-dichloro-1H-pyrazolo[3,4-d]pyrimidin-1-yl)propan-1-ol.

An alcohol intermediate of type VII can be reacted with an intermediate of type V under Mitsunobu-type conditions employing e.g. diisopropyl azodicarboxylate and triphenylphosphine in a solvent such as tetrahydrofuran to afford an intermediate of type III, as detailed in for example the synthesis of 3,6-dichloro-1-(3-((5-cyclopropyl-4-nitro-1-(tetrahydro-2H-pyran-4-yl)-1H-pyrazol-3-yl)oxy)propyl)-1H-pyrazolo[3,4-d]pyrimidine.

Alternatively, an intermediate of type VII can be converted into an intermediate of type VI (wherein $LG_1$ is for example OTs) using p-toluenesulfonyl chloride in the presence of an appropriate base such as triethylamine in a suitable solvent for example dichloromethane. An intermediate of type VI can be reacted with intermediates of type V in the presence of base for example potassium carbonate in a solvent such as N,N-dimethylformamide to afford an intermediate of type III as for example described in the synthesis of 3,6-dichloro-1-(3-((5-methyl-1-(3-methyloxetan-3-yl)-4-nitro-1H-pyrazol-3-yl)oxy)propyl)-1H-pyrazolo[3,4-d]pyrimidine.

Method 4:

Scheme 4

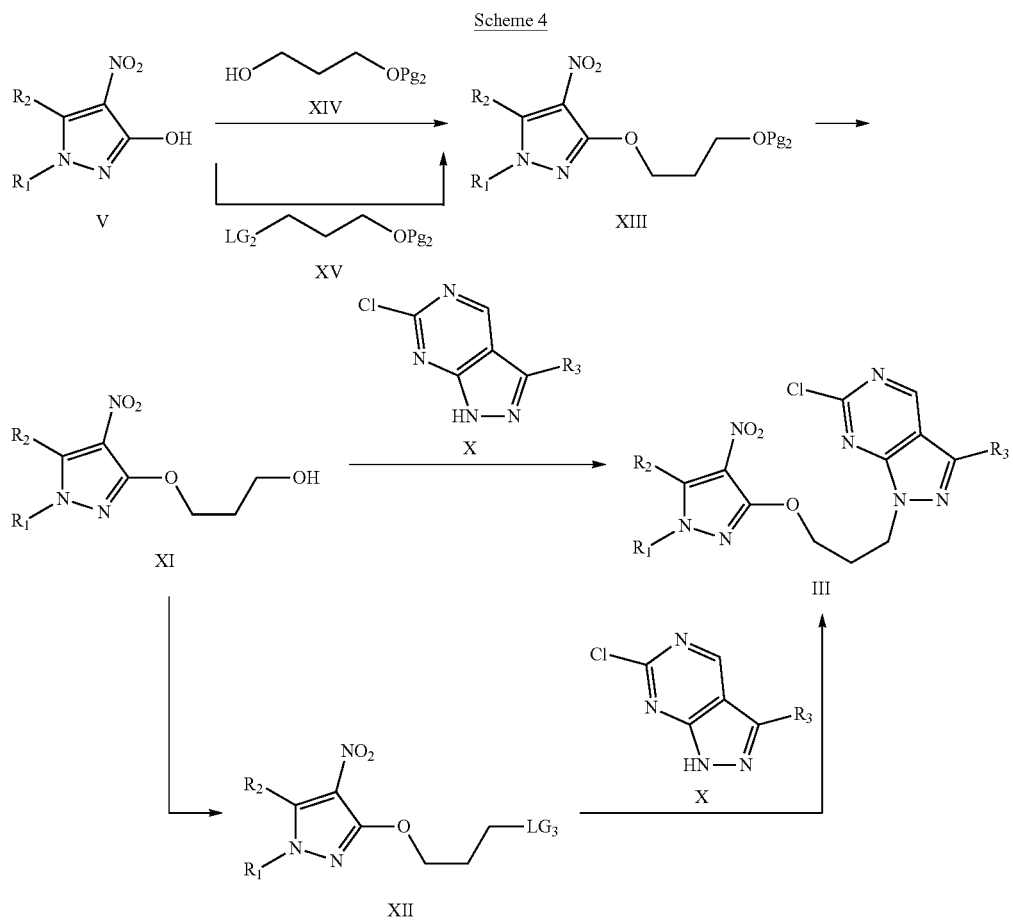

An alternative method to prepare a nitropyrazole intermediate of type III is described in scheme 4 starting from a pyrazole intermediate of type V. Intermediates of type XIII can be prepared from an intermediate of type V through a Mitsunobu-type reaction with an alcohol like XIV (wherein $PG_2$ is for example TBS) using for example diisopropyl azodicarboxylate and triphenylphosphine in a suitable solvent such as tetrahydrofuran. Alternatively, an intermediate of type XIII can be prepared from intermediates of type V through alkylation with an intermediate of type XV (wherein for example $LG_2$ is OTs and $PG_2$ is TBS) in the presence of a base such as cesium carbonate in a suitable solvent e.g. N,N-dimethylformamide. An intermediate of type XIII (wherein $PG_2$ is for example TBS) can be converted into intermediates of type XI employing for example aqueous HCl in a solvent such as tetrahydrofuran.

It is understood that an intermediate of type XIII (wherein $PG_2$ is for example TBS) can be transformed into another intermediate of type XIII wherein $R^2$ has been modified: For example an intermediate of XIII (wherein $R^2$=cyclopropyl and $PG_2$=TBS) can be reacted with a base such as lithium diisopropylamide and N-Fluorobis(phenylsulfonyl)amine in a suitable solvent such as tetrahydrofuran to afford an intermediate of type XIII (wherein $R^2$=1-fluorocyclopropyl and $PG_2$=TBS), as detailed in the synthesis of 3,6-dichloro-1-(3-((5-(1-fluorocyclopropyl)-4-nitro-1-(tetrahydro-2H-pyran-4-yl)-1H-pyrazol-3-yl)oxy)propyl)-1H-pyrazolo[3,4-d]pyrimidine.

It is furthermore understood that an intermediate of type XIII can be converted into an intermediate of type XI wherein $R^2$ has been modified: For example an intermediate of type XIII (wherein $R^2$=$CH_3$ and $PG_2$=TBS) can be transformed into an intermediate of type XI (wherein $R^2$=$CD_3$) through reaction with a base such as potassium tert-butoxide in hexadeuterodimethyl sulfoxide, as described in the synthesis of 3,6-dichloro-1-(3-((5-(methyl-$d_3$)-4-nitro-1-(tetrahydro-2H-pyran-4-yl)-1H-pyrazol-3-yl)oxy)propyl)-1H-pyrazolo[3,4-d]pyrimidine Finally, an intermediate of type XI can be reacted with a pyrazolopyrimidine intermediate of type X using a Mitsunobu-type reaction employing for example 1-(azodicarbonyl)-dipiperidine and tributylphosphine in a solvent such as tetrahydrofuran to afford intermediates of type III, as detailed in the synthesis of (±)-3,6-dichloro-1-(3-((5-methyl-4-nitro-1-(tetrahydro-2H-pyran-3-yl)-1H-pyrazol-3-yl)oxy)propyl)-1H-pyrazolo[3,4-d]pyrimidine.

Alternatively, an intermediate of type XI can be reacted with for example methanesulfonyl chloride in the presence of a base such as triethylamine in a suitable solvent e.g. dichloromethane to afford and intermediate of type XII (wherein $LG_3$ is OMs). Intermediates of type XII can be converted into a an intermediate of type III through reaction with a pyrazolopyrimidine intermediate of type X in the presence of a base for example N,N-diisopropylethylamine, an additive such as sodium iodide in a suitable solvent e.g.

N,N-dimethylformamide, as described in the synthesis of 3,6-dichloro-1-(3-((1,5-dimethyl-4-nitro-1H-pyrazol-3-yl)oxy)propyl)-1H-pyrazo-lo[3,4-d]pyrimidine.
Method 5:

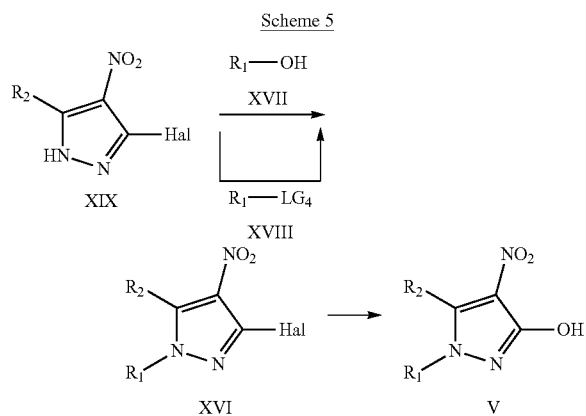

An intermediate of type V can be prepared according to scheme 5 through a two-step sequence employing alkylation and subsequent hydrolysis. Intermediates of type XIX can be converted into intermediates of type XVI in the presence of an alcohol intermediate such as XVII using for example Mitsunobu-type reaction conditions employing di-tert-butyl azodicarboxylate and triphenylphosphine in a solvent such as tetrahydrofuran, as described in the synthesis of 3,6-dichloro-1-(3-((5-methyl-4-nitro-1-(tetrahydro-2H-pyran-4-yl)-1H-pyrazol-3-yl)oxy)propyl)-1H-pyrazolo[3,4-d]pyrimidine.

Alternatively, an intermediate of type XIX can be reacted with and intermediate like XVIII (wherein LG$_4$ is for example a halogen) in the presence of a suitable base such as potassium carbonate in a solvent like acetonitrile to afford an intermediate of type XVI, as described in the synthesis of 1-(3-((1-((2-oxabicyclo[2.1.1]hexan-4-yl)methyl)-5-methyl-4-nitro-1H-pyrazol-3-yl)oxy)propyl)-3,6-dichloro-1H-pyrazolo[3,4-d]pyrimidine.

Intermediates of type XVI can be transformed into intermediates of type V using a base like potassium hydroxide in a suitable solvent such as water, as detailed in the synthesis of 3,6-dichloro-1-(3-((5-(methyl-d$_3$)-4-nitro-1-(tetrahydro-2H-pyran-4-yl-4-d)-1H-pyrazol-3-yl)oxy)propyl)-1H-pyrazolo[3,4-d]pyrimidine
Method 6:

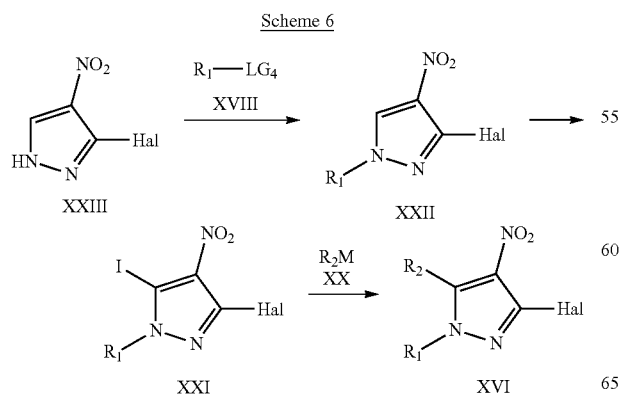

An alternative way to prepare an intermediate of type XVI is described in scheme 6. Intermediates of type XXIII can be reacted with an alkylating agent of type XVIII (wherein LG$_4$ is for example a halogen) in the presence of a base such as cesium carbonate in a solvent such as N,N-dimethylformamide to afford an intermediate of type XXII. Intermediates of type XXII can be modified into an intermediate of type XXI employing for example iodine and a base such as lithium bis(trimethylsilyl)amide in a suitable solvent such as tetrahydrofuran. Intermediates of type XXI can be converted into an intermediate of type XVI through reaction with a reagent of type XX (wherein M is for example Bpin, B(OH)$_2$, Sn(n-Bu)$_3$ or SnMe$_3$, ZnBr). The coupling is exemplified by but not limited to a Suzuki-Miyaura-type cross-coupling reaction. The reaction can be mediated employing a boronic acid in which M=(OH)$_2$ in the presence of a catalyst system consisting of e.g. tris(dibenzylideneacetone)dipalladium(0) and tricyclohexylphosphine, a base such as potassium carbonate in a suitable solvent e.g. N,N-dimethylformamide, as described for 3,6-dichloro-1-(3-((5-cyclopropyl-4-nitro-1-(tetrahydro-2H-pyran-4-yl)-1H-pyrazol-3-yl)oxy)propyl)-1H-pyrazolo[3,4-d]pyrimidine.
Method 7:

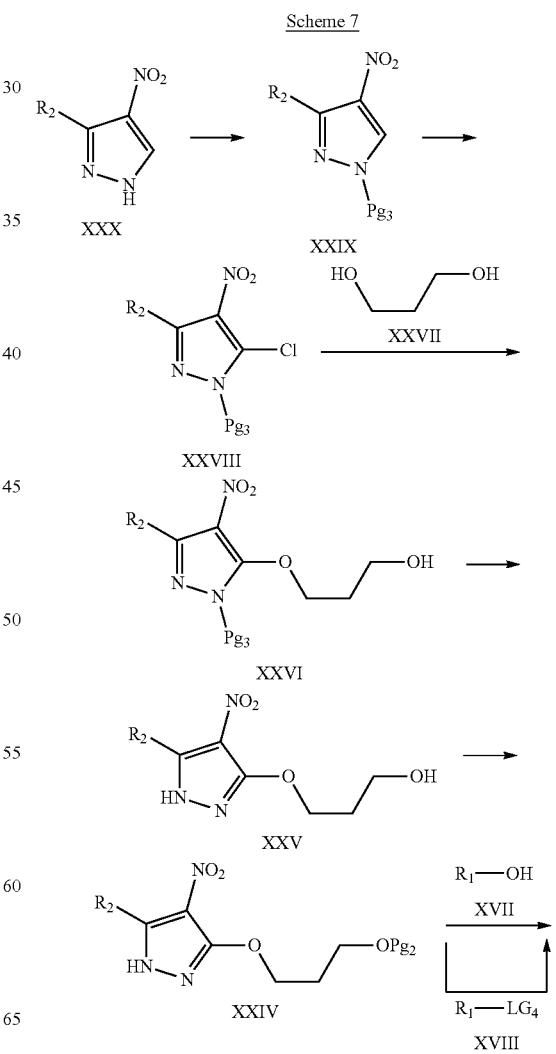

-continued

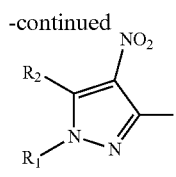

XIII

An alternative method to prepare an intermediate of type XIII (wherein $R_2$ is e.g. Me or Et) is depicted in scheme 7. Intermediates of type XIII (wherein $Pg_2$ is for example TBS) can be prepared from a pyrazole intermediate of type XXIV through reaction with an alcohol such as XVII under Mitsunobu-like reaction conditions employing 2-(tributyl-$\lambda^5$-phosphanylidene)acetonitrile in a solvent like toluene as described in the synthesis of intermediate cis-3,6-Dichloro-1-(3-((5-methyl-1-(2-methyltetrahydro-2H-pyran-4-yl)-4-nitro-1H-pyrazol-3-yl)oxy)propyl)-1H-pyrazolo[3,4-d]pyrimidine. Alternatively, intermediates if type XIII can be prepared through reaction of pyrazole intermediates such as XXIV employing an alkylating agent of type XVIII (wherein, $LG_4$ is for example OTs or Br) in the presence of a base like potassium carbonate in an appropriate solvent for example N,N-dimethylformamide, as detailed in the synthesis of trans-3-((1-(4-fluorocyclohexyl)-5-methyl-4-nitro-1H-pyrazol-3-yl)oxy)propan-1-ol.

Intermediates of type XXIV (wherein $Pg_2$ is e.g. TBS) can be synthesized from an alcohol such as XXV using for example tert-butyldimethylsilyl chloride in the presence of a base such as imidazole and a catalyst such as 4-dimethylaminopyridine in an appropriate solvent such as dichloromethane. An alcohol intermediate such as XXV can be prepared from a nitropyazole such as XXVI (wherein $Pg_3$ is for example, 2-tetrahydropyranyl) by treatment with an acid such as aqueous hydrochloric acid in a suitable solvent for example methanol.

Alcohol intermediates of type XXVI can be prepared by reacting a chloro intermediate XXVIII with propane-1,3-diol XXVII in the presence of a base for example cesium fluoride in a solvent such as N,N-dimethylacetamide.

Chloro intermediates such as XXVIII (wherein $Pg_3$ is for example, 2-tetrahydropyranyl) can be prepared from a nitropyrazole intermediate XXIX (wherein $Pg_3$ is for example, 2-tetrahydropyranyl) using a strong base for example lithium bis(trimethylsilyl)amide, and an electrophile for example hexachloroethane in a suitable solvent such as tetrahydrofuran.

A nitropyazole intermediate of type XXIX (wherein $Pg_3$ is for example, 2-tetrahydropyranyl) can be prepared from a pyrazole such as XXX employing 3,4-dihydro-2H-pyran in the presence of an acid for example para-toluenesulfonic acid monohydrate in an appropriate solvent for example tetrahydrofuran. The general synthetic sequence to prepare XXIV is for example described in the preparation of 3-(3-((tert-butyldimethylsilyl)oxy)propoxy)-5-methyl-4-nitro-1H-pyrazole.

Method 8:

Scheme 8

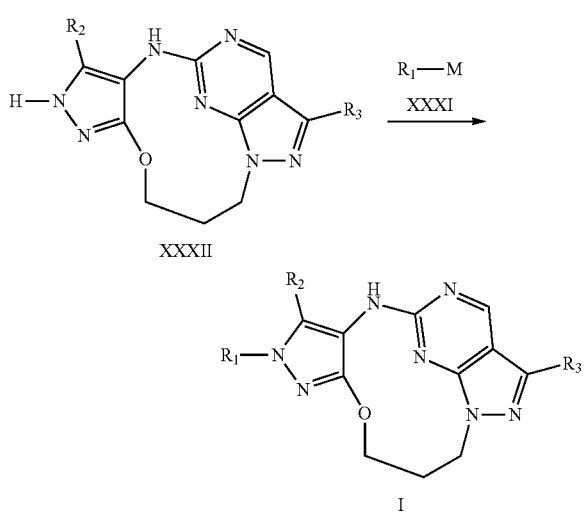

Alternatively, compounds of formula I can be prepared from a compound of formula XXXII according to scheme 8. The compounds of formula I can be prepared by employing e.g. a copper-mediated coupling between an intermediate of type XXXII and an intermediate of type XXXI (wherein M is for example $B(OH)_2$). The coupling is exemplified by but not limited to a Chan-Lam type coupling. The reaction can be performed by reacting an intermediate of type XXXII with a boronic acid intermediate XXXI in which $M=B(OH)_2$ in the presence of a copper salt such as copper(II) acetate, a base for example pyridine, a drying agent such as 4 Å molecular sieves under an oxygen atmosphere and a suitable solvent such as 1,2-dichloroethane as described for Example 39 and 40.

Method 9:

Scheme 9

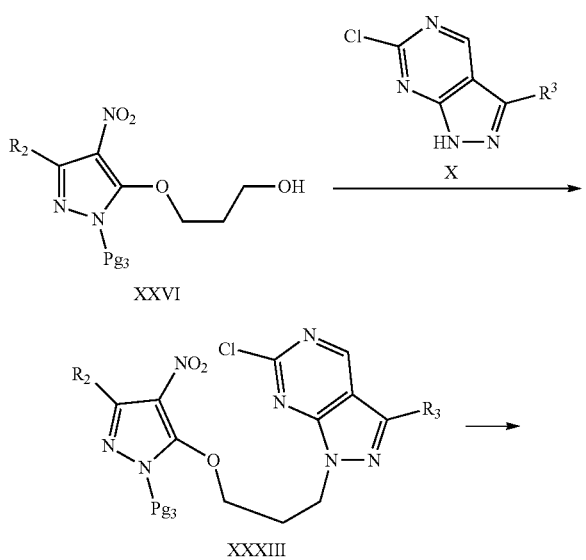

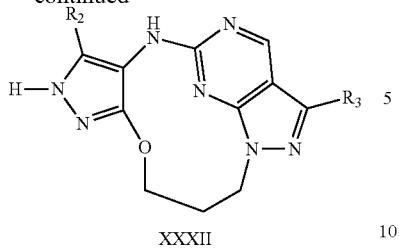

XXXII

An intermediate such as XXXII can be prepared according to scheme 9. The intermediates of type XXXII can for example be prepared through a one pot procedure by reducing an intermediate of type XXXIII (wherein $Pg_3$ is for example, 2-tetrahydropyrany) with iron and ammonium chloride in a suitable solvent e.g. a mixture of ethanol and water.

Nitropyrazole intermediates like XXXIII can be prepared by reaction of a pyrazolopyrimidine like X with an alcohol such as XXVI (wherein $Pg_3$ is for example, 2-tetrahydropyranyl) employing Mitsunobu-like reaction conditions for example diisopropyl azodicarboxylate and triphenylphosphine in a solvent such as tetrahydrofuran.

The general synthetic sequence in scheme 9 is for example described in the synthesis of intermediate 8-chloro-3-methyl-2,4,12,13-tetrahydro-11H-5,7-(azenometheno)dipyrazolo[3,4-b:5',1'-g][1]oxa[4,6,8]triazacycloundecine.

Method 10:

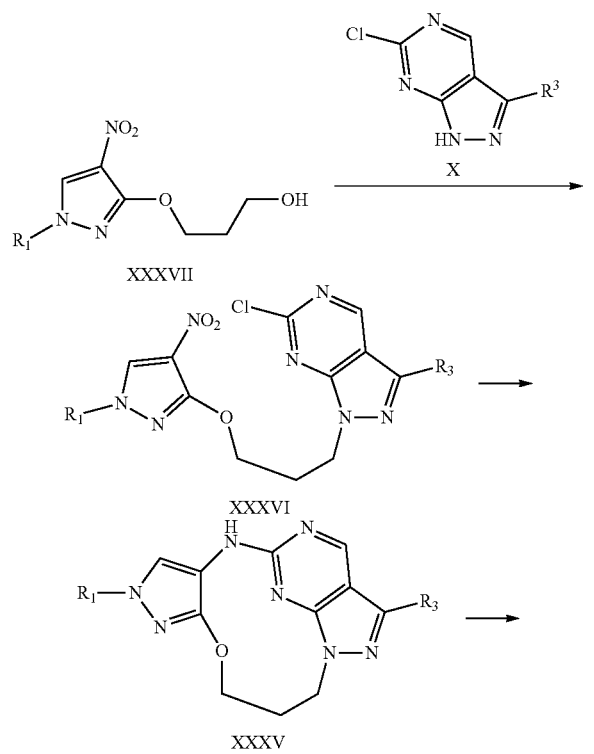

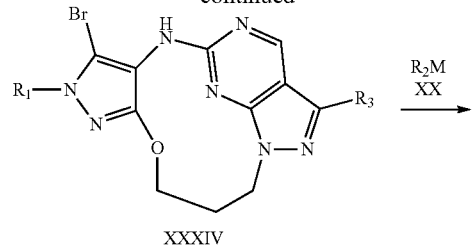

XXXIV

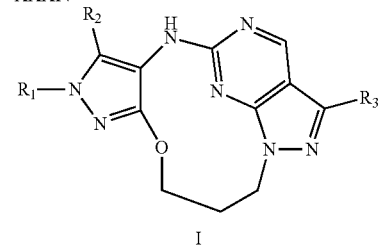

I

Alternatively, compounds of formula I can be prepared according to scheme 10. A bromo intermediate of type XXXIV can be reacted with an organometallic species such as XX (wherein M is for example Bpin, $B(OH)_2$, $Sn(n-Bu)_3$ or $SnMe_3$, Zn, ZnBr or ZnCl). The coupling is exemplified by but not limited to a Negishi-type cross-coupling. The reaction can be performed by reacting an intermediate of type XXXIV with an organozinc species such as $(CD_3)_2Zn$ in the presence of a catalyst like bis[tris(tert-butyl)phosphine]palladium, a base such as lithium bis(trimethylsilyl) amide in an appropriate solvent such as tetrahydrofuran as described for Example 50.

A bromo intermediate such as XXXIV can be prepared from a pyrazole like XXXV using a brominating agent for example N-bromosuccinimide in a suitable solvent such as tetrahydrofuran. Intermediates of type XXXV can in turn be synthesized from a nitropyrazole intermediate such as XXXVI employing a one-pot reduction and cyclization procedure. The reduction and subsequent cyclization can be performed using for example iron in the presence of ammonium chloride in a suitable solvent such as a mixture of ethanol and water. Nitropyrazole intermediates such as XXXVI can for example be synthesized through reaction of a pyrazolopyrimidine such as X and an alcohol like XXXVII employing Mitsunobu-like reaction conditions. The Mitsunobu-like coupling can for example be conducted using diisopropyl azodicarboxylate in the presence of triphenylphosphine in an appropriate solvent such as tetrahydrofuran. The synthesis of an intermediate like XXXIV is exemplified in the preparation of 3-bromo-8-chloro-2-((1r,4r)-4-methoxycyclohexyl)-2,4,12,13-tetrahydro-11H-5,7-(azenometheno)dipyrazolo[3,4-b:5',1'-g][1]oxa[4,6,8]triazacycloundecine.

Method 11:

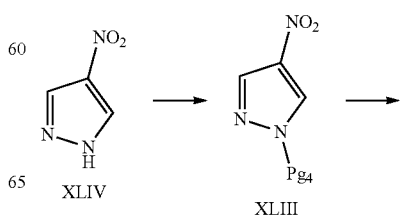

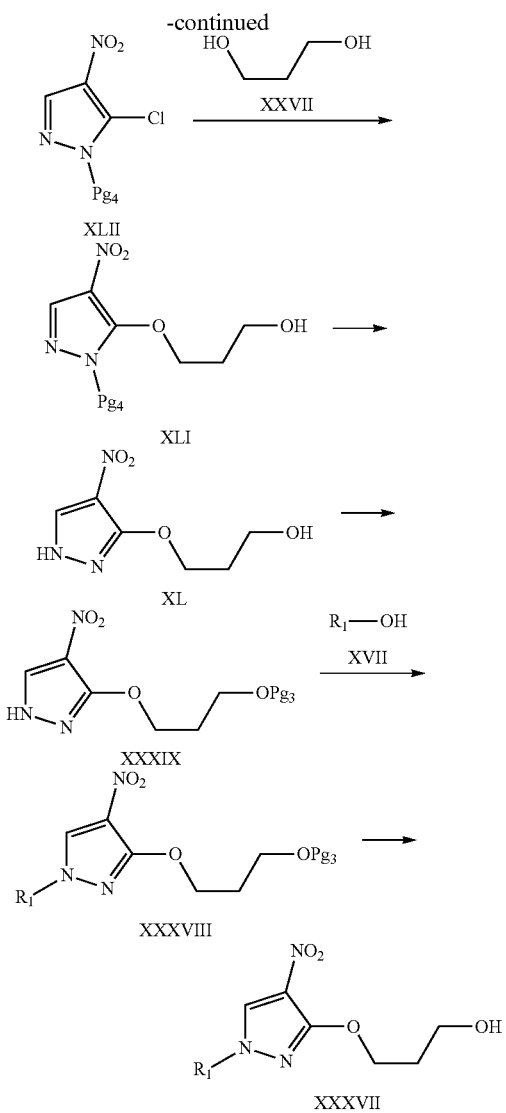

A method to prepare an intermediate of type XXXVII is depicted in scheme 11. Alcohol intermediates of type XXXVII can be prepared from a nitro pyrazole intermediate of type XXXVIII (wherein Pg₃ is e.g. TBS) using tetra-n-butyl ammonium fluoride in a suitable solvent such as tetrahydrofuran. Nitropyrazole intermediates of type XXXVIII can synthesized from pyrazole intermediates such as XXXIX and an alcohols such as XVII under Mitsunobu-like reaction conditions employing 2-(tributyl-X⁵-phosphanylidene)acetonitrile in a solvent like toluene as described in the synthesis of intermediate 3-((1-((1r,4r)-4-methoxycyclohexyl)-4-nitro-1H-pyrazol-3-yl)oxy)propan-1-ol.

Intermediates of type XXXIX (wherein Pg₃ is e.g. TBS) can be synthesized from an alcohol such as XL using for example tert-butyldimethylsilyl chloride in the presence of a base such as imidazole and a catalyst such as 4-dimethylaminopyridine in an appropriate solvent such as dichloromethane. An alcohol intermediate such as XL can be prepared from a nitropyazole such as XLI (wherein Pg₄ is for example, 2-tetrahydropyranyl) by treatment with an acid such as aqueous hydrochloric acid in a suitable solvent for example methanol.

Alcohol intermediates of type XLI can be prepared by reacting a chloro intermediate XLII with propane-1,3-diol XXVII in the presence of a base for example cesium fluoride in a solvent such as N,N-dimethylacetamide.

Chloro intermediates such as XLII (wherein Pg₄ is for example, 2-tetrahydropyranyl) can be prepared from a nitropyrazole intermediate XLIII (wherein Pg₄ is for example, 2-tetrahydropyranyl) using a strong base for example lithium bis(trimethylsilyl)amide, and an electrophile for example hexachloroethane in a suitable solvent such as tetrahydrofuran.

Abbreviations

Abbreviations used in the experimental may include, but are not limited to the following:
Boc: tert-butyloxycarbonyl; BRIJ-35: polyoxyethylene (23) lauryl ether; C: Celsius; CPME: cyclopentyl methyl ether; cPr: cyclopropyl; dba: dibenzylideneacetone; DBAD: di-tert-butyl azodicarboxylate; DCM: dichloromethane; DIAD: diisopropyl azodicarboxylate; DIPEA: N,N-diisopropylethylamine; DMA: N,N-dimethylacetamide; DMF: N'N-dimethylformamid; DMSO: dimethylsulfoxide; DTT: dithiothreitol; EGTA: ethylene glycol-bis(3-aminoethyl ether)-N,N,N,N'-tetraacetic acid; Et: ethyl; EtOAc: ethyl acetate; g: gram; h: hour(s); HMDS: hexamethyldisilazane; L: liter; LDA: lithium diisopropylamide; M: molar; Me: methyl; mg: milligram; mL: milliliter; mmol: millimole; Ms: methanesulfonyl; n-Bu: n-butyl; NFSI: N-fluorobenzenesulfonimide; NMR: nuclear magnetic resonance; Ph: phenyl; Pin: pinacol; PG: protecting group; SFC: supercritical fluid chromatography; TBS: tert-butyl(dimethyl)silyl; TEA: triethylamine; THF: tetrahydrofuran; THP: tetrahydropyran; TMS: trimethylsilyl; Tris: trisaminomethane; Ts: toluenesulfonyl.

Chemical Names

The chemical names for the Examples of the invention were generated using ChemDraw, version 20.0.0.41 by PerkinElmer Informatics, Inc.

Analytical Methods

LC-MS Methods

Method A: LC-MS were run on Agilent LC1200-MS6110 UPLC-MS or a consisting of Agilent LC1200 including column manager, binary solvent manager, sample organizer, PDA detector (operating at 220&254 nM), ELS detector, and MS6110 equipped with APPI-source operating in positive ion mode. LC-conditions: The column was Xtimate C18 2.1×30 mm, 3 μm operating at 50° C. with 1.2 mL/min of a binary gradient consisting of water+0.037% trifluoroacetic acid (A) and acetonitrile+0.018% trifluoroacetic acid(B). The retention times ($t_R$) are expressed in minutes based on UV-trace at 220&254 nm.

Gradient: 0.00 min 10% B
  0.9 min 80% B
  1.5 min 80% B
  1.51 min 10% B
  2.00 min 10% B
Total run time: 2.0 min Method B: LC-MS were run on Agilent LC1200-MS6150 or LC1200-MS6110 UPLC-MS consisting of Agilent LC1200 including column manager, binary solvent manager, sample organizer, PDA detector (operating at 220&254 nM), ELS detector, and MS6150 or MS6110 equipped with APPI-source operating in positive ion mode. LC-conditions: The column was MERCK, RP-18e 25×3.0 mm operating at 50° C. with 1.5 mL/min of a binary gradient consisting of water+0.037% trifluoroacetic acid (A) and acetonitrile+ 0.018% trifluoroacetic acid(B). The retention times ($t_R$) are expressed in minutes based on UV-trace at 220&254 nm.

Gradient: 0.00 min 5% B
  0.7 min 95% B
  1.1 min 95% B
  1.11 min 5% B
  1.5 min 5% B
Total run time: 1.5 min Method C: LC-MS were run on Agilent Prime-6125B UPLC-MS consisting of Agilent Prime including column manager, binary solvent manager, sample organizer, PDA detector (operating at 254 nM), ELS detector, and 6125B equipped with APPI-source operating in positive ion mode. LC-conditions: The column was Agilent Poroshell 120 EC-C18 1.9 μm; 3.0×30 mm operating at 50° C. with 1.5 mL/min of a binary gradient consisting of water+0.037% trifluoroacetic acid (A) and acetonitrile+0.018% trifluoroacetic acid(B). The retention times ($t_R$) are expressed in minutes based on UV-trace at 254 nm.
Gradient: 0.00 min 5% B
  1.20 min 80% B
  2.5 min 95% B
  2.51 min 5% B
  3.00 min 5% B
Total run time: 3.0 min Method D: LC-MS were run on Agilent Prime-6125B UPLC-MS consisting of Agilent Prime including column manager, binary solvent manager, sample organizer, PDA detector (operating at 254 nM), ELS detector, and 6125B equipped with APPI-source operating in positive ion mode. LC-conditions: The column was Agilent Poroshell 120 EC-C18 1.9 μm; 3.0×30 mm operating at 50° C. with 1.5 mL/min of a binary gradient consisting of water+0.037% trifluoroacetic acid (A) and acetonitrile+0.018% trifluoroacetic acid(B). The retention times ($t_R$) are expressed in minutes based on UV-trace at 254 nm.
Gradient: 0.00 min 0% B
  1.20 min 30% B
  2.5 min 95% B
  2.51 min 0% B
  3.00 min 0% B
Total run time: 3.0 min Method E: LC-MS were run on Waters Aquity UPLC-MS consisting of Waters Aquity including column manager, binary solvent manager, sample organizer, PDA detector (operating at 254 nM), ELS detector, and SQD-MS equipped with APPI-source operating in positive ion mode. LC-conditions: The column was Acquity UPLC BEH C18 1.7 μm; 2.1×50 mm operating at 60° C. with 1.2 ml/min of a binary gradient consisting of water+0.05% trifluoroacetic acid (A) and acetonitrile+5% water+0.035% trifluoroacetic acid. The retention times ($t_R$) are expressed in minutes based on UV-trace at 254 nm.
Gradient: 0.00 min 10% B
  1.00 min 100% B
  1.01 min 10% B
  1.15 min 10% B
Total run time: 1.15 min Method F: LC-MS were run on Waters Aquity UPLC-MS consisting of Waters Aquity including column manager, binary solvent manager, sample organizer, PDA detector (operating at 254 nM), ELS detector, and TQD-MS equipped with APPI-source operating in positive ion mode. LC-conditions: The column was Acquity UPLC BEH C18 1.7 μm; 2.1×50 mm operating at 60° C. with 1.2 ml/min of a binary gradient consisting of water+0.05% trifluoroacetic acid (A) and acetonitrile+5% water+0.05% trifluoroacetic acid. The retention times ($t_R$) are expressed in minutes based on UV-trace at 254 nm.
Gradient: 0.00 min 10% B
  1.00 min 100% B
  1.01 min 10% B
  1.15 min 10% B
Total run time: 1.15 min Method G: LC-MS were run on Agilent Prime-6125B UPLC-MS consisting of Agilent Prime including column manager, binary solvent manager, sample organizer, PDA detector (operating at 254 nM), ELS detector, and 6125B equipped with APPI-source operating in positive ion mode. LC-conditions: The column was Agilent Poroshell 120 EC-C18 1.9 μm; 3.0×30 mm operating at 30° C. with 1.5 mL/min of a binary gradient consisting of water+0.05% $NH_3 \cdot H_2O$ (A) and acetonitrile (B). The retention times ($t_R$) are expressed in minutes based on UV-trace at 254 nm.
Gradient: 0.00 min 5% B
  1.20 min 80% B
  2.5 min 95% B
  2.51 min 5% B
  3.00 min 5% B
Total run time: 3.0 min Method H: method PHQA: LC-MS were run on a Shimadzu LCMS-2020. PDA detector operating at 190-400 nM, ESI+ with a mass scan range 90-900 (m/z). The column was a EVO C18 1.9 μm; 3.0×50 mm operating at 40° C. with 1.2 mL/min of a binary gradient consisting of water+5 mM $NH_4HCO_3$ in water (A) and acetonitrile (B). The retention times ($t_R$) are expressed in minutes based on UV-trace at 254 nm.
Gradient: 0.0 min 10% B
  2.0 min 95% B
  2.6 min 95% B
  2.7 min 10% B
Total run time: 2.8 min Method I: LC-MS were run on Shimadzu LC-20AD; LCMS-2020 consisting of Shimadzu LC-20AD including column manager, binary solvent manager, sample organizer, PDA detector (operating at 220&254 nM), ELS detector, and MS6150 equipped with APPI-source operating in positive ion mode. LC-conditions: The column was Chromolith© Flash RP-18e 25-3 mm operating at 50° C. with 1.5 mL/min of a binary gradient consisting of water+0.037% trifluoroacetic acid (A) and acetonitrile+0.018% trifluoroacetic acid (B). The retention times (tR) are expressed in minutes based on UV-trace at 220&254 nm.
Gradient: 0 min 5% B
  0.4 min 95% B
  0.7 min 95% B
  0.71 min 5% B
  1.0 min 5% B
Total run time: 1.0 min Method J: LC-MS were run on Shimadzu LC20-MS2010 UPLC-MS consisting of Shimadzu LC20 including column manager, binary solvent manager, sample organizer, PDA detector (operating at 220&254 nm), ELS detector, and MS2010 equipped with APPI-source operating in positive ion mode. LC-conditions: The column was Xtimate, C18, 2.1×30 mm, 3 μm operating at 50° C. with 0.8 mL/min of a binary gradient consisting of water+0.037% trifluoroacetic acid (A) and acetonitrile+0.018% trifluoroacetic acid(B). The retention times ($t_R$) are expressed in minutes based on UV-trace at 220&254 nm.
Gradient: 0.00 min 10% B
  1.35 min 80% B
  2.25 min 80% B
  2.26 min 10% B
  3 min 10% B
Total run time: 3 min Method K: LC-MS were run on Shimadzu LC20-MS2010 UPLC-MS consisting of Shimadzu LC20 including column manager, binary solvent manager, sample organizer, PDA detector (operating at 220&254 nm), ELS detector, and MS2010 equipped with APPI-source operating in positive ion mode. LC-conditions: The column was Xtimate, C18, 2.1×30 mm, 3 μm operating at 50° C. with 0.8 mL/min of a binary gradient consisting of water+0.037% trifluoroacetic acid (A) and acetonitrile+0.018% trifluoroacetic acid(B). The retention times (tR) are expressed in minutes based on UV-trace at 220&254 nm.

Gradient: 0.00 min 0% B 1.35 min 60% B 2.25 min 60% B 2.26 min 0% B 3 min 0% B

Total run time: 3 min

NMR $^1$H NMR spectra were recorded at 600 MHz on a Bruker 600-Avance-III spectrometer, at 500 MHz on a Bruker 500-Avance DRX spectrometer, at 400 MHz on Bruker Avance AV-III-400 or a Varian MR400 spectrometers or at 300 MHZ using a Bruker Avance III HD.

Chemical shift values are expressed in ppm-values relative to tetramethylsilane. The following abbreviations or their combinations are used for multiplicity of NMR signals: br=broad, d=doublet, m=multiplet, q=quartet, quint=quintet, s=singlet and t=triplet.

Preparation of Reagents

Reagent: Bis(Methyl-d$_3$)Zinc in THF-Dibutyl Ether-Toluene

To a mixture of magnesium turnings (3.51 g, 145 mmol) and n-butyl ether (39.0 mL) was added DIBAL-H in toluene (1.00 mL, 1.00 molar, 1.00 mmol) at room temperature. The mixture was stirred for 15 min then iodomethane-d$_3$ (0.62 mL, 10 mmol) was added. The mixture was then heated to 40° C. and stirred for 15 minutes. Then additional iodomethane-d$_3$ (5.6 mL, 90 mmol) was added dropwise over a period of 30 minutes. The mixture was further stirred at 40° C. for 1.5 h. The mixture was cooled, and an aliquot was subjected to iodometric titration (I$_2$ in 2-MeTHF; slow addition of Grignard reagent) to determine the concentration=1.38 M.

To dried zinc(II) bromide (2.20 g, 9.77 mmol) under N$_2$ was added THF (4.40 mL). This was stirred for 10 min. Then n-Butyl ether (4.40 mL) was slowly added to form a white suspension. Then D$_3$CMgI (1.38 M in n-Bu$_2$O) (14.2 mL, 1.38 M, 19.6 mmol) was added slowly over a period of 5 minutes at ~5° C. (ice-water cooling) to form a white suspension. The mixture was stirred for 30 minutes at room temperature. Then toluene (5.52 mL) was added, and the suspension was stirred for 15 min. The mixture was filtered under an inert atmosphere, and the filtrate was used in the subsequent reaction. Iodometric titration (I$_2$ in 2-MeTHF) to determine the concentration=0.71 M.

Preparation of Intermediates

Intermediate: 3,6-Dichloro-1H-pyrazolo[3,4-d]pyrimidine

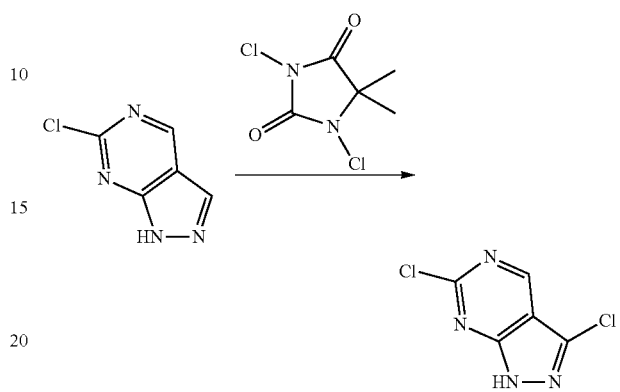

Three reactions were run in parallel: To a solution of 6-chloro-1H-pyrazolo[3,4-d]pyrimidine (8 g, 51.8 mmol) in MeCN (240 mL) was added 1,3-dichloro-5,5-dimethylimidazolidine-2,4-dione (7.14 g, 36.23 mmol). The mixture was stirred at 85° C. for 24 h. The reaction mixture was concentrated under reduced pressure. The residues from the three reactions were combined and purified by chromatography on silica gel (eluent: petroleum ether:EtOAc 100:0→80:20) to afford 3,6-dichloro-1H-pyrazolo[3,4-d]pyrimidine (4.3 g) of sufficient purity for the subsequent step. $^1$H NMR (DMSO-d$_6$, 400 MHz) δ 14.55 (br s, 1H), 9.29 (s, 1H).

Intermediate: 3-(3,6-Dichloro-1H-pyrazolo[3,4-d]pyrimidin-1-yl)propan-1-ol

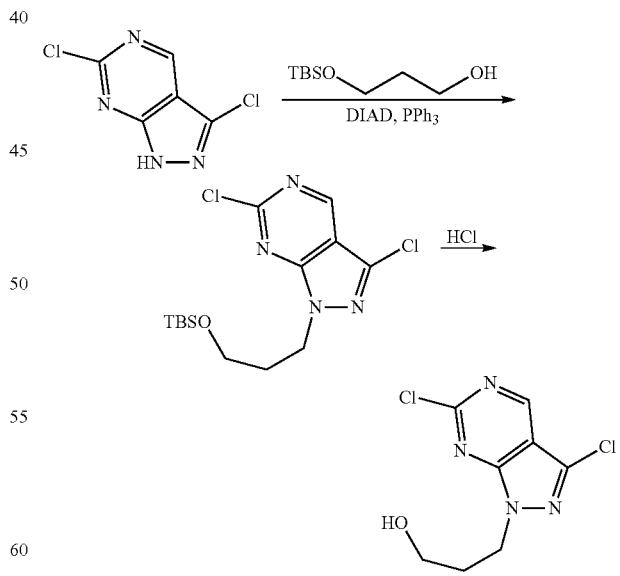

To a solution of 3-((tert-butyldimethylsilyl)oxy)propan-1-ol (4.4 g, 23.1 mmol), 3,6-dichloro-1H-pyrazolo[3,4-d]pyrimidine (5.24 g, 27.7 mmol), and PPh$_3$ (12.1 g, 46.2 mmol) in THF (45 mL) was added DIAD (9.35 g, 46.2 mmol) in a dropwise manner at 0° C. The mixture was stirred at 20° C. for 16 h. The mixture was concentrated under reduced pressure. The residue was purified by chromatography on silica gel (eluent: petroleum ether:EtOAc 95:5→90:10) to afford 1-(3-((tert-butyldimethylsilyl)oxy)propyl)-3,6-dichloro-1H-pyrazolo[3,4-d]pyrimidine (4.4 g) of sufficient purity for the subsequent step. ¹H NMR (CDCl₃, 400 MHz) δ8.97 (s, 1H), 4.53 (t, J=6.8 Hz, 2H), 3.66 (t, J=5.6 Hz, 2H), 2.20-2.12 (m, 2H), 0.88 (s, 9H), 0.01 (s, 6H).

To a solution of 1-(3-((tert-butyldimethylsilyl)oxy)propyl)-3,6-dichloro-1H-pyrazolo[3,4-d]pyrimidine (7 g, 19 mmol) in THF (20 mL) was added HCl (16 mL, 12M in H₂O). The mixture was stirred at 20° C. for 16 h. The mixture was concentrated under reduced pressure. The residue was treated with saturated aqueous NaHCO₃, final pH~7 and extracted with EtOAc (3×30 mL). The combined organic layers were washed with brine (3×30 mL), dried over Na₂SO₄, and concentrated under reduced pressure. The residue was purified by chromatography on silica gel (eluent: petroleum ether:EtOAc 80:20→50:50) to afford 3-(3,6-dichloro-1H-pyrazolo[3,4-d]pyrimidin-1-yl)propan-1-ol (2.1 g) of sufficient purity for the subsequent step. ¹H NMR (CDCl₃, 400 MHz) δ9.00 (s, 1H), 4.59 (t, J=6.8 Hz, 2H), 3.66 (q, J=5.6 Hz, 2H), 2.20-2.10 (m, 3H).

Intermediate: 3-(3,6-Dichloro-1H-pyrazolo[3,4-d]pyrimidin-1-yl)propyl 4-methylbenzenesulfonate

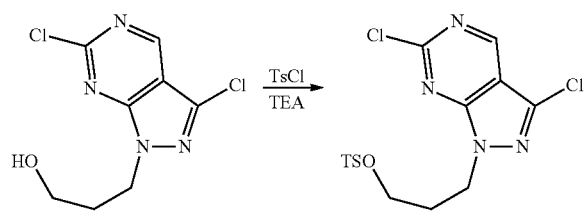

To a solution of 3-(3,6-dichloro-1H-pyrazolo[3,4-d]pyrimidin-1-yl)propan-1-ol (580 mg, 2.35 mmol) in DCM (10 mL) was added TEA (713 mg, 7.04 mmol) and TsCl (671 mg, 3.52 mmol). The mixture was stirred at 15° C. for 16 h. The mixture was concentrated under reduced pressure. The residue was purified by chromatography on silica gel (eluent: petroleum ether:EtOAc 100:0→70:30) to afford 3-(3,6-dichloro-1H-pyrazolo[3,4-d]pyrimidin-1-yl)propyl 4-methylbenzenesulfonate (800 mg). ¹H NMR (CDCl₃, 400 MHz) δ 8.95 (s, 1H), 7.75 (d, J=8.0 Hz, 2H), 7.33 (d, J=8.0 Hz, 2H), 4.47 (t, J=6.8 Hz, 2H), 4.09 (t, J=6.0 Hz, 2H), 2.45 (s, 3H), 2.37-2.29 (m, 2H).

Intermediate: 3-(3-Bromo-6-chloro-1H-pyrazolo[3,4-d]pyrimidin-1-yl)propan-1-ol

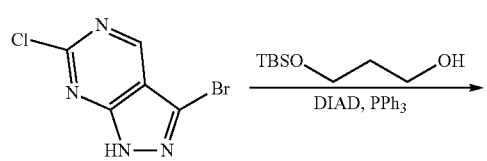

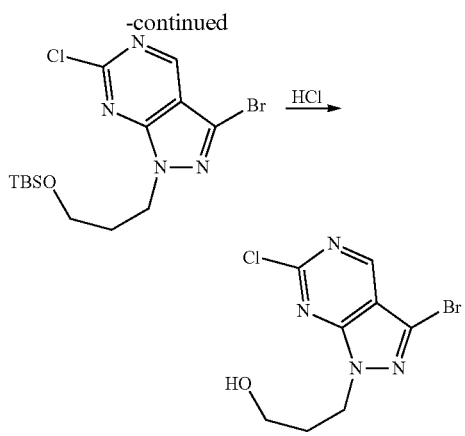

A solution of DIAD (1.96 g, 1.89 mL, 9.71 mmol) in THF (65 mL) was cooled to 0° C. PPh₃ (2.55 g, 9.71 mmol) was added portionwise and the mixture was stirred for 15 minutes. 3-Bromo-6-chloro-1H-pyrazolo[3,4-d]pyrimidine (1.60 g, 6.85 mmol) was then added in portions followed by a solution of 3-((tert-butyldimethylsilyl)oxy)propan-1-ol (1.09 g, 5.71 mmol) in THF (10 mL). The cooling bath was allowed to expire upon overnight stirring. The reaction mixture was concentrated under reduced pressure. The residue was purified by chromatography on silica gel (eluent: petroleum ether:EtOAc 100:0→70:30) to afford 3-bromo-1-(3-((tertbutyldimethylsilyl)oxy)propyl)-6-chloro-1H-pyrazolo[3,4-d]pyrimidine (2.17 g) of sufficient purity for the subsequent step. ¹H NMR (CDCl₃, 600 MHz) δ8.89 (s, 1H), δ 4.54 (t, J=6.9 Hz, 2H), 3.65 (t, J=5.8 Hz, 2H), 2.15 (m, 2H), 0.88 (s, 9H), 0.01 (s, 6H).

To a dry flask was added 3-bromo-1-(3-((tert-butyldimethylsilyl)oxy)propyl)-6-chloro-1H-pyrazolo[3,4-d]pyrimidine (1.00 g, 2.46 mmol) and THF (25 mL). The flask was capped and the atmosphere was exchanged for argon. HCl (3M in CPME) (3.02 mL, 9.1 mmol) was added and the mixture was stirred at 50° C. overnight. The reaction mixture was diluted with water (10 mL), and pH adjusted using saturated aqueous potassium carbonate, pH~11, and extracted with EtOAc (3×50 mL). The combined organic layers were washed with brine, dried over sodium sulfate, and concentrated under reduced pressure. The residue was purified by chromatography on silica gel (eluent: petroleum ether:EtOAc 80:20→20:80) to afford 3-(3-bromo-6-chloro-1H-pyrazolo[3,4-d]pyrimidin-1-yl)propan-1-ol (650 mg) of sufficient purity for the subsequent step. ¹H NMR (CDCl₃, 600 MHz) δ 8.91 (s, 1H), 4.60 (t, J=6.6 Hz, 2H), 3.65 (q, J=5.8 Hz, 2H), 2.18-2.13 (m, 2H), 2.11 (t, J=5.8 Hz, 1H).

Intermediate: 3,6-Dichloro-1-(3-((1,5-dimethyl-4-nitro-1H-pyrazol-3-yl)oxy)propyl)-1H-pyrazolo[3,4-d]pyrimidine

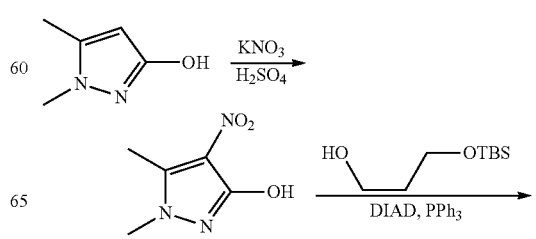

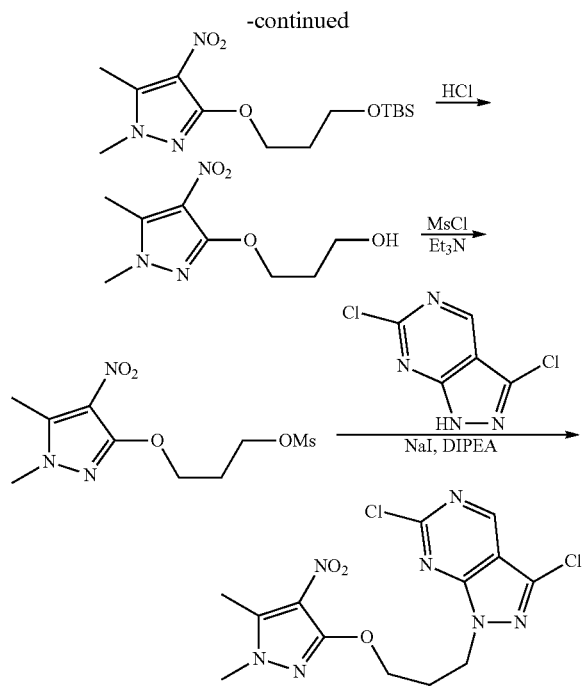

To a solution of 1,5-dimethyl-1H-pyrazol-3-ol hydrochloride (5 g, 33.7 mmol, HCl salt) in H$_2$SO$_4$ (40 mL) was added KNO$_3$ (4.08 g, 40.4 mmol) at 0° C. The mixture was stirred at 0° C. for 1 h. The reaction mixture was poured onto ice water (200 mL) and adjusted to pH 5-6 with saturated aqueous NaOH. The mixture was extracted with EtOAc (3×200 mL) and the combined organic layers were concentrated to afford 1,5-dimethyl-4-nitro-1H-pyrazol-3-ol (2.8 g) as a solid of sufficient purity for the subsequent step. $^1$H NMR (CDCl$_3$, 400 MHz) δ 3.72 (s, 3H), 2.61 (s, 3H).

To a solution of 1,5-dimethyl-4-nitro-pyrazol-3-ol (500 mg, 3.18 mmol), 3-[tertbutyl(dimethyl)silyl]oxypropan-1-ol (727 mg, 3.82 mmol), and PPh$_3$ (1.09 g, 4.14 mmol) in THF (10 mL) was added dropwise DIAD (837 mg, 4.14 mmol) at 0° C. The mixture was stirred at 15° C. for 16 h. The mixture was concentrated. The residue was purified by chromatography on silica gel (eluent: petroleum ether:EtOAc 70:30→60:40) to afford give 3-(3-((tertbutyldimethylsilyl)oxy)propoxy)-1,5-dimethyl-4-nitro-1H-pyrazole (700 mg) of sufficient purity for the subsequent step. $^1$H NMR (CDCl$_3$, 400 MHz) δ 4.38 (t, J=6.0 Hz, 2H), 3.82 (t, J=6.0 Hz, 2H), 3.69 (s, 3H), 2.60 (s, 3H), 2.07-1.97 (m, 2H), 0.89 (s, 9H), 0.05 (s, 6H).

To a solution of tert-butyl-[3-(1,5-dimethyl-4-nitro-pyrazol-3-yl)oxypropoxy]-dimethylsilane (560 mg, 1.70 mmol) in THF (5 mL) were added saturated aqueous HCl (12 M, 1.42 mL). The reaction mixture was stirred at 10° C. for 16 h. The solvent was removed under reduced pressure to afford 3-((1,5-dimethyl-4-nitro-1H-pyrazol-3-yl)oxy)propan-1-ol (365.7 mg) of sufficient purity for the subsequent step. LC-MS (method A) (m/z)=216.2 (MH)$^+$ t$_R$=0.42 minutes.

To a solution of 3-(1,5-dimethyl-4-nitro-pyrazol-3-yl)oxypropan-1-ol (200 mg, 0.93 mmol) in DCM (5 mL) were added MsCl (266 mg, 2.32 mmol) and TEA (282 mg, 2.79 mmol) at 0° C. The reaction mixture was stirred at 15° C. for 16 h. The reaction mixture was diluted with water (10 mL) and extracted with DCM (3×10 mL). The combined organic layers were washed with brine (3×10 mL), dried over Na$_2$SO$_4$, and concentrated under reduced pressure. The residue was purified by chromatography on silica gel (eluent: petroleum ether:EtOAc 70:30→60:40) to afford 3-((1,5-dimethyl-4-nitro-1H-pyrazol-3-yl)oxy)propyl methanesulfonate (150 mg) of sufficient purity for the subsequent step. $^1$H NMR (CDCl$_3$, 400 MHz) δ 4.67-4.40 (m, 4H), 3.69 (s, 3H), 3.03 (s, 3H), 2.60 (s, 3H), 2.30-2.24 (m, 2H).

To a solution of 3,6-dichloro-1H-pyrazolo[3,4-d]pyrimidine (170 mg, 0.90 mmol) in DMF (2 mL) were added 3-((1,5-dimethyl-4-nitro-1H-pyrazol-3-yl)oxy)propyl methanesulfonate (264 mg, 0.90 mmol), NaI (135 mg, 0.90 mmol), and DIPEA (581 mg, 4.50 mmol). The reaction mixture was stirred at 80° C. for 16 h. The reaction mixture was diluted with water (10 mL) and extracted with EtOAc (3×10 mL). The combined organic layers were washed with brine (3×10 mL), dried over Na$_2$SO$_4$, and concentrated under reduced. The residue was purified by chromatography on silica gel (eluent: petroleum ether:EtOAc 60:40→50:50) to afford 3,6-dichloro-1-(3-((1,5-dimethyl-4-nitro-1H-pyrazol-3-yl)oxy)propyl)-1H-pyrazolo[3,4-d]pyrimidine (100 mg) of sufficient purity for the subsequent step. $^1$H NMR (CDCl$_3$, 400 MHz) δ 8.95 (s, 1H), 4.65 (t, J=6.0 Hz, 2H), 4.32 (t, J=6.0 Hz, 2H), 3.64 (s, 3H), 2.58 (s, 3H), 2.50-2.44 (m, 2H).

Intermediate: 3,6-Dichloro-1-(3-((5-methyl-4-nitro-1-(tetrahydro-2H-pyran-4-yl)-1H-pyrazol-3-yl)oxy)propyl)-1H-pyrazolo[3,4-d]pyrimidine

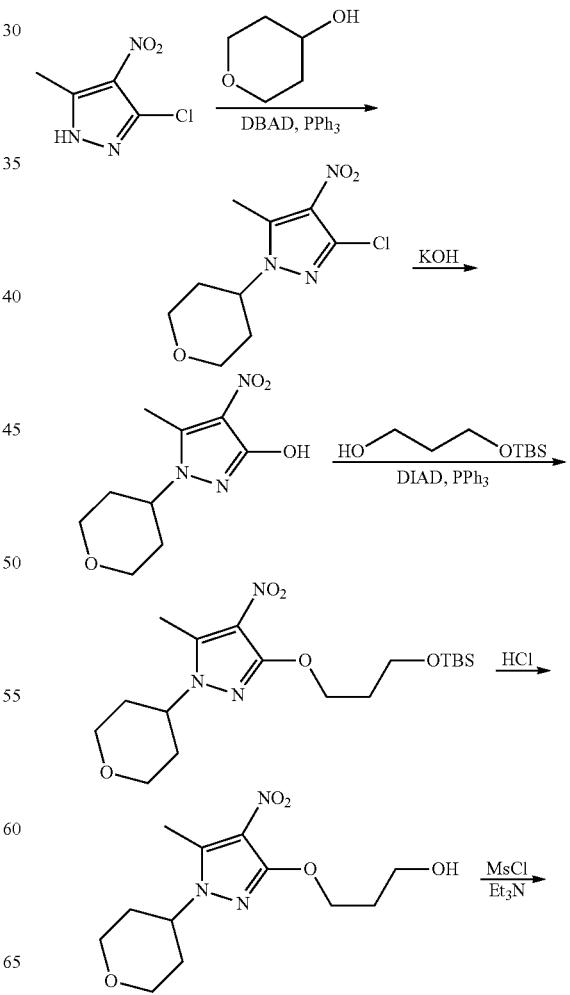

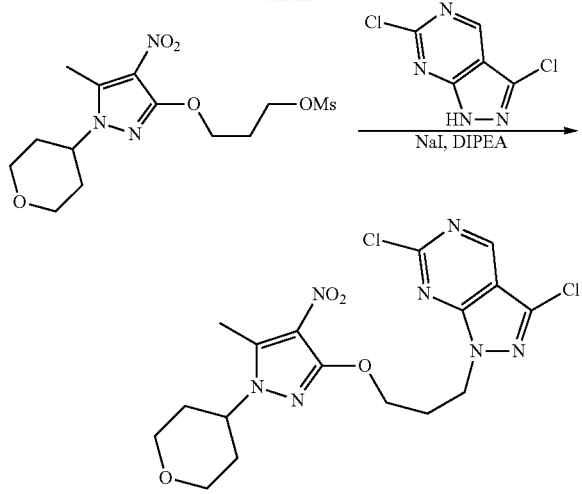

To a solution of 5-chloro-3-methyl-4-nitro-1H-pyrazole (10.8 g, 66.85 mmol), tetrahydro-2H-pyran-4-ol (13.66 g, 133.7 mmol) and PPh₃ (21.04 g, 80.22 mmol) in THF (100 mL) was added a solution of DBAD (18.47 g, 80.22 mmol) in THF (40 mL) dropwise at 0° C. The resulting mixture was stirred at 20° C. for 16 h. The mixture was concentrated under reduced pressure. The residue was purified by chromatography on silica gel (eluent: heptane:EtOAc 100:0→20:80) twice to afford 3-chloro-5-methyl-4-nitro-1-(tetrahydro-2H-pyran-4-yl)-1H-pyrazole (11 g) of sufficient purity for the next step. $^1$H NMR (CDCl₃, 400 MHz) δ 4.35-4.26 (m, 1H), 4.17-4.13 (m, 2H), 3.56-3.49 (m, 2H), 2.62 (s, 3H), 2.38-2.26 (m, 2H), 1.83-1.78 (m, 2H).

3-Chloro-5-methyl-4-nitro-1-(tetrahydro-2H-pyran-4-yl)-1H-pyrazole (2.5 g, 10.2 mmol) and KOH (9 g, 160 mmol) in H₂O (40 mL) was heated at 140° C. for 8 hours. The mixture was adjusted to pH~3 with aqueous HCl (12M). The precipitate was filtered. The filter cake was dried to afford 5-methyl-4-nitro-1-(tetrahydro-2H-pyran-4-yl)-1H-pyrazol-3-ol (2.2 g) of sufficient purity for the subsequent step. $^1$H NMR (CDCl₃, 400 MHz) δ 8.44 (s, 1H), 4.23-4.16 (m, 1H), 4.13-4.09 (m, 2H), 3.52-3.45 (m, 2H), 2.64 (s, 3H), 2.37-2.26 (m, 2H), 1.76-1.72 (m, 2H).

A solution of DIAD (4.16 g, 20.6 mmol) was added to a solution of 5-methyl-4-nitro-1-(tetrahydro-2H-pyran-4-yl)-1H-pyrazol-3-ol (3.6 g, 15 mmol), 3-((tertbutyldimethylsilyl)oxy)propan-1-ol (3.62 g, 19.0 mmol) and PPh₃ (5.40 g, 20.6 mmol) in THF (50 mL) at 0° C. Then the mixture was stirred at 20° C. for 40 h. The reaction mixture was concentrated under reduced pressure. The residue was purified by chromatography on silica gel (eluent: heptane:EtOAc 100:0→80:20) to afford 3-(3-((tert-butyldimethylsilyl)oxy)propoxy)-5-methyl-4-nitro-1-(tetrahydro-2H-pyran-4-yl)-1H-pyrazole (4 g) of sufficient purity for the next step. $^1$H NMR (CDCl₃, 400 MHz) δ 4.40 (t, J=6.4 Hz, 2H), 4.27-4.17 (m, 1H), 4.16-4.11 (m, 2H), 3.52 (t, J=6.4 Hz, 2H), 3.59-3.43 (m, 2H), 2.63 (s, 3H), 2.38-2.20 (m, 2H), 2.04-1.99 (m, 2H), 1.80-1.70 (m, 2H), 0.88 (s, 9H), 0.04 (s, 6H).

To a solution of 3-(3-((tert-butyldimethylsilyl)oxy)propoxy)-5-methyl-4-nitro-1-(tetrahydro-2H-pyran-4-yl)-1H-pyrazole (4 g, 10 mmol) in THF (40 mL) was added HCl (12 M, 8.34 mL, 100 mmol). The mixture was stirred at 20° C. for 16 h. The reaction mixture was concentrated under reduced pressure. The reaction mixture was diluted with water (50 mL) and the pH adjusted to 9~10 using saturated aqueous Na₂CO₃ and extracted with EtOAc (3×100 mL). The combined organics were dried over Na₂SO₄, filtered, and concentrated under reduced pressure.

The residue was purified by chromatography on silica gel (eluent: heptane:EtOAc 100:0→20:80) to afford 3-((5-methyl-4-nitro-1-(tetrahydro-2H-pyran-4-yl)-1H-pyrazol-3-yl)oxy)propan-1-ol (1.4 g) of sufficient purity for the next step. $^1$H NMR (CDCl₃, 400 MHz) δ 4.50 (t, J=6.0 Hz, 2H), 4.28-4.17 (m, 1H), 4.17-4.12 (m, 2H), 3.91-3.78 (m, 2H), 3.57-3.46 (m, 2H), 2.65 (s, 3H), 2.36-2.23 (m, 2H), 2.11-2.05 (m, 2H), 1.81-1.73 (m, 2H).

To a solution of 3-((5-methyl-4-nitro-1-(tetrahydro-2H-pyran-4-yl)-1H-pyrazol-3-yl)oxy)propan-1-ol (1.4 g, 4.91 mmol) in DCM (20 mL) was added MsCl (1.41 g, 12.31 mmol) and TEA (1.49 g, 14.7 mmol) at 0° C. The mixture was stirred at 20° C. for 16 h. The reaction mixture was diluted with water (50 mL) and extracted with DCM (3×100 mL). The combined organic layers were washed with brine (3×100 mL), dried over Na₂SO₄, and concentrated under reduced pressure. The residue was purified by chromatography on silica gel (eluent: heptane:EtOAc 100:0→20:80) to afford 3-((5-methyl-4-nitro-1-(tetrahydro-2H-pyran-4-yl)-1H-pyrazol-3-yl)oxy)propylmethanesulfonate (1.5 g) of sufficient purity for the next step. $^1$H NMR (CDCl₃, 400 MHz) δ 4.49-4.42 (m, 4H), 4.27-4.17 (m, 1H), 4.16-4.11 (m, 2H), 3.58-3.47 (m, 2H), 3.04 (s, 3H), 2.65 (s, 3H), 2.36-2.22 (m, 4H), 1.80-1.72 (m, 2H).

To a solution of 3,6-dichloro-1H-pyrazolo[3,4-d]pyrimidine (810 mg, 4.29 mmol) in DMF (20 mL) were added 3-((5-methyl-4-nitro-1-(tetrahydro-2H-pyran-4-yl)-1H-pyrazol-3-yl)oxy)propyl methanesulfonate (1.5 g, 4.13 mmol), NaI (619 mg, 4.13 mmol) and DIPEA (2.67 g, 20.6 mmol). The mixture was stirred at 80° C. for 16 h. The reaction mixture was diluted with water (50 mL) and extracted with EtOAc (3×100 mL). The combined organic layers were washed with brine (3×100 mL), dried over Na₂SO₄, and concentrated under reduced pressure. The residue was purified by chromatography on silica gel (eluent: heptane:EtOAc 100:0→60:40) to afford 3,6-dichloro-1-(3-((5-methyl-4-nitro-1-(tetrahydro-2H-pyran-4-y)-1H-pyrazol-3-yl)oxy)propyl)-1H-pyrazolo[3,4-d]pyrimidine (840 mg) of sufficient purity for the next step. $^1$H NMR (CDCl₃, 400 MHz) δ 8.96 (s, 1H), 4.65 (t, J=6.4 Hz, 2H), 4.35 (t, J=6.4 Hz, 2H), 4.23-4.15 (m, 1H), 4.12-4.07 (m, 2H), 3.54-3.46 (m, 2H), 2.63 (s, 3H), 2.51-2.43 (m, 2H), 2.25-2.14 (m, 2H), 1.76-1.69 (m, 2H).

Intermediate: (±)-3,6-Dichloro-1-(3-((5-methyl-4-nitro-1-(tetrahydro-2H-pyran-3-yl)-1H-pyrazol-3-yl)oxy)propyl)-1H-pyrazolo[3,4-d]pyrimidine

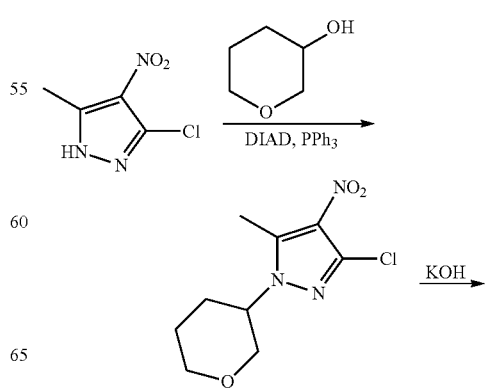

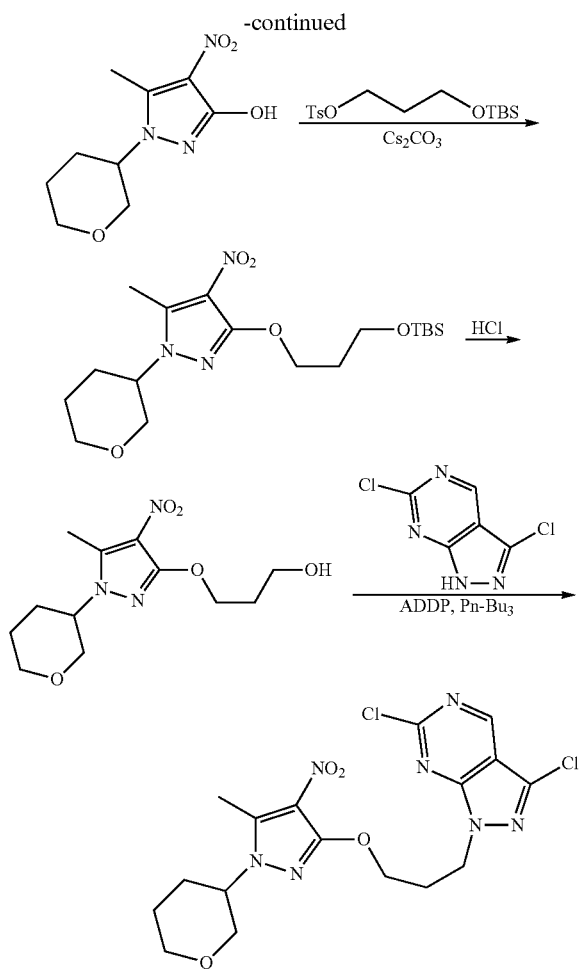

To a dry flask fitted with a stirbar and capped with a septum was added DIAD (2.69 mL, 13.8 mmol) and the atmosphere was exchanged for argon. THF (200 mL) was added and the solution was cooled to 0° C. Then, PPh₃ (on resin, loading: 1.6 mmol/g) (3.62 g, 13.8 mmol, 8.625 g resin used), was added and the mixture was stirred under argon for 5 minutes. 3-Chloro-5-methyl-4-nitro-1H-pyrazole (1.80 g, 11.1 mmol) was added followed by the addition of tetrahydro-2H-pyran-3-ol (1.71 g, 16.7 mmol) as a solution in THF (10 mL). The mixture was allowed to reach room temperature and was stirred for 4 h. The reaction was diluted with THF and was filtered while washing with THF. The filtrate was concentrated under reduced pressure. The residue was purified by chromatography on silica gel (eluent: heptane:EtOAc 100:0→25:75) to afford (±)-3-chloro-5-methyl-4-nitro-1-(tetrahydro-2H-pyran-3-yl)-1H-pyrazole (600 mg) of sufficient purity for the subsequent step. ¹H NMR (CDCl₃, 600 MHz) δ 4.27-4.22 (m, 1H), 4.01-3.92 (m, 2H), 3.73 (t, J=11.1 Hz, 1H), 3.48-3.42 (m, 1H), 2.68 (s, 3H), 2.32-2.23 (m, 1H), 2.11-2.05 (m, 1H), 1.89-1.78 (m, 2H).

To a vial was added (±)-3-chloro-5-methyl-4-nitro-1-(tetrahydro-2H-pyran-3-yl)-1H-pyrazole (725 mg, 2.95 mmol), potassium hydroxide (1.16 g, 20.7 mmol), and water (11.7 mL, 649 mmol). The vial was capped, and the reaction mixture was heated using a microwave reactor at 152° C. for 3 h. The mixture was cooled to room temperature and was diluted with water (50 mL). The mixture was washed with EtOAc (10 mL). The aqueous phase was then acidified by slow addition of 2 M aqueous HCl and the mixture was extracted with EtOAc (3×100 mL). The combined organic phases were washed with saturated NaCl, dried over sodium sulfate, filtered, and concentrated under reduced pressure to afford (±)-5-methyl-4-nitro-1-(tetrahydro-2H-pyran-3-yl)-1H-pyrazol-3-ol (510 mg) as a solid of sufficient purity for the next step. ¹H NMR (CDCl₃, 600 MHz) δ 4.21-4.15 (m, 1H), 3.99-3.95 (m, 1H), 3.93-3.89 (m, 1H), 3.75 (t, J=10.7 Hz, 1H), 3.46-3.40 (m, 1H), 2.69 (s, 1H), 2.64 (s, 3H), 2.31-2.22 (m, 1H), 2.06-1.99 (m, 1H), 1.88-1.79 (m, 2H).

To a dry flask was added 3-((tert-butyldimethylsilyl)oxy)propyl 4-methylbenzenesulfonate (1.45 g, 4.20 mmol), DMF (15 mL), and (±) 5-methyl-4-nitro-1-(tetrahydro-2H-pyran-3-yl)-1H-pyrazol-3-ol (510 mg, 2.24 mmol). The flask was flushed with argon before cesium carbonate (1.40 g, 4.30 mmol) was added in a portionwise manner. The reaction was stirred at room temperature for 16 h. The mixture was concentrated under reduced pressure. The residue was purified by chromatography on silica gel (eluent: heptane:EtOAc 100:0→25:75) twice to afford (±)-3-(3-((tert-butyldimethylsilyl)oxy)propoxy)-5-methyl-4-nitro-1-(tetrahydro-2H-pyran-3-yl)-1H-pyrazole (401 mg) of sufficient purity for the next step. ¹H NMR (CDCl₃, 600 MHz) δ 4.38 (t, J=6.3 Hz, 2H), 4.18-4.11 (m, 1H), 3.99-3.95 (m, 1H), 3.93-3.88 (m, 1H), 3.80 (t, J=6.0 Hz, 2H), 3.70 (t, J=10.7 Hz, 1H), 3.46-3.40 (m, 1H), 2.62 (s, 3H), 2.26-2.17 (m, 1H), 2.05-1.97 (m, 3H), 1.85-1.79 (m, 2H), 0.88 (s, 9H), 0.04 (s, 6H).

To a dry flask was added (±)-3-(3-((tert-butyldimethylsilyl)oxy)propoxy)-5-methyl-4-nitro-1-(tetrahydro-2H-pyran-3-yl)-1H-pyrazole (400 mg, 1.00 mmol) and DCM (10 mL). The flask was capped and the atmosphere was exchanged for argon. HCl (3M in CPME) (2.67 mL, 8.01 mmol) was added and the mixture was briefly heated and then stirred for 1 h at room temperature. HCl (3M in CPME) (2.67 mL, 8.01 mmol) was added and the flask was stirred overnight at room temperature. The reaction mixture was concentrated under reduced pressure. The reaction mixture was diluted with water (10 mL) and saturated aqueous potassium carbonate adjusting pH⁻11. The mixture was extracted with EtOAc (3×50 mL), and the combined organics were washed with brine, and dried over sodium sulfate, filtered and concentrated under reduced pressure. The residue was purified by chromatography on silica gel (eluent: Heptane:EtOAc 100:0→20:80) to afford (±)-3-((5-methyl-4-nitro-1-(tetrahydro-2H-pyran-3-yl)-1H-pyrazol-3-yl)oxy)propan-1-ol (248 mg) of sufficient purity for the next step. ¹H NMR (CDCl₃, 600 MHz) δ 4.52-4.44 (m, 2H), 4.16 (tt, J=11.0, 4.3 Hz, 1H), 3.99-3.95 (m, 1H), 3.94-3.88 (m, 1H), 3.86-3.80 (m, 2H), 3.69 (t, J=11.2 Hz, 1H), 3.47-3.41 (m, 1H), 2.63 (s, 3H), 2.55-2.50 (m, 1H), 2.24-2.16 (m, 1H), 2.09-2.00 (m, 3H), 1.88-1.79 (m, 2H).

A solution of 3,6-dichloro-1H-pyrazolo[3,4-d]pyrimidine (201 mg, 1.06 mmol) and (±)-3-((5-methyl-4-nitro-1-(tetrahydro-2H-pyran-3-yl)-1H-pyrazol-3-yl)oxy)propan-1-ol (243 mg, 0.852 mmol) in THF (25 mL) was degassed thoroughly with argon in a dry vial. The vial was capped and 1,1-(Azodicarbonyl)-Dipiperidine (484 mg, 1.92 mmol), and tributylphosphine (476 µL, 1.92 mmol) were added sequentially. The reaction mixture was stirred at room temperature for 1 h. The reaction mixture was quenched with MeOH (0.5 mL) and diluted with EtOAc (25 mL). Celite was added and the mixture was concentrated under reduced pressure. The residue was purified by chromatography on silica gel (eluent: heptane:EtOAc 100:0→20:80) twice to afford (±)-3,6-dichloro-1-(3-((5-methyl-4-nitro-1-(tetrahydro-2H-pyran-3-yl)-1H-pyrazol-3-yl)oxy)propyl)-

1H-pyrazolo[3,4-d]pyrimidine (244 mg) as a solid of sufficient purity for the next step. ¹H NMR (CDCl₃, 600 MHz) δ 8.95 (s, 1H), 4.68-4.60 (m, 2H), 4.34 (t, J=5.8 Hz, 2H), 4.16-4.10 (m, 1H), 3.99-3.94 (m, 1H), 3.91-3.86 (m, 1H), 3.62 (t, J=10.7 Hz, 1H), 3.43-3.37 (m, 1H), 2.61 (s, 3H), 2.46 (p, J=6.2 Hz, 2H), 2.17-2.09 (m, 1H), 2.01-1.96 (m, 1H), 1.84-1.78 (m, 2H).

Intermediate: 6-Chloro-1-(3-((5-methyl-4-nitro-1-(tetrahydro-2H-pyran-4-yl)-1H-pyrazol-3-yl)oxy)propyl)-3-(trifluoromethyl)-1H-pyrazolo[3,4-d]pyrimidine

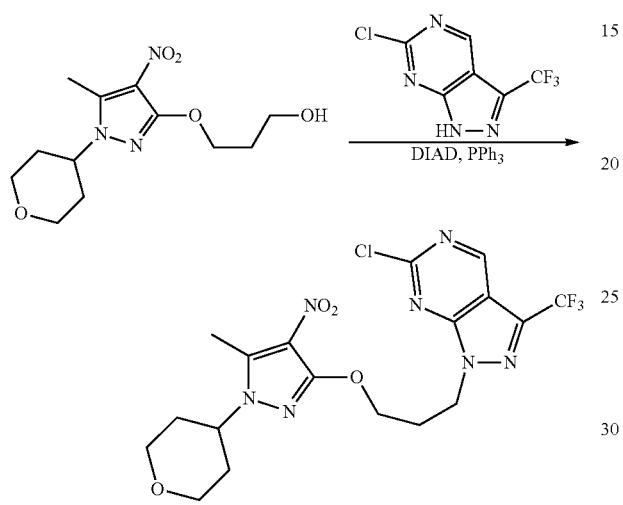

A solution of DIAD (218 µL, 1.12 mmol) in THF (1 mL) was cooled to 0° C. under an atmosphere of argon. PPh₃ (294 mg, 1.12 mmol) was added and the mixture was stirred for 10 minutes. 6-Chloro-3-(trifluoromethyl)-1H-pyrazolo[3,4-d]pyrimidine (156 mg, 0.701 mmol) was then added followed by a solution of 3-((5-methyl-4-nitro-1-(tetrahydro-2H-pyran-4-yl)-1H-pyrazol-3-yl)oxy)propan-1-ol (160 mg, 0.561 mmol, prepared as previously described) in THF (0.25 mL). The reaction mixture was stirred at 0° C. for 2 minutes and then at room temperature overnight. The reaction mixture was concentrated under reduced pressure. The residue was purified by chromatography on silica gel (eluent: heptane:EtOAc 100:0→20:80) to afford 6-chloro-1-(3-((5-methyl-4-nitro-1-(tetrahydro-2H-pyran-4-yl)-1H-pyrazol-3-yl)oxy)propyl)-3-(trifluoromethyl)-1H-pyrazolo[3,4-d]pyrimidine (190 mg) as a solid of sufficient purity for the subsequent step. ¹H NMR (CDCl₃, 600 MHz) δ 9.12 (s, 1H), 4.76 (t, J=6.5 Hz, 2H), 4.38 (t, J=5.8 Hz, 2H), 4.21-4.14 (m, 1H), 4.12-4.07 (m 2H), 3.52-3.46 (m, 2H), 2.61 (s, 3H), 2.52 (p, J=6.2 Hz, 2H), 2.23-2.16 (m, 2H), 1.75-1.69 (m, 2H).

Intermediate: 3,6-Dichloro-1-(3-((5-cyclopropyl-4-nitro-1-(tetrahydro-2H-pyran-4-yl)-1H-pyrazol-3-yl)oxy)propyl)-1H-pyrazolo[3,4-d]pyrimidine

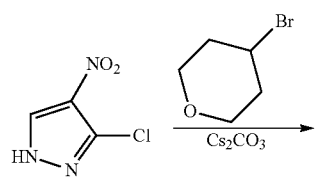

A mixture of 3-chloro-4-nitro-1H-pyrazole (10 g, 68 mmol), 4-bromotetrahydro-2H-pyran (22.37 g, 135.6 mmol) and Cs₂CO₃ (55.22 g, 169.5 mmol) in DMF (100 mL) was degassed and purged with N₂ (×3), and then the mixture was stirred at 80° C. for 16 h. The reaction mixture was diluted with water (100 mL) and extracted with EtOAc (4×200 mL). The combined organic layers were washed with brine (3×300 mL), dried over Na₂SO₄, and concentrated under reduced pressure. The residue was purified by chromatography on silica gel (eluent: petroleum ether:EtOAc 80:20→70:30) to afford 3-chloro-4-nitro-1-(tetrahydro-2H-pyran-4-yl)-1H-pyrazole (8.7 g) of sufficient purity for the subsequent step. ¹H NMR (CDCl₃, 400 MHz) δ8.22 (s, 1H), 4.38-4.28 (m, 1H), 4.15 (dd, J=3.2, 10.8 Hz, 2H), 3.59-3.49 (m, 2H), 2.19-2.00 (m, 4H).

Three reactions were run in parallel on the same scale. To a solution of 3-chloro-4-nitro-1-(tetrahydro-2H-pyran-4-yl)-1H-pyrazole (2.2 g, 9.5 mmol) in THF (100 mL) was added LiHMDS (28.49 mL, 1M in THF) in a dropwise manner at −78° C. After stirring for 0.5 h at −78° C. a solution of I$_2$ (7.23 g, 28.5 mmol) in THF (20 mL) was added in a dropwise manner. The reaction mixture was stirred at −78° C. for 1.5 h. The reaction was quenched with saturated aqueous NH$_4$Cl (50 mL) and extracted with EtOAc (5×50 mL). The combined organic layers were washed with saturated aqueous Na$_2$SO$_3$ (3×50 mL), dried over Na$_2$SO$_4$, and concentrated under reduced pressure. The residue from the three reactions were combined and purified by chromatography on silica gel (eluent: petroleum ether:EtOAc 80:20→70:30) to afford 3-chloro-5-iodo-4-nitro-1-(tetrahydro-2H-pyran-4-yl)-1H-pyrazole (8.6 g) for the three reactions of sufficient purity for the subsequent step. $^1$H NMR (CDCl$_3$, 400 MHz) δ4.68-4.58 (m, 1H), 4.17-4.14 (m, 2H), 3.60-3.51 (m, 2H), 2.36-2.23 (m, 2H), 1.90 (dd, J=2.4, 12.8 Hz, 2H).

Four reactions were run in parallel on the same scale. A mixture of 3-chloro-5-iodo-4-nitro-1-(tetrahydro-2H-pyran-4-yl)-1H-pyrazole (1.15 g, 3.22 mmol), cyclopropylboronic acid (553 mg, 6.43 mmol), Pd$_2$(dba)$_3$ (185 mg, 0.20 mmol), PCy$_3$ (90 mg, 0.32 mmol), and K$_2$CO$_3$ (1.33 g, 9.65 mmol) in DMF (10 mL) was stirred at 140° C. for 2 h using a microwave reactor. The reaction mixture was quenched with water (40 mL) and extracted with EtOAc (3×50 mL). The combined organic layers were washed with brine (3×60 mL), dried over Na$_2$SO$_4$, and concentrated under reduced pressure. The residues from the four reactions were combined and purified by chromatography on silica gel (eluent: petroleum ether:EtOAc 80:20→70:30) followed by preparative HPLC (Instrument: Gilson GX-281 Liquid Handler, SHIMADZU LC-8A; Column: Phenomenex C18 150×40 mm×5 μm; Mobile Phase A: water (NH$_3$H$_2$O+NH$_4$HCO$_3$), Mobile phase B: MeCN; Gradient: B from 26% to 56% in 10 min then hold at 100% for 2 min; Flow Rate (mL/min): 60; Column temperature: 30° C.; Wavelength: 220 nm 254 nm basic condition) to afford 3-chloro-5-cyclopropyl-4-nitro-1-(tetrahydro-2H-pyran-4-yl)-1H-pyrazole (2 g) for the four reactions of sufficient purity for the next step. $^1$H NMR (CDCl$_3$, 400 MHz) δ4.77-4.68 (m, 1H), 4.15 (dd, J=4.0, 11.2 Hz, 2H), 3.58-3.49 (m, 2H), 2.41-2.28 (m, 2H), 1.92-1.83 (m, 1H), 1.83-1.75 (m, 2H), 1.34-1.27 (m, 2H), 0.81-0.75 (m, 2H).

A mixture of 3-chloro-5-cyclopropyl-4-nitro-1-(tetrahydro-2H-pyran-4-yl)-1H-pyrazole (2.9 g, 10.67 mmol), and KOH (8.98 g, 160.10 mmol) in H$_2$O (50 mL) was degassed and purged with N$_2$ (×3), and then the mixture was stirred at 140° C. for 16 h. The mixture was acidified with concentrated HCl to pH=3 and extracted with EtOAc (3×100 mL). The combined organic layers were washed with brine (3×150 mL), dried over Na$_2$SO$_4$, and concentrated under reduced pressure to afford 5-cyclopropyl-4-nitro-1-(tetrahydro-2H-pyran-4-yl)-1H-pyrazol-3-ol (1.13 g) of sufficient purity for the subsequent step. $^1$H NMR (CDCl$_3$, 400 MHz) δ 8.62 (br s, 1H), 4.71-4.61 (m, 1H), 4.14 (dd, J=5.2, 12.0 Hz, 2H), 3.57-3.47 (m, 2H), 2.42-2.29 (m, 2H), 1.87-1.78 (m, 1H), 1.74 (dd, J=3.2, 12.8 Hz, 2H), 1.35-1.28 (m, 2H), 0.91-0.84 (m, 2H). LC-MS (method C) (m/z)=254.2 (MH)$^+$ t$_R$=1.59 minutes.

To a solution of 5-cyclopropyl-4-nitro-1-(tetrahydro-2H-pyran-4-yl)-1H-pyrazol-3-ol (200 mg, 0.79 mmol), 3-(3,6-dichloro-1H-pyrazolo[3,4-d]pyrimidin-1-yl)propan-1-ol (195 mg, 0.79 mmol, prepared as described previously), and PPh$_3$ (621 mg, 2.37 mmol) in THF (10 mL) was added DIAD (479 mg, 2.37 mmol) in a dropwise manner at 0° C. The mixture was stirred at 20° C. for 16 h. The mixture was concentrated under reduced pressure. The residue was purified by chromatography on silica gel (eluent: petroleum ether:EtOAc 80:20→70:30) to afford 3,6-dichloro-1-(3-((5-cyclopropyl-4-nitro-1-(tetrahydro-2H-pyran-4-yl)-1H-pyrazol-3-yl)oxy)propyl)-1H-pyrazolo[3,4-d]pyrimidine (140 mg) of sufficient purity for the subsequent step. LC-MS (method B) (m/z)=428.1 (MH)$^+$ t$_R$=0.87 minutes.

Intermediate: 1-(3-((1-((2-Oxabicyclo[2.1.1]hexan-1-yl)methyl)-5-methyl-4-nitro-1H-pyrazol-3-yl)oxy) propyl)-3,6-dichloro-1H-pyrazolo[3,4-d]pyrimidine

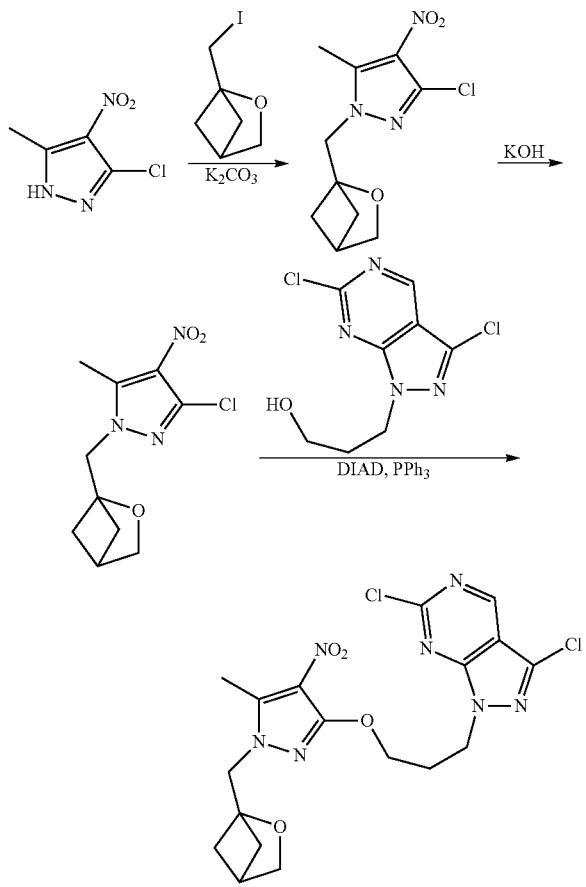

A mixture of 1-(iodomethyl)-2-oxabicyclo[2.1.1]hexane (17.93 g, 80.02 mmol), 3-chloro-5-methyl-4-nitro-1H-pyrazole (10.8 g, 66.9 mmol), and K$_2$CO$_3$ (27.7 g, 201 mmol) in MeCN (350 mL) was stirred at 70° C. for 16 h. The mixture was filtered and concentrated under reduced pressure. The residue was purified by chromatography on silica gel (eluent: petroleum ether:EtOAc 100:0→70:30) to afford 1-((2-oxabicyclo[2.1.1]hexan-1-yl)methyl)-3-chloro-5-methyl-4-nitro-1H-pyrazole (8.4 g) of sufficient purity for the subsequent step. $^1$H NMR (CDCl$_3$, 400 MHz) δ4.40 (s, 2H), 3.74 (s, 2H), 2.98-2.92 (m, 1H), 2.71 (s, 3H), 1.87-1.79 (m, 2H), 1.48-1.44 (m, 2H).

To a solution of 1-((2-oxabicyclo[2.1.1]hexan-1-yl)methyl)-3-chloro-5-methyl-4-nitro-1H-pyrazole (1 g, 3.88 mmol) in H$_2$O (80 mL) was added KOH (4.35 g, 77.6 mmol). The mixture was stirred at 120° C. for 23 h. Then additional KOH (1.58 g, 28.2 mmol) was added and the mixture was stirred at 140° C. for 40 h. The mixture was adjusted to pH~2 with concentrated aqueous HCl and extracted with EtOAc (3×50 mL). The combined organic layers were dried over Na$_2$SO$_4$, filtered, and concentrated under reduced pressure to afford 1-((2-oxabicyclo[2.1.1]hexan-1-yl)methyl)-5-methyl-4-nitro-1H-pyrazol-3-ol (880 mg) of sufficient purity for the subsequent step. $^1$H NMR (DMSO-d$_6$, 400 MHz) δ11.37 (s, 1H), 4.30 (s, 2H), 3.63 (s, 2H), 2.86 (t, J=6.4 Hz, 1H), 2.53 (s, 3H), 1.875-1.75 (m, 2H), 1.40-1.27 (m, 2H).

To a solution of 1-((2-oxabicyclo[2.1.1]hexan-1-yl)methyl)-5-methyl-4-nitro-1H-pyrazol-3-ol (200 mg, 0.84 mmol) and 3-(3,6-dichloro-1H-pyrazolo[3,4-d]pyrimidin-1-yl)propan-1-ol (248 mg, 1.00 mmol, prepared as described previously) in THF (6 mL) was added DIAD (686 mg, 3.39 mmol) and PPh$_3$ (877 mg, 3.34 mmol). The mixture was stirred at 20° C. for 16 h. The mixture was concentrated under reduced pressure. The residue was purified by chromatography on silica gel (eluent: petroleum ether:EtOAc 100:0→50:50) to afford 1-(3-((1-((2-oxabicyclo[2.1.1]hexan-1-yl)methyl)-5-methyl-4-nitro-1H-pyrazol-3-yl)oxy)propyl)-3,6-dichloro-1H-pyrazolo[3,4-d]pyrimidine (230 mg) of sufficient purity for the subsequent step.

Intermediate: 3,6-Dichloro-1-(3-((5-methyl-1-((3-methyloxetan-3-yl)methyl)-4-nitro-1H-pyrazol-3-yl)oxy)propyl)-1H-pyrazolo[3,4-d]pyrimidine

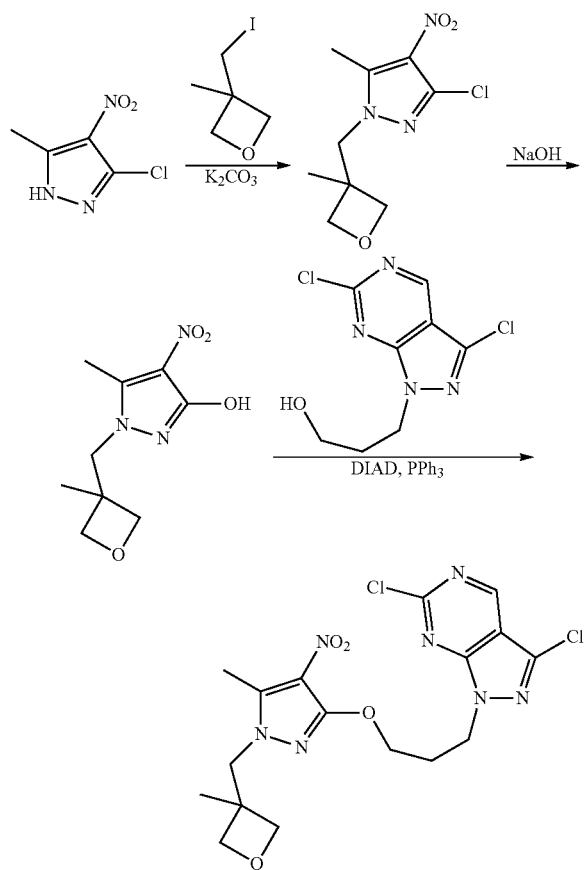

To a solution of 3-chloro-5-methyl-4-nitro-1H-pyrazole (10 g, 61.9 mmol) in MeCN (100 mL) were added 3-(iodomethyl)-3-methyl-oxetane (14.44 g, 68.1 mmol) and K$_2$CO$_3$ (25.7 g, 186 mmol). The reaction mixture was stirred at 80° C. for 16 h. The reaction mixture was concentrated under reduced pressure. The mixture was diluted with water (30 mL) and extracted with EtOAc (3×30 mL). The combined organic layers were washed with brine (3×30 mL), dried over Na$_2$SO$_4$ and concentrated under reduced pressure. The residue was purified by chromatography on silica gel (eluent: petroleum ether:EtOAc 80:20→75:25) to afford 3-chloro-5-methyl-1-((3-methyloxetan-3-yl)methyl)-4-nitro-1H-pyrazole (6.3 g) of sufficient purity for the subsequent step. $^1$H NMR (CDCl$_3$, 400 MHz) δ4.73 (d, J=6.4 Hz, 2H), 4.44 (d, J=6.4 Hz, 2H), 4.29 (s, 2H), 2.67 (s, 3H), 1.28 (s, 3H).

To a solution of 3-chloro-5-methyl-1-((3-methyloxetan-3-yl)methyl)-4-nitro-1H-pyrazole (500 mg, 2.04 mmol) in H$_2$O (25 mL) was added NaOH (2.44 g, 61.1 mmol). The mixture was stirred at 140° C. for 1.5 h. The reaction mixture was extracted with EtOAc (3×100 mL), the combined organic layers were discarded. The water phase was adjusted to pH=3 with aqueous HCl (12M), extracted with EtOAc (3×100 mL), dried over Na$_2$SO$_4$, and concentrated under reduced pressure to afford 5-methyl-1-((3-methyloxetan-3-yl)methyl)-4-nitro-1H-pyrazol-3-ol (100 mg) of sufficient purity for the subsequent step. $^1$H NMR (CDCl$_3$, 400 MHz) δ4.78 (d, J=6.4 Hz, 2H), 4.37 (d, J=6.4 Hz, 2H), 4.22 (s, 2H), 2.59 (s, 3H), 1.22 (s, 3H).

To a solution of 5-methyl-1-((3-methyloxetan-3-yl)methyl)-4-nitro-1H-pyrazol-3-ol (140 mg, 0.62 mmol), 3-(3,6-dichloropyrazolo[3,4-d]pyrimidin-1-yl)propan-1-ol (152 mg, 0.62 mmol, prepared as described previously), and PPh$_3$ (485 mg, 1.85 mmol) in THF (4 mL) was added DIAD (374 mg, 1.85 mmol) at 0° C. The mixture was stirred at 20° C. for 15 h. The reaction mixture was concentrated under reduced pressure. The residue was purified by chromatography on silica gel (eluent: petroleum ether:EtOAc 100:0→40:60) and further purified by preparative HPLC (Instrument: Gilson GX-281 Liquid Handler, Gilson 322 Pump, Gilson 156 UV Detector; Column: Xtimate C18 150×40 mm×5 um; Mobile Phase A: water (NH$_3$H$_2$O), Mobile phase B: MeCN; Gradient: B from 38% to 68% in 8 min then hold at 100% for 1 min; Flow Rate (mL/min): 60; Column temperature: 30° C.; Wavelength: 220 nm 254 nm) to afford 3,6-dichloro-1-(3-((5-methyl-1-((3-methyloxetan-3-yl)methyl)-4-nitro-1H-pyrazol-3-yl)oxy)propyl)-1H-pyrazolo[3,4-d]pyrimidine (75 mg) of sufficient purity for the subsequent step. $^1$H NMR (CDCl$_3$, 400 MHz) δ 8.96 (s, 1H), 4.70 (d, J=6.4 Hz, 2H), 4.64 (t, J=6.4 Hz, 2H), 4.37 (d, J=6.4 Hz, 2H), 4.30 (t, J=5.6 Hz, 2H), 4.11 (s, 2H), 2.59 (s, 3H), 2.49-2.44 (m, 2H), 1.22 (s, 3H).

Intermediate: 3,6-Dichloro-1-(3-((5-(methyl-d$_3$)-4-nitro-1-(tetrahydro-2H-pyran-4-yl)-1H-pyrazol-3-yl)oxy)propyl)-1H-pyrazolo[3,4-d]pyrimidine

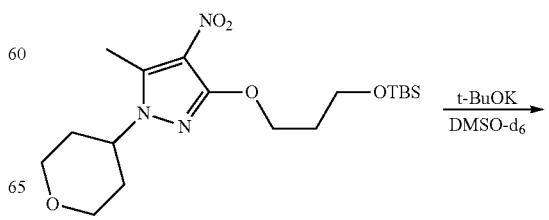

-continued

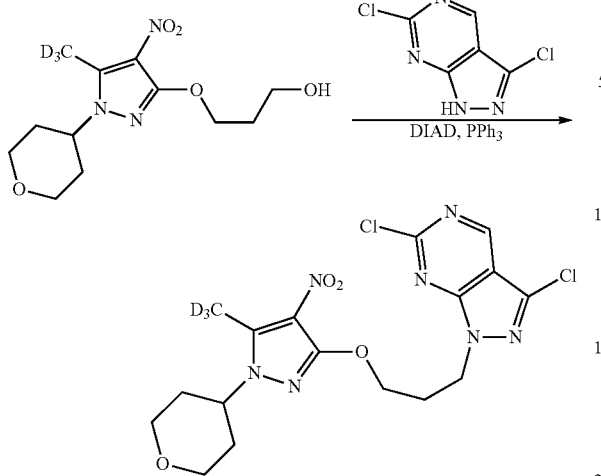

To a dry vial containing 3-(3-((tert-butyldimethylsilyl)oxy)propoxy)-5-methyl-4-nitro-1-(tetrahydro-2H-pyran-4-yl)-1H-pyrazole (200 mg, 0.501 mmol) in DMSO-$d_6$ (8 mL) under an atmosphere of argon was added potassium tert-butoxide (28.1 mg, 0.250 mmol). The solution turned dark orange. The reaction mixture was stirred at 30° C. for 72 h. The mixture was diluted with deuterium oxide (10 mL) and was extracted with EtOAc (3×25 mL). The combined organics were dried over sodium sulfate, filtered, and concentrated under reduced pressure. The residue was dried thoroughly via freeze drying to remove residual solvent to afford 3-((5-(methyl-$d_3$)-4-nitro-1-(tetrahydro-2H-pyran-4-yl)-1H-pyrazol-3-yl)oxy)propan-1-ol (140 mg) of sufficient purity for the next step. $^1$H NMR (CDCl$_3$, 600 MHz) δ4.49 (t, J=5.9 Hz, 2H), 4.23-4.17 (m, 1H), 4.13-4.08 (m, 2H), 3.86-3.80 (m, 2H), 3.54-3.47 (m, 2H), 2.55 (t, J=6.0 Hz, 1H), 2.33-2.23 (m, 2H), 2.10-2.03 (m, 2H), 1.78-1.73 (m, 2H).

A solution of DIAD (113 μL, 0.583 mmol) in THF (7 mL) was cooled to 0° C. under an atmosphere of argon. PPh$_3$ (153 mg, 0.583 mmol) (on resin, ~3 mmol/g: employed 194 mg=0.583 mmol) was added and the mixture was stirred for 10 minutes. 3,6-Dichloro-1H-pyrazolo[3,4-d]pyrimidine (118 mg, 0.624 mmol) was then added followed by a solution of 3-((5-(methyl-$d_3$)-4-nitro-1-(tetrahydro-2H-pyran-4-yl)-1H-pyrazol-3-yl)oxy)propan-1-ol (120 mg, 0.416 mmol) in THF (1.5 mL). The reaction mixture was stirred at 0° C. for 2 minutes and then at room temperature overnight. The reaction mixture was filtered and the filtrate was concentrated under reduced pressure. The residue was purified by chromatography on silica gel (eluent: petroleum ether:EtOAc 100:0→20:80) to afford 3,6-dichloro-1-(3-((5-(methyl-$d_3$)-4-nitro-1-(tetrahydro-2H-pyran-4-yl)-1H-pyrazol-3-yl)oxy)propyl)-1H-pyrazolo[3,4-d]pyrimidine (133 mg) as a solid of sufficient purity for the subsequent step. $^1$H NMR (CDCl$_3$, 600 MHz) δ 8.95 (s, 1H), 4.64 (t, J=6.4 Hz, 2H), 4.35 (t, J=5.8 Hz, 2H), 4.20-4.13 (m, 1H), 4.12-4.07 (m, 2H), 3.53-3.44 (m, 2H), 2.51-2.44 (m, 2H), 2.23-2.14 (m, 2H), 1.76-1.68 (m, 2H).

Intermediate: 3,6-Dichloro-1-(3-((5-methyl-1-(3-methyloxetan-3-yl)-4-nitro-1H-pyrazol-3-yl)oxy)propyl)-1H-pyrazolo[3,4-d]pyrimidine

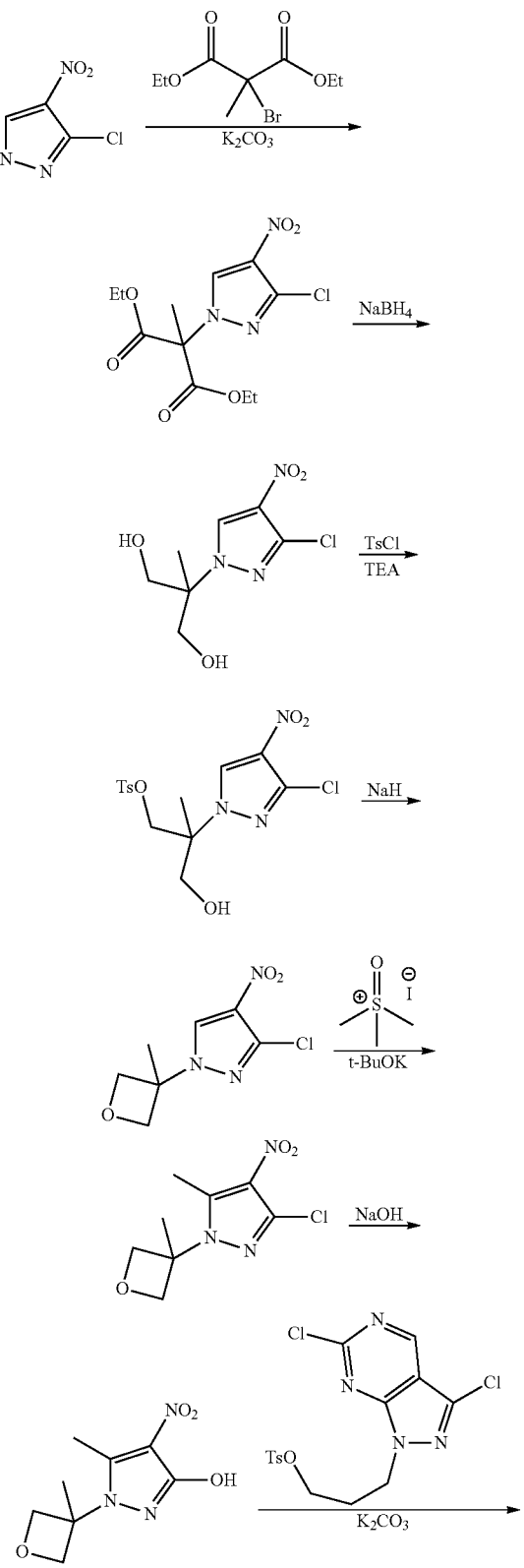

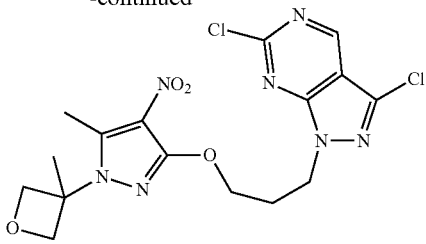

To a solution of 3-chloro-4-nitro-1H-pyrazole (5 g, 33.9 mmol) in DMF (50 mL) was added diethyl 2-bromo-2-methylmalonate (17.16 g, 67.79 mmol) and $K_2CO_3$ (9.39 g, 68.0 mmol) and the reaction was stirred at 100° C. for 12 h. The mixture was diluted with $H_2O$ (50 mL) and extracted with EtOAc (2×50 mL). The organic phase was washed with brine (2×50 mL), dried over $Na_2SO_4$, and concentrated under reduced pressure. The residue was purified by chromatography on silica gel (eluent: petroleum ether:EtOAc 100:0→70:30) to afford diethyl 2-(3-chloro-4-nitro-1H-pyrazol-1-yl)-2-methylmalonate (7.25 g) of sufficient purity for the subsequent step. $^1$H NMR ($CDCl_3$, 400 MHz) δ 8.60 (s, 1H), 4.33 (q, J=7.2 Hz, 4H), 2.12 (s, 3H), 1.31 (t, J=7.2 Hz, 6H).

To a solution of diethyl 2-(3-chloro-4-nitro-1H-pyrazol-1-yl)-2-methylmalonate (3.6 g, 11.3 mmol) in MeOH (80 mL) was added $NaBH_4$ (854 mg, 22.6 mmol) in portions at 0° C. and the reaction was stirred at 0° C. for 1 h. The mixture was concentrated under reduced pressure. The residue was diluted with $H_2O$ (10 mL), saturated aqueous $NH_4Cl$ (10 mL), and extracted with EtOAc (3×20 mL). The organic phase was washed with brine (20 mL), dried over $Na_2SO_4$, and concentrated under reduced pressure. The residue was purified by chromatography on silica gel (eluent: petroleum ether:EtOAc 100:0→20:80) to afford 2-(3-chloro-4-nitro-1H-pyrazol-1-yl)-2-methylpropane-1,3-diol (1.55 g) of sufficient purity for the subsequent step. $^1$H NMR ($CDCl_3$, 400 MHz) δ 8.48 (s, 1H), 4.01 (d, J=4.4 Hz, 4H), 2.83-2.72 (m, 2H), 1.53 (s, 3H).

To a solution of 2-(3-chloro-4-nitro-1H-pyrazol-1-yl)-2-methylpropane-1,3-diol (1.55 g, 6.58 mmol) in DCM (20 mL) was added TsCl (1.32 g, 6.91 mmol) and TEA (998 mg, 9.87 mmol), the reaction was stirred at 20° C. for 12 h. The reaction was concentrated under reduced pressure. The residue was purified by chromatography on silica gel (eluent: petroleum ether:EtOAc 100:0→70:30) to afford 2-(3-chloro-4-nitro-1H-pyrazol-1-yl)-3-hydroxy-2-methylpropyl 4-methylbenzenesulfonate (1.5 g) of sufficient purity for the subsequent step. $^1$H NMR ($CDCl_3$, 400 MHz) δ 8.22 (s, 1H), 7.65 (d, J=8.4 Hz, 2H), 7.32 (d, J=8.4 Hz, 2H), 4.40 (d, J=10.8 Hz, 1H), 4.27 (d, J=10.8 Hz, 1H), 3.95 (s, 2H), 2.64 (br s, 1H), 2.46 (s, 3H), 1.62 (s, 3H).

To a solution of 2-(3-chloro-4-nitro-1H-pyrazol-1-yl)-3-hydroxy-2-methylpropyl 4-methylbenzenesulfonate (1.1 g, 2.8 mmol) in THF (20 mL) was added NaH (170 mg, 4.25 mmol, 60% in mineral oil) at 0° C. and the reaction was stirred at 70° C. for 2 h. The mixture was quenched with $H_2O$ (20 mL) at 0° C. and extracted with EtOAc (2×20 mL). The combined organic phases were washed with brine (20 mL), dried over $Na_2SO_4$, and concentrated under reduced pressure. The residue was purified by chromatography on silica gel (eluent: petroleum ether:EtOAc 100:0→60:40) to afford 3-chloro-1-(3-methyloxetan-3-yl)-4-nitro-1H-pyrazole (360 mg) of sufficient purity for the subsequent step. $^1$H NMR ($CDCl_3$, 400 MHz) δ 8.32 (s, 1H), 5.13 (d, J=6.4 Hz, 2H), 4.68 (d, J=6.8 Hz, 2H), 1.99 (s, 3H).

To a solution of trimethylsulfoxonium iodide (1.76 g, 8.00 mmol) in DMSO (7 mL) was added t-BuOK (897 mg, 7.99 mmol) at 25° C. and the reaction was stirred at 25° C. for 1 h. Then a solution of 3-chloro-1-(3-methyloxetan-3-yl)-4-nitro-1H-pyrazole (870 mg, 4.00 mmol) in DMSO (3 mL) was added dropwise at 35° C. and the mixture was stirred at 35° C. for 12 h. The mixture was diluted with $H_2O$ (10 mL) and extracted with EtOAc (4×10 mL). The organic phase was washed with brine (10 mL), dried over $Na_2SO_4$, and concentrated under reduced pressure. The residue was purified by chromatography on silica gel (eluent: petroleum ether:EtOAc 100:0→60:40) to afford 3-chloro-5-methyl-1-(3-methyloxetan-3-yl)-4-nitro-1H-pyrazole (605 mg) of sufficient purity for the subsequent step. LC-MS (method B) (m/z)=232.0 $(MH)^+$ $t_R$=0.69 minutes.

A mixture of 3-chloro-5-methyl-1-(3-methyloxetan-3-yl)-4-nitro-1H-pyrazole (600 mg, 2.59 mmol) in a solution of NaOH (1.20 g, 30 mmol) in $H_2O$ (15 mL) was stirred at 100° C. for 4 h. The reaction was cooled to room temperature (20° C.) and acidified with saturated aqueous $KHSO_4$ to pH 5. The solid was filtered, washed with $H_2O$ (2×1 mL) and dried to afford 5-methyl-1-(3-methyloxetan-3-yl)-4-nitro-1H-pyrazol-3-ol (405 mg) of sufficient purity for the subsequent step, which was used in the next step directly. $^1$H NMR ($CDCl_3$, 400 MHz) δ 8.40 (br s, 1H), 5.19 (d, J=6.8 Hz, 2H), 4.59 (d, J=7.2 Hz, 2H), 2.46 (s, 3H), 1.87 (s, 3H).

5-methyl-1-(3-methyloxetan-3-yl)-4-nitro-1H-pyrazol-3-ol (150 mg, 0.7 mmol), 3-(3,6-dichloro-1H-pyrazolo[3,4-d]pyrimidin-1-yl)propyl 4-methylbenzenesulfonate (283 mg, 0.71 mmol, prepared as described previously) and $K_2CO_3$ (292 mg, 2.11 mmol) were taken up into a sealed tube in DMF (3 mL) and the reaction was stirred at 85° C. for 2 h. The mixture was diluted with $H_2O$ (3 mL) and extracted with EtOAc (2×3 mL). The organic phase was washed with brine (2×3 mL), dried over $Na_2SO_4$, and concentrated under reduced pressure. The residue was purified by chromatography on silica gel (eluent: petroleum ether:EtOAc 100:0→50:50) to afford 3,6-dichloro-1-(3-((5-methyl-1-(3-methyloxetan-3-yl)-4-nitro-1H-pyrazol-3-yl)oxy)propyl)-1H-pyrazolo[3,4-d]pyrimidine (201 mg) of sufficient purity for the subsequent step. $^1$H NMR ($CDCl_3$, 400 MHz) δ 8.96 (s, 1H), 5.11 (d, J=6.4 Hz, 2H), 4.65 (t, J=6.4 Hz, 2H), 4.54 (d, J=7.2 Hz, 2H), 4.31 (t, J=5.6 Hz, 2H), 2.51-2.44 (m, 2H), 2.41 (s, 3H), 1.80 (s, 3H).

Intermediate: 3,6-Dichloro-1-(3-((5-(methyl-ds)-4-nitro-1-(tetrahydro-2H-pyran-4-yl-4-d)-1H-pyrazol-3-yl)oxy)propyl)-1H-pyrazolo[3,4-d]pyrimidine

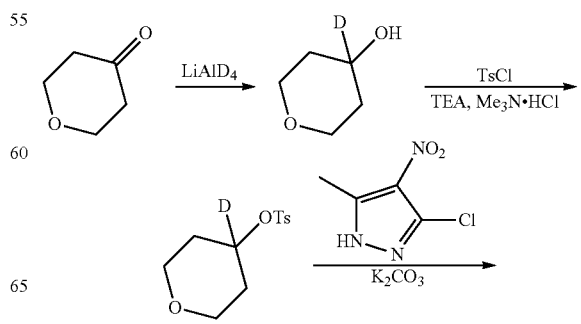

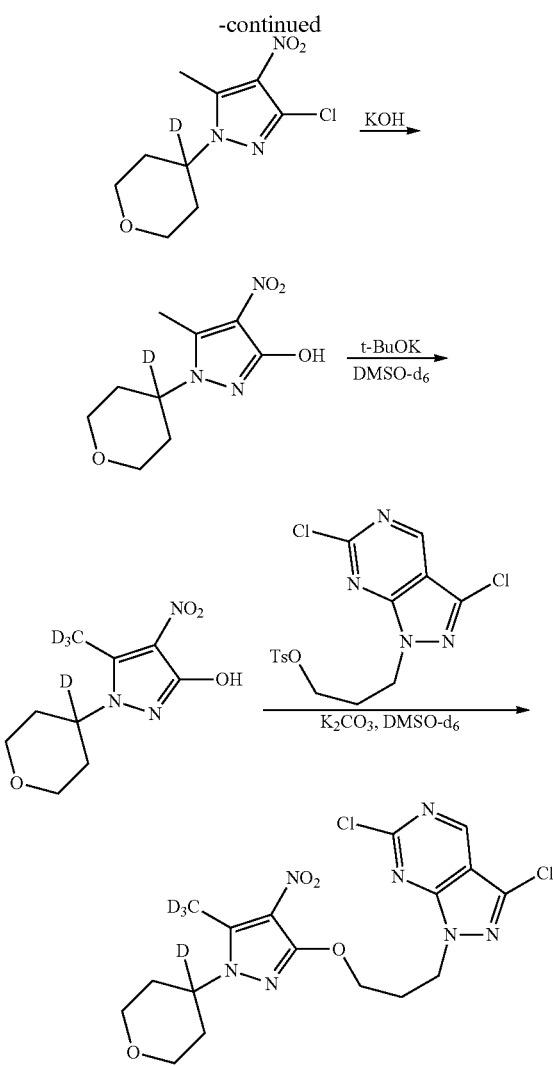

A mixture of dihydro-2H-pyran-4(3H)-one (17 g, 170 mmol) in THF (200 mL) was degassed and purged with N₂ (×3), lithium aluminum deuteride (9.67 g, 255 mmol) was added portionwise at 0° C. and then the mixture was stirred at 0° C. for 1 h. The reaction mixture was quenched with water (10 mL), followed by aqueous 10% NaOH (30 mL) and water (10 mL). The mixture was filtered, and the filtrate was concentrated to afford tetrahydro-2H-pyran-4-d-4-ol (17.5 g) of sufficient purity for the subsequent step. ¹H NMR (CDCl₃, 400 MHz) δ 3.99-3.91 (m, 2H), 3.48-3.39 (m, 2H), 1.94-1.86 (m, 2H), 1.61-1.49 (m, 2H).

To a solution of tetrahydro-2H-pyran-4-d-4-ol (15 g, 145 mmol), TEA (22.08 g, 218 mmol) and N,N-dimethylmethanamine hydrochloride (1.39 g, 14.5 mmol) in DCM (450 mL) was added TsCl (33.3 g, 175 mmol) at 0° C. The mixture was stirred at 20° C. for 17 h. The reaction mixture was concentrated under reduced pressure. The residue was purified by chromatography on silica gel (eluent: petroleum ether:EtOAc 100:0→80:20) to afford tetrahydro-2H-pyran-4-yl-4-d 4-methylbenzenesulfonate (30.9 g) of sufficient purity for the subsequent step. ¹H NMR (CDCl₃, 400 MHz) δ 7.81 (d, J=8.4 Hz, 2H), 7.35 (d, J=8.4 Hz, 2H), 3.93-3.80 (m, 2H), 3.52-3.43 (m, 2H), 2.45 (s, 3H), 1.89-1.82 (m, 2H), 1.79-1.70 (m, 2H).

To a solution of 5-chloro-3-methyl-4-nitro-1H-pyrazole (16 g, 99.0 mmol) and tetrahydro-2H-pyran-4-yl-4-d 4-methylbenzenesulfonate (30.9 g, 120 mmol) in DMF (300 mL) was added K₂CO₃ (41.1 g, 297 mmol). The mixture was stirred at 80° C. for 20 h. The reaction mixture was concentrated under reduced pressure. The residue was purified by chromatography on silica gel (eluent: petroleum ether: EtOAc 100:0→80:20) three times to afford 3-chloro-5-methyl-4-nitro-1-(tetrahydro-2H-pyran-4-yl-4-d)-1H-pyrazole (11 g) of sufficient purity for the subsequent step. ¹H NMR (CDCl₃, 400 MHz) δ 4.18-4.12 (m, 2H), 3.57-3.49 (m, 2H), 2.70 (s, 3H), 2.38-2.28 (m, 2H), 1.85-1.79 (m, 2H).

To a solution of 3-chloro-5-methyl-4-nitro-1-(tetrahydro-2H-pyran-4-yl-4-d)-1H-pyrazole (11 g, 44.6 mmol) in H₂O (150 mL) was added KOH (25 g, 446 mmol). The mixture was stirred at 140° C. for 22 h. The mixture was acidified with aqueous HCl (12 M), pH=3. The precipitate was filtered. The filter cake was dried to afford 5-methyl-4-nitro-1-(tetrahydro-2H-pyran-4-yl-4-d)-1H-pyrazol-3-ol (8 g). The filtrate was extracted with EtOAc (3×300 mL). The combined organic layers were washed with brine (3×300 mL), dried over Na₂SO₄, and concentrated to afford 5-methyl-4-nitro-1-(tetrahydro-2H-pyran-4-yl-4-d)-1H-pyrazol-3-ol (2 g). The two crops of material were combined to afford 5-methyl-4-nitro-1-(tetrahydro-2H-pyran-4-yl-4-d)-1H-pyrazol-3-ol (10 g) of sufficient purity for the subsequent step. ¹H NMR (CDCl₃, 400 MHz) δ 11.37 (br s, 1H), 3.97-3.90 (m, 2H), 3.50-3.42 (m, 2H), 2.59 (s, 3H), 1.99-1.89 (m, 2H), 1.79-1.70 (m, 2H).

To a solution of 5-methyl-4-nitro-1-(tetrahydro-2H-pyran-4-yl-4-d)-1H-pyrazol-3-ol (6.0 g, 26 mmol) in DMSO-d₆ (240 mL) was added t-BuOK (3.25 g, 28.9 mmol). The mixture was stirred at 30° C. for 64 h. The mixture was diluted with deuterium oxide (100 mL) and adjusted to pH=3 with aqueous HCl (2M). The aqueous phase was extracted with EtOAc (6×300 mL). The combined organic layers were washed with brine (2×200 mL), dried over Na₂SO₄, and concentrated. Water (100 mL) was added to the residue and the mixture was lyophilized to afford 5-(methyl-d₃)-4-nitro-1-(tetrahydro-2H-pyran-4-yl-4-d)-1H-pyrazol-3-ol (5 g) of sufficient purity for the subsequent step. ¹H NMR (CDCl₃, 400 MHz) δ 11.36 (br s, 1H), 3.97-3.89 (m, 2H), 3.51-3.41 (m, 2H), 1.99-1.89 (m, 2H), 1.79-1.69 (m, 2H). LC-MS: t$_R$=1.653 min (Method D), m/z=232.1 [M+H]⁺.

To a solution of 3-(3,6-dichloro-1H-pyrazolo[3,4-d]pyrimidin-1-yl)propyl 4-methylbenzenesulfonate (760 mg, 1.89 mmol, prepared as described previously) in DMSO-d₆ (20 mL) was added K₂CO₃ (288 mg, 2.08 mmol) and 5-(methyl-d₃)-4-nitro-1-(tetrahydro-2H-pyran-4-yl-4-d)-1H-pyrazol-3-ol (438 mg, 1.89 mmol). The mixture was stirred at 80° C. for 1 h. The reaction mixture was diluted with aqueous HCl (2 M), pH=6~7, and extracted with EtOAc (3×30 mL). The combined organic layers were washed with brine (3×40 mL), dried over Na₂SO₄, and concentrated under reduced pressure. The residue was purified by chromatography on silica gel (eluent: petroleum ether:EtOAc 100:0→50:50) to afford 3,6-dichloro-1-(3-((5-(methyl-d₃)-4-nitro-1-(tetrahydro-2H-pyran-4-yl-4-d)-1H-pyrazol-3-yl)oxy)propyl)-1H-pyrazolo[3,4-d]pyrimidine (540 mg) of sufficient purity for the subsequent step. ¹H NMR (CDCl₃, 400 MHz) δ 8.94 (s, 1H), 4.64 (t, J=6.4 Hz, 2H), 4.34 (t, J=6.0 Hz, 2H), 4.10-4.05 (m, 2H), 3.53-3.44 (m, 2H), 2.50-2.42 (m, 2H), 2.22-2.12 (m, 2H), 1.76-1.67 (m, 2H).

Intermediate: 3,6-Dichloro-1-(3-((5-(1-fluorocyclopropyl)-4-nitro-1-(tetrahydro-2H-pyran-4-yl)-1H-pyrazol-3-yl)oxy)propyl)-1H-pyrazolo[3,4-d]pyrimidine

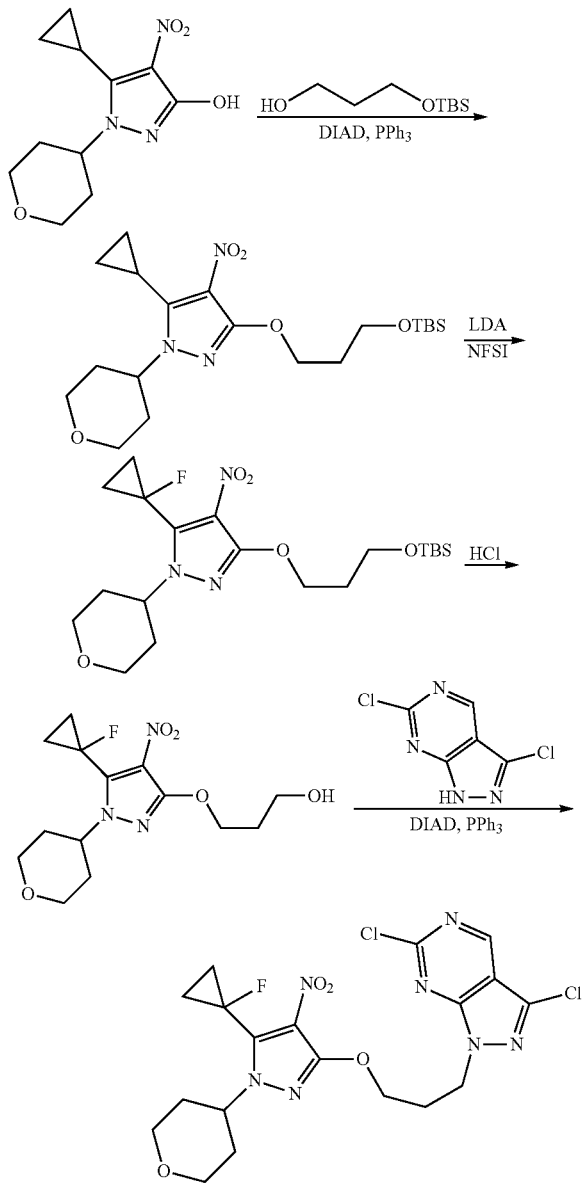

A solution of DIAD (576 μL, 2.96 mmol) in THF (60 mL) was cooled to 0° C. under an atmosphere of argon. PPh₃ (~3 mmol/g on resin) (777 mg, 2.96 mmol, employed 1.0 g resin) was added in portions and the mixture was stirred for 15 minutes. 5-Cyclopropyl-4-nitro-1-(tetrahydro-2H-pyran-4-yl)-1H-pyrazol-3-ol (500 mg, 1.97 mmol, prepared as described previously) was then added followed by a solution of 3-((tert-butyldimethylsilyl)oxy)propan-1-ol (376 mg, 1.97 mmol) in THF (1 mL). The cooling bath was removed and the reaction mixture was stirred at room temperature for 3 h. The mixture was filtered and concentrated under reduced pressure. The residue was purified by chromatography on silica gel (eluent: petroleum ether:EtOAc 100:0→65:35) to afford 3-(3-((tert-butyldimethylsilyl)oxy) propoxy)-5-cyclopropyl-4-nitro-1-(tetrahydro-2H-pyran-4-yl)-1H-pyrazole (518 mg) of sufficient purity for the subsequent step. ¹H NMR (CDCl₃, 600 MHz) δ 4.66-4.59 (m, 1H), 4.38 (t, J=6.3 Hz, 2H), 4.15-4.09 (m, 2H), 3.79 (t, J=6.1 Hz, 2H), 3.55-3.48 (m, 2H), 2.34-2.25 (m, 2H), 2.04-1.98 (m, 2H), 1.85-1.79 (m, 1H), 1.74-1.68 (m, 2H), 1.26-1.21 (m, 2H), 0.88 (s, 9H), 0.78-0.73 (m, 2H), 0.04 (s, 6H).

A solution of 3-(3-((tert-butyldimethylsilyl)oxy) propoxy)-5-cyclopropyl-4-nitro-1-(tetrahydro-2H-pyran-4-yl)-1H-pyrazole (318 mg, 0.747 mmol), lithium chloride (158 mg, 3.74 mmol, dried overnight at 90° C. in vacuum oven) and N-Fluorobis(phenylsulfonyl)amine (530 mg, 1.68 mmol) in THF (20 mL) was cooled to −78° C. under an atmosphere of argon. LDA (1.5M in hexanes) (1.74 mL, 2.62 mmol) was added dropwise by syringe to form a dark orange solution.

Immediately following, was added a solution of N-Fluorobis(phenylsulfonyl)amine (707 mg, 2.24 mmol) in THF (2.5 mL) over the course of 20 seconds. The orange color was quenched during the addition. The mixture was stirred for 5 min. The mixture was quenched with water (~0.1 mL) and was concentrated to dryness. The residue was suspended DCM, filtered, and concentrated under reduced pressure. The residue was purified by chromatography on silica gel (eluent: petroleum ether:EtOAc 100:0→50:50) to afford 3-(3-((tert-butyldimethylsilyl)oxy)propoxy)-5-(1-fluorocyclopropyl)-4-nitro-1-(tetrahydro-2H-pyran-4-yl)-1H-pyrazole (204 mg) of sufficient purity for the subsequent step. ¹H NMR (CDCl₃, 500 MHz) δ 4.78-4.70 (m, 1H), 4.43 (t, J=6.3 Hz, 2H), 4.17-4.10 (m, 2H), 3.80 (t, J=6.0 Hz, 2H), 3.57-3.49 (m, 2H), 2.39-2.28 (m, 2H), 2.05-1.98 (m, 2H), 1.83-1.76 (m, 2H), 1.74-1.65 (m, 2H), 1.14-1.07 (m, 2H), 0.88 (s, 9H), 0.05 (s, 6H).

To a dry flask was added 3-(3-((tert-butyldimethylsilyl) oxy)propoxy)-5-(1-fluorocyclopropyl)-4-nitro-1-(tetrahydro-2H-pyran-4-yl)-1H-pyrazole (204 mg, 0.460 mmol), DCM (20 mL) and HCl (3M in diethyl ether) (1.61 mL, 3.22 mmol). The flask was flushed with argon and stirred overnight at room temperature. The reaction mixture was concentrated under reduced pressure. The residue was purified by chromatography on silica gel (eluent: petroleum ether: EtOAc 100:0→0:100) to afford 3-((5-(1-fluorocyclopropyl)-4-nitro-1-(tetrahydro-2H-pyran-4-yl)-1H-pyrazol-3-yl)oxy) propan-1-ol (108 mg) of sufficient purity for the subsequent step. ¹H NMR (CDCl₃, 600 MHz) δ 4.78-4.71 (m, 1H), 4.52 (t, J=5.9 Hz, 2H), 4.17-4.11 (m, 2H), 3.86 (t, J=5.6 Hz, 2H), 3.57-3.51 (m, 2H), 2.38-2.28 (m, 2H), 2.22 (br s, 1H), 2.11-2.05 (m, 2H), 1.84-1.77 (m, 2H), 1.73-1.66 (m, 2H), 1.15-1.08 (m, 2H).

A solution of DIAD (121 μL, 0.623 mmol) in THF (15 mL) was cooled to 0° C. under an atmosphere of argon. PPh₃ (on resin, ~3 mmol/g) (163 mg, 0.623 mmol, 207 mg resin used), was added and the mixture was stirred for 2 minutes. 3,6-Dichloro-1H-pyrazolo[3,4-d]pyrimidine (77.5 mg, 0.410 mmol) was then added followed by a solution of 3-((5-(1-fluorocyclopropyl)-4-nitro-1-(tetrahydro-2H-pyran-4-yl)-1H-pyrazol-3-yl)oxy)propan-1-ol (108 mg, 1.0 Eq, 328 μmol) in THF (1 mL). The cooling bath was removed and the reaction mixture was stirred for 2 h. The reaction mixture was filtered and the filtrate was concentrated under reduced pressure. The residue was purified by chromatography on silica gel (eluent: petroleum ether:EtOAc 100:0→0:100) to afford 3,6-dichloro-1-(3-((5-(1-fluorocyclopropyl)-4-nitro-1-(tetrahydro-2H-pyran-4-yl)-1H-pyrazol-3-yl)oxy)propyl)-1H-pyrazolo[3,4-d]pyrimidine (129 mg) of sufficient purity for the subsequent step. ¹H NMR (CDCl₃, 600 MHz) δ 8.95 (s, 1H), 4.75-4.68 (m, 1H), 4.65 (t, J=6.4 Hz, 2H), 4.41-4.36 (m, 2H), 4.13-4.08 (m, 2H), 3.56-3.49 (m, 2H), 2.50-2.44 (m, 2H), 2.27-2.18 (m, 2H), 1.81-1.75 (m, 2H), 1.73-1.66 (m, 2H), 1.15-1.09 (m, 2H).

Intermediate: 3,6-Dichloro-1-(3-((5-ethyl-4-nitro-1-(tetrahydro-2H-pyran-4-yl)-1H-pyrazol-3-yl)oxy)propyl)-1H-pyrazolo[3,4-d]pyrimidine

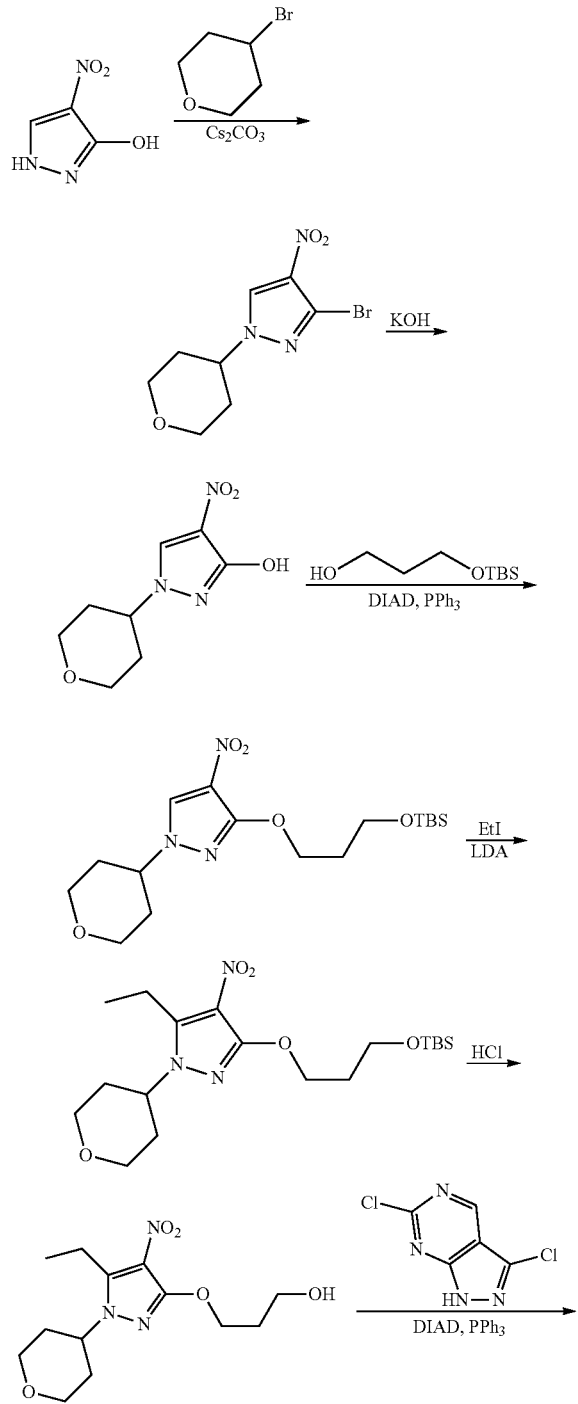

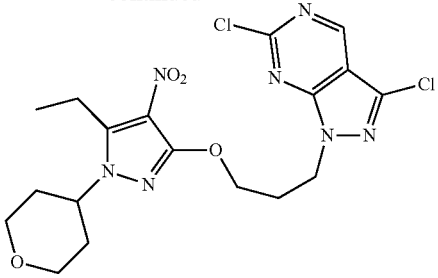

-continued

To a dry flask were added 3-bromo-4-nitro-1H-pyrazole (14.00 g, 72.93 mmol) and DMF (anhydrous) (150 mL). Cs₂CO₃ (59.4 g, 182 mmol) was added followed by 4-bromooxane (24.07 g, 146 mmol). The mixture was stirred at 80° C. for 16 h. The mixture was cooled to room temperature and water (120 mL) and EtOAc (150 mL) were added. The phases were separated, and the organic phase was washed with aqueous NH₄Cl (2×150 mL), dried over Na₂SO₄, and concentrated under reduced pressure. The residue was purified by chromatography on silica gel (eluent: petroleum ether:EtOAc 83:17) to afford 3-bromo-4-nitro-1-(oxan-4-yl)pyrazole (9.49 g) of sufficient purity for the subsequent step.

A mixture of 3-bromo-4-nitro-1-(oxan-4-yl)pyrazole (8.44 g, 30.6 mmol) and KOH (33.76 g, 601.7 mmol) in H₂O (330 mL) was stirred at 100° C. for 16 hours. The mixture was acidified to pH=3 with HCl (aq.), extracted with EtOAc (130 mL×3) and concentrated under reduced pressure. The residue was purified by chromatography on silica gel (eluent: petroleum ether:EtOAc 33:67) to afford 4-nitro-1-(oxan-4-yl)pyrazol-3-ol (5 g) of sufficient purity for the subsequent step.

To a stirred solution of 4-nitro-1-(oxan-4-yl)pyrazol-3-ol (5 g, 23 mmol) and 3-[(tertbutyldimethylsilyl)oxy]propan-1-ol (8.93 g, 46.9 mmol) in THF (100 mL) was added PPh₃ (12.30 g, 46.9 mmol) in one portion at room temperature under argon atmosphere. Then DIAD (9.48 g, 46.9 mmol) was added at 0° C. The resulting mixture was stirred for 2 h at room temperature. The reaction was quenched with water (15 mL) and extracted with EtOAc (2×25 mL). The combined organic layers were dried over Na₂SO₄ and concentrated under reduced pressure. The residue was purified by chromatography on silica gel (eluent: petroleum ether:EtOAc 83:17) to afford 3-{3-[(tert-butyldimethylsilyl)oxy]propoxy}-4-nitro-1-(oxan-4-yl)pyrazole (6 g) of sufficient purity for the subsequent step.

To a stirred solution of 3-{3-[(tert-butyldimethylsilyl)oxy]propoxy}-4-nitro-1-(oxan-4-yl)pyrazole (500 mg, 1.30 mmol) and 15-crown-5 (3.43 g, 15.6 mmol) in THF (25 mL) was added LDA (6.48 mL, 13.0 mmol, 2 M) dropwise at −78° C. The mixture was stirred for 60 minutes at −78° C. Then ethyl iodide (1.01 g, 6.49 mmol) was added and the resulting mixture was stirred for 2 h at −78° C. The reaction was quenched with aqueous NH₄Cl (25 mL) and the resulting mixture was extracted with EtOAc (3×30 mL). The combined organic layers were dried over Na₂SO₄, filtered, and concentrated under reduced pressure. The residue was purified by preparative TLC (eluent: petroleum ether:EtOAc 83:17) to afford 3-{3-[(tert-butyldimethylsilyl)oxy]propoxy}-5-ethyl-4-nitro-1-(oxan-4-yl)pyrazole (320 mg) of sufficient purity for the subsequent step.

To a stirred solution of 3-{3-[(tert-butyldimethylsilyl)oxy]propoxy}-5-ethyl-4-nitro-1-(oxan-4-yl)pyrazole (50 mg, 0.12 mmol) in DCM (0.8 mL) was added HCl in 1,4-dioxane (0.10 mL, 0.40 mmol, 4 M) dropwise at room temperature. The resulting mixture was stirred for 2 h at room temperature. The residue was purified by preparative TLC (eluent: petroleum ether:EtOAc 33:67) to afford 3-{[5-ethyl-4-nitro-1-(oxan-4-yl)pyrazol-3-yl]oxy}propan-1-ol (23 mg) of sufficient purity for the subsequent step.

To a stirred mixture of 3-{[5-ethyl-4-nitro-1-(oxan-4-yl)pyrazol-3-yl]oxy}propan-1-ol (170 mg, 0.57 mmol), 3,6-dichloro-1H-pyrazolo[3,4-d]pyrimidine (215 mg, 1.14 mmol) and PPh₃ (298 mg, 1.14 mmol) in THF (12 mL) was added DIAD (230 mg, 1.14 mmol) dropwise at 0° C. under argon atmosphere. The resulting mixture was stirred for 2 h at room temperature and concentrated under reduced pressure. The residue was purified by preparative TLC (eluent: petroleum ether:EtOAc 80:20) to afford 3,6-dichloro-1-(3-((5-ethyl-4-nitro-1-(tetrahydro-2H-pyran-4-yl)-1H-pyrazol-3-yl)oxy)propyl)-1H-pyrazolo[3,4-d]pyrimidine desired product (230 mg) of sufficient purity for the subsequent step.

Intermediate: 3-(3-((tert-Butyldimethylsilyl)oxy)propoxy)-5-methyl-4-nitro-1H-pyrazole

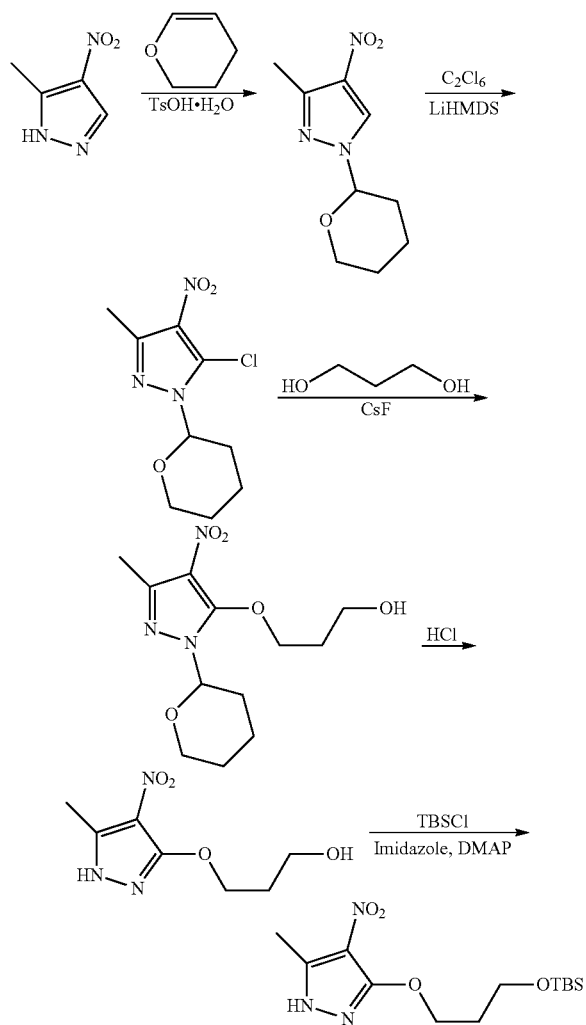

To a solution of 5-methyl-4-nitro-1H-pyrazole (12 g, 94 mmol) in THF (140 mL) was added TsOH·H₂O (898 mg, 4.7 mmol) and the reaction was stirred at 20° C. for 30 minutes. The reaction was cooled to 0° C. and 3,4-dihydro-2H-pyran (10.2 g, 121 mmol) was added. The mixture was stirred at 20° C. for 16 h. The mixture was concentrated under reduced pressure. The residue was purified by chromatography on silica gel (eluent: petroleum ether:EtOAc 100:0→80:20) to afford 3-methyl-4-nitro-1-(tetrahydro-2H-pyran-2-y)-1H-pyrazole (12 g) of sufficient purity for the subsequent step.

To a solution of 3-methyl-4-nitro-1-(tetrahydro-2H-pyran-2-yl)-1H-pyrazole (12 g, 57 mmol) in THF (100 mL) was added LiHMDS (1 M in THF, 62.5 mL) at −65° C. and stirred at −65° C. for 30 minutes. Then 1,1,1,2,2,2-hexachloroethane (14.80 g, 62.5 mmol) dissolved in THF (50 mL) was added and the mixture was stirred at −65° C. for 60 minutes and then warmed to 20° C. for 10 minutes. The mixture was quenched with saturated aqueous NH₄Cl (200 mL) at 0° C. and then warmed to 20° C. After 20 min stirring the mixture was extracted with EtOAc (3×150 mL). The combined organic layers were washed with brine (80 mL) and concentrated under reduced pressure. The residue was purified by chromatography on silica gel (eluent: petroleum ether:EtOAc 100:0→90:10) to afford 5-chloro-3-methyl-4-nitro-1-tetrahydropyran-2-yl-pyrazole (7.9 g) of sufficient purity for the subsequent step.

To a solution of 5-chloro-3-methyl-4-nitro-1-(tetrahydro-2H-pyran-2-yl)-1H-pyrazole (19 g, 77 mmol) in DMA (150 mL) was added CsF (41.1 g, 271 mmol) and propane-1,3-diol (29.4 g, 387 mmol). The mixture was stirred at 50° C. for 16 h. The mixture was added water (200 mL) and extracted with EtOAc (3×100 mL). The combined organic layers were washed with brine (3×100 mL), and concentrated under reduced pressure. The residue was purified by chromatography on silica gel (eluent: petroleum ether:EtOAc 100:0→69:31) to afford 3-((3-methyl-4-nitro-1-(tetrahydro-2H-pyran-2-yl)-1H-pyrazol-5-yl)oxy)propan-1-ol (13.7 g) of sufficient purity for the subsequent step.

To a solution of 3-((3-methyl-4-nitro-1-(tetrahydro-2H-pyran-2-yl)-1H-pyrazol-5-yl)oxy)propan-1-ol (4 g, 14 mmol) in MeOH (20 mL) was added aqueous HCl (12 M, 14 mL). The mixture was stirred at 20° C. for 16 h and then heated to 60° C. for 2 h. The mixture was concentrated under reduced pressure and pH adjusted to 10 with 4M aqueous NaOH. The resulting mixture was concentrated under reduced pressure. The residue was purified by chromatography on silica gel (eluent: petroleum ether:EtOAc 100:0→80:20) to afford 3-((5-methyl-4-nitro-1H-pyrazol-3-yl)oxy)propan-1-ol (2.7 g) of sufficient purity for the subsequent step. ¹H NMR (DMSO-d₆, 400 MHz) δ 12.94 (br s, 1H), 4.55 (t, J=4.8 Hz, 1H), 4.28 (t, J=6.4 Hz, 2H), 3.60-3.49 (m, 2H), 2.47 (s, 3H), 1.92-1.82 (m, 2H).

To a solution of 3-((5-methyl-4-nitro-1H-pyrazol-3-yl)oxy)propan-1-ol (2.7 g, 13 mmol) in DCM (30 mL) was added imidazole (1.46 g, 21.5 mmol), TBSCl (4.05 g, 26.8 mmol) and DMAP (820 mg, 6.71 mmol). The mixture was stirred at 20° C. for 16 h. The mixture was concentrated under reduced pressure. The residue was purified by chromatography on silica gel (eluent: petroleum ether:EtOAc 100:0→79:21 to afford 3-(3-((tert-butyldimethylsilyl)oxy)propoxy)-5-methyl-4-nitro-1H-pyrazole (3.7 g) of sufficient purity for the subsequent step. ¹H NMR (CD₃OD, 400 MHz) δ 4.40 (t, J=6.4 Hz, 2H), 3.84 (t, J=6.0 Hz, 2H), 2.61 (s, 3H), 2.03 (t, J=6.0 Hz, 2H), 0.89 (s, 9H), 0.05 (s, 6H).

Intermediate: 3-(3-((tert-Butyldimethylsilyl)oxy)propoxy)-5-ethyl-4-nitro-1H-pyrazole 5

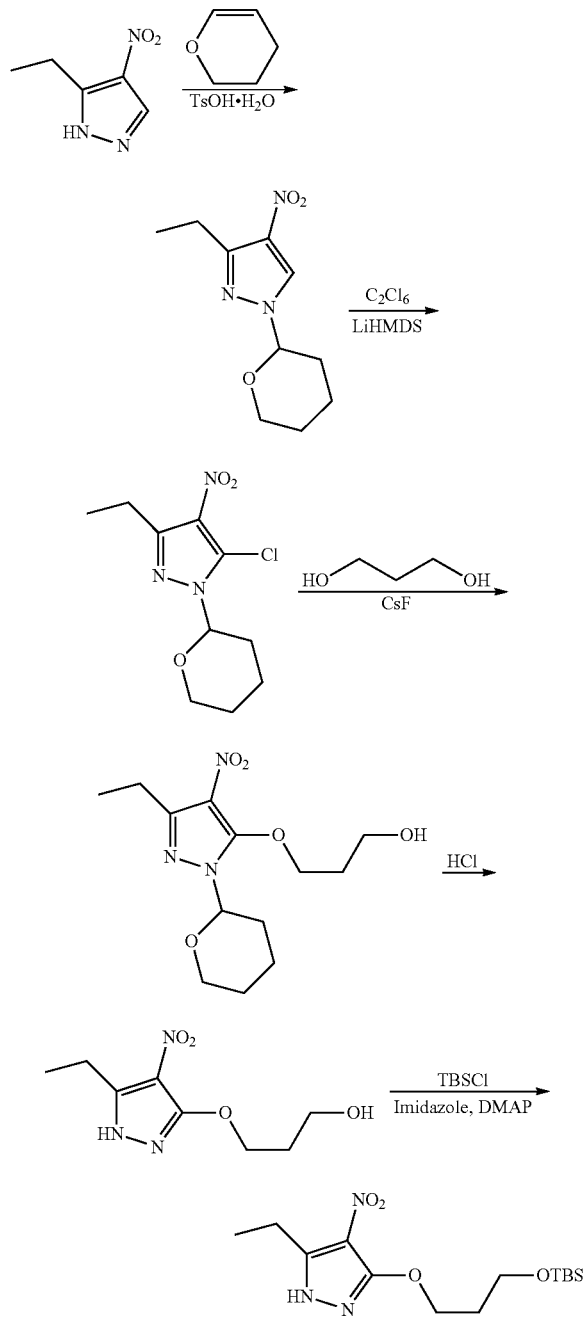

To a solution of 5-ethyl-4-nitro-1H-pyrazole (12.5 g, 88.6 mmol) in THF (150 mL) was added TsOH·H₂O (843 mg, 4.43 mmol). The mixture was stirred at 25° C. for 15 minute and then 3,4-dihydro-2H-pyran (9.54 g, 113 mmol) was added at 0° C. The mixture was stirred at 25° C. for 16 h. The mixture was concentrated. The residue was purified by chromatography on silica gel (eluent: petroleum ether:EtOAc 100:0→90:10) to afford 3-ethyl-4-nitro-1-tetrahydropyran-2-yl-pyrazole (19 g) of sufficient purity for the subsequent step. $^{1}$H NMR (CDCl$_3$, 400 MHz) δ 8.33 (s, 1H), 5.34-5.30 (m, 1H), 4.13-4.06 (m, 1H), 3.76-3.66 (m, 1H), 2.98 (q, J=7.6 Hz, 2H), 2.19-2.09 (m, 1H), 2.02-1.96 (m, 1H), 1.77-1.63 (m, 4H), 1.28 (t, J=7.6 Hz, 3H).

To a solution of 3-ethyl-4-nitro-1-tetrahydropyran-2-yl-pyrazole (19 g, 84.4 mmol) in THF (80 mL) was added LiHMDS (1 M in THF, 92.8 mL) at −65° C. and stirred at −65° C. for 30 minutes. Then 1,1,1,2,2,2-hexachloroethane (22 g, 93 mmol) dissolved in THF (60 mL) was added and the mixture was stirred at −65° C. for 2 h and then warmed to 20° C. for 10 minutes. The mixture was quenched with saturated aqueous NH$_4$Cl solution (200 mL) at 0° C. then warmed to 20° C. for 20 minutes and extracted with EtOAc (3×200 mL). The combined organic layers were washed with brine (3×80 mL) and concentrated under reduced pressure. The residue was purified by chromatography on silica gel (eluent: petroleum ether:EtOAc 100:0→95:5) to afford 5-chloro-3-ethyl-4-nitro-1-tetrahydropyran-2-yl-pyrazole (17 g) of sufficient purity for the subsequent step. $^{1}$H NMR (CDCl$_3$, 400 MHz) δ 5.52 (dd, J=2.8, 10.0 Hz, 1H), 4.13-4.03 (m, 1H), 3.76-3.64 (m, 1H), 2.98 (q, J=7.2 Hz, 2H), 2.51-2.36 (m, 1H), 2.22-2.10 (m, 1H), 1.95-1.85 (m, 1H), 1.81-1.60 (m, 3H), 1.29 (t, J=7.2 Hz, 3H).

To a solution of 5-chloro-3-ethyl-4-nitro-1-(tetrahydro-2H-pyran-2-yl)-1H-pyrazole (12 g, 46 mmol) and propane-1,3-diol (17.58 g, 231.1 mmol) in DMA (150 mL) was added CsF (21.06 g, 138.6 mmol). The mixture was stirred at 50° C. for 16 h. The mixture was diluted with water (200 mL) and extracted with EtOAc (4×150 mL). The combined organic layers were washed with brine (4×100 mL) and concentrated under reduced pressure. The residue was purified by chromatography on silica gel (eluent: petroleum ether:EtOAc 100:0→60:40) to afford 3-((3-ethyl-4-nitro-1-(tetrahydro-2H-pyran-2-yl)-1H-pyrazol-5-yl)oxy)propan-1-ol (14 g) of sufficient purity for the subsequent step.

To a solution of 3-((3-ethyl-4-nitro-1-(tetrahydro-2H-pyran-2-yl)-1H-pyrazol-5-yl)oxy)propan-1-ol (14 g, 47 mmol) in MeOH (140 mL) was added concentrated aqueous HCl (24 mL, 12 M). The mixture was stirred at 60° C. for 3 h. The mixture was cooled to 0° C., pH was adjusted to 8 using NaOH and then the mixture was concentrated under reduced pressure. The residue was purified by chromatography on silica gel (eluent: petroleum ether:EtOAc 100: 0→10:90) to afford 3-((5-ethyl-4-nitro-1H-pyrazol-3-yl)oxy)propan-1-ol (8.5 g) of sufficient purity for the subsequent step. $^{1}$H NMR (DMSO-d$^6$, 400 MHz) δ 12.95 (br s, 1H), 4.54 (br, 1H), 4.29 (t, J=6.8 Hz, 2H), 3.54 (t, J=6.0 Hz, 2H), 2.89 (q, J=7.6 Hz, 2H), 1.92-1.83 (m, 2H), 1.20 (t, J=7.6 Hz, 3H).

To a solution of 3-((5-ethyl-4-nitro-1H-pyrazol-3-yl)oxy) propan-1-ol (8.5 g, 40 mmol) in DCM (70 mL) was added DMAP (1.45 g, 11.9 mmol) and imidazole (4.30 g, 63.2 mmol), and TBSCl (11.9 g, 79.0 mmol). The mixture was stirred at 25° C. for 16 h. The mixture was concentrated under reduced pressure. The residue was purified by chromatography on silica gel (eluent: petroleum ether:EtOAc 100:0→10:90) to afford 3-(3-((tertbutyldimethylsilyl)oxy)propoxy)-5-ethyl-4-nitro-1H-pyrazole 5 (8.5 g) of sufficient purity for the subsequent step. $^{1}$H NMR (CDCl$_3$, 400 MHz) δ 4.40 (t, J=6.4 Hz, 2H), 3.83 (t, J=6.0 Hz, 2H), 3.04 (q, J=7.6 Hz, 2H), 2.09-1.99 (m, 2H), 1.33 (t, J=7.6 Hz, 3H), 0.88 (s, 9H), 0.05 (s, 6H).

Intermediate: 3-(3-((tert-Butyldimethylsilyl)oxy)propoxy)-4-nitro-1H-pyrazole

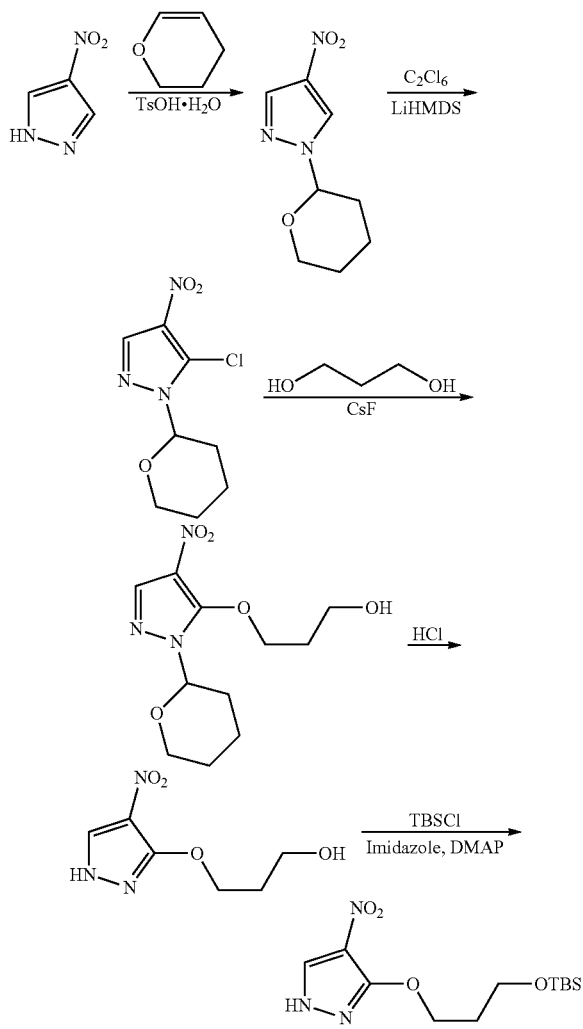

To a solution of 4-nitro-1H-pyrazole (10 g, 88 mmol) in THF (100 mL) was added 3,4-dihydro-2H-pyran (22.3 g, 265 mmol) and TsOH·H₂O (841 mg, 4.4 mmol). The mixture was stirred at 20° C. for 15 h. The reaction mixture was concentrated under reduced pressure. The residue was purified by chromatography on silica gel (eluent: petroleum ether:EtOAc 100:0→90:10) to afford 4-nitro-1-tetrahydropyran-2-yl-pyrazole (17 g) of sufficient purity for the subsequent step. $^1$H NMR (CDCl$_3$, 400 MHz) δ 8.37 (s, 1H), 8.10 (s, 1H), 5.41 (dd, J=9.2 Hz, 2.8 Hz, 1H), 4.10-4.06 (m, 1H), 3.80-3.70 (m, 1H), 2.16-2.10 (m, 1H), 2.05-1.90 (m, 2H), 1.80-1.60 (m, 3H).

To a solution of 4-nitro-1-tetrahydropyran-2-yl-pyrazole (15 g, 76 mmol) in THF (150 mL) was added dropwise LiHMDS (1 M in THF, 83.7 mL) at −78° C. After addition, the mixture was stirred at this temperature for 0.5 h, and then 1,1,1,2,2,2-hexachloroethane (19.81 g, 83.7 mmol) in THF (50 mL) was added dropwise at −78° C. The resulting mixture was stirred at 20° C. for 1.5 h. The reaction mixture was quenched with saturated aqueous NH₄Cl (100 mL) at 0° C., extracted with EtOAc (3×100 mL). The combined organic layers were washed with brine (3×100 mL), dried over Na₂SO₄, and concentrated under reduced pressure. The residue was purified by chromatography on silica gel (eluent: petroleum ether:EtOAc 100:0→90:10) to afford 5-chloro-4-nitro-1-tetrahydropyran-2-yl-pyrazole (11.4 g) of sufficient purity for the subsequent step. $^1$H NMR (CDCl$_3$, 400 MHz) δ 8.21 (s, 1H), 5.57 (dd, J=2.8, 9.6 Hz, 1H), 4.15-3.98 (m, 1H), 3.77-3.64 (m, 1H), 2.50-2.35 (m, 1H), 2.24-2.10 (m, 1H), 1.99-1.91 (m, 1H), 1.80-1.60 (m, 2H), 1.60-1.52 (m, 1H).

To a solution of 5-chloro-4-nitro-1-tetrahydropyran-2-yl-pyrazole (10 g, 43 mmol) in DMA (150 mL) was added CsF (26.23 g, 172.7 mmol) and propane-1,3-diol (16.42 g, 215.9 mmol). The mixture was stirred at 50° C. for 15 h. The reaction mixture was diluted with water (100 mL), extracted with EtOAc (3×200 mL). The combined organic layers were washed with brine (5×300 mL), dried over Na₂SO₄, and concentrated under reduced pressure. The residue was purified by chromatography on silica gel (eluent: petroleum ether:EtOAc 100:0→60:40) to afford 3-((4-nitro-1-(tetrahydro-2H-pyran-2-yl)-1H-pyrazol-5-yl)oxy)propan-1-ol (6.7 g) of sufficient purity for the subsequent step. $^1$H NMR (CDCl$_3$, 400 MHz) δ 8.03 (s, 1H), 5.45 (dd, J=2.8, 9.2 Hz, 1H), 4.68-4.62 (m, 1H), 4.55-4.48 (m, 1H), 4.10-4.03 (m, 1H), 3.92 (t, J=6.0 Hz, 2H), 3.74-3.65 (m, 1H), 2.47-2.29 (m, 1H), 2.18-2.13 (m, 1H), 2.13-2.07 (m, 2H), 1.76-1.57 (m, 4H).

To a solution of 3-((4-nitro-1-(tetrahydro-2H-pyran-2-yl)-1H-pyrazol-5-yl)oxy)propan-1-ol (19.8 g, 73.0 mmol) in MeOH (200 mL) was added concentrated aqueous HCl (12 M, 73 mL). The mixture was stirred at 60° C. for 16 h. The mixture was concentrated under reduced pressure and pH adjusted to 10 with 4M aqueous NaOH. The mixture was concentrated under reduced pressure. The residue was purified by chromatography on silica gel (eluent: petroleum ether:EtOAc (10 v % MeOH) 100:0→50:50) to afford 3-((4-nitro-1H-pyrazol-5-yl)oxy)propan-1-ol (10.5 g) of sufficient purity for the subsequent step. LC-MS (method K) (m/z)=187.7 (MH)$^+$ t$_R$=0.96 minutes.

To a solution of 3-((4-nitro-1H-pyrazol-5-yl)oxy)propan-1-ol (10.5 g, 56.1 mmol), imidazole (6.11 g, 89.8 mmol) and DMAP (3.43 g, 28.1 mmol) in DCM (200 mL) was added TBSCl (16.91 g, 112.2 mmol). The mixture was stirred at 20° C. for 12 hours. The mixture was concentrated. The residue was purified by chromatography on silica gel (eluent: petroleum ether:EtOAc (10 v % MeOH) 100:0→50:50) to afford 3-(3-((tert-butyldimethylsilyl)oxy)propoxy)-4-nitro-1H-pyrazole (13.6 g) of sufficient purity for the subsequent step. 1H NMR (CDCl$_3$, 400 MHz) δ8.20 (s, 1H), 4.46 (t, J=6.0 Hz, 2H), 3.86 (t, J=5.6 Hz, 2H), 2.11-2.07 (m, 2H), 0.91 (s, 9H), 0.11-0.03 (m, 6H).

Intermediate: cis-3,6-Dichloro-1-(3-((5-methyl-1-(2-methyltetrahydro-2H-pyran-4-yl)-4-nitro-1H-pyrazol-3-yl)oxy)propyl)-1H-pyrazolo[3,4-d]pyrimidine

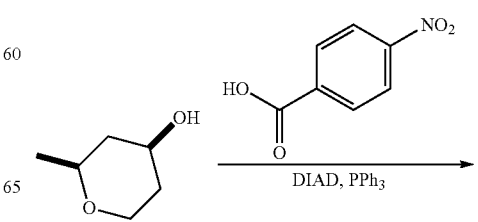

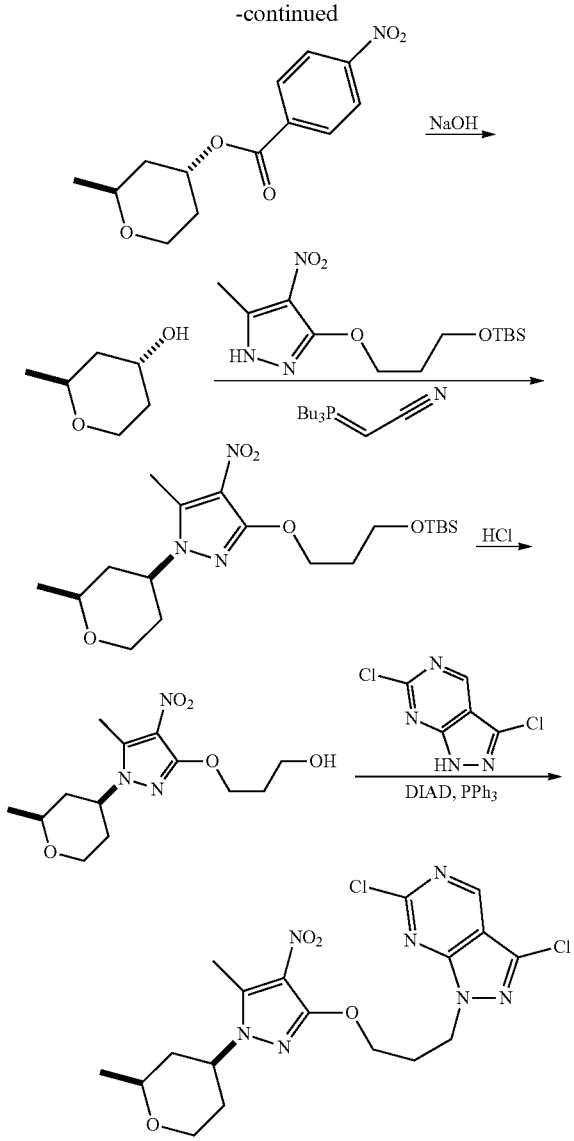

A solution of DIAD (5.22 g, 25.8 mmol) was added to a solution of cis-2-methyltetrahydro-2H-pyran-4-ol (2 g, 17.2 mmol), 4-nitrobenzoic acid (3.31 g, 19.8 mmol) and PPh$_3$ (6.77 g, 25.8 mmol) in THF (50 mL) at 0° C. The mixture was stirred at 20° C. for 15 h. The reaction mixture was concentrated under reduced pressure. The residue was purified by chromatography on silica gel (eluent: petroleum ether:EtOAc 100:0→90:10) to afford trans-2-methyltetrahydro-2H-pyran-4-yl 4-nitrobenzoate (6.5 g) of sufficient purity for the subsequent step. $^1$H NMR (CDCl$_3$, 400 MHz) δ 8.32 (d, J=6.8 Hz, 2H), 8.24 (d, J=6.8 Hz, 2H), 5.52-5.41 (m, 1H), 3.99-3.84 (m, 3H), 2.04-1.91 (m, 2H), 1.90-1.81 (m, 1H), 1.71-1.63 (m, 1H), 1.22 (d, J=6.4 Hz, 3H).

To a solution of trans-2-methyltetrahydro-2H-pyran-4-yl 4-nitrobenzoate (6.5 g, 24 mmol) in THF (50 mL) and MeOH (50 mL) was added aqueous NaOH (2 M, 37 mL). The mixture was stirred at 20° C. for 2 h. The reaction mixture was concentrated under reduced pressure. The residue was purified by chromatography on silica gel (eluent: petroleum ether:EtOAc 100:0→40:60) to afford trans-2-methyltetrahydro-2H-pyran-4-ol (1.3 g) of sufficient purity for the subsequent step. $^1$H NMR (CDCl$_3$, 400 MHz) δ 4.25-4.19 (m, 1H), 3.93-3.84 (m, 2H), 3.81-3.74 (m, 1H), 1.89-1.80 (m, 1H), 1.66-1.63 (m, 1H), 1.58-1.50 (m, 2H), 1.15 (d, J=6.4 Hz, 3H).

To a solution of 3-(3-((tert-butyldimethylsilyl)oxy)propoxy)-5-methyl-4-nitro-1H-pyrazole (1 g, 3.17 mmol) in toluene (20 mL) was added trans-2-methyltetrahydro-2H-pyran-4-ol (553 mg, 4.76 mmol) and 2-(tributyl-X-phosphanylidene)acetonitrile (3.06 g, 12.68 mmol). The mixture was stirred at 110° C. for 15 h. The reaction mixture was concentrated under reduced pressure. The residue was purified by chromatography on silica gel (eluent: petroleum ether:EtOAc 100:0→40:60) to afford cis-3-(3-((tert-butyldimethylsilyl)oxy)propoxy)-5-methyl-1-(2-methyltetrahydro-2H-pyran-4-yl)-4-nitro-1H-pyrazole (1 g) of sufficient purity for the subsequent step. LC-MS (method B) (m/z) =414.3 (MH)$^+$ t$_R$=1.10 minutes.

A solution of cis-3-(3-((tert-butyldimethylsilyl)oxy)propoxy)-5-methyl-1-(2-methyltetrahydro-2H-pyran-4-yl)-4-nitro-1H-pyrazole (1.0 g, 2.4 mmol) in HCl/1,4-dioxane (4 M, 10 mL) was stirred at 20° C. for 15 h. The reaction mixture was concentrated under reduced pressure. The residue was purified by chromatography on silica gel (eluent: petroleum ether:EtOAc 100:0→50:50) to afford cis-3-((5-methyl-1-(2-methyltetrahydro-2H-pyran-4-yl)-4-nitro-1H-pyrazol-3-yl)oxy)propan-1-ol (430 mg) of sufficient purity for the subsequent step. $^1$H NMR (CDCl$_3$, 400 MHz,) δ 4.50 (t, J=6.0 Hz, 2H), 4.29-4.19 (m, 1H), 4.13-4.05 (m, 1H), 3.85 (t, J=5.2 Hz, 2H), 3.61-3.51 (m, 2H), 2.65 (s, 3H), 2.61-2.49 (m, 1H), 2.30-2.16 (m, 1H), 2.12-2.06 (m, 2H), 2.01-1.89 (m, 1H), 1.84-1.70 (m, 2H), 1.28 (d, J=6.0 Hz, 3H).

To a solution of cis-3-((5-methyl-1-(2-methyltetrahydro-2H-pyran-4-yl)-4-nitro-1H-pyrazol-3-yl)oxy)propan-1-ol (412 mg, 1.38 mmol), 3,6-dichloro-1H-pyrazolo[3,4-d]pyrimidine (260 mg, 1.38 mmol), and PPh$_3$ (1.08 g, 4.13 mmol) in THF (20 mL) was added DIAD (835 mg, 4.13 mmol) at 0° C. The mixture was stirred at 20° C. for 15 h. The reaction mixture was concentrated under reduced pressure. The residue was purified by chromatography on silica gel (eluent: petroleum ether:EtOAc 100:0→60:40) to afford cis-3,6-dichloro-1-(3-((5-methyl-1-(2-methyltetrahydro-2H-pyran-4-yl)-4-nitro-1H-pyrazol-3-yl)oxy)propyl)-1H-pyrazolo[3,4-d]pyrimidine (500 mg) of sufficient purity for the subsequent step. $^1$H NMR (CDCl$_3$, 400 MHz) δ 8.95 (s, 1H), 4.65 (t, J=6.4 Hz, 2H), 4.35 (t, J=6.0 Hz, 2H), 4.25-4.15 (m, 1H), 4.12-4.07 (m, 1H), 3.61-3.48 (m, 2H), 2.62 (s, 3H), 2.52-2.42 (m, 2H), 2.20-2.08 (m, 1H), 1.91-1.80 (m, 1H), 1.79-1.73 (m, 1H), 1.72-1.67 (m, 1H), 1.27 (d, J=6.0 Hz, 3H).

Intermediate: 3,6-Dichloro-1-(3-((5-methyl-4-nitro-1-(tetrahydro-2H-pyran-4-yl)-1H-pyrazol-3-yl)oxy)propyl-1,1,2,2,3,3-d$_6$)-1H-pyrazolo[3,4-d]pyrimidine

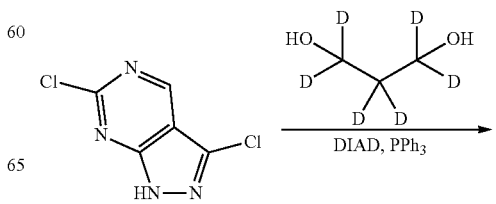

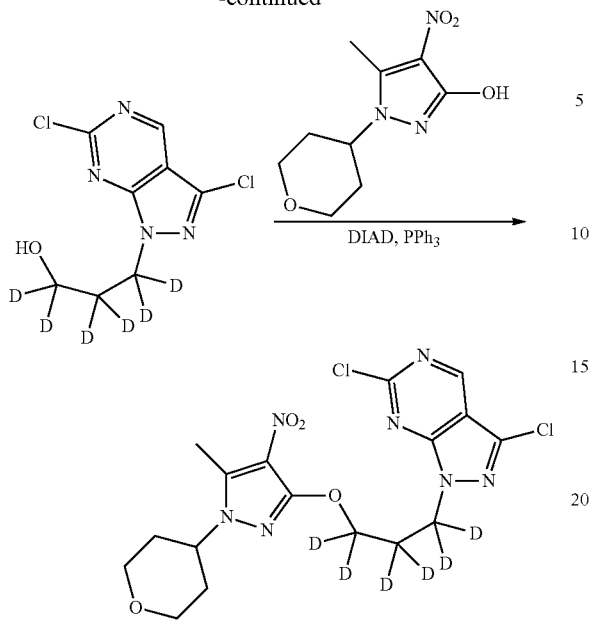

To a stirred mixture of 3,6-dichloro-1H-pyrazolo[3,4-d]pyrimidine (200 mg, 1.05 mmol) and propane-$d_6$-1,3-diol (130 mg, 1.58 mmol) in THF (2 mL) were added PPh$_3$ (555 mg, 2.11 mmol) and DIAD (427 mg, 2.11 mmol) portionwise at 0° C. under an argon atmosphere. The resulting mixture was stirred for 2 h at room temperature. The resulting mixture was concentrated under reduced pressure. The residue was purified by chromatography on silica gel (eluent: petroleum ether:EtOAc 50:50) to afford 3-(3,6-dichloro-1H-pyrazolo[3,4-d]pyrimidin-1-yl)propan-1,1,2,2,3,3-$d_6$-1-ol (124.8 mg) of sufficient purity for the subsequent step. $^1$H NMR (DMSO-$d_6$, 400 MHz) δ 9.30 (s, 1H), 4.53 (s, 1H).

To a stirred mixture of 3-(3,6-dichloro-1H-pyrazolo[3,4-d]pyrimidin-1-yl)propan-1,1,2,2,3,3-$d_6$-1-ol (700 mg, 2.76 mmol) and 5-methyl-4-nitro-1-(tetrahydro-2H-pyran-4-yl)-1H-pyrazol-3-ol (754 mg, 3.31 mmol) in THF (10 mL) were added PPh$_3$ (1.45 g, 5.53 mmol) and DIAD (1.12 g, 5.53 mmol) at 0° C. under an argon atmosphere. The resulting mixture was stirred for 2 h at room temperature. The residue was purified by chromatography on silica gel (eluent: petroleum ether:EtOAc 50:50) to afford 3,6-dichloro-1-(3-((5-methyl-4-nitro-1-(tetrahydro-2H-pyran-4-yl)-1H-pyrazol-3-yl)oxy)propyl-1,1,2,2,3,3-$d_6$)-1H-pyrazolo[3,4-d]pyrimidine (750 mg) of sufficient purity for the subsequent step.

Intermediate: 3,6-Dichloro-1-(3-((5-methyl-1-(3-methyltetrahydro-2H-pyran-4-yl)-4-nitro-1H-pyrazol-3-yl)oxy)propyl)-1H-pyrazolo[3,4-d]pyrimidine

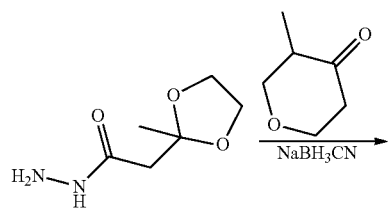

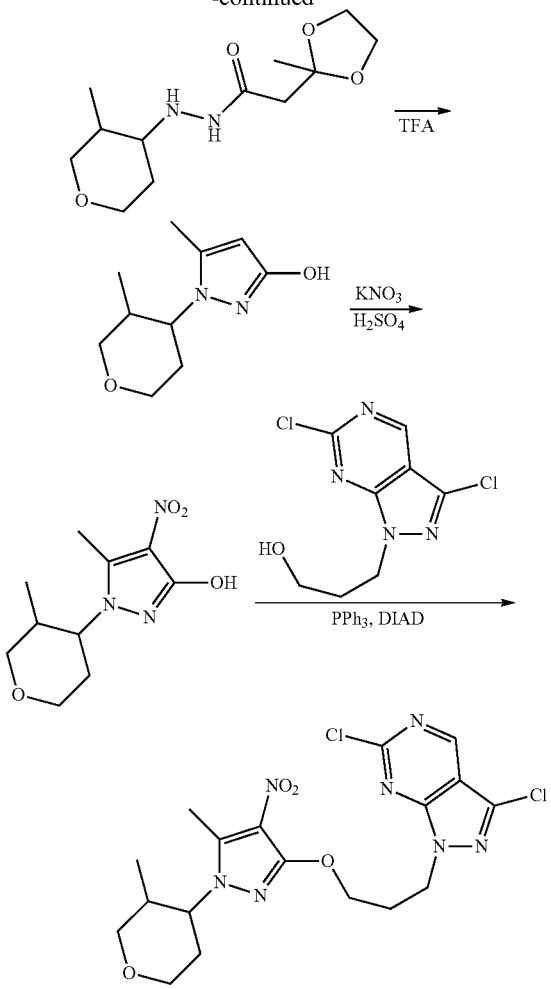

To a solution of 2-(2-methyl-1,3-dioxolan-2-yl)acetohydrazide (5 g, 31 mmol) in MeOH (50 mL) was added 3-methyltetrahydro-4H-pyran-4-one (3.57 g, 31.3 mmol) at 25° C. The mixture was stirred at 25° C. for 1 h. NaBH$_3$CN (5.89 g, 93.7 mmol) was added into the mixture and the mixture was stirred at 25° C. for 1 h. The mixture was concentrated under reduced pressure. The residue was diluted with EtOAc (100 mL) and washed with saturated aqueous NH$_4$Cl (2×50 mL), H$_2$O (50 mL) and brine (50 mL), dried over Na$_2$SO$_4$, filtered and concentrated to give 2-(2-methyl-1,3-dioxolan-2-yl)-N'-(3-methyltetrahydro-2H-pyran-4-yl)acetohydrazide (8.06 g) of sufficient purity for the subsequent step.

To a solution of 2-(2-methyl-1,3-dioxolan-2-yl)-N'-(3-methyltetrahydro-2H-pyran-4-yl)acetohydrazide (8.06 g, 31 mmol) in EtOH (100 mL) was added TFA (4.63 mL, 62.6 mmol) and the mixture was stirred at 90° C. 12 h. Additional TFA (4.63 mL) was added at 25° C. and the reaction was stirred at 90° C. for another 12 h. The mixture was concentrated under reduced pressure. The residue was purified by chromatography on silica gel (eluent: petroleum ether:EtOAc 100:0→20:80) to afford 5-methyl-1-(3-methyltetrahydro-2H-pyran-4-yl)-1H-pyrazol-3-ol (3.8 g) of sufficient purity for the subsequent step.

To a solution of 5-methyl-1-(3-methyltetrahydro-2H-pyran-4-yl)-1H-pyrazol-3-ol (3.8 g, 19 mmol) in H$_2$SO$_4$ (40 mL) was added KNO$_3$ (5.97 g, 59.1 mmol) slowly at 0° C.

The mixture was stirred at 0° C. for 0.5 h. The mixture was poured into ice-water (150 mL) and extracted with EtOAC (4×50 mL). The organic phase was washed with saturated aqueous NaHCO$_3$ (100 mL), brine (2×100 mL), dried over Na$_2$SO$_4$ and concentrated under reduced pressure to give 5-methyl-1-(3-methyltetrahydro-2H-pyran-4-yl)-4-nitro-1H-pyrazol-3-ol (2.9 g) of sufficient purity for the subsequent step.

A mixture of 3-(3,6-dichloro-1H-pyrazolo[3,4-d]pyrimidin-1-yl)propan-1-ol (1.53 g, 6.19 mmol), 5-methyl-1-(3-methyltetrahydro-2H-pyran-4-yl)-4-nitro-1H-pyrazol-3-ol (1.5 g, 6.22 mmol), DIAD (3.76 g, 18.6 mmol), and PPh$_3$ on resin (6.18 g, 18.58 mmol, 3 mmol/g) in THF (30 mL) was stirred at 20° C. for 16 h. The mixture was concentrated under reduced pressure. The residue was purified by chromatography on silica gel (eluent: petroleum ether:EtOAc 100:0→40:60) to afford 3,6-dichloro-1-(3-((5-methyl-1-(3-methyltetrahydro-2H-pyran-4-yl)-4-nitro-1H-pyrazol-3-yl)oxy)propyl)-1H-pyrazolo[3,4-d]pyrimidine (1.7 g) of sufficient purity for the subsequent step.

Intermediate: trans-3,6-Dichloro-1-(3-((1-(4-fluorocyclohexyl)-5-methyl-4-nitro-1H-pyrazol-3-yl)oxy)propyl)-1H-pyrazolo[3,4-d]pyrimidine

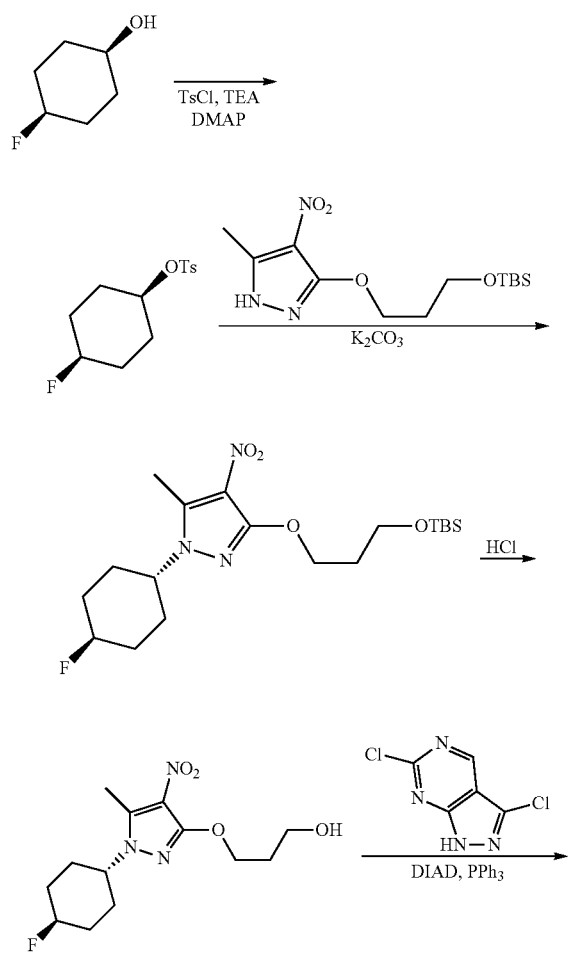

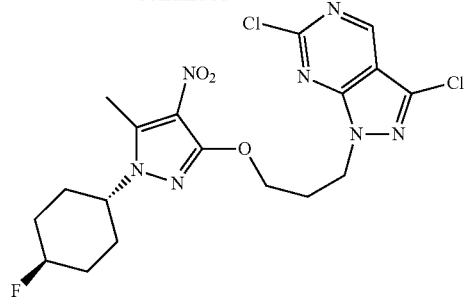

To a solution of 4-fluorocyclohexanol (500 mg, 4.23 mmol, cis:trans=3:1) in DCM (7 mL) was added TEA (727 mg, 7.18 mmol) and DMAP (52 mg, 0.43 mmol) followed by TsCl (888 mg, 4.66 mmol) at 0° C. The mixture was stirred at 20° C. for 16 h. The mixture was concentrated under reduced pressure. The residue was purified by chromatography on silica gel (eluent: petroleum ether:EtOAc 100:0→80:20) to afford cis-4-fluorocyclohexyl 4-methylbenzenesulfonate(720 mg) of sufficient purity for the subsequent step. $^1$H NMR (CDCl$_3$, 400 MHz) δ 7.80 (d, J=8.4 Hz, 2H), 7.34 (d, J=8.0 Hz, 2H), 4.72-4.50 (m, 2H), 2.45 (s, 3H), 2.02-1.87 (m, 4H), 1.74-1.57 (m, 4H).

To a solution of cis-(4-fluorocyclohexyl) 4-methylbenzenesulfonate (342 mg, 1.25 mmol) and 3-(3-((tert-butyldimethylsilyl)oxy)propoxy)-5-methyl-4-nitro-1H-pyrazole (350 mg, 1.11 mmol) in DMF (6 mL) was added K$_2$CO$_3$ (467 mg, 3.38 mmol). The mixture was stirred at 80° C. for 24 h. The mixture was diluted with water (20 mL) and extracted with EtOAc (3×20 mL). The combined organic layers were washed with brine (3×20 mL) and concentrated under reduced pressure. The residue was purified by chromatography on silica gel (eluent: petroleum ether:EtOAc 100:0→60:40) to afford trans-3-(3-((tert-butyldimethylsilyl)oxy)propoxy)-1-(4-fluorocyclohexyl)-5-methyl-4-nitro-1H-pyrazole (220 mg) of sufficient purity for the subsequent step. $^1$H NMR (400 MHz, CDCl$_3$) δ 4.75-4.53 (m, 1H), 4.38 (t, J=6.4 Hz, 2H), 4.12-3.97 (m, 1H), 3.81 (t, J=6.0 Hz, 2H), 2.62 (s, 3H), 2.37-2.23 (m, 2H), 2.13-1.98 (m, 4H), 1.97-1.88 (m, 2H), 1.76-1.64 (m, 2H), 0.89 (s, 9H), 0.05 (s, 6H).

To a solution of trans-3-(3-((tert-butyldimethylsilyl)oxy)propoxy)-1-(4-fluorocyclohexyl)-5-methyl-4-nitro-1H-pyrazole (220 mg, 0.53 mmol) in DCM (1 mL) was added HCl/dioxane (4 M, 5 mL). The mixture was stirred at 20° C. for 2 h. The mixture was concentrated under reduced pressure. The residue was purified by chromatography on silica gel (eluent: petroleum ether:EtOAc 100:0→60:40) to afford trans-3-((1-(4-fluorocyclohexyl)-5-methyl-4-nitro-1H-pyrazol-3-yl)oxy)propan-1-ol (110 mg) of sufficient purity for the subsequent step. $^1$H NMR (400 MHz, CDCl$_3$) δ 4.76-4.54 (m, 1H), 4.48 (t, J=5.6 Hz, 2H), 4.11-3.99 (m, 1H), 3.84 (t, J=5.2 Hz, 2H), 2.63 (s, 3H), 2.35-2.25 (m, 2H), 2.10-1.90 (m, 6H), 1.71-1.63 (m, 2H).

A mixture of trans-3-[1-(4-fluorocyclohexyl)-5-methyl-4-nitro-pyrazol-3-yl]oxypropan-1-ol (100 mg, 0.4 mmol), 3,6-dichloro-1H-pyrazolo[3,4-d]pyrimidine (63 mg, 0.4 mmol), PPh$_3$ (261 mg, 1.0 mol), and DIAD (201 mg, 1.0 mmol) in THF (1 mL) was stirred at 20° C. for 16 h. The mixture was concentrated under reduced pressure. The residue was purified by chromatography on silica gel (eluent: petroleum ether:EtOAc 100:0→60:40) to afford trans-3,6-dichloro-1-(3-((1-(4-fluorocyclohexyl)-5-methyl-4-nitro-1H-pyrazol- 3-yl)oxy)propyl)-1H-pyrazolo[3,4-d]pyrimidine (170 mg) of sufficient purity for the subsequent step.

Intermediate: 3,6-Dichloro-1-(3-((1-(4,4-difluorocyclohexyl)-5-methyl-4-nitro-1H-pyrazol-3-yl)oxy)propyl)-1H-pyrazolo[3,4-d]pyrimidine

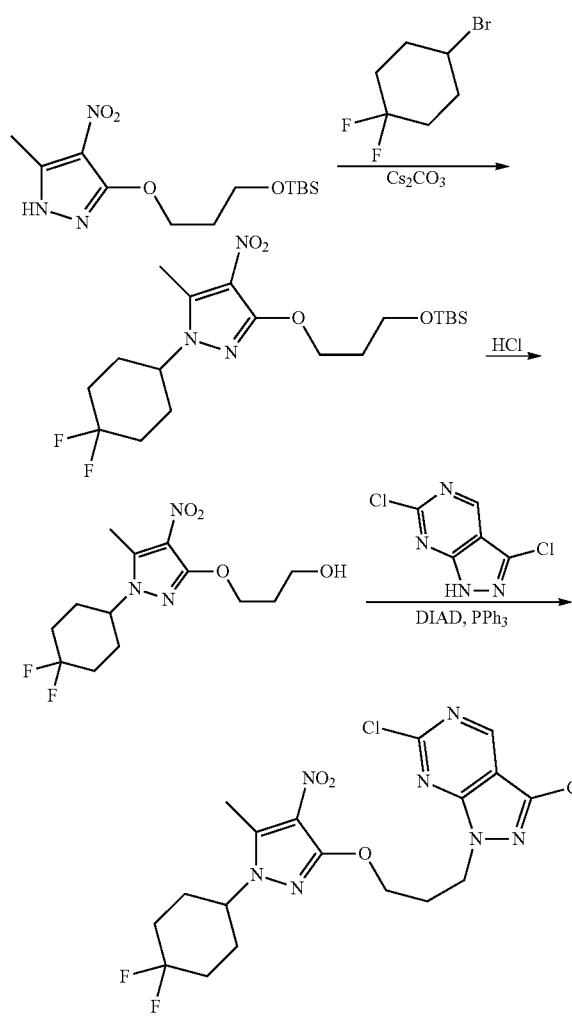

To a mixture of 3-(3-((tert-butyldimethylsilyl)oxy)propoxy)-5-methyl-4-nitro-1H-pyrazole (0.3 g, 0.95 mmol) and 4-bromo-1,1-difluoro-cyclohexane (1.33 g, 6.66 mmol) in DMF (6 mL) was added Cs$_2$CO$_3$ (620 mg, 1.90 mmol) at 20° C. The reaction mixture was stirred at 80° C. for 16 h. The mixture was concentrated under reduced pressure. The residue was purified by chromatography on silica gel (eluent: petroleum ether:EtOAc 100:0→70:30) to afford 3-(3-((tert-butyldimethylsilyl)oxy)propoxy)-1-(4,4-difluorocyclohexyl)-5-methyl-4-nitro-1H-pyrazole (0.32 g) of sufficient purity for the subsequent step. $^1$H NMR (CDCl$_3$, 400 MHz) δ 4.41 (t, J=6.4 Hz, 2H), 4.19-4.12 (m, 1H), 3.83 (t, J=6.0 Hz, 2H), 2.65 (s, 3H), 2.41-2.24 (m, 4H), 2.08-2.03 (m, 2H), 2.01-1.86 (m, 4H), 0.90 (s, 9H), 0.06 (s, 6H).

To a mixture of 3-(3-((tert-butyldimethylsilyl)oxy)propoxy)-1-(4,4-difluorocyclohexyl)-5-methyl-4-nitro-1H-pyrazole (0.31 g, 0.72 mmol) in THF (5 mL) was added HCl/dioxane (4 M, 5 mL) and then the mixture was stirred at 25° C. for 1 h. The mixture was concentrated under reduced pressure. The residue was purified by chromatography on silica gel (eluent: petroleum ether:EtOAc 100:0→50:50) to afford 3-((1-(4,4-difluorocyclohexyl)-5-methyl-4-nitro-1H-pyrazol-3-yl)oxy)propan-1-ol (0.21 g) of sufficient purity for the subsequent step. LC-MS (method B) (m/z)=320.2 (MH)$^+$ t$_R$=0.81 minutes.

To a mixture of 3-((1-(4,4-difluorocyclohexyl)-5-methyl-4-nitro-1H-pyrazol-3-yl)oxy)propan-1-ol (0.2 g, 0.63 mmol), 3,6-dichloro-1H-pyrazolo[3,4-d]pyrimidine (118 mg, 0.63 mmol), and PPh$_3$ (329 mg, 1.25 mmol) in THF (20 mL) was added DIAD (253 mg, 1.25 mmol) at 0° C. The mixture was stirred at 25° C. for 16 h. The mixture was concentrated under reduced pressure. The residue was purified by chromatography on silica gel (eluent: petroleum ether:EtOAc 100:0→70:30) to afford 3,6-dichloro-1-(3-((1-(4,4-difluorocyclohexyl)-5-methyl-4-nitro-1H-pyrazol-3-yl)oxy)propyl)-1H-pyrazolo[3,4-d]pyrimidine (0.28 g) of sufficient purity for the subsequent step. $^1$H NMR (CDCl$_3$, 400 MHz) δ 8.97 (s, 1H), 4.66 (t, J=6.8 Hz, 2H), 4.36 (t, J=5.6 Hz, 2H), 4.13-4.04 (m, 1H), 2.63 (s, 3H), 2.53-2.43 (m, 2H), 2.36-2.17 (m, 4H), 2.00-1.83 (m, 4H).

Intermediate: 3,6-Dichloro-1-(3-((5-methyl-4-nitro-1-(oxepan-3-yl)-1H-pyrazol-3-yl)oxy)propyl)-1H-pyrazolo[3,4-d]pyrimidine

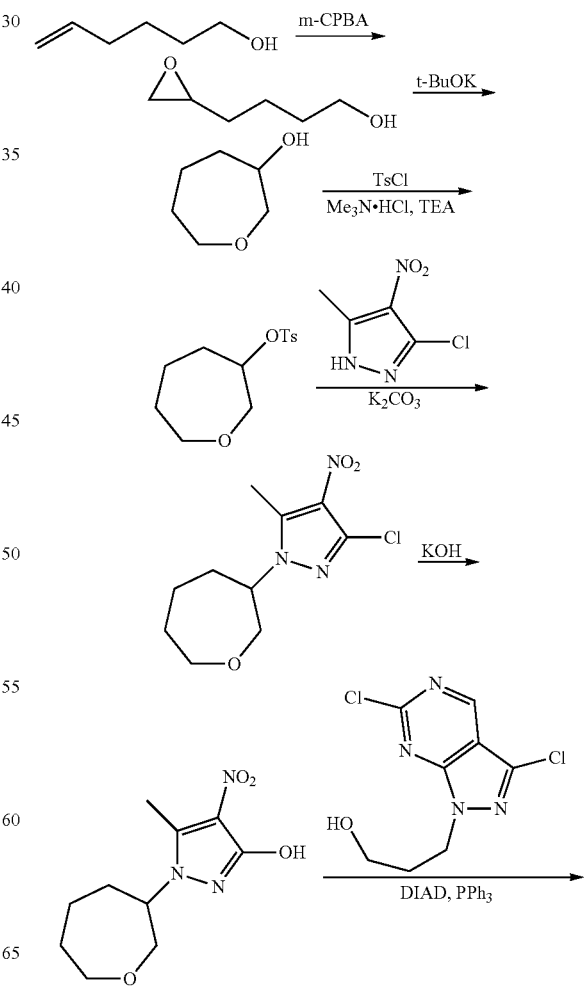

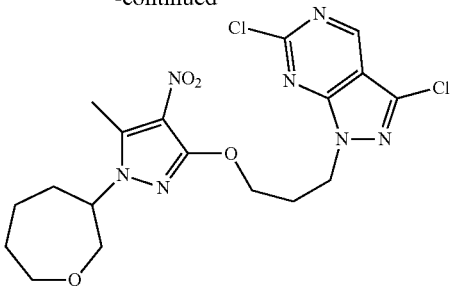

To a solution of hex-5-en-1-ol (9.0 g, 89 mmol) in DCM (150 mL) were added m-CPBA (29.08 g, 135 mmol, 80% purity) at 0° C. The reaction mixture was stirred at 20° C. for 16 h. The reaction was cooled to 0° C. and quenched with aqueous NaOH (1 M, 140 ml). The reaction mixture was diluted with water (100 mL) and extracted with DCM (3×100 mL). The combined organic layers were washed with brine (3×100 mL), dried over $Na_2SO_4$, and concentrated under reduced pressure. The residue was purified by chromatography on silica gel (eluent: petroleum ether:EtOAc 60:40→50:50) to afford 4-(oxiran-2-yl)butan-1-ol (8 g) of sufficient purity for the subsequent step.

To a solution of 4-(oxiran-2-yl)butan-1-ol (7.5 g, 65 mmol) in THF (100 mL) was added tBuOK (8.69 g, 77.5 mmol). The reaction mixture was stirred at 50° C. for 16 h. The reaction mixture was added water (50 mL) and extracted with EtOAc (3×50 mL). The combined organic layers were washed with brine (3×50 mL), dried over $Na_2SO_4$, and concentrated under reduced pressure. The residue was purified by chromatography on silica gel (eluent: petroleum ether:EtOAc 30:70→20:80) to give a mixture of oxepan-3-ol and (tetrahydro-2H-pyran-2-yl)methanol (4 g). The mixture of tetrahydropyran-2-ylmethanol and oxepan-3-ol was dissolved in DCM (40 mL). TEA (5.23 g, 51.65 mmol) and N,N-dimethylmethanamine; hydrochloride (329 mg, 3.44 mmol) were added followed by TsCl (7.88 g, 41.3 mmol) at 0° C. The mixture was stirred at 20° C. for 16 h. The solvent was removed under reduced pressure. The residue was purified by chromatography on silica gel (eluent: petroleum ether:EtOAc 80:20→70:30) to afford a mixture of oxepan-3-yl 4-methylbenzenesulfonate and (tetrahydro-2H-pyran-2-yl)methyl 4-methylbenzenesulfonate (5 g). The mixture of oxepan-3-yl 4-methylbenzenesulfonate and (tetrahydro-2H-pyran-2-yl)methyl 4-methylbenzenesulfonate (4 g) was added to a solution of 3-chloro-5-methyl-4-nitro-1H-pyrazole (2 g, 12.38 mmol) in DMF (10 mL). $K_2CO_3$ (5.13 g, 37.1 mmol) was added and the reaction mixture was stirred at 80° C. for 16 h. The reaction mixture was diluted with water (10 mL) and extracted with EtOAc (3×10 mL). The combined organic layers were washed with brine (3×10 mL), dried over $Na_2SO_4$, and concentrated under reduced pressure. The residue was purified by chromatography on silica gel (eluent: petroleum ether:EtOAc 100:0→85:15) to afford 3-chloro-5-methyl-4-nitro-1-(oxepan-3-yl)pyrazole (700 mg) of sufficient purity for the subsequent step. $^1$H NMR (CDCl$_3$, 400 MHz) δ 4.42-4.32 (m, 1H), 4.02-3.94 (m, 1H), 3.92-3.77 (m, 3H), 2.67 (s, 3H), 2.13-2.04 (m, 2H), 1.99-1.86 (m, 3H), 1.72-1.63 (m, 1H).

To a solution of 3-chloro-5-methyl-4-nitro-1-(oxepan-3-yl)pyrazole (200 mg, 0.77 mmol) in H$_2$O (10 mL) was added KOH (1.1 g, 20 mmol). The reaction mixture was stirred at 155° C. for 16 h using a microwave reactor. The reaction mixture was washed with EtOAc (10 mL). The aqueous phase was adjusted to pH=2~3, and extracted with EtOAc (3×10 mL), dried over Na$_2$SO$_4$, and concentrated under reduced pressure to afford 5-methyl-4-nitro-1-(oxepan-3-yl)pyrazol-3-ol (150 mg) of sufficient purity for the subsequent step. $^1$H NMR (CDCl$_3$, 400 MHz) δ 4.37-4.24 (m, 1H), 4.02-3.94 (m, 1H), 3.91-3.84 (m, 1H), 3.84-3.78 (m, 2H), 2.63 (s, 3H), 2.15-2.01 (m, 2H), 1.99-1.84 (m, 3H), 1.72-1.62 (m, 1H).

To a solution of 5-methyl-4-nitro-1-(oxepan-3-yl)pyrazol-3-ol (150 mg, 0.62 mmol) in THF (10 mL) were added 3-(3,6-dichloropyrazolo[3,4-d]pyrimidin-1-yl)propan-1-ol (169 mg, 0.68 mmol), DIAD (754 mg, 3.73 mmol) and PPh$_3$ on resin (975 mg, 3.73 mmol) at 0° C. The reaction mixture was stirred at 25° C. for 16 h. The solvent was removed. The residue was purified by chromatography on silica gel (eluent: petroleum ether:EtOAc 70:30→60:40) to afford 3,6-dichloro-1-(3-((5-methyl-4-nitro-1-(oxepan-3-yl)-1H-pyrazol-3-yl)oxy)propyl)-1H-pyrazolo[3,4-d]pyrimidine (250 mg) of sufficient purity for the subsequent step. $^1$H NMR (CDCl$_3$, 400 MHz) δ 8.95 (s, 1H), 4.65 (t, J=6.4 Hz, 2H), 4.34 (t, J=6.0 Hz, 2H), 4.31-4.23 (m, 1H), 3.86 (d, J=7.2 Hz, 2H), 3.82-3.78 (m, 2H), 2.60 (s, 3H), 2.50-2.44 (m, 2H), 2.02-1.96 (m, 2H), 1.92-1.79 (m, 3H), 1.69-1.62 (m, 1H).

Intermediate: 3,6-Dichloro-1-(3-((5-methyl-4-nitro-1-(oxepan-4-yl)-1H-pyrazol-3-yl)oxy)propyl)-1H-pyrazolo[3,4-d]pyrimidine

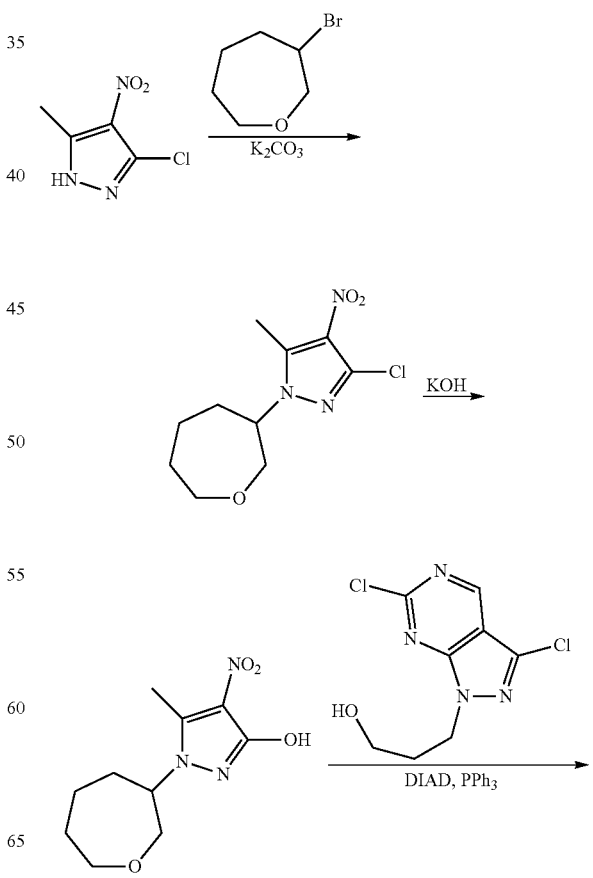

155

-continued

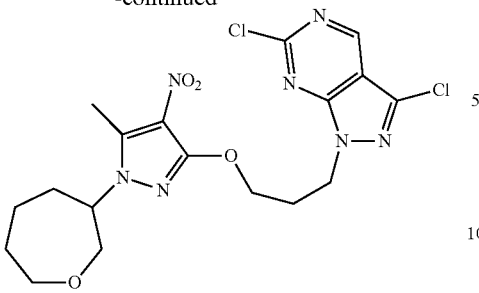

To a solution of 3-chloro-5-methyl-4-nitro-1H-pyrazole (2 g, 12 mmol) and 4-bromooxepane (2.44 g, 13.6 mmol) in MeCN (50 mL) was added K₂CO₃ (5.13 g, 37.1 mmol). The mixture was stirred at 80° C. for 15 h. The reaction mixture was concentrated under reduced pressure. The residue was purified by chromatography on silica gel (eluent: petroleum ether:EtOAc 100:0→80:20) to afford 3-chloro-5-methyl-4-nitro-1-(oxepan-4-yl)-1H-pyrazole (1.2 g) of sufficient purity for the subsequent step. ¹H NMR (CDCl₃, 400 MHz) δ4.49-4.39 (m, 1H), 3.98-3.91 (m, 1H), 3.90-3.77 (m, 2H), 3.69-3.61 (m, 1H), 2.68 (s, 3H), 2.45-2.35 (m, 1H), 2.35-2.24 (m, 1H), 2.19-2.08 (m, 1H), 2.04-1.96 (m, 1H), 1.96-1.88 (m, 1H), 1.87-1.73 (m, 1H).

To a solution of 3-chloro-5-methyl-4-nitro-1-(oxepan-4-yl)-1H-pyrazole (200 mg, 770 µmol) in H₂O (10 mL) was added KOH (1.12 g, 20.02 mmol). The mixture was stirred at 155° C. for 3 h using a microwave reactor. The reaction mixture was washed with EtOAc (50 mL×3). The aqueous phase was adjusted to pH=3 using HCl (12M) and extracted with EtOAc (100 mL×3). The combined organic layers were dried over Na₂SO₄ and concentrated under reduced pressure to afford 5-methyl-4-nitro-1-(oxepan-4-yl)-1H-pyrazol-3-ol (200 mg) of sufficient purity for the subsequent step. ¹H NMR (CDCl₃, 400 MHz) δ11.31 (br s, 1H), 4.57-4.35 (m, 1H), 3.80-3.69 (m, 2H), 3.66-3.54 (m, 2H), 2.57 (s, 3H), 2.14-2.06 (m, 1H), 2.06-1.93 (m, 2H), 1.92-1.84 (m, 1H), 1.83-1.73 (m, 2H).

DIAD (1.37 g, 6.80 mmol) was added to a solution of 3-(3,6-dichloro-1H-pyrazolo[3,4-d]pyrimidin-1-yl)propan-1-ol (280 mg, 1.13 mmol), 5-methyl-4-nitro-1-(oxepan-4-yl)-1H-pyrazol-3-ol (273 mg, 1.13 mmol) and PPh₃ on resin (2.26 g, 6.80 mmol, 3 mmol/g) in THF (20 mL) at 0° C. The mixture was stirred at 20° C. for 15 h. The reaction mixture was concentrated under reduced pressure. The residue was purified by chromatography on silica gel (eluent: petroleum ether:EtOAc 100:0→50:50) to afford 3,6-dichloro-1-(3-((5-methyl-4-nitro-1-(oxepan-4-yl)-1H-pyrazol-3-yl)oxy)propyl)-1H-pyrazolo[3,4-d]pyrimidine (330 mg) of sufficient purity for the subsequent step. ¹H NMR (CDCl₃, 400 MHz) δ 8.99 (s, 1H), 4.65 (t, J=6.4 Hz, 2H), 4.35 (t, J=6.0 Hz, 2H), 4.32-4.23 (m, 1H), 3.96-3.81 (m, 2H), 3.79-3.71 (m, 1H), 3.69-3.59 (m, 1H), 2.61 (s, 3H), 2.53-2.42 (m, 2H), 2.34-2.24 (m, 1H), 2.24-2.14 (m, 1H), 2.04-1.98 (m, 1H), 1.95-1.86 (m, 2H), 1.83-1.73 (m, 1H).

156

Intermediate: trans-3,6-Dichloro-1-(3-((1-(3-fluorotetrahydro-2H-pyran-4-yl)-5-methyl-4-nitro-1H-pyrazol-3-yl)oxy)propyl)-1H-pyrazolo[3,4-d]pyrimidine

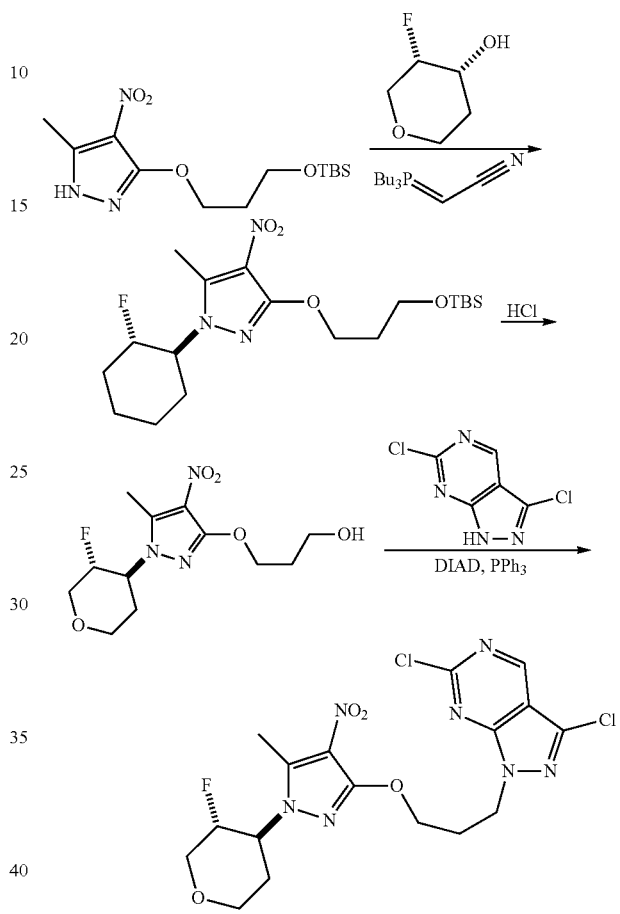

To a solution of 3-(3-((tert-butyldimethylsilyl)oxy)propoxy)-5-methyl-4-nitro-1H-pyrazole (1.6 g, 5.1 mmol) in toluene (20 mL) was added cis-3-fluorotetrahydropyran-4-ol (914 mg, 7.61 mmol) and 2-(tributyl-X-phosphanylidene)acetonitrile (4.90 g, 20.3 mmol). The mixture was stirred at 110° C. for 15 h. The reaction mixture was concentrated under reduced pressure. The residue was purified by chromatography on silica gel (eluent: petroleum ether:EtOAc 100:0→80:20) to afford trans-3-(3-((tert-butyldimethylsilyl)oxy)propoxy)-1-(3-fluorotetrahydro-2H-pyran-4-yl)-5-methyl-4-nitro-1H-pyrazole (1.6 g) of sufficient purity for the subsequent step. ¹H NMR (CDCl₃, 400 MHz) δ 5.00-4.75 (m, 1H), 4.41 (t, J=6.4 Hz, 2H), 4.31-4.18 (m, 2H), 4.11-4.04 (m, 1H), 3.82 (t, J=6.0 Hz, 2H), 3.56-3.46 (m, 1H), 3.43-3.34 (m, 1H), 2.66 (s, 3H), 2.57-2.45 (m, 1H), 2.05-1.99 (m, 2H), 1.98-1.89 (m, 1H), 0.89 (s, 9H), 0.05 (s, 6H).

A solution of trans-3-(3-((tert-butyldimethylsilyl)oxy)propoxy)-1-(3-fluorotetrahydro-2H-pyran-4-yl)-5-methyl-4-nitro-1H-pyrazole (1.6 g, 3.8 mmol) in HCl/dioxane (4 M, 10 mL) was stirred at 20° C. for 15 h. The reaction mixture was concentrated under reduced pressure. The residue was purified by chromatography on silica gel (eluent: petroleum ether:EtOAc 100:0→40:60) to afford trans-3-((1-(3-fluorotetrahydro-2H-pyran-4-yl)-5-methyl-4-nitro-1H-pyrazol-3-yl)oxy)propan-1-ol (850 mg) of sufficient purity for the subsequent step. LC-MS (method B) (m/z)=304.2 (MH)+ $t_R$=0.73 minutes.

DIAD (800 mg, 3.96 mmol) was added to a solution of trans-3-((1-(3-fluorotetrahydro-2H-pyran-4-yl)-5-methyl-4-nitro-1H-pyrazol-3-yl)oxy)propan-1-ol (400 mg, 1.32 mmol) 3,6-dichloro-1H-pyrazolo[3,4-d]pyrimidine (249 mg, 1.32 mmol), and PPh$_3$ (1.04 g, 3.96 mmol) in THF (20 mL) at 0° C. Then the mixture was stirred at 20° C. for 15 h. The reaction mixture was concentrated under reduced pressure. The residue was purified by chromatography on silica gel (eluent: petroleum ether:EtOAc 100:0→70:30) to afford trans-3,6-dichloro-1-(3-((1-(3-fluorotetrahydro-2H-pyran-4-yl)-5-methyl-4-nitro-1H-pyrazol-3-yl)oxy)propyl)-1H-pyrazolo[3,4-d]pyrimidine (450 mg) of sufficient purity for the subsequent step. LC-MS (method B) (m/z)=474.2 (MH)+ $t_R$=0.92 minutes.

Intermediate: 3-(8-Chloro-3-methyl-4,11,12,13-tetrahydro-2H-5,7-(azenometheno)dipyrazolo[3,4-b:5',1'-g][1,4,6,8]oxatriazacycloundecin-2-yl)bicyclo[1.1.1]pentane-1-carboxamide

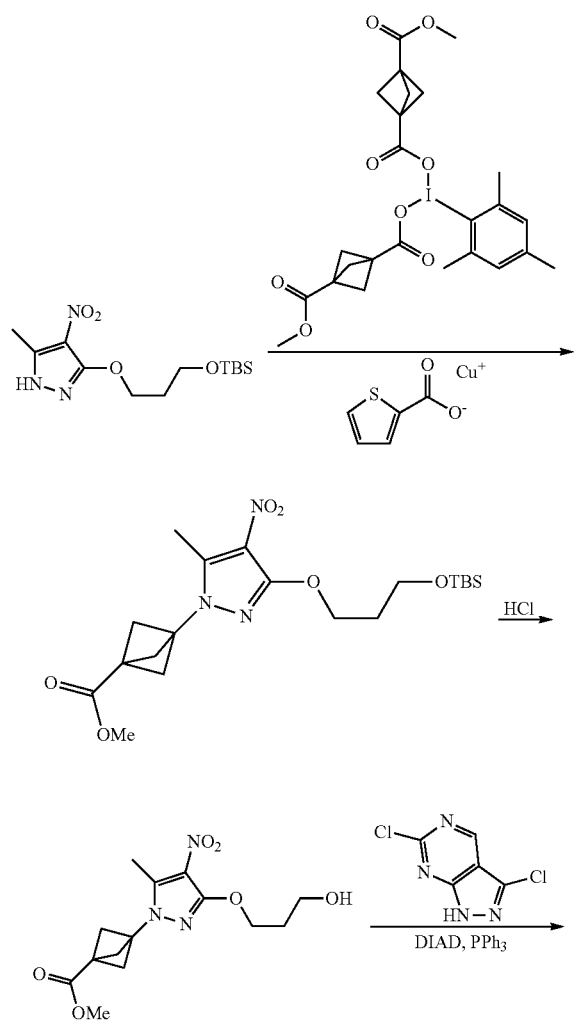

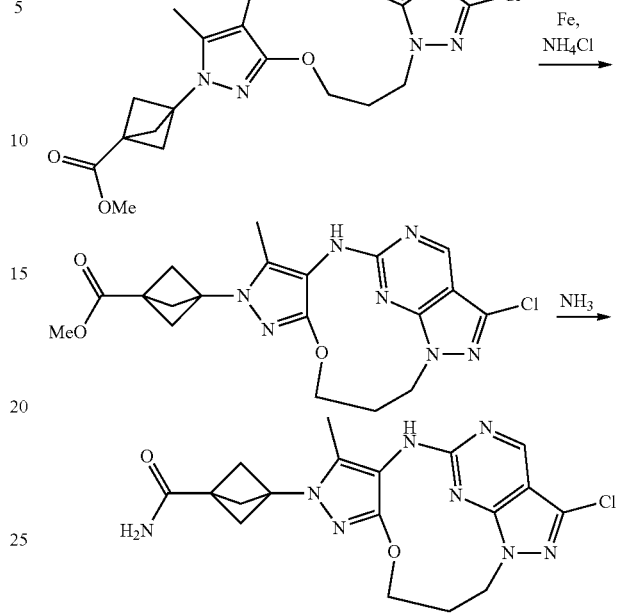

A mixture of O3-[(3-methoxycarbonylbicyclo[1.1.1]pentane-1-carbonyl)oxy-(2,4,6-trimethylphenyl)-V-iodanyl] O1-methyl bicyclo[1.1.1]pentane-1,3-dicarboxylate (600 mg, 1.03 mmol), 3-(3-((tert-butyldimethylsilyl)oxy)propoxy)-5-methyl-4-nitro-1H-pyrazole (300 mg, 0.951 mmol), pentane-2,4-dione (114 mg, 1.14 mmol), thiophene-2-carbonyloxycopper (218 mg, 1.14 mmol), 4,7-diphenyl-1,10-phenanthroline (632 mg, 1.90 mmol), and DBU (145 mg, 0.951 mmol) in 1,4-dioxane (15 mL) was degassed and purged with N$_2$ for 3 times and then the mixture was stirred at 20° C. for 60 h in the dark. The reaction mixture was diluted with aqueous NH$_4$Cl (50 mL) and extracted with DCM (3×100 mL). The combined organic layers were dried over Na$_2$SO$_4$ and concentrated under reduced pressure. The residue was purified by chromatography on silica gel (eluent: petroleum ether:EtOAc 100:0→80:20) to afford 3-(3-(3-((tertbutyldimethylsilyl)oxy)propoxy)-5-methyl-4-nitro-1H-pyrazol-1-yl)bicyclo[1.1.1]pentane-1-carboxylate (300 mg) of sufficient purity for the subsequent step. $^1$H NMR (CDCl$_3$, 400 MHz) δ 4.39 (t, J=6.4 Hz, 2H), 3.80 (t, J=6.4 Hz, 2H), 3.75 (s, 3H), 2.67 (s, 3H), 2.63 (s, 6H), 2.04-1.98 (m, 2H), 0.89 (s, 9H), 0.05 (s, 6H).

A solution of methyl 3-(3-(3-((tert-butyldimethylsilyl)oxy)propoxy)-5-methyl-4-nitro-1H-pyrazol-1-yl)bicyclo[1.1.1]pentane-1-carboxylate (570 mg, 1.30 mmol) in HCl/MeOH (4M, 10 mL) was stirred at 20° C. for 1 hour. The reaction mixture was concentrated under reduced pressure. The residue was purified by chromatography on silica gel (eluent: petroleum ether:EtOAc 100:0→60:40) to afford methyl-3-(3-(3-hydroxypropoxy)-5-methyl-4-nitro-1H-pyrazol-1-yl)bicyclo[1.1.1]pentane-1-carboxylate (250 mg) of sufficient purity for the subsequent step. $^1$H NMR (DMSO-d$^6$, 400 MHz) δ 4.53 (s, 1H), 4.28 (t, J=6.4 Hz, 2H), 3.66 (s, 3H), 3.53 (t, J=6.0 Hz, 2H), 2.63 (s, 3H), 2.61 (s, 6H), 1.94-1.81 (m, 2H).

DIAD (448 mg, 2.21 mmol) was added to a solution of methyl-3-(3-(3-hydroxypropoxy)-5-methyl-4-nitro-1H-pyrazol-1-yl)bicyclo[1.1.1]pentane-1-carboxylate (240 mg, 0.738 mmol), 3,6-dichloro-1H-pyrazolo[3,4-d]pyrimidine (139 mg, 0.738 mmol), and PPh₃ on resin (736 mg, 2.21 mmol, 3 mmol/g) in THF (10 mL) at 0° C. The mixture was stirred at 20° C. for 15 h. The reaction mixture was concentrated under reduced pressure. The residue was purified by chromatography on silica gel (eluent: petroleum ether: EtOAc 100:0→40:60) to afford methyl 3-(3-(3-(3,6-dichloro-1H-pyrazolo[3,4-d]pyrimidin-1-yl)propoxy)-5-methyl-4-nitro-1H-pyrazol-1-yl)bicyclo[1.1.1]pentane-1-carboxylate (270 mg) of sufficient purity for the subsequent step. ¹H NMR (CDCl₃, 400 MHz) δ8.96 (s, 1H), 4.65 (t, J=6.4 Hz, 2H), 4.33 (t, J=6.0 Hz, 2H), 3.75 (s, 3H), 2.66 (s, 3H), 2.60 (s, 6H), 2.51-2.41 (m, 2H).

To a solution of methyl 3-(3-(3-(3,6-dichloro-1H-pyrazolo[3,4-d]pyrimidin-1-yl)propoxy)-5-methyl-4-nitro-1H-pyrazol-1-yl)bicyclo[1.1.1]pentane-1-carboxylate (260 mg, 0.524 mmol) in EtOH (40 mL) and H₂O (8 mL) was added Fe (146 mg, 2.61 mmol) and NH₄Cl (140 mg, 2.62 mmol). The mixture was stirred at 80° C. for 15 h. The reaction mixture was concentrated under reduced pressure. The residue was purified by chromatography on silica gel (eluent: petroleum ether:EtOAc 100:0→50:50) to afford methyl 3-(8-chloro-3-methyl-4,11,12,13-tetrahydro-2H5,7-(azenometheno)dipyrazolo[3,4-b:5',1'-g][1,4,6,8]oxatriazacycloundecin-2-yl)bicyclo[1.1.1]pentane-1-carboxylate (100 mg) of sufficient purity for the subsequent step. ¹H NMR (CDCl₃, 400 MHz) δ 8.65 (s, 1H), 6.82 (br s, 1H), 4.54-4.46 (m, 2H), 4.46-4.38 (m, 2H), 3.74 (s, 3H), 2.61 (s, 6H), 2.33 (s, 3H), 2.01-1.85 (m, 2H).

NH₃/MeOH (7 M, 15 mL) was added to methyl 3-(8-chloro-3-methyl-4,11,12,13-tetrahydro-2H-5,7-(azenometheno)dipyrazolo[3,4-b:5',1'-g][1,4,6,8]oxatriazacycloundecin-2-yl)bicyclo[1.1.1]pentane-1-carboxylate (90 mg, 0.209 mmol) in a sealed flask. The reaction mixture was stirred at 80° C. for 15 h. The reaction mixture was concentrated under reduced pressure to afford 3-(8-chloro-3-methyl-4,11,12,13-tetrahydro-2H-5,7-(azenometheno)dipyrazolo[3,4-b:5',1'-g][1,4,6,8]oxatriazacycloundecin-2-yl)bicyclo[1.1.1]pentane-1-carboxamide (80 mg) of sufficient purity for the subsequent step.

Intermediate: 3,6-Dichloro-1-(3-((5-methyl-4-nitro-1-(2-oxaspiro[3.3]heptan-6-yl)-1H-pyrazol-3-yl)oxy)propyl)-1H-pyrazolo[3,4-d]pyrimidine

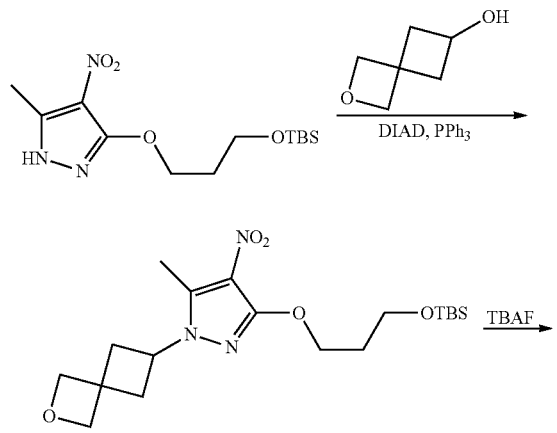

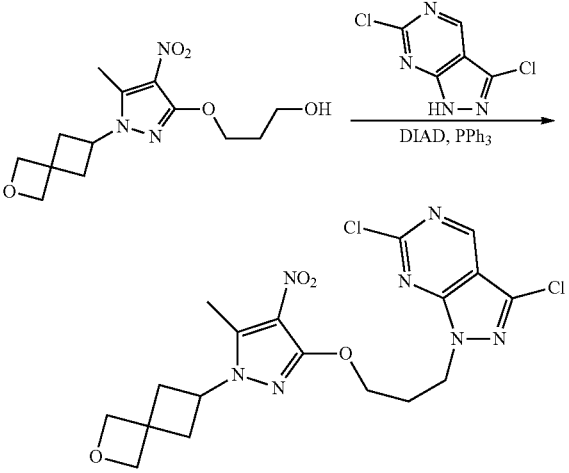

A mixture of 3-(3-((tert-butyldimethylsilyl)oxy)propoxy)-5-methyl-4-nitro-1H-pyrazole (350 mg, 1.11 mmol), 2-oxaspiro[3.3]heptan-6-ol (152 mg, 1.33 mmol), PPh₃ on resin (553 mg, 1.66 mmol, 3 mmol/g), and DIAD (337 mg, 1.66 mmol) in THF (5 mL) was stirred at 20° C. for 16 h. The mixture was concentrated under reduced pressure. The residue was purified by chromatography on silica gel (eluent: petroleum ether:EtOAc 100:0→70:30) to afford 3-(3-((tert-butyldimethylsilyl)oxy)propoxy)-5-methyl-4-nitro-1-(2-oxaspiro[3.3]heptan-6-y)-1H-pyrazole (295 mg) of sufficient purity for the subsequent step. H NMR (CDCl₃, 400 MHz) δ 4.77 (d, J=4.8 Hz, 4H), 4.56-4.49 (m, 1H), 4.41 (t, J=6.0 Hz, 2H), 3.82 (t, J=6.0 Hz, 2H), 2.87-2.79 (m, 2H), 2.77-2.69 (m, 2H), 2.56 (s, 3H), 2.07-2.02 (m, 2H), 0.89 (s, 9H), 0.05 (s, 6H).

To a solution of 3-(3-((tert-butyldimethylsilyl)oxy)propoxy)-5-methyl-4-nitro-1-(2-oxaspiro[3.3]heptan-6-yl)-1H-pyrazole (260 mg, 0.63 mmol) in THF (5 mL) was added TBAF (1 M, 1 mL). The mixture was stirred at 20° C. for 2 h. The mixture was diluted with water (10 mL) and extracted with EtOAc (15 mL×3). The combined organic layers were concentrated under reduced pressure. The residue was purified by chromatography on silica gel (eluent: petroleum ether:EtOAc 100:0→0:100) to afford 3-((5-methyl-4-nitro-1-(2-oxaspiro[3.3]heptan-6-yl)-1H-pyrazol-3-yl)oxy)propan-1-ol (179 mg) of sufficient purity for the subsequent step. ¹H NMR (CDCl₃, 400 MHz) δ4.77 (d, J=9.2 Hz, 4H), 4.56-4.47 (m, 3H), 3.86 (t, J=5.6 Hz, 2H), 2.86-2.78 (m, 2H), 2.77-2.70 (m, 2H), 2.57 (s, 3H), 2.14-2.06 (m, 2H).

A mixture of 3-((5-methyl-4-nitro-1-(2-oxaspiro[3.3]heptan-6-yl)-1H-pyrazol-3-yl)oxy)propan-1-ol (160 mg, 0.54 mmol), 3,6-dichloro-1H-pyrazolo[3,4-d]pyrimidine (101.71 mg, 0.54 mmol), PPh₃ on resin (304 mg, 0.92 mmol) (3 mmol/g), and DIAD (185 mg, 0.92 mmol) in THF (5 mL) was stirred at 20° C. for 16 h. The mixture was concentrated under reduced pressure. The residue was purified by chromatography on silica gel (eluent: petroleum ether:EtOAc 100:0→20:80) to afford 3,6-dichloro-1-(3-((5-methyl-4-nitro-1-(2-oxaspiro[3.3]heptan-6-yl)-1H-pyrazol-3-yl)oxy)propyl)-1H-pyrazolo[3,4-d]pyrimidine (170 mg) of sufficient purity for the subsequent step. ¹H NMR (CDCl₃, 400 MHz) δ 8.96 (s, 1H), 4.77 (s, 2H), 4.72 (s, 2H), 4.66 (t, J=6.4 Hz, 2H), 4.52-4.45 (m, 1H), 4.37 (t, J=5.6 Hz, 2H), 2.78-2.69 (m, 4H), 2.55 (s, 3H), 2.50-2.44 (m, 2H).

Intermediate: 3,6-Dichloro-1-(3-((5-(methyl-d$_3$)-4-nitro-1-(tetrahydro-2H-pyran-4-yl)-1H-pyrazol-3-yl)oxy)propyl-1,1,2,2,3,3-d$_6$)-1H-pyrazolo[3,4-d]pyrimidine

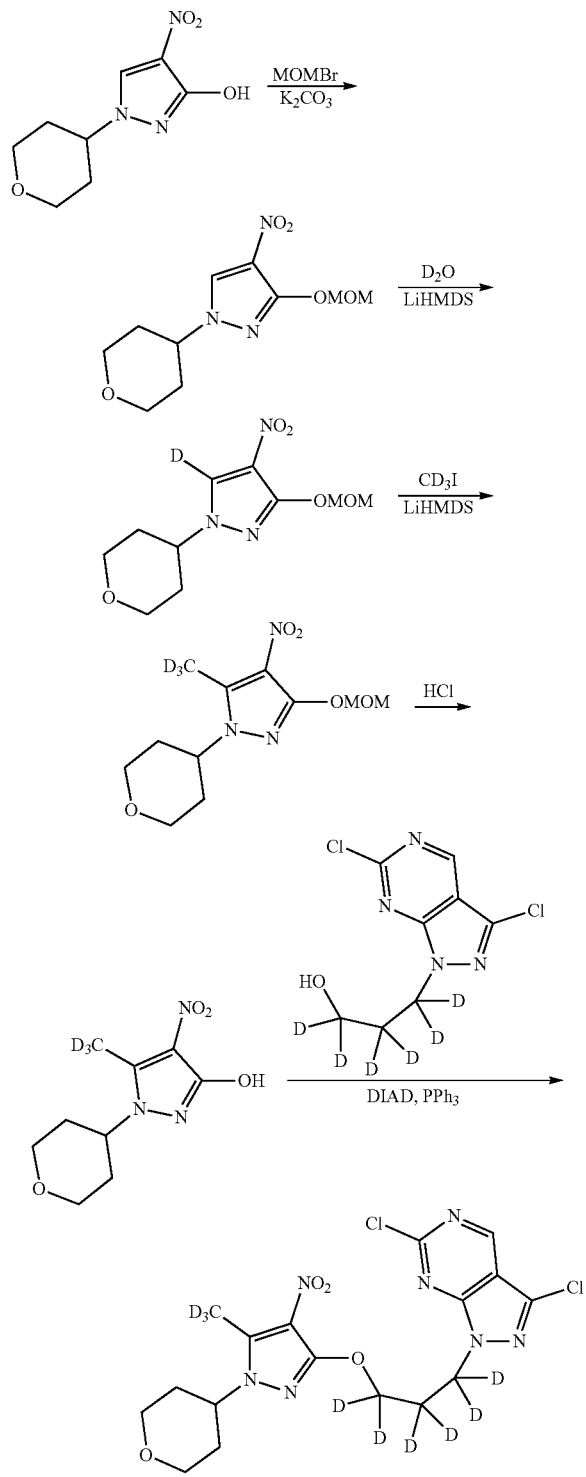

To a stirred mixture of 4-nitro-1-(tetrahydro-2H-pyran-4-yl)-1H-pyrazol-3-ol (100 mg, 0.469 mmol) and K$_2$CO$_3$ (259 mg, 1.87 mmol) in DMF (3 mL) was added bromo(methoxy)methane (117 mg, 0.938 mmol) in portions at 0° C. The resulting mixture was stirred for 16 h at room temperature. The reaction was quenched by the addition of water (100 mL) and extracted with EtOAc (3×50 mL). The combined organic layers were washed with brine (50 mL), dried over Na$_2$SO$_4$, and concentrated under reduced pressure. The residue was purified by chromatography on silica gel (eluent: petroleum ether:EtOAc 50:50) afford 3-(methoxymethoxy)-4-nitro-1-(tetrahydro-2H-pyran-4-yl)-1H-pyrazole (40 mg) of sufficient purity for the subsequent step.

To a stirred solution of 3-(methoxymethoxy)-4-nitro-1-(tetrahydro-2H-pyran-4-yl)-1H-pyrazole (200 mg, 0.777 mmol) in THF (2 mL) was added LiHMDS (1.55 mL, 1.55 mmol, 1M in THF) dropwise at −78° C. under. The resulting mixture was stirred for 2 h at −78° C. D$_2$O (4 mL) was added at −78° C. The resulting mixture was diluted with water (100 mL) and extracted with EtOAc (3×50 mL). The combined organic layers were dried over Na$_2$SO$_4$ and concentrated under reduced pressure. The residue was purified by chromatography on silica gel (eluent: petroleum ether:EtOAc 50:50) to afford 3-(methoxymethoxy)-4-nitro-1-(tetrahydro-2H-pyran-4-yl)-1H-pyrazole-5-d (180 mg) of sufficient purity for the subsequent step.

To a stirred solution 3-(methoxymethoxy)-4-nitro-1-(tetrahydro-2H-pyran-4-yl)-1H-pyrazole-5-d (50 mg) in THF (1.5 mL) was added LiHMDS (0.39 mL, 0.39 mmol, 1M in THF) in a dropwise manner at −78° C. The resulting mixture was stirred for 1 h at −78° C. CD$_3$I (113 mg, 0.776 mmol) was added in a dropwise manner at −78° C. The resulting mixture was stirred for 2 h at −78° C. followed by dropwise addition of D$_2$O (2 mL) dropwise at −78° C. The residue was purified by chromatography on silica gel (eluent: petroleum ether:EtOAc 67:33) to afford 3-(methoxymethoxy)-5-(methyl-d$_3$)-4-nitro-1-(tetrahydro-2H-pyran-4-yl)-1H-pyrazole (40 mg) of sufficient purity for the subsequent step.

A solution of 3-(methoxymethoxy)-5-(methyl-d$_3$)-4-nitro-1-(tetrahydro-2H-pyran-4-yl)-1H-pyrazole (150 mg, 0.547 mmol) and HCl in 1,4-dioxane (4 mL, 16 mmol, 4M) in DCM (2 mL) was stirred at room temperature for 2 h. The resulting mixture was concentrated under reduced pressure to afford 5-(methyl-d$_3$)-4-nitro-1-(tetrahydro-2H-pyran-4-yl)-1H-pyrazol-3-ol (101 mg) of sufficient purity for the subsequent step. $^1$H NMR (DMSO-d$_6$, 400 MHz) δ 11.35 (s, 1H), 4.47 (tt, J=11.2, 4.0 Hz, 1H), 3.96-3.92 (m, 2H), 3.46 (t, J=12.0 Hz, 2H), 1.97-1.93 (m, 2H), 1.77-1.74 (m, 2H).

To a stirred solution of 5-(methyl-ds)-4-nitro-1-(tetrahydro-2H-pyran-4-yl)-1H-pyrazol-3-ol (95.5 mg, 0.416 mmol) in THF (5 mL) were added 3-(3,6-dichloro-1H-pyrazolo[3,4-d]pyrimidin-1-yl)propan-1,1,2,2,3,3-d$_6$-1-ol (70 mg, 0.277 mmol) and PPh$_3$ (145 mg, 0.554 mmol) in portions at room temperature under argon atmosphere. To the above mixture was added DIAD (0.11 mL, 0.554 mmol) dropwise at 0° C. The resulting mixture was stirred for 2 h at room temperature and concentrated under reduced pressure. The residue was purified by chromatography on silica gel (eluent: petroleum ether:EtOAc 50:50) to afford 3,6-dichloro-1-(3-((5-(methyl-d$_3$)-4-nitro-1-(tetrahydro-2H-pyran-4-yl)-1H-pyrazol-3-yl)oxy)propyl-1,1,2,2,3,3-d$_6$)-1H-pyrazolo[3,4-d]pyrimidine (110 mg) of sufficient purity for the subsequent step.

Intermediate: 1-(8-Chloro-3-methyl-4,11,12,13-tetrahydro-2H-5,7-(azenometheno)dipyrazolo[3,4-b:5', 1'-g][1,4,6,8]oxatriazacycloundecin-2-yl)cyclopropanecarboxamide

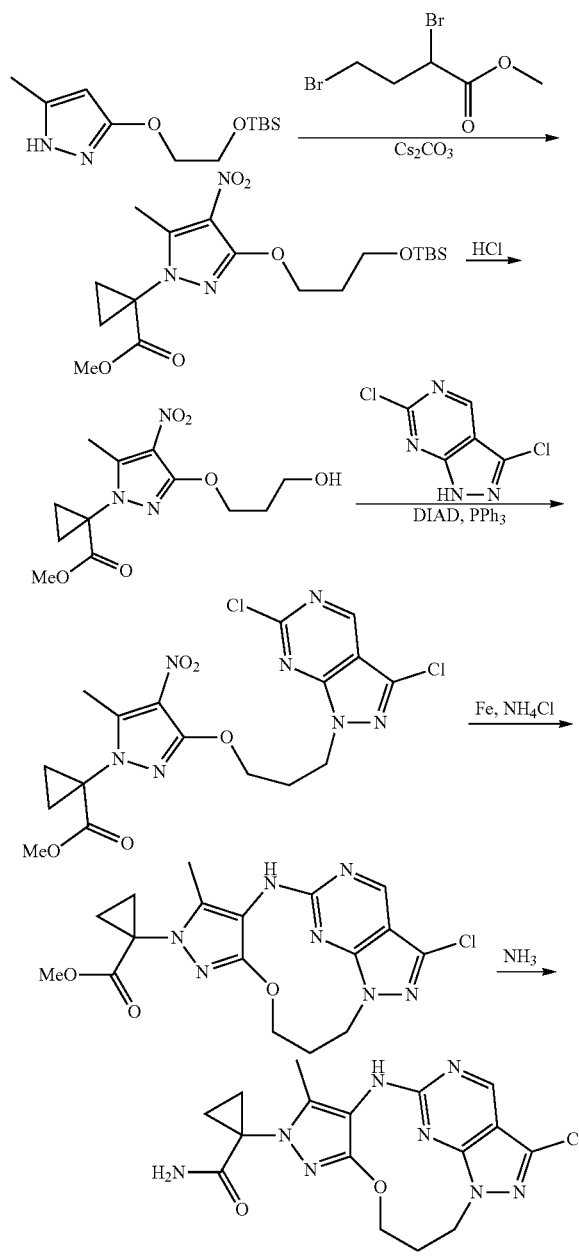

To a solution of 3-(3-((tert-butyldimethylsilyl)oxy) propoxy)-5-methyl-4-nitro-1H-pyrazole (600 mg, 1.90 mmol) in DMF (24 mL) was added Cs$_2$CO$_3$ (2.48 g, 7.62 mmol) and methyl 2,4-dibromobutanoate (552 mg, 2.12 mmol). The mixture was stirred at 45° C. for 16 h. The reaction mixture was diluted with water (15 mL) and extracted with EtOAc (3×15 mL). The combined organic layers were washed with brine (3×15 mL), dried over Na$_2$SO$_4$, and concentrated under reduced pressure. The residue was purified by chromatography on silica gel (eluent: petroleum ether:EtOAc 100:0→90:10) to afford 1-(3-(3-(3-((tertbutyldimethylsilyl)oxy)propoxy)-5-methyl-4-nitro-1H-pyrazol-1-yl)cyclopropanecarboxylate (440 mg) of sufficient purity for the subsequent step. $^1$H NMR (DMSO-d$_6$, 400 MHz) δ 4.28 (t, J=6.0 Hz, 2H), 3.73 (t, J=6.0 Hz, 2H), 3.65 (s, 3H), 2.54 (s, 3H), 1.95-1.85 (m, 2H), 1.86-1.78 (m, 2H), 1.77-1.70 (m, 2H), 0.84 (s, 9H), 0.01 (s, 6H).

To methyl 1-(3-(3-((tert-butyldimethylsilyl)oxy) propoxy)-5-methyl-4-nitro-1H-pyrazol-1-yl)cyclopropanecarboxylate (440 mg, 1.06 mmol) was added HCl/dioxane (4 M, 5 mL) and the mixture was stirred at 20° C. for 16 h. The reaction mixture was concentrated under reduced pressure. The residue was purified by chromatography on silica gel (eluent: DCM:MeOH 100:0→97:3) to afford a residue that was suspended in water (10 mL), extracted with EtOAc (3×40 mL) and the combined organic layers were dried over Na$_2$SO$_4$ and concentrated under reduced pressure to afford methyl 1-(3-(3-hydroxypropoxy)-5-methyl-4-nitro-1H-pyrazol-1-yl)cyclopropanecarboxylate (320 mg) of sufficient purity for the subsequent step.

To a solution of methyl 1-(3-(3-hydroxypropoxy)-5-methyl-4-nitro-1H-pyrazol-1-yl)cyclopropanecarboxylate (300 mg, 1.00 mmol), 3,6-dichloro-1H-pyrazolo[3,4-d]pyrimidine (202 mg, 1.07 mmol), and DIAD (608 mg, 3.01 mmol) in THF (5 mL) was added PPh$_3$ (789 mg, 3.01 mmol) at 0° C. The mixture was stirred at 20° C. for 16 h. The reaction mixture was concentrated under reduced pressure. The residue was purified by chromatography on silica gel (eluent: petroleum ether:EtOAc 100:0→70:30) to afford methyl 1-(3-(3-(3,6-dichloro-1H-pyrazolo[3,4-d]pyrimidin-1-yl)propoxy)-5-methyl-4-nitro-1H-pyrazol-1-yl)cyclopropanecarboxylate (230 mg) of sufficient purity for the subsequent step. $^1$H NMR (DMSO-d$_6$, 400 MHz) δ 9.27 (s, 1H), 4.55 (t, J=6.4 Hz, 2H), 4.26 (t, J=5.6 Hz, 2H), 3.65 (s, 3H), 2.54 (s, 3H), 2.35-2.25 (m, 2H), 1.85-1.77 (m, 2H), 1.70-1.65 (m, 2H).

A mixture of methyl 1-(3-(3-(3,6-dichloro-1H-pyrazolo[3,4-d]pyrimidin-1-yl)propoxy)-5-methyl-4-nitro-1H-pyrazol-1-yl)cyclopropanecarboxylate (190 mg, 0.340 mmol), Fe (95 mg, 1.70 mmol), and NH$_4$Cl (91 mg, 1.7 mmol) in EtOH (4 mL) and H$_2$O (1 mL) was degassed and purged with N$_2$ for 3 times, and then the mixture was stirred at 80° C. for 16 h. The reaction mixture was concentrated under reduced pressure. The residue was purified by chromatography on silica gel (eluent: petroleum ether:EtOAc 100:0→50:50) to afford methyl 1-(8-chloro-3-methyl-4,11,12,13-tetrahydro-2H-5,7-(azenometheno)dipyrazolo[3,4-b:5', 1'-g][1,4,6,8]oxatriazacycloundecin-2-yl) cyclopropanecarboxylate (63 mg) of sufficient purity for the subsequent step. LC-MS (method B) (m/z)=404.2 (MH)$^+$ t$_R$=0.79 minutes.

A mixture of NH$_3$/MeOH (7 M, 8 mL) and methyl 1-(8-chloro-3-methyl-4,11,12,13-tetrahydro-2H-5,7-(azenometheno)dipyrazolo[3,4-b:5',1'-g][1,4,6,8]oxatriazacycloundecin-2-yl)cyclopropanecarboxylate (60 mg, 0.15 mmol) in a sealed tube was heated at 80° C. for 2 h using a microwave reactor. The reaction mixture was concentrated under reduced pressure. The residue was purified by chromatography on silica gel (eluent: petroleum ether:EtOAc 100:0→80:20) to afford 1-(8-chloro-3-methyl-4,11,12,13-tetrahydro-2H-5,7-(azenometheno)dipyrazolo[3,4-b:5',1'-g] [1,4,6,8]oxatriazacycloundecin-2-yl)cyclopropanecarboxamide (40 mg) of sufficient purity for the subsequent step. LC-MS (method B) (m/z)=389.2 (MH)$^+$ t$_R$=0.70 minutes.

Intermediate: 3,6-Dichloro-1-(3-((1-((1r,4r)-4-methoxycyclohexyl)-5-methyl-4-nitro-1H-pyrazol-3-yl)oxy)propyl)-1H-pyrazolo[3,4-d]pyrimidine

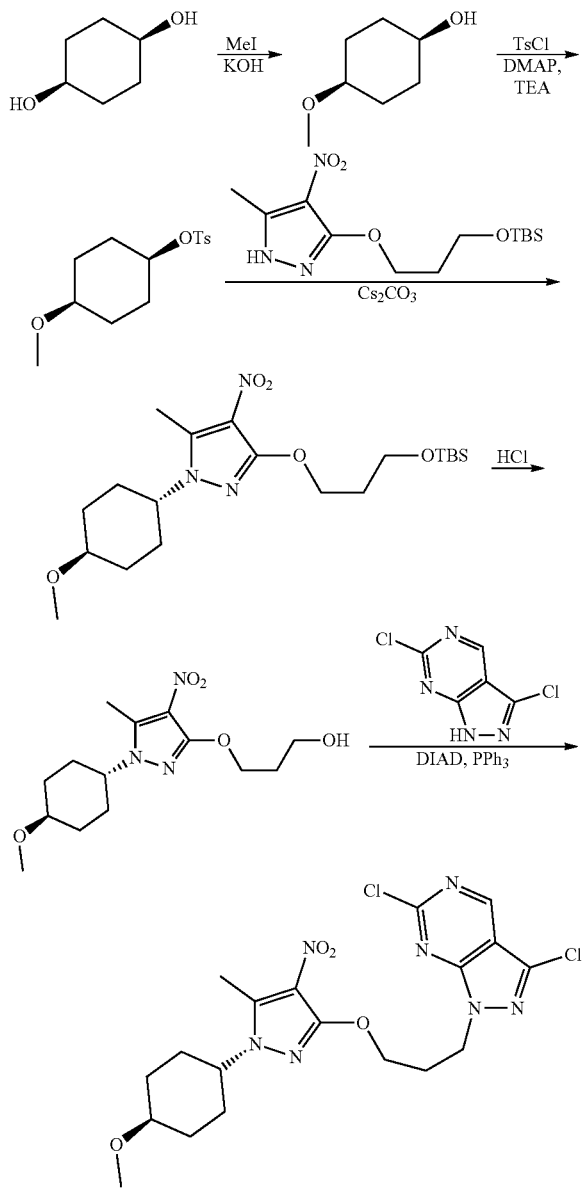

To a solution of (1s,4s)-cyclohexane-1,4-diol (2 g, 17 mmol) in water (10 mL) was added KOH (1.06 g, 18.94 mmol) and MeI (3.67 g, 25.8 mmol). The mixture was stirred at 100° C. for 5 h. The reaction mixture was concentrated under reduced pressure. The residue was purified by chromatography on silica gel (eluent: petroleum ether:EtOAc 95:5→50:50) to afford (1s,4s)-4-methoxycyclohexanol (500 mg) of sufficient purity for the subsequent step. $^1$H NMR (CDCl$_3$, 400 MHz) δ3.79-3.69 (m, 1H), 3.38-3.21 (m, 4H), 1.89-1.75 (m, 2H), 1.70-1.62 (m, 4H), 1.58-1.50 (m, 2H).

To a solution of (1s,4s)-4-methoxycyclohexanol (400 mg, 3.07 mmol) in DCM (6 mL) at 0° C. were successively added Et$_3$N (684 mg, 6.76 mmol), DMAP (38 mg, 0.31 mmol), and TsCl (820 mg, 4.30 mmol). The mixture was allowed to warm to 15° C. and stirred for 16 h. The reaction mixture was concentrated under reduced pressure. The residue was purified by chromatography on silica gel (eluent: petroleum ether:EtOAc 100:0→70:30) to afford (1s,4s)-4-methoxycyclohexyl 4-methylbenzenesulfonate (350 mg) of sufficient purity for the subsequent step. $^1$H NMR (CDCl$_3$, 400 MHz) δ7.80 (d, J=8.4 Hz, 2H), 7.33 (d, J=8.0 Hz, 2H), 4.65-4.56 (m, 1H), 3.30 (s, 3H), 3.26-3.18 (m, 1H), 2.45 (s, 3H), 1.94-1.82 (m, 2H), 1.80-1.70 (m, 2H), 1.63-1.56 (m, 4H).

A mixture of 3-(3-((tert-butyldimethylsilyl)oxy)propoxy)-5-methyl-4-nitro-1H-pyrazole (400 mg, 1.27 mmol), (1s,4s)-4-methoxycyclohexyl 4-methylbenzenesulfonate (400 mg, 1.41 mmol), and Cs$_2$CO$_3$ (826 mg, 2.54 mmol) in DMF (10 mL) was degassed and purged with N$_2$×3, and then stirred at 80° C. for 16 h. The mixture was concentrated under reduced pressure. The residue was purified by chromatography on silica gel (eluent: petroleum ether:EtOAc 95:5→70:30) to afford 3-(3-((tert-butyldimethylsilyl)oxy)propoxy)-1-((1r,4r)-4-fluorocyclohexyl)-5-methyl-4-nitro-1H-pyrazole (240 mg) of sufficient purity for the subsequent step. $^1$H NMR (CDCl$_3$, 400 MHz) δ4.39 (t, J=6.0 Hz, 2H), 4.03-3.94 (m, 1H), 3.81 (t, J=6.0 Hz, 2H), 3.39 (s, 3H), 3.30-3.20 (m, 1H), 2.62 (s, 3H), 2.28-2.19 (m, 2H), 2.06-2.04 (m, 2H), 2.02-1.97 (m, 2H), 1.95-1.84 (m, 2H), 1.42-1.30 (m, 2H), 0.89 (s, 9H), 0.05 (s, 6H).

A mixture of 3-(3-((tert-butyldimethylsilyl)oxy)propoxy)-1-((1r,4r)-4-fluorocyclohexyl)-5-methyl-4-nitro-1H-pyrazole (240 mg, 0.56 mmol) in HCl/dioxane (4 M, 5 mL) was degassed and purged with N$_2$×3, and then the mixture was stirred at 15° C. for 1 h. The mixture was concentrated under reduced pressure. The residue was purified by chromatography on silica gel (eluent: petroleum ether:EtOAc 95:5→0:100) to afford 3-((1-((1r,4r)-4-methoxycyclohexyl)-5-methyl-4-nitro-1H-pyrazol-3-yl)oxy)propan-1-ol (130 mg) of sufficient purity for the subsequent step. $^1$H NMR (400 MHz, CDCl$_3$) δ 4.50 (t, J=6.4 Hz, 2H), 4.06-3.95 (m, 1H), 3.82 (t, J=5.6 Hz, 2H), 3.38 (s, 3H), 3.30-3.18 (m, 1H), 2.63 (s, 3H), 2.31-2.17 (m, 2H), 2.10-2.05 (m, 2H), 2.04-1.95 (m, 2H), 1.94-1.82 (m, 2H), 1.43-1.30 (m, 2H).

To a solution of 3-((1-((1r,4r)-4-methoxycyclohexyl)-5-methyl-4-nitro-1H-pyrazol-3-yl)oxy)propan-1-ol (130 mg, 0.41 mmol), 3,6-dichloro-1H-pyrazolo[3,4-d]pyrimidine (78 mg, 0.41 mmol) and PPh$_3$ (218 mg, 0.83 mmol) in THF (10 mL) was added DIAD (168 mg, 0.83 mmol) in a dropwise manner at 0° C. The mixture was stirred at 15° C. for 16 h. The mixture was concentrated under reduced pressure. The residue was purified by chromatography on silica gel (eluent: petroleum ether:EtOAc 80:20→50:50) to afford 3,6-dichloro-1-(3-((1-((1r,4r)-4-methoxycyclohexyl)-5-methyl-4-nitro-1H-pyrazol-3-yl)oxy)propyl)-1H-pyrazolo[3,4-d]pyrimidine (160 mg) of sufficient purity for the subsequent step. LC-MS (method B) (m/z)=484.2 (MH)$^+$ t$_R$=0.95 minutes.

Intermediate: 1-(3-((1-(3-Oxabicyclo[3.1.0]hexan-6-yl)-5-methyl-4-nitro-1H-pyrazol-3-yl)oxy)propyl)-3,6-dichloro-1H-pyrazolo[3,4-d]pyrimidine

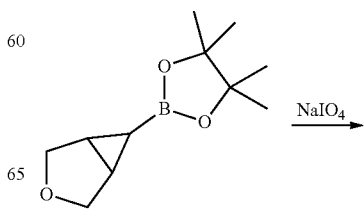

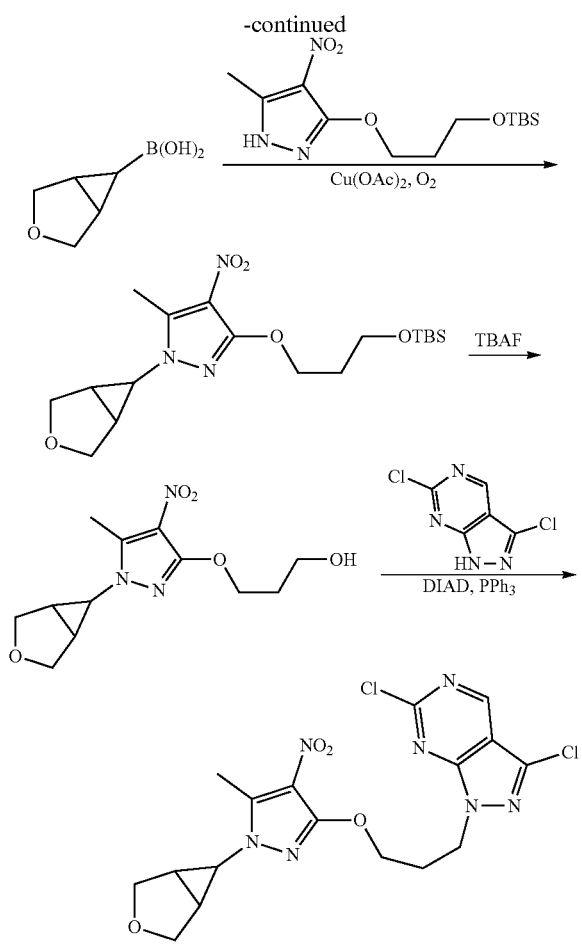

To 2-(3-oxabicyclo[3.1.0]hexan-6-yl)-4,4,5,5-tetramethyl-1,3,2-dioxaborolane (950 mg, 4.52 mmol) in THF (20 mL) and H₂O (5 mL) was added sodium periodate (2.91 g, 13.6 mmol) and the reaction was stirred at 20° C. for 30 minutes. Then aqueous HCl (1 M, 5 mL) was added and the reaction was stirred at 20° C. for 12 h. The reaction was filtered and the filter cake was washed with THF (20 mL×2). The filtrate was concentrated under reduced pressure. The residue was diluted with EtOAc (30 mL), washed with brine (10 mL), dried over Na₂SO₄, and concentrated under reduced pressure to afford 3-oxabicyclo[3.1.0]hexan-6-yl-boronic acid (579 mg) of sufficient purity for the subsequent step.

A mixture of 3-(3-((tert-butyldimethylsilyl)oxy)propoxy)-5-methyl-4-nitro-1H-pyrazole (700 mg, 2.22 mmol), 3-oxabicyclo[3.1.0]hexan-6-ylboronic acid (579 mg, 4.53 mmol), Cu(OAc)₂ (613 mg, 3.37 mmol) and 4 Å MS (700 mg) in DCE (50 mL) was stirred at 65° C. under oxygen (15 psi) for 36 h. The reaction mixture was filtered and concentrated under reduced pressure. The residue was purified by chromatography on silica gel (eluent: petroleum ether:EtOAc 100:0→70:30) to afford 1-(3-oxabicyclo[3.1.0]hexan-6-yl)-3-(3-((tert-butyldimethylsilyl)oxy)propoxy)-5-methyl-4-nitro-1H-pyrazole (730 mg) of sufficient purity for the subsequent step. LC-MS (method B) (m/z)=398.2 (MH)⁺ $t_R$=0.96 minutes.

To a solution of 1-(3-oxabicyclo[3.1.0]hexan-6-yl)-3-(3-((tertbutyldimethylsilyl)oxy)propoxy)-5-methyl-4-nitro-1H-pyrazole (700 mg, 1.76 mmol) in THF (5 mL) was added TBAF (1 M in THF, 2.64 mL) at 0° C. and the reaction was stirred at 20° C. for 1 h. The mixture was concentrated under reduced pressure. The residue was purified by chromatography on silica gel (eluent: petroleum ether:EtOAc 100:0→0:100) to afford 3-((1-(3-oxabicyclo[3.1.0]hexan-6-yl)-5-methyl-4-nitro-1H-pyrazol-3-yl)oxy)propan-1-ol (310 mg) of sufficient purity for the subsequent step. ¹H NMR (CDCl₃, 400 MHz) δ 4.46 (t, J=5.6 Hz, 2H), 4.18-4.11 (m, 2H), 3.87-3.79 (m, 4H), 3.18 (t, J=2.0 Hz, 1H), 2.66 (s, 3H), 2.64-2.59 (m, 1H), 2.39-2.35 (m, 2H), 2.09-2.05 (m, 2H).

To a mixture of 3-((1-(3-oxabicyclo[3.1.0]hexan-6-yl)-5-methyl-4-nitro-1H-pyrazol-3-yl)oxy)propan-1-ol 300 mg, 1.06 mmol), 3,6-dichloro-1H-pyrazolo[3,4-d]pyrimidine (210 mg, 1.11 mmol) and PPh₃ (555 mg, 2.12 mmol) in THF (10 mL) was added DIAD (428 mg, 2.12 mmol) at 0° C. and the reaction was stirred at 20° C. for 12 h. The reaction was concentrated under reduced pressure. The residue was purified by chromatography on silica gel (eluent: petroleum ether:EtOAc 100:0→50:50) to afford 1-(3-((1-(3-oxabicyclo[3.1.0]hexan-6-yl)-5-methyl-4-nitro-1H-pyrazol-3-yl)oxy)propyl)-3,6-dichloro-1H-pyrazolo[3,4-d]pyrimidine (250 mg) of sufficient purity for the subsequent step. LC-MS (method B) (m/z)=454.1 (MH) $t_R$=0.78 minutes.

Intermediate: 8-Chloro-3-methyl-2,4,12,13-tetrahydro-11H-5,7-(azenometheno)dipyrazolo[3,4-b:5',1'-g][1]oxa[4,6,8]-triazacycloundecine

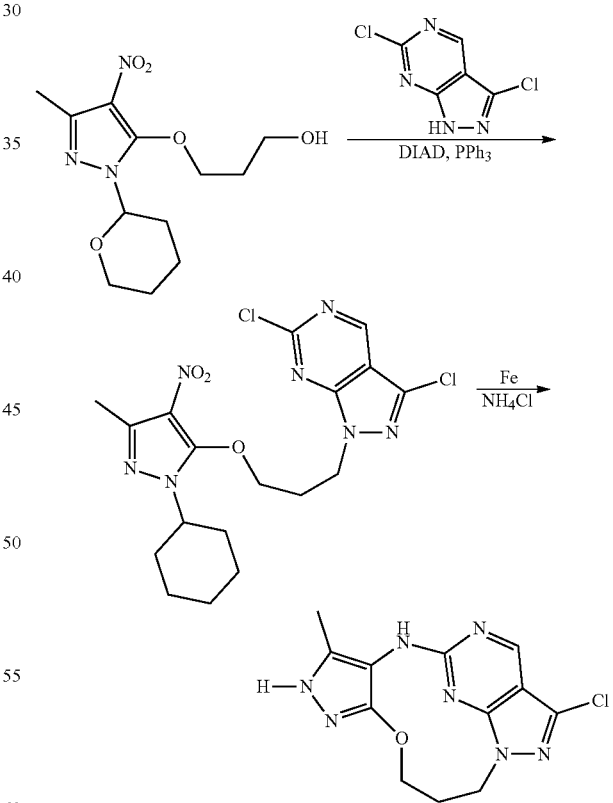

A mixture of 3-((3-methyl-4-nitro-1-(tetrahydro-2H-pyran-2-yl)-1H-pyrazol-5-yl)oxy)propan-1-ol (2 g, 7.0 mmol), 3,6-dichloro-1H-pyrazolo[3,4-d]pyrimidine (1.32 g, 7.01 mmol), PPh₃ (2.76 g, 10.52 mmol), and DIAD (2.13 g, 10.52 mmol) in THF (20 mL) was stirred at 15° C. for 16 h. The mixture was concentrated under reduced pressure. The residue was purified by chromatography on silica gel (eluent: petroleum ether:EtOAc 100:0→70:30). The crude product was dissolved in a mixture of EtOAc 40 mL and Petroleum ether 20 mL at 50° C. for 20 minutes. The mixture was allowed to cool to 20° C., filtered, and the filter cake was dried to afford 3,6-dichloro-1-(3-((3-methyl-4-nitro-1-(tetrahydro-2H-pyran-2-yl)-1H-pyrazol-5-yl)oxy)propyl)-1H-pyrazolo[3,4-d]pyrimidine (2.3 g) of sufficient purity for the subsequent step. $^1$H NMR (CDCl$_3$, 400 MHz) δ 9.01 (s, 1H), 5.43 (dd, J=2.8, 10.4 Hz, 1H), 4.70 (t, J=6.8 Hz, 2H), 4.59-4.46 (m, 1H), 4.44-4.34 (m, 1H), 4.08-4.00 (m, 1H), 3.74-3.60 (m, 1H), 2.57-2.47 (m, 5H), 2.43-2.31 (m, 1H), 2.17-2.06 (m, 1H), 1.93-1.79 (m, 1H), 1.78-1.67 (m, 2H), 1.27 (d, J=6.4 Hz, 1H).

To a solution of 3,6-dichloro-1-(3-((3-methyl-4-nitro-1-(tetrahydro-2H-pyran-2-yl)-1H-pyrazol-5-yl)oxy)propyl)-1H-pyrazolo[3,4-d]pyrimidine (2.3 g, 5.0 mmol) in EtOH (300 mL) was added Fe (1.41 g, 25.2 mmol) and then a solution of NH$_4$Cl (1.35 g, 25.2 mmol) in H$_2$O (20 mL). The mixture was stirred at 80° C. for 32 h. The mixture was concentrated under reduced pressure. The residue was purified by chromatography on silica gel (eluent: petroleum ether:EtOAc 100:0:→0:100 followed by DCM:MeOH 100:0→90:10) to afford 8-chloro-3-methyl-2,4,12,13-tetrahydro-11H-5,7-(azenometheno)dipyrazolo[3,4-b:5',1'-g][1]oxa[4,6,8]-triazacycloundecine (500 mg) of sufficient purity for the subsequent step. $^1$H NMR (DMSO-d$_6$, 400 MHz) δ 11.68 (br s, 1H), 9.33 (s, 1H), 8.77 (s, 1H), 4.44-4.24 (m, 4H), 2.18 (s, 3H), 1.82-1.72 (m, 2H). LC-MS (method C) (m/z)=306.1 (MH)$^+$ t$_R$=1.19 minutes.

Intermediate: 3,6-Dichloro-1-(3-((1-((2R,4r,6S)-2,6-dimethyltetrahydro-2H-pyran-4-yl)-5-methyl-4-nitro-1H-pyrazol-3-yl)oxy)propyl)-1H-pyrazolo[3,4-d]pyrimidine

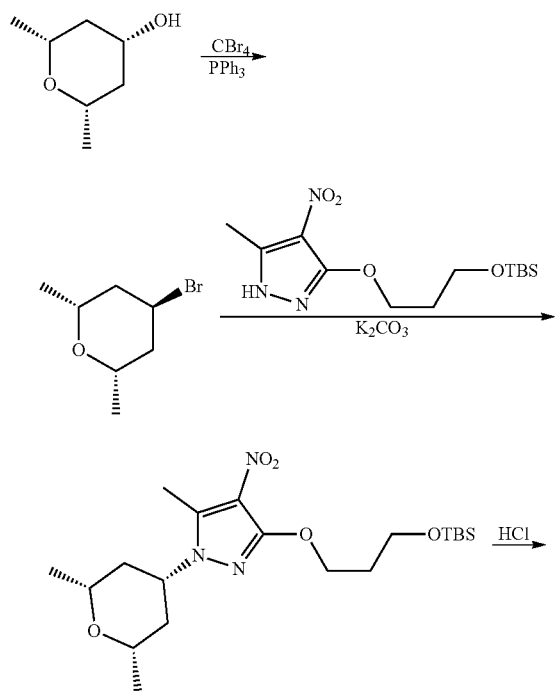

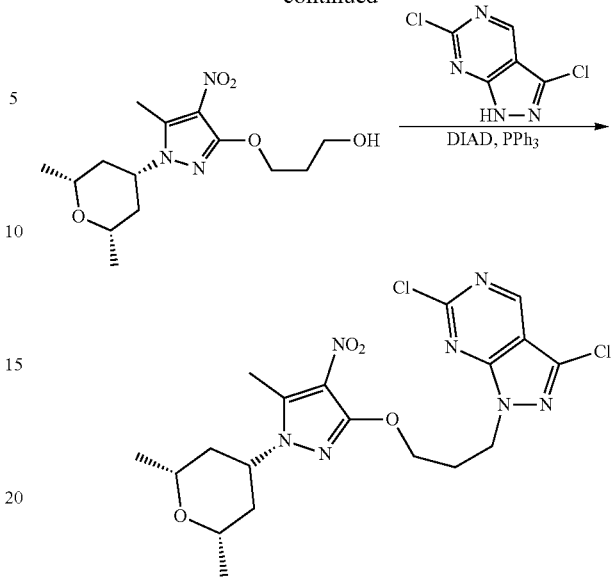

To a solution of (2R,4r,6S)-2,6-dimethyltetrahydro-2H-pyran-4-ol (5 g, 38 mmol) in DCM (150 mL) was added PPh$_3$ (30.2 g, 115 mmol) and CBr$_4$ (19.11 g, 57.61 mmol). The mixture was stirred at 20° C. for 16 h. The reaction mixture was poured into MTBE (100 mL) and filtered. The filter cake was washed with MTBE (50 mL) and the filtrate was concentrated under reduced pressure. The residue was purified by chromatography on silica gel (eluent: petroleum ether:EtOAc 100:0→91:9) to afford (2R,4s,6S)-4-bromo-2,6-dimethyltetrahydro-2H-pyran (2.6 g) of sufficient purity for the subsequent step. $^1$H NMR (CDCl$_3$, 400 MHz) δ 4.73-4.68 (m, 1H), 4.05-4.01 (m, 2H), 1.99-1.94 (m, 2H), 1.72-1.67 (m, 2H), 1.22 (d, J=6.0 Hz, 6H).

To a solution of 3-(3-((tert-butyldimethylsilyl)oxy)propoxy)-5-methyl-4-nitro-1H-pyrazole (500 mg, 1.59 mmol) in DMF (15 mL) was added (2R,4s,6S)-4-bromo-2,6-dimethyltetrahydro-2H-pyran (461 mg, 2.38 mmol), and K$_2$CO$_3$ (659 mg, 4.77 mmol). The mixture was stirred at 80° C. for 16 h. The reaction mixture was diluted with water (20 mL) and extracted with EtOAc (3×40 mL). The combined organic layers were washed with brine (3×40 mL), dried over Na$_2$SO$_4$, and concentrated under reduced pressure. The residue was purified by chromatography on silica gel (eluent: petroleum ether:EtOAc 100:0→40:60) to afford 3-(3-((tert-butyldimethylsilyl)oxy)propoxy)-1-((2R,4r,6S)-2,6-dimethyltetrahydro-2H-pyran-4-yl)-5-methyl-4-nitro-1H-pyrazole (410 mg) of sufficient purity for the subsequent step. $^1$H NMR (CDCl$_3$, 400 MHz) δ4.40 (t, J=6.4 Hz, 2H), 4.29-4.18 (m, 1H), 3.81 (t, J=6.0 Hz, 2H), 3.63-3.58 (m, 2H), 2.62 (s, 3H), 2.05-1.99 (m, 2H), 1.95-1.83 (m, 2H), 1.79-1.71 (m, 2H), 1.28 (d, J=6.4 Hz, 6H), 0.89 (s, 9H), 0.05 (s, 6H).

3-(3-((tert-butyldimethylsilyl)oxy)propoxy)-1-((2R,4r,6S)-2,6-dimethyltetrahydro-2H-pyran-4-yl)-5-methyl-4-nitro-1H-pyrazole (400 mg, 0.935 mmol) was dissolved in HCl/dioxane (4 M, 3 mL) and stirred at 20° C. for 2 h. The reaction mixture was concentrated under reduced pressure. The residue was purified by chromatography on silica gel (eluent: petroleum ether:EtOAc 100:0→55:45) to afford 3-((1-((2R,4r,6S)-2,6-dimethyltetrahydro-2H-pyran-4-yl)-5-methyl-4-nitro-1H-pyrazol-3-yl)oxy)propan-1-ol (223 mg) of sufficient purity for the subsequent step. $^1$H NMR (CDCl$_3$, 400 MHz) δ 4.51 (t, J=6.0 Hz, 2H), 4.32-4.22 (m, 1H), 3.86 (t, J=5.6 Hz, 2H), 3.70-3.55 (m, 2H), 2.65 (s, 3H), 2.14-2.06 (m, 2H), 1.95-1.73 (m, 4H), 1.30 (d, J=6.0 Hz, 6H).

To a solution of 3-((1-((2R,4r,6S)-2,6-dimethyltetrahydro-2H-pyran-4-yl)-5-methyl-4-nitro-1H-pyrazol-3-yl)oxy)propan-1-ol (208 mg, 0.664 mmol) and 3,6-dichloro-1H-pyrazolo[3,4-d]pyrimidine (125 mg, 0.664 mmol) in THF (6 mL) was added PPh$_3$ (522 mg, 1.99 mmol). The mixture was cooled to 0° C. then DIAD (403 mg, 1.99 mmol) was added. The resulting mixture was stirred at 20° C. for 12 h. The reaction mixture was filtered and the filtrate was concentrated under reduced pressure. The residue was purified by chromatography on silica gel (eluent: petroleum ether:EtOAc 100:0→75:25) to afford 3,6-dichloro-1-(3-((1-((2R,4r,6S)-2,6-dimethyltetrahydro-2H-pyran-4-yl)-5-methyl-4-nitro-1H-pyrazol-3-yl)oxy)propyl)-1H-pyrazolo[3,4-d]pyrimidine (170 mg) of sufficient purity for the subsequent step.

Intermediate: 3,6-Dichloro-1-(3-((1-(2,2-dimethyltetrahydro-2H-pyran-4-yl)-5-methyl-4-nitro-1H-pyrazol-3-yl)oxy)propyl)-1H-pyrazolo[3,4-d]pyrimidine

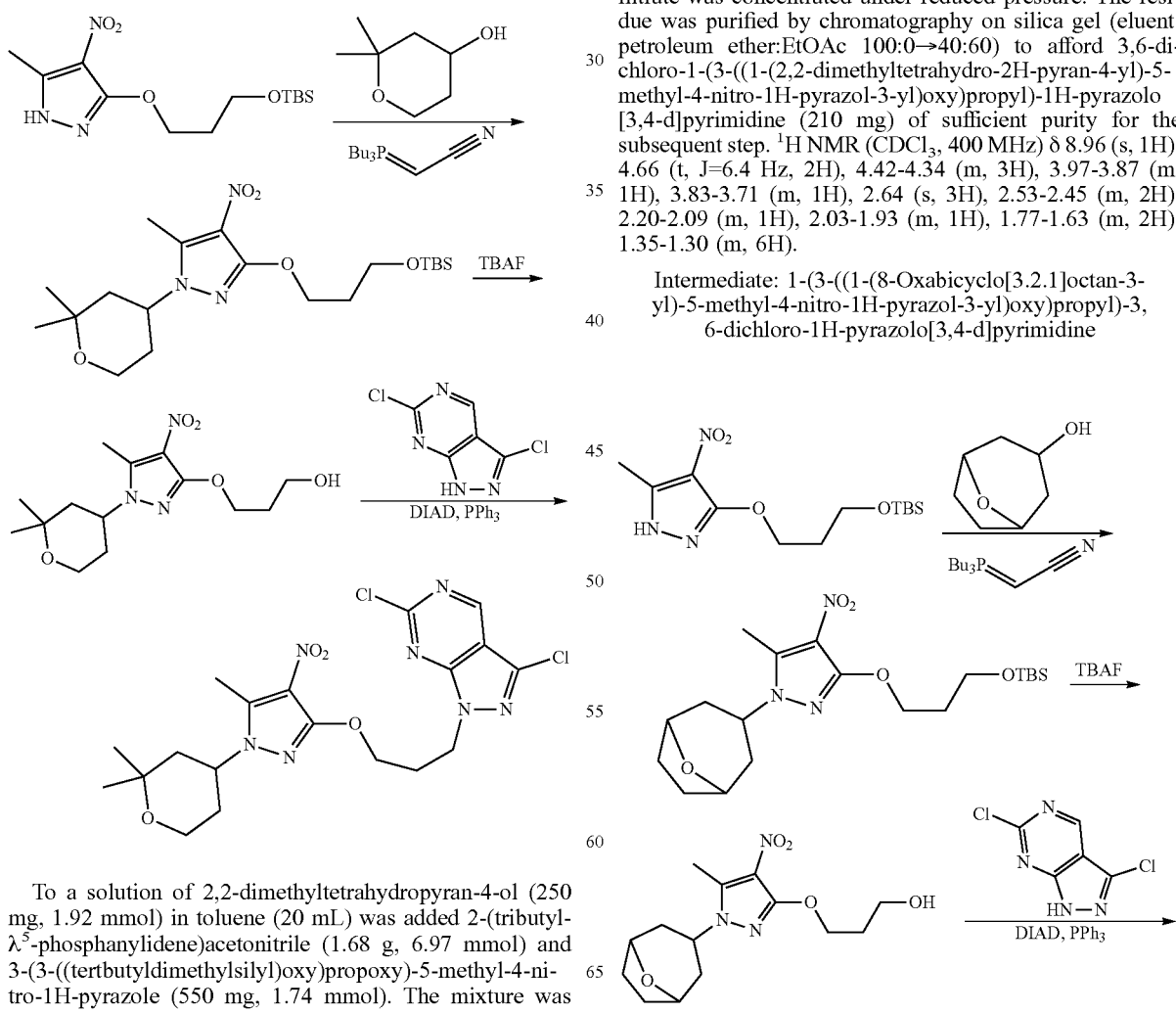

To a solution of 2,2-dimethyltetrahydropyran-4-ol (250 mg, 1.92 mmol) in toluene (20 mL) was added 2-(tributyl-λ$^5$-phosphanylidene)acetonitrile (1.68 g, 6.97 mmol) and 3-(3-((tertbutyldimethylsilyl)oxy)propoxy)-5-methyl-4-nitro-1H-pyrazole (550 mg, 1.74 mmol). The mixture was stirred at 110° C. for 15 h. The solvent was removed under reduced pressure. The residue was purified by chromatography on silica gel (eluent: petroleum ether:EtOAc 100: 0→70:30) to afford 3-(3-((tert-butyldimethylsilyl)oxy)propoxy)-1-(2,2-dimethyltetrahydro-2H-pyran-4-yl)-5-methyl-4-nitro-1H-pyrazole (230 mg) of sufficient purity for the subsequent step. LC-MS (method B) (m/z)=428.2 (MH)$^+$ t$_R$=1.11 minutes.

To a solution of 3-(3-((tert-butyldimethylsilyl)oxy)propoxy)-1-(2,2-dimethyltetrahydro-2H-pyran-4-yl)-5-methyl-4-nitro-1H-pyrazole (450 mg, 1.05 mmol) in THF (8 mL) was added TBAF (1 M, 1.58 mL) at 25° C. The resulting solution was stirred at 25° C. for 2 h. The reaction mixture was concentrated under reduced pressure. The residue was purified by chromatography on silica gel (eluent: petroleum ether:EtOAc 80:20-30:70) to afford 3-((1-(2,2-dimethyltetrahydro-2H-pyran-4-yl)-5-methyl-4-nitro-1H-pyrazol-3-yl)oxy)propan-1-ol (285 mg) of sufficient purity for the subsequent step. $^1$H NMR (CDCl$_3$, 400 MHz) δ4.51 (t, J=6.0 Hz, 2H), 4.45-4.33 (m, 1H), 3.99-3.75 (m, 4H), 2.66 (s, 3H), 2.61-2.52 (m, 1H), 2.31-2.16 (m, 1H), 2.12-2.07 (m, 3H), 1.81-1.67 (m, 2H), 1.33 (s, 6H).

To a solution of 3-((1-(2,2-dimethyltetrahydro-2H-pyran-4-yl)-5-methyl-4-nitro-1H-pyrazol-3-yl)oxy)propan-1-ol (275 mg, 0.878 mmol) and 3,6-dichloro-1H-pyrazolo[3,4-d]pyrimidine (166 mg, 0.878 mmol) in THF (15 mL) was added PPh$_3$ (691 mg, 2.63 mmol) followed by DIAD (532 mg, 2.63 mmol) at 5° C. The resulting mixture was stirred at 25° C. for 12 h. The reaction mixture was filtered and the filtrate was concentrated under reduced pressure. The residue was purified by chromatography on silica gel (eluent: petroleum ether:EtOAc 100:0→40:60) to afford 3,6-dichloro-1-(3-((1-(2,2-dimethyltetrahydro-2H-pyran-4-yl)-5-methyl-4-nitro-1H-pyrazol-3-yl)oxy)propyl)-1H-pyrazolo[3,4-d]pyrimidine (210 mg) of sufficient purity for the subsequent step. $^1$H NMR (CDCl$_3$, 400 MHz) δ 8.96 (s, 1H), 4.66 (t, J=6.4 Hz, 2H), 4.42-4.34 (m, 3H), 3.97-3.87 (m, 1H), 3.83-3.71 (m, 1H), 2.64 (s, 3H), 2.53-2.45 (m, 2H), 2.20-2.09 (m, 1H), 2.03-1.93 (m, 1H), 1.77-1.63 (m, 2H), 1.35-1.30 (m, 6H).

Intermediate: 1-(3-((1-(8-Oxabicyclo[3.2.1]octan-3-yl)-5-methyl-4-nitro-1H-pyrazol-3-yl)oxy)propyl)-3,6-dichloro-1H-pyrazolo[3,4-d]pyrimidine

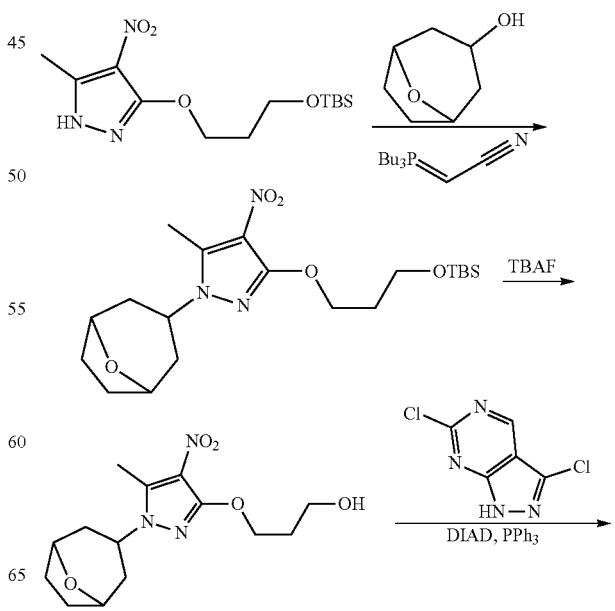

-continued

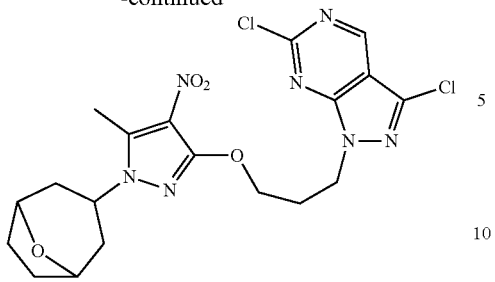

A mixture of 8-oxabicyclo[3.2.1]octan-3-ol (609 mg, 4.76 mmol), tert-butyl-dimethyl-[3-[(5-methyl-4-nitro-1H-pyrazol-3-yl)oxy]propoxy]silane (1.0 g, 3.17 mmol) and 2-(tributyl-X⁵-phosphanylidene)acetonitrile (3.06 g, 12.7 mmol) in toluene (20 mL) was stirred at 110° C. for 16 h. The reaction mixture was concentrated under reduced pressure. The residue was purified by chromatography on silica gel (eluent: petroleum ether:EtOAc 100:0→75:25) to afford 1-(8-oxabicyclo[3.2.1]octan-3-yl)-3-(3-((tert-butyldimethylsilyl)oxy)propoxy)-5-methyl-4-nitro-1H-pyrazole (1.7 g) of sufficient purity for the subsequent step.

To 1-(8-oxabicyclo[3.2.1]octan-3-yl)-3-(3-((tert-butyldimethylsilyl)oxy)propoxy)-5-methyl-4-nitro-1H-pyrazole (1.5 g, 2.5 mmol, ~70 mol % purity) in THF (35 mL) was slowly added TBAF (1 M in THF, 6.17 mL). The mixture was stirred at 25° C. for 16 h. The reaction mixture was extracted with EtOAc (50 mL×3). The combined organic layers were washed with brine (50 mL×2), dried over Na₂SO₄, filtered, and concentrated under reduced pressure. The residue was purified by chromatography on silica gel (eluent: petroleum ether:EtOAc 100:0→50:50) to afford 3-((1-(8-oxabicyclo[3.2.1]octan-3-yl)-5-methyl-4-nitro-1H-pyrazol-3-yl)oxy)propan-1-ol (370 mg) of sufficient purity for the subsequent step. $^1$H NMR (CDCl$_3$, 400 MHz) δ 4.57-4.56 (m, 1H), 4.51-4.46 (m, 3H), 4.45-4.38 (m, 1H), 3.86-3.83 (m, 2H), 2.63-2.61 (m, 3H), 2.46-2.37 (m, 2H), 2.13-2.06 (m, 2H), 2.04-1.98 (m, 1H), 1.96-1.93 (m, 2H), 1.91-1.86 (m, 1H), 1.84-1.80 (m, 1H), 1.70-1.66 (m, 1H).

To a solution of 3-((1-(8-oxabicyclo[3.2.1]octan-3-yl)-5-methyl-4-nitro-1H-pyrazol-3-yl)oxy)propan-1-ol (325 mg, 1.04 mmol), 3,6-dichloro-1H-pyrazolo[3,4-d]pyrimidine (197 mg, 1.04 mmol), and PPh$_3$ (821 mg, 3.13 mmol) in THF (14 mL) was added DIAD (633 mg, 3.13 mmol) at 0° C. The mixture was then stirred at 25° C. for 16 h. The reaction mixture was concentrated under reduced pressure. The residue was purified by chromatography on silica gel (eluent: petroleum ether:EtOAc 100:0→50:50) to afford 1-(3-((1-(8-oxabicyclo[3.2.1]octan-3-yl)-5-methyl-4-nitro-1H-pyrazol-3-yl)oxy)propyl)-3,6-dichloro-1H-pyrazolo[3,4-d]pyrimidine (620 mg) of sufficient purity for the subsequent step. LC-MS (method I) (m/z)=482.0 (MH)⁺ $t_R$=0.55 minutes.

Intermediate: 3,6-Dichloro-1-[1,1-dideuterio-3-(5-methyl-4-nitro-1-tetrahydropyran-4-yl-pyrazol-3-yl)oxy-propyl]pyrazolo[3,4-d]pyrimidine

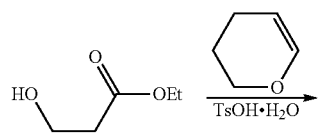

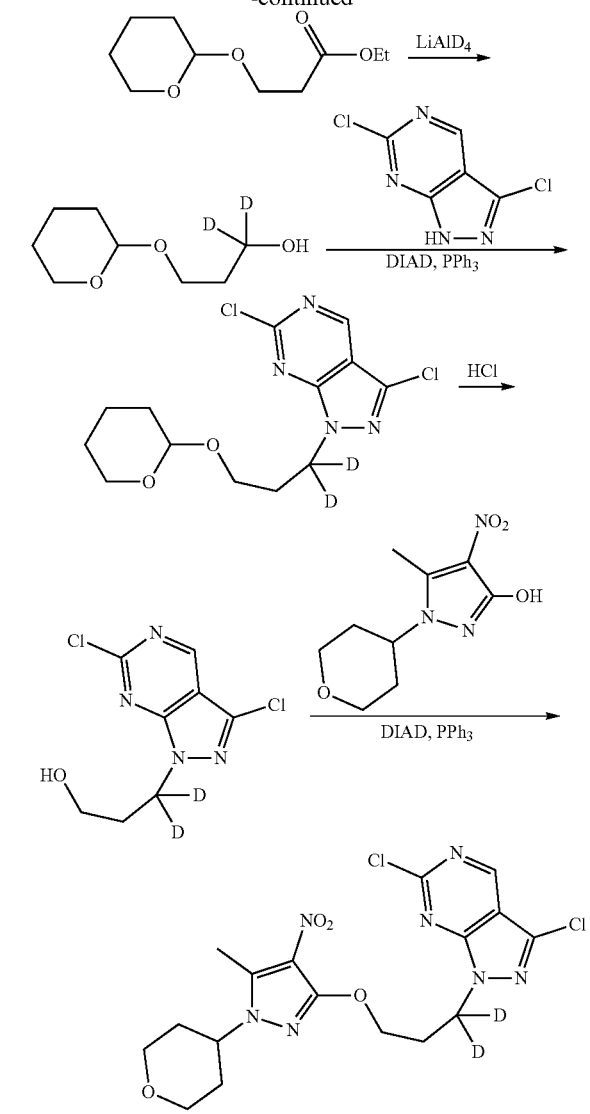

To a solution of ethyl 3-hydroxypropanoate (5 g, 42 mmol) in THF (60 mL) was added TsOH·H₂O (403 mg, 2.12 mmol) and stirred at 20° C. for 30 minutes. Then 3,4-dihydro-2H-pyran (4.56 g, 54.2 mmol) was added at 0° C. and the mixture was stirred at 20° C. for 16 h. The mixture was concentrated under reduced pressure. The residue was purified by chromatography on silica gel (eluent: petroleum ether:EtOAc 100:0→92:8) to afford ethyl 3-((tetrahydro-2H-pyran-2-yl)oxy)propanoate (7.3 g) of sufficient purity for the subsequent step. $^1$H NMR (CDCl$_3$, 400 MHz) δ 4.64 (t, J=2.8 Hz, 1H), 4.20-4.13 (m, 2H), 4.05-3.95 (m, 1H), 3.89-3.65 (m, 1H), 3.55-3.45 (m, 1H), 3.57-3.47 (m, 1H), 2.61 (t, J=6.4 Hz, 2H), 1.87-1.75 (m, 1H), 1.74-1.65 (m, 1H), 1.62-1.48 (m, 4H), 1.27 (t, J=7.2 Hz, 3H).

A solution of ethyl 3-((tetrahydro-2H-pyran-2-yl)oxy)propanoate (7.85 g, 38.8 mmol) in THF (50 mL) was added dropwise to a solution of LiAlD$_4$ (2.95 g, 77.6 mmol) in THF (80 mL) at 0° C. and then the mixture was stirred at 20° C. for 2 h. The reaction mixture was quenched with water (2 mL), followed by aqueous 10% NaOH (2 mL) and water (2 mL). Then the mixture was filtered, and the filtrate was concentrated under reduced pressure to afford 1,1-dideuterio-3-tetrahydropyran-2-yloxy-propan-1-ol (6.28 g) of sufficient purity for the subsequent step. ¹H NMR (CDCl₃, 400 MHz) δ 4.60 (t, J=2.8 Hz, 1H), 3.99-3.84 (m, 2H), 3.65-3.50 (m, 2H), 2.49-2.23 (m, 1H), 1.89-1.70 (m, 4H), 1.62-1.52 (m, 4H).

To a solution of 1,1-dideuterio-3-tetrahydropyran-2-yloxy-propan-1-ol (3.09 g, 19.1 mmol) in THF (180 mL) was added 3,6-dichloro-1H-pyrazolo[3,4-d]pyrimidine (3 g, 16 mmol), PPh₃ (12.49 g, 47.62 mmol) and DIAD (9.63 g, 47.6 mmol) at 0° C. The mixture was stirred at 20° C. for 16 h. The reaction mixture was concentrated under reduced pressure. The residue was purified by chromatography on silica gel (eluent: petroleum ether:EtOAc 100:0→80:20) to afford 3,6-dichloro-1-(1,1-dideuterio-3-tetrahydropyran-2-yloxy-propyl)pyrazolo[3,4-d]pyrimidine (4.2 g) of sufficient purity for the subsequent step. ¹H NMR (CDCl₃, 400 MHz) δ 8.97 (s, 1H), 4.50 (t, J=3.6 Hz, 1H), 3.82-3.74 (m, 2H), 3.51-3.41 (m, 1H), 3.38-3.25 (m, 1H), 2.22 (t, J=6.0 Hz, 2H), 1.79-1.65 (m, 2H), 1.61-1.49 (m, 4H).

To 3,6-dichloro-1-(1,1-dideuterio-3-tetrahydropyran-2-yloxy-propyl)pyrazolo[3,4-d]pyrimidine (4.1 g, 12 mmol) in MeOH (100 mL) was added concentrated aqueous HCl (12 M, 10 mL) and stirred at 20° C. for 16 h. The reaction mixture was concentrated under reduced pressure. The residue was purified by chromatography on silica gel (eluent: petroleum ether:EtOAc 100:0→79:21) to afford 3,3-dideuterio-3-(3,6-dichloropyrazolo[3,4-d]pyrimidin-1-yl)propan-1-ol (2.6 g) of sufficient purity for the subsequent step. ¹H NMR (CDCl₃, 400 MHz) δ 8.99 (s, 1H), 3.65 (t, J=6.0 Hz, 2H), 2.30 (br, 1H), 2.14 (t, J=6.0 Hz, 2H).

To a solution of 3,3-dideuterio-3-(3,6-dichloropyrazolo[3,4-d]pyrimidin-1-yl)propan-1-ol (200 mg, 0.803 mmol) in THF (15 mL) was added 5-methyl-4-nitro-1-(tetrahydro-2H-pyran-4-yl)-1H-pyrazol-3-ol (182 mg, 0.803 mmol), DIAD (487 mg, 2.41 mmol), and PPh₃ (632 mg, 2.41 mmol) at 0° C. The mixture was stirred at 20° C. for 16 h. The reaction mixture was concentrated under reduced pressure. The residue was purified by chromatography on silica gel (eluent: petroleum ether:EtOAc 100:0→35:65) to afford 3,6-dichloro-1-[1,1-dideuterio-3-(5-methyl-4-nitro-1-tetrahydropyran-4-yl-pyrazol-3-yl)oxy-propyl]pyrazolo[3,4-d]pyrimidine (680 mg) of sufficient purity for the subsequent step.

Intermediate: 3,6-Dichloro-1-[3,3-dideuterio-3-(5-methyl-4-nitro-1-tetrahydropyran-4-yl-pyrazol-3-yl)oxy-propyl]pyrazolo[3,4-d]pyrimidine

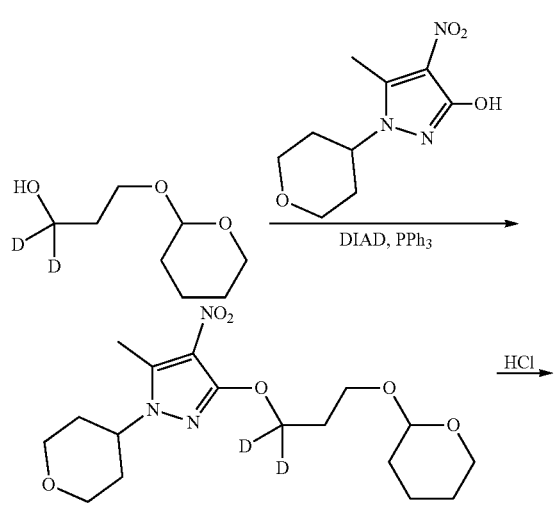

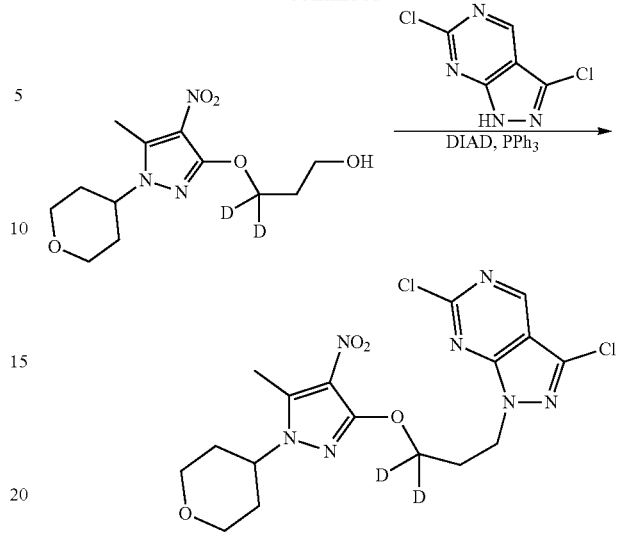

DIAD (1.33 g, 6.60 mmol) was added to a solution of 5-methyl-4-nitro-1-(tetrahydro-2H-pyran-4-yl)-1H-pyrazol-3-ol (500 mg, 2.20 mmol), 1,1-dideuterio-3-tetrahydropyran-2-yloxy-propan-1-ol (428 mg, 2.64 mmol), and PPh₃ (1.73 g, 6.60 mmol) in THF (20 mL) at 0° C. Then the mixture was stirred at 20° C. for 15 h. The reaction mixture was concentrated under reduced pressure. The residue was purified by chromatography on silica gel (eluent: petroleum ether:EtOAc 100:0→65:35) to afford 3-(1,1-dideuterio-3-tetrahydropyran-2-yloxy-propoxy)-5-methyl-4-nitro-1-tetrahydropyran-4-yl-pyrazole (1 g) of sufficient purity for the subsequent step. All of the material was dissolved in MeOH (10 mL) and aqueous HCl (12 M, 5 mL) was added. The mixture was stirred at 20° C. for 15 h. The reaction mixture was concentrated under reduced pressure. The residue was purified by chromatography on silica gel (eluent: petroleum ether:EtOAc 100:0→0:100) and then preparative HPLC (instrument: Gilson GX-281 Liquid Handler, Gilson 322 Pump, Gilson 156 UV detector, column: Xtimate C18 150× 40 mm×10 μm, mobile Phase: A: water (NH₃—H₂O+ NH₄HCO₃), mobile phase B: MeCN, gradient: B from 25% to 55% in 8 min, flow rate (mL/min): 55, column temperature: 35° C., wavelengths: 220 nm, 254 nm) to afford 3,3-dideuterio-3-(5-methyl-4-nitro-1-tetrahydropyran-4-yl-pyrazol-3-yl)oxy-propan-1-ol (260 mg) of sufficient purity for the subsequent step. ¹H NMR (CDCl₃, 400 MHz) δ 4.28-4.18 (m, 1H), 4.17-4.09 (m, 2H), 3.92-3.78 (m, 2H), 3.58-3.45 (m, 2H), 2.65 (s, 3H), 2.57-2.48 (m, 1H), 2.38-2.22 (m, 2H), 2.06 (t, J=5.6 Hz, 2H), 1.81-1.72 (m, 2H).

DIAD (450 mg, 2.23 mmol) was added to a solution of 3,6-dichloro-1H-pyrazolo[3,4-d]pyrimidine (140 mg, 0.741 mmol), 3,3-dideuterio-3-(5-methyl-4-nitro-1-tetrahydropyran-4-yl-pyrazol-3-yl)oxy-propan-1-ol(235 mg, 0.812 mmol), and PPh₃ (583 mg, 2.22 mmol) in THF (20 mL) at 0° C. Then the mixture was stirred at 20° C. for 15 h. The reaction mixture was concentrated under reduced pressure. The residue was purified by chromatography on silica gel (eluent: petroleum ether:EtOAc 100:0→60:40) to afford 3,6-dichloro-1-[3,3-dideuterio-3-(5-methyl-4-nitro-1-tetrahydropyran-4-yl-pyrazol-3-yl)oxy-propyl]pyrazolo[3,4-d]pyrimidine (700 mg) of sufficient purity for the subsequent step.

Intermediate: 3,6-Dichloro-1-(3-((1-(3-fluoro-3-methyltetrahydro-2H-pyran-4-yl)-5-methyl-4-nitro-1H-pyrazol-3-yl)oxy)propyl)-1H-pyrazolo[3,4-d]pyrimidine

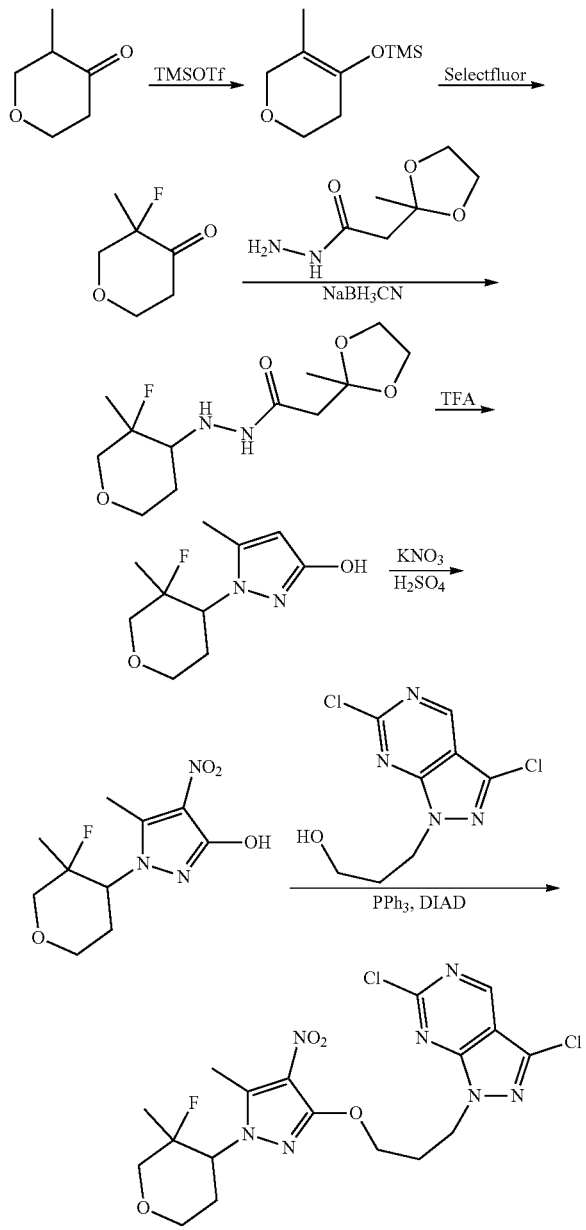

To a solution of 3-methyltetrahydropyran-4-one (5 g, 44 mmol) and TEA (8.87 g, 87.6 mmol) in DCM (50 mL) was added TMSOTf (14.6 g, 65.7 mmol) at 0° C. The mixture was stirred at 0° C. for 2 h. The reaction mixture was quenched with saturated aqueous NaCl (15 mL) and extracted with EtOAc (3×20 mL). The combined organic layers were dried over $Na_2SO_4$ and concentrated under reduced pressure. The residue was purified by distillation (temperature:80° C., pressure: 0.26 mbar) to afford trimethyl((5-methyl-3,6-dihydro-2H-pyran-4-yl)oxy)silane (6.7 g) of sufficient purity for the subsequent step. $^1$H NMR (CDCl$_3$, 400 MHz) δ 4.03-3.98 (m, 2H), 3.84-3.80 (m, 2H), 2.20-2.11 (m, 2H), 1.51 (s, 3H), 0.20 (s, 9H).

To a solution of trimethyl((5-methyl-3,6-dihydro-2H-pyran-4-yl)oxy)silane (6.7 g, 36 mmol) in CH$_3$CN (70 mL) was added Selectfluor (15.29 g, 43.15 mmol) at 0° C. The mixture was stirred at 0° C. for 2 h. The reaction mixture was diluted with saturated aqueous NaCl (150 mL) and extracted with Et$_2$O (4×50 mL). The combined organic layers were dried over Na$_2$SO$_4$ and concentrated under reduced pressure. The residue was purified by distillation (temperature: 25° C., pressure: 20 mBar) to afford 3-fluoro-3-methyltetrahydro-4H-pyran-4-one (3.9 g) of sufficient purity for the subsequent step. $^1$H NMR (CDCl$_3$, 400 MHz) δ 4.00-3.93 (m, 2H), 3.92-3.88 (m, 1H), 3.73-3.69 (m, 1H), 2.89-2.80 (m, 1H), 2.62-2.58 (m, 1H), 1.55-1.46 (m, 3H).

To a solution of 2-(2-methyl-1,3-dioxolan-2-yl)acetohydrazide (1.3 g, 8.12 mmol) and 3-fluoro-3-methyltetrahydro-4H-pyran-4-one (2.15 g, 16.2 mmol) in MeOH (30 mL) was added AcOH (975 mg, 16.2 mmol). The reaction mixture was stirred at 20° C. for 1 h. NaBH$_3$CN (1.53 g, 24.4 mmol) was added, and the reaction was stirred at 60° C. for 15 h. The mixture was concentrated under reduced pressure and the residue was diluted with EtOAc (50 mL) and washed with H$_2$O (20 mL) and brine (20 mL), dried over Na$_2$SO$_4$, filtered, and concentrated under reduced pressure to afford N'-(3-fluoro-3-methyltetrahydro-2H-pyran-4-yl)-2-(2-methyl-1,3-dioxolan-2-yl)acetohydrazide (1.65 g) of sufficient purity for the subsequent step. LC-MS (method B) (m/z)=277.2 (MH)$^+$ t$_R$=0.57 minutes.

To a solution of N'-(3-fluoro-3-methyltetrahydro-2H-pyran-4-yl)-2-(2-methyl-1,3-dioxolan-2-yl)acetohydrazide (1.62 g, 5.86 mmol) in EtOH (20 mL) was added TFA (2.67 g, 23.5 mmol), and the reaction was stirred at 90° C. for 15 h. TFA (2.7 g, 24 mmol) was added to the mixture and the reaction was stirred at 90° C. for another 16 h. The mixture was concentrated under reduced pressure to afford 1-(3-fluoro-3-methyltetrahydro-2H-pyran-4-yl)-5-methyl-1H-pyrazol-3-ol (1.9 g). All of the material was dissolved in H$_2$SO$_4$ (20 mL) and KNO$_3$ (2.95 g, 29.2 mmol) was added at 0° C., and the reaction was stirred at 0° C. for 0.5 h. The mixture was poured into ice-water (100 mL) and extracted with EtOAc (4×50 mL). The combined organic phases were washed with brine (50 mL), dried over Na$_2$SO$_4$, and concentrated under reduced pressure. The residue was purified by chromatography on silica gel (eluent: petroleum ether:EtOAc (10 v % MeOH) 100:0→70:30) to afford 1-(3-fluoro-3-methyltetrahydro-2H-pyran-4-yl)-5-methyl-4-nitro-1H-pyrazol-3-ol (0.14 g) of sufficient purity for the subsequent step. $^1$H NMR (CDCl$_3$, 400 MHz) δ8.47 (br s, 1H), 4.46-4.37 (m, 1H), 4.21-4.14 (m, 1H), 3.94-3.89 (m, 1H), 3.60-3.52 (m, 1H), 3.51-3.46 (m, 1H), 2.70 (d, J=1.6 Hz, 3H), 2.67-2.65 (m, 1H), 1.99-1.92 (m, 1H), 1.36 (d, J=23.6 Hz, 3H).

To a mixture of 3-(3,6-dichloropyrazolo[3,4-d]pyrimidin-1-yl)propan-1-ol (0.12 g, 0.49 mmol), 1-(3-fluoro-3-methyltetrahydro-2H-pyran-4-yl)-5-methyl-4-nitro-1H-pyrazol-3-ol (126 mg, 0.49 mmol), and PPh$_3$ (382 mg, 1.46 mmol) in THF (20 mL) was added DIAD (295 mg, 1.46 mmol) at 0° C. The mixture was stirred at 20° C. for 12 h. The mixture was concentrated under reduced pressure. The residue was purified by chromatography on silica gel (eluent: petroleum ether:EtOAc 100:0→60:40, repeated twice) to afford 3,6-dichloro-1-(3-((1-(3-fluoro-3-methyltetrahydro-2H-pyran-4-yl)-5-methyl-4-nitro-1H-pyrazol-3-yl)oxy)propyl)-1H-pyrazolo[3,4-d]pyrimidine (0.2 g) of sufficient purity for the subsequent step. LC-MS (method J) (m/z)=488.0 (MH)$^+$ t$_R$=1.64 minutes.

179

Intermediate: 3,6-Dichloro-1-(3-((5-methyl-4-nitro-1-((tetrahydro-2H-pyran-4-yl)methyl)-1H-pyrazol-3-yl)oxy)propyl)-1H-pyrazolo[3,4-d]pyrimidine

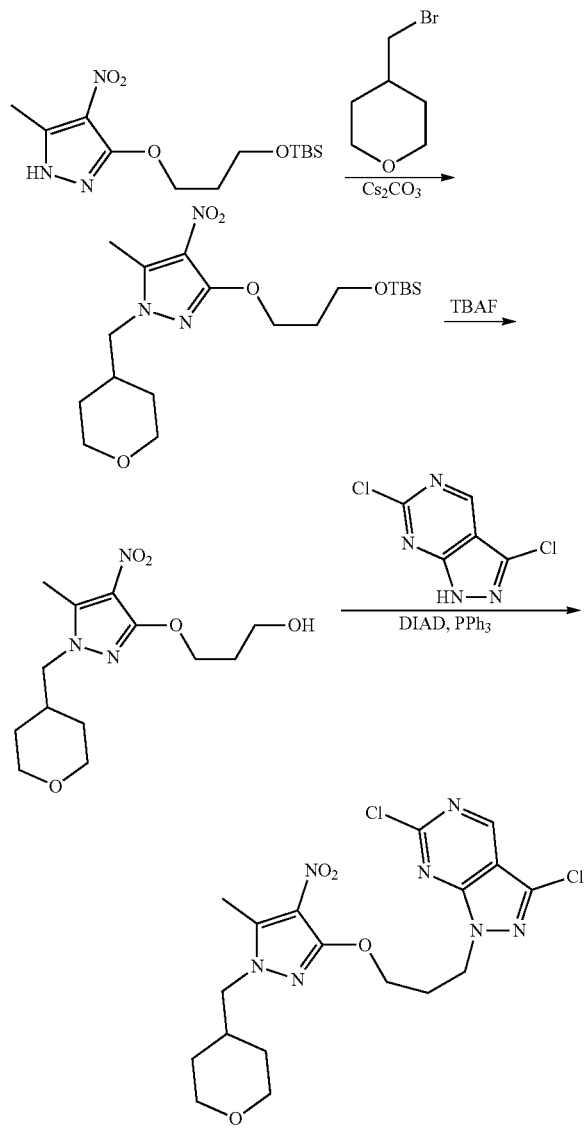

To a solution of 3-(3-((tert-butyldimethylsilyl)oxy)propoxy)-5-methyl-4-nitro-1H-pyrazole (600 mg, 1.90 mmol) and $Cs_2CO_3$ (1.86 g, 5.71 mmol) in DMF (10 mL) was added 4-(bromomethyl)tetrahydro-2H-pyran (511 mg, 2.85 mmol). The mixture was stirred at 80° C. for 16 h. The reaction mixture was diluted with EtOAc (50 mL) and extracted with $H_2O$ (3×40 mL). The combined organic layers were washed with brine (50 mL), dried over $Na_2SO_4$, filtered, and concentrated under reduced pressure. The residue was purified by chromatography on silica gel (eluent: petroleum ether:EtOAc 100:0→70:30) to afford 3-(3-((tert-butyldimethylsilyl)oxy)propoxy)-5-methyl-4-nitro-1-((tetrahydro-2H-pyran-4-yl)methyl)-1H-pyrazole (480 mg) of sufficient purity for the subsequent step. $^1$H NMR (CDCl$_3$, 400 MHz) δ 4.38 (t, J=6.0 Hz, 2H), 4.01-3.97 (m, 2H), 3.85-3.79 (m, 4H), 3.41-3.33 (m, 2H), 2.61 (s, 3H), 2.23-2.11 (m, 1H), 2.07-1.99 (m, 2H), 1.59-1.49 (m, 2H), 1.44-1.32 (m, 2H), 0.88 (s, 9H), 0.04 (s, 6H).

180

To a solution of 3-(3-((tert-butyldimethylsilyl)oxy)propoxy)-5-methyl-4-nitro-1-((tetrahydro-2H-pyran-4-yl)methyl)-1H-pyrazole (470 mg, 1.14 mmol) in THF (7 mL) was added TBAF (1 M in THF, 1.70 mL). The mixture was stirred at 25° C. for 1 h. The mixture was concentrated under reduced pressure. The residue was purified by chromatography on silica gel (eluent: petroleum ether:EtOAc 100:0→40:60) to afford 3-((5-methyl-4-nitro-1-((tetrahydro-2H-pyran-4-yl)methyl)-1H-pyrazol-3-yl)oxy)propan-1-ol (300 mg) of sufficient purity for the subsequent step. $^1$H NMR (400 MHz, CDCl$_3$) δ 4.50 (t, J=6.0 Hz, 2H), 4.01-3.97 (m, 2H), 3.87-3.79 (m, 4H), 3.40-3.34 (m, 2H), 2.61 (s, 3H), 2.22-2.12 (m, 1H), 2.10-2.05 (m, 2H), 1.55-1.48 (m, 2H), 1.44-1.32 (m, 2H).

To a solution of 3-((5-methyl-4-nitro-1-((tetrahydro-2H-pyran-4-yl)methyl)-1H-pyrazol-3-yl)oxy)propan-1-ol (290 mg, 0.97 mmol) and 3,6-dichloro-1H-pyrazolo[3,4-d]pyrimidine (183 mg, 0.97 mmol,) in THF (7 mL) was added PPh$_3$ (762 mg, 2.91 mmol), and DIAD (588 mg, 2.91 mmol). The mixture was stirred at 25° C. for 16 h. The mixture was filtered and concentrated under reduced pressure. The residue was purified by chromatography on silica gel (eluent: petroleum ether:EtOAc 100:0→50:50) to afford 3,6-dichloro-1-(3-((5-methyl-4-nitro-1-((tetrahydro-2H-pyran-4-yl)methyl)-1H-pyrazol-3-yl)oxy)propyl)-1H-pyrazolo[3,4-d]pyrimidine (690 mg) of sufficient purity for the subsequent step.

Intermediate: 3-Bromo-8-chloro-2-((1r,4r)-4-methoxycyclohexyl)-2,4,12,13-tetrahydro-11H-5,7-(azenometheno)dipyrazolo[3,4-b:5',1'-g][1]oxa[4,6,8]triazacycloundecine

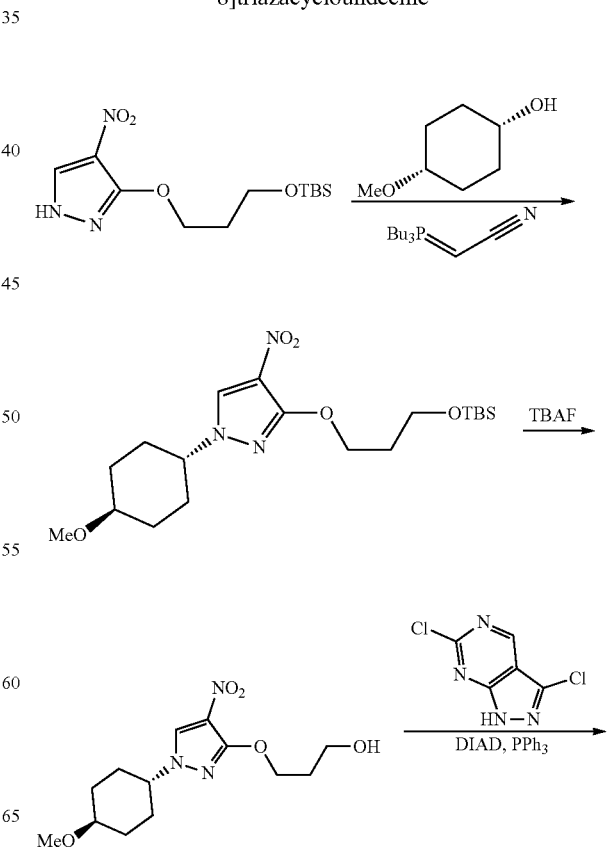

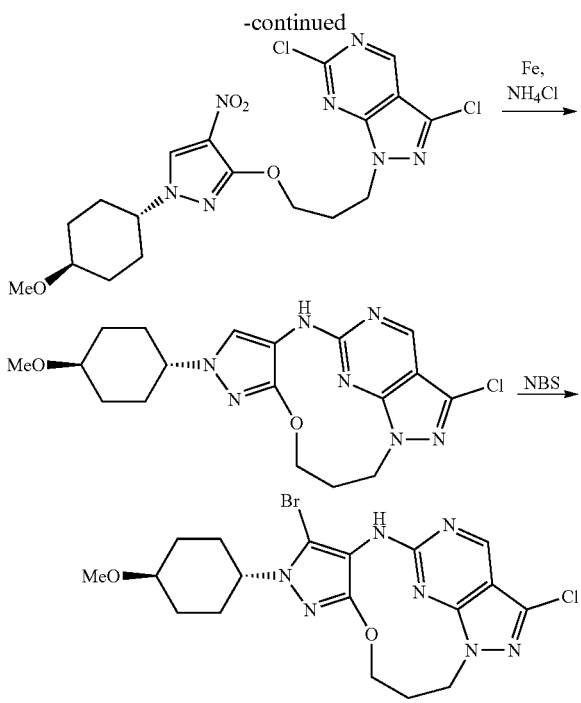

To a solution of 3-(3-((tert-butyldimethylsilyl)oxy) propoxy)-1-((1r,4r)-4-methoxycyclohexyl)-4-nitro-1H-pyrazole (2.4 g, 5.8 mmol) in THF (50 mL) was added TBAF (1 M in THF, 8.7 mL) and then stirred at 20° C. for 1 h. The mixture was concentrated under reduced pressure. The residue was purified by chromatography on silica gel (eluent: petroleum ether:EtOAc (MeOH 10v %) 100:0→50:50) to afford 3-((1-((1r,4r)-4-methoxycyclohexyl)-4-nitro-1H-pyrazol-3-yl)oxy)propan-1-ol (1.7 g) of sufficient purity for the subsequent step. $^1$H NMR (CDCl$_3$, 400 MHz) δ 8.03 (s, 1H), 4.51 (t, J=6.0 Hz, 2H), 4.02-3.93 (m, 1H), 3.85 (t, J=5.6 Hz, 2H), 3.39 (s, 3H), 3.29-3.20 (m, 1H), 2.28-2.18 (m, 4H), 2.14-2.06 (m, 2H), 1.84-1.71 (m, 2H), 1.47-1.36 (m, 2H).

To a mixture of 3-((1-((1r,4r)-4-methoxycyclohexyl)-4-nitro-1H-pyrazol-3-yl)oxy)propan-1-ol (1.7 g, 5.7 mmol), 3,6-dichloro-1H-pyrazolo[3,4-d]pyrimidine (1.07 g, 5.68 mmol) and PPh$_3$ (4.47 g, 17.0 mmol) in THF (120 mL) was added DIAD (3.45 g, 17.0 mmol) at 0° C. The mixture was stirred at 20° C. for 11 h. The mixture was concentrated under reduced pressure. The residue was purified by chromatography on silica gel (eluent: petroleum ether:EtOAc 100:0→60:40) to afford 3,6-dichloro-1-(3-((1-((1r,4r)-4-methoxycyclohexyl)-4-nitro-1H-pyrazol-3-yl)oxy)propyl)-1H-pyrazolo[3,4-d]pyrimidine (1.24 g) of sufficient purity for the subsequent step. LC-MS (method J) (m/z)=470.0 (MH)$^+$ t$_R$=1.60 minutes.

To a mixture of 3,6-dichloro-1-(3-((1-((1r,4r)-4-methoxycyclohexyl)-4-nitro-1H-pyrazol-3-yl)oxy)propyl)-1H-pyrazolo[3,4-d]pyrimidine (1.24 g, 2.64 mmol) and NH$_4$Cl (705 mg, 13.2 mmol) in a mixture of EtOH (150 mL) and H$_2$O (15 mL) was added Fe (736 mg, 13.2 mmol) at 20° C. The reaction was stirred at 80° C. for 16 h. The mixture was filtered and concentrated under reduced pressure. The residue was purified by chromatography on silica gel (eluent: petroleum ether:EtOAc (MeOH 10v %) 100:0→50:50) to afford 8-chloro-2-((1r,4r)-4-methoxycyclohexyl)-2,4,12,13-tetrahydro-11H-5,7-(azenometheno)dipyrazolo[3,4-b:5',1'-g][1]oxa[4,6,8]triazacycloundecine (0.8 g) of sufficient purity for the subsequent step. LC-MS (method J) (m/z)=404.0 (MH)$^+$ t$_R$=1.40 minutes.

A solution of NBS (463 mg, 2.60 mmol) in THF (10 mL) was added dropwise to a solution of 8-chloro-2-((1r,4r)-4-methoxycyclohexyl)-2,4,12,13-tetrahydro-11H-5,7-(azenometheno)dipyrazolo[3,4-b:5',1'-g][1]oxa[4,6,8]triazacycloundecine (0.7 g, 1.73 mmol) in THF (70 mL) over 0.5 h at 5° C. The mixture was stirred for 0.5 h at 5° C. and concentrated under reduced pressure. The residue was diluted with EtOAc (100 mL) and washed with brine (50 mL×3), dried, and concentrated under reduced pressure. The residue was purified by chromatography on silica gel (eluent: petroleum ether:EtOAc (DCM 10v %) 100:0→50:50) and preparative SFC (instrument: Thar 200, column: DAICEL CHIRALCEL OJ-H 250×30 mm, 5 μm, mobile phase: supercritical CO$_2$/EtOH (0.1% NH$_3$·H$_2$O, v %)=80/20, flow rate: 60 mL/min, column temperature: 38° C., nozzle pressure: 100 bar, nozzle temperature: 60° C., evaporator temperature: 20° C., trimmer temperature: 25° C., wavelength: 220 nm) to afford 3-Bromo-8-chloro-2-((1r,4r)-4-methoxycyclohexyl)-2,4,12,13-tetrahydro-11H-5,7-(azenometheno) dipyrazolo[3,4-b:5',1'-g][1]oxa[4,6,8]triazacycloundecine (0.26 g) of sufficient purity for the subsequent step. $^1$H NMR (CDCl$_3$, 400 MHz) δ 8.62 (s, 1H), 6.79 (s, 1H), 4.43 (t, J=4.4 Hz, 2H), 4.36 (t, J=4.8 Hz, 2H), 4.15-4.04 (m, 1H), 3.31 (s, 3H), 3.24-3.12 (m, 1H), 2.26-2.09 (m, 2H), 2.04-1.80 (m, 6H), 1.39-1.24 (m, 2H). LC-MS (method C) (m/z)=484.1 (MH)$^+$ t$_R$=1.69 minutes.

Intermediate: (+)-cis-8-Chloro-2-(2-methyltetrahydro-2H-pyran-4-yl)-2,4,12,13-tetrahydro-11H-5,7-(azenometheno)dipyrazolo[3,4-b:5',1'-g][1]oxa[4,6,8]triazacycloundecine and (−)-cis-8-Chloro-2-(2-methyltetrahydro-2H-pyran-4-yl)-2,4,12,13-tetrahydro-11H-5,7-(azenometheno)dipyrazolo[3,4-b:5',1'-g][1]oxa[4,6,8]triazacycloundecine

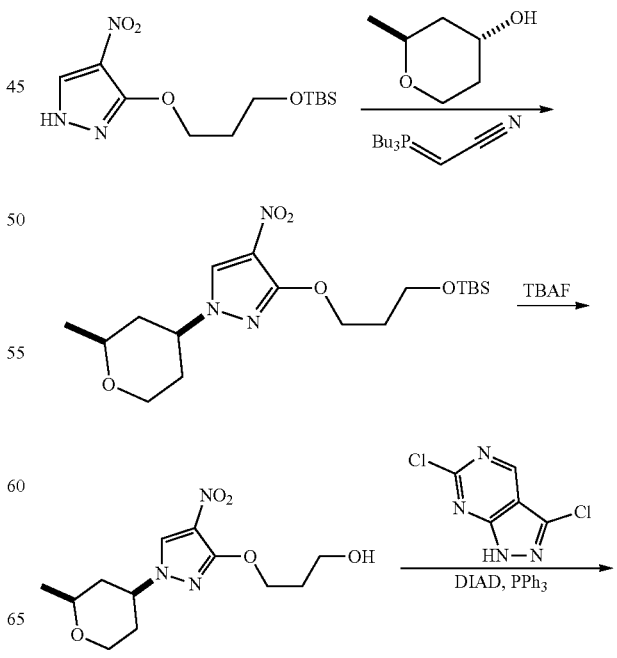

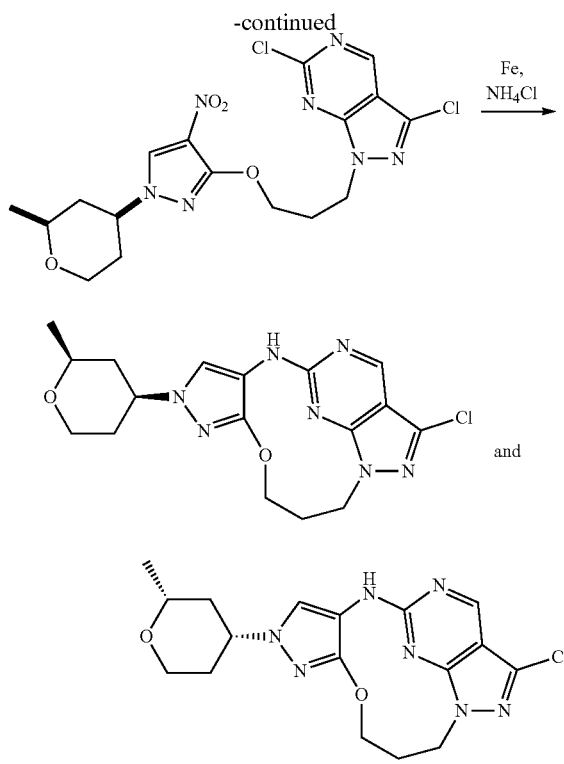

To a solution of 3-(3-((tert-butyldimethylsilyl)oxy)propoxy)-4-nitro-1H-pyrazole (5 g, 16.6 mmol) and trans-2-methyltetrahydro-2H-pyran-4-ol (2.31 g, 19.9 mmol) in toluene (150 mL) was added 2-(tributyl-X'-phosphanylidene)acetonitrile (16.01 g, 66.35 mmol). The resulting mixture was stirred at 110° C. for 16 h. The reaction mixture was concentrated under reduced pressure. The residue was purified by chromatography on silica gel (eluent: petroleum ether:EtOAc 100:0+65:35) to afford cis-3-(3-((tert-butyldimethylsilyl)oxy)propoxy)-1-(2-methyltetrahydro-2H-pyran-4-yl)-4-nitro-1H-pyrazole (4.6 g) of sufficient purity for the subsequent step.

To a solution of cis-3-(3-((tert-butyldimethylsilyl)oxy)propoxy)-1-(2-methyltetrahydro-2H-pyran-4-yl)-4-nitro-1H-pyrazole (4.6 g, 11.5 mmol) in THF (90 mL) was added TBAF (1 M in THF, 17.3 mL). The mixture was stirred at 20° C. for 2 h. The mixture was concentrated under reduced pressure. The residue was purified by chromatography on silica gel (eluent: petroleum ether:EtOAc 100:0→0:100) to afford cis-3-((1-(2-methyltetrahydro-2H-pyran-4-yl)-4-nitro-1H-pyrazol-3-yl)oxy)propan-1-ol (3 g) of sufficient purity for the subsequent step. $^1$H NMR (CDCl$_3$, 400 MHz) δ 8.05 (s, 1H), 4.51 (t, J=6.0 Hz, 2H), 4.25-4.13 (m, 2H), 3.85 (t, J=5.6 Hz, 2H), 3.63-3.47 (m, 2H), 2.19-2.13 (m, 1H), 2.11-2.06 (m, 3H), 2.00-1.88 (m, 1H), 1.71-1.59 (m, 1H), 1.29 (d, J=6.4 Hz, 3H).

To a solution of cis-3-((1-(2-methyltetrahydro-2H-pyran-4-yl)-4-nitro-1H-pyrazol-3-yl)oxy)propan-1-ol (3.25 g, 11.4 mmol) and 3,6-dichloro-1H-pyrazolo[3,4-d]pyrimidine (2.15 g, 11.4 mmol) in THF (250 mL) was added PPh$_3$ (8.96 g, 34.2 mmol) followed by DIAD (6.91 g, 34.2 mmol) at 5° C. The resulting mixture was stirred at 20° C. for 16 h. The reaction mixture was filtered, and the filtrate was concentrated under reduced pressure. The residue was purified by chromatography on silica gel (eluent: petroleum ether:EtOAc 100:0→50:50) to afford cis-3,6-dichloro-1-(3-((1-(2-methyltetrahydro-2H-pyran-4-yl)-4-nitro-1H-pyrazol-3-yl)oxy)propyl)-1H-pyrazolo[3,4-d]pyrimidine (2.75 g) of sufficient purity for the subsequent step. $^1$H NMR (CDCl$_3$, 400 MHz) δ 8.97 (s, 1H), 8.03 (s, 1H), 4.67 (t, J=6.4 Hz, 2H), 4.38 (t, J=6.0 Hz, 2H), 4.19-4.12 (m, 2H), 3.62-3.51 (m, 2H), 2.53-2.45 (m, 2H), 2.15-2.10 (m, 1H), 2.08-2.01 (m, 1H), 1.97-1.84 (m, 1H), 1.67-1.62 (m, 1H), 1.30 (d, J=6.8 Hz, 3H).

To a suspension of cis-3,6-dichloro-1-(3-((1-(2-methyltetrahydro-2H-pyran-4-yl)-4-nitro-1H-pyrazol-3-yl)oxy)propyl)-1H-pyrazolo[3,4-d]pyrimidine (1.87 g, 4.10 mmol) in EtOH (200 mL) and H$_2$O (50 mL) was added Fe (1.14 g, 20.5 mmol) and NH$_4$Cl (1.10 g, 20.5 mmol). The mixture was stirred at 80° C. for 16 h. The reaction mixture was filtered and the filtrate was concentrated under reduced pressure. The material was suspended in DCM (100 mL), filtered and concentrated under reduced pressure. The residue was purified by chromatography on silica gel (eluent: petroleum ether:EtOAc (MeOH 10 v %) 80:20→20:80) to afford and cis-8-chloro-2-(2-methyltetrahydro-2H-pyran-4-yl)-2,4,12,13-tetrahydro-11H-5,7-(azenometheno)dipyrazolo[3,4-b:5',1'-g][1]oxa[4,6,8]triazacycloundecine (1.1 g). cis-8-Chloro-2-(2-methyltetrahydro-2H-pyran-4-yl)-2,4,12,13-tetrahydro-11H-5,7-(azenometheno)dipyrazolo[3,4-b:5',1'-g][1]oxa[4,6,8]triazacycloundecine (1.5 g) was separated using preparative SFC (instrument: Berger MultiGram II, column: DAICEL CHIRALPAK AD 250×30 mm, 10 μm, mobile phase: supercritical CO$_2$/EtOH (0.1% NH$_3$·H$_2$O, v %)=45/55, flow rate: 80 mL/min, column temperature: 38° C., nozzle pressure: 100 bar, nozzle temperature: 60° C., evaporator temperature: 20° C., trimmer temperature: 25° C., wavelength: 220 nm) to afford: (+)-cis-8-Chloro-2-(2-methyltetrahydro-2H-pyran-4-yl)-2,4,12,13-tetrahydro-11H-5,7-(azenometheno)dipyrazolo[3,4-b:5',1'-g][1]oxa[4,6,8]triazacycloundecine (500 mg). $^1$H NMR (CDCl$_3$, 400 MHz) δ 8.66 (s, 1H), 7.27 (s, 1H), 7.06 (br s, 1H), 4.54-4.47 (m, 2H), 4.47-4.41 (m, 2H), 4.23-4.10 (m, 2H), 3.62-3.51 (m, 2H), 2.18-2.12 (m, 1H), 2.10-2.04 (m, 1H), 2.03-1.87 (m, 3H), 1.71-1.60 (m, 1H), 1.28 (d, J=6.0 Hz, 3H). LC-MS (method C) (m/z)=390.2 (MH)$^+$ t$_R$=1.43 minutes. Chiral analytical SFC conditions (instrument: Waters UPCC with PDA Detector, column: Chiralpak AD-3 50×4.6 mm I.D., 3 μm, mobile phase: A: CO$_2$ B: ethanol (0.05% DEA), gradient: from 5% to 40% of B in 2 min and hold 40% for 1.2 min, then 5% of B for 0.8 min, flow rate: 4 mL/min, column temperature: 35° C., ABPR: 1500 psi, run time: 4 min, wavelength: 220 nm), ee>99%, t$_R$=2.39 minutes. [α]$_D^{20}$=+1.6 (c=0.5 g/100 mL, CHCl$_3$) and the corresponding enantiomer (−)-cis-8-Chloro-2-(2-methyltetrahydro-2H-pyran-4-yl)-2,4,12,13-tetrahydro-11H-5,7-(azenometheno)dipyrazolo[3,4-b:5',1'-g][1]oxa[4,6,8]triazacycloundecine (550 mg). $^1$H NMR (CDCl$_3$, 400 MHz) δ 8.66 (s, 1H), 7.28 (s, 1H), 7.01 (br s, 1H), 4.55-4.47 (m, 2H), 4.47-4.42 (m, 2H), 4.22-4.11 (m, 2H), 3.61-3.53 (m, 2H), 2.20-2.11 (m, 1H), 2.10-2.04 (m, 1H), 2.03-1.88 (m, 3H), 1.65-1.60 (m, 1H), 1.28 (d, J=6.0 Hz, 3H). LC-MS (method C) (m/z)=390.2 (MH)$^+$ t$_R$=1.42 minutes. Chiral analytical SFC conditions (instrument: Waters UPCC with PDA Detector, column: Chiralpak AD-3 50×4.6 mm I.D., 3 μm, mobile phase: A: CO$_2$ B: ethanol (0.05% DEA), gradient: from 5% to 40% of B in 2 min and hold 40% for 1.2 min, then 5% of B for 0.8 min, flow rate: 4 mL/min, column temperature: 35° C., ABPR: 1500 psi, run time: 4 min, wavelength: 220 nm), ee>99%, t$_R$=2.85 minutes. [α]$_D^{20}$=−12 (c=0.2 g/100 mL, CHCl$_3$).

185

Intermediate: 3-Bromo-8-chloro-2-((2R,4R) or (2S,4S)-2-methyltetrahydro-2H-pyran-4-yl)-2,4,12,13-tetrahydro-11H-5,7-(azenometheno)dipyrazolo[3,4-b:5',1'-g][1]oxa[4,6,8]triazacycloundecine, peak 1

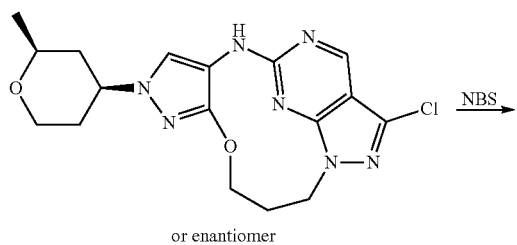

or enantiomer

NBS

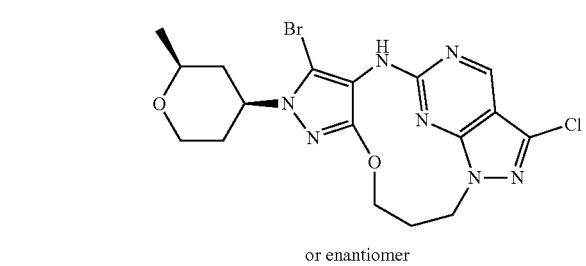

or enantiomer

To a solution of (+)-cis-8-chloro-2-(2-methyltetrahydro-2H-pyran-4-yl)-2,4,12,13-tetrahydro-11H-5,7-(azenometheno)dipyrazolo[3,4-b:5',1'-g][1]oxa[4,6,8]triazacycloundecine (520 mg, 1.33 mmol) in THF (19 mL,) was added, over a period of 13 min, a solution of NBS (268 mg, 1.51 mmol) in THF (4 mL) at room temperature. The mixture was stirred at room temperature for 1 h. Water (5 mL) was slowly added at room temperature, and the reaction mixture was concentrated under reduced pressure to remove most of the THF. The mixture was filtered and the filter cake was washed with water and dried before being concentrated under reduced pressure to afford 3-bromo-8-chloro-2-((2R,4R) or (2S,4S)-2-methyltetrahydro-2H-pyran-4-yl)-2,4,12,13-tetrahydro-11H-5,7-(azenometheno)dipyrazolo[3,4-b:5',1'-g][1]oxa[4,6,8]triazacycloundecine, peak1 (559 mg) of sufficient purity for the next step.

Intermediate: 3-Bromo-8-chloro-2-((2R,4R) or (2S,4S)-2-methyltetrahydro-2H-pyran-4-yl)-2,4,12,13-tetrahydro-11H-5,7-(azenometheno)dipyrazolo[3,4-b:5',1'-g][1]oxa[4,6,8]triazacycloundecine, peak 2

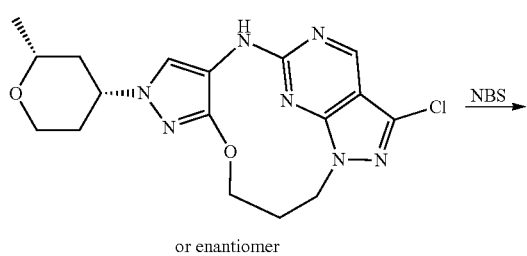

or enantiomer

NBS

186

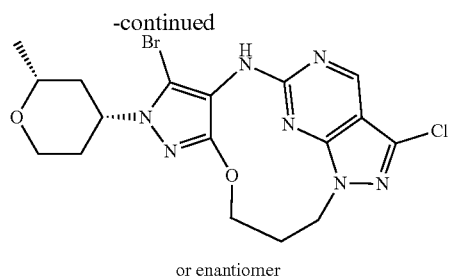

or enantiomer

To a solution of (−)-cis-8-chloro-2-(2-methyltetrahydro-2H-pyran-4-yl)-2,4,12,13-tetrahydro-11H-5,7-(azenometheno)dipyrazolo[3,4-b:5',1'-g][1]oxa[4,6,8]triazacycloundecine (475 mg, 1.22 mmol) in THF (19 mL,) was added, over a period of 13 min, a solution of NBS (239 mg, 1.34 mmol) in THF (4 mL) at room temperature. The mixture was stirred at room temperature for 1 h. Water (5 mL) was slowly added at room temperature, and the reaction mixture was concentrated on to remove most of the THF. The mixture was filtered and the filter cake was washed with water and dried before being concentrated to afford 3-bromo-8-chloro-2-((2R,4R) or (2S,4S)-2-methyltetrahydro-2H-pyran-4-yl)-2,4,12,13-tetrahydro-11H-5,7-(azenometheno)dipyrazolo[3,4-b:5',1'-g][1]oxa[4,6,8]triazacycloundecine, peak2 (473 mg) of sufficient purity for the next step.

Intermediate: 3,6-Dichloro-1-(3-((5-methyl-4-nitro-1-(4-oxaspiro[2.5]octan-7-yl)-1H-pyrazol-3-yl)oxy)propyl)-1H-pyrazolo[3,4-d]pyrimidine

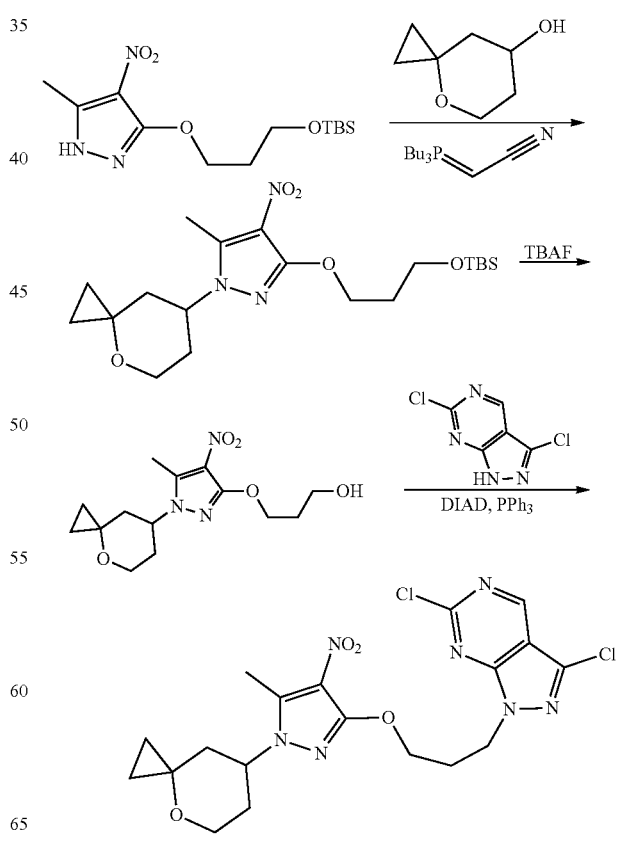

To a solution of 3-(3-((tert-butyldimethylsilyl)oxy)propoxy)-5-methyl-4-nitro-1H-pyrazole (900 mg, 2.85 mmol) in toluene (30 mL) was added 2-(tributyl-λ⁵-phosphanylidene)acetonitrile (2.75 g, 11.4 mmol) and 4-oxaspiro[2.5]octan-7-ol (439 mg, 3.42 mmol, prepared in a manner similar to Mathur, A. et al. J. Org. Chem., 2017, 82, 10376-10387). The mixture was stirred at 110° C. for 15 h. The reaction mixture was concentrated under reduced pressure. The residue was purified by chromatography on silica gel (eluent: petroleum ether:EtOAc 100:0→80:20) to afford 3-(3-((tert-butyldimethylsilyl)oxy)propoxy)-5-methyl-4-nitro-1-(4-oxaspiro[2.5]octan-7-yl)-1H-pyrazole (600 mg) of sufficient purity for the subsequent step. LC-MS (method B) (m/z)=426.2 (MH) $t_R$=1.11 minutes.

To a solution of 3-(3-((tert-butyldimethylsilyl)oxy)propoxy)-5-methyl-4-nitro-1-(4-oxaspiro[2.5]octan-7-yl)-1H-pyrazole (590 mg, 1.39 mmol) in THF (10 mL) was added TBAF (1 M in THF, 2.08 mL). The mixture was stirred at 20° C. for 1 h. The reaction mixture was concentrated under reduced pressure. The residue was purified by chromatography on silica gel (eluent: petroleum ether:EtOAc 100:0→50:50) to afford give 3-((5-methyl-4-nitro-1-(4-oxaspiro[2.5]octan-7-yl)-1H-pyrazol-3-yl)oxy)propan-1-ol (400 mg) of sufficient purity for the subsequent step. LC-MS (method B) (m/z)=312.1 (MH) $t_R$=0.77 minutes.

DIAD (760 mg, 3.76 mmol) was added to a solution of 3-((5-methyl-4-nitro-1-(4-oxaspiro[2.5]octan-7-yl)-1H-pyrazol-3-yl)oxy)propan-1-ol (390 mg, 1.25 mmol), 3,6-dichloro-1H-pyrazolo[3,4-d]pyrimidine (237 mg, 1.25 mmol), and PPh₃ (986 mg, 3.76 mmol) in THF (20 mL) at 0° C. Then the mixture was stirred at 20° C. for 15 h. The reaction mixture was concentrated under reduced pressure. The residue was purified by chromatography on silica gel (eluent: petroleum ether:EtOAc 100:0→60:40) to afford 3,6-dichloro-1-(3-((5-methyl-4-nitro-1-(4-oxaspiro[2.5]octan-7-yl)-1H-pyrazol-3-yl)oxy)propyl)-1H-pyrazolo[3,4-d]pyrimidine (500 mg) of sufficient purity for the subsequent step.

Intermediate: trans-3,6-Dichloro-1-(3-((5-ethyl-1-(3-fluorotetrahydro-2H-pyran-4-yl)-4-nitro-1H-pyrazol-3-yl)oxy)propyl)-1H-pyrazolo[3,4-d]pyrimidine

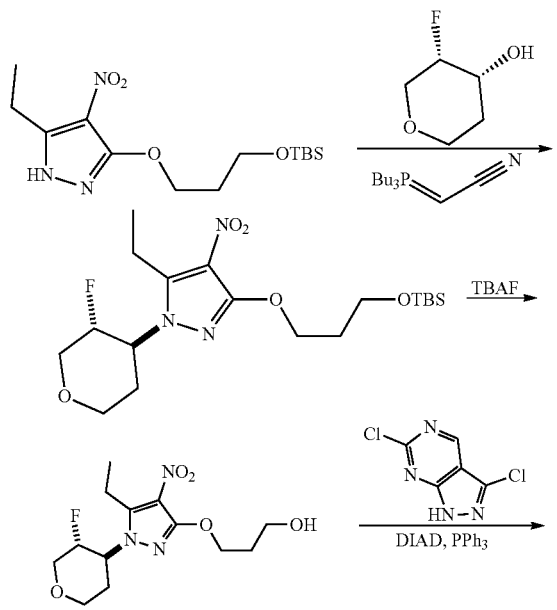

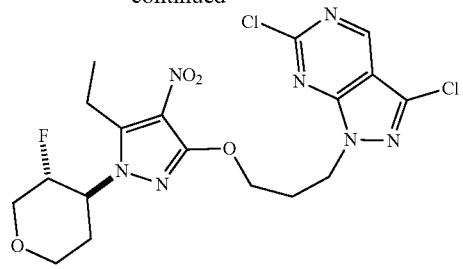

A solution of 3-(3-((tert-butyldimethylsilyl)oxy)propoxy)-5-ethyl-4-nitro-1H-pyrazole (1 g, 3.0 mmol), cis-3-fluorotetrahydro-2H-pyran-4-ol (547 mg, 4.55 mmol) and 2-(tributylphosphoranylidene)acetonitrile (2.93 g, 12.1 mmol) in toluene (40 mL) was stirred at 110° C. for 15 h. The mixture was concentrated under reduced pressure. The residue was purified by chromatography on silica gel (eluent: petroleum ether:EtOAc 95:5→80:20) to afford trans-3-(3-((tert-butyldimethylsilyl)oxy)propoxy)-5-ethyl-1-(3-fluorotetrahydro-2H-pyran-4-yl)-4-nitro-1H-pyrazole (950 mg) of sufficient purity for the subsequent step. ¹H NMR (CDCl₃, 400 MHz) δ5.07-4.83 (m, 1H), 4.42 (t, J=6.4 Hz, 2H), 4.34-4.15 (m, 2H), 4.13-4.02 (m, 1H), 3.82 (t, J=6.0 Hz, 2H), 3.55-3.46 (m, 1H), 3.44-3.34 (m, 1H), 3.15-2.98 (m, 2H), 2.55-2.42 (m, 1H), 2.09-2.00 (m, 2H), 1.95-1.86 (m, 1H), 1.28 (t, J=7.6 Hz, 3H), 0.89 (s, 9H), 0.05 (s, 6H).

To a solution of trans-3-(3-((tert-butyldimethylsilyl)oxy)propoxy)-5-ethyl-1-(3-fluorotetrahydro-2H-pyran-4-yl)-4-nitro-1H-pyrazole (950 mg, 2.20 mmol) in THF (15 mL) was added TBAF (3.30 mL, 1M in THF) at 0° C. and the reaction was stirred at 25° C. for 2 h. The mixture was concentrated under reduced pressure. The residue was purified by chromatography on silica gel (eluent: petroleum ether:EtOAc 95:5→50:50) to afford trans-3-((5-ethyl-1-(3-fluorotetrahydro-2H-pyran-4-yl)-4-nitro-1H-pyrazol-3-yl)oxy)propan-1-ol (600 mg) of sufficient purity for the subsequent step. ¹H NMR (CDCl₃, 400 MHz) δ5.06-4.83 (m, 1H), 4.50 (t, J=6.0 Hz, 2H), 4.34-4.16 (m, 2H), 4.13-4.04 (m, 1H), 3.88 (t, J=5.6 Hz, 2H), 3.56-3.46 (m, 1H), 3.44-3.34 (m, 1H), 3.21-2.94 (m, 2H), 2.55-2.40 (m, 1H), 2.18-2.02 (m, 2H), 1.97-1.87 (m, 1H), 1.28 (t, J=7.6 Hz, 3H).

To a solution of trans-3-((5-ethyl-1-(3-fluorotetrahydro-2H-pyran-4-yl)-4-nitro-1H-pyrazol-3-yl)oxy)propan-1-ol (600 mg, 1.89 mmol), 3,6-dichloro-1H-pyrazolo[3,4-d]pyrimidine (357 mg, 1.89 mmol) and PPh₃ (992 mg, 3.78 mmol) in THF (20 mL) was added DIAD (765 mg, 3.78 mmol) in a dropwise manner at 0° C. The mixture was stirred at 25° C. for 16 h. The mixture was concentrated under reduced pressure. The residue was purified by chromatography on silica gel (eluent: petroleum ether:EtOAc 80:20→50:50) to afford trans-3,6-dichloro-1-(3-((5-ethyl-1-(3-fluorotetrahydro-2H-pyran-4-yl)-4-nitro-1H-pyrazol-3-yl)oxy)propyl)-1H-pyrazolo[3,4-d]pyrimidine (830 mg) of sufficient purity for the subsequent step. LC-MS (method B) (m/z)=488.1 (MH)⁺ $t_R$=0.94 minutes.

Intermediate: 3,6-Dichloro-1-(3-((5-ethyl-1-((1r,4r)-4-meth oxycyclohexyl)-4-nitro-1H-pyrazol-3-yl)oxy)propyl)-1H-pyrazolo[3,4-d]pyrimidine

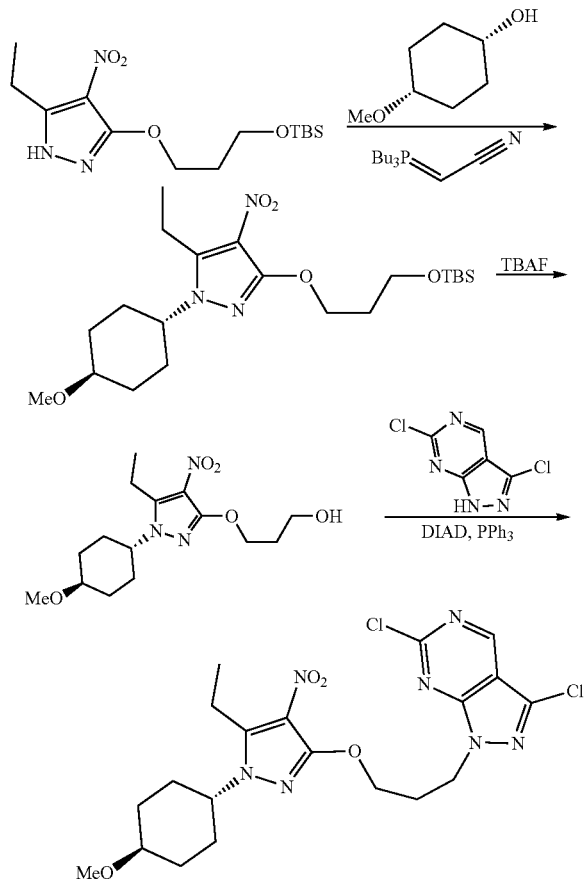

A mixture of 3-(3-((tert-butyldimethylsilyl)oxy)propoxy)-5-ethyl-4-nitro-1H-pyrazole (1 g, 3.0 mmol), cis-4-methoxycyclohexanol (790 mg, 6.07 mmol) and 2-(tributylphosphoranylidene)acetonitrile (2.93 g, 12.1 mmol) in toluene (40 mL) was stirred at 110° C. for 15 h. The mixture was concentrated under reduced pressure. The residue was purified by chromatography on silica gel (eluent: petroleum ether:EtOAc 95:5→80:20) to afford 3-(3-((tert-butyldimethylsilyl)oxy)propoxy)-5-ethyl-1-((1r,4r)-4-methoxycyclohexyl)-4-nitro-1H-pyrazole (700 mg) of sufficient purity for the subsequent step. $^1$H NMR (CDCl$_3$, 400 MHz) δ4.39 (t, J=6.4 Hz, 2H), 4.03-3.91 (m, 1H), 3.82 (t, J=6.4 Hz, 2H), 3.39 (s, 3H), 3.33-3.20 (m, 1H), 3.03 (q, J=7.6 Hz, 2H), 2.30-2.19 (m, 2H), 2.15-2.01 (m, 4H), 1.91-1.81 (m, 2H), 1.46-1.34 (m, 2H), 1.26 (t, J=6.8 Hz, 3H), 0.89 (s, 9H), 0.05 (s, 6H).

To a solution of 3-(3-((tert-butyldimethylsilyl)oxy)propoxy)-5-ethyl-1-((1r,4r)-4-methoxycyclohexyl)-4-nitro-1H-pyrazole (700 mg, 1.59 mmol) in THF (15 mL) was added TBAF (2.38 mL, 1M in THF) at 0° C. and the reaction was stirred at 30° C. for 2 h. The mixture was concentrated under reduced pressure. The residue was purified by chromatography on silica gel (eluent: petroleum ether:EtOAc 95:5→50:50) to afford 3-((5-ethyl-1-((1r,4r)-4-methoxycyclohexyl)-4-nitro-1H-pyrazol-3-yl)oxy)propan-1-ol (500 mg) of sufficient purity for the subsequent step. $^1$H NMR (CDCl$_3$, 400 MHz) δ4.50 (t, J=6.0 Hz, 2H), 4.05-3.93 (m, 1H), 3.83 (t, J=5.6 Hz, 2H), 3.39 (s, 3H), 3.31-3.19 (m, 1H), 3.04 (q, J=7.6 Hz, 2H), 2.30-2.20 (m, 2H), 2.09-2.04 (m, 4H), 1.93-1.83 (m, 2H), 1.42-1.32 (m, 2H), 1.27 (t, J=7.2 Hz, 3H).

To a solution of 3-((5-ethyl-1-((1r,4r)-4-methoxycyclohexyl)-4-nitro-1H-pyrazol-3-yl)oxy)propan-1-ol (500 mg, 1.53 mmol), 3,6-dichloro-1H-pyrazolo[3,4-d]pyrimidine (289 mg, 1.53 mmol), and PPh$_3$ (801 mg, 3.05 mmol) in THF (20 mL) was added dropwise DIAD (618 mg, 3.05 mmol) at 0° C. The mixture was stirred at 25° C. for 16 h. The mixture was concentrated under reduced pressure. The residue was purified by chromatography on silica gel (eluent: petroleum ether:EtOAc 80:20→50:50) to afford 3,6-dichloro-1-(3-((5-ethyl-1-((1r,4r)-4-methoxycyclohexyl)-4-nitro-1H-pyrazol-3-yl)oxy)propyl)-1H-pyrazolo[3,4-d]pyrimidine (1 g) of sufficient purity for the subsequent step. LC-MS (method B) (m/z)=498.1 (MH)$^+$ t$_R$=0.97 minutes.

Intermediate: 3-Bromo-8-chloro-2-(oxepan-4-yl)-2,4,12,13-tetrahydro-11H-5,7-(azenometheno)dipyrazolo[3,4-b:5',1'-g][1]oxa[4,6,8]triazacycloundecine

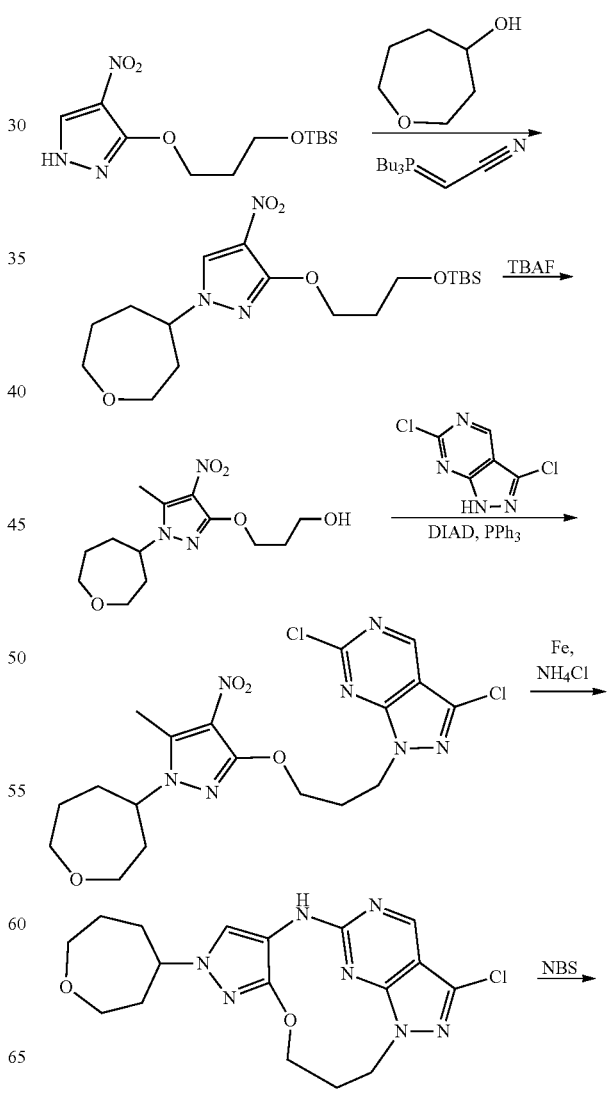

-continued

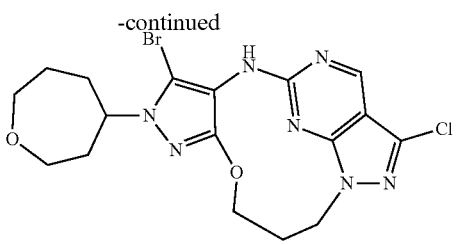

To a solution of 3-(3-((tert-butyldimethylsilyl)oxy)propoxy)-4-nitro-1H-pyrazole (6 g, 20 mmol) and oxepan-4-ol (3.47 g, 29.9 mmol) in toluene (120 mL) was added 2-(tributyl-λ⁵-phosphanylidene)acetonitrile (19.22 g, 79.6 mmol). The mixture was stirred at 110° C. for 15 h. The mixture was concentrated under reduced pressure. The residue was purified by chromatography on silica gel (eluent: petroleum ether:EtOAc 100:0-30:70) to afford 3-(3-((tert-butyldimethylsilyl)oxy)propoxy)-4-nitro-1-(oxepan-4-yl)-1H-pyrazole (7.2 g) of sufficient purity for the subsequent step. $^1$H NMR (CDCl$_3$, 400 MHz) δ 8.04 (s, 1H), 4.47-4.37 (m, 2H), 4.29-4.20 (m, 1H), 3.94-3.79 (m, 4H), 3.77-3.67 (m, 2H), 2.30-2.10 (m, 4H), 2.05-1.99 (m, 2H), 1.95-1.79 (m, 2H), 0.91-0.87 (m, 9H), 0.09-0.02 (m, 6H)

To a solution of 3-(3-((tert-butyldimethylsilyl)oxy)propoxy)-4-nitro-1-(oxepan-4-yl)-1H-pyrazole (7.4 g, 18.5 mmol) in THF (150 mL) was added TBAF (1 M in THF, 28 mL) and then stirred at 20° C. for 1 h. The mixture was concentrated under reduced pressure. The residue was purified by chromatography on silica gel (eluent: petroleum ether:EtOAc (MeOH 10 v %) 100:0→50:50) to afford 3-((4-nitro-1-(oxepan-4-yl)-1H-pyrazol-3-yl)oxy)propan-1-ol (5.1 g) of sufficient purity for the subsequent step. $^1$H NMR (CDCl$_3$, 400 MHz) δ 8.06 (s, 1H), 4.51 (t, J=6.0 Hz, 2H), 4.31-4.19 (m, 1H), 3.94-3.80 (m, 4H), 3.77-3.67 (m, 2H), 2.58 (br s, 1H), 2.31-2.06 (m, 6H), 1.94-1.79 (m, 2H).

To a mixture of 3-((4-nitro-1-(oxepan-4-yl)-1H-pyrazol-3-yl)oxy)propan-1-ol (1.7 g, 6.0 mmol), 3,6-dichloro-1H-pyrazolo[3,4-d]pyrimidine (1.13 g, 6.0 mmol) and PPh$_3$ (4.69 g, 17.9 mmol) in THF (100 mL) was added DIAD (3.61 g, 17.9 mmol) at 0° C. The mixture was stirred at 20° C. for 16 h. The mixture was concentrated under reduced pressure. The residue was purified by chromatography on silica gel (eluent: petroleum ether:EtOAc 100:0→40:60) to afford 3,6-dichloro-1-(3-((4-nitro-1-(oxepan-4-yl)-1H-pyrazol-3-yl)oxy)propyl)-1H-pyrazolo[3,4-d]pyrimidine (3.3 g) of sufficient purity for the subsequent step. LC-MS (method J) (m/z)=455.9 (MH)$^+$ t$_R$=1.54 minutes.

To a mixture of 3,6-dichloro-1-(3-((4-nitro-1-(oxepan-4-yl)-1H-pyrazol-3-yl)oxy)propyl)-1H-pyrazolo[3,4-d]pyrimidine (3.5 g, 7.7 mmol) and NH$_4$Cl (1.02 g, 19.1 mmol) in EtOH (150 mL) and H$_2$O (30 mL) was added Fe (1.07 g, 19.1 mmol) at 20° C. The mixture was stirred at 80° C. for 16 h, filtered, and concentrated under reduced pressure. The residue was purified by chromatography on silica gel (eluent: petroleum ether:EtOAc (DCM 10v %) 100:0→50:50) to afford 8-chloro-2-(oxepan-4-yl)-2,4,12,13-tetrahydro-11H-5,7-(azenometheno)dipyrazolo[3,4-b:5',1'-g][1]oxa[4,6,8]triazacycloundecine (1.5 g) of sufficient purity for the subsequent step. $^1$H NMR (DMSO-d$_6$, 400 MHz) δ 9.63 (s, 1H), 8.84 (s, 1H), 7.53 (s, 1H), 4.53-4.37 (m, 4H), 4.35-4.25 (m, 1H), 3.88-3.74 (m, 2H), 3.74-3.59 (m, 2H), 2.21-2.11 (m, 2H), 2.09-2.01 (m, 2H), 2.0-1.88 (m, 2H), 1.87-1.75 (m, 2H).

A solution of NBS (685 mg, 3.85 mmol) in THF (5 mL) was added dropwise to a solution of 8-chloro-2-(oxepan-4-yl)-2,4,12,13-tetrahydro-11H-5,7-(azenometheno)dipyrazolo[3,4-b:5',1'-g][1]oxa[4,6,8]triazacycloundecine (1 g, 2.6 mmol) in THF (50 mL) at 25° C. The mixture was stirred for 1 h at 25° C. The mixture was concentrated under reduced pressure. The residue was diluted with EtOAc (50 mL). The organic phase was washed with brine (20 mL×3), dried and concentrated under reduced pressure. The residue was purified by chromatography on silica gel (eluent: petroleum ether:EtOAc (DCM 10v %) 100:0→80:20) to afford 3-bromo-8-chloro-2-(oxepan-4-yl)-2,4,12,13-tetrahydro-11H-5,7-(azenometheno)dipyrazolo[3,4-b:5',1'-g][1]oxa[4,6,8]triazacycloundecine (0.8 g) of sufficient purity for the subsequent step. $^1$H NMR (400 MHz, CDCl$_3$) δ 8.63 (s, 1H), 6.90-6.71 (m, 1H), 4.50-4.39 (m, 3H), 4.38-4.32 (m, 2H), 3.88-3.76 (m, 2H), 3.75-3.66 (m, 1H), 3.65-3.56 (m, 1H), 2.36-2.23 (m, 1H), 2.23-2.13 (m, 1H), 2.13-2.02 (m, 1H), 2.0-1.9 (m, 3H), 1.88-1.73 (m, 2H).

Intermediate: 3-Bromo-8-chloro-2-(tetrahydro-2H-pyran-3-yl)-2,4,12,13-tetrahydro-11H-5,7-(azenometheno)dipyrazolo[3,4-b:5',1'-g][1]oxa[4,6,8]triazacycloundecine

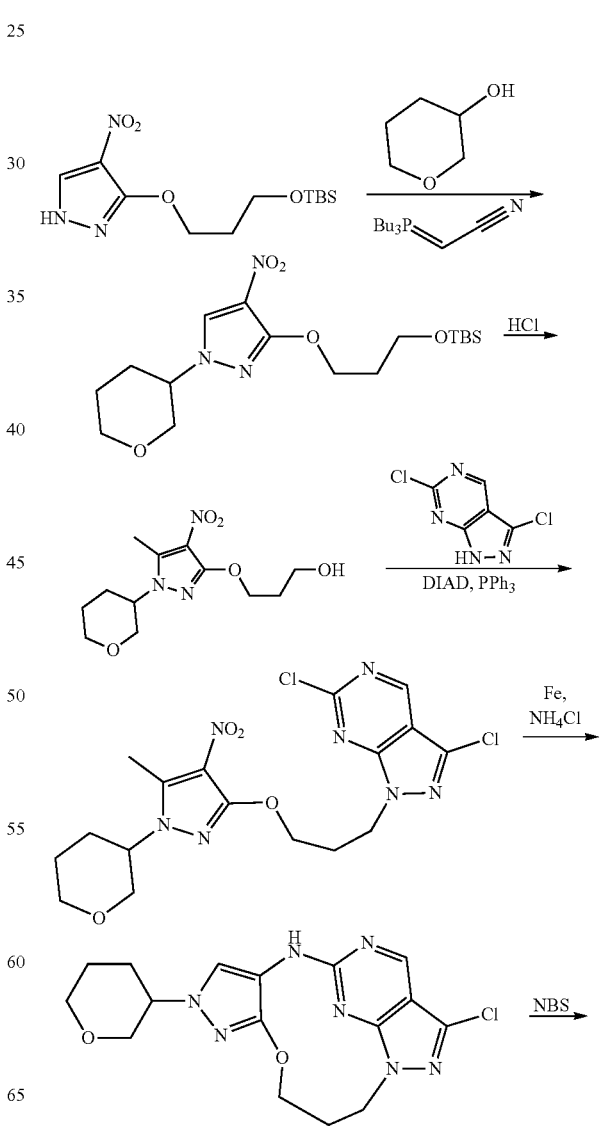

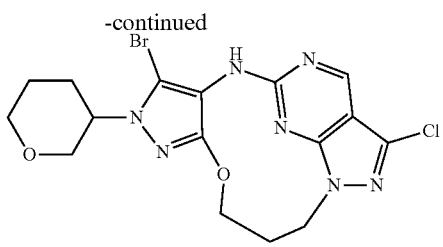

To a solution of 3-(3-((tert-butyldimethylsilyl)oxy)propoxy)-4-nitro-1H-pyrazole (0.56 g, 1.84 mmol) in toluene (11 mL) was added tetrahydro-2H-pyran-3-ol (0.261 mL, 2.76 mmol) and 2-(tributyl-X-phosphanylidene)acetonitrile (1.98 g, 8.20 mmol). The mixture was stirred at 110° C. for 15 h. The reaction mixture was concentrated under reduced pressure. The residue was purified by chromatography on silica gel (eluent: heptane:EtOAc 100:0→0:100) to afford 3-(3-((tert-butyldimethylsilyl)oxy)propoxy)-4-nitro-1-(tetrahydro-2H-pyran-3-yl)-1H-pyrazole (412 mg) of sufficient purity for the subsequent step.

To a solution of 3-(3-((tert-butyldimethylsilyl)oxy)propoxy)-4-nitro-1-(tetrahydro-2H-pyran-3-yl)-1H-pyrazole (412 mg, 0.930 mmol) in THF (15.1 mL) was added aqueous HCl (0.80 mL, 12 M, 9.6 mmol). The mixture was stirred at room temperature for 30 minutes. The mixture was concentrated under reduced pressure and saturated aqueous NaHCO$_3$ was added to adjust pH=8-9, extracted with EtOAc. The combined organic phases were washed with brine, dried over Na$_2$SO$_4$, and concentrated under reduced pressure. The residue was purified by chromatography on silica gel (eluent: heptane:EtOAc 100:0→0:100) to afford 3-((4-nitro-1-(tetrahydro-2H-pyran-3-yl)-1H-pyrazol-3-yl)oxy)propan-1-ol (261 mg) of sufficient purity for the subsequent step.

To a reaction vessel was added DIAD (355 µL, 1.83 mmol) and the atmosphere was exchanged for argon. THF (12 mL) was added, and the solution was cooled to 0° C. Then, triphenylphosphine (on resin, loading: 1.6 mmol/g) (1.18 g, 1.89 mmol), was added and the solution was stirred under argon for 5 minutes. At this point 3,6-dichloro-1H-pyrazolo[3,4-d]pyrimidine (223 mg, 1.09 mmol) was added followed by the addition of 3-((4-nitro-1-(tetrahydro-2H-pyran-3-yl)-1H-pyrazol-3-yl)oxy)propan-1-ol (261 mg, 0.914 mmol) as a solution in THF (4 mL). The mixture was allowed to reach room temperature and was stirred overnight at room temperature. The mixture was filtered and concentrated under reduced pressure. The residue was purified by chromatography on silica gel (eluent: heptane:EtOAc 100:0→0:100) to afford 3,6-dichloro-1-(3-((4-nitro-1-(tetrahydro-2H-pyran-3-yl)-1H-pyrazol-3-yl)oxy)propyl)-1H-pyrazolo[3,4-d]pyrimidine (498 mg) of sufficient purity for the subsequent step.

To a solution of 3,6-dichloro-1-(3-((4-nitro-1-(tetrahydro-2H-pyran-3-yl)-1H-pyrazol-3-yl)oxy)propyl)-1H-pyrazolo[3,4-d]pyrimidine (430 mg, 0.914 mmol) in EtOH (130 mL) and H$_2$O (10 mL,) was added Fe (570 mg, 10.2 mmol) and NH$_4$Cl (500 mg, 9.35 mmol). The mixture was stirred at 60° C. overnight, followed by 80° C. for 23 h. The reaction mixture was filtered through celite and then concentrated under reduced pressure. The residue was purified by chromatography on silica gel (eluent: heptane:EtOAc 100:0→0:100) to afford 8-chloro-2-(tetrahydro-2H-pyran-3-yl)-2,4,12,13-tetrahydro-11H-5,7-(azenometheno)dipyrazolo[3,4-b:5',1'-g][1]oxa[4,6,8]triazacycloundecine (214 mg) of sufficient purity for the subsequent step.

To a solution of 8-chloro-2-(tetrahydro-2H-pyran-3-yl)-2,4,12,13-tetrahydro-11H-5,7-(azenometheno)dipyrazolo[3,4-b:5',1'-g][1]oxa[4,6,8]triazacycloundecine (532 mg, 1.37 mmol) in THF (19 mL) was added NBS (276 mg, 1.55 mmol) as a solution in THF (4 mL) over a period of 13 minutes at room temperature. The mixture was stirred at room temperature for 1 h. Water (5 mL) was slowly added at room temperature, and the reaction mixture was concentrated under reduced pressure to remove most of the THF. The mixture was filtered and the filter cake was washed with water and dried to afford 3-bromo-8-chloro-2-(tetrahydro-2H-pyran-3-yl)-2,4,12,13-tetrahydro-11H-5,7-(azenometheno)dipyrazolo[3,4-b:5',1'-g][1]oxa[4,6,8]triazacycloundecine (492 mg) of sufficient purity for the subsequent step.

Intermediate: 8-Chloro-2-((3R,4S) or (3R,4S)-3-fluorotetrahydro-2H-pyran-4-yl)-2,4,12,13-tetrahydro-11H-5,7-(azenometheno)dipyrazolo[3,4-b:5',1'-g][1]oxa[4,6,8]triazacycloundecine, peak 1 and 8-Chloro-2-((3R,4S) or (3R,4S)-3-fluorotetrahydro-2H-pyran-4-yl)-2,4,12,13-tetrahydro-11H-5,7-(azenometheno)dipyrazolo[3,4-b:5',1'-g][1]oxa[4,6,8]triazacycloundecine, peak 2

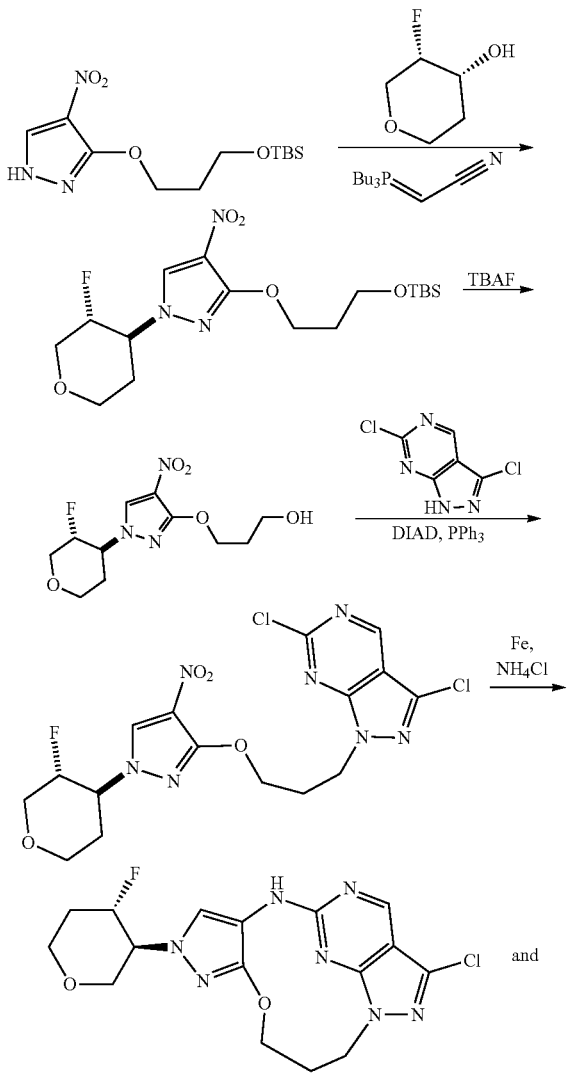

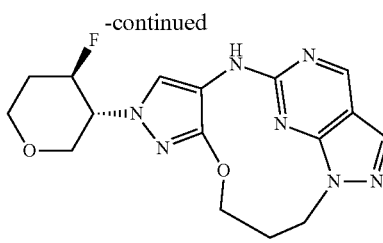

To a solution of 3-(3-((tert-butyldimethylsilyl)oxy)propoxy)-4-nitro-1H-pyrazole (6 g, 20 mmol) and cis-3-fluorotetrahydro-2H-pyran-4-ol:trans-3-fluorotetrahydro-2H-pyran-4-ol (cis/trans=3:1, 3.59 g, 29.9 mmol) in toluene (120 mL) was added 2-(tributyl-λ⁵-phosphanylidene)acetonitrile (19.22 g, 79.6 mmol). The mixture was stirred at 110° C. for 16 h. The mixture was concentrated under reduced pressure. The residue was purified by chromatography on silica gel (eluent: Petroleum ether:EtOAc 100:0→30:70) to afford trans-3-(3-((tert-butyldimethylsilyl)oxy)propoxy)-1-(3-fluorotetrahydro-2H-pyran-4-yl)-4-nitro-1H-pyrazole (5.6 g) of sufficient purity for the subsequent step. $^1$H NMR (CDCl$_3$, 400 MHz) δ 8.12 (s, 1H), 4.93-4.72 (m, 1H), 4.44 (t, J=6.4 Hz, 2H), 4.27 (dd, J=5.6, 11.6 Hz, 1H), 4.12-4.04 (m, 2H), 3.83 (t, J=5.6 Hz, 2H), 3.55-3.45 (m, 1H), 3.43-3.34 (m, 1H), 2.44-2.33 (m, 1H), 2.18-2.09 (m, 1H), 2.06-2.00 (m, 2H), 0.89 (s, 9H), 0.05 (s, 6H).

To a solution of trans-3-(3-((tert-butyldimethylsilyl)oxy)propoxy)-1-(3-fluorotetrahydro-2H-pyran-4-yl)-4-nitro-1H-pyrazole (5.47 g, 13.6 mmol) in THF (100 mL) was added TBAF (1 M in THF, 20 mL) and then stirred at 20° C. for 1 h. The reaction mixture was concentrated under reduced pressure. The residue was purified by chromatography on silica gel (eluent: Petroleum ether:EtOAc (MeOH, 10 v %) 100:0→50:50) to afford trans-3-((1-(3-fluorotetrahydro-2H-pyran-4-yl)-4-nitro-1H-pyrazol-3-yl)oxy)propan-1-ol (3.6 g) of sufficient purity for the subsequent step. $^1$H NMR (CDCl$_3$, 400 MHz) δ 8.14 (s, 1H), 4.93-4.71 (m, 1H), 4.51 (t, J=6.0 Hz, 2H), 4.27 (dd, J=5.2, 11.2 Hz, 1H), 4.21-4.14 (m, 1H), 4.10-4.04 (m, 1H), 3.87 (t, J=6.0 Hz, 2H), 3.55-3.45 (m, 1H), 3.43-3.33 (m, 1H), 2.43-2.33 (m, 1H), 2.18-2.13 (m, 1H), 2.12-2.07 (m, 2H).

To a mixture of trans-3-((1-(3-fluorotetrahydro-2H-pyran-4-yl)-4-nitro-1H-pyrazol-3-yl)oxy)propan-1-ol (3.6 g, 135 mmol), 3,6-dichloro-1H-pyrazolo[3,4-d]pyrimidine (2.35 g, 12.5 mmol), and PPh$_3$ (9.79 g, 37.3 mmol) in THF (200 mL) was added DIAD (7.55 g, 37.3 mmol) at 0° C. The mixture was stirred at 20° C. for 11 h. The mixture was concentrated under reduced pressure. The residue was purified by chromatography on silica gel (eluent: Petroleum ether:EtOAc (MeOH, 10 v %) 100:0→50:50) to afford trans-3,6-dichloro-1-(3-((1-(3-fluorotetrahydro-2H-pyran-4-yl)-4-nitro-1H-pyrazol-3-yl)oxy)propyl)-1H-pyrazolo[3,4-d]pyrimidine (3 g) of sufficient purity for the subsequent step. LC-MS (method J) (m/z)=482.0 (M+Na)+t$_R$=1.54 minutes.

To a mixture of trans-3,6-dichloro-1-(3-((1-(3-fluorotetrahydro-2H-pyran-4-yl)-4-nitro-1H-pyrazol-3-yl)oxy)propyl)-1H-pyrazolo[3,4-d]pyrimidine (3 g, 6.5 mmol) and NH$_4$Cl (1.74 g, 32.6 mmol) in a mixture of EtOH (600 mL) and H$_2$O (100 mL) was added Fe (1.82 g, 32.6 mmol) at 20° C. under. The mixture was stirred at 80° C. for 16 h. Additional Fe (1.82 g) and NH$_4$Cl (1.74 g) were added to the mixture and stirred at 80° C. for another 16 h. The mixture was filtered and concentrated under reduced pressure. The residue was purified by chromatography on silica gel (eluent: Petroleum ether:EtOAc (DCM, 10 v %) 100:0→50:50) to afford trans-8-chloro-2-(3-fluorotetrahydro-2H-pyran-4-yl)-2,4,12,13-tetrahydro-11H-5,7-(azenometheno)dipyrazolo[3,4-b:5',1'-g][1]oxa[4,6,8]triazacycloundecine (1.6 g). trans-8-Chloro-2-(3-fluorotetrahydro-2H-pyran-4-yl)-2,4,12,13-tetrahydro-11H-5,7-(azenometheno)dipyrazolo[3,4-b:5',1'-g][1]oxa[4,6,8]triazacycloundecine (1.6 g) was separated using preparative SFC (instrument: Thar SFC Prep 200, column: DAICEL CHIRALPAK AD 250×30 mm, 10 μm, mobile phase: supercritical CO$_2$/ETOH (0.1% NH$_3$·H$_2$O, v %)=50/50, flow rate: 200 mL/min, column temperature: 38° C., nozzle pressure: 100 bar, nozzle temperature: 60° C., evaporator temperature: 20° C., trimmer temperature: 25° C., wavelength: 220 nm) to afford: 8-Chloro-2-((3R,4S) or (3R,4S)-3-fluorotetrahydro-2H-pyran-4-yl)-2,4,12,13-tetrahydro-11H-5,7-(azenometheno)dipyrazolo[3,4-b:5',1'-g][1]oxa[4,6,8]triazacycloundecine, peak 1 (0.62 g) of sufficient purity for the subsequent step. LC-MS (method B) (m/z)=394.1 (MH)$^+$ t$_R$=0.77 minutes. Chiral analytical SFC conditions (instrument: Waters UPCC with PDA Detector, column: Chiralpak AD-3 50×4.6 mm I.D., 3 μm, mobile phase: A: CO$_2$ B: ethanol (0.05% DEA), isocratic: 40% B, flow rate: 4 mL/min, column temperature: 35° C., ABPR: 1500 psi, run time: 4 min, wavelength: 220 nm), ee>99%, t$_R$=1.42 minutes, and the corresponding enantiomer 8-Chloro-2-((3R,4S) or (3R,4S)-3-fluorotetrahydro-2H-pyran-4-yl)-2,4,12,13-tetrahydro-11H-5,7-(azenometheno)dipyrazolo[3,4-b:5',1'-g][1]oxa[4,6,8]triazacycloundecine, peak 2 (0.53 g) of sufficient purity for the next step. LC-MS (method B) (m/z)=394.1 (MH)$^+$ t$_R$=0.77 minutes. Chiral analytical SFC conditions (instrument: Waters UPCC with PDA Detector, column: Chiralpak AD-3 50×4.6 mm I.D., 3 μm, mobile phase: A: CO$_2$ B: ethanol (0.05% DEA), isocratic: 40% B, flow rate: 4 mL/min, column temperature: 35° C., ABPR: 1500 psi, run time: 4 min, wavelength: 220 nm), ee>99%, t$_R$=1.97 minutes.

Intermediate: (+)-3-Bromo-8-chloro-2-((3R,4S) or (3S,4R)-3-fluorotetrahydro-2H-pyran-4-yl)-2,4,12,13-tetrahydro-11H-5,7-(azenometheno)dipyrazolo[3,4-b:5',1'-g][1]oxa[4,6,8]triazacycloundecine

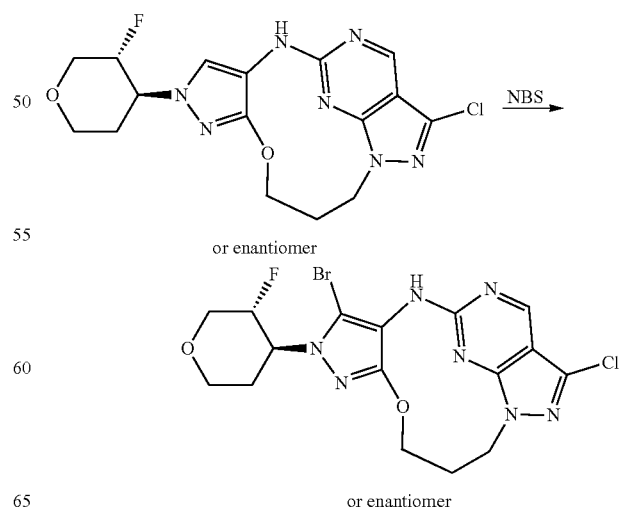

A solution of NBS (470 mg, 2.64 mmol) in THF (5 mL) was added dropwise to a solution of 8-chloro-2-((3R,4S) or (3R,4S)-3-fluorotetrahydro-2H-pyran-4-yl)-2,4,12,13-tetrahydro-11H5,7-(azenometheno)dipyrazolo[3,4-b:5',1'-g][1]oxa[4,6,8]triazacycloundecine, peak 1 (0.52 g, 1.32 mmol) in THF (50 mL) at 20° C. The mixture was stirred for 1 h at 20° C. The mixture was concentrated under reduced pressure. The residue was diluted with EtOAc (10 mL). The organic phase was washed with brine (5 mL×2), dried, and concentrated under reduced pressure. The residue was purified by chromatography on silica gel (eluent: Petroleum ether:EtOAc (DCM 10v %) 100:0→50:50) and preparative SFC (instrument: Thar SFC Prep 80, column: DAICEL CHIRALCEL OD-H 250×30 mm, 10 μm, mobile phase: supercritical $CO_2$/EtOH (0.1% $NH_3·H_2O$, v %)=70/30, flow rate: 80 mL/min, column temperature: 38° C., nozzle pressure: 100 bar, nozzle temperature: 60° C., evaporator temperature: 20° C., trimmer temperature: 25° C., wavelength: 220 nm) to afford (+)-3-bromo-8-chloro-2-((3S, 4R)-3-fluorotetrahydro-2H-pyran-4-yl)-2,4,12,13-tetrahydro-11H-5,7-(azenometheno)dipyrazolo[3,4-b:5',1'-g][1]oxa[4,6,8]triazacycloundecine (0.2 g) of sufficient purity for the subsequent step. $^1$H NMR (CDCl$_3$, 400 MHz) δ8.73 (s, 1H), 6.82 (br s, 1H), 5.09-4.87 (m, 1H), 4.60-4.40 (m, 5H), 4.34-4.26 (m, 1H), 4.12-4.04 (m, 1H), 3.60-3.50 (m, 1H), 3.49-3.39 (m, 1H), 2.43-2.30 (m, 1H), 2.12-1.95 (m, 3H). LC-MS (method C) (m/z)=474.1 (MH)$^+$ $t_R$=1.60 minutes. Chiral analytical SFC conditions (instrument: Waters UPCC with PDA Detector, column: Chiralpak AD-3 50×4.6 mm I.D., 3 μm, mobile phase: A: $CO_2$ B: ethanol (0.05% DEA), gradient: from 5% to 40% of B in 2 min and hold 40% for 1.2 min, then 5% of B for 0.8 min, flow rate: 4 mL/min, column temperature: 35° C., ABPR: 1500 psi, run time: 4 min, wavelength: 254 nm), ee>99%, $t_R$=0.78 minutes. $[α]_D^{20}$=+18.7 (c=0.3 g/100 mL, CHCl$_3$).

Intermediate: (−)-3-Bromo-8-chloro-2-((3R,4S) or (3S,4R)-3-fluorotetrahydro-2H-pyran-4-yl)-2,4,12,13-tetrahydro-11H-5,7-(azenometheno)dipyrazolo[3,4-b:5',1'-g][1]oxa[4,6,8]triazacycloundecine (azenometheno)dipyrazolo[3,4-b:5',1'-g][1]oxa[4,6,8]triazacycloundecine using NBS (434 mg, 2.44 mmol) in THF (5 mL), 8-chloro-2-((3R,4S or 3S,4R)-3-fluorotetrahydro-2H-pyran-4-yl)-2,4,12,13-tetrahydro-11H-5,7-(azenometheno)dipyrazolo[3,4-b:5',1'-g][1]oxa[4,6,8]triazacycloundecine, peak 2 (0.48 g, 1.22 mmol) in THF (50 mL) at 20° C. for 1 h, followed by work-up, and purification by chromatography on silica gel (eluent: Petroleum ether:EtOAc (DCM 10v %) 100:0→50:50) and preparative SFC (instrument: Thar SFC Prep 80, column: DAICEL CHIRALCEL OD-H 250×30 mm, 10 μm, mobile phase: supercritical $CO_2$/EtOH (0.1% $NH_3·H_2O$, v %)=70/30, flow rate: 80 mL/min, column temperature: 38° C., nozzle pressure: 100 bar, nozzle temperature: 60° C., evaporator temperature: 20° C., trimmer temperature: 25° C., wavelength: 220 nm) to afford (−)-3-bromo-8-chloro-2-((3R,4S) or (3S,4R)-3-fluorotetrahydro-2H-pyran-4-yl)-2,4,12,13-tetrahydro-11H-5,7-(azenometheno)dipyrazolo[3,4-b:5',1'-g][1]oxa[4,6,8]triazacycloundecine (0.23 g) of sufficient purity for the subsequent step. $^1$H NMR (CDCl$_3$, 400 MHz) δ8.72 (s, 1H), 6.91 (br s, 1H), 5.09-4.87 (m, 1H), 4.60-4.41 (m, 5H), 4.34-4.25 (m, 1H), 4.12-4.04 (m, 1H), 3.56-3.50 (m, 1H), 3.49-3.39 (m, 1H), 2.43-2.29 (m, 1H), 2.12-1.95 (m, 3H). LC-MS (method C) (m/z)=474.0 (MH)$^+$ $t_R$=1.60 minutes. Chiral analytical SFC conditions (instrument: Waters UPCC with PDA Detector, column: Chiralpak AD-3 50×4.6 mm I.D., 3 μm, mobile phase: A: $CO_2$ B: ethanol (0.05% DEA), gradient: from 5% to 40% of B in 2 min and hold 40% for 1.2 min, then 5% of B for 0.8 min, flow rate: 4 mL/min, column temperature: 35° C., ABPR: 1500 psi, run time: 4 min, wavelength: 254 nm), ee>99%, $t_R$=0.99 minutes. $[α]_D^{20}$=−20 (c=0.3 g/100 mL, CHCl$_3$).

Intermediate: (−)-(R) or (S)-3-bromo-8-chloro-2-(4-oxaspiro[2.5]octan-7-yl)-2,4,12,13-tetrahydro-11H-5,7-(azenometheno)dipyrazolo[3,4-b:5',1'-g][1]oxa[4,6,8]triazacycloundecine and (+)-(R) or (S)-3-bromo-8-chloro-2-(4-oxaspiro[2.5]octan-7-yl)-2,4,12,13-tetrahydro-11H5,7-(azenometheno)dipyrazolo[3,4-b:5',1'-g][1]oxa[4,6,8]triazacycloundecine

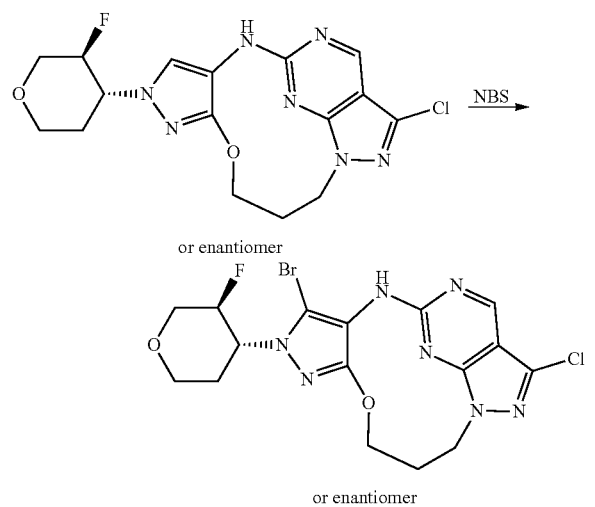

or enantiomer

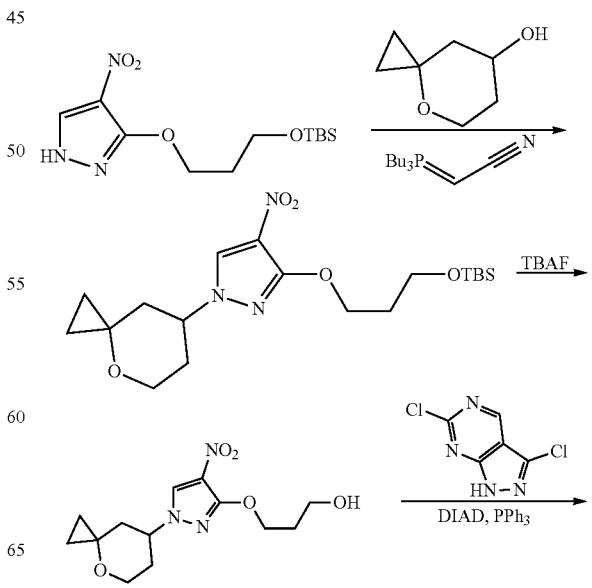

The intermediate was prepared in a manner similar to (+)-3-Bromo-8-chloro-2-((3R,4S) or (3S,4R)-3-fluorotetrahydro-2H-pyran-4-yl)-2,4,12,13-tetrahydro-11H-5,7-

-continued

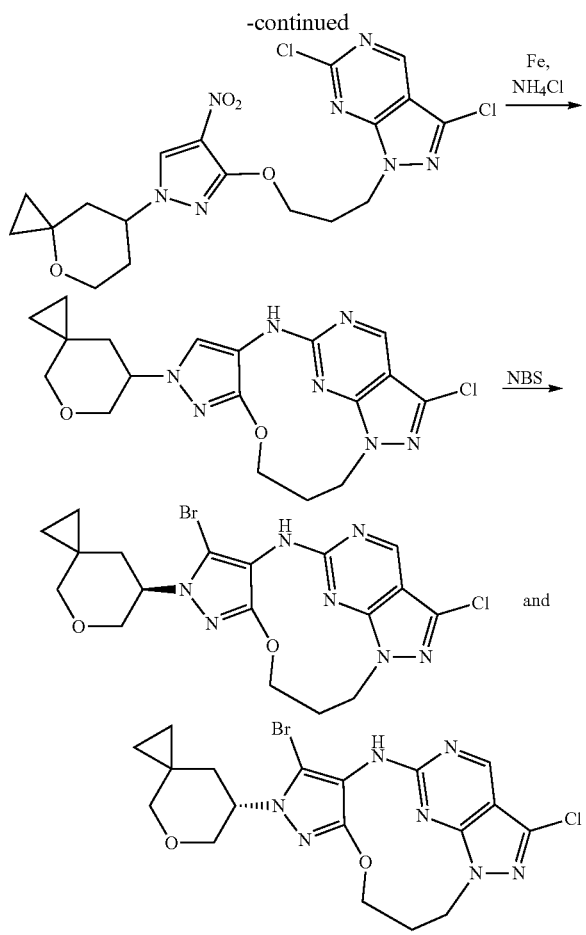

To a solution of 3-(3-((tert-butyldimethylsilyl)oxy)propoxy)-4-nitro-1H-pyrazole (7.6 g, 25 mmol) and 4-oxaspiro[2.5]octan-7-ol (4.2 g, 33 mmol, prepared in a manner similar to Mathur, A. et al. J. Org. Chem., 2017, 82, 10376-10387) in toluene (220 mL) was added 2-(tributyl-X-phosphanylidene)acetonitrile (24.34 g, 100.9 mmol). The mixture was stirred at 110° C. for 15 h. The mixture was concentrated under reduced pressure. The residue was purified by chromatography on silica gel (eluent: Petroleum ether:EtOAc 100:0→70:30) to afford 3-(3-((tertbutyldimethylsilyl)oxy)propoxy)-4-nitro-1-(4-oxaspiro[2.5]octan-7-yl)-1H-pyrazole (6.3 g) of sufficient purity for the subsequent step. $^1$H NMR (CDCl$_3$, 400 MHz) δ7.99 (s, 1H), 4.37 (t, J=6.4 Hz, 2H), 4.32-4.22 (m, 1H), 4.0-3.93 (m, 1H), 3.77 (t, J=6.4 Hz, 2H), 3.64-3.55 (m, 1H), 2.47-2.39 (m, 1H), 2.14-2.02 (m, 2H), 2.00-1.94 (m, 2H), 1.57-1.52 (m, 1H), 0.96-0.90 (m, 1H), 0.84 (s, 9H), 0.75-0.66 (m, 1H), 0.60-0.53 (m, 1H), 0.49-0.40 (m, 1H), 0.03 (s, 6H).

To a solution of 3-(3-((tert-butyldimethylsilyl)oxy)propoxy)-4-nitro-1-(4-oxaspiro[2.5]octan-7-yl)-1H-pyrazole (6.3 g, 15 mmol) in THF (120 mL) was added TBAF (1 M in THF, 23 mL) and then stirred at 25° C. for 1 h. The reaction mixture was concentrated under reduced pressure. The residue was purified by chromatography on silica gel (eluent: Petroleum ether:EtOAc (MeOH 10 v %) 100:0→50:50) to afford 3-((4-nitro-1-(4-oxaspiro[2.5]octan-7-yl)-1H-pyrazol-3-yl)oxy)propan-1-ol (4.4 g) of sufficient purity for the subsequent step. $^1$H NMR (CDCl$_3$, 400 MHz) δ 8.07 (s, 1H), 4.51 (t, J=6.0 Hz, 2H), 4.39-4.28 (m, 1H), 4.06-3.99 (m, 1H), 3.86 (t, J=5.6 Hz, 2H), 3.70-3.60 (m, 1H), 2.53-2.45 (m, 1H), 2.22-2.08 (m, 4H), 1.70 (br s, 1H), 1.63-1.57 (m, 1H), 1.01-0.95 (m, 1H), 0.82-0.71 (m, 1H), 0.68-0.58 (m, 1H), 0.54-0.44 (m, 1H).

To a mixture of 3-((4-nitro-1-(4-oxaspiro[2.5]octan-7-yl)-1H-pyrazol-3-yl)oxy)propan-1-ol (4.3 g, 14.5 mmol), 3,6-dichloro-1H-pyrazolo[3,4-d]pyrimidine (2.73 g, 14.5 mmol) and PPh$_3$ (11.4 g, 43.4 mmol) in THF (180 mL) was added DIAD (8.77 g, 43.4 mmol) at 0° C. The mixture was stirred at 25° C. for 14 h. The mixture was concentrated under reduced pressure. The residue was purified by chromatography on silica gel (eluent: Petroleum ether:EtOAc 100:0→60:40) to afford 3,6-dichloro-1-(3-((4-nitro-1-(4-oxaspiro[2.5]octan-7-yl)-1H-pyrazol-3-yl)oxy)propyl)-1H-pyrazolo[3,4-d]pyrimidine (3.3 g) of sufficient purity for the subsequent step. LC-MS (method B) (m/z)=468.1 (MH)$^+$ t$_R$=0.93 minutes.

To 3,6-dichloro-1-(3-((4-nitro-1-(4-oxaspiro[2.5]octan-7-yl)-1H-pyrazol-3-yl)oxy)propyl)-1H-pyrazolo[3,4-d]pyrimidine (3.2 g, 6.8 mmol) and NH$_4$Cl (3.20 g, 59.8 mmol) in a mixture of EtOH (320 mL) and H$_2$O (60 mL) was added Fe (3.20 g, 57.3 mmol) at 20° C. The mixture was stirred at 80° C. for 16 h. The mixture was concentrated under reduced pressure.

The residue was purified by chromatography on silica gel (eluent: Petroleum ether:EtOAc (DCM 10 v %) 100:0→50:50) to afford 8-chloro-2-(4-oxaspiro[2.5]octan-7-yl)-2,4,12,13-tetrahydro-11H-5,7-(azenometheno)dipyrazolo[3,4-b:5',1'-g][1]oxa[4,6,8]triazacycloundecine (1.5 g) of sufficient purity for the subsequent step. LC-MS (method B) (m/z)=402.1 (MH)$^+$ t$_R$=0.70 minutes.

A solution of NBS (1.24 g, 6.97 mmol) in THF (20 mL) was added dropwise to a solution of 8-chloro-2-(4-oxaspiro[2.5]octan-7-yl)-2,4,12,13-tetrahydro-11H-5,7-(azenometheno)dipyrazolo[3,4-b:5',1'-g][1]oxa[4,6,8]triazacycloundecine (1.4 g, 3.5 mmol) in THF (130 mL) at 25° C. The mixture was stirred for 1 h at 25° C. The mixture was concentrated under reduced pressure. The residue was diluted with EtOAc (20 mL). The organic phase was washed with brine (3×10 mL), dried, and concentrated under reduced pressure. The residue was purified by chromatography on silica gel (eluent: Petroleum ether:EtOAc (DCM 10 v %) 100:0→80:20) to afford 3-bromo-8-chloro-2-(4-oxaspiro[2.5]octan-7-yl)-2,4,12,13-tetrahydro-11H-5,7-(azenometheno)dipyrazolo[3,4-b:5',1'-g][1]oxa[4,6,8]triazacycloundecine (0.7 g) of sufficient purity for the subsequent step. 3-Bromo-8-chloro-2-(4-oxaspiro[2.5]octan-7-yl)-2,4,12,13-tetrahydro-11H-5,7-(azenometheno)dipyrazolo[3,4-b:5',1'-g][1]oxa[4,6,8]triazacycloundecine (0.7 g) was separated using preparative SFC (instrument: SFC150AP, column: DAICEL CHIRALPAK AD 250×30 mm, 10 μm, mobile phase: supercritical CO2/EtOH (0.1% NH$_3$·H$_2$O, v %)=40/60, flow rate: 100 mL/min, column temperature: 38° C., nozzle pressure: 100 bar, nozzle temperature: 60° C., evaporator temperature: 20° C., trimmer temperature: 25° C., wavelength: 220 nm) to afford (−)-(R) or (S)-3-bromo-8-chloro-2-(4-oxaspiro[2.5]octan-7-yl)-2,4,12,13-tetrahydro-11H5,7-(azenometheno)dipyrazolo[3,4-b:5',1'-g][1]oxa[4,6,8]triazacycloundecine (0.24 g). $^1$H NMR (CDCl$_3$, 400 MHz) δ8.71 (s, 1H), 7.02 (br s, 1H), 4.60-4.50 (m, 3H), 4.49-4.42 (m, 2H), 4.06-3.99 (m, 1H), 3.72-3.63 (m, 1H), 2.78-2.69 (m, 1H), 2.40-2.27 (m, 1H), 2.10-2.01 (m, 2H), 1.98-1.90 (m, 1H), 1.41-1.33 (m, 1H), 1.00-0.93 (m, 1H), 0.81-0.73 (m, 1H), 0.63-0.56 (m, 1H), 0.52-0.45 (m, 1H). LC-MS (method C) (m/z)=482.0 (MH)$^+$ t$_R$=1.68 minutes. Chiral analytical SFC conditions (instrument: Waters UPCC with PDA Detector, column: Chiralpak AD-3 50×4.6 mm I.D., 3 μm, mobile phase: A:

CO₂ B: ethanol (0.05% DEA), gradient: from 5% to 40% of B in 2 min and hold 40% for 1.2 min, then 5% of B for 0.8 min, flow rate: 4 mL/min, column temperature: 35° C., ABPR: 1500 psi, run time: 4 min, wavelength: 254 nm), ee>99%, $t_R$=1.18 minutes. $[\alpha]_D^{20}$=−48 (c=0.35 g/100 mL, CHCl₃).

and the corresponding enantiomer (+)-(R) or (S)-3-bromo-8-chloro-2-(4-oxaspiro[2.5]octan-7-yl)-2,4,12,13-tetrahydro-11H5,7-(azenometheno) dipyrazolo[3,4-b:5',1'-g][1]oxa[4,6,8]triazacycloundecine (0.21 g) ¹H NMR (CDCl₃, 400 MHz) δ 8.71 (s, 1H), 6.95 (br s, 1H), 4.61-4.50 (m, 3H), 4.48-4.43 (m, 2H), 4.06-3.98 (m, 1H), 3.72-3.64 (m, 1H), 2.78-2.69 (m, 1H), 2.40-2.27 (m, 1H), 2.10-2.01 (m, 2H), 1.98-1.90 (m, 1H), 1.41-1.33 (m, 1H), 1.00-0.92 (m, 1H), 0.81-0.74 (m, 1H), 0.63-0.56 (m, 1H), 0.52-0.44 (m, 1H). LC-MS (method C) (m/z)=482.0 (MH)⁺ $t_R$=1.68 minutes. Chiral analytical SFC conditions (instrument: Waters UPCC with PDA Detector, column: Chiralpak AD-3 50×4.6 mm I.D., 3 μm, mobile phase: A: CO₂ B: ethanol (0.05% DEA), gradient: from 5% to 40% of B in 2 min and hold 40% for 1.2 min, then 5% of B for 0.8 min, flow rate: 4 mL/min, column temperature: 35° C., ABPR: 1500 psi, run time: 4 min, wavelength: 254 nm), ee>99%, $t_R$=3.95 minutes. $[\alpha]_D^{20}$=+49.4 (c=0.35 g/100 mL, CHCl₃).

Compounds of the Invention

Example 1: 8-Chloro-2,3-dimethyl-2,4,12,13-tetrahydro-11H-5,7-(azenometheno)dipyrazolo[3,4-b:5', 1'-g][1]oxa[4,6,8]triazacycloundecine

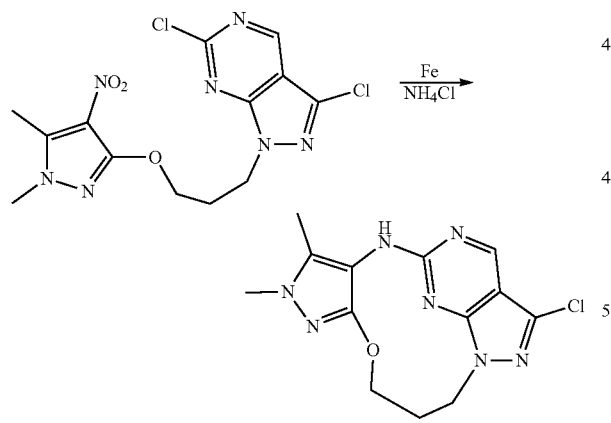

To a solution of 3,6-dichloro-1-(3-((1,5-dimethyl-4-nitro-1H-pyrazol-3-yl)oxy)propyl)-1H-pyrazolo[3,4-d]pyrimidine (90 mg, 0.23 mmol) in H₂O (1 mL) and EtOH (5 mL) was added Fe (65 mg, 1.17 mmol) and NH₄Cl (62 mg, 1.17 mmol). The reaction mixture was stirred at 100° C. for 16 h. The reaction mixture was filtered and concentrated under reduced pressure. The residue was purified by preparative HPLC ((Instrument: Gilson GX-281 Liquid Handler, Gilson 322 Pump, Gilson 156 UV Detector; Column: Phenomenex Gemini-NX C18 75×30 mm×3 μm; Mobile Phase: A: water (0.05% NH₃·H₂O v/v+10 mM NH₄HCO₃), Mobile phase B: MeCN; Gradient: B from 30% to 60% in 7 min then hold at 100% for 2 min; Flow Rate (mL/min): 25; Column temperature: 25° C.; Wavelength: 220 nm 254 nm) to afford the title compound (30 mg). ¹H NMR (CDCl₃, 400 MHz) δ 8.67 (s, 1H), 6.76 (br s, 1H), 4.54-4.42 (m, 4H), 3.70 (s, 3H), 2.29 (s, 3H), 1.99-1.95 (m, 2H). LC-MS (method C) (m/z)=320.2 (MH)⁺ $t_R$=1.67 minutes.

Example 2: 8-Chloro-3-methyl-2-(tetrahydro-2H-pyran-4-yl)-2,4,12,13-tetrahydro-11H-5,7-(azenometheno)dipyrazolo[3,4-b:5',1'-g][1]oxa[4,6,8]triazacycloundecine

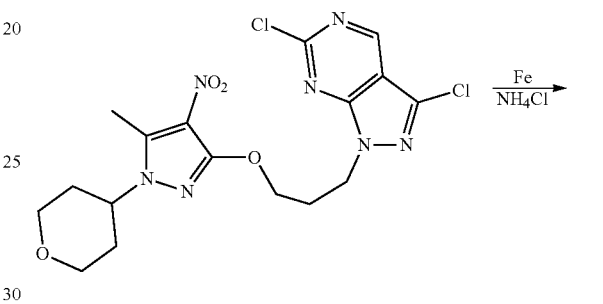

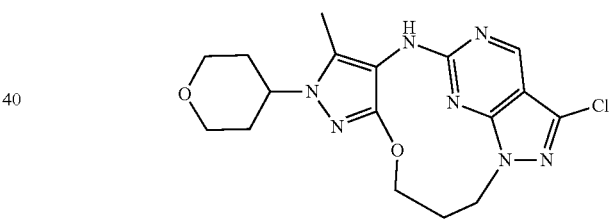

The compound was prepared in a manner similar to Example 1 using 3,6-dichloro-1-(3-((5-methyl-4-nitro-1-(tetrahydro-2H-pyran-4-yl)-1H-pyrazol-3-yl)oxy)propyl)-1H-pyrazolo[3,4-d]pyrimidine (840 mg, 1.84 mmol), Fe (514 mg, 9.20 mmol), and NH₄Cl (492 mg, 9.20 mmol) in EtOH (40 mL) and H₂O (4 mL) at 100° C. for 15 h, followed by work-up, and preparative HPLC (Instrument: Gilson GX-281 Liquid Handler, Gilson 322 Pump, Gilson 156 UV Detector; Column: Xtimate C18 150×40 mm×5 μm; Mobile Phase A: water (0.05% NH₃H₂O) Mobile phase B: MeCN; Gradient: B from 28% to 53% in 6 min then hold at 100% for 1 min Flow Rate (mL/min); Column temperature: 25° C.; Wavelength: 220 nm 254 nm) to afford the title compound. ¹H NMR (CDCl₃, 400 MHz) δ 8.65 (s, 1H), 6.85 (br s, 1H), 4.57-4.35 (m, 4H), 4.17-4.06 (m, 3H), 3.59-3.46 (m, 2H), 2.36-2.21 (m, 5H), 2.01-1.90 (m, 2H), 1.85-1.77 (m, 2H). LC-MS (method C) (m/z)=390.2 (MH)⁺ $t_R$=1.79 minutes.

Example 3: (R) or (S)-8-Chloro-3-methyl-2-(tetrahydro-2H-pyran-3-yl)-2,4,12,13-tetrahydro-11H-5,7-(azenometheno)dipyrazolo[3,4-b:5',1'-g][1]oxa[4,6,8]triazacycloundecine peak 1 and Example 4: (R) or (S)-8-Chloro-3-methyl-2-(tetrahydro-2H-pyran-3-yl)-2,4,12,13-tetrahydro-11H-5,7-(azenometheno)dipyrazolo[3,4-b:5',1'-g][1]oxa[4,6,8]triazacycloundecine peak 2

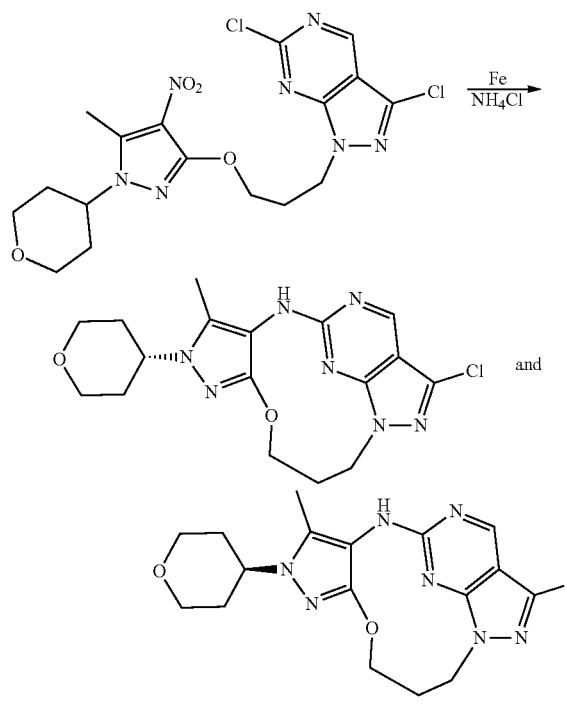

The racemic mixture of Example 3 and Example 4 was prepared in a manner similar to Example 1 using (±)-3,6-dichloro-1-(3-((5-methyl-4-nitro-1-(tetrahydro-2H-pyran-3-yl)-1H-pyrazol-3-yl)oxy)propyl)-1H-pyrazolo[3,4-d]pyrimidine (218 mg, 0.478 mmol), Fe (133 mg, 2.39 mmol) and NH$_4$Cl (128 mg, 2.39 mmol) in EtOH (17 mL) and H$_2$O ((1.7 mL) at 94° C. for 4 h, followed by work-up and purification by chromatography on silica gel (eluent: Heptane:EtOAc 80:20→10:90) to afford (±)-8-chloro-3-methyl-2-(tetrahydro-2H-pyran-3-yl)-2,4,12,13-tetrahydro-11H-5,7-(azenometheno)dipyrazolo[3,4-b:5',1'-g][1]oxa[4,6,8]triazacycloundecine (140 mg). The racemic mixture (140 mg) was separated into the two enantiomers by preparative chiral SFC (instrument: Berger Multigram II, column: Chiralpak-IA, 250 mm×20 mm, particle size 5 μm, mobile phase: CO$_2$/EtOH (96% containing 0.1% DEA, v/v)=60/40, flow rate 50 mL/min, column temperature: 35° C., pressure: 100 bar) to afford:

Example 3, Peak 1: (R) or (S)-8-chloro-3-methyl-2-(tetrahydro-2H-pyran-3-yl)-2,4,12,13-tetrahydro-11H-5,7-(azenometheno)dipyrazolo[3,4-b:5',1'-g][1]oxa[4,6,8]triazacycloundecine (35 mg). $^1$H NMR (600 MHz, CDCl$_3$) δ 8.66 (s, 1H), 6.52 (br s, 1H), 4.53-4.37 (m, 4H), 4.07 (tt, J=11.1, 4.4 Hz, 1H)), 3.98-3.91 (m, 2H), 3.69 (t, J=10.8 Hz, 1H), 3.48-3.40 (m, 1H), 2.28 (s, 3H), 2.28-2.18 (m, 1H), 2.09-2.04 (m, 1H), 2.00-1.88 (m, 2H), 1.86-1.78 (m, 2H). LC-MS (method E) (m/z)=390.4 (MH)$^+$ t$_R$=0.59 minutes.

Chiral analytical SFC conditions (instrument: Aurora SFC Fusion5/Agilent, column: Chiralpak-IA, 150×4.6 mm, 5 μm particle size, mobile phase; CO$_2$/EtOH (96% containing 0.1% DEA, v/v)=60/40, isocratic elution 7 minutes, flow rate 4 mL/min, column temperature 40° C., UV detection: 254 nm), ee>99%, t$_R$=1.92 minutes.

and the corresponding enantiomer

Example 4, Peak 2: Example 4: (R) or (S)-8-chloro-3-methyl-2-(tetrahydro-2H-pyran-3-yl)-2,4,12,13-tetrahydro-11H-5,7-(azenometheno)dipyrazolo[3,4-b:5',1'-g][1]oxa[4,6,8]triazacycloundecine (50 mg). $^1$H NMR (600 MHz, CDCl$_3$) δ 8.66 (s, 1H), 6.52 (br s, 1H), 4.53-4.37 (m, 4H), 4.07 (tt, J=11.1, 4.4 Hz, 1H)), 3.98-3.91 (m, 2H), 3.69 (t, J=10.8 Hz, 1H), 3.48-3.40 (m, 1H), 2.28 (s, 3H), 2.28-2.18 (m, 1H), 2.09-2.04 (m, 1H), 2.00-1.88 (m, 2H), 1.86-1.78 (m, 2H). LC-MS (method E) (m/z)=390.4 (MH)$^+$ t$_R$=0.59 minutes. Chiral analytical SFC conditions (instrument: Aurora SFC Fusion5/Agilent, column: Chiralpak-IA, 150×4.6 mm, 5 μm particle size, mobile phase; CO$_2$/EtOH (96% containing 0.1% DEA, v/v)=60/40, isocratic elution 7 minutes, flow rate 4 mL/min, column temperature 40° C., UV detection: 254 nm), ee>99%, t$_R$=2.53 minutes.

Example 5: 3-Methyl-2-(tetrahydro-2H-pyran-4-yl)-8-(trifluoromethyl)-2,4,12,13-tetrahydro-11H-5,7-(azenometheno)dipyrazolo[3,4-b:5',1'-g][1]oxa[4,6,8]triazacycloundecine

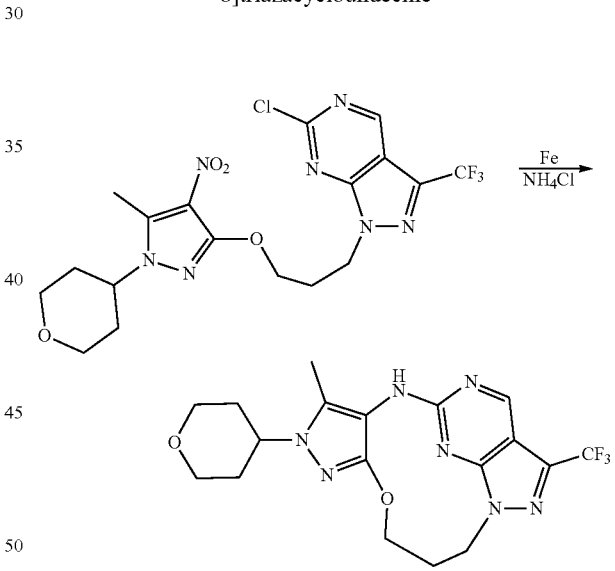

The compound was prepared in a manner similar to Example 1 using 6-chloro-1-(3-((5-methyl-4-nitro-1-(tetrahydro-2H-pyran-4-yl)-1H-pyrazol-3-yl)oxy)propyl)-3-(trifluoromethyl)-1H-pyrazolo[3,4-d]pyrimidine (95 mg, 0.19 mmol), Fe (54 mg, 0.97 mmol), and NH$_4$Cl (52 mg, 5 Eq, 0.97 mmol) in EtOH (15 mL) and H$_2$O (1.5 mL) at 85° C. for 72 h, followed by work-up, and purification by chromatography on silica gel (eluent: Heptane:EtOAc 80:20→10:90) to afford the title compound (42 mg). $^1$H NMR (CDCl$_3$, 600 MHz) δ 8.81 (s, 1H), 6.57 (br s, 1H), 4.60-4.42 (m, 4H), 4.17-4.06 (m, 3H), 3.52 (td, J=12.1, 2.1 Hz, 2H), 2.33-2.24 (m, 2H), 2.30 (s, 3H), 2.08-1.94 (m, 2H), 1.84-1.78 (m, 2H). $^{19}$F NMR (CDCl$_3$, 470 MHz) δ−61.5 (s). LC-MS (method E) (m/z)=424.4 (MH)$^+$ t$_R$=0.64 minutes.

Example 6: 8-Bromo-3-methyl-2-(tetrahydro-2H-pyran-4-yl)-2,4,12,13-tetrahydro-11H-5,7-(azenometheno)dipyrazolo[3,4-b:5',1'-g][1]oxa[4,6,8]triazacycloundecine

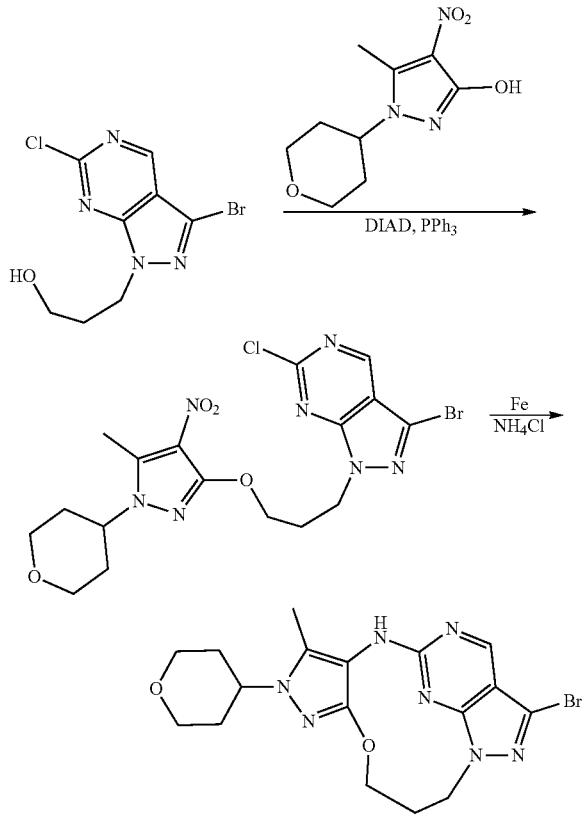

A solution of DIAD (87 μL, 0.45 mmol) in THF (5 mL) was cooled to 0° C. PPh₃ (on resin, ~3 mmol/g) (118 mg, 0.449 mmol)(employed 150 mg resin (~3 mmol/g)=0.449 mmol)), was added portionwise and the mixture was stirred for 10 minutes. 5-methyl-4-nitro-1-(tetrahydro-2H-pyran-4-yl)-1H-pyrazol-3-ol (60.0 mg, 0.264 mmol, prepared as previously described) was then added followed by a solution of 3-(3-bromo-6-chloro-1H-pyrazolo[3,4-d]pyrimidin-1-yl)propan-1-ol (77.0 mg, 0.26 mmol) in THF (1 mL). The cooling bath was removed and the reaction mixture was stirred for 2 h. The mixture was filtered while washing with THF, and the filtrate was concentrated to dryness under reduced pressure. The residue obtained was redissolved in ethanol (5 mL) and water (0.5 mL). Fe (73.7 mg, 1.32 mmol) and NH₄Cl (70.6 mg, 1.32 mmol) was added and the flask was briefly flushed with argon and stirred while heating to 90° C. for 2 h and then at 60° C. overnight. The reaction mixture was filtered while washing with EtOAc and the filtrate was concentrated to dryness under reduced pressure. The residue was purified by chromatography on silica gel (eluent: heptane:EtOAc (w. 1% MeOH) 100:0→10:90) to afford the title compound (32 mg). $^1$H NMR (CDCl₃, 600 MHz) δ 8.57 (s, 1H), 6.57 (br s, 1H), 4.60-4.34 (m, 4H), 4.17-4.00 (m, 3H), 3.51 (t, J=11.9, 2H), 2.36-2.19 (m, 5H), 2.02-1.86 (m, 2H), 1.85-1.74 (m, 2H). LC-MS (method E) (m/z)=420.3 (MH)⁺ $t_R$=0.56 minutes.

Example 7: 8-Cyclopropyl-3-methyl-2-(tetrahydro-2H-pyran-4-yl)-2,4,12,13-tetrahydro-11H5,7-(azenometheno)dipyrazolo[3,4-b:5',1'-g][1]oxa[4,6,8]triazacycloundecine

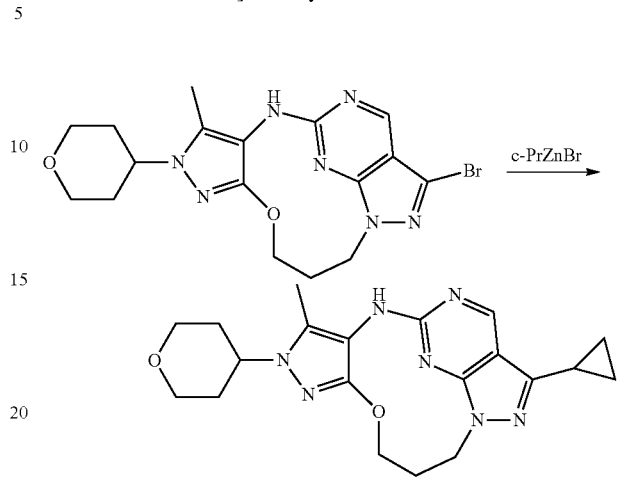

To a dry vial was added Example 6 (60 mg, 0.14 mmol) and the vial was evacuated and backfilled with argon. Toluene (0.25 mL) and THF (2.5 mL) were added and the mixture stirred for a few minutes before di-μ-iodobis(tri-t-butylphosphino)dipalladium(I) (18 mg, 0.021 mmol) was added. The mixture was stirred for an additional 2 minutes at which point cyclopropylzinc(II) bromide (0.5 M in THF) (1.1 mL, 0.55 mmol) was added in one portion. The reaction was stirred for 1 h at room temperature. The mixture was concentrated under reduced pressure. The residue was purified by chromatography on silica gel (eluent: heptane:EtOAc (w. 1% MeOH) 100:0→10:90) to afford the title compound (48 mg). $^1$H NMR (CDCl₃, 600 MHz) δ 8.97 (br s, 1H), 8.80 (s, 1H), 4.55-4.28 (m, 4H), 4.16-4.05 (m, 3H), 3.57-3.45 (m, 2H), 2.36 (s, 3H), 2.31-2.21 (m, 2H), 2.03 (tt, J=8.3, 5.0 Hz, 1H), 2.00-1.88 (m, 2H), 1.83-1.75 (m, 2H), 1.06-0.93 (m, 4H). LC-MS (method E) (m/z)=396.4 (MH)⁺ $t_R$=0.51 minutes.

Example 8: 3,8-Dimethyl-2-(tetrahydro-2H-pyran-4-yl)-2,4,12,13-tetrahydro-11H-5,7-(azenometheno)dipyrazolo[3,4-b:5',1'-g][1]oxa[4,6,8]triazacycloundecine

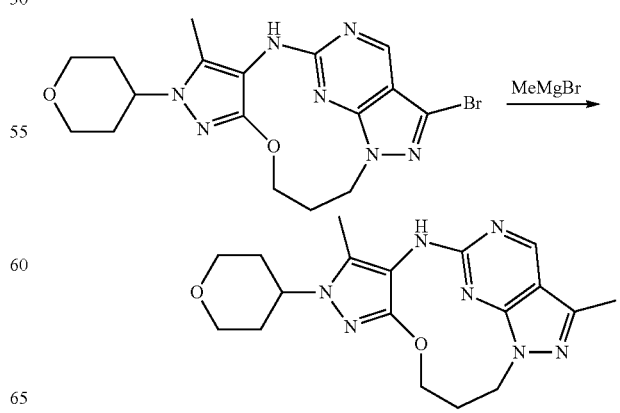

To a dry vial containing THF (2 mL) under argon atmosphere was added bromomethylmagnesium (3M in diethylether) (537 μL, 1.61 mmol) and zinc chloride (1.9M in THF) (1.02 mL, 1.93 mmol). The mixture was stirred for 5 minutes at room temperature which led to formation of a white precipitate. The solids were allowed to settle and the top solution (approx. 2 mL, clear solution) was taken out by syringe. The above prepared solution was added to a second vial containing Example 6 (70.0 mg, 0.161 mmol) and di-μ-iodobis(tri-t-butylphosphino)dipalladium(I) (17.6 mg, 0.0201 mmol) in a mixture of toluene (0.4 mL) and THF (10 mL). The mixture was stirred at room temperature overnight. The reaction mixture was concentrated under reduced pressure. The residue was purified by chromatography on silica gel (eluent: heptane:EtOAc (w. 2% MeOH) 90:10→0:100) to afford the title compound (13 mg). $^1$H NMR (CDCl$_3$, 600 MHz) δ 8.71 (s, 1H), 4.52-4.34 (m, 4H), 4.15-4.09 (m, 2H), 3.52 (t, J=12.1 Hz, 2H), 2.46 (s, 3H), 2.33 (s, 3H), 2.32-2.23 (m, 2H), 2.01-1.90 (m, 2H), 1.84-1.77 (m, 2H). LC-MS (method E) (m/z)=370.4 (MH)$^+$ $t_R$=0.41 minutes.

Example 9: 3-Methyl-2-(tetrahydro-2H-pyran-4-yl)-2,4,12,13-tetrahydro-11H-5,7-(azenometheno)dipyrazolo[3,4-b:5',1'-g][1]oxa[4,6,8]triazacycloundecine-8-carbonitrile

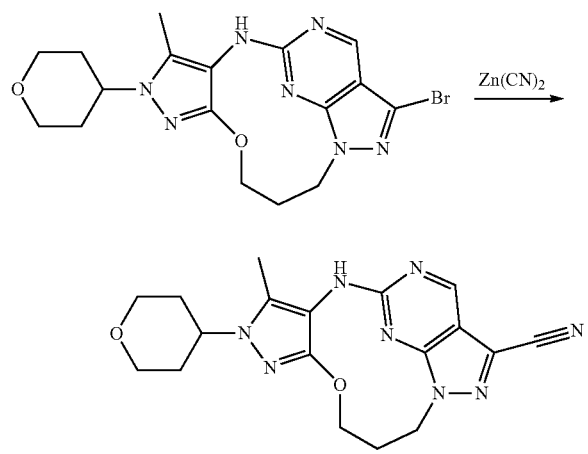

To a dry vial fitted with a stirbar under an atmosphere of argon was added Example 6 (15 mg, 0.035 mmol), Zinc cyanide (4.1 mg, 0.035 mmol) and methanesulfonato[9,9-dimethyl-4,5-bis(diphenylphosphino)xanthene][2'-amino-1,1'-biphenyl]palladium(II) dichloromethane adduct (2.5 mg, 0.0026 mmol). The vial was capped and the atmosphere was exchanged for argon before DMA (0.35 mL) was added. The solution was purged with argon for 1 minute before DIPEA (1.8 μL, 0.010 mmol) was added. The mixture was stirred at 85° C. overnight. The reaction mixture was concentrated under reduced pressure. The residue was purified by chromatography on silica gel (eluent: heptane:EtOAc (w. 2% MeOH) 90:10→0:100) to afford the title compound (2.3 mg). $^1$H NMR (CDCl$_3$, 600 MHz) δ8.84 (s, 1H), 6.69 (s, 1H), 4.59-4.42 (m, 4H), 4.15-4.07 (m, 3H), 3.56-3.48 (m, 2H), 2.32-2.23 (m, 5H), 2.07-1.91 (m, 2H), 1.84-1.77 (m, 2H). LC-MS (method F) (m/z)=381.2 (MH)$^+$ $t_R$=0.60 minutes.

Example 10: 8-Chloro-3-cyclopropyl-2-(tetrahydro-2H-pyran-4-yl)-2,4,12,13-tetrahydro-11H5,7-(azenometheno)dipyrazolo[3,4-b:5',1'-g][1]oxa[4,6,8]triazacycloundecine

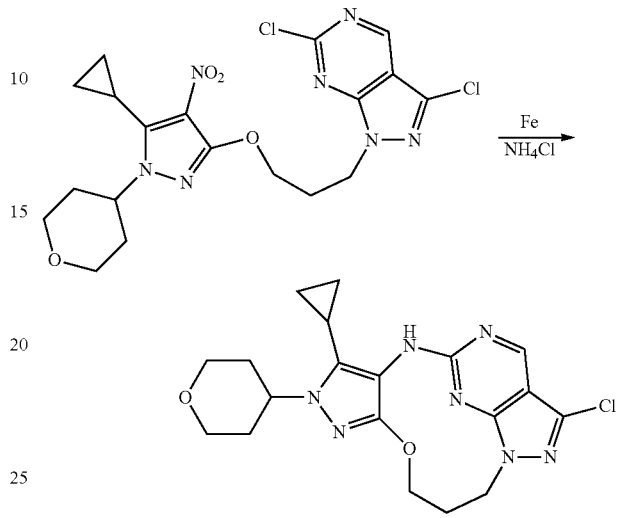

The compound was prepared in a manner similar to Example 1 using of 3,6-dichloro-1-(3-((5-cyclopropyl-4-nitro-1-(tetrahydro-2H-pyran-4-yl)-1H-pyrazol-3-yl)oxy)propyl)-1H-pyrazolo[3,4-d]pyrimidine (140 mg, 0.29 mmol), Fe (81 mg, 1.5 mmol), and NH$_4$Cl (78 mg, 1.5 mmol) in EtOH (70 mL) and H$_2$O (10 mL) at 100° C. for 16 h, followed by work-up, and preparative HPLC ((Instrument: Gilson GX-281 Liquid Handler, Gilson 322 Pump, Gilson 156 UV Detector; Column: Boston Prime C18 150× 30 mm×5 μm; Mobile Phase: A: water (0.05% NH$_3$·H$_2$O+10 mM NH$_4$HCO$_3$ v/v), Mobile phase B: MeCN; Gradient: B from 40% to 70% in 7 min then hold at 100% for 2 min; Flow Rate (mL/min): 25; Column temperature: 35° C.; Wavelength: 220 nm 254 nm) to afford the title compound (50 mg). $^1$H NMR (CDCl$_3$, 400 MHz) δ 8.66 (s, 1H), 6.76 (br s, 1H), 4.56-4.39 (m, 5H), 4.13 (dd, J=3.6, 10.8 Hz, 2H), 3.54 (t, J=10.4 Hz, 2H), 2.36-2.23 (m, 2H), 2.04-1.93 (m, 2H), 1.79 (dd, J=2.0, 12.8 Hz, 2H), 1.70-1.63 (m, 1H), 1.12-1.04 (m, 2H), 0.87-0.79 (m, 2H). LC-MS (method C) (m/z)=416.1 (MH)$^+$ $t_R$=1.56 minutes.

Example 11: 2-((2-Oxabicyclo[2.1.1]hexan-1-yl)methyl)-8-chloro-3-methyl-2,4,12,13-tetrahydro-11H-5,7-(azenometheno)dipyrazolo[3,4-b:5',1'-g][1]oxa[4,6,8]triazacycloundecine

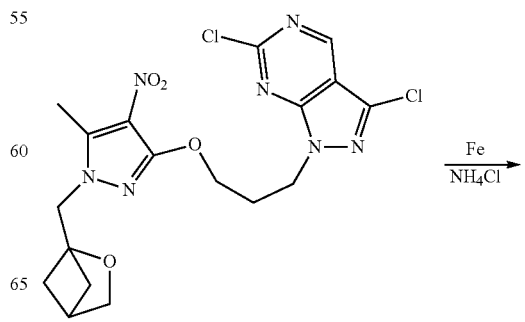

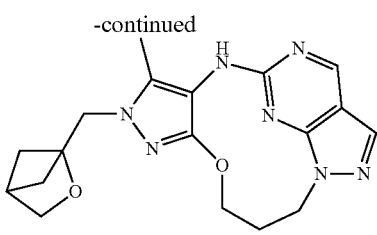

The compound was prepared in a manner similar to Example 1 using 1-(3-((1-((2-oxabicyclo[2.1.1]hexan-1-yl)methyl)-5-methyl-4-nitro-1H-pyrazol-3-yl)oxy)propyl)-3,6-dichloro-1H-pyrazolo[3,4-d]pyrimidine (230 mg, 0.49 mmol), Fe (137 mg, 2.5 mmol), and NH$_4$Cl (131 mg, 2.5 mmol) in EtOH (93 mL) and H$_2$O (13 mL) at 100° C. for 16 h, followed by work-up, and preparative HPLC (Instrument: Gilson GX-215 Liquid Handler, SHIMADZU LC-20AP, SHIMADZU SPD-20A; Column: Welch Xtimate C18 150×30 mm×5 μm; Mobile Phase A: water (0.05% NH$_3$H$_2$O+10 mM NH$_4$HCO$_3$) Mobile phase B: MeCN; Gradient: B from 27% to 57% in 9 min then hold at 100% for 3 min Flow Rate (mL/min): 30; Column temperature: 30° C.; Wavelength: 220 nm 254 nm) to afford the title compound (37 mg). $^1$H NMR (CDCl$_3$, 400 MHz) δ 8.66 (s, 1H), 6.68 (br s, 1H), 4.51-4.38 (m, 4H), 4.27 (s, 2H), 3.77 (s, 2H), 2.89 (t, J=3.2 Hz, 1H), 2.31 (s, 3H), 2.01-1.96 (m, 2H), 1.82-1.75 (m, 2H), 1.51-1.43 (m, 2H). LC-MS (method C) (m/z)=402.1 (MH)$^+$ t$_R$=1.45 minutes.

Example 12: 8-Chloro-3-methyl-2-((3-methyl-oxetan-3-yl)methyl)-2,4,12,13-tetrahydro-11H5,7-(azenometheno)dipyrazolo[3,4-b:5',1'-g][1]oxa[4,6,8]triazacycloundecine

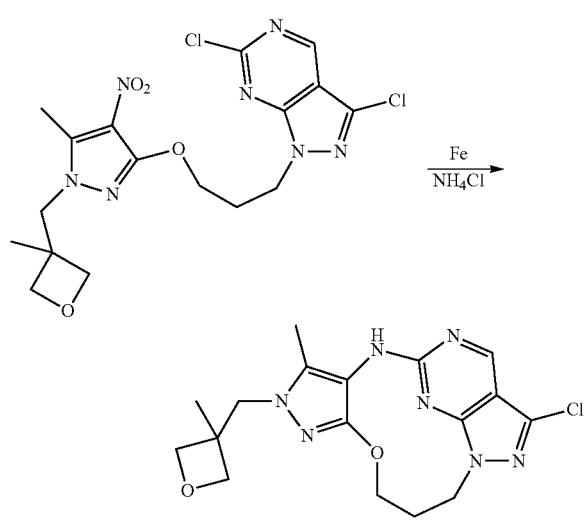

The compound was prepared in a manner similar to Example 1 using 3,6-dichloro-1-(3-((5-methyl-1-((3-methyloxetan-3-yl)methyl)-4-nitro-1H-pyrazol-3-yl)oxy)propyl)-1H-pyrazolo[3,4-d]pyrimidine (50 mg, 0.11 mmol), Fe (31 mg, 0.55 mmol), and NH$_4$Cl (29 mg, 0.55 mmol) in EtOH (10 mL) and H$_2$O (10 mL) at 80° C. for 5 h, followed by work-up, and preparative HPLC (Instrument: Gilson GX-281 Liquid Handler, Gilson 322 Pump, Gilson 156 UV; Detector Column: Boston Prime C18 150×30 mm×5 μm; Mobile Phase A: water (0.05% NH$_3$H$_2$O+10 mM NH$_4$HCO$_3$) Mobile phase B: MeCN; Gradient: B from 30% to 60% in 7 min then hold at 100% for 2 min; Flow Rate (mL/min): 25; Column temperature: 30° C.; Wavelength: 220 nm 254 nm) to afford the title compound (15 mg). $^1$H NMR (CDCl$_3$, 400 MHz) δ8.71 (br s, 1H), 7.30 (s, 1H), 4.78 (d, J=6.0 Hz, 2H), 4.46-4.39 (m, 6H), 4.10 (s, 2H), 2.28 (s, 3H), 2.02-1.93 (m, 2H), 1.29 (s, 3H). LCMS (method G) (m/z)=390.3 (MH)$^+$ t$_R$=1.75 minutes.

Example 13: 8-Chloro-3-(methyl-d$_3$)-2-(tetrahydro-2H-pyran-4-yl)-2,4,12,13-tetrahydro-11H5,7-(azenometheno)dipyrazolo[3,4-b:5',1'-g][1]oxa[4,6,8]triazacycloundecine

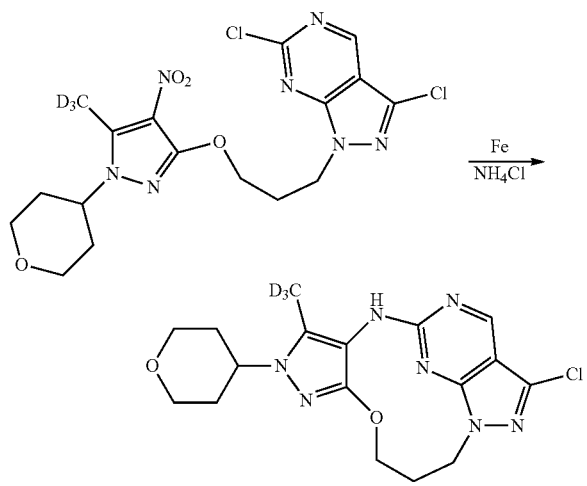

3,6-Dichloro-1-(3-((5-(methyl-d$_3$)-4-nitro-1-(tetrahydro-2H-pyran-4-yl)-1H-pyrazol-3-yl)oxy)propyl)-1H-pyrazolo[3,4-d]pyrimidine (100 mg, 0.217 mmol) was dissolved in Ethanol (15 mL) and deuterium oxide (1.5 mL) in a vial. Fe (48.5 mg, 0.869 mmol) and NH$_4$Cl (46.5 mg, 0.869 mmol) was added and the flask was thoroughly flushed with argon and stirred while heating to 85° C. overnight. The reaction mixture was cooled and filtered while washing with EtOAc and DCM and the filtrate was concentrated under reduced pressure. The residue was purified by chromatography on silica gel (eluent: heptane:EtOAc (w. 2% MeOH) 90:10→0:100) to afford the title compound (49.7 mg). $^1$H NMR (CDCl$_3$, 600 MHz) δ 8.66 (s, 1H), 6.54 (s, 1H), 4.53-4.38 (m, 4H), 4.14-4.07 (m, 3H), 3.52 (td, J=12.1, 2.1 Hz, 2H), 2.32-2.23 (m, 2H), 2.02-1.87 (m, 2H), 1.84-1.77 (m, 2H). LC-MS (method F) (m/z)=393.2 (MH)$^+$ t$_R$=0.55 minutes Example 14: 8-Chloro-3-methyl-2-(3-methyloxetan-3-yl)-2,4,12,13-tetrahydro-11H-5,7-(azenometheno)dipyrazolo[3,4-b:5',1'-g][1]oxa[4,6,8]triazacycloundecine

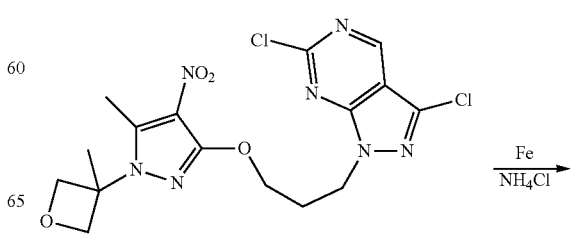

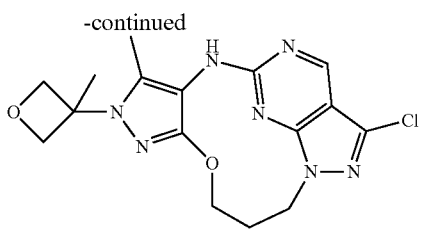

The compound was prepared in a manner similar to Example 1 using 3,6-dichloro-1-(3-((5-methyl-1-(3-methyloxetan-3-yl)-4-nitro-1H-pyrazol-3-yl)oxy)propyl)-1H-pyrazolo[3,4-d]pyrimidine (190 mg, 0.43 mmol), Fe (120 mg, 2.15 mmol), and NH$_4$Cl (115 mg, 2.15 mmol) in EtOH (40 mL) and H$_2$O (40 mL) at 80° C. for 16 h, followed by work-up, and preparative HPLC (Instrument: Gilson GX-281 Liquid Handler, Gilson 322 Pump, Gilson 156; UV Detector; Column: Boston Prime C18 150×30 mm×5 μm; Mobile Phase A: water (0.05% NH$_3$·H$_2$O+10 mM NH$_4$HCO$_3$) Mobile phase B: MeCN; Gradient: B from 30% to 60% in 7 min then hold at 100% for 2 min; Flow Rate (mL/min): 25; Column temperature: 30° C.; Wavelength: 220 nm 254 nm) to afford the title compound (51 mg). $^1$H NMR (CDCl$_3$, 400 MHz) δ 8.67 (s, 1H), 6.55 (s, 1H), 5.25 (d, J=6.4 Hz, 2H), 4.59 (d, J=6.8 Hz, 2H), 4.48-4.43 (m, 4H), 2.15 (s, 3H), 2.01-1.91 (m, 2H), 1.80 (s, 3H). LC-MS (method C) (m/z)=376.1 (MH)$^+$ t$_R$=1.37 minutes.

Example 15: 8-Chloro-3-(methyl-d$_3$)-2-(tetrahydro-2H-pyran-4-yl-4-d)-2,4,12,13-tetrahydro-11H-5,7-(azenometheno)dipyrazolo[3,4-b:5',1'-g][1]oxa[4,6,8]triazacycloundecine

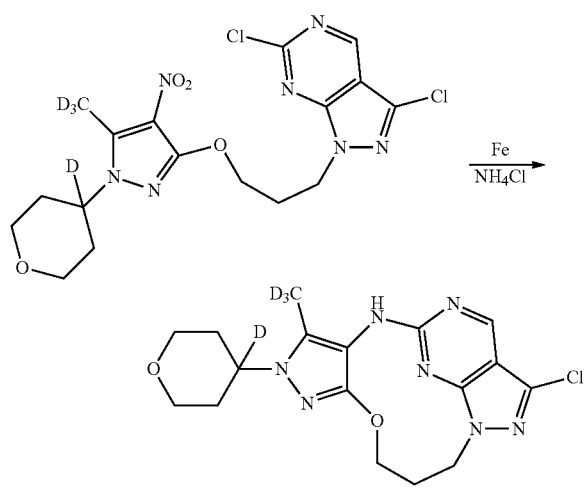

The compound was prepared in a manner similar to Example 1 using 3,6-dichloro-1-(3-((5-(methyl-d$_3$)-4-nitro-1-(tetrahydro-2H-pyran-4-yl-4-d)-1H-pyrazol-3-yl)oxy)propyl)-1H-pyrazolo[3,4-d]pyrimidine (520 mg, 1.13 mmol), Fe (315 mg, 5.65 mmol), and NH$_4$Cl (302 mg, 5.65 mmol) in EtOH (100 mL) and H$_2$O (100 mL) at 90° C. for 16 h, followed by work-up, and preparative HPLC (Instrument: Gilson GX-281 Liquid Handler, Gilson 322 Pump, Gilson 156 UV Detector; Column: Boston Prime C18 150×30 mm×5 μm; Mobile Phase: A: water (0.05% NH$_3$·H$_2$O+10 mM NH$_4$HCO$_3$ v/v), Mobile phase B: MeCN; Gradient: B from 30% to 60% in 7 min then hold at 100% for 2 min; Flow Rate (mL/min): 25; Column temperature: 35° C.; Wavelength: 220 nm 254 nm) to afford the title compound (250 mg). $^1$H NMR (CDCl$_3$, 400 MHz) δ8.66 (s, 1H), 6.74 (s, 1H), 4.55-4.37 (m, 4H), 4.12 (dd, J=4.0, 11.2 Hz, 2H), 3.58-3.47 (m, 2H), 2.35-2.23 (m, 2H), 2.01-1.88 (m, 2H), 1.84-1.77 (m, 2H). LC-MS (method G) (m/z)=394.2 (MH)$^+$ t$_R$=1.39 minutes.

Example 16: 8-Chloro-3-(1-fluorocyclopropyl)-2-(tetrahydro-2H-pyran-4-yl)-2,4,12,13-tetrahydro-11H-5,7-(azenometheno)dipyrazolo[3,4-b:5',1'-g][1]oxa[4,6,8]triazacycloundecine

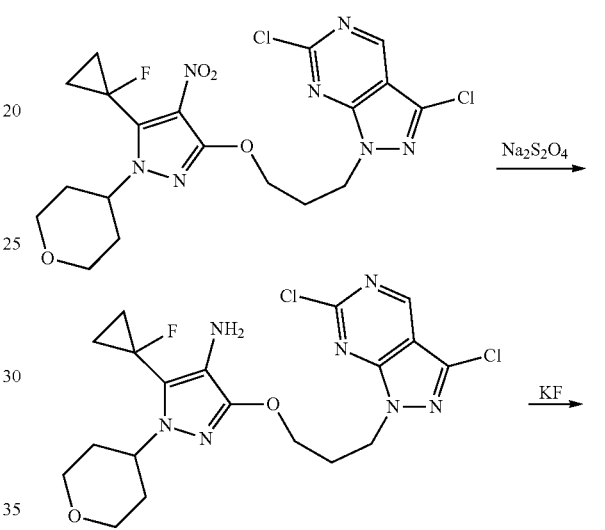

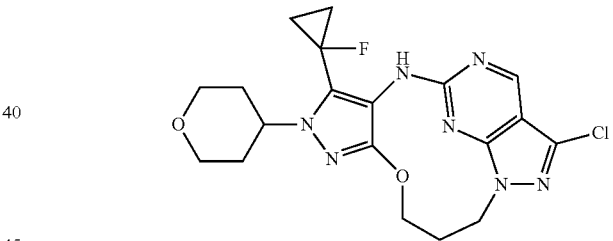

To a flask was added potassium hydrogen carbonate (120 mg, 1.20 mmol) and water (6.4 mL). The vial was cooled to 0° C. and the solution was purged with argon before sodium dithionite (120 mg, 0.688 mmol) was added. The solution was purged with argon for 5 minutes before 3,6-dichloro-1-(3-((5-(1-fluorocyclopropyl)-4-nitro-1-(tetrahydro-2H-pyran-4-yl)-1H-pyrazol-3-yl)oxy)propyl)-1H-pyrazolo[3,4-d]pyrimidine (80.0 mg, 0.160 mmol) was added along with THF (6.4 mL). The reaction mixture was stirred at 0° C. for 2.5 h, and then from 0-10° C. for an additional 1 h. The mixture was diluted with water (10 mL) and EtOAc (20 mL). The phases were separated, and the aqueous phase was extracted with EtOAc (3×20 mL). The combined organics washed with brine, dried over sodium sulfate, filtered, and concentrated under reduced pressure. The residue was transferred to a dry vial and DMSO (7 mL), 1,4-Dioxane (7 mL) and potassium fluoride (37.2 mg, 0.640 mmol) were added. The vial was flushed with argon, capped and stirred at 77° C. for 16 h. The reaction mixture was diluted with water (5 mL) and extracted with EtOAc (3×20 mL). The combined organics were washed with brine repeatedly, dried over Example 17: 8-Chloro-3-ethyl-2-(tetrahydro-2H-pyran-4-yl)-2,4,12,13-tetrahydro-11H-5,7-(azenometheno)dipyrazolo[3,4-b:5',1'-g][1]oxa[4,6,8]triazacycloundecine

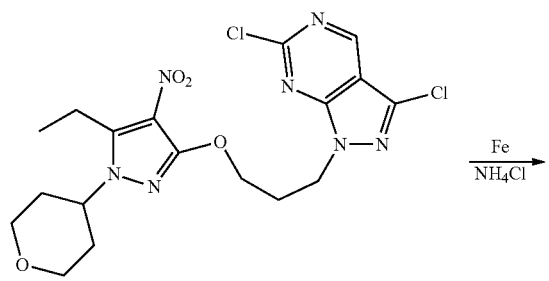

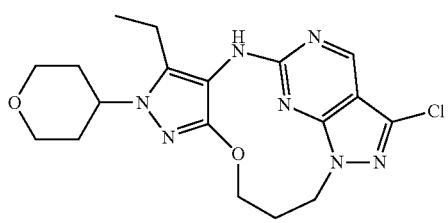

The compound was prepared in a manner similar to Example 1 using 3,6-dichloro-1-(3-((5-ethyl-4-nitro-1-(tetrahydro-2H-pyran-4-yl)-1H-pyrazol-3-yl)oxy)propyl)-1H-pyrazolo[3,4-d]pyrimidine (50 mg, 0.11 mmol), Fe (30 mg, 0.53 mmol), and NH$_4$Cl (28 mg, 0.53 mmol) in EtOH (2 mL) and H$_2$O (0.2 mL) at 100° C. for 3 h, followed by work-up, and preparative HPLC (Column: YMC-Actus Triart C18 ExRS, 30×150 mm, particle size 5 µm, mobile phase A: Water(10 mmol/L NH$_4$HCO$_3$), mobile phase B: ACN; flow rate: 25 mL/min, gradient: 34% B to 50% B in 7 minutes, 50% B; wave length: 254/220 nm) to afford the title compound (15 mg). $^1$H NMR (CDCl$_3$, 300 MHz) δ 8.67 (s, 1H), 6.93 (s, 1H), 4.51-4.43 (m, 4H), 4.17-4.07 (m, 3H), 3.61-3.50 (m, 2H), 2.74 (q, J=7.6 Hz, 2H), 2.35 (qd, J=12.5, 4.6 Hz, 2H), 2.08-1.92 (m, 2H), 1.92-1.71 (m, 2H), 1.28 (t, J=7.6 Hz, 3H). LC-MS (method H) (m/z)=404.2 (MH)$^+$ t$_R$=1.28 minutes.

Example 18 (+)-8-Chloro-3-methyl-2-((2R,4R)-or-(2S,4S)-2-methyltetrahydro-2H-pyran-4-yl)-2,4,12,13-tetrahydro-11H-5,7-(azenometheno)dipyrazolo[3,4-b:5',1'-g][1]oxa[4,6,8]triazacycloundecine and Example 19: (−)-8-Chloro-3-methyl-2-((2R,4R)-or-(2S,4S)-2-methyltetrahydro-2H-pyran-4-yl)-2,4,12,13-tetrahydro-11H-5,7-(azenometheno)dipyrazolo[3,4-b:5',1'-g][1]oxa[4,6,8]triazacycloundecine

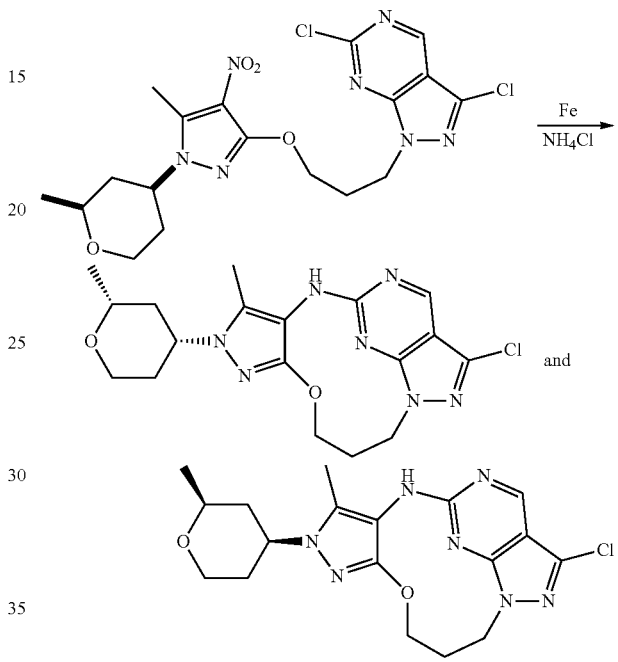

The racemic mixture of Example 18 and Example 19 was prepared in a manner similar to Example 1 using cis-3,6-dichloro-1-(3-((5-methyl-1-(2-methyltetrahydro-2H-pyran-4-yl)-4-nitro-1H-pyrazol-3-yl)oxy)propyl)-1H-pyrazolo[3,4-d]pyrimidine (500 mg, 1.1 mmol), Fe (297 mg, 5.32 mmol), and NH$_4$Cl (284 mg, 5.32 mmol) in EtOH (30 mL) and H$_2$O (5 mL) at 80° C. for 15 h, followed by work-up and purification by chromatography on silica gel (eluent: Petroleum ether:EtOAc 100:0→30:70) to afford 8-chloro-3-methyl-2-((2R,4R and 2S,4S)-2-methyltetrahydro-2H-pyran-4-yl)-2,4,12,13-tetrahydro-11H-5,7-(azenometheno)dipyrazolo[3,4-b:5',1'-g][1]oxa[4,6,8]triazacycloundecine (350 mg). The racemic mixture (350 mg) was separated into the two enantiomers by preparative chiral SFC (instrument: Berger MultiGram II, column: DAICEL CHIRALPAK AS 250×30 mm, particle size 10 µm, mobile phase: supercritical CO$_2$/MeOH (0.1% NH$_3$·H$_2$O, v %)=70/30, flow rate: 80 mL/min, column temperature: 38° C., nozzle pressure: 100 bar, nozzle temperature: 60° C., evaporator temperature: 20° C., trimmer temperature: 25° C., wavelength: 220 nm) to afford:

Example 18 (+)-8-Chloro-3-methyl-2-((2R,4R)-or-(2S,4S)-2-methyltetrahydro-2H-pyran-4-yl)-2,4,12,13-tetrahydro-11H-5,7-(azenometheno)dipyrazolo[3,4-b:5',1'-g][1]oxa[4,6,8]triazacycloundecine (70 mg). $^1$H NMR (CDCl$_3$, 400 MHz) δ 8.68 (s, 1H), 6.70 (br s, 1H), 4.59-4.36 (m, 4H), 4.23-4.04 (m, 2H), 3.66-3.48 (m, 2H), 2.30 (s, 3H), 2.27-2.16 (m, 1H), 2.07-1.89 (m, 3H), 1.88-1.82 (m, 1H), 1.81-1.76 (m, 1H), 1.27 (d, J=6.4 Hz, 3H). LC-MS (method C)

(m/z)=404.1 (MH)+ $t_R$=1.46 minutes. Chiral analytical SFC (instrument: Waters UPCC with PDA Detector, column: Chiralpak AS-3 150×4.6 mm I.D., particle size 3 μm, mobile phase: A: $CO_2$ B: methanol (0.05% DEA), gradient: from 5% to 40% of B in 5 min and hold 40% for 2.5 min, then 5% of B for 2.5 min, flow rate: 2.5 mL/min, column temperature: 35° C., ABPR: 1500 psi, run time: 10 min, wavelength: 220 nm), ee=>99%, $t_R$=4.05 minutes. $[\alpha]_D^{20}$=+16 (c=0.1 g/100 mL, $CHCl_3$) and the corresponding enantiomer Example 19: (−)-8-Chloro-3-methyl-2-((2R,4R)-or-(2S,4S)-2-methyltetrahydro-2H-pyran-4-yl)-2,4,12,13-tetrahydro-11H-5,7-(azenometheno)dipyrazolo[3,4-b:5',1'-g][1]oxa[4,6,8]triazacycloundecine (80 mg). $^1$H NMR ($CDCl_3$, 400 MHz) δ 8.67 (s, 1H), 6.69 (br s, 1H), 4.64-4.31 (m, 4H), 4.21-4.04 (m, 2H), 3.66-3.47 (m, 2H), 2.30 (s, 3H), 2.28-2.15 (m, 1H), 2.07-1.89 (m, 3H), 1.88-1.82 (m, 1H), 1.80-1.76 (m, 1H), 1.27 (d, J=6.0 Hz, 3H). LC-MS (method C) (m/z)=404.2 (MH)+ $t_R$=1.46 minutes. Chiral analytical SFC (instrument: Waters UPCC with PDA Detector, column: Chiralpak AS-3 150×4.6 mm I.D., particle size 3 μm, mobile phase: A: $CO_2$ B: methanol (0.05% DEA), gradient: from 5% to 40% of B in 5 min and hold 40% for 2.5 min, then 5% of B for 2.5 min, flow rate: 2.5 mL/min, column temperature: 35° C., ABPR: 1500 psi, run time: 10 min, wavelength: 220 nm), ee=99%, $t_R$=4.34 minutes. $[\alpha]^{2o}$=−17.3 (c=0.15 g/100 mL, $CHCl_3$).

Example 20: 8-Chloro-3-methyl-2-(tetrahydro-2H-pyran-4-yl)-2,4,12,13-tetrahydro-11H-5,7-(azenometheno)dipyrazolo[3,4-b:5',1'-g][1]oxa[4,6,8]triazacycloundecine-11,11,12,12,13,13-$d_6$

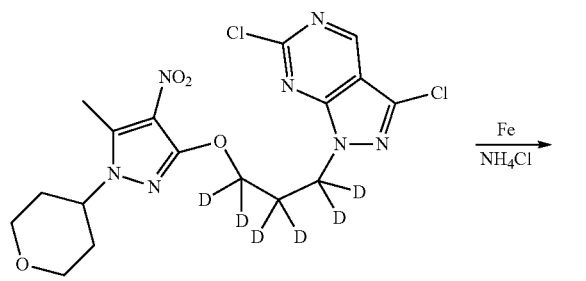

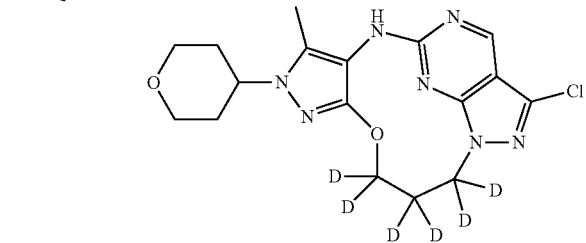

The compound was prepared in a manner similar to Example 1 using 3,6-dichloro-1-(3-((5-methyl-4-nitro-1-(tetrahydro-2H-pyran-4-yl)-1H-pyrazol-3-yl)oxy)propyl-1,1,2,2,3,3-$d_6$)-1H-pyrazolo[3,4-d]pyrimidine (270 mg, 0.584 mmol), Fe (163 mg, 2.92 mmol), and $NH_4Cl$ (156 mg, 2.92 mmol) in EtOH (27 mL) and $D_2O$ (2.7 mL) at 100° C. for 16 h, followed by work-up, and preparative HPLC ((instrument: waters sample manager 2767, waters 2545 pump, waters UV Detector 2545, Column: YMC-Actus Triart C18 ExRS, 30×150 mm, particle size 5 μm, mobile phase A: water, mobile phase B: ACN, gradient: B from 28% to 41% in 9 min, flow rate: 25 mL/min, column temperature: 30° C., wavelength: 220 nm, 254 nm) to afford the title compound (112 mg). $^1$H NMR (DMSO-$d_6$, 300 MHz) δ 9.37 (s, 1H), 8.78 (s, 1H), 4.30-4.22 (m, 1H), 3.98-3.92 (m, 2H), 3.50-3.41 (m, 2H), 2.26 (s, 3H), 2.05-1.90 (m, 2H), 1.76-1.71 (m, 2H). LC-MS (method H) (m/z)=396.2 (MH)+ $t_R$=1.15 minutes.

Example 21 8-Chloro-3-methyl-2-((3R,4S) or (3S,4R) or (3S,4S) or (3R,4R)-3-methyltetrahydro-2H-pyran-4-yl)-2,4,12,13-tetrahydro-11H-5,7-(azenometheno)dipyrazolo[3,4-b:5',1'-g][1]oxa[4,6,8] triazacycloundecine peak 1 and Example 22 8-Chloro-3-methyl-2-((3R,4S) or (3S,4R) or (3S,4S) or (3R,4R)-3-methyltetrahydro-2H-pyran-4-yl)-2,4,12,13-tetrahydro-11H-5,7-(azenometheno)dipyrazolo[3,4-b:5',1'-g][1]oxa[4,6,8] triazacycloundecine peak 3 and Example 23 8-Chloro-3-methyl-2-((3R,4S) or (3S,4R) or (3S,4S) or (3R,4R)-3-methyltetrahydro-2H-pyran-4-yl)-2,4,12,13-tetrahydro-11H-5,7-(azenometheno)dipyrazolo[3,4-b:5',1'-g][1]oxa[4,6,8] triazacycloundecine peak 4 and Example 24 8-Chloro-3-methyl-2-((3R,4S) or (3S,4R) or (3S,4S) or (3R,4R)-3-methyltetrahydro-2H-pyran-4-yl)-2,4,12,13-tetrahydro-11H-5,7-(azenometheno)dipyrazolo[3,4-b:5',1'-g][1]oxa[4,6,8] triazacycloundecine peak 2

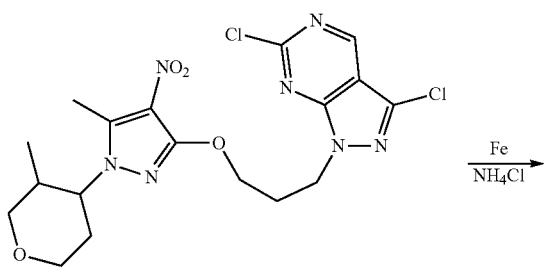

-continued

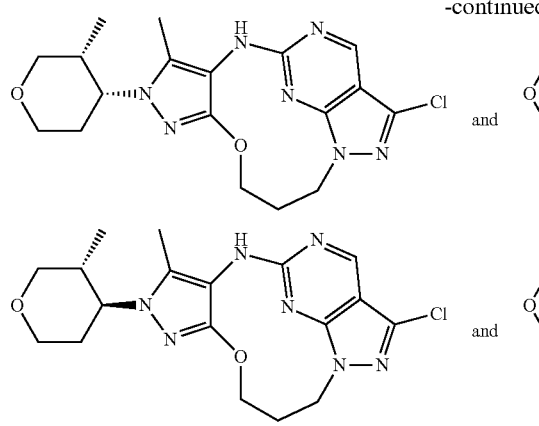 and 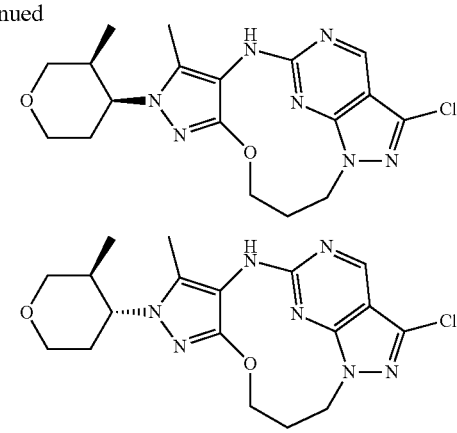

The mixture of Example 21, Example 22, Example 23, and Example 24 was prepared in a manner similar to Example 1 using 3,6-dichloro-1-(3-((5-methyl-1-(3-methyltetrahydro-2H-pyran-4-yl)-4-nitro-1H-pyrazol-3-yl)oxy)propyl)-1H-pyrazolo[3,4-d]pyrimidine (1.1 g, 2.34 mmol), Fe (660 mg, 11.82 mmol), and $NH_4Cl$ (625 mg, 11.69 mmol) in EtOH (40 mL) and $H_2O$ (20 mL) at 80° C. for 16 h, followed by work-up and purification by chromatography on silica gel (eluent: Petroleum ether:EtOAc 100:0→0:100) to afford 8-chloro-3-methyl-2-(3-methyltetrahydro-2H-pyran-4-yl)-2,4,12,13-tetrahydro-11H-5,7-(azenometheno)dipyrazolo[3,4-b:5',1'-g][1]oxa[4,6,8]triazacycloundecine (590 mg). The mixture (580 mg) was separated into the four isomers by preparative chiral SFC (instrument: Berger MultiGram II, column: DAICEL CHIRALPAK AD 250×30 mm, 10 μm, mobile phase: supercritical $CO_2$/IPA (0.1% $NH_3·H_2O$, v %)=65/35, flow rate: 80 mL/min, column temperature: 38° C., nozzle pressure: 100 bar, nozzle temperature: 60° C., evaporator temperature: 20° C., trimmer temperature: 25° C., wavelength: 220 nm) to afford:

Example 21 8-Chloro-3-methyl-2-((3R,4S) or (3S,4R) or (3S,4S) or (3R,4R)-3-methyltetrahydro-2H-pyran-4-yl)-2,4,12,13-tetrahydro-11H-5,7-(azenometheno)dipyrazolo[3,4-b:5',1'-g][1]oxa[4,6,8]triazacycloundecine peak 1 (100 mg). $^1H$ NMR (CDCl$_3$, 400 MHz) δ 8.67 (s, 1H), 6.56 (br s, 1H), 4.57-4.40 (m, 4H), 4.12 (dd, J=4.8, 11.6 Hz, 1H), 4.00 (dd, J=4.4, 12.0 Hz, 1H), 3.69-3.61 (m, 1H), 3.57-3.46 (m, 1H), 3.14 (t, J=11.6 Hz, 1H), 2.50-2.37 (m, 1H), 2.35-2.25 (m, 4H), 2.09-1.98 (m, 1H), 1.96-1.86 (m, 1H), 1.81-1.73 (m, 1H), 0.68 (d, J=6.8 Hz, 3H). LC-MS (method C) (m/z)=404.2 (MH)$^+$ $t_R$=1.44 minutes. Chiral analytical SFC (instrument: Waters UPCC with PDA Detector, Column: Chiralpak AD-3 150×4.6 mm I.D., particle size 3 μm, mobile phase: A: $CO_2$ B: Methanol (0.05% DEA), gradient: 40% of iso-propanol (0.05% DEA) in $CO_2$, flow rate: 2.5 mL/min, column temp.: 35° C., ABPR: 1500 psi, run time: 6 min, wavelength: 220 nm), ee>99%, $t_R$=3.08 minutes.
and isomer Example 22 8-Chloro-3-methyl-2-((3R,4S) or (3S,4R) or (3S,4S) or (3R,4R)-3-methyltetrahydro-2H-pyran-4-yl)-2,4,12,13-tetrahydro-11H-5,7-(azenometheno)dipyrazolo[3,4-b:5',1'-g][1]oxa[4,6,8]triazacycloundecine peak 3 (110 mg). $^1H$ NMR (CDCl$_3$, 400 MHz) δ 8.67 (s, 1H), 6.56 (br s, 1H), 4.57-4.40 (m, 4H), 4.12 (dd, J=4.8, 11.6 Hz, 1H), 4.00 (dd, J=4.4, 12.0 Hz, 1H), 3.69-3.61 (m, 1H), 3.57-3.46 (m, 1H), 3.14 (t, J=11.6 Hz, 1H), 2.50-2.37 (m, 1H), 2.35-2.25 (m, 4H), 2.09-1.98 (m, 1H), 1.96-1.86 (m, 1H), 1.81-1.73 (m, 1H), 0.68 (d, J=6.8 Hz, 3H). LC-MS (method C) (m/z)=404.2 (MH)$^+$ $t_R$=1.44 minutes. Chiral analytical SFC (instrument: Waters UPCC with PDA Detector, Column: Chiralpak AD-3 150×4.6 mm I.D., particle size 3 μm, mobile phase: A: $CO_2$ B: Methanol (0.05% DEA), gradient: 40% of iso-propanol (0.05% DEA) in $CO_2$, flow rate: 2.5 mL/min, column temp.: 35° C., ABPR: 1500 psi, run time: 6 min, wavelength: 220 nm), ee>99%, $t_R$=3.90 minutes.
and isomer Example 23 8-Chloro-3-methyl-2-((3R,4S) or (3S,4R) or (3S,4S) or (3R,4R)-3-methyltetrahydro-2H-pyran-4-yl)-2,4,12,13-tetrahydro-11H-5,7-(azenometheno)dipyrazolo[3,4-b:5',1'-g][1]oxa[4,6,8]triazacycloundecine peak 4 (120 mg). $^1H$ NMR (CDCl$_3$, 400 MHz) δ 8.67 (s, 1H), 6.56 (br s, 1H), 4.52-4.47 (m, 2H), 4.45-4.40 (m, 2H), 4.33-4.22 (m, 2H), 3.93 (dd, J=4.4, 11.2 Hz, 1H), 3.68-3.58 (m, 2H), 2.54-2.43 (m, 1H), 2.30 (s, 3H), 2.15-2.05 (m, 1H), 2.03-1.95 (m, 2H), 1.89-1.81 (m, 1H), 0.88 (d, J=7.2 Hz, 3H). LC-MS (method C) (m/z)=404.2 (MH)$^+$ $t_R$=1.48 minutes. Chiral analytical SFC (instrument: Waters UPCC with PDA Detector, Column: Chiralpak AD-3 150×4.6 mm I.D., particle size 3 μm, mobile phase: A: $CO_2$ B: Methanol (0.05% DEA), gradient: 40% of iso-propanol (0.05% DEA) in $CO_2$, flow rate: 2.5 mL/min, column temp.: 35° C., ABPR: 1500 psi, run time: 6 min, wavelength: 220 nm), ee>99%, $t_R$=4.31 minutes.
and isomer Example 24 8-Chloro-3-methyl-2-((3R,4S) or (3S,4R) or (3S,4S) or (3R,4R)-3-methyltetrahydro-2H-pyran-4-yl)-2,4,12,13-tetrahydro-11H-5,7-(azenometheno)dipyrazolo[3,4-b:5',1'-g][1]oxa[4,6,8]triazacycloundecine peak 2 (110 mg). $^1H$ NMR (400 MHz, CDCl$_3$) δ 8.66 (s, 1H), 6.59 (br s, 1H), 4.52-4.47 (m, 2H), 4.45-4.40 (m, 2H), 4.33-4.22 (m, 2H), 3.93 (dd, J=4.4, 11.2 Hz, 1H), 3.68-3.58 (m, 2H), 2.54-2.43 (m, 1H), 2.30 (s, 3H), 2.15-2.05 (m, 1H), 2.03-1.95 (m, 2H), 1.89-1.81 (m, 1H), 0.88 (d, J=7.2 Hz, 3H). LC-MS (method C) (m/z)=404.2 (MH)$^+$ $t_R$=1.48 minutes. Chiral analytical SFC (instrument: Waters UPCC with PDA Detector, Column: Chiralpak AD-3 150×4.6 mm I.D., particle size 3 μm, mobile phase: A: $CO_2$ B: Methanol (0.05% DEA), gradient: 40% of iso-propanol (0.05% DEA) in $CO_2$, flow rate: 2.5 mL/min, column temp.: 35° C., ABPR: 1500 psi, run time: 6 min, wavelength: 220 nm), ee>99%, $t_R$=3.48 minutes.

Example 25: 8-Chloro-2-((1r,4r)-4-fluorocyclohexyl)-3-methyl-2,4,12,13-tetrahydro-11H-5,7-(azenometheno)dipyrazolo[3,4-b:5',1'-g][1]oxa[4,6,8]triazacycloundecine

Example 26: 8-Chloro-2-(4,4-difluorocyclohexyl)-3-methyl-2,4,12,13-tetrahydro-11H-5,7-(azenometheno)dipyrazolo[3,4-b:5',1'-g][1]oxa[4,6,8]triazacycloundecine

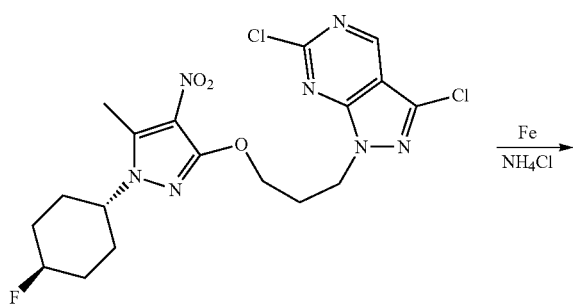
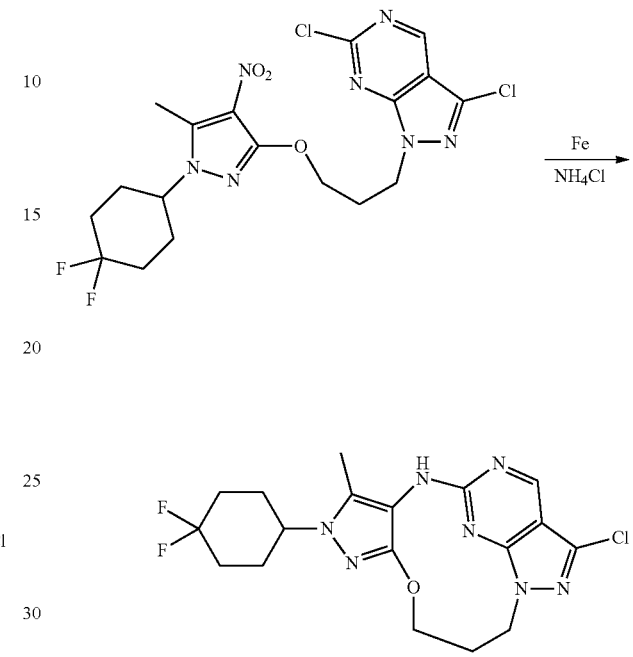

The compound was prepared in a manner similar to Example 1 using trans-3,6-dichloro-1-(3-((1-(4-fluorocyclohexyl)-5-methyl-4-nitro-1H-pyrazol-3-yl)oxy)propyl)-1H-pyrazolo[3,4-d]pyrimidine (110 mg, 0.27 mmol), Fe (65 mg, 1.2 mmol), and $NH_4Cl$ (62 mg, 1.2 mmol) in EtOH (14 mL) and $H_2O$ (7 mL) at 80° C. for 16 h, followed by work-up, and purification by chromatography on silica gel (eluent: Petroleum ether:EtOAc 100:0→0:100) and them preparative SFC (instrument: SFC150AP, column: DAICEL CHIRALPAK AD(250 mm×30 mm, particle size 10 μm), mobile phase: supercritical $CO_2$/EtOH (0.1% $NH_3H_2O$, v %)=65/35, flow rate: 80 mL/min, column temperature: 38° C., nozzle pressure: 100 bar, nozzle temperature: 60° C., evaporator temperature: 20° C., trimmer temperature: 25° C., wavelength: 220 nm) to afford the title compound (25 mg)$^1$H NMR (CDCl$_3$, 400 MHz) δ 8.67 (br s, 1H), 6.71 (br s, 1H), 4.77-4.53 (m, 1H), 4.52-4.37 (m, 4H), 4.03-3.86 (m, 1H), 2.29-2.23 (m, 5H), 2.13-2.01 (m, 2H), 2.01-1.91 (m, 4H), 1.73-1.68 (m, 1H), 1.65-1.59 (m, 1H). LC-MS (method C) (m/z)=406.1 (MH)$^+$ $t_R$=1.58 minutes.

The compound was prepared in a manner similar to Example 1 using 3,6-dichloro-1-(3-((1-(4,4-difluorocyclohexyl)-5-methyl-4-nitro-1H-pyrazol-3-yl)oxy)propyl)-1H-pyrazolo[3,4-d]pyrimidine (0.26 g, 0.53 mmol), Fe (148 mg, 2.65 mmol), and $NH_4Cl$ (142 mg, 2.65 mmol) in EtOH (50 mL) and $H_2O$ (10 mL) at 80° C. for 16 h, followed by work-up, and purification by chromatography on silica gel (eluent: Petroleum ether:EtOAc (10v % MeOH) 100:0→50:50) to afford the title compound (90 mg). $^1$H NMR (CDCl$_3$, 400 MHz) δ 8.67 (s, 1H), 6.68 (s, 1H), 4.55-4.38 (m, 4H), 4.11-4.00 (m, 1H), 2.40-2.23 (m, 7H), 2.03-1.82 (m, 6H). LC-MS (method C) (m/z)=424.2 (MH)$^+$ $t_R$=1.64 minutes.

Example 27: (−)-(R) or (S)-8-Chloro-3-methyl-2-(oxepan-3-yl)-2,4,12,13-tetrahydro-11H-5,7-(azenometheno)dipyrazolo[3,4-b:5',1'-g][1]oxa[4,6,8]triazacycloundecine and

Example 28 (+)-8-(R) or (S)-Chloro-3-methyl-2-(oxepan-3-yl)-2,4,12,13-tetrahydro-11H-5,7-(azenometheno)dipyrazolo[3,4-b:5',1'-g][1]oxa[4,6,8]triazacycloundecine

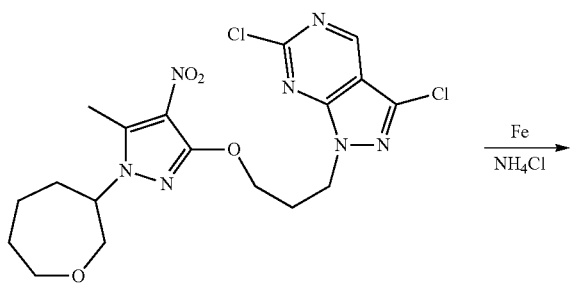

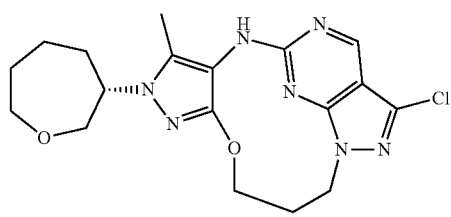
and
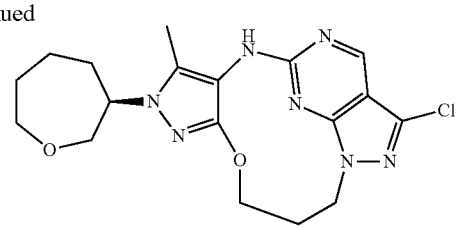

-continued

The racemic mixture of Example 27 and Example 28 was prepared in a manner similar to Example 1 using 3,6-dichloro-1-(3-((5-methyl-4-nitro-1-(oxepan-3-yl)-1H-pyrazol-3-yl)oxy)propyl)-1H-pyrazolo[3,4-d]pyrimidine (240 mg, 0.51 mmol), Fe (143 mg, 2.55 mmol), and NH$_4$Cl (137 mg, 2.55 mmol) in EtOH (15 mL) and H$_2$O (5 mL) at 80° C. for 16 h, followed by workup and purification by chromatography on silica gel (eluent: Petroleum ether:EtOAc 30:70->20:80) to afford 8-Chloro-3-methyl-2-(oxepan-3-yl)-2,4,12,13-tetrahydro-11H-5,7-(azenometheno)dipyrazolo[3,4-b:5',1'-g][1]oxa[4,6,8]triazacycloundecine (120 mg). The racemic mixture (120 mg) was separated into the two enantiomers by preparative chiral SFC (instrument: Berger MultiGram II, column: DAICEL CHIRALPAK AD(250 mm×30 mm, particle size 10 μm), mobile phase: supercritical CO$_2$/IPA(0.1% ammonium hydroxide)=55/45, flow rate: 80 mL/min, column temperature: 38° C., nozzle pressure: 100 bar, nozzle temperature: 60° C., evaporator temperature: 20° C., trimmer temperature: 25° C., wavelength: 220 nm) to afford:

Example 27 (−)-(R) or (S)-8-Chloro-3-methyl-2-(oxepan-3-yl)-2,4,12,13-tetrahydro-11H5,7-(azenometheno)dipyrazolo[3,4-b:5',1'-g][1]oxa[4,6,8]triazacycloundecine (55 mg). $^1$H NMR (CDCl$_3$, 400 MHz) δ8.66 (s, 1H), 6.62 (br s, 1H), 4.49-4.45 (m, 2H), 4.45-4.41 (m, 2H), 4.27-4.18 (m, 1H), 3.97-3.90 (m, 2H), 3.85-3.80 (m, 2H), 2.28 (s, 3H), 2.14-2.03 (m, 2H), 1.98-1.92 (m, 3H), 1.91-1.85 (m, 2H), 1.70-1.64 (m, 1H). LC-MS (method G) (m/z)=404.2 (MH)$^+$ t$_R$=1.50 minutes. Chiral analytical SFC (instrument: Agilent 1260 with DAD detector, column: ChiralPak AD-3 50×4.6 mm I.D., particle size 31 μm, mobile phase: A: CO$_2$ B: iso-propanol (0.05% DEA), gradient: hold 40% for 3 min, flow rate: 4 mL/min, column temperature: 40° C., ABPR: 1500 psi, run time: 3 minutes, wavelength: 220 nm) ee=>99%, t$_R$=0.88 minutes. [α]$_D$$^{20}$=−10.0 (c=0.1 g/100 mL, MeOH) and the corresponding enantiomer Example 28 (+)-(R) or (S)-8-Chloro-3-methyl-2-(oxepan-3-yl)-2,4,12,13-tetrahydro-11H5,7-(azenometheno)dipyrazolo[3,4-b:5',1'-g][1]oxa[4,6,8]triazacycloundecine (50 mg). $^1$H NMR (CDCl$_3$, 400 MHz) δ8.65 (s, 1H), 6.69 (br s, 1H), 4.49-4.45 (m, 2H), 4.45-4.41 (m, 2H), 4.27-4.18 (m, 1H), 3.97-3.90 (m, 2H), 3.85-3.80 (m, 2H), 2.28 (s, 3H), 2.14-2.03 (m, 2H), 1.98-1.92 (m, 3H), 1.91-1.85 (m, 2H), 1.70-1.64 (m, 1H). LC-MS (method G) (m/z)=404.2 (MH)$^+$ t$_R$=1.50 minutes. Chiral analytical SFC (instrument: Agilent 1260 with DAD detector, column: ChiralPak AD-3 50×4.6 mm I.D., particle size 31 μm, mobile phase: A: CO$_2$ B: iso-propanol (0.05% DEA), gradient: hold 40% for 3 min, flow rate: 4 mL/min, column temperature: 40° C., ABPR: 1500 psi, run time: 3 minutes, wavelength: 220 nm) ee=>99%, t$_R$=1.98 minutes. [α]$_D$$^{20}$=+8.0 (c=0.1 g/100 mL, MeOH)

Example 29: (−)-(R) or (S)-8-Chloro-3-methyl-2-(oxepan-4-yl)-2,4,12,13-tetrahydro-11H-5,7-(azenometheno)dipyrazolo[3,4-b:5',1'-g][1]oxa[4,6,8]triazacycloundecine and Example 30 (+)-8-(R) or (S)-Chloro-3-methyl-2-(oxepan-4-yl)-2,4,12,13-tetrahydro-11H-5,7-(azenometheno)dipyrazolo[3,4-b:5',1'-g][1]oxa[4,6,8]triazacycloundecine

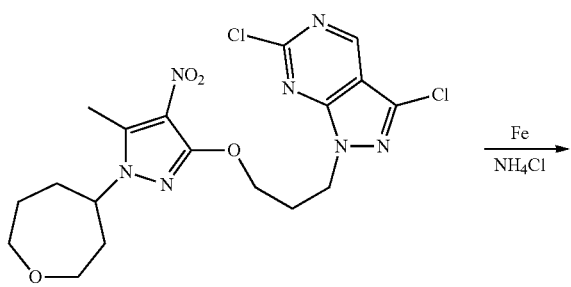

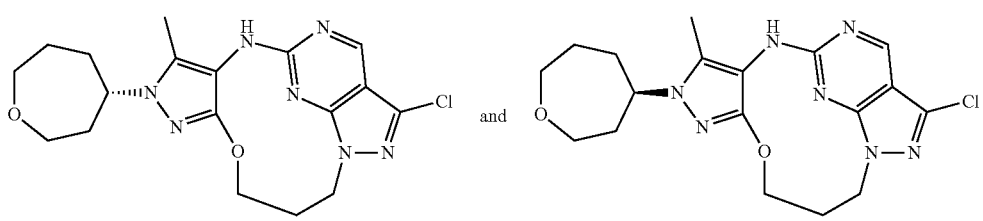

The racemic mixture of Example 29 and Example 30 was prepared in a manner similar to Example 1 using 3,6-dichloro-1-(3-((5-methyl-4-nitro-1-(oxepan-4-yl)-1H-pyrazol-3-yl)oxy)propyl)-1H-pyrazolo[3,4-d]pyrimidine (330 mg, 0.702 mmol) Fe (196 mg, 3.51 mmol), and NH$_4$Cl (188 mg, 3.51 mmol) in EtOH (20 mL) and H$_2$O (4 mL) at 80° C. for 15 h, followed by workup and purification by chromatography on silica gel (eluent: Petroleum ether:EtOAc 100:0->0:100) to afford 8-chloro-3-methyl-2-(oxepan-4-yl)-2,4,12,13-tetrahydro-11H-5,7-(azenometheno)dipyrazolo[3,4-b:5',1'-g][1]oxa[4,6,8]triazacycloundecine (120 mg). The racemic mixture (120 mg) was separated into the two enantiomers by preparative chiral SFC (instrument: SFC-80Q, column: DAICEL CHIRALPAK AD 250×30 mm, particle size 10 µm, mobile phase: supercritical CO$_2$/IPA (0.1% NH$_3$·H$_2$O, v %)=55/45, flow rate: 80 mL/min, column temperature: 38° C., nozzle pressure: 100 bar, nozzle temperature: 60° C., evaporator temperature: 20° C., trimmer temperature: 25° C., wavelength: 220 nm) to afford:

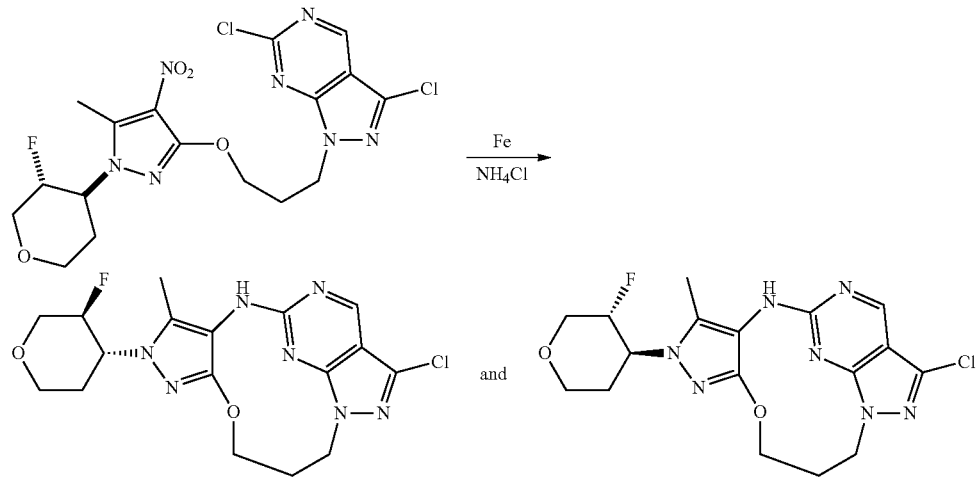

Example 29: (−)-(R) or (S)-8-Chloro-3-methyl-2-(oxepan-4-yl)-2,4,12,13-tetrahydro-11H5,7-(azenometheno)dipyrazolo[3,4-b:5',1'-g][1]oxa[4,6,8]triazacycloundecine (45 mg). $^1$H NMR (CDCl$_3$, 400 MHz) δ8.64 (s, 1H), 6.85 (br s, 1H), 4.59-4.36 (m, 4H), 4.32-4.20 (m, 1H), 3.97-3.84 (m, 2H), 3.83-3.74 (m, 1H), 3.71-3.61 (m, 1H), 2.45-2.32 (m, 1H), 2.27 (s, 3H), 2.26-2.18 (m, 1H), 2.17-2.07 (m, 1H), 2.04-1.92 (m, 3H), 1.92-1.85 (m, 1H), 1.84-1.75 (m, 1H). LC-MS (method C) (m/z)=404.2 (MH)$^+$ t$_R$=1.45 minutes. Chiral analytical SFC (instrument: Waters UPCC with PDA Detector, column: Chiralpak AD-3 50×4.6 mm I.D., particle size 31 µm, mobile phase: A: CO$_2$ B: iso-propanol (0.05% DEA), gradient: from 5% to 40% of B in 2 min and hold 40% for 1.2 min, then 5% of B for 0.8 min, flow rate: 4 mL/min, column temperature: 35° C., ABPR: 1500 psi, run time: 4 min, wavelength: 220 nm) ee=98%, t$_R$=2.48 minutes. [α]$_D$$^{20}$ O=−4.0 (c=0.1 g/100 mL, MeOH) and the corresponding enantiomer Example 30 (+)-(R) or (S)-8-Chloro-3-methyl-2-(oxepan-4-yl)-2,4,12,13-tetrahydro-11H5,7-(azenometheno)dipyrazolo[3,4-b:5',1'-g][1]oxa[4,6,8]triazacycloundecine (50 mg). $^1$H NMR (CDCl$_3$, 400 MHz) δ8.65 (s, 1H), 6.71 (br s, 1H), 4.57-4.35 (m, 4H), 4.32-4.18 (m, 1H), 3.96-3.84 (m, 2H), 3.83-3.74 (m, 1H), 3.71-3.62 (m, 1H), 2.45-2.32 (m, 1H), 2.28 (s, 3H), 2.27-2.18 (m, 1H), 2.17-2.08 (m, 1H), 2.06-1.92 (m, 3H), 1.92-1.85 (m, 1H), 1.84-1.72 (m, 1H). LC-MS (method C) (m/z)=404.2 (MH)$^+$ t$_R$=1.45 minutes. Chiral analytical SFC (instrument: Waters UPCC with PDA Detector, column: Chiralpak AD-3 50×4.6 mm I.D., particle size 31 µm, mobile phase: A: CO$_2$ B: iso-propanol (0.05% DEA), gradient: from 5% to 40% of B in 2 min and hold 40% for 1.2 min, then 5% of B for 0.8 min, flow rate: 4 mL/min, column temperature: 35° C., ABPR: 1500 psi, run time: 4 min, wavelength: 220 nm) ee=>99%, t$_R$=2.34 minutes. [α]$_D$$^{20}$=+4.0 (c=0.1 g/100 mL, MeOH).

Example 31 (−)-8-Chloro-2-((3S,4R) or (3R,4S)-3-fluorotetrahydro-2H-pyran-4-yl)-3-methyl-2,4,12,13-tetrahydro-11H-5,7-(azenometheno)dipyrazolo[3,4-b:5',1'-g][1]oxa[4,6,8]triazacycloundecine and Example 32 (+)-8-Chloro-2-((3S,4R) or (3R,4S)-3-fluorotetrahydro-2H-pyran-4-yl)-3-methyl-2,4,12,13-tetrahydro-11H-5,7-(azenometheno)dipyrazolo[3,4-b:5',1'-g][1]oxa[4,6,8]triazacycloundecine The racemic mixture of Example 31 and Example 32 was prepared in a manner similar to Example 1 using trans-3,6-dichloro-1-(3-((1-(3-fluorotetrahydro-2H-pyran-4-yl)-5-methyl-4-nitro-1H-pyrazol-3-yl)oxy)propyl)-1H-pyrazolo[3,4-d]pyrimidine (450 mg, 0.95 mmol), Fe (265 mg, 4.74 mmol), and NH$_4$Cl (254 mg, 4.74 mmol) in EtOH (40 mL) and H$_2$O (4 mL) at 80° C. for 15 h, followed by work-up and purification by chromatography on silica gel (eluent: Petroleum ether:EtOAc 100:0→50:50) to afford 8-Chloro-2-((3S, 4R and 3R,4S)-3-fluorotetrahydro-2H-pyran-4-yl)-3-methyl-2,4,12,13-tetrahydro-11H-5,7-(azenometheno)dipyrazolo[3,4-b:5',1'-g][1]oxa[4,6,8]triazacycloundecine (200 mg). The racemic mixture (200 mg) was separated into the two enantiomers by preparative chiral SFC (instrument: Berger MultiGram II, column: DAICEL CHIRALPAK AS 250×30 mm, particle size 10 µm, mobile phase: supercritical CO$_2$/IPA (0.1% NH$_3$·H$_2$O, v %)=75/25, flow rate: 70 mL/min, column temperature: 38° C., nozzle pressure: 100 bar, nozzle temperature: 60° C., evaporator temperature: 20° C., trimmer temperature: 25° C., wavelength: 220 nm) to afford:

Example 31 (−)-8-Chloro-2-((3S,4R) or (3R,4S)-3-fluorotetrahydro-2H-pyran-4-yl)-3-methyl-2,4,12,13-tetrahydro-11H-5,7-(azenometheno)dipyrazolo[3,4-b:5',1'-g][1]oxa[4,6,8]triazacycloundecine (60 mg). $^1$H NMR (CDCl$_3$, 400 MHz) δ 8.67 (s, 1H), 6.57 (br s, 1H), 4.99-4.76 (m, 1H), 4.58-4.35 (m, 4H), 4.31-4.23 (m, 1H), 4.22-3.98 (m, 2H), 3.58-3.45 (m, 1H), 3.44-3.32 (m, 1H), 2.59-2.43 (m, 1H), 2.31 (s, 3H), 2.13-1.81 (m, 3H). LC-MS (method G) (m/z)= 408.1 (MH)$^+$ $t_R$=1.43 minutes. Chiral analytical SFC (instrument: Waters UPCC with PDA Detector, column: Chiralpak AS-3 100×4.6 mm I.D., particle size 3 µm, mobile phase: A: $CO_2$ B: ethanol (0.05% DEA), gradient: from 5% to 40% of B in 4 min and hold 40% for 0.5 min, then 5% of B for 1.5 min, flow rate: 2.8 mL/min, column temperature: 35° C., ABPR: 1500 psi, run time: 6 min, wavelength: 220 nm), ee>99%, $t_R$=2.77 minutes. $[\alpha]^{20}$=−42 (c=0.5 g/100 mL, $CHCl_3$).
and the corresponding enantiomer Example 32 (+)-8-Chloro-2-((3S,4R) or (3R,4S)-3-fluorotetrahydro-2H-pyran-4-yl)-3-methyl-2,4,12,13-tetrahydro-11H-5,7-(azenometheno)dipyrazolo[3,4-b:5',1'-g][1]oxa[4,6,8]triazacycloundecine (60 mg). $^1$H NMR ($CDCl_3$, 400 MHz) δ 8.67 (s, 1H), 6.64 (br s, 1H), 5.03-4.75 (m, 1H), 4.59-4.37 (m, 4H), 4.31-4.23 (m, 1H), 4.20-4.01 (m, 2H), 3.59-3.46 (m, 1H), 3.44-3.33 (m, 1H), 2.61-2.41 (m, 1H), 2.31 (s, 3H), 2.11-1.84 (m, 3H). LC-MS (method G) (m/z)= 408.1 (MH)$^+$ $t_R$=1.43 minutes. Chiral analytical SFC (instrument: Waters UPCC with PDA Detector, column: Chiralpak AS-3 100×4.6 mm I.D., particle size 3 µm, mobile phase: A: $CO_2$ B: ethanol (0.05% DEA), gradient: from 5% to 40% of B in 4 min and hold 40% for 0.5 min, then 5% of B for 1.5 min, flow rate: 2.8 mL/min, column temperature: 35° C., ABPR: 1500 psi, run time: 6 min, wavelength: 220 nm), ee=98.5%, $t_R$=3.30 minutes. $[\alpha]_D^{20}$=+48.5 (c=0.8 g/100 mL, $CHCl_3$)

Example 33 3-(8-Chloro-3-methyl-12,13-dihydro-11H-5,7-(azenometheno)dipyrazolo[3,4-b:5',1'-g][1]oxa[4,6,8]triazacycloundecin-2(4H)-yl)bicyclo[1.1.1]pentane-1-carbonitrile

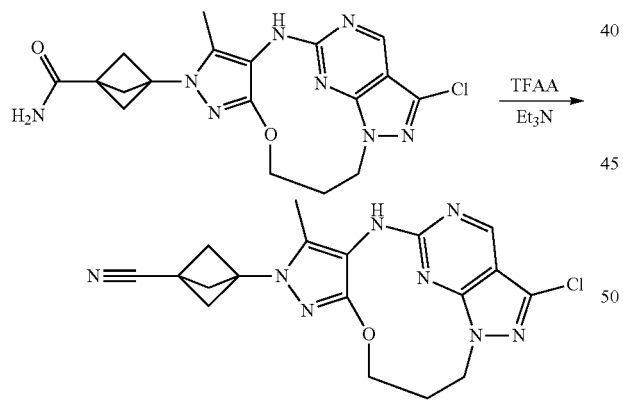

To a solution of 3-(8-chloro-3-methyl-4,11,12,13-tetrahydro-2H-5,7-(azenometheno)dipyrazolo[3,4-b:5',1'-g][1,4,6,8]oxatriazacycloundecin-2-yl)bicyclo[1.1.1]pentane-1-carboxamide (70 mg, 0.17 mmol) in DCM (10 mL) were added TFAA (53.16 mg, 0.253 mmol) and TEA (68 mg, 0.68 mmol) at 0° C. The reaction mixture was stirred at 0° C. for 1 h. Then additional TFAA (106 mg, 0.50 mmol) and TEA (70 mg, 0.69 mmol) was added to the mixture and the mixture was stirred at 0° C. for 1 h. The reaction mixture was diluted with water (20 mL) and extracted with DCM (3×20 mL). The combined organic layers were washed with brine (3×20 mL), dried over $Na_2SO_4$, filtered, and concentrated under reduced pressure. The residue was purified using preparative SFC (instrument: Berger MultiGram II, column: DAICEL CHIRALCEL OD-H 250×30 mm, particle size 5 µm, mobile phase: supercritical $CO_2$/ETOH (0.1% $NH_3 \cdot H_2O$, v %)=60/40, flow rate: 80 mL/min, column temperature: 38° C., nozzle pressure: 100 bar, nozzle temperature: 60° C., evaporator temperature: 20° C., trimmer temperature: 25° C., wavelength: 220 nm) to afford the title compound (35 mg). $^1$H NMR ($CDCl_3$, 400 MHz) δ 8.66 (s, 1H), 6.70 (br s, 1H), 4.53-4.36 (m, 4H), 2.79 (s, 6H), 2.32 (s, 3H), 2.03-1.85 (m, 2H). LC-MS (method G) (m/z)=397.1 (MH)$^+$ $t_R$=1.47 minutes.

Example 34: 8-Chloro-3-methyl-2-(2-oxaspiro[3.3]heptan-6-yl)-2,4,12,13-tetrahydro-11H-5,7-(azenometheno)dipyrazolo[3,4-b:5',1'-g][1]oxa[4,6,8]triazacycloundecine

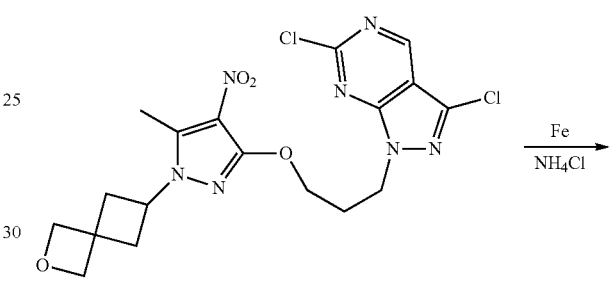

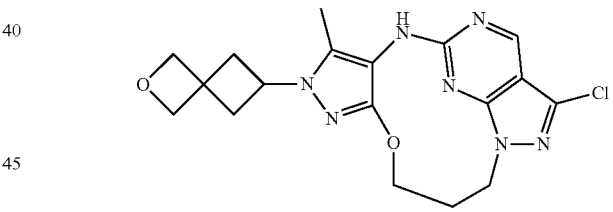

The compound was prepared in a manner similar to Example 1 using 3,6-dichloro-1-(3-((5-methyl-4-nitro-1-(2-oxaspiro[3.3]heptan-6-yl)-1H-pyrazol-3-yl)oxy)propyl)-1H-pyrazolo[3,4-d]pyrimidine (70 mg, 0.15 mmol), Fe (42 mg, 0.75 mmol), and $NH_4Cl$ (42 mg, 0.78 mmol) in EtOH (7 mL) and $H_2O$ (3.5 mL) at 54° C. for 16 h, followed by work-up, and purification by preparative HPLC (instrument: Gilson GX-215, Gilson 322 Pump, Gilson 156 UV Detector, column: Welch Xtimate C18 150×30 mm×5 µm, mobile Phase A: water (0.05% $NH_3H_2O$+10 mM $NH_4HCO_3$), mobile phase B: MeCN, gradient: B from 28% to 58% in 9 min then hold at 100% for 2 min, flow rate (mL/min): 35, column temperature: 30° C., wavelengths: 220 nm and 254 nm) to afford the title compound (12 mg). $^1$H NMR ($CDCl_3$, 400 MHz) δ 8.66 (s, 1H), 6.59 (br s, 1H), 4.80 (s, 2H), 4.75 (s, 2H), 4.54-4.47 (m, 2H), 4.45-4.36 (m, 3H), 2.89-2.80 (m, 2H), 2.73-2.66 (m, 2H), 2.23 (s, 3H), 1.98-1.85 (m, 2H). LC-MS (method G) (m/z)=402.1 (MH)$^+$ $t_R$=1.38 minutes.

Example 35: 8-Chloro-3-(methyl-d₃)-2-(tetrahydro-2H-pyran-4-yl)-2,4,12,13-tetrahydro-11H5,7-(azenometheno)dipyrazolo[3,4-b:5',1'-g][1]oxa[4,6,8]triazacycloundecine-11,11,12,12,13,13-d₆

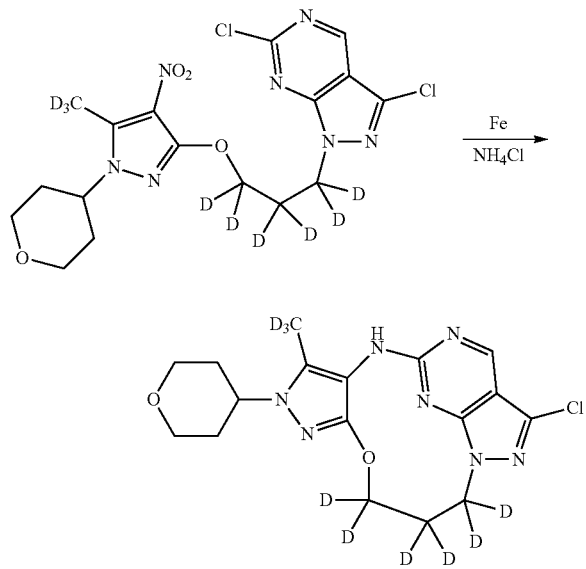

The compound was prepared in a manner similar to Example 1 using 3,6-dichloro-1-(3-((5-(methyl-d₃)-4-nitro-1-(tetrahydro-2H-pyran-4-yl)-1H-pyrazol-3-yl)oxy)propyl-1,1,2,2,3,3-d₆)-1H-pyrazolo[3,4-d]pyrimidine (100 mg, 0.215 mmol), Fe (60.0 mg, 1.07 mmol), and NH₄Cl (57.5 mg, 1.07 mmol) in EtOH (1 mL) and H₂O (0.1 mL) at 100° C. for 2 h, followed by work-up, and purification by preparative HPLC (instrument: Waters sample manager 2767; Waters 2545 pump, Waters UV Detector 2545, column: Sunfire prep C18 column, 30×150 mm, particle size 5 μm, mobile phase A: Water(0.1% FA), mobile phase B: CAN, gradient: 18% B to 53% B in 7 min, flow rate: 60 mL/min, column temperature: 30° C., wavelengths: 220 nm, 254 nm) to afford the title compound (20 mg). ¹H NMR (400 MHz, DMSO-d₆) δ 8.62 (s, 1H), 7.74 (s, 1H), 4.14-4.08 (m, 3H), 3.52 (t, J=11.2 Hz, 2H), 2.27 (tt, J=12.4, 8.0 Hz, 2H), 1.80 (d, J=11.6 Hz, 2H). LC-MS (method E) (m/z)=399.7 (MH)⁺ t$_R$=0.56 minutes.

Example 36: 1-(8-Chloro-3-methyl-12,13-dihydro-11H-5,7-(azenometheno)dipyrazolo[3,4-b:5',1'-g][1]oxa[4,6,8]triazacycloundecin-2(4H)-yl)cyclopropane-1-carbonitrile

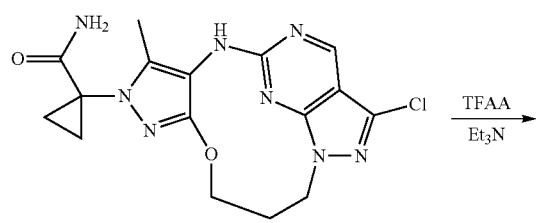

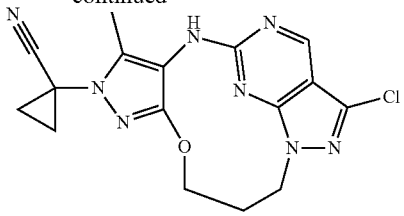

The compound was prepared in a manner similar to Example 33 using 1-(8-chloro-3-methyl-4,11,12,13-tetrahydro-2H-5,7-(azenometheno)dipyrazolo[3,4-b:5',1'-g][1,4,6,8]oxatriazacycloundecin-2-yl)cyclopropanecarboxamide (35 mg, 0.090 mmol), TFAA (28 mg, 0.135 mmol) and TEA (36.4 mg, 0.360 mmol) in DCM (14 mL) at 0° C. for 1 h, followed by work-up and preparative SFC (instrument: SFC-80Q, column: DAICEL CHIRALCEL OD-H (250 mm×30 mm, particle size 5 μm), mobile phase: supercritical CO₂/EtOH (0.1% NH₃·H₂O, v %)=30/30, flow rate: 80 mL/min, column temperature: 38° C., nozzle pressure: 100 bar, nozzle temperature: 60° C., evaporator temperature: 20° C., trimmer temperature: 25° C., wavelength: 220 nm) to afford the title compound (12 mg). ¹H NMR (CDCl₃, 400 MHz) δ 8.67 (s, 1H), 7.01 (br s, 1H), 4.63-4.28 (m, 4H), 2.44 (s, 3H), 1.95-1.90 (m, 2H), 1.85-1.75 (m, 4H). LC-MS (method G) (m/z)=371.1 (MH)⁺ t$_R$=1.40 minutes.

Example 37: 8-Chloro-2-((1r,4r)-4-methoxycyclohexyl)-3-methyl-2,4,12,13-tetrahydro-11H-5,7-(azenometheno)dipyrazolo[3,4-b:5',1'-g][1]oxa[4,6,8]triazacycloundecine

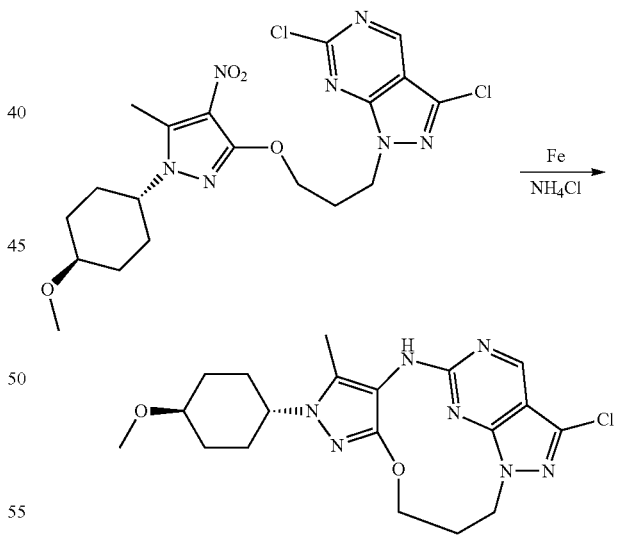

The compound was prepared in a manner similar to Example 1 using 3,6-dichloro-1-(3-((1-((1r,4r)-4-methoxycyclohexyl)-5-methyl-4-nitro-1H-pyrazol-3-yl)oxy)propyl)-1H-pyrazolo[3,4-d]pyrimidine (160 mg, 0.33 mmol), Fe (92 mg, 1.7 mmol), and NH₄Cl (88 mg, 1.7 mmol) in EtOH (16 mL) and H₂O (4 mL) at 80° C. for 16 h, followed by work-up, and purification by chromatography on silica gel (eluent: Petroleum ether:EtOAc 83:17→0:100) and preparative SFC (instrument: Thar SFC Prep 80, column: DAICEL CHIRALCEL OJ (250 mm×30 mm, 10 μm), mobile phase:

supercritical CO$_2$/EtOH (0.1% NH$_3$·H$_2$O, v %)=70/30, flow rate: 70 mL/min, column temperature: 38° C., nozzle pressure: 100 bar, nozzle temperature: 60° C., evaporator temperature: 20° C., trimmer temperature: 25° C., wavelength: 220 nm) to afford the title compound (80 mg). $^1$H NMR (CDCl$_3$, 400 MHz) δ 8.66 (s, 1H), 6.63 (br, 1H), 4.59-4.36 (m, 4H), 4.03-3.82 (m, 1H), 3.39 (s, 3H), 3.31-3.16 (m, 1H), 2.28 (s, 3H), 2.26-2.17 (m, 2H), 2.09-1.86 (m, 6H), 1.42-1.26 (m, 2H). LC-MS (method C) (m/z)=418.2 (MH)$^+$ t$_R$=1.52 minutes.

Example 38: 2-((1R,5S,6r)-3-Oxabicyclo[3.1.0]hexan-6-yl)-8-chloro-3-methyl-2,4,12,13-tetrahydro-11H-5,7-(azenometheno)dipyrazolo[3,4-b:5',1'-g][1]oxa[4,6,8]triazacycloundecine

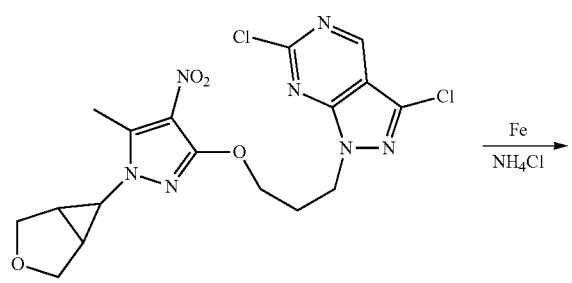

followed by work-up, and purification by chromatography on silica gel (eluent: Petroleum ether:EtOAc 100:0→0:100) and preparative (instrument: Gilson GX-215, Gilson 322 Pump, Gilson 156 UV Detector, column: Welch Xtimate C18 150×30 mm×5 µm, mobile Phase A: water (NH$_3$H$_2$O+NH$_4$HCO$_3$), mobile phase B: MeCN, gradient: B from 30% to 60% in 7 min, flow rate (mL/min): 25 mL/min, column temperature: 30° C., wavelengths: 220 nm 254 nm) to afford the title compound (61 mg). $^1$H NMR (DMSO-d$_6$, 400 MHz) δ 9.41 (br s, 1H), 8.78 (s, 1H), 4.35-4.31 (m, 2H), 4.29-4.25 (m, 2H), 3.98 (d, J=8.4 Hz, 2H), 3.70 (d, J=8.4 Hz, 2H), 3.10-3.04 (m, 1H), 2.33-2.28 (m, 2H), 2.28 (s, 3H), 1.79-1.75 (m, 2H). LC-MS (method G) (m/z)=388.1 (MH)$^+$ t$_R$=1.37 minutes.

Example 39 (−)-(R) or (S)-8-Chloro-2-(2,2-difluorocyclopropyl)-3-methyl-2,4,12,13-tetrahydro-11H-5,7-(azenometheno)dipyrazolo[3,4-b:5',1'-g][1]oxa[4,6,8]triazacycloundecine and Example 40 (+)-(R) or (S)-8-Chloro-2-(2,2-difluorocyclopropyl)-3-methyl-2,4,12,13-tetrahydro-11H-5,7-(azenometheno)dipyrazolo[3,4-b:5',1'-g][1]oxa[4,6,8]triazacycloundecine

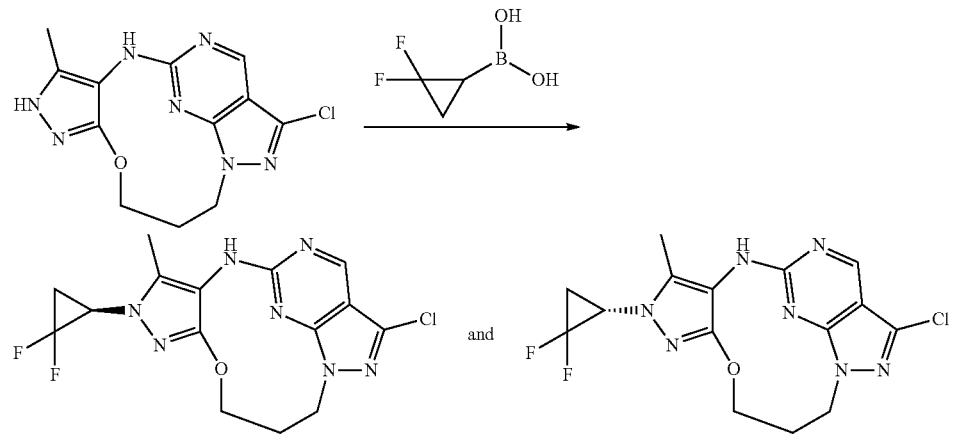

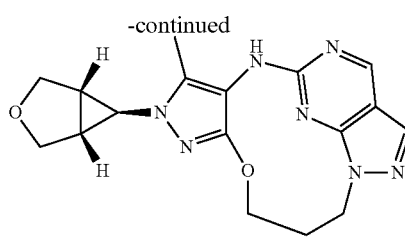

The compound was prepared in a manner similar to Example 1 using 1-(3-((1-(3-oxabicyclo[3.1.0]hexan-6-yl)-5-methyl-4-nitro-1H-pyrazol-3-yl)oxy)propyl)-3,6-dichloro-1H-pyrazolo[3,4-d]pyrimidine (230 mg, 0.51 mmol), Fe (142 mg, 2.54 mmol), and NH$_4$Cl (136 mg, 2.54 mmol) in EtOH (10 mL) and H$_2$O (2.5 mL) at 80° C. for 12 h, A mixture of 8-chloro-3-methyl-2,4,12,13-tetrahydro-11H-5,7-(azenometheno)dipyrazolo[3,4-b:5',1'-g][1]oxa[4,6,8]-triazacycloundecine (300 mg, 0.981 mmol), (2,2-difluorocyclopropyl)boronic acid (120 mg, 0.981 mmol), pyridine (315 mg, 3.98 mmol), Cu(OAc)$_2$ (270 mg, 1.49 mmol) and 4 Å MS (300 mg) in DCE (10 mL) was stirred at 65° C. under oxygen (15 psi) for 12 h. The mixture was filtered, the filter cake was washed with DCM (3×10 mL), and the combined filtrate was concentrated under reduced pressure. The residue was purified by chromatography on silica gel (eluent: Petroleum ether:EtOAc 100:0→40:60) to afford 8-Chloro-2-(2,2-difluorocyclopropyl)-3-methyl-2,4,12,13-tetrahydro-11H-5,7-(azenometheno)dipyrazolo[3,4-b:5',1'-g][1]oxa[4,6,8]triazacycloundecine (80 mg). The racemic mixture (80 mg) was separated into the two enantiomers by preparative chiral SFC (instrument: Berger MultiGram II, column: Phenomenex-Cellulose-2 250×30 mm, 10 μm, mobile phase: supercritical CO₂/EtOH (0.1% NH₃·H₂O, v %)=70/30, flow rate: 80 mL/min, column temperature: 38° C., nozzle pressure: 100 bar, nozzle temperature: 60° C., evaporator temperature: 20° C., trimmer temperature: 25° C., wavelength: 220 nm) to afford:

Example 39 (−)-(R) or (S)-8-Chloro-2-(2,2-difluorocyclopropyl)-3-methyl-2,4,12,13-tetrahydro-11H-5,7-(azenometheno)dipyrazolo[3,4-b:5′,1′-g][1]oxa[4,6,8]triazacycloundecine (30 mg). $^1$H NMR (CDCl₃, 400 MHz) δ8.66 (s, 1H), 6.85 (br s, 1H), 4.63-4.34 (m, 4H), 3.84-3.69 (m, 1H), 2.41-2.24 (m, 4H), 2.13-1.95 (m, 2H), 1.94-1.81 (m, 1H). LC-MS (method C) (m/z)=382.1 (MH)⁺ $t_R$=1.51 minutes. Chiral analytical SFC (instrument: Waters UPCC with PDA Detector and QDa Detector, column: Cellulose-2 100×4.6 mm I.D., particle size 3 μm, mobile phase: A: CO₂ B: ethanol (0.05% DEA), gradient: from 5% to 40% of B in 4 min and hold 40% for 0.5 min, then 5% of B for 1.5 min, flow rate: 2.8 mL/min, column temperature: 35° C., ABPR: 1500 psi, run time: 6 min, wavelength: 220 nm), ee>99%, $t_R$=2.62 minutes. $[α]_D^{20}$=−68 (c=0.1 g/100 mL, MeOH). and the corresponding enantiomer Example 40 (+)-(R) or (S)-8-Chloro-2-(2,2-difluorocyclopropyl)-3-methyl-2,4,12,13-tetrahydro-11H-5,7-(azenometheno)dipyrazolo[3,4-b:5′,1′-g][1]oxa[4,6,8]triazacycloundecine (30 mg). $^1$H NMR (CDCl₃, 400 MHz) δ 8.68 (s, 1H), 6.66 (br s, 1H), 4.58-4.36 (m, 4H), 3.83-3.71 (m, 1H), 2.40-2.26 (m, 4H), 2.13-1.95 (m, 2H), 1.95-1.77 (m, 1H). LC-MS (method C) (m/z)=382.1 (MH)⁺ $t_R$=1.51 minutes. Chiral analytical SFC (instrument: Waters UPCC with PDA Detector and QDa Detector, column: Cellulose-2 100×4.6 mm I.D., particle size 3 μm, mobile phase: A: CO₂ B: ethanol (0.05% DEA), gradient: from 5% to 40% of B in 4 min and hold 40% for 0.5 min, then 5% of B for 1.5 min, flow rate: 2.8 mL/min, column temperature: 35° C., ABPR: 1500 psi, run time: 6 min, wavelength: 220 nm), ee=95.3%, $t_R$=2.97 minutes. $[α]_D^{20}$=+68 (c=0.1 g/100 mL, MeOH)

Example 41: 8-chloro-2-((2R,4r,6S)-2,6-dimethyltetrahydro-2H-pyran-4-yl)-3-methyl-2,4,12,13-tetrahydro-11H-5,7-(azenometheno)dipyrazolo[3,4-b:5′,1′-g][1]oxa[4,6,8]triazacycloundecine

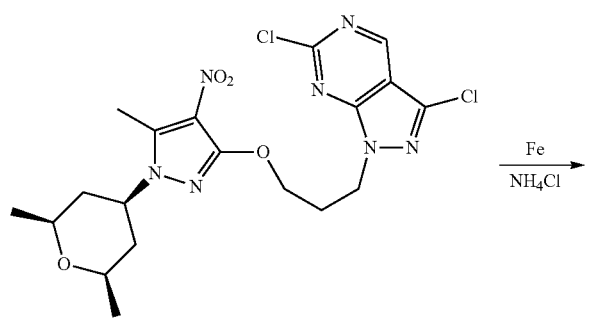

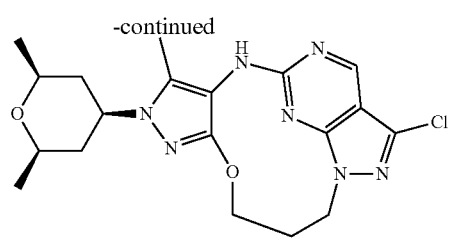

The compound was prepared in a manner similar to Example 1 using 3,6-dichloro-1-(3-((1-((2R,4r,6S)-2,6-dimethyltetrahydro-2H-pyran-4-yl)-5-methyl-4-nitro-1H-pyrazol-3-yl)oxy)propyl)-1H-pyrazolo[3,4-d]pyrimidine (140 mg, 0.29 mmol), Fe (129 mg, 2.31 mmol), and NH₄Cl (124 mg, 2.31 mmol) in EtOH (20 mL) and H₂O (5 mL) at 80° C. for 12 h, followed by workup, and purification by chromatography on silica gel (eluent: Petroleum ether:EtOAc70:30 4 70:30) to afford the title compound (40 mg). $^1$H NMR (CDCl₃, 400 MHz) δ 8.68 (s, 1H), 6.68 (br s, 1H), 4.49-4.45 (m, 4H), 4.18-4.15 (m, 1H), 3.63 (m, 2H), 2.30 (s, 3H), 2.05-1.76 (m, 6H), 1.30 (d, J=3.6 Hz, 6H). LC-MS (method C) (m/z)=418.2 (MH)⁺ $t_R$=1.56 minutes.

Example 42 (+)-(R) or (S)-8-Chloro-2-(2,2-dimethyltetrahydro-2H-pyran-4-yl)-3-methyl-2,4,12,13-tetrahydro-11H-5,7-(azenometheno)dipyrazolo[3,4-b:5′,1′-g][1]oxa[4,6,8]triazacycloundecine and Example 43 (−)-(R) or (S)-8-Chloro-2-(2,2-dimethyltetrahydro-2H-pyran-4-yl)-3-methyl-2,4,12,13-tetrahydro-11H-5,7-(azenometheno)dipyrazolo[3,4-b:5′,1′-g][1]oxa[4,6,8]triazacycloundecine

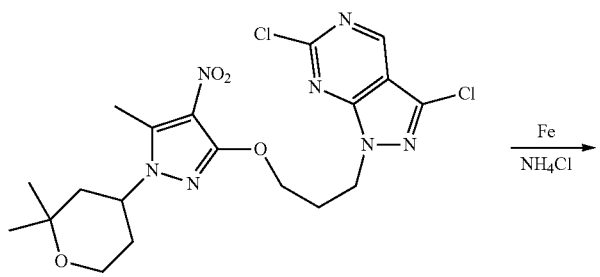

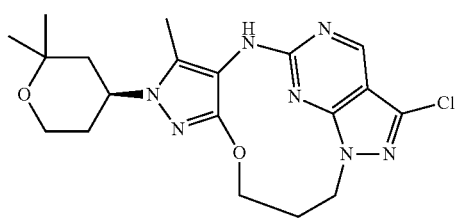
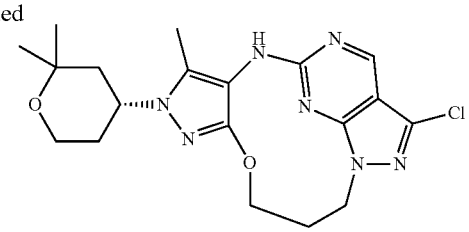

and

The racemic mixture of Example 42 and Example 43 was prepared in a manner similar to Example 1 using 3,6-dichloro-1-(3-((1-(2,2-dimethyltetrahydro-2H-pyran-4-yl)-5-methyl-4-nitro-1H-pyrazol-3-yl)oxy)propyl)-1H-pyrazolo[3,4-d]pyrimidine (210 mg, 0.43 mmol), Fe (121 mg, 2.17 mmol), and NH$_4$Cl (116 mg, 2.17 mmol) in EtOH (25 mL) and H$_2$O (6 mL) at 80° C. for 12 h, followed by work-up and purification by chromatography on silica gel (eluent: Petroleum ether:EtOAc 80:20→25:75) to afford 8-Chloro-2-(2,2-dimethyltetrahydro-2H-pyran-4-yl)-3-methyl-2,4,12,13-tetrahydro-11H-5,7-(azenometheno)dipyrazolo[3,4-b:5',1'-g][1]oxa[4,6,8]triazacycloundecine (112 mg). The racemic mixture (112 mg) was separated into the two enantiomers by preparative chiral SFC (instrument: Berger MultiGram II, column: DAICEL CHIRALCEL OD 250×30 mm, 10 μm, mobile phase: supercritical CO$_2$/EtOH (0.1% NH$_3$·H$_2$O, v %)=70/30, flow rate: 80 mL/min, column temperature: 38° C., nozzle pressure: 100 bar, nozzle temperature: 60° C., evaporator temperature: 20° C., trimmer temperature: 25° C., wavelength: 220 nm) to afford:

Example 42 (+)-(R) or (S)-8-Chloro-2-(2,2-dimethyltetrahydro-2H-pyran-4-yl)-3-methyl-2,4,12,13-tetrahydro-11H-5,7-(azenometheno)dipyrazolo[3,4-b:5',1'-g][1]oxa[4,6,8]triazacycloundecine (34 mg). $^1$H NMR (CDCl$_3$, 400 MHz) δ8.67 (s, 1H), 6.66 (br s, 1H), 4.60-4.38 (m, 4H), 4.36-4.22 (m, 1H), 3.99-3.88 (m, 1H), 3.86-3.76 (m, 1H), 2.31 (s, 3H), 2.27-2.15 (m, 1H), 2.15-2.06 (m, 1H), 2.04-1.90 (m, 2H), 1.84-1.71 (m, 2H), 1.33 (d, J=4.0 Hz, 6H). LC-MS (method C) (m/z)=418.2 (MH)$^+$ t$_R$=1.52 minutes. Chiral analytical SFC (instrument: Waters UPCC with PDA Detector, column: Chiralcel OD-3 150×4.6 mm I.D., 3 μm, mobile phase: 40% of ethanol (0.05% DEA) in CO$_2$, flow rate: 2.5 mL/min, column temperature: 35° C., ABPR: 1500 psi, run time: 3.5 min, wavelength: 220 nm), ee>99%, t$_R$=2.14 minutes. [α]$_D^{20}$=+27.5 (c=0.24 g/100 mL, MeOH) and the corresponding enantiomer Example 43 (−)-(R) or (S)-8-Chloro-2-(2,2-dimethyltetrahydro-2H-pyran-4-yl)-3-methyl-2,4,12,13-tetrahydro-11H-5,7-(azenometheno)dipyrazolo[3,4-b:5',1'-g][1]oxa[4,6,8]triazacycloundecine (37 mg). $^1$H NMR (CDCl$_3$, 400 MHz) δ8.70 (s, 1H), 6.66 (br s, 1H), 4.56-4.42 (m, 4H), 4.34-4.25 (m, 1H), 3.97-3.90 (m, 1H), 3.86-3.76 (m, 1H), 2.31 (s, 3H), 2.27-2.15 (m, 1H), 2.14-2.06 (m, 1H), 2.04-1.90 (m, 2H), 1.84-1.72 (m, 2H), 1.33 (d, J=4.0 Hz, 6H). LC-MS (method C) (m/z)=418.2 (MH)$^+$ t$_R$=1.52 minutes. Chiral analytical SFC (instrument: Waters UPCC with PDA Detector, column: Chiralcel OD-3 150×4.6 mm I.D., 3 μm, mobile phase: 40% of ethanol (0.05% DEA) in CO$_2$, flow rate: 2.5 mL/min, column temperature: 35° C., ABPR: 1500 psi, run time: 3.5 min, wavelength: 220 nm), ee>99%, t$_R$=1.55 minutes. [α]$_D^{20}$=−24 (c=0.2 g/100 mL, MeOH).

Example 44: 2-((1R,3s,5S)-8-Oxabicyclo[3.2.1]octan-3-yl)-8-chloro-3-methyl-2,4,12,13-tetrahydro-11H-5,7-(azenometheno)dipyrazolo[3,4-b:5',1'-g][1]oxa[4,6,8]triazacycloundecine

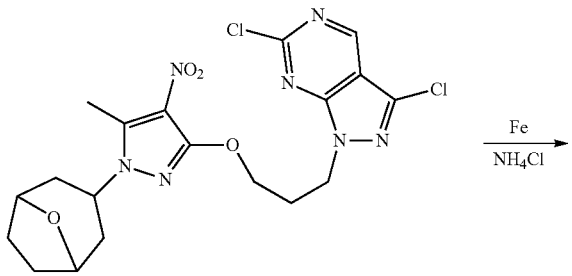

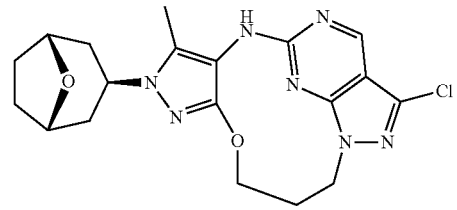

The compound was prepared in a manner similar to Example 1 using 1-(3-((1-(8-oxabicyclo[3.2.1]octan-3-yl)-5-methyl-4-nitro-1H-pyrazol-3-yl)oxy)propyl)-3,6-dichloro-1H-pyrazolo[3,4-d]pyrimidine (0.62 g, 1.3 mmol), Fe (162 mg, 2.89 mmol), and NH$_4$Cl (155 mg, 2.89 mmol) in EtOH (24 mL) and H$_2$O (6 mL) at 80° C. for 16 h, followed by work-up, and purification by preparative HPLC (SHIMADZU LH-40, column: Xtimate C18 100×30 mm×10 μm), mobile phase A: water (FA), mobile phase B: MeCN, gradient: B from 50% to 80% in 10 min, hold 100% B for 2 min, flow rate: 25 mL/min, column temperature: 25° C., wavelengths: 220 nm, 254 nm) to afford the title compound (30 mg). $^1$H NMR (CDCl$_3$, 400 MHz) δ 8.66 (s, 1H), 6.89 (br s, 1H), 4.58-4.54 (m, 2H), 4.52-4.40 (m, 4H), 4.39-4.27 (m, 1H), 2.47-2.34 (m, 2H), 2.29 (s, 3H), 2.15-2.04 (m, 2H), 2.00-1.92 (m, 2H), 1.85-1.82 (m, 2H), 1.78-1.73 (m, 2H). LCMS (method C) (m/z)=416.2 (MH)$^+$ t$_R$=1.45 minutes.

Example 45: 8-Chloro-3-methyl-2-(tetrahydro-2H-pyran-4-yl)-2,4,12,13-tetrahydro-11H-5,7-(azenometheno)dipyrazolo[3,4-b:5',1'-g][1]oxa[4,6,8]triazacycloundecine-11,11-$d_2$

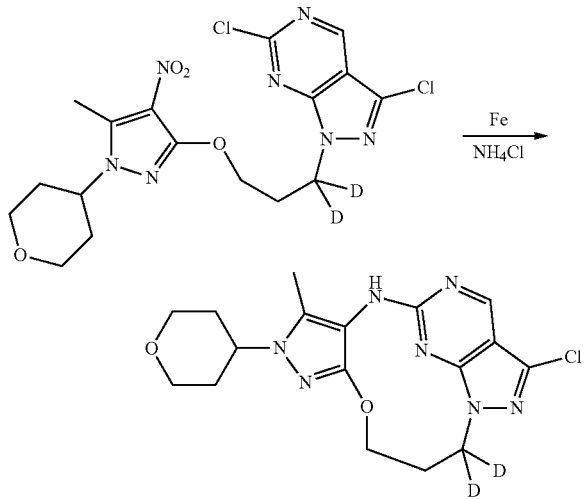

The compound was prepared in a manner similar to Example 1 using 3,6-dichloro-1-[1,1-dideuterio-3-(5-methyl-4-nitro-1-tetrahydropyran-4-yl-pyrazol-3-yl)oxypropyl]pyrazolo[3,4-d]pyrimidine (680 mg, 1.48 mmol), Fe (415 mg, 7.43 mmol), and NH$_4$Cl (397 mg, 7.42 mmol) in EtOH (20 mL) and H$_2$O (2 mL) at 80° C. for 16 h, followed by work-up, and purification by chromatography on silica gel (eluent: Petroleum ether:EtOAc 100:0→0:100) and preparative HPLC (instrument: Gilson GX-215, Gilson 322 Pump, Gilson 156 UV Detector, column: Welch Xtimate C18 150×30 mm×5 μm, mobile phase A: water (NH$_3$H$_2$O+NH$_4$HCO$_3$), mobile phase B: MeCN, gradient: B from 28% to 58% in 25 min then hold at 100% for 2 min, flow rate (mL/min): 35 mL/min, column temperature: 30° C., wavelengths: 220 nm, 254 nm) to afford the title compound (65 mg). $^1$H NMR (CDCl$_3$, 400 MHz) δ 8.66 (s, 1H), 6.67 (br s, 1H), 4.62-4.45 (m, 2H), 4.16-4.08 (m, 3H), 3.62-3.44 (m, 2H), 2.34-2.24 (m, 5H), 1.97-1.92 (m, 2H), 1.84-1.78 (m, 2H). LC-MS (method G) (m/z)=392.2 (MH)$^+$ $t_R$=1.38 minutes.

Example 46: 8-Chloro-3-methyl-2-(tetrahydro-2H-pyran-4-yl)-2,4,12,13-tetrahydro-11H-5,7-(azenometheno)dipyrazolo[3,4-b:5',1'-g][1]oxa[4,6,8]triazacycloundecine-13,13-$d_2$

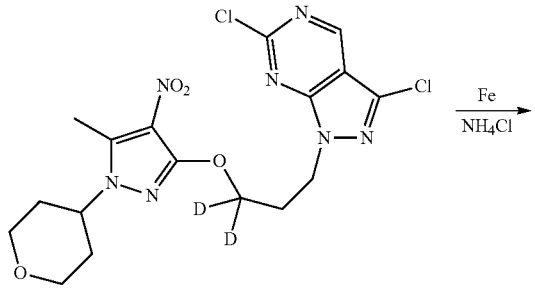

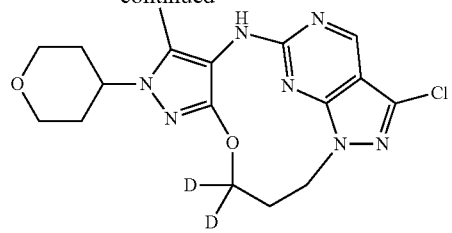

The compound was prepared in a manner similar to Example 1 using 3,6-dichloro-1-[3,3-dideuterio-3-(5-methyl-4-nitro-1-tetrahydropyran-4-yl-pyrazol-3-yl)oxypropyl]pyrazolo[3,4-d]pyrimidine (700 mg, 1.5 mmol), Fe (427 mg, 7.64 mmol), and NH$_4$Cl (409 mg, 7.64 mmol) in EtOH (30 mL) and H$_2$O (5 mL) at 80° C. for 15 h, followed by work-up, and purification by chromatography on silica gel (eluent: Petroleum ether:EtOAc 100:0→30:70) and preparative HPLC (instrument: Gilson GX-281 Liquid Handler, Gilson 322 Pump, Gilson 156 UV Detector, column: Welch Xtimate C18 150×30 mm×5 μm, mobile phase: A: water (NH$_3$H$_2$O+NH$_4$HCO$_3$), mobile phase B: MeCN, gradient: B from 28% to 58% in 25 min then hold at 100% for 2 min, flow rate (mL/min): 35, column temperature: 35° C., wavelengths: 220 nm, 254 nm) to afford the title compound (50 mg). $^1$H NMR (CDCl$_3$, 400 MHz) δ8.65 (s, 1H), 6.89 (br s, 1H), 4.43 (t, J=4.8 Hz, 2H), 4.17-4.06 (m, 3H), 3.52 (t, J=10.8 Hz, 2H), 2.35-2.22 (m, 5H), 2.01-1.88 (m, 2H), 1.85-1.77 (m, 2H). LC-MS (method G) (m/z)=392.1 (MH)$^+$ $t_R$=1.38 minutes.

Example 47 (+)-8-Chloro-2-((3R,4S) or (3S,4R)-3-Fluoro-3-methyltetrahydro-2H-pyran-4-yl)-3-methyl-2,4,12,13-tetrahydro-11H-5,7-(azenometheno)dipyrazolo[3,4-b:5',1'-g][1]oxa[4,6,8]triazacycloundecine and Example 48 (−)-8-Chloro-2-((3R,4S) or (3S,4R)-3-Fluoro-3-methyltetrahydro-2H-pyran-4-yl)-3-methyl-2,4,12,13-tetrahydro-11H-5,7-(azenometheno)dipyrazolo[3,4-b:5',1'-g][1]oxa[4,6,8]triazacycloundecine

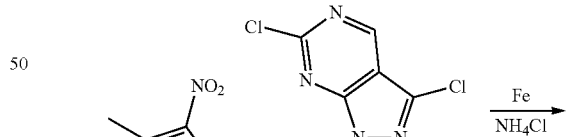

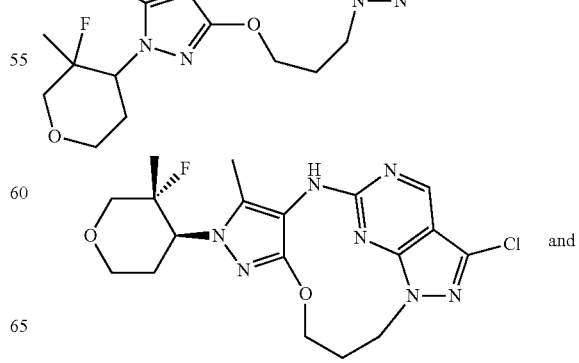

and

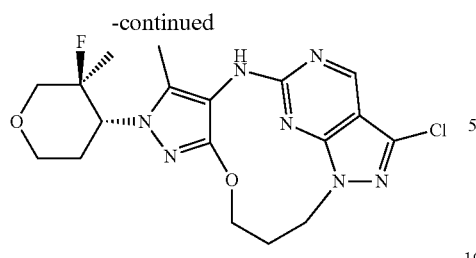

The racemic mixture of Example 47 and Example 48 was prepared in a manner similar to Example 1 using 3,6-dichloro-1-(3-((1-(3-fluoro-3-methyltetrahydro-2H-pyran-4-yl)-5-methyl-4-nitro-1H-pyrazol-3-yl)oxy)propyl)-1H-pyrazolo[3,4-d]pyrimidine (0.16 g, 0.33 mmol), Fe (91 mg, 1.64 mmol), and NH$_4$Cl (88 mg, 1.64 mmol) in EtOH (40 mL) and H$_2$O (4 mL) at 80° C. for 14 h, followed by work-up and purification by chromatography on silica gel (eluent: Petroleum ether:EtOAc (10 v % MeOH) 100:0→50:50) to afford 8-chloro-2-(3-fluoro-3-methyltetrahydro-2H-pyran-4-yl)-3-methyl-2,4,12,13-tetrahydro-11H-5,7-(azenometheno)dipyrazolo[3,4-b:5',1'-g][1]oxa[4,6,8]triazacycloundecine (65 mg). The mixture (65 mg) was separated using preparative chiral SFC (instrument: Waters 150, column: DAICEL CHIRALPAK AD 150×30 mm, 10 μm, mobile phase: supercritical CO$_2$/EtOH (0.1% NH$_3$·H$_2$O, v %)=50/50, flow rate: 130 mL/min, column temperature: 38° C., nozzle pressure: 100 bar, nozzle temperature: 60° C., evaporator temperature: 20° C., trimmer temperature: 25° C., wavelength: 220 nm) to afford:

Example 47 (+)-8-Chloro-2-((3R,4S) or (3S,4R)-3-Fluoro-3-methyltetrahydro-2H-pyran-4-yl)-3-methyl-2,4,12,13-tetrahydro-11H-5,7-(azenometheno)dipyrazolo[3,4-b:5',1'-g][1]oxa[4,6,8]triazacycloundecine (20 mg). $^1$H NMR (CDCl$_3$, 400 MHz) δ 8.66 (s, 1H), 6.75 (br s, 1H), 4.53-4.39 (m, 4H), 4.34-4.24 (m, 1H), 4.22-4.13 (m, 1H), 3.96-3.88 (m, 1H), 3.63-3.53 (m, 1H), 3.52-3.46 (m, 1H), 2.66-2.50 (m, 1H), 2.32 (s, 3H), 2.07-1.90 (m, 3H), 1.32 (d, J=23.6 Hz, 3H). LC-MS (method C) (m/z)=422.2 (MH)$^+$ t$_R$=1.53 minutes. Chiral analytical SFC ((instrument: Waters UPCC with PDA Detector, column: Chiralpak AD-3 50×4.6 mm I.D., 3 μm, mobile phase: A: CO$_2$ B: ethanol (0.05% DEA), gradient: isocratic 40% B, flow rate: 4 mL/min, column temperature: 35° C., ABPR: 1500 psi, run time: 5 min, wavelength: 220 nm), ee>99%, t$_R$=1.06 minutes. [α]$_D^{20}$=+39.3 (c=0.3 g/100 mL, MeOH) and the corresponding enantiomer Example 48 (−)-8-Chloro-2-((3R,4S) or (3S,4R)-3-Fluoro-3-methyltetrahydro-2H-pyran-4-yl)-3-methyl-2,4,12,13-tetrahydro-11H-5,7-(azenometheno)dipyrazolo[3,4-b:5',1'-g][1]oxa[4,6,8]triazacycloundecine (23 mg). $^1$H NMR (CDCl$_3$, 400 MHz) δ 8.66 (s, 1H), 6.76 (br s, 1H), 4.53-4.39 (m, 4H), 4.34-4.24 (m, 1H), 4.22-4.13 (m, 1H), 3.96-3.88 (m, 1H), 3.63-3.53 (m, 1H), 3.52-3.46 (m, 1H), 2.66-2.50 (m, 1H), 2.32 (s, 3H), 2.07-1.90 (m, 3H), 1.32 (d, J=24.0 Hz, 3H). LC-MS (method C) (m/z)=422.2 (MH)$^+$ t$_R$=1.53 minutes. Chiral analytical SFC ((instrument: Waters UPCC with PDA Detector, column: Chiralpak AD-3 50×4.6 mm I.D., 3 μm, mobile phase: A: CO$_2$ B: ethanol (0.05% DEA), gradient: isocratic 40% B, flow rate: 4 mL/min, column temperature: 35° C., ABPR: 1500 psi, run time: 5 min, wavelength: 220 nm), ee>99%, t$_R$=3.00 minutes. [α]$_D^{20}$=−38 (c=0.3 g/100 mL, MeOH).

Example 49 8-Chloro-3-methyl-2-((tetrahydro-2H-pyran-4-yl)methyl)-2,4,12,13-tetrahydro-11H-5,7-(azenometheno)dipyrazolo[3,4-b:5',1'-g][1]oxa[4,6,8]triazacycloundecine

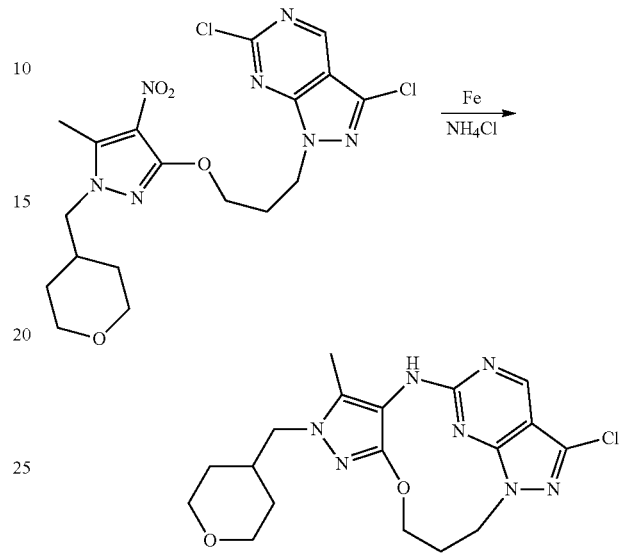

The compound was prepared in a manner similar to Example 1 using 3,6-dichloro-1-(3-((5-methyl-4-nitro-1-((tetrahydro-2H-pyran-4-yl)methyl)-1H-pyrazol-3-yl)oxy)propyl)-1H-pyrazolo[3,4-d]pyrimidine (670 mg, 1.4 mmol), Fe (398 mg, 7.12 mmol), and NH$_4$Cl (381 mg, 7.12 mmol) in EtOH (10 mL) and H$_2$O (1 mL) at 80° C. for 16 h, followed by work-up, and purification by chromatography on silica gel (eluent: Petroleum ether:EtOAc 100:0→0:100) and preparative SFC (instrument: Thar SFC Prep 80, column: DAICEL CHIRALCEL OD-H (250×30 mm, 5 μm), mobile phase: supercritical CO$_2$/ETOH (0.1% NH$_3$·H$_2$O, v %)=70/30, flow rate: 80 mL/min, column temperature: 38° C., nozzle pressure: 100 bar, nozzle temperature: 60° C., evaporator temperature: 20° C., trimmer temperature: 25° C., wavelength: 220 nm) to afford the title compound (50 mg). $^1$H NMR (DMSO-d$_6$, 400 MHz) δ9.36 (s, 1H), 8.78 (br s, 1H), 4.39-4.21 (m, 4H), 3.91-3.74 (m, 4H), 3.28-3.21 (m, 2H), 2.22 (s, 3H), 2.04-1.96 (m, 1H), 1.93-1.65 (m, 2H), 1.47-1.38 (m, 2H), 1.33-1.20 (m, 2H). LC-MS (method C) (m/z)=404.2 (MH)$^+$ t$_R$=1.39 minutes.

Example 50: 8-Chloro-2-((1r,4r)-4-methoxycyclohexyl)-3-(methyl-d$_3$)-2,4,12,13-tetrahydro-11H5,7-(azenometheno)dipyrazolo[3,4-b:5',1'-g][1]oxa[4,6,8]triazacycloundecine

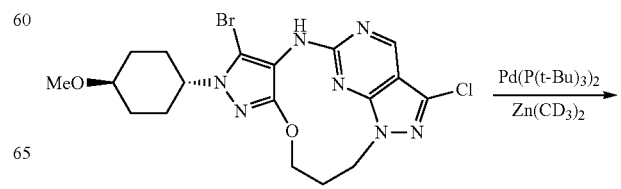

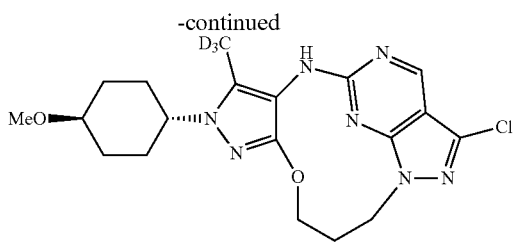

To a mixture of 3-bromo-8-chloro-2-((1r,4r)-4-methoxy-cyclohexyl)-2,4,12,13-tetrahydro-11H-5,7-(azenometheno)dipyrazolo[3,4-b:5',1'-g][1]oxa[4,6,8]triazacycloundecine (235 mg, 0.487 mmol) and bis[tris(tert-butyl)phosphine]palladium (3.3 mg, 0.0065 mmol) was added THF (3 mL) at room temperature. Then LiHMDS in THF (490 μL, 1 M, 0.490 mmol) was added at room temperature. The mixture was stirred for 20 minutes. Then bis(methyl-d₃)zinc in THF-dibutyl ether-Toluene (1.40 mL, 0.47 M, 0.658 mmol) was added. The reaction mixture was heated at 50° C. for 20 h. Additional bis(methyl-d₃)zinc in THF-dibutyl ether-Toluene (0.25 mL, 0.83 molar, 0.21 mmol) was added and then reaction was stirred at 50° C. overnight. The mixture was cooled to room temperature, saturated aqueous NH₄Cl (5 mL) and water (5 mL) were added. The mixture was stirred for 15 minutes at room temperature. The mixture was extracted with EtOAc. The organic phase was washed with saturated aqueous NaCl, dried over Na₂SO₄, and concentrated under reduced pressure. The residue was purified by chromatography on silica gel (eluent: heptane:EtOAc 100:0→0:100) to afford the title compound (152 mg). $^1$H NMR (DMSO-d₆, 600 MHz) δ 9.34 (s, 1H), 8.77 (s, 1H), 4.44-4.12 (m, 4H), 4.02 (td, J=10.0, 4.7 Hz, 1H), 3.25 (s, 3H), 3.19 (td, J=10.8, 5.2 Hz, 1H), 2.52 (m, 1H), 2.08 (m, 2H), 1.80 (m, 5H), 1.29 (qd, J=11.9, 5.2 Hz, 2H). LC-MS (method F) (m/z)=421.3 (MH)⁺ $t_R$=0.64 minutes.

Example 51 (+)-8-Chloro-3-(methyl-d₃)-2-((2R,4R) or (2S,4S)-2-methyltetrahydro-2H-pyran-4-yl)-2,4,12,13-tetrahydro-11H-5,7-(azenometheno)dipyrazolo[3,4-b:5',1'-g][1]oxa[4,6,8]triazacycloundecine

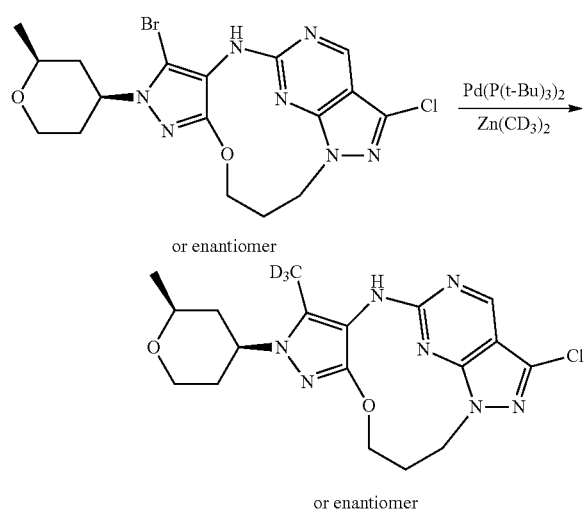

or enantiomer

The compound was prepared in a manner similar to Example 50 using 3-bromo-8-chloro-2-((2R,4R) or (2S,4S)-2-methyltetrahydro-2H-pyran-4-yl)-2,4,12,13-tetrahydro-11H-5,7-(azenometheno)dipyrazolo[3,4-b:5',1'-g][1]oxa[4,6,8]triazacycloundecine, peak1 (559 mg, 1.13 mmol), bis[tris(tert-butyl)phosphine]palladium (6.7 mg, 0.013 mmol), LiHMDS (1.20 mL, 1 M, 1.20 mmol), and bis(methyl-d₃)zinc in THF-dibutyl ether-Toluene (3.20 mL, 0.47 M, 1.5 mmol) in THF (5 mL) at 50° C. for 20 h followed by additional bis(methyl-d₃)zinc in THF-dibutyl ether-Toluene (1.5 mL, 0.83 M, 1.2 mmol) and stirring at 50° C. overnight, work-up and purification by chromatography on silica gel (eluent heptane:EtOAc 100:0→0:100) to afford the title compound (213 mg). $^1$H NMR (DMSO-d₆, 600 MHz) δ 9.37 (s, 1H), 8.78 (s, 1H), 4.44-4.19 (m, 5H), 3.94 (dd, J=11.5, 4.6 Hz, 1H), 3.57-3.52 (m, 1H), 3.52-3.46 (m, 1H), 2.52-2.48 (m, 2H), 1.90 (qd, J=12.4, 4.8 Hz, 1H), 1.85-1.76 (m, 1H), 1.76-1.69 (m, 1H), 1.65 (q, J=11.8 Hz, 1H), 1.14 (dd, J=6.3, 1.2 Hz, 3H). LC-MS (method F) (m/z)=407.3 (MH)⁺ $t_R$=0.60 minutes. $[\alpha]_D^{20}$=+16.1 (c=1.0 g/100 mL, CHCl₃).

Example 52 (−)-8-Chloro-3-(methyl-d₃)-2-((2R,4R) or (2S,4S)-2-methyltetrahydro-2H-pyran-4-yl)-2,4,12,13-tetrahydro-11H-5,7-(azenometheno)dipyrazolo[3,4-b:5',1'-g][1]oxa[4,6,8]triazacycloundecine

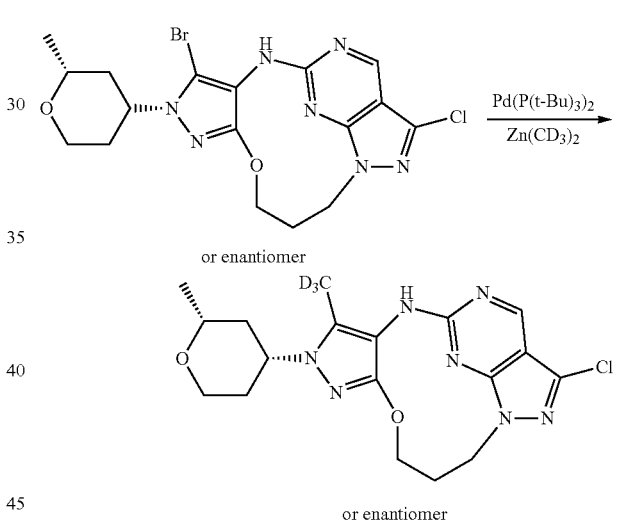

or enantiomer

The compound was prepared in a manner similar to Example 50 using 3-bromo-8-chloro-2-((2R,4R) or (2S,4S)-2-methyltetrahydro-2H-pyran-4-yl)-2,4,12,13-tetrahydro-11H-5,7-(azenometheno)dipyrazolo[3,4-b:5',1'-g][1]oxa[4,6,8]triazacycloundecine, peak2 (473 mg, 0.868 mmol), bis[tris(tert-butyl)phosphine]palladium (6.6 mg, 0.013 mmol), LiHMDS (0.99 mL, 1 M, 0.99 mmol), and bis(methyl-d₃) zinc in THF-dibutyl ether-Toluene (2.40 mL, 0.47 molar, 1.13 mmol) in THF (5 mL) at 50° C. for 22 h followed by additional bis(methyl-d₃)zinc in THF-dibutyl ether-Toluene (1.2 mL, 0.83 molar, 1.0 mmol) and stirring at 50° C. overnight, work-up and purification by chromatography on silica gel (eluent heptane:EtOAc 100:0→0:100) to afford the title compound (192 mg). $^1$H NMR (DMSO-d₆, 600 MHz) δ 9.37 (s, 1H), 8.78 (s, 1H), 4.44-4.13 (m, 5H), 3.94 (m, 1H), 3.59-3.45 (m, 2H), 2.52-2.48 (m, 2H), 1.90 (qd, J=12.4, 4.7 Hz, 1H), 1.84-1.76 (m, 1H), 1.74-1.70 (m, 1H), 1.65 (q, J=11.8 Hz, 1H), 1.14 (dd, J=6.2, 1.0 Hz, 3H). LC-MS (method F) (m/z)=407.3 (MH)⁺ $t_R$=0.61 minutes. $[\alpha]_D^{20}$=−25.0 (c=1.0 g/100 mL, CHCl₃).

Example 53 (+)-(R) or (S)-8-Chloro-3-methyl-2-(4-oxaspiro[2.5]octan-7-yl)-2,4,12,13-tetrahydro-11H-5,7-(azenometheno)dipyrazolo[3,4-b:5',1'-g][1]oxa[4,6,8]triazacycloundecine and Example 54 (−)-(R) or (S)-8-Chloro-3-methyl-2-(4-oxaspiro[2.5]octan-7-yl)-2,4,12,13-tetrahydro-11H-5 7-azenometheno)dipyrazolo[3,4-b:5',1'-g][1]oxa[4,6,8]triazacycloundecine

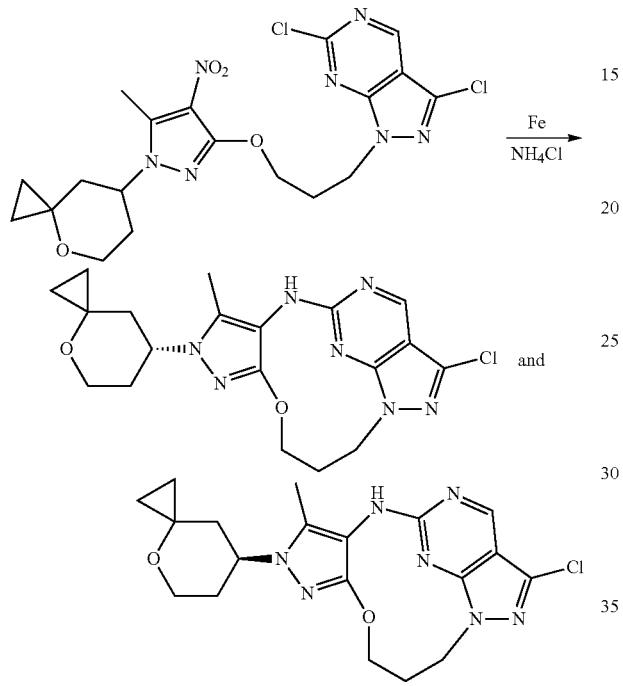

The racemic mixture of Example 53 and Example 54 was prepared in a manner similar to Example 1 using 3,6-dichloro-1-(3-((5-methyl-4-nitro-1-(4-oxaspiro[2.5]octan-7-yl)-1H-pyrazol-3-yl)oxy)propyl)-1H-pyrazolo[3,4-d]pyrimidine (490 mg, 1.0 mmol), Fe (490 mg, 8.77 mmol), and NH$_4$Cl (490 mg, 9.16 mmol) in EtOH (30 mL) and H$_2$O (3 mL) at 80° C. for 15 h, followed by work-up and purification by chromatography on silica gel (eluent: Petroleum ether: EtOAc 100:0→40:60) to afford 8-chloro-3-methyl-2-(4-oxaspiro[2.5]octan-7-yl)-2,4,12,13-tetrahydro-11H-5,7-(azenometheno)dipyrazolo[3,4-b:5',1'-g][1]oxa[4,6,8]triazacycloundecine (270 mg). The racemic mixture (270 mg) was separated into the two enantiomers by preparative chiral SFC (instrument: SFC150AP, column: DAICEL CHIRALCEL OD 250×30 mm, 10 μm, mobile phase: supercritical CO$_2$/IPA (0.1% NH$_3$·H$_2$O, v %)=65/35, flow rate: 100 mL/min, column temperature: 38° C., nozzle pressure: 100 bar, nozzle temperature: 60° C., evaporator temperature: 20° C., trimmer temperature: 25° C., wavelength: 220 nm) to afford:

Example 53 (+)-(R) or (S)-8-Chloro-3-methyl-2-(4-oxaspiro[2.5]octan-7-yl)-2,4,12,13-tetrahydro-11H-5,7-(azenometheno)dipyrazolo[3,4-b:5',1'-g][1]oxa[4,6,8]triazacycloundecine (90 mg). $^1$H NMR (CDCl$_3$, 400 MHz) δ 8.66 (s, 1H), 6.80 (br s, 1H), 4.60-4.37 (m, 4H), 4.36-4.22 (m, 1H), 4.06-3.94 (m, 1H), 3.77-3.53 (m, 1H), 2.89-2.65 (m, 1H), 2.43-2.24 (m, 4H), 2.05-1.91 (m, 2H), 1.89-1.83 (m, 1H), 1.32-1.25 (m, 1H), 0.98-0.90 (m, 1H), 0.80-0.69 (m, 1H), 0.63-0.53 (m, 1H), 0.49-0.36 (m, 1H). LC-MS (method C) (m/z)=416.2 (MH)$^+$ t$_R$=1.54 minutes. Chiral analytical SFC ((instrument: Waters UPCC with PDA Detector, column: Chiralcel OD-3 150×4.6 mm I.D., 3 μm, mobile phase: 40% of iso-propanol (0.05% DEA) in CO$_2$, flow rate: 2.5 mL/min, column temperature: 35° C., ABPR: 1500 psi, run time: 7 min, wavelength: 220 nm), ee=98.3%, t$_R$=2.99 minutes. [α]$_D^{20}$=+68.0 (c=0.1 g/100 mL, MeOH) and the corresponding enantiomer Example 54 (−)-(R) or (S)-8-Chloro-3-methyl-2-(4-oxaspiro[2.5]octan-7-yl)-2,4,12,13-tetrahydro-11H-5,7-(azenometheno)dipyrazolo[3,4-b:5',1'-g][1]oxa[4,6,8]triazacycloundecine (90 mg). $^1$H NMR (CDCl$_3$, 400 MHz) δ 8.65 (s, 1H), 6.80 (br s, 1H), 4.54-4.39 (m, 4H), 4.35-4.20 (m, 1H), 4.07-3.95 (m, 1H), 3.71-3.58 (m, 1H), 2.84-2.71 (m, 1H), 2.40-2.24 (m, 4H), 2.04-1.91 (m, 2H), 1.90-1.83 (m, 1H), 1.33-1.25 (m, 1H), 0.98-0.90 (m, 1H), 0.78-0.69 (m, 1H), 0.62-0.53 (m, 1H), 0.47-0.38 (m, 1H). LC-MS (method C) (m/z)=416.2 (MH)$^+$ t$_R$=1.54 minutes. Chiral analytical SFC ((instrument: Waters UPCC with PDA Detector, column: Chiralcel OD-3 150×4.6 mm I.D., 3 μm, mobile phase: 40% of iso-propanol (0.05% DEA) in CO$_2$, flow rate: 2.5 mL/min, column temperature: 35° C., ABPR: 1500 psi, run time: 7 min, wavelength: 220 nm), ee>99%, t$_R$=2.04 minutes. [α]$^0$=−72 (c=0.25 g/100 mL, MeOH).

Example 55 (+)-8-Chloro-3-ethyl-2-((3R,4S) or (3S,4R)-3-fluorotetrahydro-2H-pyran-4-yl)-2,4,12,13-tetrahydro-11H-5,7-(azenometheno)dipyrazolo[3,4-b:5',1'-g][1]oxa[4,6,8]triazacycloundecine and Example 56 (−)-8-Chloro-3-ethyl-2-((3R,4S) or (3S,4R)-3-fluorotetrahydro-2H-pyran-4-yl)-2,4,12,13-tetrahydro-11H-5,7-(azenometheno)dipyrazolo[3,4-b:5',1'-g][1]oxa[4,6,8]triazacycloundecine

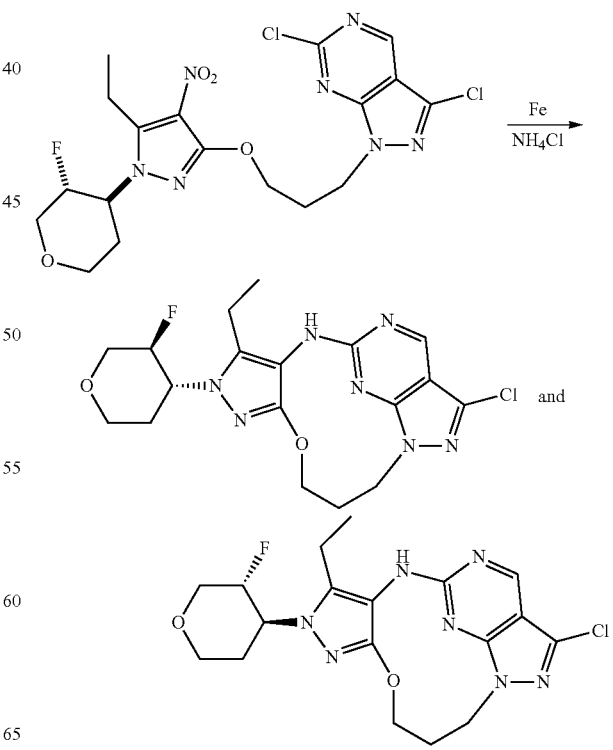

The racemic mixture of Example 55 and Example 56 was prepared in a manner similar to Example 1 using trans-3,6-dichloro-1-(3-((5-ethyl-1-(3-fluorotetrahydro-2H-pyran-4-yl)-4-nitro-1H-pyrazol-3-yl)oxy)propyl)-1H-pyrazolo[3,4-d]pyrimidine (830 mg, 1.70 mmol), Fe (475 mg, 8.50 mmol), and $NH_4Cl$ (455 mg, 8.50 mmol) in EtOH (45 mL) and $H_2O$ (6 mL) at 80° C. for 16 h, followed by work-up and purification by chromatography on silica gel (eluent: Petroleum ether:EtOAc 83:17→50:50) to afford 8-chloro-3-ethyl-2-((3R,4S and 3S,4R)-3-fluorotetrahydro-2H-pyran-4-yl)-2,4,12,13-tetrahydro-11H-5,7-(azenometheno)dipyrazolo[3,4-b:5',1'-g][1]oxa[4,6,8]triazacycloundecine (310 mg). The racemic mixture (310 mg) was separated into the two enantiomers by preparative chiral SFC ((Instrument: SFC-80Q, column: DAICEL CHIRALPAK AD (250 mm×30 mm, 10 μm), mobile phase: supercritical $CO_2$/EtOH (0.1% $NH_3·H_2O$, v %)=45/55, flow rate: 80 mL/min, column temperature: 38° C., nozzle pressure: 100 bar, nozzle temperature: 60° C., evaporator temperature: 20° C., trimmer temperature: 25° C., wavelength: 220 nm) to afford:

Example 55 (+)-8-Chloro-3-ethyl-2-((3R,4S) or (3S,4R)-3-fluorotetrahydro-2H-pyran-4-yl)-2,4,12,13-tetrahydro-11H-5,7-(azenometheno)dipyrazolo[3,4-b:5',1'-g][1]oxa[4,6,8]triazacycloundecine (90 mg). $^1$H NMR ($CDCl_3$, 400 MHz) δ8.66 (s, 1H), 6.69 (br s, 1H), 5.14-4.79 (m, 1H), 4.71-4.36 (m, 4H), 4.28 (dd, J=5.2, 11.2 Hz, 1H), 4.21-3.98 (m, 2H), 3.57-3.45 (m, 1H), 3.44-3.35 (m, 1H), 2.85-2.60 (m, 2H), 2.55-2.38 (m, 1H), 2.02-1.79 (m, 3H), 1.26 (t, J=7.6 Hz, 3H). LC-MS (method C) (m/z)=422.2 (MH)$^+$ $t_R$=1.54 minutes. Chiral analytical SFC (instrument: Waters UPCC with PDA Detector and QDa Detector, column: Chiralpak AD-3 50×4.6 mm I.D., 3 μm, mobile phase: A: $CO_2$ B: ethanol (0.05% DEA), gradient: 40% B, column temperature: 35° C., flow rate: 4 mL/min, ABPR: 1500 psi, wavelength: 220 nm, run time: 3 min). ee>99%, $t_R$=0.98 minutes. $[α]_D^{20}$=+26.0 (c=0.1 g/100 mL, MeOH) and the corresponding enantiomer Example 56 (−)-8-Chloro-3-ethyl-2-((3R,4S) or (3S,4R)-3-fluorotetrahydro-2H-pyran-4-yl)-2,4,12,13-tetrahydro-11H-5,7-(azenometheno)dipyrazolo[3,4-b:5',1'-g][1]oxa[4,6,8]triazacycloundecine (85 mg). $^1$H NMR ($CDCl_3$, 400 MHz) δ8.66 (s, 1H), 6.75 (br s, 1H), 5.08-4.79 (m, 1H), 4.60-4.35 (m, 4H), 4.28 (dd, J=5.2, 11.2 Hz, 1H), 4.21-4.00 (m, 2H), 3.57-3.46 (m, 1H), 3.45-3.35 (m, 1H), 2.83-2.61 (m, 2H), 2.55-2.40 (m, 1H), 2.04-1.90 (m, 3H), 1.26 (t, J=7.6 Hz, 3H). LC-MS (method C) (m/z)=422.2 (MH)$^+$ $t_R$=1.54 minutes. Chiral analytical SFC (instrument: Waters UPCC with PDA Detector and QDa Detector, column: Chiralpak AD-3 50×4.6 mm I.D., 3 μm, mobile phase: A: $CO_2$ B: ethanol (0.05% DEA), gradient: 40% B, column temperature: 35° C., flow rate: 4 mL/min, ABPR: 1500 psi, wavelength: 220 nm, run time: 3 min), ee>99%, $t_R$=1.71 minutes. $[α]_D^{20}$=−28.0 (c=0.1 g/100 mL, MeOH)

Example 57: 8-Chloro-3-ethyl-2-((1r,4r)-4-methoxycyclohexyl)-2,4,12,13-tetrahydro-11H-5,7-(azenometheno)dipyrazolo[3,4-b:5',1'-g][1]oxa[4,6,8]triazacycloundecine

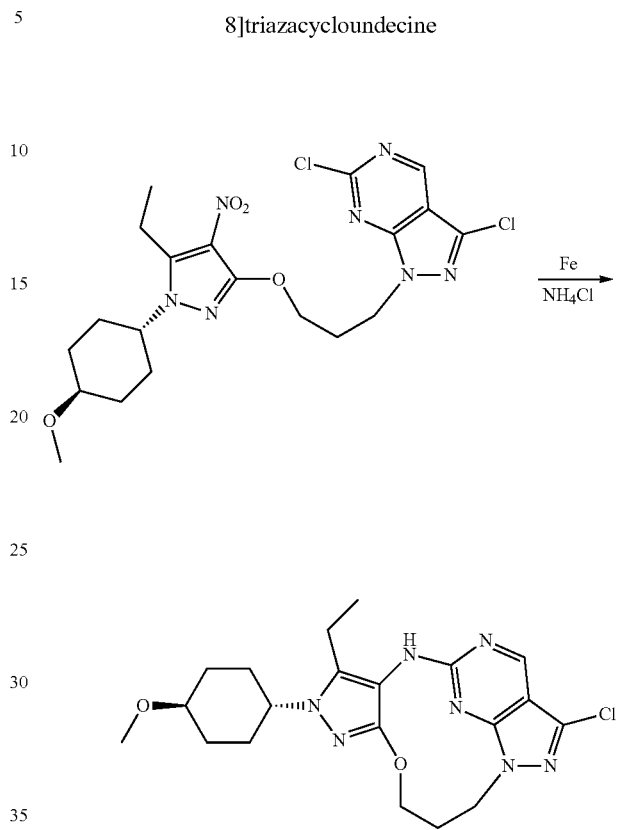

The compound was prepared in a manner similar to Example 1 using 3,6-dichloro-1-(3-((5-ethyl-1-((1r,4r)-4-methoxycyclohexyl)-4-nitro-1H-pyrazol-3-yl)oxy)propyl)-1H-pyrazolo[3,4-d]pyrimidine (1 g, 2 mmol), Fe (560 mg, 10.0 mmol), and $NH_4Cl$ (537 mg, 10.0 mmol) in EtOH (40 mL) and $H_2O$ (6 mL) at 80° C. for 16 h, followed by work-up, and purification by chromatography on silica gel (eluent: Petroleum ether:EtOAc 83:17→50:50) and preparative SFC (instrument: SFC-80Q, column: DAICEL CHIRALCEL OD (250 mm×30 mm, 10 μm), mobile phase: supercritical $CO_2$/EtOH (0.1% $NH_3·H_2O$, v %)=75/25, flow rate: 100 mL/min, column temperature: 38° C., nozzle pressure: 100 bar, nozzle temperature: 60° C., evaporator temperature: 20° C., trimmer temperature: 25° C., wavelength: 220 nm) to afford the title compound (60 mg). $^1$H NMR ($CDCl_3$, 400 MHz) δ8.65 (s, 1H), 6.72 (br s, 1H), 4.52-4.37 (m, 4H), 3.98-3.81 (m, 1H), 3.39 (s, 3H), 3.33-3.23 (m, 1H), 2.69 (q, J=7.6 Hz, 2H), 2.28-2.18 (m, 2H), 2.14-1.86 (m, 6H), 1.41-1.30 (m, 2H), 1.25 (t, J=7.6 Hz, 3H). LC-MS (method C) (m/z)=432.2 (MH)$^+$ $t_R$=1.61 minutes.

Example 58 (+)-(R) or (S)-8-Chloro-3-(methyl-d₃)-
2-(oxepan-4-yl)-2,4,12,13-tetrahydro-11H-5,7-
(azenometheno)dipyrazolo[3,4-b:5',1'-g][1]oxa[4,6,
8]triazacycloundecine and Example 59 (−)-(R) or (S)-8-Chloro-3-(methyl-d₃)-
2-(oxepan-4-yl)-2,4,12,13-tetrahydro-11H-5,7-
(azenometheno)dipyrazolo[3,4-b:5',1'-g][1]oxa[4,6,
8]triazacycloundecine

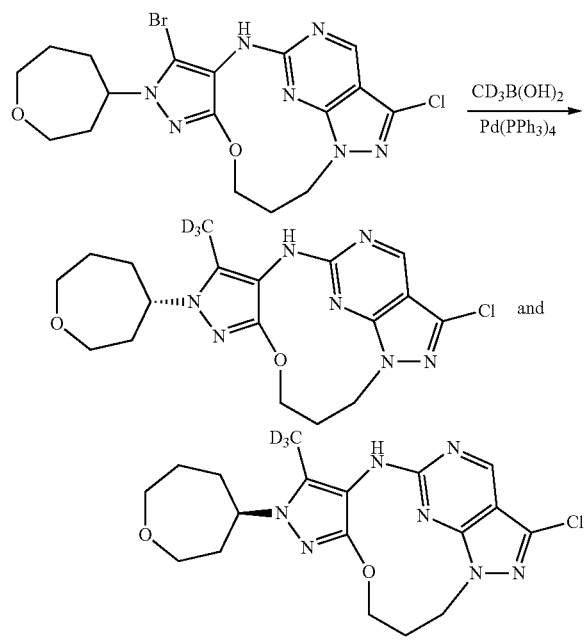

To a mixture of 3-bromo-8-chloro-2-(oxepan-4-yl)-2,4,
12,13-tetrahydro-11H-5,7-(azenometheno)dipyrazolo[3,4-b:5',1'-g][1]oxa[4,6,8]triazacycloundecine (0.48 g, 1.02 mmol), trideuteriomethylboronic acid (129 mg, 2.05 mmol) and K₂CO₃ (283 mg, 2.05 mmol) in a mixture of 1,4-dioxane (50 mL) and H₂O (12.5 mL) at 20° C. was added Pd(PPh₃)₄ (118 mg, 0.1 mmol). The reaction mixture was heated at 100° C. for 16 h. The reaction mixture was concentrated under reduced pressure. The residue was purified by chromatography on silica gel (eluent: heptane:EtOAc (10 v % MeOH and 10 v % DCM) 100:0→50:50) to afford a racemic mixture of Example 58 and Example 59 (0.29 g). The racemic material (330 mg) was separated into the two enantiomers by preparative chiral SFC (instrument: SFC-80Q, column: CHIRALPAK AD 250×30 mm, 10 μm, mobile phase: supercritical CO₂/IPA (0.1% NH₃—H₂O, v %)=55/45, flow Rate: 80 mL/min, column temperature: 38, ° C., nozzle pressure: 100 bar, nozzle temperature: 60° C., evaporator temperature: 20° C., trimmer temperature: 25° C., wavelength: 220 nm) to afford:

Example 58 (+)-(R) or (S)-8-Chloro-3-(methyl-d₃)-2-(oxepan-4-yl)-2,4,12,13-tetrahydro-11H-5,7-(azenometheno)dipyrazolo[3,4-b:5',1'-g][1]oxa[4,6,8]triazacycloundecine (128 mg). $^1$H NMR (DMSO-d₆, 400 MHz) δ 9.37 (s, 1H), 8.78 (s, 1H), 4.38-4.22 (m, 5H), 3.80-3.70 (m, 2H), 3.68-3.56 (m, 2H), 2.20-2.09 (m, 1H), 2.08-2.00 (m, 1H), 1.99-1.92 (m, 1H), 1.91-1.68 (m, 5H). LC-MS (method C) (m/z)=407.2 (MH)⁺ $t_R$=1.45 minutes. Chiral analytical SFC (instrument: Agilent 1260 with DAD Detector, column: Chiralpak AD-3 100×4.6 mm I.D., 3 μm, mobile phase: A: CO₂ B: IPA (0.05% DEA), gradient: from 5% to 40% of B in 1.5 min and hold 40% for 3 min, then 5% of B for 1.5 min, flow rate: 2.5 mL/min, column temperature: 40° C., ABPR: 1500 psi, run time: 10 min, wavelength: 220 nm) ee>99%, $t_R$=8.03 minutes. $[α]_D^{20}$=+6.5 (c=0.4 g/100 mL, CHCl₃) and the corresponding enantiomer Example 59: (−)-(R) or (S)-8-chloro-3-(methyl-d₃)-2-(oxepan-4-yl)-2,4,12,13-tetrahydro-11H-5,7-(azenometheno)dipyrazolo[3,4-b:5',1'-g][1]oxa[4,6,8]triazacycloundecine (137 mg). $^1$H NMR (DMSO-d₆, 400 MHz) δ 9.37 (s, 1H), 8.78 (s, 1H), 4.37-4.23 (m, 5H), 3.78-3.70 (m, 2H), 3.67-3.56 (m, 2H), 2.20-2.10 (m, 1H), 2.08-2.00 (m, 1H), 1.99-1.92 (m, 1H), 1.92-1.69 (m, 5H). LC-MS (method C) (m/z)=407.2 (MH) $t_R$=1.45 minutes. Chiral analytical SFC (instrument: Agilent 1260 with DAD Detector, column: Chiralpak AD-3 100×4.6 mm I.D., 3 μm, mobile phase: A: CO₂ B: IPA (0.05% DEA), gradient: from 5% to 40% of B in 1.5 min and hold 40% for 3 min, then 5% of B for 1.5 min, flow rate: 2.5 mL/min, column temperature: 40° C., ABPR: 1500 psi, run time: 10 min, wavelength: 220 nm) ee=98.3%, $t_R$=8.57 minutes. $[α]^{20}$=−7.5 (c=0.4 g/100 mL, CHCl₃).

Example 60 (R) or (S)-8-Chloro-3-(methyl-d₃)-2-
(tetrahydro-2H-pyran-3-yl)-2,4,12,13-tetrahydro-
11H-5,7-(azenometheno)dipyrazolo[3,4-b:5',1'-g][1]
oxa[4,6,8]triazacycloundecine, peak 1 and Example 61 (R) or (S)-8-Chloro-3-(methyl-d₃)-2-
(tetrahydro-2H-pyran-3-yl)-2,4,12,13-tetrahydro-
11H-5,7-(azenometheno)dipyrazolo[3,4-b:5',1'-g][1]
oxa[4,6,8]triazacycloundecine, peak 2

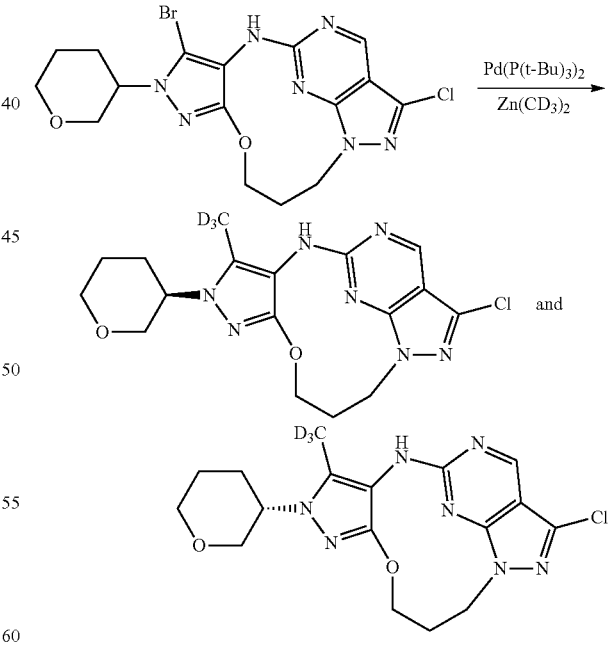

The racemic mixture of Example 60 and Example 61 was prepared in a manner similar to Example 50 using 3-bromo-8-chloro-2-(tetrahydro-2H-pyran-3-yl)-2,4,12,13-tetrahydro-11H5,7-(azenometheno)dipyrazolo[3,4-b:5',1'-g][1]oxa[4,6,8]triazacycloundecine (492 mg, 0.909 mmol), bis[tris(tert-butyl)phosphine]palladium (5.5 mg, 0.011 mmol), LiHMDS (1.05 mL, 1 M, 1.05 mmol), and bis(methyl-d$_3$) zinc in THF-dibutyl ether-toluene (2.60 mL, 0.47 M, 1.22 mmol) in THF (5 mL) at 50° C. for 20 h followed by additional bis(methyl-d$_3$)zinc in THF-dibutyl ether-toluene (1 mL, 0.83 M, 0.8 mmol) and stirring at 50° C. overnight, work-up and purification by chromatography on silica gel (eluent heptane:EtOAc 100:0→0:100) to afford 8-chloro-3-(methyl-d3)-2-(tetrahydro-2H-pyran-3-yl)-2,4,12,13-tetrahydro-11H-5,7-(azenometheno)dipyrazolo[3,4-b:5',1'-g][1]oxa[4,6,8]triazacycloundecine (243 mg). The racemic mixture was separated using preparative SFC (instrument: Shimadzu Nexera Prep SFC, column: Chiralpack-IA 50×250 mm, 5 μm, mobile phase: supercritical CO$_2$/EtOH (0.1% DEA, v %)=60/40, flow rate: 60 mL/min, column temperature: 40° C., nozzle pressure: 100 bar, nozzle temperature: 40° C., wavelength: 254 nm) to afford:

Example 60 (R) or (S)-8-Chloro-3-(methyl-d$_3$)-2-(tetrahydro-2H-pyran-3-yl)-2,4,12,13-tetrahydro-11H-5,7-(azenometheno)dipyrazolo[3,4-b:5',1'-g][1]oxa[4,6,8]triazacycloundecine, peak 1 (94 mg). $^1$H NMR (DMSO-d$_6$, 600 MHz) δ 9.49 (s, 1H), 8.89 (s, 1H), 4.53-4.33 (m, 4H), 4.21 (m, 1H), 3.96 (td, J=10.4, 3.7 Hz, 2H), 3.58 (t, J=10.6 Hz, 1H), 3.44-3.41 (m, 1H), 2.65 (m, 2H), 2.20-2.01 (m, 2H), 1.97-1.69 (m, 2H). LC-MS (method F) (m/z)=393.3 (MH)$^+$ t$_R$=0.59 minutes. Chiral analytical SFC (instrument: AuroraSFC Fusion5/Agilent, column: Chiralpack-IA 6×150 mm, 5 μm, mobile phase: supercritical CO$_2$/EtOH (96% containing 0.1% DEA, v %)=60/40, flow rate: 4.0 mL/min, column temperature: 35° C., ABPR: 150 bar, run time: 5 min, wavelength: 254 nm) ee=96.8%, t$_R$=1.85 minutes.
and the corresponding enantiomer Example 61 (R) or (S)-8-Chloro-3-(methyl-d$_3$)-2-(tetrahydro-2H-pyran-3-yl)-2,4,12,13-tetrahydro-11H-5,7-(azenometheno)dipyrazolo[3,4-b:5',1'-g][1]oxa[4,6,8]triazacycloundecine, peak 2 (90 mg). $^1$H NMR (DMSO-d$_6$, 600 MHz) δ 9.39 (s, 1H), 8.78 (s, 1H), 4.46-4.26 (m, 4H), 4.11 (tt, J=10.1, 4.6 Hz, 1H), 3.86 (td, J=10.3, 3.6 Hz, 2H), 3.48 (t, J=10.6 Hz, 1H), 3.34-3.30 (m, 1H), 2.55 (m, 2H), 2.11-1.95 (m, 2H), 1.91-1.63 (m, 2H). LC-MS (method F) (m/z)=393.3 (MH)$^+$ t$_R$=0.61 minutes. Chiral analytical SFC (instrument: AuroraSFC Fusion5/Agilent, column: Chiralpack-IA 6×150 mm, 5 μm, mobile phase: supercritical CO$_2$/EtOH (96% containing 0.1% DEA, v %)=60/40, flow rate: 4.0 mL/min, column temperature: 35° C., ABPR: 150 bar, run time: 5 min, wavelength: 254 nm) ee>99%, t$_R$=2.52 minutes.

Example 62: (−)-8-Chloro-2-((3R,4S) or (3S,4R)-3-fluorotetrahydro-2H-pyran-4-yl)-3-(methyl-d$_3$)-2,4,12,13-tetrahydro-11H-5,7-(azenometheno)dipyrazolo[3,4-b:5',1'-g][1]oxa[4,6,8]triazacycloundecine

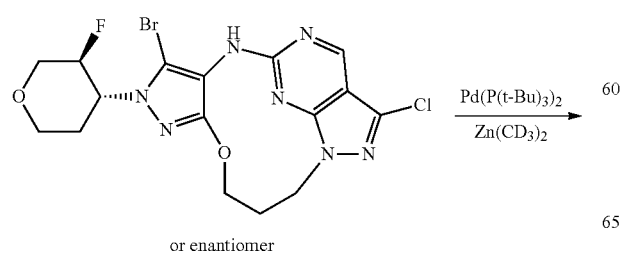

or enantiomer

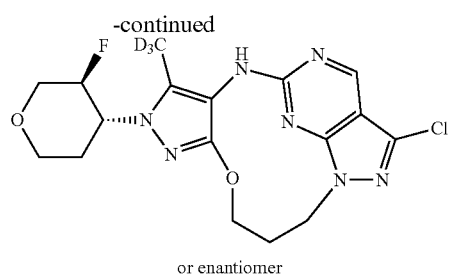

or enantiomer

The compound was prepared in a manner similar to Example 50 using (−)-3-bromo-8-chloro-2-((3R,4S) or (3S,4R)-3-fluorotetrahydro-2H-pyran-4-yl)-2,4,12,13-tetrahydro-11H-5,7-(azenometheno)dipyrazolo[3,4-b:5',1'-g][1]oxa[4,6,8]triazacycloundecine (101 mg, 0.214 mmol), bis[tris(tert-butyl)phosphine]palladium (14 mg, 0.027 mmol), LiHMDS (0.220 mL, 1 M, 0.220 mmol), and bis(methyl-d$_3$)zinc in THF-dibutyl ether-toluene (0.40 mL, 0.81 M, 0.324 mmol) in THF (2.0 mL) at 50° C. for 20 h followed by additional bis(methyl-d$_3$)zinc in THF-dibutyl ether-toluene (1.5 mL, 0.83 M, 1.2 mmol) and stirring at 50° C. overnight, work-up and purification by chromatography on silica gel (eluent heptane:EtOAc 100:0→0:100) and preparative SFC (instrument: Shimadzu Nexera Prep SFC, column: 2-ethylpyridin 21.2×150 mm, 3 μm, mobile phase: supercritical CO$_2$/EtOH (0.1% DEA, v %)=90/10, flow rate: 60 mL/min, column temperature: 40° C., nozzle pressure: 100 bar, nozzle temperature: 40° C., wavelength: 254 nm) to afford the title compound (20 mg). $^1$H NMR (CDCl$_3$, 600 MHz) δ 8.67 (s, 1H), 6.59 (s, 1H), 4.98-4.75 (m, 1H), 4.62-4.37 (m, 4H), 4.27 (m, 1H), 4.20-4.03 (m, 2H), 3.51 (m, 1H), 3.39 (td, J=10.5, 9.0, 5.3 Hz, 1H), 2.49 (m, 1H), 2.09-1.84 (m, 3H). LC-MS (method F) (m/z)=411.2 (MH)$^+$ t$_R$=0.59 minutes. [α]$_D^{20}$=−11.4 (c=1.0 g/100 mL, CHCl$_3$).

Example 63: (+)-8-Chloro-2-((3R,4S) or (3S,4R)-3-fluorotetrahydro-2H-pyran-4-yl)-3-(methyl-d$_3$)-2,4,12,13-tetrahydro-11H-5,7-(azenometheno)dipyrazolo[3,4-b:5',1'-g][1]oxa[4,6,8]triazacycloundecine

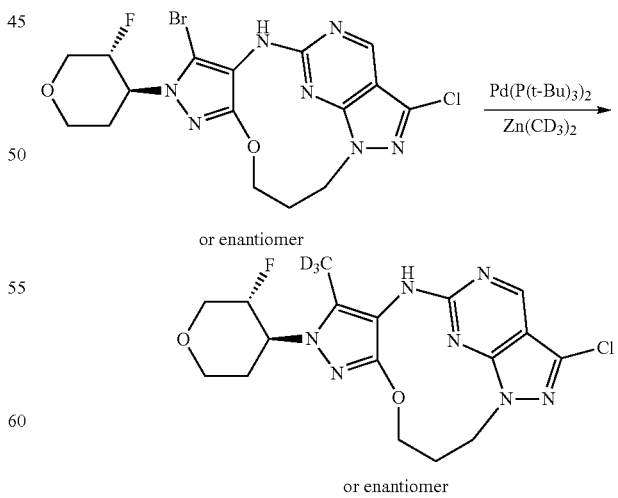

or enantiomer

The compound was prepared in a manner similar to Example 50 using (+)-3-bromo-8-chloro-2-((3R,4S) or (3S,4R)-3-fluorotetrahydro-2H-pyran-4-yl)-2,4,12,13-tetrahydro-11H-5,7-(azenometheno)dipyrazolo[3,4-b:5',1'-g][1]oxa[4,6,8]triazacycloundecine (127 mg, 0.268 mmol), bis[tris(tert-butyl)phosphine]palladium (16 mg, 0.031 mmol), LiHMDS (0.28 mL, 1 M, 0.28 mmol), and bis(methyl-d$_3$) zinc in THF-dibutyl ether-toluene (0.500 mL, 0.81 M, 0.41 mmol) in THF (2.5 mL) at 50° C. for 18 h, work-up and purification by chromatography on silica gel (eluent heptane:EtOAc 100:0→0:100) and preparative SFC (instrument: Shimadzu Nexera Prep SFC, column: Chiralcel-OD-H 21.2×250 mm, 5 μm, mobile phase: supercritical CO$_2$/EtOH (0.1% DEA, v %)=80/20, flow rate: 60 mL/min, column temperature: 40° C., nozzle pressure: 100 bar, nozzle temperature: 40° C., wavelength: 254 nm) to afford the title compound (15 mg). $^1$H NMR (CDCl$_3$, 600 MHz) δ 8.67 (s, 1H), 6.58 (s, 1H), 4.98-4.75 (m, 1H), 4.65-4.34 (m, 4H), 4.26 (m, 1H), 4.21-4.02 (m, 2H), 3.51 (ddd, J=14.2, 11.1, 2.1 Hz, 1H), 3.38 (m, 1H), 2.49 (qd, J=11.3, 9.5, 6.4 Hz, 1H), 2.12-1.84 (m, 3H). LC-MS (method F) (m/z)=411.2 (MH)$^+$ t$_R$=0.59 minutes. [α]$_D^{20}$=+42 (c=1.0 g/100 mL, CHCl$_3$).

Example 64: (−)-(R) or (S)-8-Chloro-3-(methyl-d$_3$)-2-(4-oxaspiro[2.5]octan-7-yl)-2,4,12,13-tetrahydro-11H-5,7-(azenometheno)dipyrazolo[3,4-b:5',1'-g][1]oxa[4,6,8]triazacycloundecine

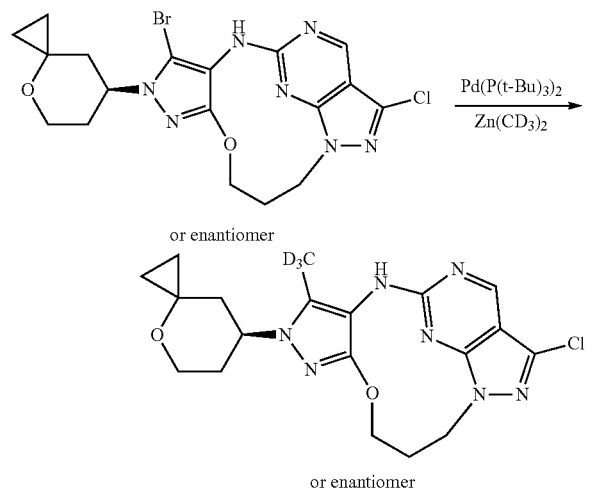

or enantiomer

The compound was prepared in a manner similar to Example 50 using (−)-(R) or (S)-3-bromo-8-chloro-2-(4-oxaspiro[2.5]octan-7-yl)-2,4,12,13-tetrahydro-11H-5,7-(azenometheno)dipyrazolo[3,4-b:5',1'-g][1]oxa[4,6,8]triazacycloundecine (102 mg, 0.213 mmol), bis[tris(tert-butyl)phosphine]palladium (16 mg, 0.031 mmol), LiHMDS (0.22 mL, 1 M, 0.22 mmol), and bis(methyl-d$_3$)zinc in THF-dibutyl ether-toluene (0.400 mL, 0.80 M, 0.32 mmol) in THF (2.0 mL) at 50° C. for 18 h, followed by additional bis(methyl-d$_3$)zinc in THF-dibutyl ether-toluene (0.45 mL, 0.80 M, 0.36 mmol), stirring at 50° C. overnight, followed by a third batch of bis(methyl-d$_3$)zinc in THF-dibutyl ether-toluene (0.45 mL, 0.80 M, 0.36 mmol) and stirring overnight at 50° C., work-up and purification by chromatography on silica gel (eluent heptane:EtOAc 100:0→0:100) to afford the title compound (35 mg). $^1$H NMR (CDCl$_3$, 600 MHz) δ 8.66 (s, 1H), 6.60 (br s, 1H), 4.63-4.35 (m, 4H), 4.27 (m, 1H), 3.99 (ddd, J=11.8, 4.7, 2.6 Hz, 1H), 3.64 (m, 1H), 2.77 (m, 1H), 2.33 (m, 1H), 1.96 (m, 2H), 1.86 (dq, J=13.2, 2.2 Hz, 1H), 1.28 (ddt, J=14.9, 4.2, 2.0 Hz, 1H), 0.93 (td, J=10.0, 6.1 Hz, 1H), 0.74 (ddq, J=8.6, 4.5, 2.2 Hz, 1H), 0.57 (m, 1H), 0.42 (dt, J=9.5, 3.5 Hz, 1H). LC-MS (method F) (m/z)=419.2 (MH)$^+$ t$_R$=0.64 minutes. [α]$_D^{20}$=−78.4 (c=0.98 g/100 mL, CHCl$_3$).

Example 65: (+)-(R) or (S)-8-Chloro-3-(methyl-d$_3$)-2-(4-oxaspiro[2.5]octan-7-yl)-2,4,12,13-tetrahydro-11H-5,7-(azenometheno)dipyrazolo[3,4-b:5',1'-g][1]oxa[4,6,8]triazacycloundecine

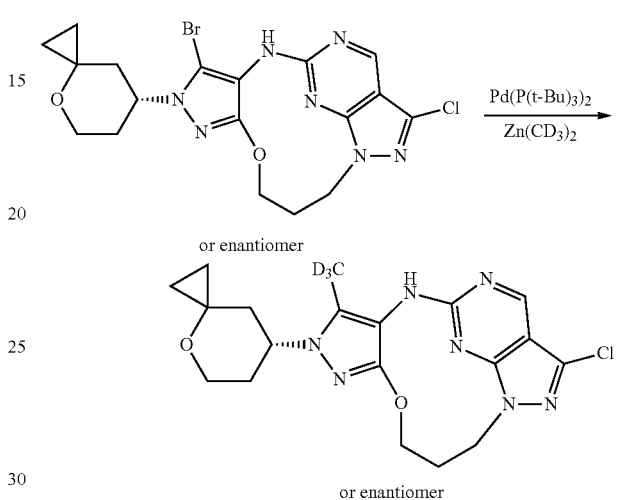

or enantiomer

The compound was prepared in a manner similar to Example 50 using (+)-(R) or (S)-3-bromo-8-chloro-2-(4-oxaspiro[2.5]octan-7-yl)-2,4,12,13-tetrahydro-11H-5,7-(azenometheno)dipyrazolo[3,4-b:5',1'-g][1]oxa[4,6,8]triazacycloundecine (102 mg, 0.21 mmol), bis[tris(tert-butyl)phosphine]palladium (21 mg, 0,041 mmol), LiHMDS (0.22 mL, 1 M, 0.22 mmol), and bis(methyl-d$_3$)zinc in THF-dibutyl ether-toluene (0.400 mL, 0.80 M, 0.32 mmol) in THF (2.0 mL) at 50° C. for 18 h, followed by additional bis(methyl-d$_3$)zinc in THF-dibutyl ether-toluene (0.45 mL, 0.80 M, 0.36 mmol), stirring at 50° C. overnight, followed by a third batch of bis(methyl-d$_3$)zinc in THF-dibutyl ether-toluene (0.45 mL, 0.80 M, 0.36 mmol) and stirring overnight at 50° C., work-up and purification by chromatography on silica gel (eluent heptane:EtOAc 100:0→0:100) to afford the title compound (30 mg). $^1$H NMR (CDCl$_3$, 600 MHz) δ 8.66 (s, 1H), 6.59 (br s, 1H), 4.55-4.36 (m, 4H), 4.27 (td, J=9.8, 8.2, 5.8 Hz, 1H), 4.00 (ddd, J=11.5, 4.5, 2.4 Hz, 1H), 3.64 (m, 1H), 2.77 (t, J=12.4 Hz, 1H), 2.33 (m, 1H), 1.96 (m, 2H), 1.86 (dq, J=13.2, 2.2 Hz, 1H), 1.28 (m, 1H), 0.93 (m, 1H), 0.74 (ddd, J=8.6, 4.4, 2.1 Hz, 1H), 0.57 (dt, J=6.8, 2.7 Hz, 1H), 0.41 (m, 1H). LC-MS (method F) (m/z)=419.3 (MH)$^+$ t$_R$=0.64 minutes. [α]$_D^{20}$=+70.4 (c=0.98 g/100 mL, CHCl$_3$).

LRRK2 Wild-Type and G2019S Kinase Activity Assay

LRRK2 kinase activity was measured using a LanthaScreen kinase activity assay available from Invitrogen (Life Technologies Corporation). The assay is a homogeneous time resolved fluorescence resonance energy transfer (TR-FRET) assay that measures phosphorylation of a fluorescein-labelled peptide substrate Fluorescein-ERM LRRKtide obtainable from Life Technologies Corporation as a result of LRRK2 kinase activity. The phosphorylated peptide is recognized by a terbium-labelled phospho-specific anti-LRRKtide antibody (pLRRKtide antibody), obtainable from Life Technologies Corporation and, subsequently, the phosphorylated LRRKtide can be quantified by the extent of TR-FRET between the terbium donor and fluorescein acceptor.

The LRRK2 kinase was obtained from Invitrogen (Life Technologies Corporation) and comprises residue 970 to 2527 of the full length human wild-type LRRK2 kinase, or a similar sequence with the G2019S mutation. As discussed above, this mutation increases the kinase activity relative to the wild type. The kinase reactions were performed in a 20 µL volume in 384-well plates. The kinase reaction buffer consisted of 50 mM Tris pH 8.5, 0.01% BRIJ-35, 10 mM $MgCl_2$, 1 mM EGTA, and 2 mM DTT.

In the assay, 1 nM LRRK2 WT or 250 µM LRRK2 G2019S kinase in kinase reaction buffer was incubated with the test compound (typically at 0 to 30 µM) for 30 minutes before the kinase reaction was initiated by addition of 1.3 mM ATP and 0.4 µM fluorescein-LRRKtide. The reaction mixture (20 µl total volume) was incubated for 3.5 h (for LRRK2 WT) and 3 h (for LRRK2 G2019S) at 30° C., before the reaction was terminated by addition of 10 mM EDTA and 1 nM terbium-labelled anti-phospho-LRRKtide antibody (final volume 20 µl). The mixture was further incubated for 30 minutes at RT. TR-FRET was measured by excitation of the terbium-donor with 340 nm light and subsequent (delay time 100 s) measurement of terbium and fluorescein emission at 495 nm and 520 nm, respectively, over a time window of 1000 s. The measurement was repeated 30 times for fluorescein and 30 times for terbium emission with a 1000 s time window between repeats. TR-FRET measurements were performed on a Biotek Synergy plate. The TR-FRET signal was calculated as the emission-ratio at 520 nm over 495 nm.

The TR-FRET ratio readout for test compounds was normalized to 0% inhibition corresponding to TR-FRET ratio measured in control wells with no inhibition of the kinase activity and 100% inhibition corresponding to TR-FRET ratio measured in control wells with inhibitor. Test compound potency ($IC_{50}$) was estimated by nonlinear regression using the sigmoidal dose-response (variable slope) using XIfit 4 (IDBS, Guildford, Surrey, UK, model 205). Were the $IC_{50}$ could not be determined the % inhibition at the highest tested concentration is given by equation 1.

$$y = (A + ((B-A)/(1+((C/x)^D)))) \quad (1)$$

where y is the normalized TR-TRET ratio measurement for a given concentration of test compound, x is the concentration of test compound, A is the estimated efficacy (% inhibition) at infinite compound dilution, and B is the maximal efficacy (% inhibition). C is the $IC_{50}$ value and D is the Hill slope coefficient. $IC_{50}$ estimates were obtained from independent experiment and the logarithmic average was calculated.

Table 2 below shows the $IC_{50}$ values in nM obtained as described above for the exemplified compounds, data is based on n≥2 tests.

TABLE 2

| LRRK2 wild-type and G2019S kinase activity | | |
|---|---|---|
| Example Number | LRRK2 G2019S $IC_{50}$ (nM) | LRRK2 WT $IC_{50}$ (nM) |
| 1 | 18 | 55 |
| 2 | 2.4 | 9.8 |
| 3 | 2.2 | 9.2 |
| 4 | 2.8 | 12 |
| 5 | 7.4 | 23 |

TABLE 2-continued

| LRRK2 wild-type and G2019S kinase activity | | |
|---|---|---|
| Example Number | LRRK2 G2019S $IC_{50}$ (nM) | LRRK2 WT $IC_{50}$ (nM) |
| 6 | 2.2 | 8 |
| 7 | 63 | 210 |
| 8 | 21 | 93 |
| 9 | 57 | 110 |
| 10 | 6.2 | 19 |
| 11 | 4.6 | 14 |
| 12 | 12 | 32 |
| 13 | 2.5 | 9.6 |
| 14 | 4 | 16 |
| 15 | 2.4 | 6.8 |
| 16 | 16 | 60 |
| 17 | 5.8 | 15 |
| 18 | 3.6 | 11 |
| 19 | 3.9 | 13 |
| 20 | 5.1 | 14 |
| 21 | 3.7 | 10 |
| 22 | 3.5 | 10 |
| 23 | 20 | 44 |
| 24 | 4.7 | 14 |
| 25 | 5.1 | 16 |
| 26 | 5.9 | 21 |
| 27 | 7.3 | 25 |
| 28 | 5.3 | 19 |
| 29 | 4.3 | 14 |
| 30 | 4 | 12 |
| 31 | 2.4 | 5.6 |
| 32 | 6.1 | 15 |
| 33 | 5.9 | 18 |
| 34 | 5.7 | 18 |
| 35 | 5.3 | 15 |
| 36 | 7.2 | 23 |
| 37 | 3.7 | 8.5 |
| 38 | 11 | 28 |
| 39 | 7.8 | 19 |
| 40 | 12 | 28 |
| 41 | 6.4 | 17 |
| 42 | 2.9 | 7.9 |
| 43 | 5.3 | 17 |
| 44 | 4.3 | 13 |
| 45 | 3.6 | 13 |
| 46 | 3.1 | 12 |
| 47 | 3.1 | 13 |
| 48 | 18 | 90 |
| 49 | 4.7 | 9.4 |
| 50 | 5.3 | 10 |
| 51 | 5.3 | 9 |
| 52 | 10 | 19 |
| 53 | 1.3 | 3.2 |
| 54 | 0.88 | 2.6 |
| 55 | 1.5 | 5.6 |
| 56 | 2 | 4.9 |
| 57 | 6.2 | 16 |
| 58 | 7 | 19 |
| 59 | 6.2 | 17 |
| 60 | 9 | 25 |
| 61 | 10 | 34 |
| 62 | 5.9 | 17 |
| 63 | 4 | 11 |
| 64 | 5 | 11 |
| 65 | 1.7 | 4.8 |

Method I

Broad Kinase Selectivity

Protein kinase profiling of the inhibitors (Fabian, M. A. et al. inhibitors. Nat. Biotechnol. 23, 329-336 (2005)) were undertaken at a concentration of 0.1 µM and carried out Eurofins DiscoverX scanMAX panel of 403 wild type kinases (primarily of human origin). covering AGC (PKA, PKG, PKC family kinases), CAMK (Calcium/calmodulin-dependent protein kinases), CK1 (Casein kinase 1 kinases), CMGC (CDK, MAPK, GSK3, CLK families), STE (homologs of yeast Sterile 7, Sterile 11, Sterile 20 kinases), TK (Tyrosine kinases), TKL (Tyrosine kinase-like kinases), lipid and atypical kinase families.

Selectivity Score or S-score is a quantitative measure of compound selectivity. It was calculated by dividing the number of kinases that compounds bind to by the total number of distinct kinases tested, excluding mutant variants. S=Number of hits/Number of assays. This value can be calculated using % Ctrl as a potency threshold (below) and provides a quantitative method of describing compound selectivity to facilitate comparison of different compounds.

TABLE 3

Kinase selectivity

| Compound | Selectivity Score Type | Number of Hits | Number of Non-Mutant Kinases | Screening Concentration (nM) | Selectivity Score |
|---|---|---|---|---|---|
| Example 13 | S(35) | 38 | 403 | 100 | 0.094 |
|  | S(10) | 12 | 403 | 100 | 0.03 |
|  | S(1)* | 1 | 403 | 100 | 0.002 |

*LRRK2 WT;
S(35) = (number of non-mutant kinases with % Ctrl < 35)/(number of non-mutant kinases tested);
S(10) = (number of non-mutant kinases with % Ctrl < 10)/(number of non-mutant kinases tested);
S(1) = (number of non-mutant kinases with % Ctrl < 1)/(number of non-mutant kinases tested)

Method II
Hepatocyte Intrinsic Clearance Assay:

Test compounds (final concentration 0.1 µM, 0.05% organic) were incubated for 2 h at 37° C., with shaking, in supplemented Leibovitz L-15 media (pH7.4) containing commercially sourced, pooled donor, cryopreserved hepatocytes (final concentration 1×10$^6$ hepatocytes/mL). The $CL_{int}$ reactions (350 µL) were initiated by addition of test compound. Aliquots (25 µL) were taken at 1, 5, 10, 15, 30, 60, 90 and 120 minutes and then protein crashed with ice-cold acetonitrile containing internal standard (150 µL) then centrifuged (1960 g for 20 minutes at 4° C.). Supernatant was diluted (1:4) with deionized water then analyzed by liquid chromatography (LC)-tandem mass spectrometry (MS/MS). The intrinsic clearances ($CL_{int}$) were calculated from the slope (k) of the linear regressions of percentages of compound remaining in incubation against incubation time, according to equations 2 and 3.

Equation 2:

$$t_{1/2} = \ln(2)/k \quad (2)$$

Equation 3:

$$CL_{int}(L/h/kg \text{ body weight}) = \text{Ln}(2) \times V(L/10^6 \text{ hepatocytes})/t_{1/2}(h) \times \text{hepatocellularity}(10^6 \text{ hepatocytes/g liver}) \times \text{liver weight (g liver/kg body weight)} \quad (3)$$

V=incubation volume=0.001 L/10$^6$ hepatocytes, Human hepatocellularity=120×10$^6$ hepatocytes/g, Human liver weight=20 g/kg body weight.

TABLE 4

Hepatocyte intrinsic clearance for compounds of the invention

| Compound ID | $CL_{int}$ (L/h/kg) |
|---|---|
| Example 2* | 0.85 |
| Example 3** | 0.33 |
| Example 4* | 0.87 |

TABLE 4-continued

Hepatocyte intrinsic clearance for compounds of the invention

| Compound ID | $CL_{int}$ (L/h/kg) |
|---|---|
| Example 13* | 0.36 |
| Example 15** | 0.24 |
| Example 17* | 0.34 |
| Example 18* | <0.24 |
| Example 19* | <0.24 |
| Example 27** | 0.57 |
| Example 29* | 0.38 |
| Example 30* | 0.63 |
| Example 31* | <0.25 |
| Example 32* | <0.24 |
| Example 37* | <0.24 |
| Example 41** | 0.34 |
| Example 42* | 0.38 |
| Example 44* | <0.24 |
| Example 50** | <0.24 |
| Example 51** | <0.24 |
| Example 52** | <0.24 |
| Example 57** | 0.51 |
| Example 58** | 0.30 |
| Example 59** | 0.40 |
| Example 60** | 0.51 |
| Example 61** | <0.24 |
| Example 62** | <0.24 |

*CLint measured on 3 separate occasions;
**CLint measured on a single occasion

Summary/Conclusion: Based on the hepatocyte $CL_{int}$ values the test compounds are classified as having moderately-low to low rates of metabolism.

Method III
GSH adduct screening

Test compounds (final concentration 1 µM, 0.25% organic) were incubated for 3 h at 37° C. in commercially sourced, pooled donor, human liver microsomes (HLM, final concentration 0.5 mg/mL) with and without addition of glutathione (GSH; final concentration 1 µM). The metabolic reaction was initiated by addition of microsomal solution to the mixture of cofactor NADPH (final concentration 1 mM), test compound and GSH. After 3 h of incubation in a water bath at 37° C., the reaction was stopped by addition of 0.2% formic acid in acetonitrile, followed by mixing and centrifugation (16000 g for 5 minutes). Supernatant was diluted (1:1) with HPLC water then analyzed by liquid chromatography (LC)-quadrupole time-of-flight mass spectrometry (QTOF-MS). Accurate mass MS and MS/MS spectra from samples with GSH and without GSH, respectively, were compared to identify detectable GSH and/or cysteine related adducts.

TABLE 5

GSH adduct measurements

| Compound ID | Adduct detected in GSH supplemented HLMs |
|---|---|
| Example 2 | +GSH |
| Example 13* | None detected |
| Example 17 | None detected |
| Example 18 | +GSH |
| Example 19 | +GSH |
| Example 37 | +GSH |
| Example 50 | None detected |
| Example 51 | +GSH |
| Example 52 | +GSH |

*Measured on two separate occasions.

It was found that Examples 13, 17 and 50 did not form GSH adduct based on in vitro experiments.

Method IV
Minipig B/P:

Brain disposition of Example 13 was evaluated in female Gottingen minipigs (n=3, body weight range 13-14 kg). Briefly, test compound was formulated in vehicle (5% DMSO/95% of 20% hydroxypropyl-3-cyclodextrin solution, pH3.0) then administered as an intravenous (IV) bolus (0.28 mg/kg, 1 mL/kg) followed immediately by a constant rate IV infusion (0.60 mg/kg, 2.5 mL/kg) via an ear vein. Serial bloods were collected from the jugular vein at designated time points (0.083, 0.50, 1.00, 1.50 and 1.83 h, n=3 per time point) after IV bolus injection. At the end of infusion (2 h) the minipigs were sacrificed and terminal blood as well as brain samples were taken (n=3). Isolated plasma and brain homogenates were extracted by standard protein precipitation in acetonitrile, containing internal standard, followed by LC-MS/MS analysis using an optimized analytical method. Concentrations of test compound in plasma and brain were quantified against matrix matched calibration standards. The total plasma and brain concentration time data are presented in Table 6 alongside the calculated brain $K_p$ (total brain concentration:total plasma concentration ratio).

TABLE 6

Total concentrations, brain $K_p$ are presented (mean ± stdev from n = 3 minipigs)

| Compound ID | Time point (h) | $C_{Total, plasma}$ (ng/mL) | $C_{Total, brain}$ (ng/mL) | Brain $K_p$ |
|---|---|---|---|---|
| Example 13 | 0.083 | 95 ± 18 | — | — |
| | 0.50 | 89 ± 20 | — | — |
| | 1.00 | 91 ± 9 | — | — |
| | 1.50 | 106 ± 13 | — | — |
| | 1.83 | 105 ± 8 | — | — |
| | 2.00 | 93 ± 11 | 151 ± 11 | 1.63 ± 0.08 |

Method V
Rat B/P:

Brain disposition was evaluated for each compound in male Sprague-Dawley rats (n=3, standard body weight). Briefly, test compound was formulated as a simple suspension (0.5% HPMC in water) then administered by oral gavage (10 mg/kg, 10 mL/kg or 1 mg/kg, 1 mL/kg). At the designated time point (1 h post dose) rats were sacrificed and terminal blood and brain samples taken. Isolated plasma and brain homogenates were extracted by standard protein precipitation in acetonitrile, containing internal standard, followed by LC-MS/MS analysis using an optimized analytical method. Concentrations of test compound in plasma and brain were quantified against matrix matched calibration standards. The total plasma and brain concentration data are presented in Table 7 alongside the calculated brain $K_p$ (total brain concentration:total plasma concentration ratio).

Method VI
Free Fraction in Plasma and Brain Homogenate Methodology:

The free fractions in male Sprague-Dawley rat or female Göttingen minipig plasma ($fu_{plasma}$) and rat brain homogenate ($fu_{brain}$) were determined by equilibrium dialysis using 96-well HTD-dialysis plates with dialysis membranes (molecular weight cut off 12-14 KDa). One side of the HTD-dialysis plate was loaded with matrix (plasma or brain homogenate) and the other side with buffer (100 mM sodium phosphate buffer, pH 7.4). Test compounds were dissolved in DMSO then spiked (5 μL of 0.2 mM) into blank (995 μL) plasma or diluted brain homogenate (1:4 ratio in phosphate buffer) giving a final nominal concentration 1 μM (0.5% DMSO). The matrices were loaded into respective chambers and equilibrated against phosphate buffer for 5 h at 37° C. (in a humidified air incubator with 5% CO2 with shaking). Samples from both chambers (buffer and plasma or brain homogenate) were aliquoted to fresh 96-well polypropylene plates then matrix matched using an equal volume of opposite blank matrix before extraction with cold solvent (3 volumes acetonitrile) containing an appropriate bioanalytical internal standard. After centrifugation (20 min, 3200 g, 4° C.) the supernatants were diluted with appropriate volumes of water and compound concentrations were quantified by LC/MS-MS against matrix matched calibration standards. The $fu_{plasma}$ and $fu_{brain}$ were calculated as a percent free according to equation 4 below.

Equation 4:

$$\text{Percent free} = 100 \times \left( \frac{\frac{1}{D}}{\frac{1}{\frac{[F]}{[T]}} - 1 + \frac{1}{D}} \right) \quad (4)$$

Where [F] is the analyte concentration on the buffer (receiver) side of the membrane; [T] is the analyte concentration on the plasma or brain (donor) side of the membrane; [TO] is the analyte concentration in the plasma or brain sample at time zero; D is matrix dilution factor which is determined as 4 for brain matrix and 1 for plasma matrix in these assays.

TABLE 7

Total plasma and brain concentrations, brain $K_p$, $fu_{brain}/fu_{plasma}$ and brain $K_{p, uu}$ are presented (mean ± stdev from n = 3 rats by oral gavage)

| Compound ID | Oral dose (mg/kg) | Time point (h) | Total plasma concentration (ng/mL) | Total brain concentration (ng/g) | Brain $K_p$ | $fu_{brain}/fu_{plasma}$ (% free) | Brain $K_{p, uu}$ |
|---|---|---|---|---|---|---|---|
| Example 13 | 1 | 1.0 | 74 ± 17 | 130 ± 27 | 1.76 ± 0.04 | 6.9/32.0 | 0.38 ± 0.01 |
| | 3 | 1.0 | 340 ± 78 | 597 ± 169 | 1.74 ± 0.10 | 6.9/32.0 | 0.38 ± 0.02 |
| | 10 | 1.0 | 1639 ± 655 | 2034 ± 462 | 1.30 ± 0.22 | 6.9/32.0 | 0.28 ± 0.05 |
| Example 4 | 10 | 1.0 | 758 ± 145 | 1357 ± 186 | 1.82 ± 0.33 | 5.8/25.3 | 0.42 ± 0.07 |
| Example 5 | 10 | 1.0 | 336 ± 96 | 744 ± 281 | 2.19 ± 0.25 | 4.2/32.2 | 0.29 ± 0.03 |
| Example 6 | 10 | 1.0 | 738 ± 24 | 1459 ± 244 | 1.97 ± 0.27 | 7.7/34.3 | 0.44 ± 0.06 |
| Example 7 | 10 | 1.0 | 1549 ± 527 | 949 ± 463 | 0.63 ± 0.23 | 13/28.7 | 0.28 ± 0.10 |
| Example 10 | 10 | 1 | 314 ± 83 | 502 ± 92 | 1.62 ± 0.16 | 7.1/30.2 | 0.38 ± 0.04 |
| Example 14 | 10 | 1.0 | 280 ± 102 | 421 ± 168 | 1.52 ± 0.37 | 7.6/38.0 | 0.30 ± 0.07 |
| Example 17 | 10 | 1.0 | 653 ± 52 | 1150 ± 59 | 1.76 ± 0.08 | 9.1/27.5 | 0.59 ± 0.03 |
| Example 18 | 10 | 1.0 | 636 ± 265 | 897 ± 292 | 1.47 ± 0.22 | 6.0/25.0 | 0.35 ± 0.05 |

TABLE 7-continued

Total plasma and brain concentrations, brain $K_p$, $fu_{brain}/fu_{plasma}$ and brain $K_{p,uu}$ are presented (mean ± stdev from n = 3 rats by oral gavage)

| Compound ID | Oral dose (mg/kg) | Time point (h) | Total plasma concentration (ng/mL) | Total brain concentration (ng/g) | Brain $K_p$ | $fu_{brain}/fu_{plasma}$ (% free) | Brain $K_{p,uu}$ |
|---|---|---|---|---|---|---|---|
| Example 19 | 10 | 0.5 | 1138 ± 229 | 1433 ± 134 | 1.28 ± 0.13 | 7.6/24.0 | 0.40 ± 0.04 |
| Example 25 | 10 | 1.0 | 38 ± 6 | 110 ± 18 | 2.87 ± 0.04 | 2.7/12.0 | 0.65 ± 0.01 |
| Example 27 | 5 | 1.0 | 273 ± 36 | 443 ± 50 | 1.63 ± 0.03 | 6.4/19.9 | 0.52 ± 0.01 |
| Example 30 | 5 | 1.0 | 210 ± 50 | 427 ± 96 | 2.05 ± 0.18 | 9.5/26.5 | 0.73 ± 0.06 |
| Example 31 | 10 | 1.0 | 133 ± 54 | 215 ± 70 | 1.65 ± 0.13 | 7.5/24.9 | 0.50 ± 0.04 |
| Example 33 | 5 | 1.0 | 43 ± 9 | 37 ± 1.0 | 0.87 ± 0.15 | 5.0/11.0 | 0.40 ± 0.07 |
| Example 37 | 10 | 0.5 | 391 ± 96 | 683 ± 139 | 1.87 ± 0.76 | 4.6/18.2 | 0.47 ± 0.19 |
| Example 38 | 10 | 0.5 | 355 ± 31 | 562 ± 83 | 1.58 ± 0.10 | 9.1/30.0 | 0.48 ± 0.03 |
| Example 40 | 5 | 0.5 | 72 ± 8 | 138 ± 12 | 1.93 ± 0.22 | 4.8/12.7 | 0.72 ± 0.08 |
| Example 41 | 10 | 0.5 | 250 ± 24 | 620 ± 30 | 2.50 ± 0.31 | 4.9/25.2 | ±0.06 |
| Example 42 | 10 | 0.5 | 295 ± 145 | 550 ± 283 | 1.88 ± 0.31 | 3.7/21.7 | 0.32 ± 0.05 |
| Example 44 | 10 | 0.5 | 468 ± 117 | 731 ± 223 | 1.56 ± 0.23 | 4.9/25.5 | 0.30 ± 0.04 |
| Example 47 | 5 | 0.5 | 83 ± 27 | 235 ± 119 | 2.69 ± 0.83 | 5.2/24.8 | 0.57 ± 0.17 |
| Example 53 | 5 | 1 | 203 ± 67 | 363 ± 138 | 1.77 ± 0.16 | 6.3/17.1 | 0.65 ± 0.06 |

Based on the calculated rat brain $K_{p,uu}$ values (parameter describing the extent of brain penetration) Compounds listed in table 7 are classified as being moderately or highly brain penetrant.

Method VII

Free fraction in rat brain slice methodology:

For each test compound, the free fraction in brain was assessed using the more physiologically relevant brain slice model (Loryan et al., 2013; The brain slice method for studying drug distribution in the CNS; Fluids and Barriers of the CNS; 10(6): 1-9). In brief, freshly prepared 300 μm brain slices (n=6 slices per incubation dish) from striatum region of male Sprague-Dawley rat brain were incubated (5 h, 37° C.) in an artificial extracellular fluid (aECF) buffer (129 mM NaCl, 10 mM D-glucose, 3 mM KCl, 1.4 mM $CaCl_2$, 1.2 mM $Mg_2SO_4$, 0.4 mM $K_2HPO_4$ and 25 mM HEPES) containing compound 13 (10 nM). The slices were removed, dried on filter paper, individually weighed then transferred into 2 mL eppendorftubes. The slices were homogenized in 9 volumes (w/v) of buffer using an ultrasonic probe (GeneReady ultra cool (BSH-C2)). The buffer (aECF) was sampled directly from the dish (150 μL) into an eppendorf tube containing control rat brain homogenate (150 μL) that had been prepared with 4 volumes buffer. The matrix matched samples were extracted with cold solvent (4 volumes acetonitrile) containing an appropriate bioanalytical internal standard. After centrifugation (20 min, 3200 g, 4° C.) the supernatants were diluted with appropriate volumes of water and compound concentrations were quantified by LC/MS-MS against matrix matched calibration standards. The $V_{u,brain}$ was calculated according to equation 5 and $f_{u,brain}$ in turn from equation 6.

Equation 5:

$$V_{u,brain} = A_{slice} - V_i \times C_{buffer}/C_{buffer} \times (1-V_i) \qquad (5)$$

$V_{u,brain}$ (mL/g brain)=unbound brain volume of distribution, $A_{slice}$=compound amount in the slice (mg), $C_{buffer}$=compound concentration (μM) in the aESF buffer, $V_i$=buffer adhesion to the brain slice (value=0.0931 mL/g slice).

Equation 6:

$$f_{u,brain,slice} = (1/V_{u,brain}) \times 100 \qquad (6)$$

$f_{u,brain,slice}$=free fraction in brain calculated as a percent free.

TABLE 8

Total plasma and brain concentrations, brain $K_p$, $fu_{brain,\,slice}/fu_{plasma}$ and brain $K_{p,uu}$ are presented for Example 13 (mean ± stdev from n = 3 rats by oral gavage)

| Compound | Species | Dose (mg/kg) | Time point (h) | Total plasma concentration (ng/mL) | Total brain concentration (ng/mL) | Brain $K_p$ | $fu_{brain,\,slice}/fu_{plasma}$ (% free) | Brain $K_{p,uu}$ |
|---|---|---|---|---|---|---|---|---|
| Example 13 | Rat | 1 | 1.0 | 74 ± 17 | 130 ± 27 | 1.76 ± 0.04 | 9.8*/32.0 | 0.54 ± 0.01 |
|  |  | 3 | 1.0 | 340 ± 78 | 597 ± 169 | 1.74 ± 0.10 | 9.8*/32.0 | 0.54 ± 0.03 |
|  |  | 10 | 1.0 | 1639 ± 655 | 2034 ± 462 | 1.30 ± 0.22 | 9.8*/32.0 | 0.40 ± 0.07 |

*The brain free fraction was determined in the rat brain slice model which is a more physiologically relevant, mechanistic in vitro model.

The brain $K_{p,uu}$ values shown in table 7 are further substantiated in table 8 using a more physiologically relevant brain free fraction model supporting that Example 13 is moderately high brain penetrant.

The invention claimed is:

1. A compound of formula I, or a pharmaceutically acceptable salt thereof, wherein:

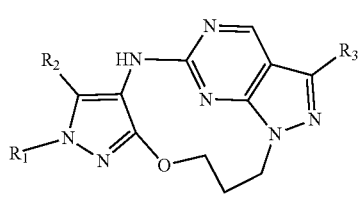

I $R_1$ is $R_4$;
$R_2$ is a $C_1$-$C_3$ alkyl, an isotopically labelled $C_1$-$C_3$ alkyl, a $C_3$-$C_6$ cycloalkyl, or a $C_1$-$C_3$ haloalkyl;

R₃ is halogen, cyano, a O-$C_1$-$C_3$ haloalkyl, a $C_1$-$C_3$ haloalkyl, a $C_3$-$C_6$ cycloalkyl, or a $C_1$-$C_3$ alkyl;

R₄ is a $C_3$-$C_6$ cycloalkyl;

wherein each cycloalkyl is unsubstituted or substituted with 1, 2, or 3 groups independently selected from the group consisting of cyano, deuterium, halogen, $C_1$-$C_3$ alkyl, an isotopically labelled $C_1$-$C_3$ alkyl, a O-$C_1$-$C_3$ haloalkyl, a O-$C_1$-$C_3$ alkyl, and a $C_1$-$C_3$ haloalkyl.

2. The compound of claim 1, or a pharmaceutically acceptable salt thereof, wherein R₂ is selected from a $C_1$-$C_3$ alkyl, an isotopically labelled $C_1$-$C_3$ alkyl and a $C_3$-$C_6$ cycloalkyl.

3. The compound of claim 1, or a pharmaceutically acceptable salt thereof, wherein R₂ is selected from —CH₃, CH₂CH₃, —CD₃ and cyclopropyl.

4. The compound of claim 1, or a pharmaceutically acceptable salt thereof, wherein R₂ is an isotopically labelled $C_1$-$C_3$ alkyl.

5. The compound of claim 1, or a pharmaceutically acceptable salt thereof, wherein R₂ is —CD₃.

6. The compound of claim 1, or a pharmaceutically acceptable salt thereof, wherein R₃ is chloro.

7. The compound of claim 1, or a pharmaceutically acceptable salt thereof, wherein R₂ is —CH₃.

8. The compound of claim 1, or a pharmaceutically acceptable salt thereof, wherein R₂ is —CH₂CH₃.

9. The compound of claim 1, or a pharmaceutically acceptable salt thereof, wherein R₄ is unsubstituted.

10. The compound of claim 1, or a pharmaceutically acceptable salt thereof, wherein R₄ is substituted with 1 or 2 groups independently selected from the group consisting of cyano, halogen, and a O-$C_1$-$C_3$ alkyl.

11. The compound of claim 1, selected from the group consisting of:

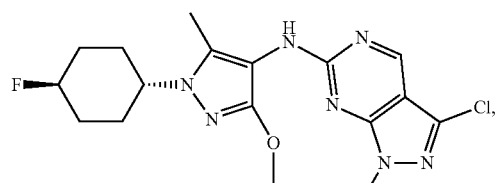

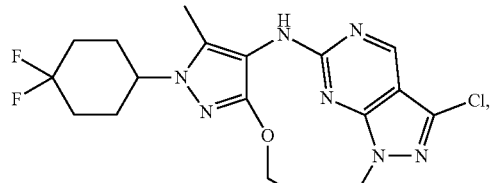

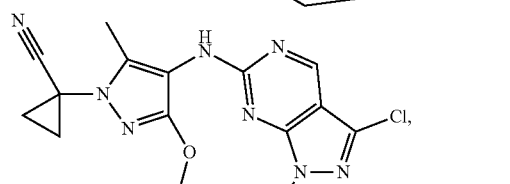

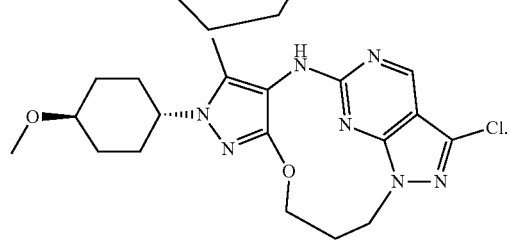

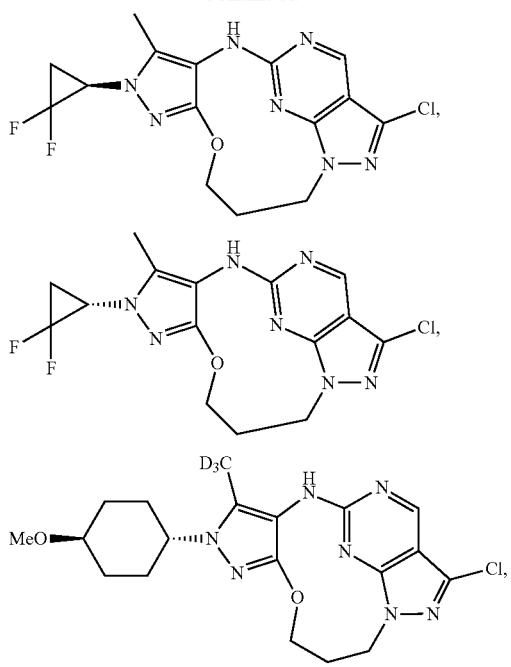

and pharmaceutically acceptable salts thereof.

12. The compound of claim 1, wherein the compound is

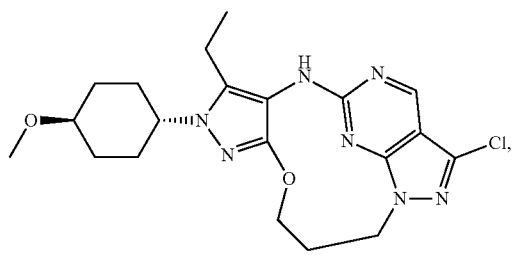

or a pharmaceutically acceptable salt thereof.

13. The compound of claim 1, wherein the compound is

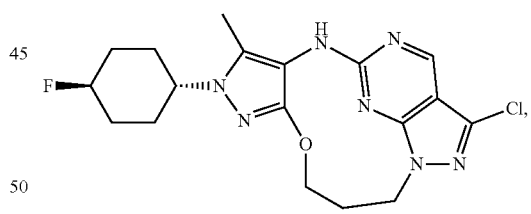

or a pharmaceutically acceptable salt thereof.

14. The compound of claim 1, wherein the compound is

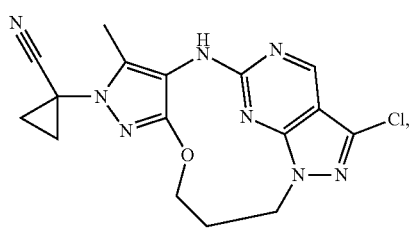 [SMILES: Cc1c2c(nn1C1(C#N)CC1)OCCCn1nc(Cl)c3cnc(nc31)N2]

or a pharmaceutically acceptable salt thereof.

15. The compound of claim 1, wherein the compound is

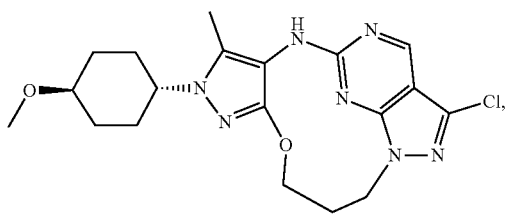 [SMILES: CO[C@H]1CC[C@H](n2nc3c(c2C)Nc2ncc4c(Cl)nn(c4n2)CCCO3)CC1]

or a pharmaceutically acceptable salt thereof.

16. The compound of claim 1, wherein the compound is

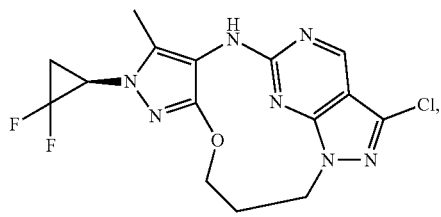 [SMILES: Cc1c2c(nn1[C@@H]1CC1(F)F)OCCCn1nc(Cl)c3cnc(nc31)N2]

or a pharmaceutically acceptable salt thereof.

17. The compound of claim 1, wherein the compound is

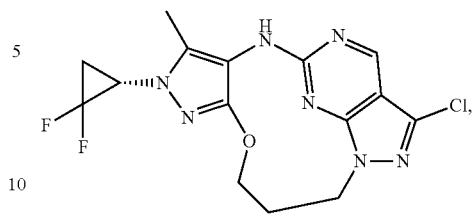

or a pharmaceutically acceptable salt thereof.

18. The compound of claim 1, wherein the compound is

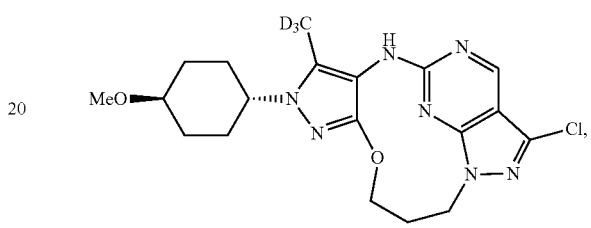

or a pharmaceutically acceptable salt thereof.

19. The compound of claim 1, wherein the compound is

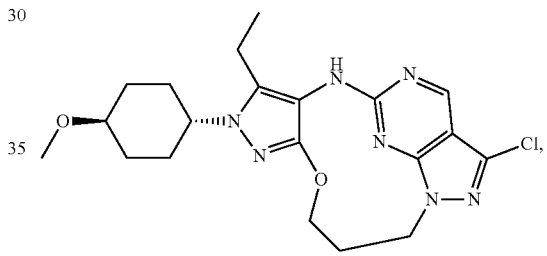

or a pharmaceutically acceptable salt thereof.

* * * * *